US008076285B2

(12) United States Patent
Von Nussbaum et al.

(10) Patent No.: US 8,076,285 B2
(45) Date of Patent: Dec. 13, 2011

(54) LYSOBACTIN AMIDES

(75) Inventors: Franz Von Nussbaum, Duesseldorf (DE); Hartmut Beck, Cologne (DE); Nina Brunner, Essen (DE); Rainer Endermann, Wuppertal (DE); Johannes Koebberling, Neuss (DE); Jacques Ragot, Duesseldorf (DE); Joachim Telser, Wuppertal (DE); Joachim Schuhmacher, Wuppertal (DE); Sonja Anlauf, Wermelskirchen (DE); Yolanda Cancho-Grande, Leverkusen (DE); Susanne Greschat, Wagenfeld (DE); Hans-Christian Militzer, Odenthal (DE); Guido Schiffer, Wuppertal (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 349 days.

(21) Appl. No.: 12/249,888

(22) Filed: Oct. 10, 2008

(65) Prior Publication Data

US 2009/0203582 A1    Aug. 13, 2009

Related U.S. Application Data

(63) Continuation of application No. PCT/EP2007/003303, filed on Apr. 13, 2007.

(30) Foreign Application Priority Data

Apr. 13, 2006    (DE) .......................... 10 2006 018 080

(51) Int. Cl.
*A61K 38/12* (2006.01)
*C07K 7/54* (2006.01)
(52) U.S. Cl. .......... 514/2.4; 514/2.8; 514/21.1; 530/317
(58) Field of Classification Search .................. None
See application file for complete search history.

(56) References Cited

U.S. PATENT DOCUMENTS

| 4,754,018 | A | 6/1988 | Tymiak et al. |
|---|---|---|---|
| 6,380,156 | B1 | 4/2002 | Rinehart et al. |
| 7,056,942 | B2 | 6/2006 | Hildesheim et al. |
| 7,368,424 | B2 | 5/2008 | Von Nussbaum et al. |
| 7,531,507 | B2 | 5/2009 | Von Nussbaum et al. |
| 2005/0075281 | A1 | 4/2005 | Von Nussbaum et al. |
| 2005/0272646 | A1 | 12/2005 | Koteva et al. |
| 2006/0264358 | A1 | 11/2006 | Von Nussbaum et al. |
| 2008/0051424 | A1 | 2/2008 | Von Nussbaum et al. |
| 2008/0058251 | A1 | 3/2008 | Von Nussbaum et al. |
| 2008/0058253 | A1 | 3/2008 | Von Nussbaum et al. |
| 2008/0070884 | A1 | 3/2008 | Von Nussbaum et al. |
| 2009/0105119 | A1 | 4/2009 | Von Nussbaum et al. |

FOREIGN PATENT DOCUMENTS

| DE | 10 2004 053410 | 5/2006 |
|---|---|---|
| EP | 0 196 042 | 10/1986 |
| JP | 01132600 | 5/1989 |
| WO | WO-01/05814 | 1/2001 |
| WO | WO-2004/099239 | 11/2004 |
| WO | WO-2006/048156 | 5/2006 |

OTHER PUBLICATIONS

A Guide to IUPAC Nomenclature of Organic Compounds (Recommendations 1993) 1993, Blackwell Scientific Publications.
Baquero, J. Antimicrob. Chemother. (1997) 39(Suppl. A):1-6.
Barret et al., Tetrahedron Letters (2001) 42(4):703-705.
Bonner et al., J. Antibiot. (1988) 41:1745-1751.
Bull et al., J. Chem. Soc. Perkin Trans. (2001) 1:3281-3287.
Cardillo et al., Synlett (1999) 1727-1730.
Cohen et al., J. Am. Chem. Soc. (2004) 124:2534-2543.
Echner et al., Liebigs Ann. Chem. (1988) 1095-1098.
Goldrick, Am. J. Nurs. (2002) 102:17.
Green, Expert Opin. Ther. Targets (2002) 6:1-19.
International Search Report and Written Opinion for PCT/EP2007/003303, dated Jul. 19, 2007, 16 pages.
Jetten et al., Tetrahedron Lett. (1991) 32:6025-6028.
Jiang et al., J. Am. Chem. Soc. (2003) 125:1877-1887.
Johnson et al., J. Hosp. Infect. (2001) 49(Suppl. A):3-11.
Kalvin et al., J. Org. Chem. (1985) 50(13):2259-2263.
Mattingly et al., J. Org. Chem. (1983) 48:3556-3559.
McGregor, J. Am. Chem. Soc. (1957) 79:6180.
Merget et al., J. Organomet. Chem. (2001) 628:183-194.
Murakami et al., Tetrahedron (2000) 56(46):9121-9128.
Nomenclature and symbolism for amino acids and peptides, Recommendations 1983, IUPAC-IUB Joint Commission on Biochemical Nomenclature, UK, Biochemical Journal (1984) 219:345-373.
Norman et al., Journal of Organic Chemistry (1998) 63(15):5288-5294.
Oliyai et al., Pharm. Res. (1995) 12(3):323-328.
O'Sullivan et al., J. Antibiot. (1988) 41:1740-1744.
Rama et al., Tetrahedron Lett. (1991) 32:4393-4396.
Rane et al., Tetrahedron Lett. (1993) 34(20):3201-3204.
Shemyakin et al., Esperienta (1966) 22(8):535-536.
Shoji et al., J. Antibiot. (1988) 41:713-718.
Schumacher et al., Journal of Pharmaceutical Sciences (2004) 93:816-830.
Tymiak et al., J. Org. Chem. (1989) 54:1149-1157.
Ulhaq et al., Bioorg. Med. Chem. (1999) 7(9):1787-1796.
Alker et al., Tetrahedron (1998) 54:6089-6098.
Anderson and McGregor, J Am Chem Soc (1957) 79:6180-6183.
Bacterial Urinary Tract Infections from the Merck Manual, 8 pages (2007).
Belokon et al., Tetrahedron: Asymmetry (2001) 12:481-485.
Blackburn et al., Drug Metabolism and Disposition (1993) 21(4):573-579.
Cellulitis from the Merck Manual, 3 pages, (2007).
Cystic Fibrosis from the Merck Manual, 7 pages, (2007).
Dikler et al., J Mass Spectrometry (1997) 32:1337-1349.
English Translation of the International Preliminary Report on Patentability for PCT/EP2005/010856, issued on Apr. 24, 2007, 10 pages.

(Continued)

*Primary Examiner* — Jeffrey E Russel
(74) *Attorney, Agent, or Firm* — Morrison & Foerster LLP

(57) ABSTRACT

The invention relates to lysobactin amides and methods for their preparation, as well as their use for manufacturing medicaments for the treatment and/or prophylaxis of diseases, in particular bacterial infectious diseases.

20 Claims, 5 Drawing Sheets

OTHER PUBLICATIONS

Harada et al., J of Chrom (2001) 932:75-81.
Hingley, retrieved from http://www.fda.gov/FDAC/features/1998/398_alz.htm on Jan. 7, 2009, 6 pages.
International Search Report for PCT/EP2005/010857, mailed on Mar. 27, 2006, 4 pages.
International Search Report for PCT/EP2005/011451, mailed on Feb. 27, 2006, 4 pages.
International Search Report for PCT/EP2007/000645, mailed on May 7, 2007, 4 pages.
International Search Report and Written Opinion for PCT/EP2007/003313, dated Jul. 20, 2007, 10 pages.
IUPAC, Nomenclature and Symbolism for Amino Acids and Peptides, Names and Symbols for Derivatives of Named Peptides, Section 3AA-22 (Recommendations 1983-1992).
Kato et al., J Antibiot (1988) 41:719-725.
Lee et al., Tetrahedron (2001) 57:2139-2145.
Maki et al., Antimicrob Agents and Chemotherapy (2001) 45(6):1823-1827.
Merino et al., Tetrahedron: Asymmetry (1998) 9:629-646.
Neises et al., Org Synth (1985) 63:183-187.
Palomo et al., Tetrahedron Lett (2001) 42:8955-8957.
Panico et al., eds., A Guide to IUPAC Nomenclature of Organic Compounds, Blackwell Science LTD., 1993, pp. 1-190 (Recommendations 1993).
Rao et al., Tetrahedron Lett (1991) 32:4393-4396.
Seebach et al., Helv Chim Acta (1996) 79:913-941.
Tenover, Am J Infect Control (2006) 34:S3-S10.
Thornber, Chem Soc Rev (1979) 8(4):563-580.
Translation of the International Preliminary Report on Patentability for PCT/EP2005/011451, mailed Jul. 12, 2007, 8 pages.
Translation of the International Preliminary Report on Patentability for PCT/EP2005/010857, Apr. 24, 2007, 11 pages.
Translation of the International Preliminary Report on Patentability for PCT/EP2005/010858, issued Apr. 24, 2007, 5 pages.
Translation of the International Preliminary Report on Patentability for PCT/EP2007/000645, issued Sep. 9, 2008, 9 pages.
Van Hof et al., Biol Chem (2001) 382:597-619.
Vippagunta et al., Adv Drug Delivery Rev (2001) 48:3-26.
U.S. Appl. No. 10/840,749, filed on May 6, 2004 [Von Nussbaum et al.].
Preliminary Amendment for U.S. Appl. No. 10/840,749, filed Dec. 17, 2004, 15 pages.
Restriction Requirement for U.S. Appl. No. 10/840,749, mailed Dec. 5, 2005, 7 pages.
Request for Extension of Time and Response to Restriction Requirement for U.S. Appl. No. 10/840,749, filed May 8, 2005, 2 pages.
Non-Final Office Action for U.S. Appl. No. 10/840,749, mailed on Aug. 8, 2006, 7 pages.
Amendment in Response to Non-Final Office Action for U.S. Appl. No. 10/840,749, filed on Nov. 8, 2006, 14 pages.
Non-Final Office Action for U.S. Appl. No. 10/840,749, mailed on Feb. 22, 2007, 11 pages.
Terminal Disclaimer for U.S. Appl. No. 10/840,749, filed on Jun. 22, 2007, 1 page.
Amendment in Response to Non-Final Office Action for U.S. Appl. No. 10/840,749, filed on Jun. 22, 2007, 16 pages.
Supplemental Amendment in Response to Non-Final Office Action for U.S. Appl. No. 10/840,749, filed on Nov. 20, 2007, 15 pages.
Notice of Allowance for U.S. Appl. No. 10/840,749, mailed on Dec. 3, 2007, 6 pages.
U.S. Appl. No. 11/267,063, filed on Nov. 4, 2005 [Von Nussbaum et al.].
Preliminary Amendment for U.S. Appl. No. 11/267,063, filed on Jul. 13, 2006, 7 pages.
Restriction Requirement for U.S. Appl. No. 11/267,063, mailed on Apr. 12, 2007, 8 pages.
Amendment in Response to Non-Final Office Action for U.S. Appl. No. 11/267,063, filed on Jul. 11, 2007, 8 pages.
Non-Final Office Action for U.S. Appl. No. 11/267,063, mailed on Aug. 17, 2007, 18 pages.
Amendment in Response to Non-Final Office Action for U.S. Appl. No. 11/267,063, filed Jan. 15, 2008, 9 pages.
Non-Final Office Action for U.S. Appl. No. 11/267,063, mailed on Apr. 14, 2008, 8 pages.
Interview Summary for U.S. Appl. No. 11/267,063, mailed on Aug. 6, 2008, 4 pages.
Amendment in Response to Non-Final Office Action for U.S. Appl. No. 11/267,063, filed Sep. 8, 2008, 8 pages.
Notice of Allowance for U.S. Appl. No. 11/267,063, mailed on Dec. 30, 2008, 7 pages.
U.S. Appl. No. 11/788,590, filed on Apr. 19, 2007 [Von Nussbaum et al.].
Restriction Requirement for U.S. Appl. No. 11/788,590, mailed on Oct. 30, 2008, 10 pages.
Response to Restriction Requirement for U.S. Appl. No. 11/788,590, filed on Dec. 29, 2008, 5 pages.
Non-Final Office Action for U.S. Appl. No. 11/788,590, mailed on Mar. 30, 2009, 19 pages.
Amendment in Response to Non-Final Office Action for U.S. Appl. No. 11/788,590, filed on Jun. 23, 2009, 17 pages.
U.S. Appl. No. 11/788,649, filed on Apr. 20, 2007 [Von Nussbaum et al.].
Restriction Requirement for U.S. Appl. No. 11/788,649, mailed on Jul. 24, 2008, 10 pages.
Response to Restriction Requirement for U.S. Appl. No. 11/788,649, filed on Sep. 19, 2008, 5 pages.
Non-Final Office Action for U.S. Appl. No. 11/788,649, mailed on Jan. 26, 2009, 15 pages.
Amendment for U.S. Appl. No. 11/788,649, filed on Jun. 26, 2009, 19 pages.
U.S. Appl. No. 11/788,690, filed on Apr. 19, 2007 [Von Nussbaum et al.].
Restriction Requirement for U.S. Appl. No. 11/788,690, mailed on Mar. 23, 2009, 12 pages.
Response to Restriction Requirement for U.S. Appl. No. 11/788,690, filed on Apr. 16, 2009, 6 pages.
U.S. Appl. No. 11/800,495, filed on May 4, 2007 [Von Nussbaum et al.].
Restriction Requirement for U.S. Appl. No. 11/800,495, mailed on Jun. 19, 2008, 7 pages.
Response to Restriction Requirement for U.S. Appl. No. 11/800,495, filed on Aug. 19, 2008, 33 pages.
Restriction Requirement for U.S. Appl. No. 11/800,495, mailed on Dec. 8, 2008, 12 pages.
Response to Restriction Requirement for U.S. Appl. No. 11/800,495, filed on Jan. 8, 2009, 5 pages.
Non-Final Office Action for U.S. Appl. No. 11/800,495, mailed on Apr. 22, 2009, 14 pages.
U.S. Appl. No. 12/180,507, filed on Jul. 25, 2008 [Von Nussbaum et al.].
U.S. Appl. No. 12/249,880, filed on Oct. 10, 2008 [Von Nussbaum et al.].

LYSOBACTIN AMIDES

CROSS-REFERENCE TO RELATED APPLICATIONS

This application is a continuation of pending international application PCT/EP2007/003303, filed Apr. 13, 2007, designating U.S., which claims priority from German patent application DE 10 2006 018 080.1, filed Apr. 13, 2006. The contents of these documents are incorporated herein by reference in their entirety.

BACKGROUND OF THE INVENTION

The invention relates to lysobactin amides and methods for their preparation, as well as their use for manufacturing medicaments for the treatment and/or prophylaxis of diseases, in particular bacterial infectious diseases.

The bacterial cell wall is synthesized by a number of enzymes (cell wall biosynthesis) and is essential for the survival and reproduction of microorganisms. The structure of this macromolecule, as well as the proteins involved in the synthesis thereof, are highly conserved within the bacteria. Due to its essential nature and uniformity, the cell wall biosynthesis is an ideal point of attack for novel antibiotics (D. W. Green, The bacterial cell wall as a source of antibacterial targets, *Expert Opin. Ther. Targets,* 2002, 6, 1-19).

Vancomycin and penicillins are inhibitors of the bacterial cell wall biosynthesis and represent successful examples of the antibiotic potency of this principle of action. They have been employed for several decades clinically for the treatment of bacterial infections, especially with Gram-positive pathogens. Due to the growing occurrence of resistant microbes, e.g. methicillin-resistant staphylococci, penicillin-resistant pneumococci and vancomycin-resistant enterococci (F. Baquero, Gram-positive resistance: challenge for the development of new antibiotics, *J. Antimicrob. Chemother.,* 1997, 39, Suppl A:1-6; A. P. Johnson, D. M. Livermore, G. S. Tillotson, Antimicrobial susceptibility of Gram-positive bacteria: what's current, what's anticipated?, *J. Hosp. Infect.,* 2001, (49), Suppl A: 3-11) and recently also for the first time vancomycin-resistant staphylococci (B. Goldrick, First reported case of VRSA in the United States, *Am. J. Nurs.,* 2002, 102, 17) these substances are increasingly losing their therapeutic efficacy.

The present invention describes a novel class of cell wall biosynthesis inhibitors without cross resistances with known antibiotic classes.

The natural product lysobactin and some derivatives are described as having antibacterial activity in U.S. Pat. No. 4,754,018. The isolation and antibacterial activity of lysobactin is also described in EP-A-196 042 and JP 01132600. WO04/099239 describes derivatives of lysobactin having antibacterial activity.

The antibacterial effect of lysobactin and katanosin A is furthermore described in O'Sullivan, J. et al., *J. Antibiot.* 1988, 41, 1740-1744, Bonner, D. P. et al., *J. Antibiot.* 1988, 41, 1745-1751, Shoji, J. et al., *J. Antibiot.* 1988, 41, 713-718 and Tymiak, A. A. et al., *J. Org. Chem.* 1989, 54, 1149-1157.

The stability of an active ingredient is an important parameter for its suitability as medicament. The stability is important inter alia in the storage and administration of medicaments. Many natural products show a stability which is insufficient for medicaments.

The depsipeptide lysobactin which has antibacterial activity is hydrolyzed in an aqueous neutral to basic medium (pH>7) within days. The result thereof is "open-lysobactin" which is opened on the lactone and has no antibacterial activity. It is therefore desirable to have active analogs of lysobactin with greater ring stability.

SUMMARY OF THE INVENTION

One object of the present invention is to provide alternative compounds to lysobactin having comparable or improved antibacterial effect, better tolerability, e.g. lower nephrotoxicity, and improved stability in aqueous neutral to basic medium for the treatment of bacterial diseases in humans and animals.

It has surprisingly been found in the context of this invention that lysobactin amides (cyclic nonapeptide amides) have an analogous antibacterial effect to lysobactin and are stable to hydrolysis in aqueous neutral to basic medium. Lysobactin amides are previously undescribed aza analogs of lysobactin in which the central lactone functionality is replaced by lactam functionality.

The invention relates to compounds of formula

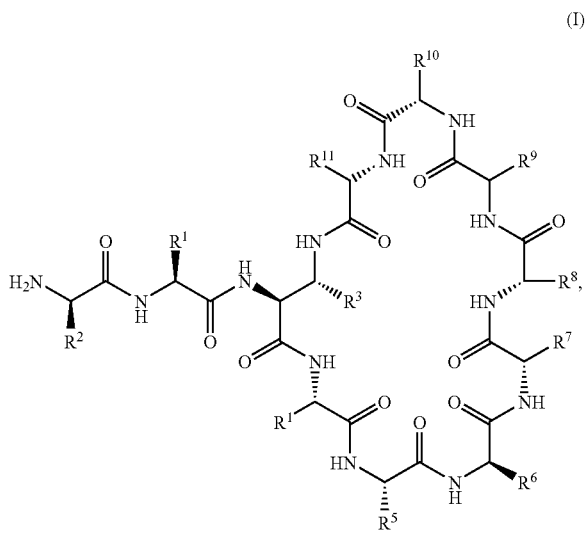

in which $R^1$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl, whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy, $R^2$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl, whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy, $R^3$ represents hydrogen, $C_1$-$C_4$-alkyl, $C_3$-$C_7$-cycloalkyl, $C_3$-$C_7$-cycloalkylmethyl, phenyl, benzyl, 5- or 6-membered heteroaryl or 5- or 6-membered heteroarylmethyl, whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl, $C_1$-$C_4$-alkylaminocarbonyl and 5- or 6-membered heterocyclyl which is bonded via nitrogen, $R^4$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^5$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^6$ represents $C_1$-$C_6$-alkyl, whereby alkyl is substituted with a substituent selected from the group consisting of amino, 1,4,5,6-tetrahydropyrimidin-2-ylamino, [amino(imino)methyl]amino, 2-pyridyl, 3-pyridyl and 4-pyridyl, $R^7$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl or trimethylsilylmethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^8$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^9$ represents hydrogen, $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^{10}$ represents hydrogen, $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^{11}$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino,
and
whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl,
and the salts thereof, the solvates thereof and the solvates of the salts thereof, except the compounds of formula (Ia)

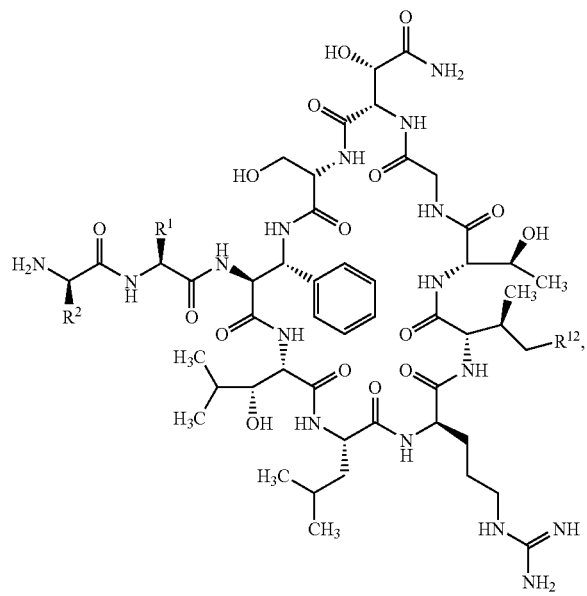

in which
$R^1$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl,
whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy,
$R^2$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl,
whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy,
and
$R^{12}$ represents hydrogen or methyl,
and the salts thereof, the solvates thereof and the solvates of the salts thereof.
Compounds of the invention are the compounds of formula (I) and the salts, solvates, solvates of the salts and prodrugs thereof, the compounds which are encompassed by formula (I) and are of the formulae mentioned below, and the salts, solvates, solvates of the salts and prodrugs thereof, as well as the compounds which are encompassed by formula (I) and are mentioned below as exemplary embodiments, and the salts, solvates, solvates of the salts and prodrugs thereof, insofar as the compounds which are encompassed by formula (I) and are mentioned below are not already salts, solvates, solvates of the salts and prodrugs.

The compounds of the invention may, depending on their structure, exist in stereoisomeric forms (enantiomers, diastereomers). The invention therefore relates to the enantiomers or diastereomers and respective mixtures thereof. The stereoisomerically uniform constituents can be isolated from such mixtures of enantiomers and/or diastereomers in a known manner.

Where the compounds of the invention can exist in tautomeric forms, the present invention encompasses all tautomeric forms.

Salts preferred for the purposes of the present invention are physiologically acceptable salts of the compounds of the invention. However, also included are salts which themselves are not suitable for pharmaceutical applications but can be used for example for the isolation or purification of the compounds of the invention or mixed salts. A mixed salt means in the context of the present invention an addition salt which comprises two or more different acids or bases, such as, for example, a trifluoroacetate-mesylate salt.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which form a complex in the solid or liquid state through coordination with solvent molecules. Hydrates are a special form of solvates in which the coordination takes place with water.

For the purposes of the present invention, the substituents have the following meaning, unless otherwise specified:

Alkyl per se and "alk" and "alkyl" in alkoxy, alkylamino, alkoxycarbonyl and alkylaminocarbonyl represents a linear or branched alkyl radical generally having 1 to 6, preferably 1 to 4, particularly preferably 1 to 3 carbon atoms, by way of example and preferably methyl, ethyl, n-propyl, isopropyl, tert-butyl, 2,2-dimethylprop-1-yl, 2,2-dimethylbut-1-yl, n-pentyl and n-hexyl.

Alkoxy by way of example and preferably represents methoxy, ethoxy, n-propoxy, isopropoxy, tert-butoxy, n-pentoxy and n-hexoxy.

Alkoxycarbonyl by way of example and preferably represents methoxycarbonyl, ethoxycarbonyl, n-propoxycarbonyl, isopropoxycarbonyl, tert-butoxycarbonyl, n-pentoxycarbonyl and n-hexoxycarbonyl.

Alkylamino represents an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino represents for example a monoalkylamino radical having 1 to 3 carbon atoms or a dialkylamino radical having 1 to 3 carbon atoms each per alkyl substituent.

Alkylaminocarbonyl represents an alkylaminocarbonyl radical having one or two alkyl substituents (chosen independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents for example a monoalkylaminocarbonyl radical having 1 to 3 carbon atoms or a dialkylaminocarbonyl radical having 1 to 3 carbon atoms each per alkyl substituent.

Cycloalkyl represents a cycloalkyl group generally having 3 to 7 carbon atoms, by way of example and preferably cyclopropyl, cyclobutyl, cyclopentyl, cyclohexyl and cycloheptyl.

Heterocyclyl represents a monocyclic, heterocyclic radical having 5 or 6 ring atoms and up to 3 heteroatoms and/or hetero groups from the series N, O, S, SO, $SO_2$, whereby a nitrogen atom can also form an N-oxide. The heterocyclyl radicals may be saturated or partly unsaturated and by way of example and preferably represent pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, thiopyranyl, morpholin-1-yl, morpholin-2-yl, morpholin-3-yl.

Heteroaryl represents an aromatic monocyclic radical having 5 or 6 ring atoms and up to 4 heteroatoms from the series S, O and N, by way of example and preferably thienyl, furyl, pyrrolyl, thiazolyl, oxazolyl, imidazolyl, pyridyl, pyrimidyl and pyridazinyl.

Halogen represents fluorine, chlorine, bromine and iodine, preferably fluorine and chlorine.

Preference is given to compounds of formula (I) in which $R^1$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^2$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^3$ represents $C_1$-$C_4$-alkyl, phenyl, benzyl, 2-pyridyl, 3-pyridyl or 4-pyridyl, whereby phenyl, benzyl, 2-pyridyl, 3-pyridyl and 4-pyridyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^4$ represents $C_1$-$C_6$-alkyl, $C_3$-$C_7$-cycloalkylmethyl, benzyl, 5- or 6-membered heteroarylmethyl or trimethylsilylmethyl, whereby alkyl may be substituted with a hydroxy substituent, and whereby cycloalkylmethyl, benzyl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^5$ represents $C_1$-$C_6$-alkyl, $C_3$-$C_7$-cycloalkylmethyl, phenyl, benzyl, 5- or 6-membered heteroarylmethyl or trimethylsilylmethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkylmethyl, phenyl, benzyl and heteroarylmethyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^6$ represents $C_1$-$C_6$-alkyl, whereby alkyl is substituted with a substituent selected from the group consisting of amino, 1,4,5,6-tetrahydropyrimidin-2-ylamino, [amino(imino)methyl]amino, 2-pyridyl, 3-pyridyl and 4-pyridyl, $R^7$ represents $C_1$-$C_6$-alkyl, $C_3$-$C_7$-cycloalkylmethyl, phenyl, benzyl, 5- or 6-membered heteroarylmethyl or trimethylsilylmethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkylmethyl, phenyl, benzyl and heteroarylmethyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^8$ represents $C_1$-$C_6$-alkyl, $C_3$-$C_7$-cycloalkylmethyl, benzyl, 5- or 6-membered heteroarylmethyl or trimethylsilylmethyl, whereby alkyl may be substituted with a hydroxy substituent, and whereby cycloalkylmethyl, benzyl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^9$ represents hydrogen, $C_1$-$C_6$-alkyl, $C_3$-$C_7$-cycloalkyl, phenyl, trimethylsilylmethyl or 2-amino-2-oxoethyl, whereby methyl may be substituted with a substituent selected from the group consisting of hydroxy, amino and mercapto, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, $R^{10}$ represents hydrogen, $C_1$-$C_6$-alkyl, $C_3$-$C_7$-cycloalkyl, phenyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, $R^{11}$ represents methyl or ethyl, whereby methyl and ethyl may be substituted with a substituent selected from the group consisting of hydroxy, amino, mercapto, 1,4,5,6-tetrahydropyrimidin-2-ylamino and [amino(imino)methyl]amino, and the salts thereof, the solvates thereof, and the solvates of the salts thereof, except the compounds of formula (Ia), in which $R^1$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^2$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, and $R^{12}$ represents hydrogen or methyl, and the salts thereof, the solvates thereof and the solvates of the salts thereof.

Preference is also given to compounds of formula (I), in which $R^1$ represents 2,2-dimethylprop-1-yl, 2,2-dimethylbut-1-yl, trimethylsilylmethyl or 3-pyridylmethyl, $R^2$ represents 2,2-dimethylprop-1-yl, 2,2-dimethylbut-1-yl, trimethylsilylmethyl or 3-pyridylmethyl, $R^3$ represents $C_1$-$C_4$-alkyl, 3-pyridyl or phenyl, whereby 3-pyridyl or phenyl may be substituted with a substituent selected from the group consisting of halogen, cyano, methyl, methoxy, dimethylamino and diethylamino, $R^4$ represents —CH(OH)—$C_1$-$C_5$-alkyl or —CH(OH)phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, $R^5$ represents $C_1$-$C_6$-alkyl, $C_3$-$C_7$-cycloalkylmethyl, benzyl or trimethylsilylmethyl, $R^6$ represents linear $C_2$-$C_4$-alkyl, whereby alkyl is substituted with a substituent selected from the group consisting of amino, 1,4,5,6-tetrahydropyrimidin-2-ylamino and [amino(imino)methyl]amino, $R^7$ represents $C_1$-$C_6$-alkyl, $C_3$-$C_7$-cycloalkylmethyl, benzyl or trimethylsilylmethyl, $R^8$ represents $C_1$-$C_4$-alkyl, —CH$_2$—OH, —CH(OH)—$C_1$-$C_5$-alkyl or —CH(OH)phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, $R^9$ represents hydrogen, $C_1$-$C_6$-alkyl, hydroxymethyl or 2-amino-2-oxoethyl, $R^{10}$ represents hydrogen, $C_1$-$C_4$-alkyl, 2-amino-2-oxoethyl or 2-amino-1-hydroxy-2-oxoethyl, whereby $C_1$-$C_4$-alkyl may be substituted with a substituent selected from the group consisting of amino and hydroxy, with the exception that $R^{10}$ is not 4-aminobut-1-yl, $R^{11}$ represents methyl, whereby methyl is substituted with a substituent selected from the group consisting of hydroxy and amino, and the salts thereof, the solvates thereof and the solvates of the salts thereof, except the compounds of formula (Ia), in which $R^1$ represents 2,2-dimethylprop-1-yl, 2,2-dimethylbut-1-yl, trimethylsilylmethyl or 3-pyridylmethyl, $R^2$ represents 2,2-dimethylprop-1-yl, 2,2-dimethylbut-1-yl, trimethylsilylmethyl or 3-pyridylmethyl, and $R^{12}$ represents hydrogen or methyl, and the salts thereof, the solvates thereof and the solvates of the salts thereof.

Preference is also given to compounds of formula (I) in which $R^1$ represents 2-methylprop-1-yl, 2,2-dimethylprop-1-yl, 2,2-dimethylbut-1-yl, trimethylsilylmethyl or benzyl, whereby benzyl may be substituted with 1 or 2 substituents selected independently of one another from the group consisting of halogen, trifluoromethyl and methyl, or one of the salts thereof, the solvates thereof or the solvates of the salts thereof.

Preference is also given to compounds of formula (I) in which $R^1$ represents 2,2-dimethylprop-1-yl, 2,2-dimethylbut-1-yl or trimethylsilylmethyl, or one of the salts thereof, the solvates thereof or the solvates of the salts thereof.

Preference is also given to compounds of formula (I) in which $R^2$ represents 2,2-dimethylprop-1-yl or 3-pyridylmethyl, or one of the salts thereof, the solvates thereof or the solvates of the salts thereof.

Preference is also given to compounds of formula (I) in which $R^3$ represents phenyl, benzyl, 2-pyridyl, 3-pyridyl or 4-pyridyl, whereby phenyl, benzyl, 2-pyridyl, 3-pyridyl and 4-pyridyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, or one of the salts thereof, the solvates thereof or the solvates of the salts thereof.

Preference is also given to compounds of formula (I) in which $R^3$ represents phenyl, whereby phenyl may be substituted with a substituent selected from the group consisting of halogen, cyano, methyl, methoxy, dimethylamino and diethylamino, or one of the salts thereof, the solvates thereof or the solvates of the salts thereof.

Preference is also given to compounds of formula (I), in which $R^8$ represents —CH(OH)—$C_1$-$C_5$-alkyl or —CH(OH) phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, and or one of the salts thereof, the solvates thereof or the solvates of the salts thereof.

Preference is also given to compounds of formula (I) in which $R^{10}$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, or one of the salts thereof, the solvates thereof or the solvates of the salts thereof.

Preference is also given to compounds of formula (I) in which $R^{10}$ represents $C_1$-$C_6$-alkyl, $C_3$-$C_7$-cycloalkyl, phenyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino) methyl]amino, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, or one of the salts thereof, the solvates thereof or the solvates of the salts thereof.

Preference is also given to compounds of formula (I) in which $R^{10}$ represents methyl, ethyl, 2-amino-2-oxoethyl or 2-amino-1-hydroxy-2-oxoethyl, whereby methyl and ethyl may be substituted with a hydroxy substituent, or one of the salts thereof, the solvates thereof or the solvates of the salts thereof.

The invention further relates to a method for preparing the compounds of formulae (I), whereby

[A] Compounds of Formula

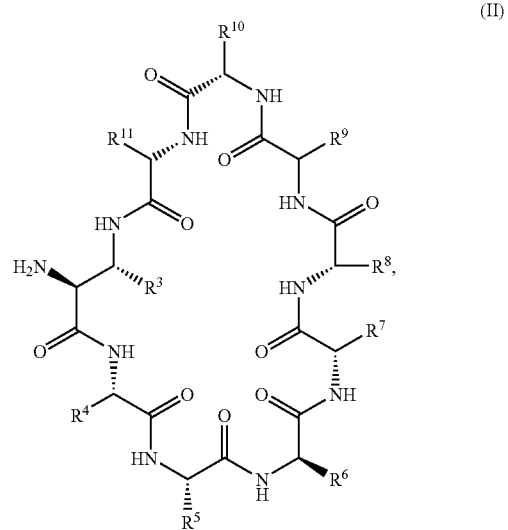

(II)

in which $R^3$, $R^4$, $R^5$, $R^6$, $R^7$, $R^8$, $R^9$, $R^{10}$ and $R^{11}$ have the meaning indicated above, are reacted first with compounds of formula

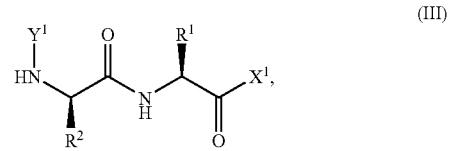

(III)

in which $R^1$ and $R^2$ have the meaning indicated above, $Y^1$ represents tert-butoxycarbonyl or benzyloxycarbonyl, and $X^1$ represents halogen, preferably bromine, chlorine or fluorine, or hydroxy, and subsequently with an acid and/or by hydrogenolysis, or

[B] Compounds of Formula

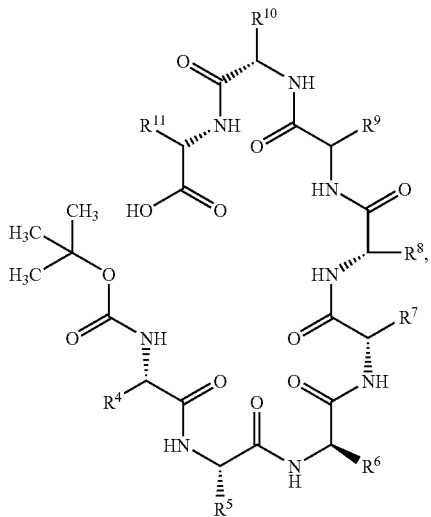

(IV)

in which
$R^4$, $R^5$, $R^6$, $R^7$, $R^8$, $R^9$, $R^{10}$ and $R^{11}$ have the meaning indicated above,
are reacted first with compounds of formula

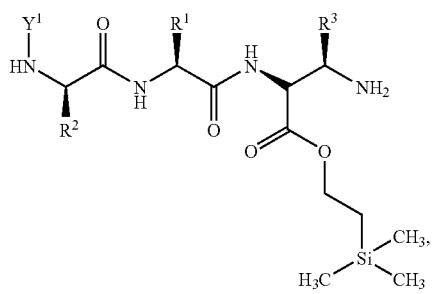

(V)

in which
$R^1$, $R^2$ and $R^3$ have the meaning indicated above, and
$Y^1$ represents tert-butoxycarbonyl or benzyloxycarbonyl,
and subsequently in a 4-stage synthesis
a) with a fluoride reagent such as tetrabutylammonium fluoride,
b) with an acid,
c) with a dehydrating reagent, where appropriate in the presence of a base, and
d) by hydrogenolysis.

Method [A]:

If $X^1$ is halogen, the reaction in the first stage generally takes place in inert solvents, where appropriate in the presence of a base, preferably in a temperature range from −30° C. to 50° C. under atmospheric pressure.

Examples of inert solvents are tetrahydrofuran, methylene chloride, pyridine, dioxane, dimethylacetamide, N-methylpyrrolidine or dimethylformamide, with preference for pyridine or dimethylformamide.

Examples of bases are triethylamine, diisopropylethylamine or N-methylmorpholine, with preference for diisopropylethylamine.

If $X^1$ is hydroxy, the reaction in the first stage generally takes place in inert solvents, in the presence of a dehydrating reagent, where appropriate in the presence of a base, preferably in a temperature range from −30° C. to 50° C. under atmospheric pressure.

Examples of inert solvents are halohydrocarbons such as dichloromethane or trichloromethane, hydrocarbons such as benzene, nitromethane, dioxane, dimethylformamide or acetonitrile. It is likewise possible to employ mixtures of these solvents. Dichloromethane or dimethylformamide is particularly preferred.

Examples of suitable dehydrating reagents hereby are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl polystyrene (PS-carbodiimide) or carbonyl compounds such as carbonyldiimidazole or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N', N'-tetramethyluronium hexafluorophosphate (HBTU), 2-(2-oxo-1-(2H)-pyridyl)-1,1,3,3-tetramethyluronium tetrafluoroborate (TPTU), O-(1H-6-chlorobenzotriazol-1-yl)-1,1,3,3-tetramethyluronium tetrafluoroborate (TCTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexa-fluorophosphate (BOP), or benzotriazol-1-yloxytris(pyrrolidino)phosphonium hexafluorophosphate (PyBOP), or N-hydroxy-succinimide, or mixtures thereof, with bases.

Examples of bases are alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

The condensation is preferably carried out with HATU or with EDC in the presence of HOBt.

The reaction with an acid in the second stage of the method preferably takes place in a temperature range from 0° C. to 40° C. under atmospheric pressure.

Suitable acids hereby are hydrogen chloride in dioxane, hydrogen bromide in acetic acid or trifluoroacetic acid in methylene chloride.

The hydrogenolysis in the second stage of the method generally takes place in a solvent in the presence of hydrogen and palladium on activated carbon, preferably in a temperature range from 0° C. to 40° C. under atmospheric pressure.

Examples of solvents are alcohols such as methanol, ethanol, n-propanol or isopropanol, in a mixture with water and acetic acid or aqueous hydrochloric acid, with preference for a mixture of ethanol, water and acetic acid or a mixture of isopropanol and aqueous hydrochloric acid.

Method [B]:

The reaction of the compounds of formula (IV) with compounds of formula (V) generally takes place in inert solvents in the presence of a dehydrating reagent, where appropriate in the presence of a base, preferably in a temperature range from −30° C. to 50° C. under atmospheric pressure.

Examples of inert solvents are halohydrocarbons such as dichloromethane or trichloromethane, hydrocarbon such as benzene, nitromethane, dioxane, dimethylformamide or acetonitrile. It is likewise possible to employ mixtures of the solvents. Dichloromethane or dimethylformamide is particularly preferred.

Examples of suitable dehydrating reagents hereby are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl polystyrene (PS-carbodiimide) or carbonyl compounds such as carbonyldiimidazole or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(1H-6-chlorobenzotriazol-1-yl)-1,1,3,3-tetramethyluronium tetrafluoroborate (TCTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures thereof, with bases.

Examples of bases are alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

The condensation is preferably carried out with HATU or with a mixture of EDC and HOBt.

The reaction with tetrabutylammonium fluoride in the first stage (a) of the further method generally takes place in inert solvents, preferably in a temperature range from 0° C. to 40° C. under atmospheric pressure.

Examples of inert solvents are halohydrocarbons such as dichloromethane or trichloromethane, or ethers such as tetrahydrofuran or dioxane. Tetrahydrofuran is particularly preferred.

The reaction with an acid in the second stage (b) of the method preferably takes place in a temperature range from 0° C. to 40° C. under atmospheric pressure.

Suitable acids hereby are hydrogen chloride in dioxane, hydrogen bromide in acetic acid or trifluoroacetic acid in methylene chloride.

The reaction in the third stage (c) of the method takes place in analogy to the reaction of compounds of formula (IV) with compounds of formula (V).

The hydrogenolysis in the fourth stage (d) of the method generally takes place in a solvent in the presence of hydrogen and palladium on activated carbon, preferably in a temperature range from 0° C. to 40° C. under atmospheric pressure.

Examples of solvents are alcohols such as methanol, ethanol, n-propanol or isopropanol, in a mixture with water and acetic acid or aqueous hydrochloric acid, with preference for a mixture of ethanol, water and acetic acid or a mixture of isopropanol and aqueous hydrochloric acid.

The compounds of formula (II) are known or can be prepared by reacting compounds of formula

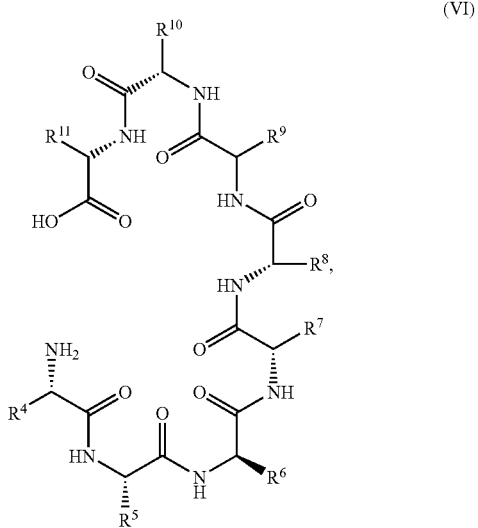

(VI)

in which $R^4$, $R^5$, $R^6$, $R^7$, $R^8$, $R^9$, $R^{10}$ and $R^{11}$ have the meaning indicated above, first with compounds of formula

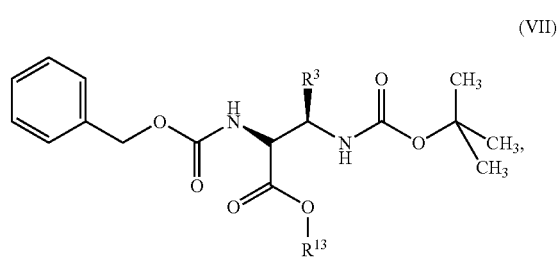

(VII)

in which $R^3$ has the meaning indicated above, and $R^{13}$ represents cyanomethyl, p-nitrophenyl, o-nitrophenyl, 2,4-dinitrophenyl, 2,4,5-trichlorophenyl, pentachlorophenyl, pentafluorophenyl (Pfp), N-hydroxyphthalimidyl, N-hydroxysuccinimidyl (O-Su), 1-hydroxypiperidinyl or 5-chloro-8-hydroxyquinolinyl, and subsequently in a 3-stage synthesis a) with an acid, b) with a dehydrating reagent, where appropriate in the presence of a base, and c) by hydrogenolysis.

The reaction of the compounds of formula (VI) with compounds of formula (VII) generally takes place in inert solvents, where appropriate in the presence of a base, preferably in a temperature range from −30° C. to 50° C. under atmospheric pressure.

Examples of inert solvents are tetrahydrofuran, methylene chloride, pyridine, dioxane, dimethylacetamide, N-methylpyrrolidine or dimethylformamide, with preference for pyridine or dimethylformamide.

The reaction with an acid in the first stage (a) of the method preferably takes place in a temperature range from 0° C. to 40° C. under atmospheric pressure.

Suitable acids hereby are hydrogen chloride in dioxane, hydrogen bromide in acetic acid or trifluoroacetic acid in methylene chloride.

The reaction in the second stage (b) of the method takes place in analogy to the reaction of compounds of formula (IV) with compounds of formula (V).

The hydrogenolysis in the third stage (c) of the method generally takes place in a solvent in the presence of hydrogen and palladium on activated carbon, preferably in a temperature range from 0° C. to 40° C. under atmospheric pressure.

Examples of solvents are alcohols such as methanol, ethanol, n-propanol or isopropanol, in a mixture with water and acetic acid or aqueous hydrochloric acid, with preference for a mixture of ethanol, water and acetic acid or a mixture of isopropanol and aqueous hydrochloric acid.

The compounds of formulae (III), (V) and (VII) are known or can be synthesized by known method, or by the methods described below, from the corresponding starting materials.

The compounds of formulae (IV) and (VI) are known or can be synthesized in solution using appropriate protecting groups or on the solid phase by known peptide synthesis methods, or by the methods described below, from the corresponding starting materials.

The preparation of the compounds of the invention can be illustrated by the following synthesis schemes.

Synthesis scheme 1:

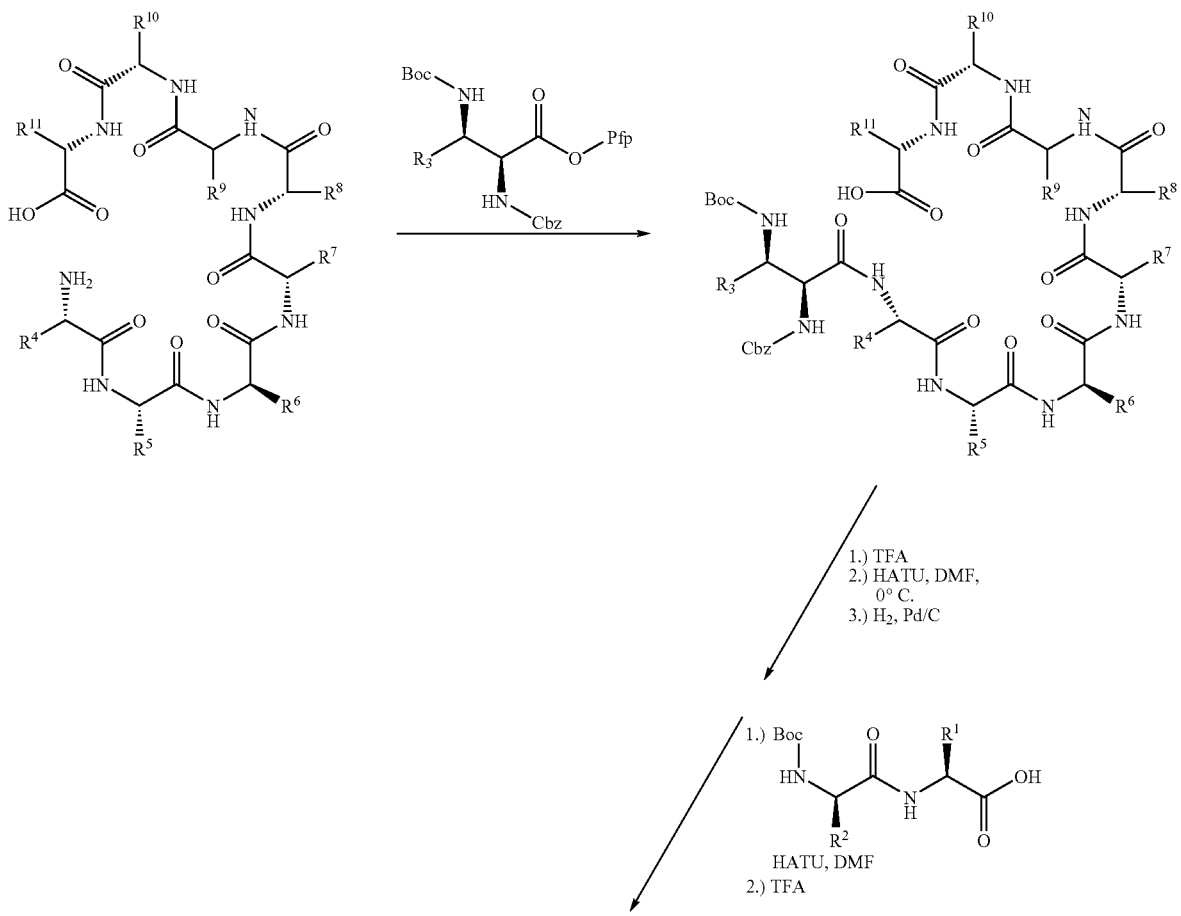

-continued
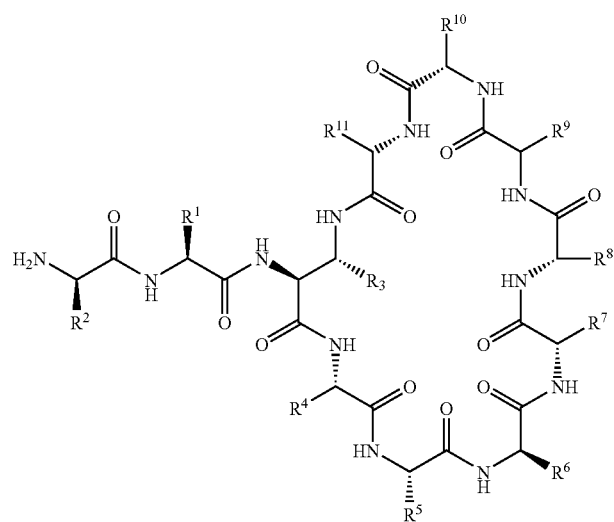
Synthesis scheme 2:
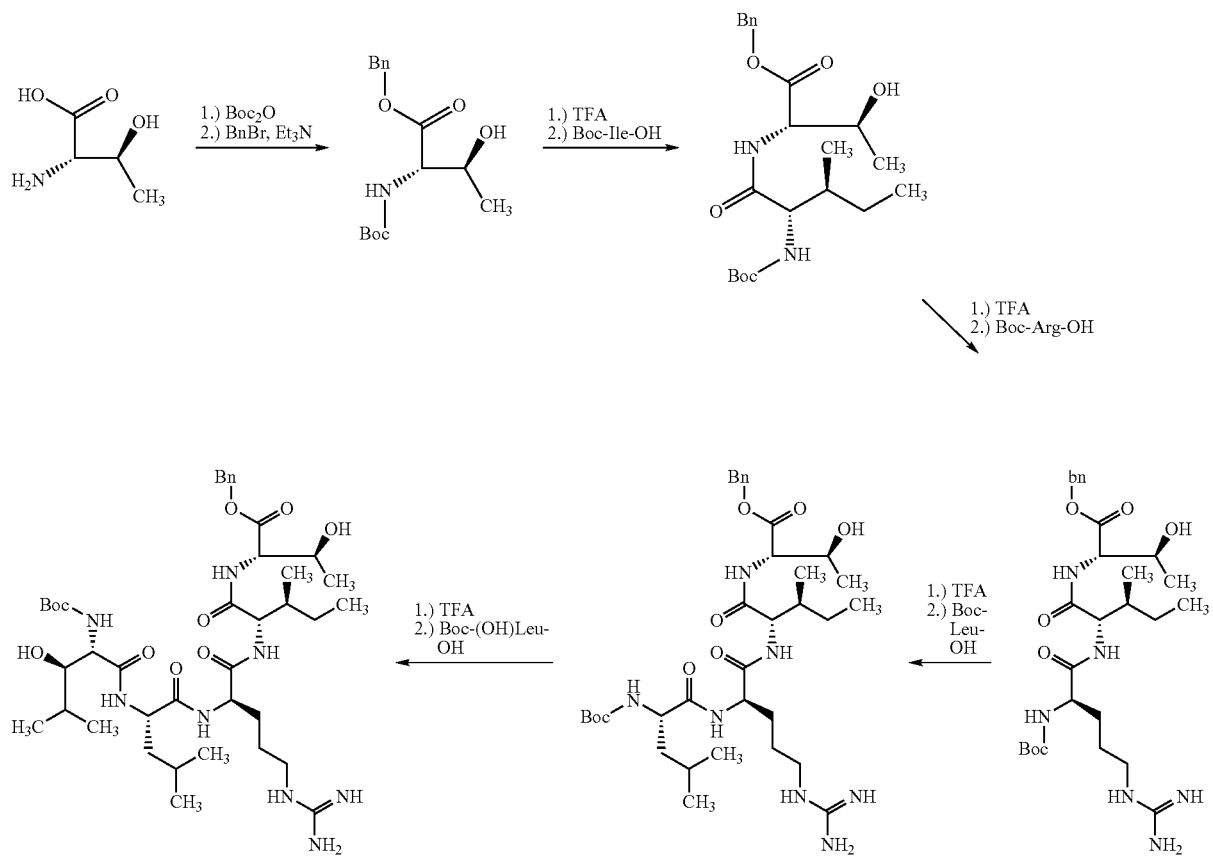

Synthesis scheme 3:

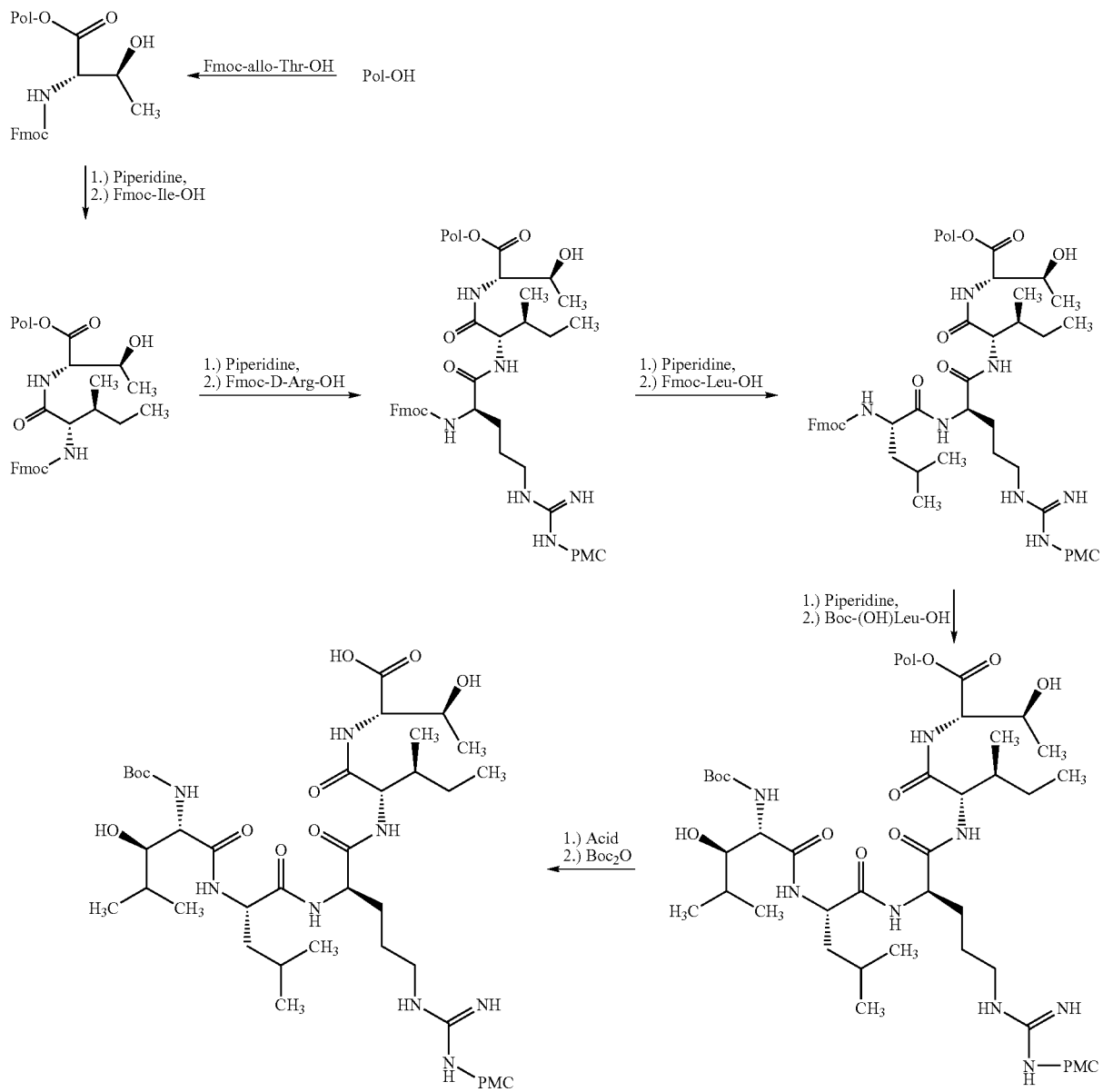

The compounds of the invention show a valuable range of pharmacological effects which could not have been predicted. They show an antibacterial effect.

They are therefore suitable for use as medicaments for the treatment and/or prophylaxis of diseases in humans and animals.

The compounds of the invention are distinguished by a lower nephrotoxicity compared with lysobactin.

The compounds of the invention are distinguished by an improved stability in aqueous neutral to basic medium. This property improves the storage of the compounds of the invention and the administration as medicaments.

The described nonadepsipeptides act as inhibitors of the bacterial cell wall biosynthesis.

The preparations of the invention are particularly effective against bacteria and bacteroid microorganisms. They are therefore particularly suitable for the prophylaxis and chemotherapy of local and systemic infections caused by these pathogens in human and veterinary medicine.

The preparations of the invention can in principle be used against all bacteria and bacteroid microorganisms possessing a bacterial cell wall (murein sacculus) and the relevant enzyme systems, for example against the following pathogens or mixtures of the following pathogens:

Gram-negative cocci (*Neisseria gonorrhoeae*) as well as Gram-negative rods such as enterobacteriaceae, e.g. *Escherichia coli*, *Haemophilus influenzae*, *Pseudomonas*, *Klebsiella*, *Citrobacter* (*C. freundii*, *C. divernis*), *Salmonella* and *Shigella*; furthermore *Enterobacter* (*E. aerogenes*, *E. agglomerans*), *Hafnia*, *Serratia* (*S. marcescens*), *Providencia*, *Yersinia*, as well as the genus *Acinetobacter*, *Branhamella* and *Chlamydia*. The antibacterial range additionally includes strictly anaerobic bacteria such as, for example, *Bacteroides fragilis*, representatives of the genus *Peptococcus*, *Peptostreptococ-*

*cus*, as well as the genus *Clostridium*; furthermore mycobacteria, e.g. *M. tuberculosis*. The compounds of the invention show a particularly pronounced effect on Gram-positive cocci, e.g. staphylococci (*S. aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is merely by way of example and is by no means to be interpreted restrictively. Examples which may be mentioned of diseases which can be caused by the pathogens mentioned or mixed infections and can be prevented, improved or healed by the preparations of the invention are:

Infectious diseases in humans such as, for example, uncomplicated and complicated urinary tract infections, uncomplicated cutaneous and superficial infections, complicated cutaneous and soft tissue infections, hospital- and community-acquired pneumonia, nosocomial pneumonias, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynecological infections, pelvic inflammatory disease, bacterial vaginosis, acute and chronic osteomyelitis, acute bacterial arthritis, empirical therapy in febrile neutropenic patients, furthermore bacteremias, MRSA infections, acute infectious diarrhea, *Helicobacter pylori* infections, postoperative infections, odontogenic infections, opthalmological infections, postoperative infections (including periproctal abscess, wound infections, biliary infections, mastitis and acute appendicitis), cystic fibrosis and bronchiectasis.

Apart from humans, bacterial infections can also be treated in other species. Examples which may be mentioned are:

Pigs: diarrhea, enterotoxemia, sepsis, dysentery, salmonellosis, metritis-mastitis-agalactiae syndrome, mastitis;

Ruminants (cattle, sheep, goats): diarrhea, sepsis, bronchopneumonia, salmonellosis, pasteurellosis, genital infections;

Horses: bronchopneumonias, joint ill, puerperal and postpuerperal infections, salmonellosis;

Dogs and cats: bronchopneumonia, diarrhea, dermatitis, otitis, urinary tract infections, prostatitis;

Poultry (hens, turkeys, quail, pigeons, ornamental birds and others): *E. coli* infections, chronic airway disorders, salmonellosis, pasteurellosis, psittacosis.

It is likewise possible to treat bacterial diseases in the rearing and management of productive and ornamental fish, in which case the antibacterial spectrum is extended beyond the pathogens mentioned above to further pathogens such as, for example, *Pasteurella, Brucella, Campylobacter, Listeria, Erysipelothris, corynebacteria, Borellia, Treponema, Nocardia, Rikettsia, Yersinia*.

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, especially of the aforementioned diseases.

The present invention further relates to the use of the compounds of the invention for the manufacture of a medicament for the treatment and/or prophylaxis of diseases, especially of the aforementioned diseases.

The compounds of the invention are preferably used for the manufacture of medicaments suitable for the prophylaxis and/or treatment of bacterial diseases.

The present invention further relates to a method for the treatment and/or prophylaxis of diseases, especially of the aforementioned diseases, using an antibacterially effective amount of the compounds of the invention.

The present invention further relates to medicaments comprising at least one compound of the invention and at least one or more further active ingredients, in particular for the treatment and/or prophylaxis of the aforementioned diseases. Preferred active ingredients for combination are compounds having an antibacterial activity and having a different range of effects, in particular a supplementary range of effects, and/or being synergistic to the compounds of the invention.

The compounds of the invention can act systemically and/or locally. For this purpose, they can be administered in a suitable way such as, for example, orally, parenterally, pulmonarily, nasally, sublingually, lingually, buccally, rectally, dermally, transdermally, conjunctivally or otically, or as an implant or stent.

For these administration routes the compounds of the invention can be administered in suitable administration forms.

Suitable for oral administration are administration forms which function according to the prior art and deliver the compounds of the invention rapidly and/or in modified fashion, and which contain the compounds of the invention in crystalline and/or amorphized and/or dissolved form, such as, for example, tablets (uncoated or coated tablets, for example having enteric coatings or coatings which dissolve with a delay or are insoluble and control the release of the compound of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for the ears or eyes, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

The compounds of the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, usually together with one or more inert, nontoxic, pharmaceutically acceptable excipients, and to the use thereof for the aforementioned purposes.

It has generally proved advantageous to administer on intravenous administration amounts of about 0.001 to 100 mg/kg, preferably about 0.1 to 10 mg/kg, of body weight to achieve effective results, and on oral administration the dosage is about 0.01 to 50 mg/kg, preferably 0.5 to 10 mg/kg, of body weight.

It may nevertheless be necessary where appropriate to deviate from the stated amounts, in particular as a function of body weight, route of administration, individual response to the active ingredient, nature of the preparation and time or interval over which the administration takes place. Thus, it may be sufficient in some cases to make do with less than the aforementioned minimum amount, whereas in other cases the stated upper limit must be exceeded. It may in the event of an administration of larger amounts be advisable to divide these into a plurality of individual doses over the day.

The percentage data in the following tests and examples are, unless indicated otherwise, percentages by weight; parts are parts by weight. Solvent ratios, dilution ratios and concentration data for the liquid/liquid solutions are in each case based on volume.

BRIEF DESCRIPTION OF THE DRAWINGS

The appended drawings show stability diagrams for selected exemplary compounds, and lysobactin as comparative example. These show.

DETAILED DESCRIPTION OF PREFERRED EMBODIMENTS

A. Examples

Figure 1:
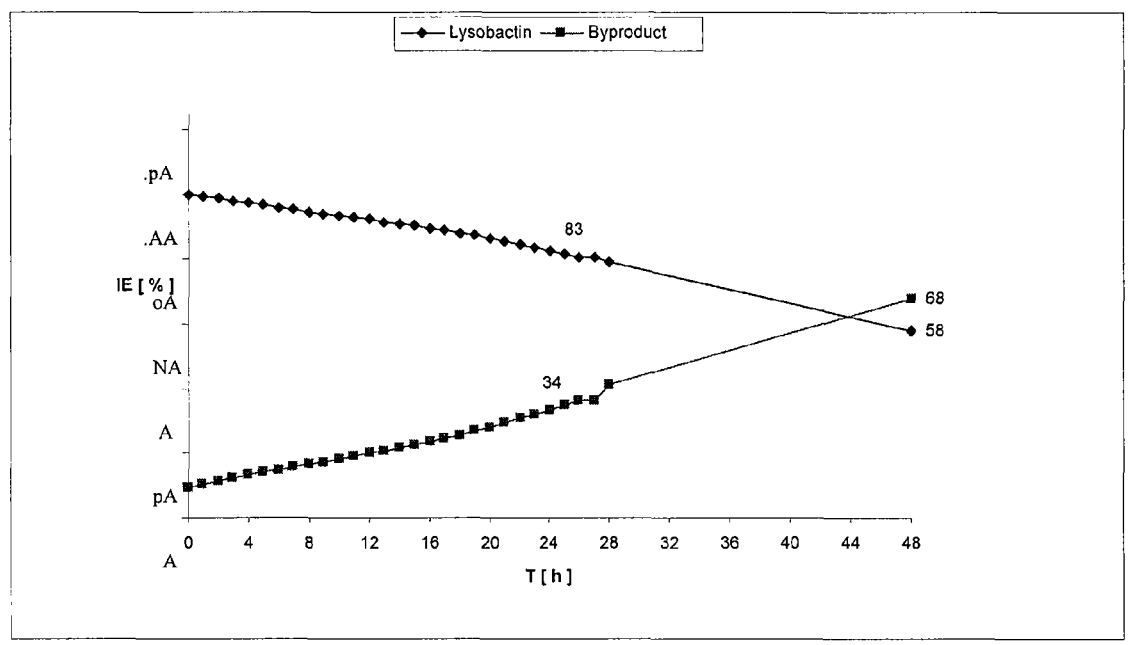
FIG. 1: A plot of the change in concentration of lysobactin and of a degradation product of lysobactin over time in an aqueous, slightly alkaline solution.

| Abbreviations | Terms |
| --- | --- |
| abs. | absolute |
| aq. | aqueous |
| BHI | brain heart infusion |
| Boc | tert-butoxycarbonyl |
| conc. | concentrated |
| DCC | dicyclohexylcarbodiimide |
| DCI | direct chemical ionization (in MS) |
| DCM | dichloromethane |
| DIEA | N,N-diisopropylethylamine |
| DMAP | 4-N,N-dimethylaminopyridine |
| DMSO | dimethyl sulfoxide |
| DMF | N,N-dimethylformamide |
| EA | ethyl acetate |

-continued

| Abbreviations | Terms |
| --- | --- |
| EDC | 1-ethyl-3-(3-dimethylaminopropyl)carbodiimide (also EDCI) |
| EDCxHCl | 1-ethyl-3-(3-dimethylaminopropyl)carbodiimide hydrochloride |
| EDTA | ethylenediaminetetraacetic acid |
| EI | electron impact ionization (in MS) |
| eq. | equivalent(s) |
| ESI | electrospray ionization (in MS) |
| Ex. | example |
| h | hour(s) |
| HATU | O-(7-azabenzotriazol-1-yl)-N,N,N',N'-tetramethyluronium hexafluorophosphate |
| HOBt | 1-hydroxybenzotriazole |
| HPLC | high pressure, high performance liquid chromatography |
| LC-MS | coupled liquid chromatography-mass spectroscopy |
| LDA | lithium diisopropylamide |
| LHMDS | lithium hexamethyldisilazide |
| LLA(3-cyclohexyl) | D-Leu-Leu-(3-cyclohexyl)Ala |
| LLF | D-Leu-Leu-Phe |
| MALDI | matrix-assisted laser desorption/ionization |
| MIC | minimum inhibitory concentration |
| Min | minute/minutes |
| MRSA | methicillin-resistant *Staphylococcus aureus* |
| MS | mass spectroscopy |
| MTBE | methyl tert-butyl ether |
| NCCLS | National Committee for Clinical Laboratory Standards |
| neg. | negative |
| NMM | N-methylmorpholine |
| NMR | nuclear magnetic resonance spectroscopy |
| org. | organic |
| p.a. | pro analysis |
| Pd | palladium |
| Pd-C | palladium on carbon |
| pos. | positive |
| PTFE | polytetrafluoroethylene |
| quant. | quantitative |
| RP-HPLC | reverse phase HPLC |
| RT | room temperature |
| $R_f$ | retention factor (in thin-layer chromatography) |
| $R_t$ | retention time (in HPLC) |
| sat. | saturated |
| TBAF | tetrabutylammonium fluoride |
| TBTU | O-(benzotriazol-1-yl)-N,N,N',N'-tetramethyluronium tetrafluoroborate |
| TCTU | O-(1H-6-chlorobenzotriazol-1-yl)-1,1,3,3-tetramethyluronium tetrafluoroborate |
| TFA | trifluoroacetic acid |
| TFE | 2,2,2-trifluoroethanol |
| THF | tetrahydrofuran |
| TMG | N,N,N,N-tetramethylguanidine |
| TMSE | 2-(trimethylsilyl)ethyl |
| TOF | time of flight |
| UV | ultraviolet |
| VRSA | vancomycin-resistant *Staphylococcus aureus* |
| XPHOS | dicyclohexyl(2',4',6'-triisopropylbiphenyl-2-yl)phosphine |
| Z, Cbz | benzyloxycarbonyl |

REFERENCES

Concerning the nomenclature of peptides and cyclodepsipeptides, compare:
1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* 1984, 219, 345-373, and cited literature.

Material and Methods
Analytical Methods
Method 1: HPLC instrument type: HP 1100 Series; UV DAD; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 2: HPLC instrument type: HP 1050 Series; UV DAD; column: Phenomenex Synergi 2μ Max-RP Mercury 20 mm×4 mm; eluent A: 1 l of water+0.05% TFA, eluent B: 1 l of acetonitrile; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 3: HPLC instrument type: HP 1050/1100 Series; UV DAD 1100 Series; column: Kromasil $C_{18}$, 60×2.1 mm, 3.5 μm; eluent A: water/0.5% perchloric acid, eluent B: acetonitrile; gradient: 0-0.5 min 2% B, 0.5-4.5 min 2-90% B, 4.5-6.5 min 90% B, 6.5-6.7 min 90-2% B, 6.7-7.5 min 2% B; flow rate: 0.75 ml/min, oven: 30° C., UV detection 210 nm.

Method 4: Instrument: HP 1100 with DAD detection; column: Kromasil 100 RP-18, 60 mm×2.1 mm, 3.5 μm; eluent A: 5 ml of perchloric acid (70%)/l of water, eluent B: acetonitrile; gradient: 0 min 2% B, 0.5 min 2% B, 4.5 min 90% B, 9 min 90% B, 9.2 min. 2% B, 10 min 2% B; flow rate: 0.75 ml/min; column temp.: 30° C.; detection: UV 210 nm.

Method 5: Instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.05% 70% perchloric acid in water; eluent B: acetonitrile; flow rate: 2.00 ml/min; gradient: 0-1 min 10% B, ramp, 4-5 min 90% B, ramp, 5.5 min 10% B.

Method 6: Instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.01% TFA in water; eluent B: 0.01% TFA in acetonitrile; flow rate: 2.00 ml/min; gradient: 0-1 min 10% B, ramp, 4-5 min 90% B, ramp, 5.5 min 10% B.

Method 7: Agilent 1100 with DAD (G1315B), binary pump (G1312A), autosampler (G1313A), degasser (G1379A) and column thermostat (G1316A); column: Synergi 4□ Hydro-RP 80A, 4.6×150×5 mm; oven temperature: 30° C.; eluent A: water+0.05% 70% perchloric acid; eluent B: acetonitrile; flow rate: 2.00 ml/min; gradient: 0-1 min 10% B, ramp, 4-5 min 90% B, ramp, 5.5 min 10% B.

Method 8: Instrument: Agilent 1100 with DAD (G1315B), binary pump (G1312A), autosampler (G1313A), solvent degasser (G1379A) and column thermostat (G1316A); column: Agilent Eclipse XDB-C8 4.6×150×5 mm; column temperature: 40° C.; eluent A: 0.05% 70% perchloric acid in water; eluent B: methanol; flow rate: 2.00 ml/min; isocratic: 0-7 min 55% B.

Method 9: HPLC instrument type: HP 1050 Series; UV DAD; column: Zorbax 300 mSB-C18 3.5μ, 4.6 mm×150 mm; eluent A: 1 l of water+0.1% TFA, eluent B: 400 ml of acetonitrile/600 ml of water+0.1% TFA; gradient: 0.0 min 100% A, 1.3 min 10% B, 18.0 min 80% B, 20.0 min 80% B, 21.0 min 100% B, 25.0 min 100% B, 26.0 min 0% B, 30.0 min 0% B. Flow rate: 1 ml/min; oven: 40° C.; UV detection: 210 nm.

Method 10: HPLC instrument type: HP 1050 Series; UV DAD; column: Zorbax 300 mSB-C18 3.5μ, 4.6 mm×150 mm; eluent A: 1 l of water+0.1% TFA, eluent B: acetonitrile; gradient: 0.0 min 100% A, 15.0 min 100% B, 17.0 min 100% B, 18.0 min 100% A. Flow rate: 1 ml/min; oven: 40° C.; UV detection: 210 nm.

Method 11: HPLC instrument type: HP 1050 Series; UV DAD; column: Zorbax 300 mSB-C18 3.5μ, 4.6 mm×150 mm; eluent A: 1 l of water+0.1% TFA, eluent B: 400 ml of acetonitrile/600 ml of water+0.1% TFA; gradient: 0.0 min 100% A, 2.0 min 10% B, 50.0 min 80% B, 52.0 min 100% B, 55.0 min 100% A, 60.0 min 100% A. Flow rate: 1 ml/min; oven: 40° C.; UV detection: 210 nm.

Method 12: HPLC instrument type: HP 1050 Series; column SymmetryPrep™C18, Waters, 50×2.1 mm, 3.5 μm; eluent A: water/0.1% TFA, eluent B: acetonitrile; gradient: 0-3 min 0% B, 3.01-9 min 100% B, 9.01-11 min 100% B, 11.01-12 min 0-100% A; oven: 40° C.; flow rate: 0.4 ml/min; UV detection: 210 nm.

Method 13: HPLC instrument type: HP 1100 Series; UV DAD; column: Chromolith Speed ROD RP18; eluent A: 1 l of water+0.05% TFA, eluent B: 1 l of acetonitrile; gradient: 0.0-0.5 min 95% A, 0.51-3.0 min 5-95% B, 3.01-3.80 min 95% A; flow rate: 5 ml/min; oven: 40° C.; UV detection: 210 nm.

Method 14: column (steel column, dimensions 250×4.6 mm); stationary phase (chiral silica/polyamide composite KBD 5326, based on the selector poly(N-methacryolyl-L-leucine dicyclopropylmethylamide); eluent: ethyl acetate, isocratic; flow rate: 1 ml/min; temperature: 25° C.; UV detection: 220 nm; sample: injection of 10 μl.

Method 15: stationary phase (Chiralcel OD); eluent: 1-hexane/1-PrOH: 9/1, isocratic; flow rate: 2 ml/min; temperature: 25° C.; UV detection: 254 nm.

Method 16: HPLC instrument type: HP 1100 Series; column: Chiralpack AD-H 250 mm×4.6 mm; eluent A: isohexane, eluent B: ethanol+0.2% TFA+1% H2O; isocratic; flow rate: 1 ml/min; oven: 40° C.; UV detection: 230 nm.

Method 17: Daicel Chiralpak AD-H 5 μm 250 mm×4.6 mm, hexane/2-propanol/methanol 85/6/9, flow rate: 2.0 ml/min, UV detection at 254 nm.

Method 18: MS instrument type: Micromass ZQ; HPLC instrument type: Waters Alliance 2795/HP 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 19: MS instrument type: Micromass ZQ; HPLC instrument type: Waters Alliance 2795/HP 1100; column: Phenomenex Gemini 3μ C-18 100 Å, 30 mm×3 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 20: UV detection: 210 nm. MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml 50% of formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 21: Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 22: Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 23: MS instrument type: Micromass LCT (ESI pos./neg.); HPLC instrument type: HP 1100 Series; UV DAD 1100 Series; column SymmetryPrep™$C_{18}$, Waters, 50×2.1 mm, 3.5 μm; eluent A: water/0.1% formic acid, eluent B: acetonitrile/0.1% formic acid; gradient: 0-1 min 0% B, 1-6 min 0-90% B, 6-8 min 90-100% B, 8-10 min 100% B, 10-10.1 min 100-0% B, 10.1-12 min 0% B, then regeneration of the chromatography column. Oven: 40° C., flow rate: 0.5 ml/min (briefly up to 1 ml/min at 10.1 min), UV detection: 210 nm.

Method 24: TOF-HR-MS-ESI+ spectra are recorded with Micromass® LCT instrument (capillary voltage: 3.2 KV, cone voltage: 42 V, source temperature: 120° C., desolvation temperature: 280° C.). A syringe pump (Harvard Apparatus) is used for the sample delivery for this purpose. Leucine-encephalin is used as standard.

Method 25: The MALDI-MS/MS investigations are carried out on a 4700 Proteomics Analyzer (Applied Biosystems, Framingham, Mass., USA) which is equipped with TOF/TOF ion optics and a 200 Hz Nd:YAG laser (355 nm). The quasi molecular ions are accelerated in the ion source with 8 kV, selected with an electric deflector (MS1), and collided with argon atoms in a collision cell which is arranged between MS1 and MS2. The resulting fragment ions are accelerated again with 15 kV and characterized with the second time of flight mass analyzer (MS2).

Preparative Chromatography

Method 26: Instrument: Gilson Abimed HPLC; binary pump system; column: Nucleodur $C_{18}$ Gravity, Macherey-Nagel, 5 μm; 250×21 mm; eluent A: water/0.05%-0.1% TFA, eluent B: acetonitrile; gradient: 0-8 min 5% B, 8-40 min 5-60% B, 40-60 min 60% B, 60-75 min 60-100% B, 75-80 min 100% B, then regeneration of the chromatography column; flow rate: 7-15 ml/min; UV detector 210 nm.

Method 27: Instrument: Gilson Abimed HPLC; binary pump system; column: Nucleodur C18 Gravity, Macherey-Nagel, 5 μm; 250×21 mm; eluent A: water/0.05%-0.1% TFA, eluent B: acetonitrile; gradient: 0-8 min 5% B, 8-40 min 5-60% B, 40-60 min 60% B, 60-75 min 60-100% B, 75-80 min 100% B, then regeneration of the chromatography column; flow rate: 7-15 ml/min; UV detector 210 nm.

Method 28: Instrument: Gilson Abimed HPLC; binary pump system; column: Nucleodur C18 Gravity, Macherey-Nagel, 5 μm; 250×40 mm; eluent A: water/0.05-0.1% TFA, eluent B: acetonitrile/0.05-0.1% TFA; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column; flow rate: 15-45 ml/min; UV detector 210 nm.

Method 29: Instrument: Gilson Abimed HPLC; binary pump system; column: Nucleodur $C_{18}$ Gravity, Macherey-Nagel, 5 μm; 250×21 mm; eluent A: water/0.2% acetic acid, eluent B: acetonitrile/0.2% acetic acid; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column; flow rate: 7-15 ml/min; UV detector 210 nm.

Method 30: Instrument: Gilson Abimed HPLC; binary pump system; column: Nucleodur C18 Gravity, Macherey-Nagel, 5 μm; 250×40 mm; eluent A: water/0.2% acetic acid, eluent B: acetonitrile/0.2% acetic acid; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column; flow rate: 15-45 ml/min; UV detector 210 nm.

Method 31: Instrument: Gilson Abimed HPLC; binary pump system; column: Kromasil-100A $C_{18}$, 5 μm; 250×30 mm; eluent A: water/0.25% acetic acid, eluent B: acetonitrile; gradient: 0-3 min 5% B, 3-30 min 5-100% B, 30-38 min 100% B, then regeneration of the chromatography column; flow rate: 25 ml/min; UV detector 210 nm.

Method 32: Instrument: Gilson Abimed HPLC; binary pump system; column: Kromasil-100A $C_{18}$, 5 μm; 250×30 mm; eluent A: water/0.05-0.5% TFA, eluent B: acetonitrile; gradient: 0-min 5% B, 5.01-10 min 10% B, 10.01-20 min 40% B, 20.01-27 min 50% B, 27.01-40 min 60% B, 40.01-45 min 90% B, 45.01-60 min 100% B; flow rate: 15-60 ml/min; UV detector 210 nm.

Method 33: Gilson Abimed HPLC; UV detector 210 nm; column: Kromasil RP-18 5 μm, 100 Å, 250×20 mm; eluent A: water+0.05% TFA, eluent B: acetonitrile+0.05% TFA: flow rate: 10 ml/min; 0-3 min 10% B, ramp, 30-38 min 90% B, 38-45 min 10% B.

Method 34: Gilson Abimed HPLC; UV detector 210 nm; column: Gromsil ODS-4HE 10 μm, 250×40 mm; eluent A: water+0.05% TFA, eluent B: acetonitrile+0.05% TFA: flow rate: 20 ml/min; 0-3 min 10% B, ramp, 30-35 min 90% B, 35-40 min 90% B.

Method 35: Instrument: Gilson Abimed HPLC; binary pump system; column: Waters Symmetry-Prep™ $C_{18}$, 7 μm, 300×19 mm; eluent A: water/0.2% glacial acetic acid, eluent B: acetonitrile; gradient: 0-8 min 5% B, 8-25 min 5-100% B, 25.01-40 min 100% B, then regeneration of the chromatography column; flow rate: 15 ml/min; UV detector 210 nm.

Method 36: Instrument: Gilson Abimed HPLC; binary pump system; column: Waters Symmetry-Prep™ $C_{18}$, 7 μm, 300×19 mm; eluent A: water/0.1% TFA, eluent B: acetonitrile; gradient: 0-5 min 5% B, 5.01-32 min 5-100% B, 32.01-35 min 100% B, then regeneration of the chromatography column; flow rate: 15 ml/min; UV detector 210 nm.

Method 37: column: Kromasil-100 $C_{18}$, 5 μm; 250×20 mm; eluent: 25% water+0.2 TFA/75% acetonitrile; isocratic; 0-8.5 min; flow rate: 25 ml/min; UV detector 220 nm; temperature 30° C.

Method 38: column (steel column, dimensions 250×30 mm); stationary phase (chiral silica/polyamide composite KBD 5326, based on the selector poly(N-methacryolyl-L-leucine dicyclopropylmethylamide); eluent ethyl acetate, isocratic; flow rate: 25 ml/min; temperature: 24° C.; UV detection: 225 nm; sample: repetitive injection of 2000 μl.

Method 39: column (steel column, dimensions 430×75 mm); stationary phase (chiral silica/polyamide based on the selector poly(N-methacryloyl-D-leucine dicyclopropylmethylamide); eluent isohexane (80%)/THF (20%), isocratic; flow rate: 200 ml/min; temperature: 24° C.; UV detection: 254 nm; sample: repetitive injection of 10000 μl.

Method 40: column (steel column, dimensions 250×20 mm); stationary phase (Daicel Chiralpak AD-H, 5 μm); eluent: isohexane (70%)/2-propanol+0.2% acetic acid+1% water (30%), isocratic; flow rate: 15 ml/min; temperature: 29° C.; UV detection: 220 nm; sample: repetitive injection of 750 μl.

Method 41: Gilson Abimed HPLC; column: Daicel Chiralpak AD-H 5 μm; 250×20 mm; eluent A: isohexane, eluent B:

0.2% acetic acid/1% water/2-propanol; isocratic; flow rate: 15 ml/min; UV-detector 212 nm Method 42: column (steel column, dimensions 500×40 mm); stationary phase (Daicel Chiralpak AD 20 μm), isohexane/isopropanol/methanol 95/2/3, flow rate: 100 ml/min, UV detection: 230 nm.

Method 43: Instrument: Gilson Abimed HPLC; UV detector 210 nm; binary pump system; column: SymmetryPrep™C$_{18}$, Waters, 7 μm; 300 mm×19 mm; flow rate: 25 ml/min; eluent A: water/0.2% TFA, eluent B: acetonitrile; gradient: 0-10 min 15-65% B, then regeneration of the chromatography column.

Method 44: Gilson Abimed HPLC; UV detector 210 nm; column: Waters Symmetry-Prep™ C-18, 7 μm, 300×19 mm; eluent A: water+0.05% TFA, eluent B: acetonitrile+0.05% TFA: flow rate: 10 ml/min; 0-3 min 10% B, ramp, 30-38 min 90% B, 38-45 min 10% B.

Method 45: Gel chromatography is carried out without pressure on Sephadex LH-20 (Pharmacia). Fractions are taken according to UV activity (UV detector for 254 nm, Knauer) (ISCO Foxy 200 fraction collector). Column dimensions: 32×7 cm (1000-100 μmol scale); 30×4 cm (100-10 μmol scale); 25×2 cm (10-1 μmol scale). Methanol is used as eluent.

Method 46: Gilson Abimed HPLC; UV detector 210 nm; column: Biotage Flash40 RP-18 or compatible module Varian Metaflash C18 40M, 35 μm, 150×40 mm; eluent A: water+0.05% TFA, eluent B: acetonitrile+0.05% TFA: flow rate: 40 ml/min; 0-3 min 10% B, ramp, 30-38 min 90% B, 38-45 min 10% B.

Method 47: Preparative separation of the chymotrypsin cleavage of fragments 1-3 and 4-11 of dihydrolysobactin by reversed phase chromatography. Column: Source 15-RPC (GE-HealthCare), diameter 5 cm, length 12 cm, volume 235 ml. Eluent A: 0.1% acetic acid in water. Eluent B: 0.1% acetic acid in methanol. Flow rate: 30 ml/min. UV detection: 215 nm, 280 nm. Loading: about 6-7 mg total protein/ml resin. Sample loading: The column is equilibrated with eluent A, the 0.2 μm-filtered cleavage mixture solution is put on and the column is washed with eluent A. Elution: 0-45% in about 18 column volumes, subsequent washing with about 1.3 column volumes of 100% B.

Fractionation: 50 ml fractions are collected from the start of the elution. CIP: Column is washed with 2 column volumes of a 1 N sodium hydroxide solution at a reduced flow rate (5 ml/min).

Specific Methods for Analyzing Amino Acids and Peptides

Method 48: The amino acid analyses are carried out using an LC 3000 amino acid analyzer from Eppendorf/Biotronik. A slightly modified standard Eppendorf/Biotronik separation program is used. The separation programs and the function of the analyzer are described in detail in the handbook for the instrument (Handbuch des Aminosaurenanalysators LC 3000, Wissenschaftliche Gerate GmbH Biotronik, Maintal, 1996).

Method 49: Capillary electrophoresis allows peptides and proteins to be separated on the basis of their charge in the electric field. The quality of the separation thereby depends on the buffer, the pH, the temperature and the additives used. The capillaries employed are so-called fused silica columns with an internal diameter of 50-100 μm. This method is a very good criterion for assessing the purity of a peptide and for monitoring the formation of enzymatic cleavage products. The peptides dihydrolysobactin and octahydrolysobactin elute at about 21 min, fragment 4-11 at about 18 min, 1-3 (LLF) at about 24 min, 1-3 (LLA(3-cyclohexyl)) at about 22 min, the deamidated forms as a double peak at about 30 min (1-11) and 24 min (4-11) from the capillary column. The large increase in the deamidated products after 24 h in the buffer is clearly seen. About 4 ng of the enzymatic cleavage products or of the starting compounds dihydrolysobactin and octahydrolysobactin or of the mixture are investigated by capillary electrophoresis on a glass column (length 72 cm, internal diameter 50 μm). Conditions: current 90 μA, column temperature 25° C., 100 mM phosphate buffer of pH 3.0, UV detection 210 nm, loading under pressure in 3 seconds.

Method 50: 3 nmol of fragments dissolved in 60% acetonitrile/0.1% TFA are loaded onto a sequencer sheet preincubated with Polybren®. The proteins are sequenced using the normal sequencer cycle. The PTH-amino acids are identified by means of online HPLC with the aid of a 40 pmol PTH standard. The non-proteinogenic amino acids are identified by their position relative to the standard amino acids. The purity of the peptides is estimated via the amino acid of the 1st PTH cycle. The various peptides are sequenced over 4 to 12 stages.

Further Analytical and Preparative Methods

Method 51: Instrument: Micromass Quattro LCZ with HPLC Agilent Series 1100; column: Phenomenex Onyx Monolithic C18, 100 mm×3 mm. Eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 52: MS instrument type: Micromass ZQ; HPLC instrument type: Waters Alliance 2795; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 53: Instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.01% TFA in water; eluent B: 0.01% TFA in acetonitrile; flow rate: 2.00 ml/min; gradient: 0-1 min 10% B, ramp, 10-14 min 90%, reconditioning.

Method 54: Instrument: Agilent 1100 with DAD (G1315B), binary pump (G1312A), autosampler (G1313A), solvent degasser (G1379A) and column thermostat (G1316A); column: Agilent Zorbax Eclipse XDB-C8 4.6×150×5 mm; column temperature: 30° C.; eluent A: 0.01% TFA in water; eluent B: 0.01% TFA in acetonitrile; flow rate: 1.40 ml/min; gradient: 0 min 10% B, ramp, 2.5-5 min 90%, reconditioning.

Method 55: Column (steel column, dimensions 250×20 mm); stationary phase (Daicel Chiralpak AD-H, 5 μm); eluent: isohexane (90%)/ethanol+0.2% AcOH+1% H2O (10%), isocratic; flow rate: 15 ml/min; temperature: 30° C.; UV detection: 220 nm; sample: repetitive injection of 500 μl.

Method 56: Column (steel column, dimensions 250×4.6 mm); stationary phase (Daicel Chiralpak AD-H, 5 μm); eluent: isohexane (90%)/ethanol+0.2% AcOH+1% H2O (10%), isocratic; flow rate: 1.0 ml/min; temperature: 30° C.; UV detection: 220 nm; sample: injection of 10 μl.

Method 57: Column: column: Kromasil 100 C18, 60×2.1 mm 3.5 μm, column oven 30° C., flow rate: 0.75 ml/min, detector: 210 nm, running time: 15 min; eluent A: water with 5 ml of HClO$_4$/liter of water), eluent B: acetonitrile; gradient: 0-1 min 2% B, ramp, 9-13 min, 98% B, reconditioning.

Method 58: (Chiral preparative HPLC, Chiralpak AD-H 40-60); column (steel column, dimensions 250×20 mm); stationary phase (Daicel Chiralpak AD-H, 5 μm); eluent: isohexane (40%)/ethanol+0.2% AcOH+1% H2O (60%), isocratic; flow rate: 15 ml/min; temperature: 30° C.; UV detection: 220 nm; sample: repetitive injection of 500 μl.

Method 59: (Chiral analytical HPLC, Chiralpak AD-H 40-60); column (steel column, dimensions 250×4.6 mm); stationary phase (Daicel Chiralpak AD-H, 5 μm); eluent: isohexane (40%)/ethanol+0.2% AcOH+1% $H_2O$ (60%), isocratic; flow rate: 1.0 ml/min; temperature: 30° C.; UV detection: 220 nm; sample: injection of 10 μl.

General Procedures

Procedure 1 (removal of Boc protecting groups with TFA): The Boc-protected compound is suspended in dichloromethane (⅕-¹/₁₀ of the reaction solution) and subsequently, under an argon protective gas atmosphere, 30% TFA in dichloromethane (approx. 1 ml/10 mg of starting material on the 100-1 millimolar scale, approx. 1 ml/1 mg on the 100-1 micromolar scale) is added, and the mixture is stirred at RT until the HPLC chromatogram shows complete conversion (e.g. method 1). The solvent is then distilled off in vacuo, during which the bath temperature should not exceed 30° C. The crude product is suspended in toluene, concentrated again on a rotary evaporator, and dried under high vacuum. This procedure is repeated several times (two to five times). If the purity of the product is insufficient, it is purified where appropriate by chromatography, e.g. by preparative HPLC or by gel chromatography.

Procedure 2 (removal of the Boc protecting group with 30% TFA in dichloromethane): The starting material is taken up in 30% TFA (solution in dichloromethane) and stirred at room temperature for 30 min. The solvent is then distilled off in vacuo, during which the bath temperature should not exceed 30° C. The product is then dried to constant weight under oil pump vacuum.

Procedure 3 (removal of the Boc protecting group with 4 N hydrochloric acid in dioxane): The N-(tert-butoxycarbonyl)-protected compound (1 mmol) is provided in dioxane (2-3 ml) under an argon protective gas atmosphere. At RT or while cooling in ice and while stirring vigorously, 4 N hydrochloric acid in dioxane (30 ml) is added dropwise. Stirring is continued until analytical HPLC (Method 1) indicates complete conversion (about 30 min to 2 h). The reaction mixture is evaporated in vacuo at RT. The crude product is taken up in a little dichloromethane and again freed of solvent in vacuo. This procedure is repeated several times with toluene (twice) and with dichloromethane (twice). Finally the crude product is lyophilized or immediately reacted further after drying under high vacuum. If the purity of the product is insufficient, it is purified where appropriate by chromatography, e.g. by preparative HPLC or by gel chromatography.

Procedure 4 (hydrogenolytic ester cleavage 1): The peptidic benzyl ester is dissolved in methanol or dioxane (about $3 \cdot 10^{-4}$-$2 \cdot 10^{-3}$ mol/l), subsequently aqueous 0.1% TFA or 0.1N hydrochloric acid (6-10 eq.) is added, and, under an argon protective gas atmosphere, 10% palladium-carbon (10 mol %) is added. Hydrogenation is carried out at RT under atmospheric pressure until the analytical HPLC (e.g. method 1) indicates complete conversion. The reaction mixture is filtered (e.g. through kieselguhr, Celite®), concentrated in vacuo and dried under high vacuum. If the purity of the product is insufficient, it is purified where appropriate by chromatography, e.g. by preparative HPLC or by gel chromatography.

Procedure 5 (hydrogenolytic ester cleavage 2): The peptidic benzyl ester is dissolved in methanol (about $3 \cdot 10^{-4}$-$2 \cdot 10^{-3}$ mol/l) and, under an argon protective gas atmosphere, 10% palladium-carbon (2-10 mol %) is added. Hydrogenation is carried out at RT under atmospheric pressure until analytical HPLC (e.g. method 1) indicates complete conversion. The reaction mixture is filtered (e.g. through kieselguhr, Celite®), concentrated in vacuo and dried under high vacuum. If the purity of the product is insufficient, it is purified where appropriate by chromatography, e.g. by preparative HPLC or by gel chromatography.

Procedure 6 (hydrolytic ester cleavage, hydrolysis): The carboxylic ester (3 mmol) is provided under an argon protective gas atmosphere in THF/water/DMF 200/100/2.5 (20 ml). At 0° C., while controlling the temperature strictly, powdered lithium hydroxide (3.6 mmol, 1.2 eq.) is added in portions to the vigorously stirred solution. If conversion is observed not to be complete after 2 h by analytical HPLC (method 13), solid lithium hydroxide is again added (3.3 mmol, 1.1 eq.). This procedure is repeated until conversion is complete, after which the reaction mixture is adjusted to pH 3-4 at 0° C. using 0.1 N aqueous hydrochloric acid, concentrated in vacuo and subsequently freeze dried. The crude product can then be gel chromatographed (e.g. method 45) and/or fine purified by preparative HPLC (e.g. method 31).

Procedure 7 (peptide coupling on a resin): The Fmoc-protected amino acid bound to chlorotrityl resin is mixed with a 20% piperidine solution in DMF and shaken for 30 min. The solution is then filtered off with suction through a frit, piperidine solution is again added, and shaking is continued for a further 30 min. The solution is filtered off with suction, and the resin is washed with DMF, methanol, THF and dichloromethane.

The deprotected polymer is suspended in DMF (1 ml of solvent per 100 mg of resin) and the Fmoc-protected amino acid (1.3-2.0 eq.), DIEA (2.0-3.0 eq.) and TBTU (1.5-2.0 eq.) dissolved in DMF are added. The resin is shaken at RT overnight. For the work up, the polymer is collected by suction filtration on a frit and subsequently washed with DMF, THF and dichloromethane.

After a sample removal in acetic acid/trifluoroethanol/dichloromethane 1:1:3, the obtained peptide can be confirmed by analysis.

Procedure 8 (automated solid-phase synthesis on a Chemspeed robot):

Instrument:

Chemspeed ASW 2000, equipped with 75 ml reactors and direct filtration with suction into the solvent waste. Mixing by vortexing.

Reagents:

Amino acids with an N-[(9H-fluoren-9-ylmethoxy)carbonyl] protecting group (Fmoc group) at the $N^2$ position are employed.

In addition to the Fmoc protecting group at the $N^2$ position, a further protecting group is used in the side chain of the following amino acids: arginine and D-arginine each carry a [(2,2,5,7,8-pentamethyl-3,4-dihydro-2H-chromen-6-yl)sulfonyl group (PMC group) on the guanidine function; serine and threonine are side-chain protected as $O^3$-tert-butylserine and -threonine, respectively. The amino groups in the side chains of lysine, ornithine, 2,4-diaminobutyric acid and 2,3-diaminobutyric acid are protected with benzyloxycarbonyl groups (Cbz groups).

Procedure:

1.7 g of 2-chlorotrityl chloride-resin (Iris Biotech, CAS No 42074-68-0) (preloaded with an α-Fmoc-protected amino acid, 0.85 mmol/g) were provided dry in each reactor, 17 ml of DMF are added and the mixture is shaken for 30 min. The DMF is removed by suction filtration.

In order to synthesize the described octapeptides 7 deprotection-coupling cycles are carried out, each of which consists of the following steps:

1.) Fmoc Elimination
12.75 ml of DMF and 4.25 ml of piperidine are added.
The mixture is shaken for 30 min.
The DMF/piperidine mixture is removed by suction filtration.
12.75 ml of DMF and 4.25 ml of piperidine are added.
The mixture is shaken for 10 min.
The DMF/piperidine mixture is removed by suction filtration.

2.) Washing Step (Repeated 5 Times)
17 ml of DMF are added.
The mixture is shaken for 30 min.
The DMF is removed by suction filtration.

3.) Amino Acid Coupling
10.2 ml of the corresponding Fmoc-amino acid (1.5 equivalents) dissolved in DMF are added.
6.8 ml of TBTU (2 equivalents) dissolved in DMF are added.
Diisopropylethylamine (3 equivalents) is added.
The reaction mixture is shaken for 2 h and then removed by suction filtration.

4.) Washing Step (Repeated 3 Times)
17 ml of DMF are added.
The mixture is shaken for 30 min.
The DMF is removed by suction filtration.

After the last reaction step, the product resins which have been collected by suction filtration are transferred with 10 ml of dichloromethane to a filter, collected by filtration and washed twice with 5 ml of dichloromethane each time.

Procedure 9 (removal with complete deprotection): The resin with the peptide is mixed in a reaction vessel with a frit base with 50% TFA in DCM (20 ml of the solution for a mixture of the size described in procedure 8), triisopropylsilane (100 μl) and water (100 μl) are added and the mixture is shaken at room temperature overnight. The dark solution is then removed by suction filtration, the resin is washed with 4 portions of DCM, shaken for 2 min each time, and again collected by suction filtration. The filtrates are combined and the solvent is distilled off. The residue is stirred with MTBE, collected by suction filtration and taken up in methanol. Finally, the methanol is distilled off in vacuo.

Procedure 10 (coupling with bridgehead active ester): The octapeptide and the active ester (compound 17A or compound 277A (1.1 equivalents) are dissolved in DMF (20-40 μl/μmol of octapeptide) at 0° C., and DIEA (4-5 eq.) is added. The reaction mixture is stirred further at room temperature for between 90 min and 2 h. The mixture is taken up in acetonitrile and purified by chromatography. Product-containing fractions are combined and lyophilized.

Procedure 11 (cyclization): The starting compound is dissolved in DMF (about 50 μl/μmol) and the solution is cooled to 0° C. 4-Methylmorpholine (6 equivalents) and HATU (3 equivalents) are added, and the mixture is stirred at 0° C. for 2 h. The workup takes place directly by loading the complete reaction mixture and separating according to method 45 or one of the HPLC methods mentioned. Product-containing fractions are combined and lyophilized or concentrated on a rotary evaporator.

Procedure 12 (removal of the Fmoc group using piperidine): The peptide is mixed at 0° C. with a mixture of THF and piperidine (4+1, approx. 20 μl/μmol). The mixture is subsequently stirred at this temperature for 1 h. The reaction mixture is purified directly according to method 45, and product-containing fractions are combined and concentrated.

Procedure 13 (peptide coupling using HATU in the liquid phase): A cyclic peptide with an unprotected N terminus (e.g. exemplary compound 407, 408, 409, etc.) and a dipeptide (for example compound 8A, 10A, etc.) (1.5 equivalents) are dissolved in DMF (about 30-80 μl/μmol of cyclopeptide) and the solution is cooled to 0° C. 4-Methylmorpholine (4 equivalents) and HATU (1.6 equivalents) are added and the mixture is stirred at room temperature for 2 h. The reaction is then stopped with 3 ml of methanol and purified by chromatography according to method 45. Product-containing fractions are combined and concentrated.

Starting Compounds

Example 1A

D-Leucyl-L-leucyl-L-phenylalanyl-[(3R)-leucyl]-L-leucyl-D-arginyl-L-isoleucyl-allothreonyl-glycyl-[(3S)-3-hydroxy-asparaginyl]-serine Trifluoroacetate (Dihydrolysobactin) and Example 2A D-Leucyl-L-leucyl-[3-cyclohexyl-L-alanyl]-[(3R)-leucyl]-L-leucyl-D-arginyl-L-isoleucyl-allothreonyl-glycyl-[(3S)-3-hydroxy-asparaginyl]-serine Trifluoroacetate (Octa-Hydrolysobactin)

Dihydrolysobaction

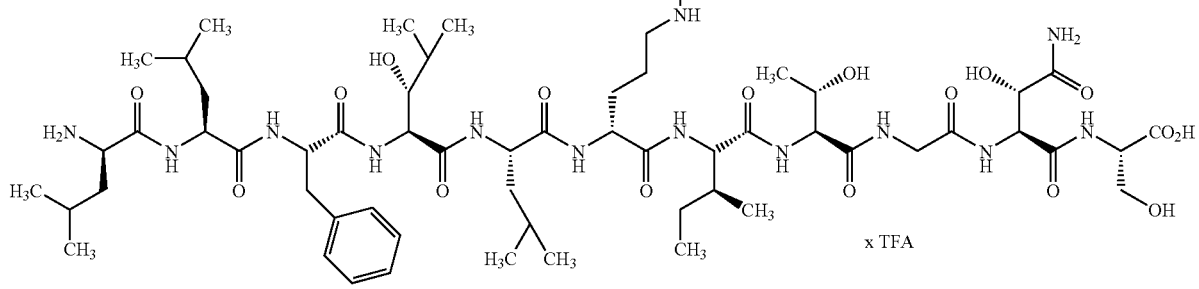

Octahydrolysobaction

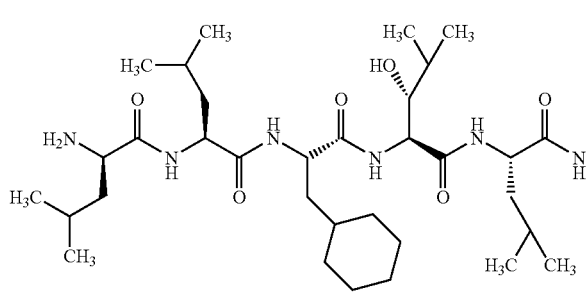

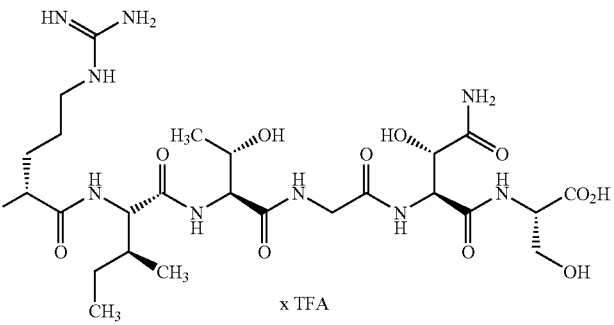

The preparation of lysobactin bistrifluoroacetate by fermentation and its isolation is described in WO 2004/099239. Lysobactin bistrifluoroacetate (20 g, 13.29 mmol) is dissolved in two portions of isopropanol/water 9:2 (110 ml each). Under an argon protective gas atmosphere, palladium on carbon (10%; 5 g in each case) is added. The reaction mixture is (after degassing) stirred under a hydrogen pressure of 80-70 bar and at 40° C. in a pressurized autoclave for 12 h. Palladium on carbon (10%; 5 g) is again added to the reaction. The reaction mixture is (after degassing) again stirred under a hydrogen pressure of 80-70 bar and at 40° C. in a pressurized autoclave for 12 h. The reaction mixture is (after degassing) once again stirred under a hydrogen pressure of 80-70 bar and at 40° C. in a pressurized autoclave for 12 h. Now no Lysobactin is detectable any longer by analytical HPLC (method 10). The reaction mixture is filtered through kieselguhr, concentrated in vacuo and dried under high vacuum. 20.10 g (99% of theory) of product (60% dihydrolysobactin, 40% octahydrolysobactin) are obtained.

Example 3A

[(3R)-Leucyl]-L-leucyl-D-arginyl-L-isoleucyl-allothreonyl-glycyl-[(3S)-3-hydroxy-asparaginyl]-serine Trifluoroacetate

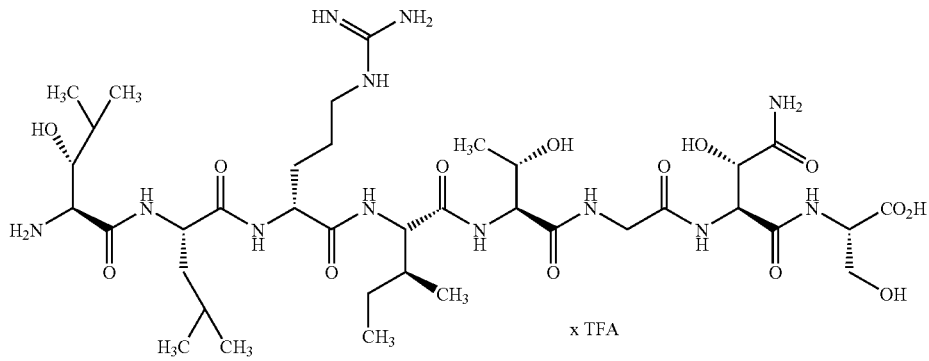

Preparative Chymotrypsin Cleavage of the Dihydro/Octahydrolysobactin Mixture Substrate Concentration 5 mg/ml 20 g of dihydro- (about 40%) and octahydrolysobactin (about 60%) are dissolved in 400 ml of methanol and then 3400 ml of cleavage buffer (0.1 M ammonium bicarbonate/ 0.5 M urea pH 8) are added. Before adding the enzyme, the solution is warmed to 37° C. in a drying oven. 800 mg of chymotrypsin (100 ml of chymotrypsin solution water/ethylene glycol 1:1, 4 mg/ml; 1:25; prewarmed to 37° C.) are added and the reaction is carried out at 37° C. 200 μl aliquots are taken after 0.5, 1 h, and the enzyme cleavage is stopped with 200 μl of 30% acetonitrile/0.1% TFA. The samples are analyzed in parallel to the enzyme cleavage by HPLC within 15 min (retention time of fragment 4-11 about 3.6 min, fragment 1-3 (LLF) about 9.6 min, fragment 1-3 (LLA(3-cyclohexyl)) about 11.3 min) (solvent A 0.1% TFA, solvent B 60% acetonitrile/0.1% TFA, gradient 0 min 30% B, 10 min 80% B, 11 min 100% B, 12 min 30% B, 15 min 30% B; flow rate: 0.7 ml/min, temperature: 40° C., UV detection 210 nm). The enzyme reaction is stopped after 60 min with 150 ml of acetonitrile and about 30 ml of TFA. The pH of the solution should be between 1 and 2. The solution can be stored at −20° C. until the preparative separation.

The activity of the chymotrypsin batch used (70 U/mg) is tested by a control cleavage with the protein interleukin-4 double mutein Arg(121)→Asp(121)/Tyr(124)→Asp(124) (Bayer Healthcare AG, D-Wuppertal).

Preparative purification: 500 ml portions of a solution of the cleavage mixture described above are first filtered through a layer of Celite under vacuum and then through a pressure filter funnel (450 μm with prefilter). The filtrate is loaded onto a Varian Metaflash C-18 40M cartridge. Elution is then carried out with the following program: solvent A: 0.05% TFA in water, solvent B: 0.05% TFA in acetonitrile. Flow rate: 50 ml/min; 0-3 min 5% B; ramp; 30 min 90% B, 33 min. 90% B. Product-containing fractions are combined and lyophilized.

11.8 g (87% of theory) of the title compound are obtained from the combined product-containing fractions.

Example 4A

Methyl (Z)-2-[(tert-butoxycarbonyl)amino]-4,4-dimethylpent-2-enoate

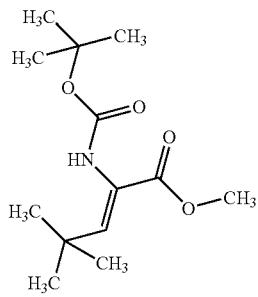

Pivalaldehyde (303.2 g, 3.41 mol, 10 eq.) and methyl {[(tert-butoxy)carbonyl]amino}-(dimethoxyphosphoryl)acetate (101.5 g, 0.341 mol, 1.0 eq.) are dissolved in THF (800 ml) and cooled to −70° C. At −70° C., TMG (78.7 g, 0.683 mmol, 6.95 ml, 2.0 eq.) is slowly added dropwise and the mixture is then stirred at −70° C. for 4 h and subsequently at RT for 4 days. The reaction mixture is concentrated and then extracted by shaking with ethyl acetate (twice 500 ml) and water, and the combined org. phases are washed with a sat. sodium chloride solution (100 ml) and dried over sodium sulfate. After concentration the crude product is chromatographed (1.5 kg of silica gel, eluent: cyclohexane/ethyl acetate 5:1). 67 g (76% of theory) of the title compound are obtained.

Alternatively, the crude product after the aqueous workup can be purified by crystallization from cyclohexane/ethyl acetate.

$R_f$ (silica gel, cyclohexane/ethyl acetate 4:1)=0.5

LC-MS (Method 18): $R_t$=2.5 min; MS (ESIpos.): m/z (%)=158 (100) $[M-C_4H_8-CO_2+H]^+$, 280 (5) $[M+Na]^+$.

$^1$H NMR (400 MHz, $d_6$-DMSO): δ 1.08 (s, 9H, C(CH$_3$)$_3$), 1.38 (s, 9H, OC(CH$_3$)$_3$), 3.61 (s, 3H, CO$_2$CH$_3$), 6.40 (s, 1H, H$^β$), 8.14 (s, 1H, NH).

$^{13}$C NMR (126 MHz, $d_6$-DMSO): δ 28.46 (3C), 29.53 (3C), 33.28, 52.22, 78.89, 125.62, 147.05, 154.67, 166.25.

HR-TOF-MS (Method 24): $C_{13}H_{23}NO_4$ $[M+H]^+$ found 258.1696, calc. 258.1700.

Example 5A $N^2$-(tert-Butoxycarbonyl)-3-tert-butyl-D-alanine Methyl Ester

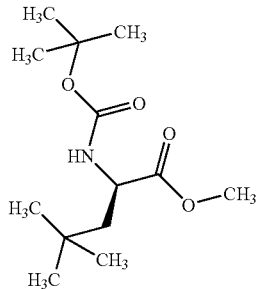

Methyl (2Z)-2-[(tert-butoxycarbonyl)amino]-4,4-dimethylpent-2-enoate (example 4A, 60 g, 233.2 mmol) is dissolved in ethanol p.a./dioxane 3:1 (1000 ml). An argon protective gas atmosphere is passed through with a needle (~10 min). The solution is placed in an ultrasonic bath (about 5 min) and (+)-1,2-bis[(2R,5R)-diethylphospholano]benzene(cyclooctadiene)rhodium(I) triflate (600 mg, 1% by weight) is added. The mixture is hydrogenated under a pressure of 3.5 bar of hydrogen and at RT for 3 days. The reaction mixture is filtered through kieselguhr, and the eluate is concentrated. The crude product is chromatographed (silica gel, eluent: cyclohexane/ethyl acetate 4:1). 60 g (99% of theory) of the title compound are obtained.

$[α]^{20}_{Na}$=+5° (c=0.33 in CHCl$_3$).

DCI-MS (NH$_3$): m/z (%)=221 (100), 260 (40) $[M+H]^+$, 277 (100) $[M+NH_4]^+$.

$^1$H NMR (400 MHz, CDCl$_3$): δ 0.93 (s, 9H, C(CH$_3$)$_3$), 1.40 (m, 10H, OC(CH$_3$)$_3$), 1.68 ("d", J=14.5 Hz, 2H, H$^β$), 3.68 (s, 3H, OCH$_3$), 4.30 (t, J=7.9 Hz, 1H, H$^α$), 4.81 (d, br, J=7.7 Hz, 1H, NH).

$^{13}$C NMR (126 MHz, CDCl$_3$): δ 28.30 (3C, CH$_2$C(CH$_3$)$_3$), 29.52 (3C, OC(CH$_3$)$_3$), 30.61 (CH$_2$C(CH$_3$)$_3$), 46.27 (C$^β$H$_2$), 51.19 (H$^α$), 52.17 (OCH$_3$), 79.79 (OC(CH$_3$)$_3$), 155.11 (NHCO$_2$), 174.39 (CO$_2$CH$_3$).

HR-TOF-MS (Method 24): $C_{26}H_{51}N_2O_8$ calc. 519.3640, found 519.3634 $[M+H]^+$.

Example 6A $N^2$-(tert-Butoxycarbonyl)-3-tert-butyl-D-alanine

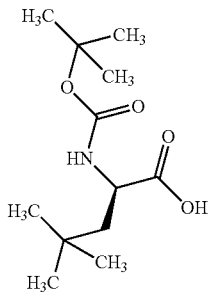

N-tert-Butoxycarbonyl-3-tert-butyl-D-alanine methyl ester (example 5A, 60 g, 231 mmol) is dissolved in THF p.a. (463 ml). At RT, a solution of lithium hydroxide monohydrate (19.4 g, 462.7 mmol) in water (463 ml) is slowly added dropwise. When the HPLC chromatogram (method 1) shows complete conversion (about 20 h), the reaction mixture is cautiously adjusted to pH 3-4 using 1 N aq. hydrochloric acid while cooling in ice. Solid sodium chloride (150 g) is added to the reaction mixture, which is then extracted twice with ethyl acetate (500 ml). The combined org. phases are washed with a sat. sodium chloride solution and then dried with sodium sulfate and filtered. The filtrate is concentrated on a rotary evaporator and dried under high vacuum. 55.4 g (98% of theory) of the title compound are obtained.

HPLC/UV-Vis (Method 3): $R_t$=4.2 min.

DCI-MS (NH$_3$): m/z (%)=263 (100) $[M+NH_4]^+$, 280 (5) $[M+N_2H_7]^+$.

$^1$H NMR (400 MHz, CDCl$_3$): δ=0.96 (s, 9H, C(CH$_3$)$_3$), 1.42 (m, 10H, OC(CH$_3$)$_3$, H$^β$), 1.79 ("d", J=14.4 Hz, 2H, H$^β$), 4.31 (t, J=8.0 Hz, 1H, H$^α$), 4.82 (d, J=8.4 Hz, 1H, NH).

$^{13}$C NMR (126 MHz, CDCl$_3$): δ=28.32 (3C), 29.54 (3C), 30.74, 45.92, 51.24, 80.19, 155.41, 178.93.

HR-TOF-MS (Method 24): C$_{24}$H$_{47}$N$_2$O$_8$ calc. 491.3327, found 491.3328 [2M+H]$^+$.

Example 7A

[N$^2$-(tert-Butoxycarbonyl)-(3-tert-butyl-D-alanyl)]-(3-tert-butyl-L-alanine) methyl ester

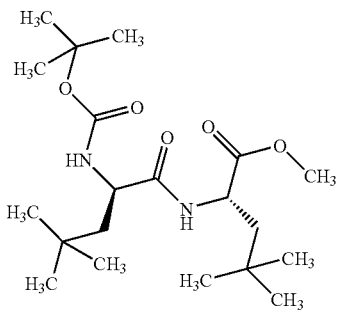

HOBt (3 eq., 39.4 g, 292 mmol), NMM (3 eq., 32.1 ml, 291.8 mmol), N-tert-butoxy-carbonyl-3-tert-butyl-D-alanine (example 6A, 1.0 eq., 97.3 mmol), EDC (2 eq., 37.3 g, 194.6 mmol) and again NMM (2 eq., 21.4 ml, 194.5 mmol) are successively added to a solution of 3-tert-butyl-L-alanine methyl ester hydrochloride (1.1 eq., 21 g, 107 mmol) in dichloromethane p.a. (1.4 l) at −20° C. The reaction mixture slowly warms to RT (about 12 h) whereby complete conversion of the amine component is observed by HPLC. The reaction mixture is then washed with a sat. aq. sodium bicarbonate solution (300 ml), 5% aq. citric acid (500 ml), a sat. aq. sodium bicarbonate solution (500 ml) and a sat. sodium chloride solution. The reaction mixture is dried over sodium sulfate and filtered. The reaction mixture is evaporated to dryness in vacuo and then dried under high vacuum. 36 g (96% of theory) of the title compound are obtained which is reacted without further purification.

[α]$^{20}_{Na}$=+24° (c=0.10 in CH$_2$Cl$_2$).

DCI-MS (NH$_3$): m/z (%) 387 (40) [M+H]$^+$, 404 (100) [M+NH$_4$]$^+$.

LC-MS (Method 20): R$_t$ 2.6 min; MS (ESIpos.): m/z (%)=287 (100) [M-C$_5$O$_2$H$_8$+H]$^+$, 387 (60) [M+H]$^+$.

$^1$H NMR (400 MHz, d$_6$-DMSO): δ 0.95 (s, br, 18H, tBu), 1.35 (dd, 1H), 1.45 (s, 9H, OtBu), 1.50 (dd, 1H), 1.65 (dd, 1H), 1.95 (dd, br, 1H), 3.70 (s, 3H, OCH$_3$), 4.15 ("t", br, 1H), 4.55 ("t", br, 1H), 4.80 (d, 1H), 6.65 (d, br, 1H).

$^{13}$C NMR (126 MHz, d$_6$-DMSO): δ 28.39 (3C, C(CH$_3$)$_3$), 29.49 (3C, C(CH$_3$)$_3$), 29.67 (3C, C(CH$_3$)$_3$), 30.40 (C(CH$_3$)$_3$), 30.44 (C(CH$_3$)$_3$), 44.25, 45.12, 49.56, 52.06, 52.21, 78.17, 154.93, 173.00, 173.35.

HR-TOF-MS (Method 24): C$_{20}$H$_{39}$N$_2$O$_5$ [M+H]$^+$ found 387.2860, calc. 387.2859.

Example 8A

[N$^2$-(tert-Butoxycarbonyl)-3-tert-butyl-D-alanyl]-3-tert-butyl-L-alanine

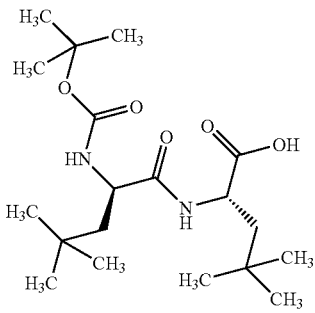

The compound of example 7A (36 g, 93.1 mmol) is dissolved in THF p.a. (279 ml). At about 10° C., a solution of lithium hydroxide monohydrate (7.82 g, 186.3 mmol, 2 eq.) in water (187 ml) is slowly added dropwise. When the HPLC chromatogram (method 1) shows complete conversion (about 20 h), the reaction mixture is freed of THF under 200 mbar and then extracted with MTBE (200 ml). The org. phase is diluted with ethyl acetate (500 ml), then mixed with water and subsequently cautiously adjusted to pH 3-4 using 1 N aq. hydrochloric acid. The combined org. phases are washed with sat. brine, dried over sodium sulfate, filtered, evaporated in vacuo and dried under high vacuum. 97.4 g (97% of theory) of the title compound are obtained.

LC-MS (Method 18): R$_t$=2.26 min; MS (ESIpos.): m/z (%)=373 (100) [M+H]$^+$.

$^1$H NMR (400 MHz, d$_6$-DMSO): δ 0.83 (s, br, 18H, tBu), 1.31 (s, 9H, OtBu), 1.40 (m, 2H, β-CH$_2$), 1.48 (dd, J=14.1, 9.4 Hz, 1H, β-CH'), 1.59 (dd, J=14.1, 2.7 Hz, 1H, β-CH'), 3.98 (m, 1H, α-CH), 4.12 (m, 1H, α-CH), 6.73 (d, J=9.1 Hz, 1H, NH), 7.72 (d, J=7.9 Hz, 1H, NH), 12.42 (s, br, 1H, CO$_2$H).

$^{13}$C NMR (126 MHz, d$_6$-DMSO): δ 28.49 (3C), 29.66 (3C), 29.78 (3C), 30.52, 30.58, 44.63 (β-CH$_2$), 45.24 (β-CH$_2$), 49.67 (α-CH), 52.40 (α-CH), 78.29, 155.05, 172.97, 174.61.

HR-TOF-MS (Method 24): C$_{19}$H$_{37}$N$_2$O$_5$ calc. 373.2702, found 373.2717 [M+H]$^+$.

Example 9A (3-tert-Butyl-D-alanyl)-3-tert-butyl-L-alanine Hydrochloride

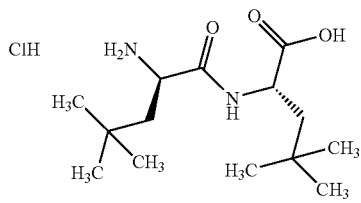

The compound of example 8A (4.5 g, 12.1 mmol) is predissolved in dioxane (3 ml). At RT, a 4 N solution of hydrochloric acid in dioxane (30.2 mmol, 120 mmol, 10 eq.) is added dropwise. The reaction mixture is stirred for 30 min, evaporated in vacuo and dried under high vacuum. The title compound is obtained as a colorless solid (3.5 g, 99% of theory).

LC-MS (Method 18): $R_t$=1.52 min; MS (ESIpos.): m/z (%)=273.6 (100) [M+H]$^+$; ESIneg: m/z=271.5 (100) [M−H]$^-$.

$^1$H NMR (500 MHz, d$_6$-DMSO): δ0.85 (s, 9H, tBu), 0.86 (s, 9H, tBu), 1.49 (dd, J=14.3, 1.6 Hz, 1H, β-CH), 1.50 (d, J=13.8 Hz, 1H, β-CH), 1.64 (dd, J=14.3, 4.0 Hz, 1H, β-CH), 1.71 (dd, J=14.3, 6.9 Hz, 1H, β-CH), 3.77 ("t", J=6.5 Hz, 1H, α-CH), 4.14 (m, 1H, α-CH), 8.27 (s, br, 3H), 8.94 (d, J=8.2 Hz, 1H, NH), 12.58 (s, br, 1H, CO$_2$H).

$^{13}$C NMR (126 MHz, d$_6$-DMSO): δ 28.41 (3C), 29.50 (3C), 30.08, 30.38, 44.46, 44.80, 50.03, 50.30, 169.10, 173.98.

HR-TOF-MS (Method 24): C$_{14}$H$_{29}$N$_2$O$_3$ calc. 273.2173, found 273.2167 [M+H]$^+$.

Example 10A

[N$^2$-(Benzyloxycarbonyl)-3-tert-butyl-D-alanyl]-3-tert-butyl-L-alanine

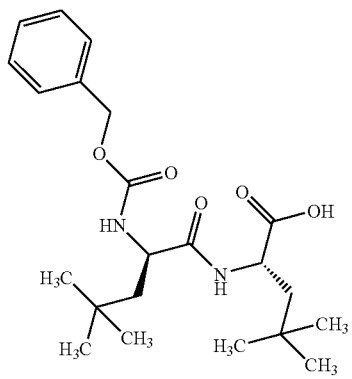

The dipeptide (example 9A, 3.73 g, 12.1 mmol) is dissolved in THF (170 ml) under an argon protective gas atmosphere. The addition of water (170 ml), benzyloxycarbonyloxysuccinimide ester (4.52 g, 18.1 mmol, 1.5 eq.) and NMM (4.28 g, 4.23 mmol, 3.5 eq.) at 0° C. is followed by vigorous stirring at RT until all the starting material has reacted (several hours, HPLC monitoring, method 1). The mixture is quenched with glacial acetic acid. The THF is removed in vacuo. The remaining aq. phase is covered with a layer of ethyl acetate, acidified to pH<3 using 4 N hydrochloric acid and then extracted several times with ethyl acetate. The org. phases are washed with a sat. sodium chloride solution, dried over sodium sulfate, filtered and concentrated. The resulting foam is stirred with acetonitrile, whereby a colorless solid forms which is collected by filtration and then washed with a little acetonitrile. This process can be repeated again several times with the filtrate after it has been concentrated. The combined solids are dried under high vacuum, whereby the title compound is obtained as a solid. The remaining mother liquor is concentrated and purified by preparative HPLC (method 26). The title compound (combined solids and purification product from the HPLC separation) is obtained as a colorless solid (3.49 g, 71% of theory).

HPLC/UV-Vis (Method 1): $R_t$=2.6 min.

LC-MS (Method 21): $R_t$=2.46 min; MS (ESIpos.): m/z (%)=363 (60), 407 (100) [M+H]$^+$. ESIneg: m/z=297 (100), 405.5 (40) [M−H]$^-$.

$^1$H NMR (500 MHz, d$_6$-DMSO): δ 0.81 (s, 9H, tBu), 0.83 (s, 9H, tBu), 1.40-1.44 (m, 2H, β-CH$_2$), 1.49 (dd, J=14.3, 9.7 Hz, 1H, β-CH), 1.58 (dd, J=13.5, 1.4 Hz, 1H, β-CH), 4.07 (m, 1H, α-CH), 4.13 (m, 1H, α-CH), 4.94 (d, J=12.3 Hz, 1H, CHHPh), 4.99 (d, J=12.5 Hz, 1H, CHHPh), 7.25-7.32 (m, 5H, ArH), 7.92 (d, J=8.5 Hz, 1H, NH).

$^{13}$C NMR (126 MHz, d$_6$-DMSO): δ29.49 (3C), 29.75 (3C), 30.41, 30.46, 44.52, 45.11, 49.55, 52.73, 65.49, 127.70 (2C), 127.91, 128.48 (2C), 137.31, 155.59, 172.52, 174.50.

HR-TOF-MS (Method 24): C$_{22}$H$_{34}$N$_2$O$_5$ calc. 407.2541, found 407.2531 [M+H]$^+$.

Example 11A

Methyl-(2R*,3R*)-N$^2$-[(benzyloxy)carbonyl]-N$^2$-[(benzyloxy)carbonylamino]-3-[(tert-butoxycarbonyl)amino]phenylalaninate

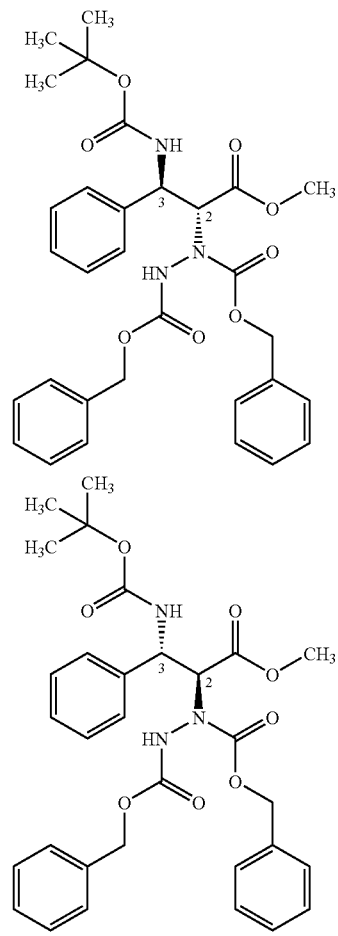

Under an argon protective gas atmosphere, a 1 N solution of lithium hexamethyldisilazide (157.5 mmol, 157.5 ml, 2.2 eq.) in THF is provided in the reaction solvent THF (300 ml). At −78° C., a solution of methyl (rac)-3-[(tert-butoxycarbonyl)amino]-3-phenylpropanoate (A. V. Rao Rama, A. K. Singh, Ch. V. N. S. Varaprasad, *Tetrahedron Lett.,* 1991, 32, 4393-4396) (20 g, 71.2 mmol) is slowly added dropwise. The mixture is stirred at −25° C. for 10 min and then again cooled to −78° C. Dibenzyl azadicarboxylate (34.2 g, 114.6 mmol, 1.6 eq.) is added in one portion to the reaction mixture. The mixture is stirred at −60 to −45° C. for 3 h. In order to stop the reaction, the mixture is again cooled to −78° C., and acetic acid (20.5 ml, 358 mmol, 5 eq.) is added, and the mixture is then warmed to 0° C. and finally to RT. The reaction mixture is evaporated in vacuo and taken up in ethyl acetate (1000 ml). The suspension is washed twice with a sat. aq. sodium bicarbonate solution, once with water, twice with 5% aq. citric acid and once with a sat. aq. sodium chloride solution. All the aq. phases are separately re-extracted with ethyl acetate. All the org. phases are evaporated in vacuo and again taken up in dichloromethane (2000 ml), filtered, dried over sodium sulfate, filtered again, evaporated in vacuo and dried under high vacuum. 7.2 g (18% of theory) of the title compound are obtained as a solid. The filtrate of the dichloromethane phase (vide supra) is concentrated and then again recrystallized from methanol, whereby 13.2 g (26% of theory) of the title compound are obtained.

LC-MS (Method 23): $R_t$=6.8 min;
MS (ESIpos.): m/z (%)=578 (40) [M+H]$^+$, 1156 (100) [2M+H]$^+$.
MS (ESIneg.): m/z (%)=576 (100) [M−H]$^-$.

Example 12A

Methyl (2S*,3R*)-N$^2$-[(benzyloxy)carbonyl]-N$^2$-[(benzyloxy)carbonylamino]-3-[(tert-butoxycarbonyl)amino]phenylalaninate

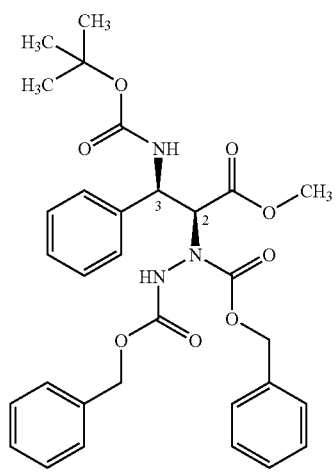

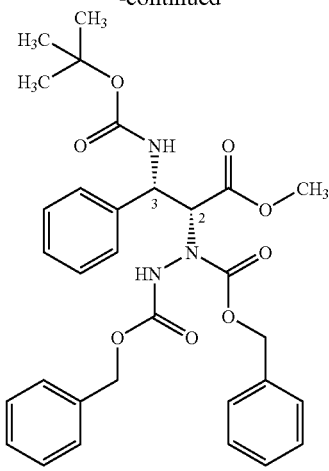

Under an argon protective gas atmosphere, TMG (50 ml, 399 mmol) is added to a solution of methyl-(2R*,3R*-N$^2$-[(benzyloxy)carbonyl]-N$^2$-[(benzyloxy)carbonylamino]-3-[(tert-butoxycarbonyl)amino]phenylalaninate (example 11A, 20.5 g, 35.5 mmol) in dry DMF p.a. (750 ml) at 0° C. The reaction mixture is allowed to thaw and is stirred until the HPLC chromatogram (method 1) indicates complete conversion (about 60% product) (about 12 h), in order to then stop the reaction by adding acetic acid (pH 4-6). The reaction mixture is evaporated in vacuo at RT and taken up in ethyl acetate. The org. phase is washed twice with water, twice with 5% citric acid, once with water, twice with a sat. aq. sodium bicarbonate solution, once with a sat. aq. sodium chloride solution, dried over sodium sulfate, filtered, evaporated in vacuo and dried under high vacuum. The crude product is purified by preparative HPLC (method 30) or flash chromatography (silica gel, cyclohexane/ethyl acetate 3:1). 7.7 g (37% of theory) of the title compound and 5 g of the starting compound (25% of theory) are obtained.

HPLC/UV-Vis (Method 1): $R_t$=3.0 min.
LC-MS (Method 10): $R_t$=3.0 min;
MS (ESIpos.): m/z (%)=478 (100) [M−Boc+H]$^+$, 578 (30) [M+H]$^+$.
LC-MS (Method 23): $R_t$=7.0 min;
MS (ESIpos.): m/z (%)=578 (40) [M+H]$^+$, 1156 (100) [2M+H]$^+$.
MS (ESIneg.): m/z (%)=576 (100) [M−H]$^-$.

Example 13A

Methyl-(2S*,3R*)-3-[(tert-butoxycarbonyl)amino]phenylalaninate

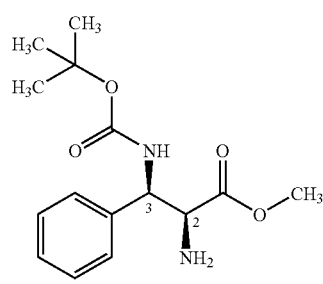

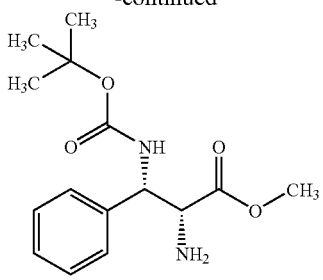

Under an argon protective gas atmosphere, Raney nickel (61 mg, about 10 mol %) is added to a solution of methyl (2S*,3R*)-N²-[(benzyloxy)carbonyl]-N²-[(benzyloxy)carbonylamino]-3-[(tert-butoxycarbonyl)amino]phenylalaninate (example 12A, 705 mg, 1.22 mmol) in methanol/dichloromethane 1:1 (42 ml). The reaction mixture is hydrogenated in a pressurized autoclave under a hydrogen pressure of 80 bar and at RT (40 h). The HPLC chromatogram shows complete conversion. The reaction mixture is filtered under an argon protective gas atmosphere through a glass frit, and the glass frit is washed several times with methanol/water/0.2% acetic acid. The filtrate is evaporated in vacuo and dried under high vacuum. A solid (about 3 g) is obtained which is then suspended in ethyl acetate in an ultrasonic bath. The suspension is mixed with a solution of EDTA (400 mg) in a 7% aq. sodium bicarbonate solution (400 ml). The aq. phase is extracted with ethyl acetate (100 ml, three times). The combined org. phases are then washed once with a sat. aq. sodium bicarbonate solution, and twice with a sat. aq. sodium chloride solution. All the aq. phases are separately re-extracted with ethyl acetate. The combined org. phases are then dried over sodium sulfate, filtered and dried under high vacuum. The product obtained is a solid (1.26 g, quantitative) which is reacted further without fine purification.

HPLC/UV-Vis (Method 2): $R_t$=1.7 min.
LC-MS (Method 23): $R_t$=4.1 min;
MS (ESIpos.): m/z (%)=239 (100), 295 (80) [M+H]⁺.

Example 14A

Methyl (2S*,3R*)-N²-[(benzyloxy)carbonyl]-3-[(tert-butoxycarbonyl)amino]phenylalaninate

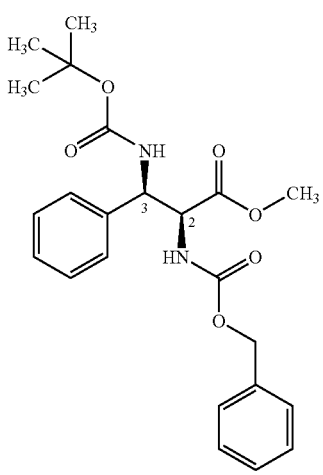

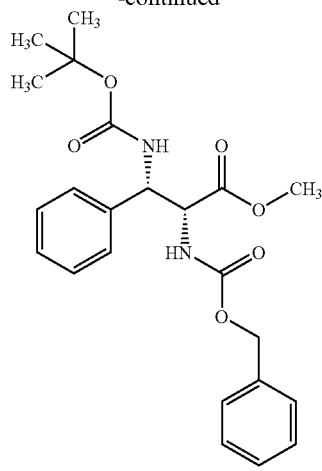

Under an argon protective gas atmosphere, NMM (260 mg, 2.6 mmol, 2.1 eq.) is added to a solution of methyl (2S*,3R*)-3-[(tert-butoxycarbonyl)amino]phenylalaninate (example 13A, 360 mg, 1.2 mmol) and N-benzyloxycarbonyloxysuccinimide ester (610 mg, 2.44 mmol, 2 eq.) in THF (25 ml) at 0° C. The reaction mixture slowly warms up (12 h), whereby complete conversion is observed by HPLC (method 2). Acetic acid (0.7 ml) is added, and the mixture is subsequently concentrated in vacuo and purified by preparative HPLC (method 31). 396 mg (76% of theory) of the title compound are obtained.

HPLC/UV-Vis (Method 2): $R_t$=2.7 min.
LC-MS (Method 23): $R_t$=6.4 min;
MS (ESIpos.): m/z (%)=329 (100) [M-C₄H₈—CO₂+H]⁺, 429 (80) [M+H]⁺, 858 (60) [2M+H]⁺.

Example 15A (2S*,3R*)-N²-[(Benzyloxy)carbonyl]-3-[(tert-butoxycarbonyl)amino]phenylalanine

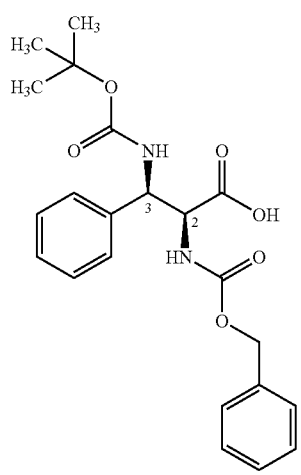

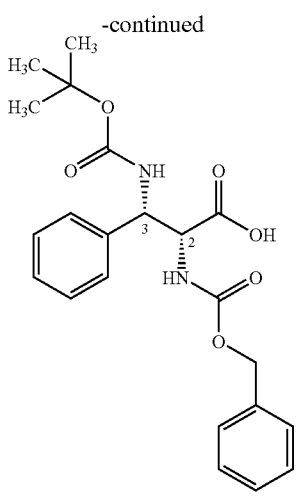

Under an argon protective gas atmosphere a solution of methyl (2S*,3R*)-N-[(benzyloxy)-carbonyl]-3-[(tert-butoxycarbonyl)amino]phenylalaninate (example 15A, 755 mg, 1.76 mmol) in THF/water 2:1 (30 ml) is provided. At 0° C., while stirring vigorously, a degassed 1% aq. solution of lithium hydroxide monohydrate (86.5 mg, 3.6 mmol, 2 eq.) is slowly added dropwise. The mixture is stirred at RT until the HPLC chromatogram (method 1) indicates complete conversion (about 1 h). Acetic acid (0.5 ml) is subsequently added, and the reaction mixture is concentrated in vacuo and covered with a layer of ethyl acetate (100 ml). The aq. phase is then acidified using 5% citric acid (pH 2-3) and then extracted three times with ethyl acetate (50 ml). The combined org. phases are washed twice with a sat. aq. sodium chloride solution (20 ml), dried over sodium sulfate, filtered, concentrated in vacuo and dried under high vacuum. 750 mg (quantitative) of crude product of the title compound are obtained which is fine purified by preparative HPLC (method 31).

HPLC/UV-Vis (Method 1): $R_t$=2.4 min.

LC-MS (Method 23): $R_t$=6.1 min;

MS (ESIpos.): m/z (%)=359 (100), 415 (60) $[M+H]^+$, 829 (60) $[2M+H]^+$.

MS (ESIneg.): m/z (%)=413 (100) $[M-H]^-$.

Example 16A (3R)-$N^2$-[(Benzyloxy)carbonyl]-3-[(tert-butoxycarbonyl)amino]-L-phenylalanine

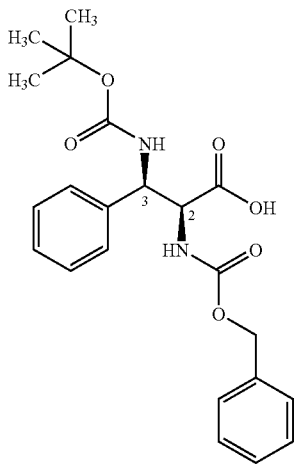

The mixture of enantiomers of (2S*,3R*)-N-[(benzyloxy)carbonyl]-3-[(tert-butoxy-carbonyl)amino]phenylalanine (example 15A, 750 mg, 1.8 mmol) is separated by preparative HPLC (method 38). 334 mg (98% ee, 45% of theory) of (2S,3R)-N-[(benzyloxy)carbonyl]-3-[(tert-butoxycarbonyl)amino]phenylalanine (title compound) and 275 mg (98% ee, 37% of theory) (2R,3S)-N-[(benzyloxy)-carbonyl]-3-[(tert-butoxycarbonyl)amino]phenylalanine (further enantiomer) are obtained.

Enantiomer determination by method 14.

$[\alpha]^{20}_{Na}$=+22° (c=0.50 in chloroform) (title compound).

$[\alpha]^{20}$Na=20° (c=0.49 in chloroform) (further enantiomer).

Example 17A

Pentafluorophenyl (3R)-$N^2$-[(benzyloxy)carbonyl]-3-[(tert-butoxycarbonyl)amino]-L-phenylalaninate

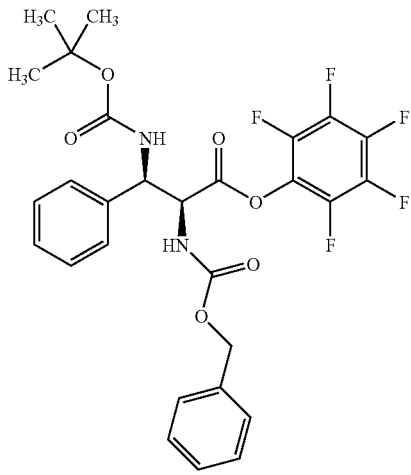

The compound of example 16A (2.0 g, 4.83 mmol) is provided in dichloromethane (30 ml), and pentafluorophenol (4.4 g, 24.13 mmol, 5 eq.) and EDC (1.4 g, 7.24 mmol, 1.5 eq.) are added at 0° C. The reaction is slowly brought to RT and stirred at this temperature overnight. For of the workup, the solvent is completely removed on a rotary evaporator at a maximum bath temperature of 30° C., and after fine purification of the residue by preparative HPLC (method 28) of 2.3 g (83.3% of theory) of product are isolated.

HPLC (Method 1) $R_t$=3.44 min.

LC-MS (Method 18): $R_t$=3.23 min; MS (ESIpos): m/z (%)=581 (13) $[M+H]^+$, 525 (100) $[M-C_4H_8+H]^+$.

$^1$H NMR (500 MHz, $d_6$-DMSO): δ=1.36 (s, 9H, 3 $CH_3$), 4.97 (d, J=7.1 Hz, 2H, $PhCH_2O$), 5.15 (dd, J=9.7, 4.8 Hz, 1H), 5.49 (dd, J=10.2, 4.6 Hz, 1H), 7.18 (d, J=10.4 Hz, 1H, ArH), 7.25-7.42 (m, 8H, ArH), 7.68 (d, J=10.4 Hz, 1H, NH), 7.90 (d, J=9.8 Hz, 1H, NH).

$^{13}$C NMR (126 MHz, d$_6$-DMSO): δ=27.97, 54.33, 58.72, 65.75, 78.65, 124.10, 126.48, 127.37 127.46, 127.82, 128.23 (2C), 136.40/138.36 (C—F), 136.54, 138.49/140.27 (C—F), 139.34/141.40 (C—F), 154.72, 156.04, 167.10.

HR-TOF-MS (Method 24): C$_{28}$H$_{26}$N$_2$O$_6$ [M+H]$^+$ found 581.1719, calc. 581.1706.

Example 18A 2,5-Dioxopyrrolidin-1-yl (3R)-N$^2$-[(benzyloxy)carbonyl]-3-[(tert-butoxycarbonyl)amino]-L-phenylalaninate

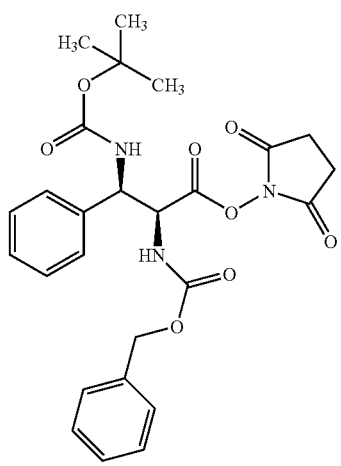

Under an argon protective gas atmosphere atmosphere, (3R)-N-[(benzyloxy)carbonyl]-3-[(tert-butoxycarbonyl)amino]-L-phenylalanine (example 16A, 100.0 mg, 241.28 μmol) is provided in methylene chloride (10 ml), the solution is cooled to 0° C., N-hydroxysuccinimide (33.3 mg, 289.53 μmol, 1.2 eq.) and EDC (55.5 mg, 289.53 μmol, 1.2 eq.) are added, and the mixture is stirred at 0° C. overnight. For the workup, the solvent is completely removed on a rotary evaporator at a bath temperature of 30° C., and after fine purification by preparative HPLC (method 32) 96.0 mg (77.8% of theory) of product are isolated.

HPLC (Method 1) R$_t$=2.53 min.

LC-MS (Method 18): R$_t$=2.58 min; MS (ESIpos): m/z (%)=529 (28) [M+NH$_4$]$^+$, 412 (100).

Example 19A

Methyl [N$^2$-[(benzyloxy)carbonyl]-3-tert-butyl-D-alanyl]-[3-tert-butyl-L-alanyl]-[(3R)-3-[(tert-butoxycarbonyl)amino]-L-phenylalaninate]

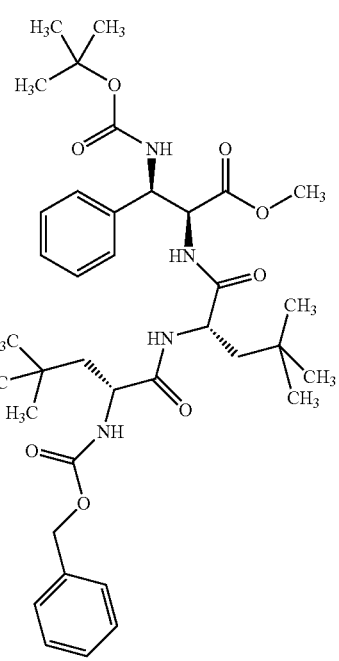

Under an argon protective gas atmosphere, N-benzyloxycarbonyl-protected dipeptide (example 10A, 58.4 mg, 0.14 mmol) is provided in methylene chloride (5 ml), the solution is subsequently cooled to −10° C., and HOBt (77.7 mg, 0.57 mmol, 4 eq.), NMM (47 μl, 43.7 mg, 0.43 mmol, 3 eq.) and EDC (55.1 mg, 0.29 mmol, 2 eq.) are successively added, and finally exemplary compound 13A (94.0 mg, 0.14 mmol, 1 eq.), and NMM 32 μl, 29.1 mg, 0.29 mmol, 2 eq.) are added. The reaction is slowly warmed to RT and stirred at this overnight. For the workup, the precipitate is filtered off, the filtrate is concentrated on a rotary evaporator at a bath temperature of 30° C., and after fine purification of the residue by preparative HPLC (method 31) 77.9 mg (79.4% of theory) of product are obtained.

HPLC (Method 1) R$_t$=3.12 min.

LC-MS (Method 23): R$_t$=7.05 min; MS (ESIpos): m/z (%)=683 (100) [M+H]$^+$, 1366 (75) [2M+2H]$^{2+}$.

$^1$H NMR (300 MHz, CDCl$_3$): δ=0.89 (d, J=4.6, 9H, CH$_2$C(CH$_3$)$_3$), 0.96 (d, J=2.9, 9H, CH$_2$C(CH$_3$)$_3$), 1.23-1.49 (m, 11H: including 1.39 (s, 9H, OC(CH$_3$)$_3$), 1.85 (m, 2H, CH$_2$C(CH$_3$)$_3$), 3.59/3.68 (2s, 3H, OCH$_3$), 4.04 (m, 1H, $^α$CH), 4.41 (m, 1H, $^α$CH), 4.88-5.42 (m, 6H), 5.99 (m, 1H, NH), 6.22 (m, 1H, NH), 7.13-7.42 (m, 10H, ArH).

HR-TOF-MS (Method 24): $C_{37}H_{55}N_4O_8$ calc. 683.4015, found 683.4033 $[M+H]^+$.

Example 20A

[$N^2$-(Benzyloxycarbonyl)-3-tert-butyl-D-alanyl]-[3-tert-butyl-L-alanyl]-[(3R)-3-{(tert-butoxycarbonyl)amino}-L-phenylalanine]

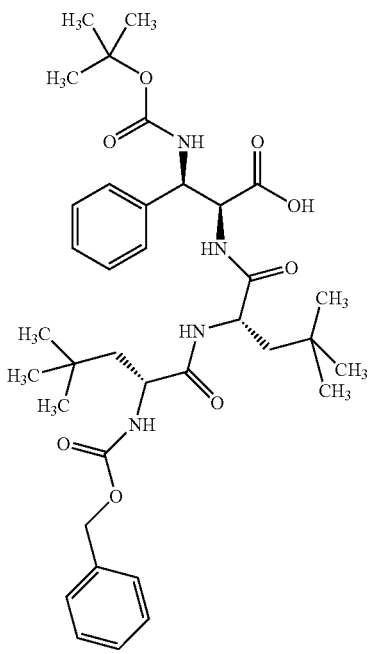

The ester (example 19A, 1.0 g, 1.46 mmol) is provided in a mixture of THF (100 ml) and water (50 ml) and, at 0° C., a 0.5% lithium hydroxide solution (12 ml, 59.6 mg, 2.49 mmol, 1.7 eq.) is added dropwise. The solution is stirred at 0° C. for 4 h until conversion is complete. For the workup, the reaction is mixed with potassium dihydrogen phosphate (996.4 mg, 7.32 mmol), the solvent is completely removed on a rotary evaporator at a bath temperature of 30° C., and the residue is purified by preparative HPLC (method 28). 737.0 mg (75.3% of theory) of product are obtained.

HPLC (Method 1) $R_t$=2.86 min.

LC-MS (Method 21): $R_t$=2.89 min; MS (ESIpos): m/z (%)=669 (20) $[M+H]^+$, 569 (100) $[M-C_4H_8-CO_2+H]^+$.

HR-TOF-MS (Method 24): $C_{36}H_{53}N_4O_8$ $[M+H]^+$ found 669.3881, calc. 669.3858.

Example 21A 2,5-Dioxopyrrolidin-1-yl [$N^2$-(benzyloxycarbonyl)-3-tert-butyl-D-alanyl]-[3-tert-butyl-L-alanyl]-[(3R)-3-{(tert-butoxycarbonyl)amino}-L-phenylalaninate]

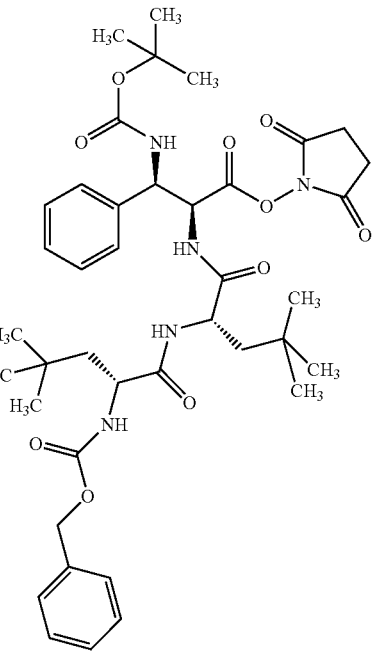

Under an argon protective gas atmosphere, exemplary compound 20A (30.0 mg, 44.85 µmol) is dissolved in dichloromethane (6 ml), the solution is cooled to 0° C., N-hydroxysuccinimide (6.2 mg, 53.83 µmol, 1.2 eq.), EDC (10.3 mg, 53.83 µmol, 1.2 eq.) and 4 Å molecular sieves are added, and the mixture is stirred at 0° C. overnight. The solvent is removed on a rotary evaporator at a maximum bath temperature of 30° C., the residue is taken up in ethyl acetate and washed successively twice with a 5% citric acid solution and twice with a sat. sodium chloride solution, the org. phase is dried over sodium sulfate and filtered, the solvent is concentrated on a rotary evaporator at a bath temperature of 30° C., and 34.0 mg (98.7% of theory) of product are isolated from the residue after fine purification on an RP cartridge (eluent: ethyl acetate).

HPLC (Method 1) $R_t$=2.99 min.

LC-MS (Method 20): $R_t$=2.88 min; MS (ESIpos): m/z (%)=766 (57) $[M+H]^+$, 666 (100) $[M+H+C_4H_8-CO_2]^+$.

Example 22A $N^2$-(tert-Butoxycarbonyl)-L-allothreonine

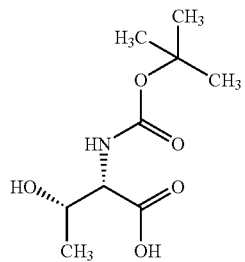

L-allo-Threonine (3.15 g, 26.44 mmol) is dissolved in water-dioxane (1+2, 75 ml), di-tert-butyl dicarbonate (6.35 g, 29.09 mmol, 1.1 equivalents) and triethylamine (4.79 ml, 34.38 mmol, 1.3 equivalents) are added and the mixture is stirred at room temperature overnight. The solvent is then removed in vacuo. The residue is taken up in ethyl acetate and extracted with 1 M citric acid. The aqueous phase is extracted several times more with ethyl acetate until no product can be detected therein any more (HPLC, method 5). The combined organic extracts are then dried over sodium sulfate, concentrated and dried under oil pump vacuum to constant weight. The product is reacted further without further purification. Yield: 6.5 g of crude product.

HPLC (Method 5): $R_t$=3.23 min.

LC-MS (Method 22): $R_t$=2.51 min, MS (ESIneg): m/z (%) 217.8 (100) [M−H]−.

$^1$H NMR (400 MHz, $d_6$-DMSO) δ (ppm)=1.08 (d, J=5.4 Hz, 3H), 1.38 (s, 9H), 3.72-3.84 (m, 2H), 6.77 (d, J=7.4 Hz, 1H).

Example 23A

Benzyl $N^2$-(tert-butoxycarbonyl)-L-allothreoninate

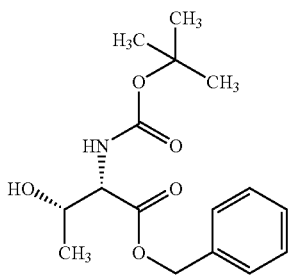

The method was carried out in analogy to the following literature: S. B. Cohen, R. Halcomb, *J. Am. Chem. Soc* 2004, 124, 2534-25M 43. W. Jiang, J. Wanner, R. J. Lee, P.-Y. Bounaud, D. L. Boger, *J. Am. Chem. Soc* 2003, 125, 1877-1887.

The compound of example 22A (6.8 g of crude product, 26.44 mmol) is taken up in methanol (177 ml), cesium carbonate (5.56 g, 17.06 mmol, 0.63 equivalents) is added, and the mixture is stirred until dissolution is complete. The solvent is then removed by distillation, DMF (42 ml) and then benzyl bromide (4.06 ml, 34.12 mmol, 1.26 equivalents) are added. The mixture is stirred for 16 h and the DMF is then substantially removed in vacuo. The residue is taken up in water and extracted with 3 portions of dichloromethane. The combined org. phases are dried over sodium sulfate, filtered and concentrated in vacuo. The crude product is purified on Biotage RP18-Flash (water-acetonitrile gradient: 0-5 min. 10% acetonitrile, 3-30 min. 10-90% acetonitrile, 30-35 min. 90% acetonitrile; flow: 20 ml/min.). Yield: 5.00 g (16.16 mmol, 52% of theory).

HPLC (Method 5): $R_t$=4.36 min.

LC-MS (Method 18): $R_t$=2.39 min, MS (ESIpos): m/z (%)=332.6 (25) [M+H]+.

$^1$H NMR (400 MHz, $d_6$-DMSO) δ (ppm)=1.09 (d, J=6.4, 3H), 1.37 (s, 9H), 3.82 (m, 1H), 3.95 (dd, J=6.4, J=8.1 Hz), 4.98 (d, J=5.4 Hz, 1H), 5.09 (d, J=12.7 Hz, 1H), 5.16 (d, J=12.7 Hz, 1H), 7.10 (d, J=8.1 Hz, 1H), 7.31-7.37 (m, 5H).

Example 24A

Benzyl L-Allothreoninate trifluoroacetate

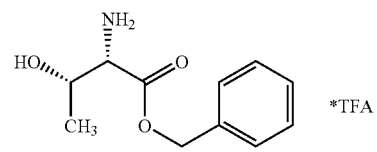

530 mg of the compound from example 23A are reacted with 8.0 ml of the TFA solution according to procedure 2. The crude product (589 mg, quant.) is reacted further without further purification.

HPLC (Method 5): $R_t$=3.18 min.

LC-MS (Method 22): $R_t$=2.24 min, MS (ESIpos): m/z (%)=210.0 (100) [M+H]+.

$^1$H NMR (400 MHz, $d_6$-DMSO) δ (ppm)=1.15 (d, J=6.6 Hz, 3H), 4.09-4.10 (m, 2H), 5.26 (s, 2H), 7.36-7.44 (m, 5H), 8.34 (br. S, 2H).

Example 25A

Benzyl [$N^2$-(tert-butoxycarbonyl)-L-isoleucyl]-L-allothreoninate

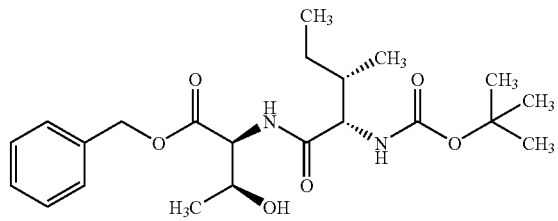

The compound of example 24A (2.30 g 7.12 mmol) and N-(tert-butoxycarbonyl)-L-isoleucine (2.14 g, 9.25 mmol, 1.3 equivalents) are dissolved in DMF (21.0 ml). 4-Methylmorpholine (1.3 ml, 12.02 mmol, 1.7 equivalents) and HATU (3.52 g, 9.25 mmol, 1.3 equivalents) are added, and the mixture is stirred at room temperature for 16 h. The complete mixture is then purified by chromatography first according to method 45 and subsequently according to method 46. Yield: 1.75 g (4.14 mmol, 58% of theory) as a pale beige-colored amorphous solid.

HPLC (Method 5): $R_t$=4.59 min.

LC-MS (Method 18): $R_t$=2.56 min, MS (ESIpos): m/z (%)=423.8 (70) [M+H]+.

$^1$H NMR (400 MHz, $d_6$-DMSO) δ (ppm)=0.74-0.78 (m, 6H), 1.01-1.07 (m, 2H), 1.10 (d, J=6.3 Hz, 3H), 1.37 (s, 9H), 1.64-1.66 (m, 1H), 3.86-3.94 (m, 1H), 4.28 (dd, J=7.3, J=7.3 Hz, 1H), 5.05 (d, J=5.6 Hz), 5.09 (d, J=12.7 Hz, 1H), 5.13 (d, J=12.7 Hz 1H), 6.70 (d, J=9.0 Hz, 1H), 7.31-7.36 (m, 5H), 8.11 (d, J=8.1 Hz).

HR-TOF-MS (Method 24): $C_{22}H_{35}N_2O_6$ calc. 423.2490, found 423.2489 [M+H]+.

Example 26A

Benzyl L-isoleucyl-L-Allothreoninate trifluoroacetate

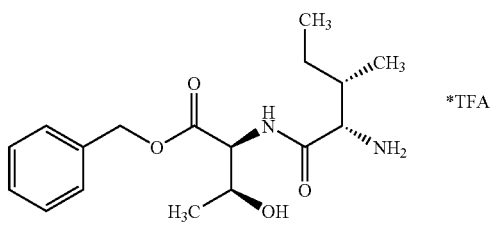

The compound of example 25A (224 mg, 0.53 mmol) is treated with 8.0 ml of the TFA solution according to procedure 2. 253 mg of crude product of example 26A (about 91% pure, 0.53 mmol, quant.) are obtained and are reacted without further purification.

HPLC (Method 5): $R_t$=3.51 min.
LC-MS (Method 18): $R_t$=1.58 min, MS (ESIpos): m/z (%)=323.6 (100) [M+H]$^+$.
$^1$H NMR (400 MHz, d$_6$-DMSO) δ (ppm)=0.77-0.86 (m, 6H), 1.02 (m, 1H), 1.15 (d, J=6.4 Hz, 3H), 1.45 (m, 1H), 1.77 (m, 1H), 3.97 (m, 1H), 4.34 (m, 1H), 5.11 (d, J=12.5 Hz, 1H), 5.16 (d, J=12.5 Hz, 1H), 7.37-7.39 (m, 5H), 7.47 (m, 1H), 8.07-8.08 (m, 3H), 8.69 (d, J=7.3 Hz, 1H).

Example 27A

Benzyl [N$^2$-(tert-butoxycarbonyl)-D-arginyl]-L-isoleucyl-L-allothreoninate

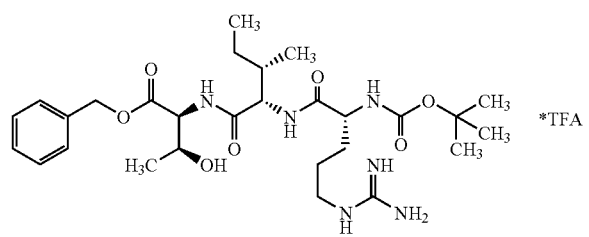

The compound of example 26A (253 mg 91% pure, 0.53 mmol) and N$^2$-(tert-butoxycarbonyl)-D-arginine (145 mg, 0.53 mmol, 1 equivalent) are dissolved in DMF (3.0 ml). 4-Methylmorpholine (76 µl, 0.70 mmol, 1.3 equivalents) and HATU (221 mg, 0.58 mmol, 1.1 equivalents) are added, and the mixture is stirred at room temperature for 16 h. The complete mixture is then put onto an HPLC column and purified by chromatography (method 34). Yield: 364 mg (0.53 mmol, 99% of theory).

HPLC (Method 5): $R_t$=3.91 min.
LC-MS (Method 18): $R_t$=2.04 min, MS (ESIpos): m/z (%)=579.9 (100) [M+H]$^+$.
$^1$H NMR (400 MHz, d$_6$-DMSO) δ (ppm)=0.72-1.16 (m, 8H), 1.37 (s, 9H), 1.46 (m, 2H), 1.60 (m, 1H), 1.69 (m, 1H), 3.06 (m, 2H), 3.93-4.01 (m, 2H), 4.25 (m, 1H), 4.33 (m, 1H), 5.07-5.14 (m, 2H), 6.96 (d, J=7.8, 1H), 7.35 (m, 5H), 7.45 (m, 1H), 7.66 (d, J=8.8), 8.33 (m, 1H).

Example 28A

Benzyl D-arginyl-L-isoleucyl-L-allothreoninate bistrifluoroacetate

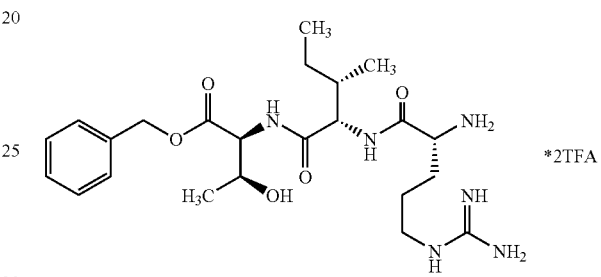

The compound of example 27A (237 mg, 0.34 mmol) is treated with 2.0 ml of the TFA solution according to procedure 2. 255 mg of crude product of example 28A (94% pure, 0.34 mmol, quant.), are obtained and are reacted without further purification.

HPLC (Method 5): $R_t$=3.42 min.
LC-MS (Method 22): $R_t$=2.42 min, MS (ESIpos): m/z (%)=479.3 (50) [M+H]$^+$.
$^1$H NMR (400 MHz, d$_6$-DMSO) δ (ppm)=0.73-0.81 (m, 5H), 1.11-1.19 (m, 5H), 1.33-1.49 (m, 3H), 1.74 (m, 3H), 3.10 (m, 2H), 3.88-3.95 (m, 2H), 4.25 (dd, J=6.8, J=7.1 Hz, 1H), 4.46 (dd, J=7.3, J=8.8 Hz, 1H), 5.09 (d, J=12.5 Hz, 1H), 5.15 (dd, J=12.5 Hz), 7.36 (m, 5H), 7.61 (m, 1H), 8.10 (m, 2H), 8.51 (d, J=7.6 Hz, 1H), 8.57 (d, J=9.0 Hz, 1H).

Example 29A

Benzyl [N$^2$-(tert-butoxycarbonyl)-L-leucyl]-D-arginyl-L-isoleucyl-L-allothreoninate trifluoroacetate

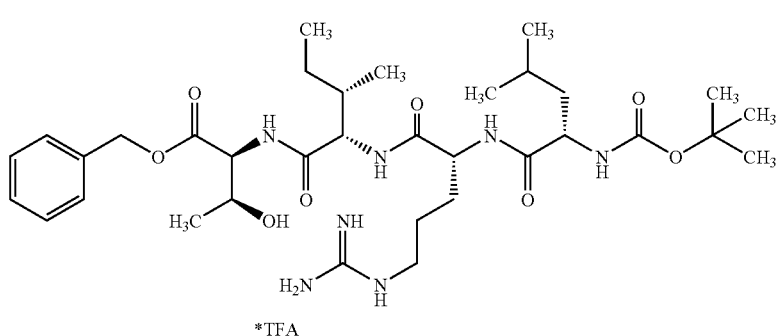

The compound of example 28A (240 mg, 0.34 mmol) and N-(tert-butoxycarbonyl)-L-leucine (79 mg, 0.34 mmol, 1 equivalent) are dissolved in dichloromethane-DMF (5+1, 6 ml). Diisopropylethylamine (296 µl, 1.70 mmol, 5 equivalents) and HATU (194 mg, 0.51 mmol, 1.5 equivalents) are added, and the mixture is stirred at room temperature for 24 h. The complete mixture is then put onto a gel chromatography column and purified by chromatography (method 45, eluent is methanol). Yield: 146 mg (0.18 mmol, 53% of theory).

HPLC (Method 5): $R_t$=4.15 min.

LC-MS (Method 18): $R_t$=1.92 min, MS (ESIpos): m/z (%)=692.8 (100), [M+H]$^+$.

$^1$H NMR (400 MHz, d$_6$-DMSO) δ (ppm)=0.72-1.23 (m, 22H), 1.37 (s, 9H), 1.38-1.71 (m, 3H), 3.08 (m, 2H), 3.91-4.00 (m, 2H), 4.26 (m, 1H), 4.33-4.42 (m, 2H), 5.07-5.15 (m, 2H), 6.92 (d, J=7.8 Hz, 1H), 7.35 (m, 5H), 7.47 (m, 1H), 7.88 (d, J=8.1 Hz, 1H), 7.93 (d, J=9.0 Hz, 1H), 8.35 (d, J=7.3 Hz, 1H).

Example 30A

Benzyl L-leucyl-D-arginyl-L-isoleucyl-L-allothreoninate bistrifluoroacetate

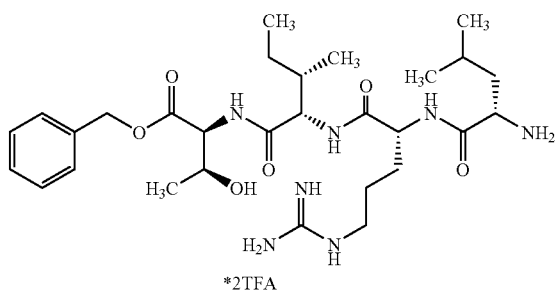

The compound of example 29A (220 mg, 0.27 mmol) is treated with 2.0 ml of the TFA solution according to procedure 2. 223 mg of crude product of example 28A (0.27 mmol, quant.), are obtained and are reacted without further purification.

HPLC (Method 4): $R_t$=3.80.

LC-MS (Method 22): $R_t$=2.54 min, MS (ESIpos): m/z (%)=592.4 (2) [M+H]$^+$.

$^1$H NMR (400 MHz, d$_6$-DMSO) δ (ppm)=0.73-1.11 (m, 13H), 1.22-1.74 (m, 12H), 3.11 (m, 4H), 3.60 (m, 2H), 3.87 (m, 1H), 3.95 (m, 1H), 4.25 (m, 1H), 4.38 (dd, J=7.8, J=8.6 Hz, 1H), 4.64 (dd, J=7.8, J=13.7 Hz, 1H), 5.09 (d, J=12.7 Hz, 1H), 5.13 (d, J=12.7 Hz, 1H), 7.35 (m, 5H), 7.58 (m, 1H), 8.07 (m, 2H), 8.25 (d, J=8.8 Hz, 1H), 8.39 (d, J=7.6 Hz, 1H), 8.77 (d, J=8.3 Hz, 1H).

Example 31A

Benzyl [(3R)-N$^2$-(tert-butoxycarbonyl)-3-hydroxy-L-leucyl]-L-leucyl-D-arginyl-L-isoleucyl-L-allothreoninate trifluoroacetate

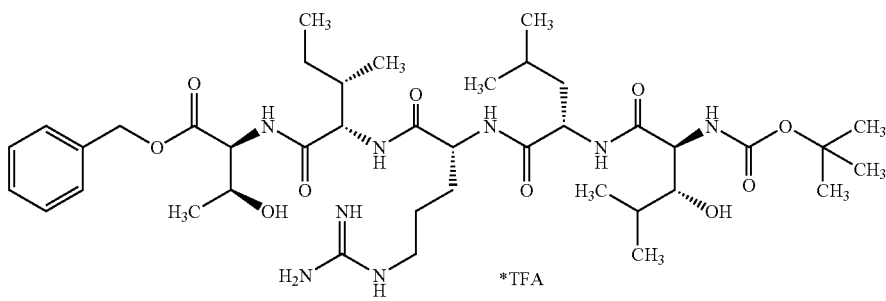

The compound of example 30A (223 mg, 0.27 mmol) and N-(tert-butoxycarbonyl)-(3R)-3-hydroxy-L-leucine (89 mg, 0.33 mmol, 1.22 equivalents) are dissolved in DMF (6 ml), and the solution is cooled to −20° C. 4-Methylmorpholine (150 µl, 1.36 mmol, 5 equivalents) and HATU (165 mg, 0.44 mmol, 1.6 equivalents) are added, and the mixture is stirred at room temperature for 16 h. The complete mixture is then put onto a gel chromatography column and purified by chromatography (method 45, eluent is methanol). Yield: 188 mg (0.20 mmol, 74% of theory).

HPLC (Method 5): $R_t$=4.24 min.

LC-MS (Method 19): $R_t$=1.99 min, MS (ESIpos): m/z (%)=821.9 (100) [M+H]$^+$.

$^1$H NMR (400 MHz, d$_6$-DMSO) δ (ppm)=0.71-0.90 (m, 15H), 1.00 (m, 1H), 1.10 (d, J=6.4 Hz, 3H), 1.24-1.26 (m, 3H), 1.38 (s, 9H), 1.42-1.71 (m, 6H), 3.06-3.17 (m, 3H), 3.45 (m, 1H), 3.61 (m, 1H), 3.93 (m, 1H), 4.05 (m, 1H), 4.26 (m, 1H), 4.35 (m, 2H), 4.54 (d, J=7.8 Hz, 1H), 5.07-5.15 (m, 2H), 5.45 (d, J=9.0 Hz, 1H), 7.35 (m, 5H), 7.46 (m, 1H), 7.85 (d, J=7.8 Hz, 1H), 7.89 (d, J=8.8 Hz, 1H), 7.97 (d, J=8.1 Hz, 1H), 8.35 (d, J=7.6 Hz, 1H).

Example 32A

[(3R)-N$^2$-(tert-Butoxycarbonyl)-3-hydroxy-L-leucyl]-L-leucyl-D-arginyl-L-isoleucyl-L-allothreonine trifluoroacetate

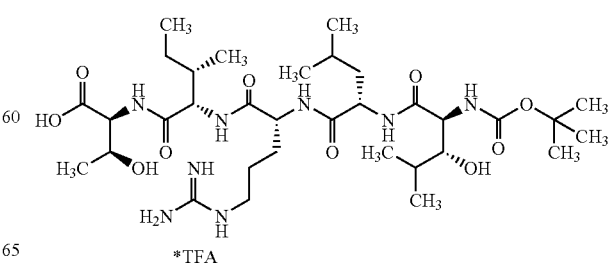

The compound of example 31A (100 mg, 0.11 mmol) is dissolved in glacial acetic acid (4.3 ml), 10% palladium on activated carbon (22 mg) is added, and the mixture is hydrogenated under atmospheric pressure at room temperature for 2 h. The catalyst is removed by filtration, and the filtrate is lyophilized. The crude product is purified by chromatography (method 33). 58 mg (60 μmol, 55% of theory) of the title compound are obtained.

HPLC (Method 5): $R_t$=3.75 min.

LC-MS (Method 1 Method 19): $R_t$=1.80 min, MS (ESI-pos): m/z (%)=731.8 (100) [M+H]$^+$.

Example 33A $O^4$-Methyl [$N^2$-(tert-butoxycarbonyl)glycyl]-(3S)-3-hydroxy-L-aspartate

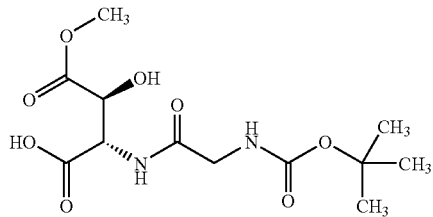

(3S)-3-Hydroxyaspartic acid is prepared by the method of G. Cardillo, L. Gentilucci, A. Tolomelli, C. Tomasini, *Synlett* 1999, 1727-1730, and converted in analogy to P. G. Mattingly, M. J. Miller, *J. Org. Chem.* 1983, 48, 3556-3559, using microwave radiation in a closed reactor into (2S,3S)-2-amino-3-hydroxy-4-methoxy-4-oxobutyric acid hydrochloride. (2S,3S)-2-Amino-3-hydroxy-4-methoxy-4-oxobutyric acid hydrochloride (447 mg, 2.24 mmol) is dissolved in DMF (9 ml). The solution is cooled to 0° C., Boc-glycin-N-hydroxysuccinimide ester (763 mg, 2.91 mmol, 1.3 equivalents), DMAP (14 mg, 0.11 mmol, 0.05 equivalents) and finally DIPEA (1170 μl, 6.72 mmol, 3 equivalents) are added. The mixture is allowed to warm slowly to room temperature and is then stirred for 2 h. The mixture is acidified with glacial acetic acid, mixed with acetonitrile and chromatographed on Sephadex LH 20 (method 45). Product-containing fractions are combined, concentrated and again chromatographed (method 46). The obtained product (761 mg, quant.) is reacted further without further purification. For analytical purposes, a pure sample is obtained by HPLC (method 44).

HPLC (Method 5): $R_t$=3.15 min

LC-MS (Method 1): $R_t$=1.17 min, MS (ESIpos)=321.2 [M+H]$^+$.

$[\alpha]^{20}_{Na}$=+39° (c=0.55, MeOH).

$^1$H NMR (300 MHz, d$_6$-DMSO) δ (ppm)=1.40 (s, 9H), 3.49-3.60 (m, 2H), 3.61 (s, 3H), 4.29 (m, 1H), 4.73 (d, J=6.6 Hz, 1H), 7.01 (m, 1H), 7.49 (d, J=6.99 Hz, 1H).

$^{13}$C-NMR (d$_6$-acetone, 126 MHz, DEPT) δ (ppm)=28.5 (CH$_3$), 42.2 (CH$_2$), 51.8 (CH$_3$), 53.7 (CH), 56.0 (CH), 79.2 (quat), 169.6 (quat), 169.7 (quat), 172.8 (quat), 173.8 (quat).

HR-TOF-MS (Method 24): $C_{12}H_{22}N_2O_8$ [M+H]$^+$ calc.: 321.1298, found: 321.1299.

Example 34A

Benzyl [$N^2$-(tert-butoxycarbonyl)glycyl]-[(3S)-3-hydroxy-$O^4$-methyl-L-aspartyl]-$O^3$-(tert-butyl)-L-serinate

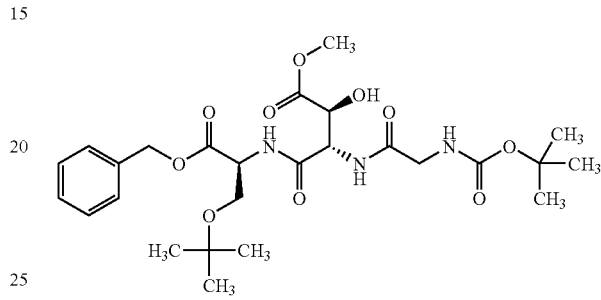

The compound of example 33A (390 mg, 1.22 mmol) and benzyl O-(tert-butyl)-L-serinate (445.14 mg, 1.22 mmol, 1 equivalent) are dissolved in DMF (9 ml). The solution is cooled to 0° C. and then 2.44 ml (2 equivalents) of a 1 M solution of 4-methylmorpholine in DMF are added, followed by HATU (925 mg, 2.44 mmol, 2 equivalents). The mixture is stirred at 0° C. for about 15 minutes, a further 2.44 ml (2 equivalents) of the 4-methylmorpholine solution are added, and the mixture is stirred at room temperature for 2 h. Water is then added and the mixture is extracted with 2 portions of ethyl acetate. The combined organic extracts are washed with 1 M citric acid, conc. sodium bicarbonate and conc. brine. The organic phase is then dried over sodium sulfate, the solvent is distilled off, and the residue is chromatographed (method 46). Yield: 413 mg (61% of theory) as a solid.

HPLC: $R_t$=4.46 min.

LC-MS: $R_t$=2.37 min. MS (ESIpos): 554.4 [M+H]$^+$.

$[\alpha]^{20}_{Na}$=−1.7 (c=0.57, CH$_3$CN).

$^1$H NMR (400 MHz, d$_6$-DMSO) δ (ppm)=1.09 (s, 9H), 1.45 (s, 9H), 3.17 (br s, 1H), 3.50-3.56 (dd, J=2.85 Hz, J=8.8 Hz, 1H), 3.59 (s, 3H), 3.61-3.67 (m, 3H), 4.66 (s, 1H), 4.70-4.72 (m, 1H), 4.97 (dd, J=2.7 Hz, J=8.65 Hz, 1H), 5.14 (d, J=12.3 Hz, 1H), 5.19 (br s, 1H), 5.23 (d, J=12.3 Hz, 1H), 7.11 (d, J=7.45 Hz, 1H), 7.19 (d, J=8.5 Hz, 1H), 7.46 (m, 5H).

$^{13}$C-NMR-DEPT (126 MHz, d$_6$-DMSO) δ (ppm)=28.5 (CH$_3$), 29.6 (CH$_3$), 45.5 (CH$_2$), 54.4 (CH$_3$), 54.5 (CH), 55.9 (CH), 62.8 (CH$_2$), 68.6 (CH$_2$), 71.7 (CH), 75.0 (quat), 81.8 (quat), 129.6 (CH), 129.7 (CH), 129.9 (CH), 136.7 (quat), 157.3 (quat), 169.9 (quat), 171.2 (quat), 173.4 (quat).

HR-TOF-MS: $C_{26}H_{40}N_3O_{10}$ [M+H]$^+$ calc.: 554.2714, found: 554.2707.

Example 35A

Benzyl [N²-(tert-butoxycarbonyl)glycyl]-[(3S)-3-hydroxy-L-asparaginyl]-O³-(tert-butyl)-L-serinate

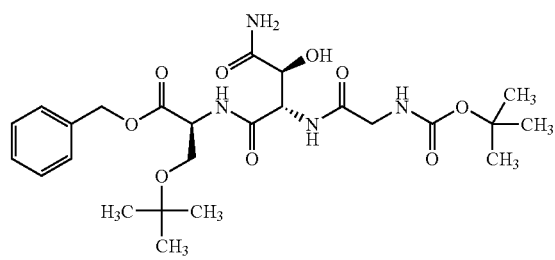

Compound 34A (430 mg, 0.78 mmol) is dissolved in acetonitrile (30 ml) and cooled to 0° C. Ammonia conc. (15 ml) is added and the mixture is stirred for about 15 min. As soon as the reaction is complete (detection by HPLC, method 5), acetic acid is added to acidify, and the mixture is diluted with water. The mixture is extracted with 2 portions of ethyl acetate. The combined organic extracts are washed with conc. brine, dried over sodium sulfate, concentrated and purified by HPLC.

Yield: 158 mg (38% of theory) as a solid.

$[\alpha]^{20}$Na=−16° (c=0.53, MeOH).

HPLC: $R_t$=4.18 min. LC-MS: $R_t$=2.14 min, MS (ESIpos) m/z=539.4 [M+H]⁺.

HR-TOF-MS: $C_{25}H_{39}N_4O_9$ [M+H]⁺ calcd: 539.2717, found: 539.2709.

¹H NMR (300 MHz, $d_6$DMSO) δ (ppm)=1.05 (s, 9H), 1.38 (s, 9H), 3.50-3.56 (m, 2H), 3.61-3.67 (m, 2H), 4.33 (s, 1H), 4.48 (m, 1H), 4.71 (m, 1H, 5.10 (d, J=12.7 Hz, 1H), 5.19 (d, J=12.7 Hz, 1H), 7.07 (m, 1H), 7.17 (br s, 1H), 7.33-7.46 (m, 6H), 7.65 (d, J=8.8 Hz, 1H), 7.83 (d, J=7.7 Hz, 1H).

¹³C-NMR-DEPT (126 MHz, $d_6$-acetone) δ (ppm)=27.54 ($CH_3$), 28.58 ($CH_3$), 44.73 ($CH_2$), 54.06 (CH), 55.67 (CH), 62.61 ($CH_2$), 67.08 ($CH_2$), 71.64 (CH), 73.90 (quat), 79.70 (quat), 128.75 (CH), 128.82 (CH), 129.25 (quat), 137.20 (quat), 157.04 (quat), 170.56, 170.62 (quat), 170.72 (quat), 174.13 (quat).

Example 36A

Benzyl glycyl-[(3S)-3-hydroxy-L-asparaginyl]-O³-(tert-butyl)-L-serine trifluoroacetate

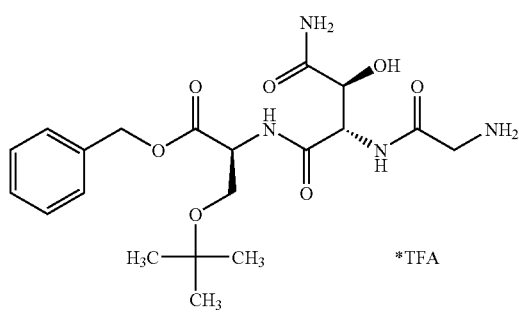

55 mg (100 μmol) of exemplary compound 35A are reacted in 2 ml of the reagent solution according to procedure 2. The product is reacted without further purification. Yield: 50 mg (quant.).

HPLC (Method 3): $R_t$=3.05 min.

LC-MS (Method 22): $R_t$=2.22 min; MS (ESIpos) m/z (%)=383.0 (100) [M+H]⁺.

Example 37A

{(3R)-N²-[(Benzyloxy)carbonyl]-3-[(tert-butoxycarbonyl)amino]-L-phenylalanyl}-[(3R)-3-hydroxy-L-leucyl]-L-leucyl-D-arginyl-L-isoleucyl-L-allothreonyl-glycyl-[(3S)-3-hydroxy-L-asparaginyl]-L-serine trifluoroacetate

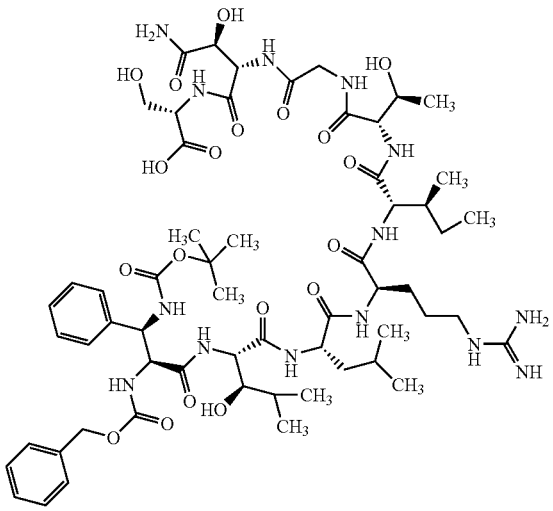

The degradation product from example 3A (2.8 g, 2.53 mmol) and the compound from example 17A (1.5 g, 2.53 mmol, 1 eq.) are provided in DMF (70 ml). The solution is cooled to 0° C., DIEA (2.64 ml, 2.0 g, 15.14 mmol, 6 eq.) is added, and the reaction mixture is slowly warmed to RT and stirred at this temperature for 3 h. The solvent is partly removed on a rotary evaporator, during which the bath temperature should not exceed 30° C. After fine purification by preparative HPLC (method 28), 2.2 g (61.4% of theory) of product are isolated.

HPLC (Method 9) $R_t$=17.03 min.

LC-MS (Method 20): $R_t$=1.79 min; MS (ESIpos): m/z (%)=1301 (28) [M+H]⁺, 601 (100) [M—$C_4H_8$—$CO_2$+2H]²⁺; MS (ESIneg.): m/z (%)=1300 (100) [M−H]⁻.

Example 38A

{(3R)-N²-[(Benzyloxy)carbonyl]-3-amino-L-phenylalanyl}-[(3R)-3-hydroxy-L-leucyl]-L-leucyl-D-arginyl-L-isoleucyl-L-allothreonyl-glycyl-[(3S)-3-hydroxy-L-asparaginyl]-L-serine trifluoroacetate

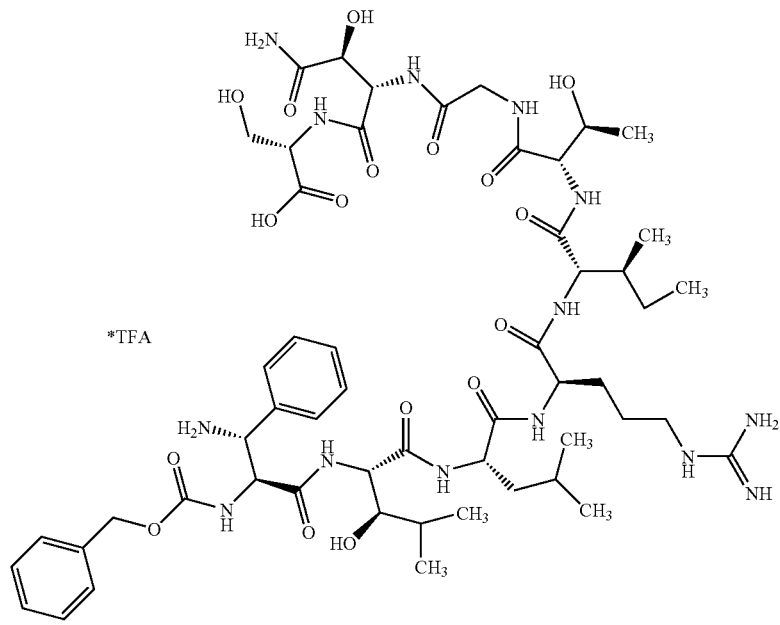

The Boc protecting group is removed from the compound of example 37A (2.2 g, 1.55 mmol) according to procedure 1. After chromatography (method 28) 1.8 g (87.1% of theory) of product are obtained.

HPLC (Method 9) $R_t$=12.37 min.

LC-MS (Method 20): $R_t$=1.17 min; MS (ESIpos): m/z (%)=1201 (8) [M+H]⁺, 601 (100) [M+2H]²⁺; MS (ESIneg.): m/z (%)=1199 (100) [M−H]⁻.

Example 39A

{(3R)-N²-[(Benzyloxy)carbonyl]-3-amino-L-phenylalanyl}-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam trifluoroacetate

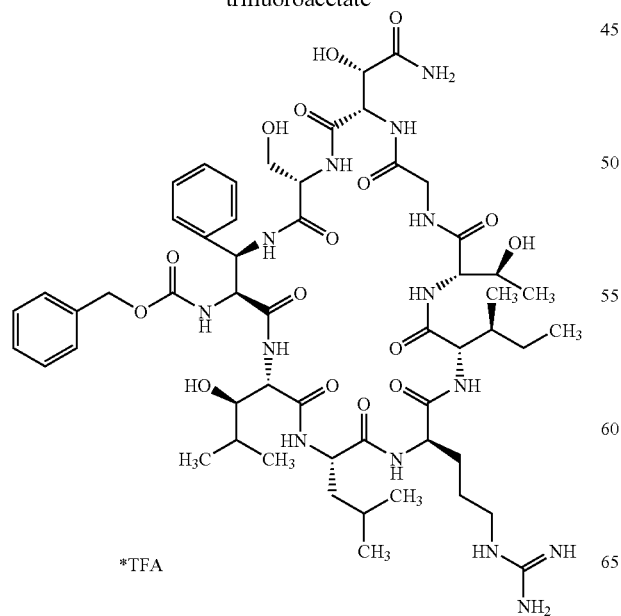

In an argon protective gas atmosphere, the compound of example 38A (1.3 g, 0.89 mmol) is provided in DMF (700 ml), the solution is cooled to 0° C. and then HATU (1.0 g, 2.68 mmol, 3 eq.) and NMM (0.8 ml, 0.7 g, 7.14 mmol, 8 eq.) are subsequently added. After stirring under a gentle stream of argon at 0° C. for 3 h, conversion is complete. For the workup, the reaction is mixed with methanol (30 ml), the solvent is removed on a rotary evaporator at a bath temperature of 30° C., the residue is suspended in methanol (30 ml) in an ultrasonic bath, and the precipitate which has separated out is removed by filtration. The filtrate is concentrated on a rotary evaporator at a maximum bath temperature of 30° C., and after fine purification by preparative HPLC (method 28) 905.6 mg (78.3% of theory) of the target compound are obtained.

HPLC (Method 9) $R_t$=15.09 min.

LC-MS (Method 18): $R_t$=1.75 min; MS (ESIpos): m/z (%)=1183 (100) [M+H]$^+$.

Example 40A

Pentafluorophenyl {N2-[(benzyloxy)carbonyl]-3-tert-butyl-D-alanyl}-{3-tert-butyl-L-alanyl}-[(3R)-3-[(tert-butoxycarbonyl)amino]-L-phenylalaninate]

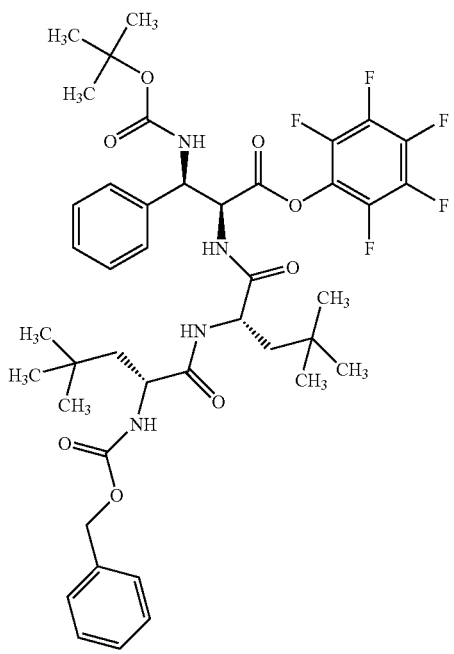

Under an argon protective gas atmosphere, the acid (example 20A, 170.0 mg, 0.25 mmol) is provided in methylene chloride (5 ml) and cooled to 0° C., and pentafluorophenyl diphenylphosphinate (146,5 mg, 0.38 mmol, 1.5 eq.) and NMM (140 µl, 128.5 mg, 1.27 mmol, 5 eq.) are subsequently added. The reaction is slowly warmed to RT and stirred at this temperature overnight. For the workup, the solvent is removed on a rotary evaporator at a bath temperature of 30° C., the residue is purified by preparative HPLC (method 32), the concentrated product fractions are again mixed with toluene and dichloromethane, the solvents are subsequently completely removed again on a rotary evaporator at a bath temperature of 30° C., the residue is lyophilized for 2 h and the product is stored at −25° C. 130.8 mg (61.6% of theory) of product are obtained.

HPLC (Method 1) $R_t$=3.30 min.

LC-MS (Method 18): $R_t$=3.42 min; MS (ESIpos): m/z (%)=835 (100) [M+H]$^+$, 735 (54) [M-C$_4$H$_8$—CO$_2$+H]$^+$, MS (ESIneg.): m/z (%)=833 (60) [M−H]$^-$, 183 (100).

Example 41A

Chlorotrityl-resin-bound O3-(tert-butyl)-N2-[(9H-fluoren-9-ylmethoxy)carbonyl]-L-serine

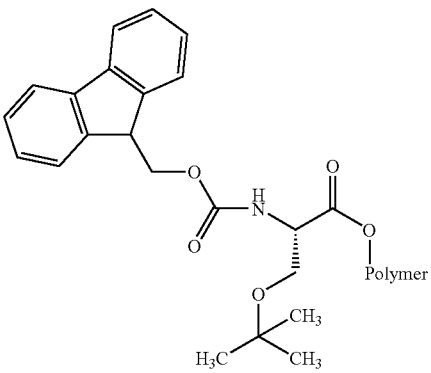

Chlorotrityl chloride-resin (4.0 g, 5.96 mmol) is provided in dichloromethane (40 ml) and O-(tert-butyl)-N-[(9H-fluoren-9-ylmethoxy)carbonyl]-L-serine (8.0 g, 20.86 mmol, 3.5 eq.) and DIEA (10.3 ml, 7.7 g, 59.60 mol, 10 eq.) are subsequently added. After shaking at RT for 20 h, the polymer is collected by suction filtration on a frit and subsequently washed successively three times with dichloromethane/methanol/DIEA 17/2/1, three times with dichloromethane, twice with DMF and three times with dichloromethane.

A sample removal with acetic acid/trifluoroethanol/dichloromethane 1:1:3 affords the corresponding fmoc-protected amino acid.

HPLC (Method 13) $R_t$=1.95 min.

LC-MS (Method 20): $R_t$=2.38 min; MS (ESIpos): m/z (%)=384 (35) [M+H]$^+$, 767 (10) [2M+H]$^+$, 105 (100); MS (ESIpos): m/z (%)=382 (25) [M−H]$^-$, 765 (10) [2M−H]$^-$, 160 (100).

Example 42A

Chlorotrityl-resin-bound {N$^2$-[(9H-fluoren-9-ylmethoxy)carbonyl]-4-trityl-L-asparaginyl}-[O$^3$-(tert-butyl)-L-serine]

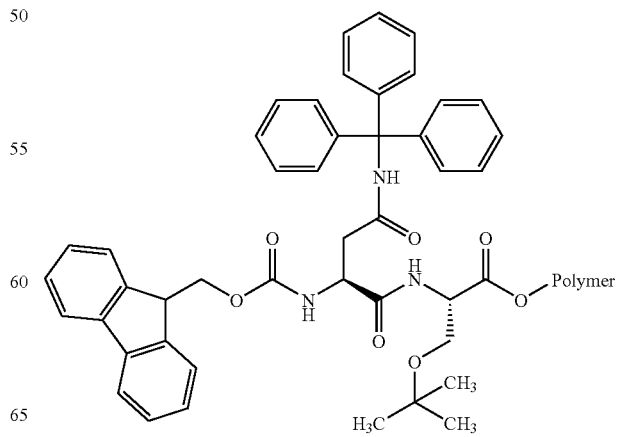

The Fmoc protecting group is removed from the polymer (example 41A, 2.0 g, 2.98 mmol), as described in procedure 7. The deprotected amino acid bound to the resin is subsequently reacted with $N^2$-[(9H-fluoren-9-ylmethoxy)carbonyl]-N-trityl-L-asparagine (3.6 g, 5.96 mmol, 2 eq.), DIEA (1.5 ml, 1.2 g, 8.94 mmol, 3 eq.) and TBTU (1.9 g, 5.96 mmol) overnight to give the Fmoc-protected dipeptide. The workup of the polymer takes place in analogy to procedure 7. The corresponding side chain-protected dipeptide is confirmed after a sample removal.

HPLC (Method 13) $R_t$=2.43 min.

LC-MS (Method 18): $R_t$=3.10 min; MS (ESIpos): m/z (%)=740 (5) [M+H]$^+$, 243 (100);

MS (ESIpos): m/z (%)=738 (40) [M−H]$^-$, 516 (85) [M-Fmoc-H]$^-$, 542 (100).

HR-TOF-MS (Method 24): $C_{45}H_{46}N_3O_7$ [M+H]$^+$ found 740.3342, calc. 740.3331.

Example 43A

Chlorotrityl-resin-bound {$N^2$-[(9H-fluoren-9-ylmethoxy)carbonyl]glycyl}-($N^4$-trityl-L-asparaginyl)-[$O^3$-(tert-butyl)-L-serine]

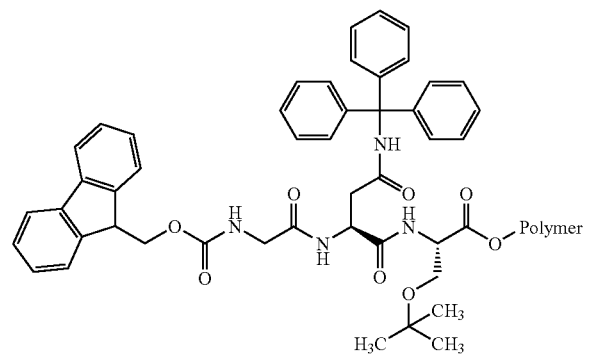

The Fmoc protecting group is removed from the polymer (example 42A, 2.0 g, 2.98 mmol), as described in procedure 7. The deprotected dipeptide bound to the resin is subsequently reacted with N-[(9H-fluoren-9-ylmethoxy)carbonyl] glycine (1.8 g, 5.96 mmol, 2 eq.), DIEA (1.5 ml, 1.2 g, 8.94 mmol, 3 eq.) and TBTU (1.9 g, 5.96 mmol, 2 eq.) overnight to give the Fmoc-protected tripeptide. The workup of the polymer takes place in analogy to procedure 7. The corresponding side chain-protected tripeptide is confirmed after a sample removal.

HPLC (Method 13) $R_t$=2.33 min.

LC-MS (Method 21): $R_t$=2.99 min; MS (ESIpos): m/z (%)=797 (5) [M+H]$^+$, 243 (100);

MS (ESIpos): m/z (%)=795 (40) [M−H]$^-$, 573 (100) [M-Fmoc-H]$^-$.

HR-TOF-MS (Method 24): $C_{47}H_{49}N_4O_8$ [M+H]$^+$ found 797.3556, calc. 797.3545.

Example 44A

Chlorotrityl-resin-bound {$O^3$-(tert-butyl)-$N^2$-[(9H-fluoren-9-ylmethoxy)carbonyl]-allothreonyl}-glycyl-($N^4$-trityl-L-asparaginyl)-[$O^3$-(tert-butyl)-L-serine]

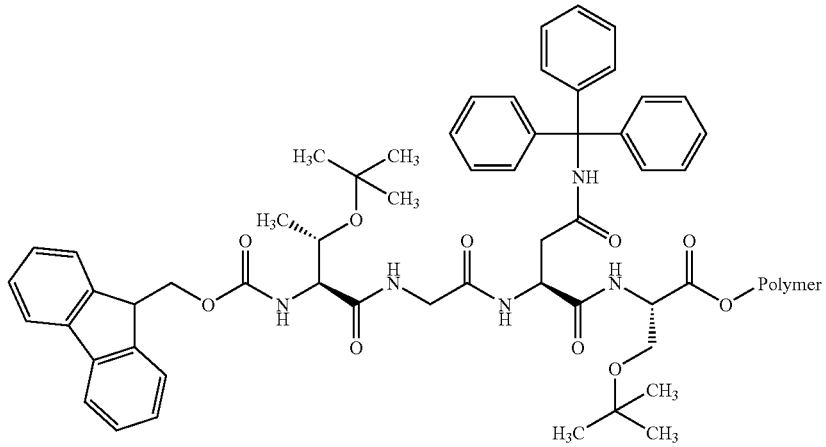

The Fmoc protecting group is removed from the polymer (example 43A, 1000.0 mg, 1.49 mmol), as described in procedure 7. The deprotected tripeptide bound to the resin is subsequently reacted with O-(tert-butyl)-N-[(9H-fluoren-9-ylmethoxy)carbonyl]allothreonine (1184.5 mg, 2.98 mmol, 2 eq.), DIEA (772 µl, 577.7 mg, 3 eq.) and TBTU (956.6 mg, 2.98 mmol, 2 eq.) overnight to give the Fmoc-protected tetrapeptide. The workup of the polymer takes place in analogy to procedure 7. The corresponding side chain-protected tetrapeptide is confirmed after a sample removal.

HPLC (Method 13) $R_f$=2.48 min.

LC-MS (Method 20): $R_t$=3.02 min; MS (ESIpos): m/z (%)=954 (100) [M+H]$^+$; MS (ESIpos): m/z (%)=752 (100) [M−H]$^-$.

HR-TOF-MS (Method 24): $C_{55}H\ N_5O_{10}$ [M+H]$^+$ found 954.4663, calc. 954.4648.

Example 45A

Chlorotrityl-resin-bound {N$^2$-[(9H-fluoren-9-ylmethoxy)carbonyl]}-L-isoleucyl-[O$^3$-(tert-butyl)]-L-allothreonyl-glycyl-(N$^3$-trityl-L-asparaginyl)-[O$^3$-(tert-butyl)-L-serine]

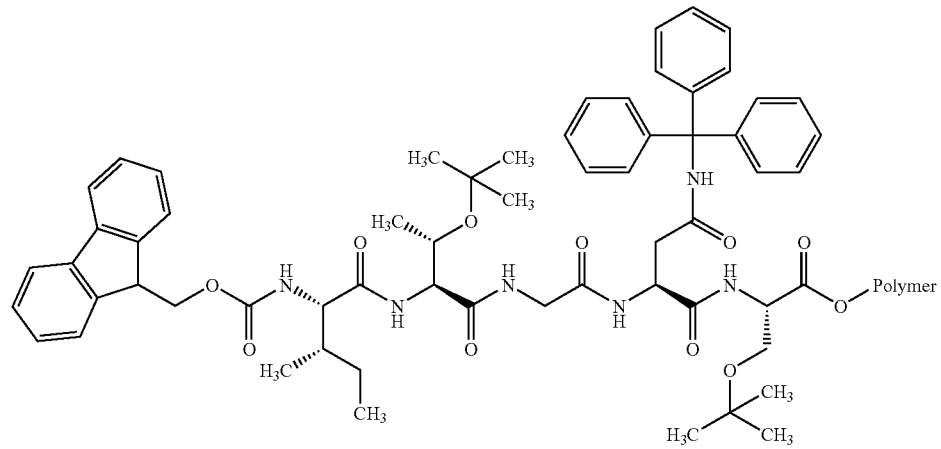

The Fmoc protecting group is removed from the polymer (example 44A, 1000.0 mg, 1.49 mmol) as described in procedure 7. The deprotected tetrapeptide bound to the resin is subsequently reacted with N-[(9H-fluoren-9-ylmethoxy)carbonyl]-L-isoleucine (1053.2 mg, 2.98 mmol, 2 eq.), DIEA (772 µl, 577.7 mg, 4.47 mmol, 3 eq.) and TBTU (956.6 mg, 2.98 mmol, 2 eq.) overnight to give the F-moc-protected pentapeptide. The workup of the polymer takes place in analogy to procedure 7. The corresponding side chain-protected pentapeptide is confirmed after a sample removal.

HPLC (Method 13) $R_f$=2.57 min.

LC-MS (Method 21): $R_t$=3.23 min; MS (ESIpos): m/z (%)=1067 (13) [M+H]$^+$, 243 (100).

HR-TOF-MS (Method 24): $C_{61}H_{75}N_6O_{11}$ [M+H]$^+$ found 1067.5488, calc. 1067.5489.

Example 46A

N$^5$-[(Benzyloxy)carbonyl]-{N$^5$-[{[(benzyloxy)carbonyl]amino}(imino)methyl]-N$^2$-[(9H-fluoren-9-ylmethoxy)carbonyl]-D-ornithine}

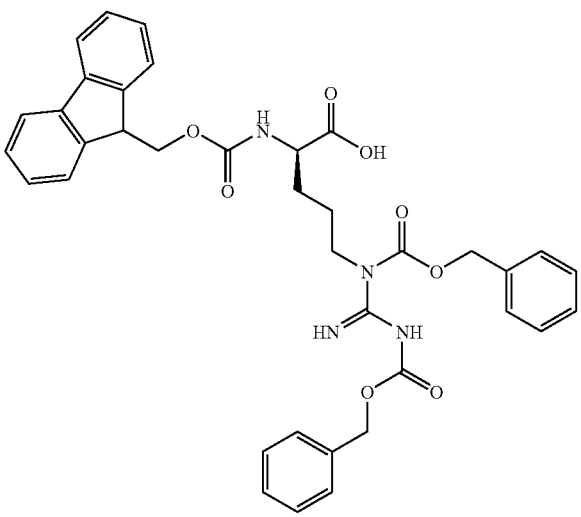

N⁵-[(Benzyloxy)carbonyl]-N⁵-[{[(benzyloxy)carbonyl]amino}(imino)methyl]-N²-(tert-butoxycarbonyl)-D-ornithine (4.90 g, 9.03 mmol) [M. Jetten et al., *Tetrahedron Lett.* 1991, 32, 6025-6028] is stirred in 4 M hydrochloric acid in dioxane (150 ml) and dichloromethane (150 ml) at RT overnight. The solvent is completely evaporated and the residue is dried in vacuo. The deprotected amine is subsequently provided in dichloromethane (180 ml), DIEA (4.5 ml, 3.5 g, 27.09 mmol, 3 eq.) and chlorotrimethylsilane (2.3 ml, 2.0 g, 18.061 mmol, 2 eq.), are added and the mixture is stirred under reflux overnight. The solution is cooled (0° C.), DIEA (3.0 ml, 2.3 g, 18.06 mmol, 2 eq.) and (9-fluorenylmethyl)chloroformate (2.3 g, 9.03 mmol, 1 eq.) are added, and the mixture is warmed to RT and stirred at this temperature overnight. For the workup, the reaction is diluted with dichloromethane and washed with a 10% aq. citric acid solution, the organic phase is dried over sodium sulfate, the solvent is removed on a rotary evaporator, and the residue is dried in vacuo. After fine purification (method 37) of the crude product 2.0 g (32.4% of theory) of the title compound are isolated.

LC-MS (Method 21): $R_t$=2.99 min; MS (ESIpos): m/z (%)=665 (100) [M+H]⁺; MS (ESIneg): m/z (%)=663 (30) [M-H]⁻, 333 (100).

Example 47A

Chlorotrityl-resin-bound [N⁵-(benzyloxycarbonyl)-N⁵-({[benzyloxycarbonyl]amino}-{imino}methyl)-N²-({9H-fluoren-9-ylmethoxy}carbonyl)-D-ornithyl]-L-isoleucyl-[O³-(tert-butyl)-L-allothreonyl]-glycyl-(N³-trityl-L-asparaginyl)-[O³-(tert-butyl)-L-serine]

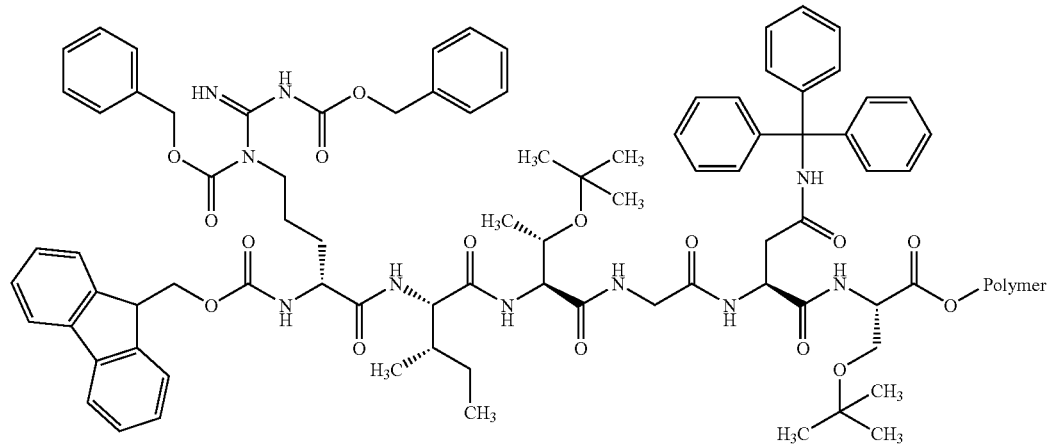

The Fmoc protecting group is removed from the polymer (example 45A, 1000.0 mg, 1.49 mmol) as described in procedure 7. The deprotected pentapeptide bound to the resin is subsequently reacted with the Fmoc-protected amino acid (example 46A, 1980.9 mg, 2.98 mmol, 2 eq.), DIEA (772 μl, 577.7 mg, 4.47 mmol, 3 eq.) and TBTU (956.6 mg, 2.98 mmol, 2 eq.) overnight to give the F-moc-protected hexapeptide. The workup of the polymer takes place in analogy to procedure 7. The polymer-bound hexapeptide is immediately processed further without analytical confirmation.

Example 48A

Chlorotrityl-resin-bound {N²-[(9H-fluoren-9-yl-methoxy)carbonyl]-L-leucyl}-[N⁵-(benzyloxycarbonyl)-N⁵-({[benzyloxycarbonyl]amino}{imino}methyl)-D-ornithyl]-L-isoleucyl-[O³-(tert-butyl)-L-allothreonyl]-glycyl-(N³-trityl-L-asparaginyl)-[O³-(tert-butyl)-L-serine]

The Fmoc protecting group is removed from the polymer (example 47A, 1000.0 mg, 1.49 mmol) as described in procedure 7. The deprotected hexapeptide bound to the resin is subsequently reacted with N-[(9H-fluoren-9-ylmethoxy)carbonyl]-L-leucine (1053.2 mg, 2.98 mmol, 2 eq.), DIEA (779 µl, 577.7 mg, 4.47 mmol, 3 eq.) and TBTU (956.7 mg, 2.98 mmol, 2 eq.) overnight to give the F-moc-protected heptapeptide. The workup of the polymer takes place in analogy to procedure 7. The corresponding side chain-protected heptapeptide is confirmed after a sample removal.

LC-MS (Method 18): $R_t$=3.51 min; MS (ESIpos): m/z (%)=1605 (100) [M+H]⁺.

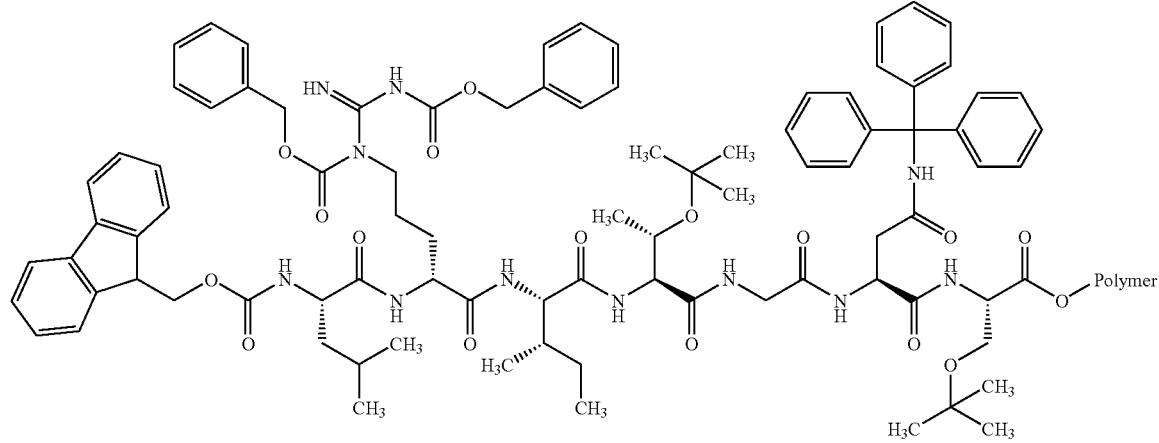

Example 49A

{N²-[tert-Butoxycarbonyl]-[(3R)-3-hydroxy-L-leucyl]}-L-leucyl}-[N⁵-(benzyloxycarbonyl)-N⁵-({[benzyloxycarbonyl]amino}{imino}methyl)-D-ornithyl]-L-isoleucyl-[O³-(tert-butyl)-L-allothreonyl]-glycyl-(N³-trityl-L-asparaginyl)-[O³-(tert-butyl)-L-serine]

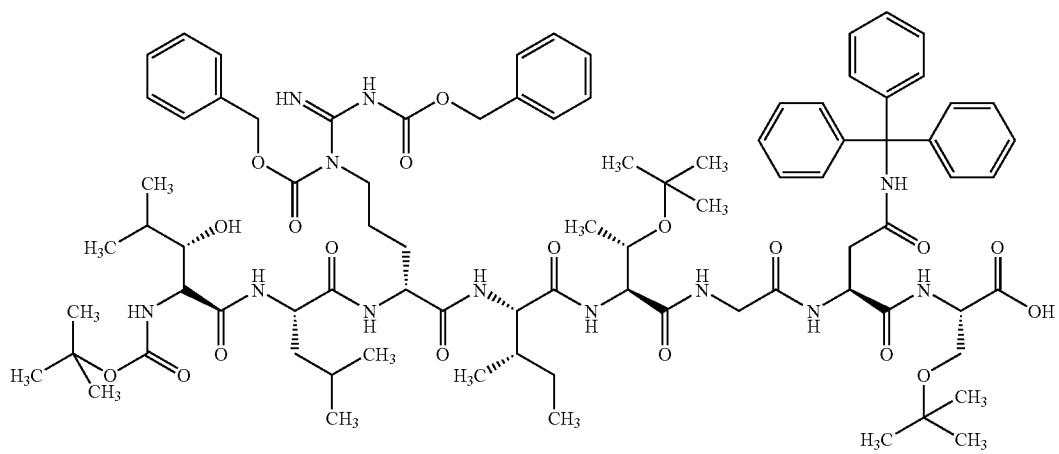

The Fmoc protecting group is removed from the polymer (example 48A, 1000.0 mg, 1.49 mmol) as described in procedure 7. The deprotected heptapeptide bound to the resin is subsequently reacted with (3R)-3-hydroxy-N-(tert-butoxycarbonyl)-L-leucine (552.7 mg, 2.24 mmol, 1.5 eq.), DIEA (597 µl, 442.9 mg, 3.43 mmol, 2.3 eq.) and TBTU (717.6 mg, 2.24 mmol, 1.5 eq.) overnight to give the F-moc-protected octapeptide. The workup of the polymer takes place in analogy to procedure 7.

The octapeptide is removed completely from the polymer in a solution of acetic acid, trifluoroethanol and dichloromethane (1:1:3). For the workup, the resin is removed by filtration on a frit, the filtrate is concentrated in vacuo and finally purified by chromatography (method 32). 56 mg (16% of theory) of the title compound are obtained.

LC-MS (Method 18): $R_f$=3.48 min; MS (ESIpos): m/z (%)=1613 (15) [M+H]$^+$, 806 (60) [M+2H]$^{2+}$, 243 (100); MS (ESIneg): m/z (%)=1611 (100) [M+H]$^+$.

Example 50A

[(3R)-3-Hydroxy-L-leucyl]-L-leucyl-{N$^5$-[benzyloxycarbonyl]-N$^5$-[{[benzyloxycarbonyl]-amino}(imino)methyl]-D-ornithyl}-L-isoleucyl-L-allothreonyl-glycyl-L-asparaginyl-L-serine

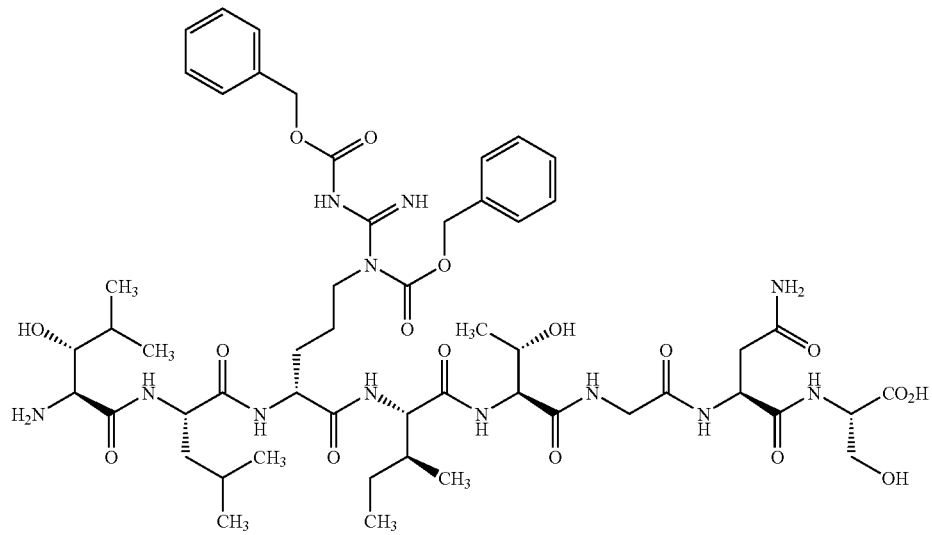

The peptide (example 49A, 22.0 mg, 13.65 µmol) is provided in TFA (5.25 ml) and water (0.25 ml), p-cresol (10.0 mg, 92.48 µmol) is subsequently added, and the solution is stirred at RT for 1 h. For the workup, the solvent is removed on a rotary evaporator at a bath temperature of 30° C. After fine purification of the residue by preparative HPLC (method 26) 4.4 mg (27.9% of theory) of product are obtained.

HPLC (Method 1) $R_f$=2.07 min

LC-MS (Method 18): $R_f$=2.12 min; MS (ESIpos): m/z (%)=1158 (5) [M+H]$^+$, 579 (100) [M+2H]$^{2+}$; MS (ESIneg.): m/z (%)=1156 (100) [M−H]$^-$.

Example 51A

[N²-(Benzyloxycarbonyl)-3-tert-butyl-D-alanyl]-[3-tert-butyl-L-alanyl]-{(3R)-3-[(tert-butoxycarbonyl)amino]-L-phenylalanyl}-{(3R)-3-hydroxy-L-leucyl}-L-leucyl-{N⁵-[benzyloxycarbonyl]-N⁵-[{[benzyloxycarbonyl]amino}(imino)methyl]-D-ornithyl}-L-isoleucyl-L-allothreonyl-glycyl-L-asparaginyl-L-serine

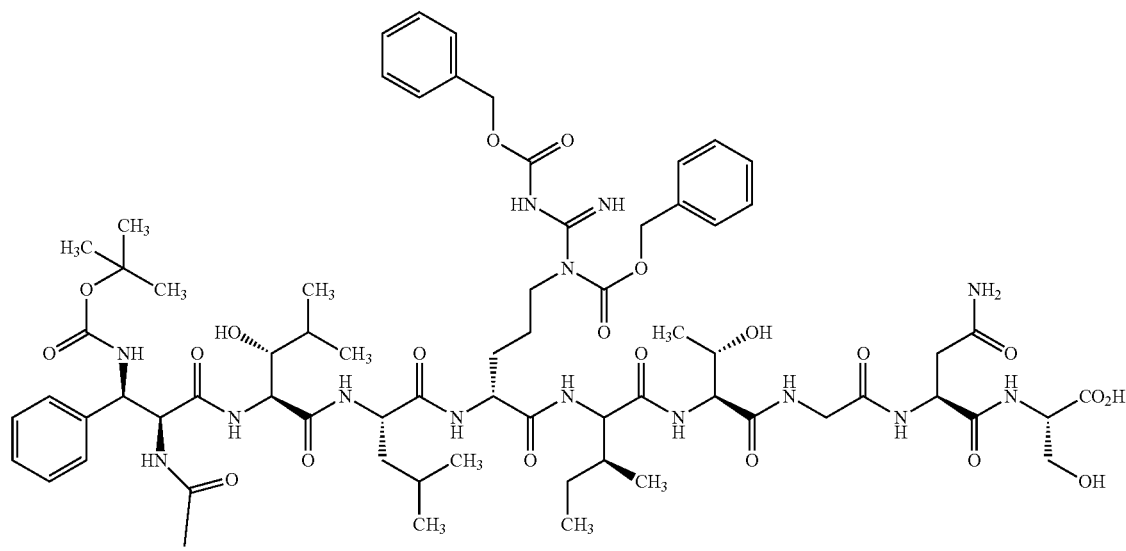

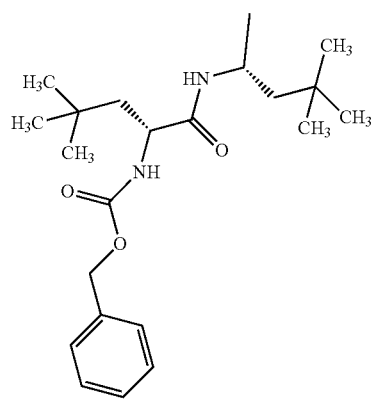

The amine (example 50A, 4.0 mg, 3.46 μmol) and the activated acid (example 40A, 3.2 mg, 3.82 μmol, 1.1 eq.) are provided in DMF (500 μl), the solution is cooled to 0° C., DIEA (4 μl, 2.7 mg, 20.74 mmol, 6 eq.) is subsequently added, and the reaction is warmed to RT and stirred at this overnight. For the workup, the solvent is removed on a rotary evaporator at a bath temperature of 30° C., the residue is prepurified by gel chromatography (method 45, eluent: methanol), and after fine purification by preparative HPLC (method 26) 3.0 mg (24.0% of theory) of product are obtained.

HPLC (Method 10) $R_t$=11.37 min

LC-MS (Method 18): $R_t$=3.37 min; MS (ESIpos): m/z (%)=904 (100) $[M+2H]^{2+}$.

Example 52A

[N²-(Benzyloxycarbonyl)-3-tert-butyl-D-alanyl]-[3-tert-butyl-L-alanyl]-{(3R)-3-amino-L-phenylalanyl}-{(3R)-3-hydroxy-L-leucyl}-L-leucyl-{N⁵-[benzyloxycarbonyl]-N⁵-[{[benzyloxycarbonyl]amino}(imino)methyl]-D-ornithyl}-L-isoleucyl-L-allothreonyl-glycyl-L-asparaginyl-L-serine Trifluoroacetate

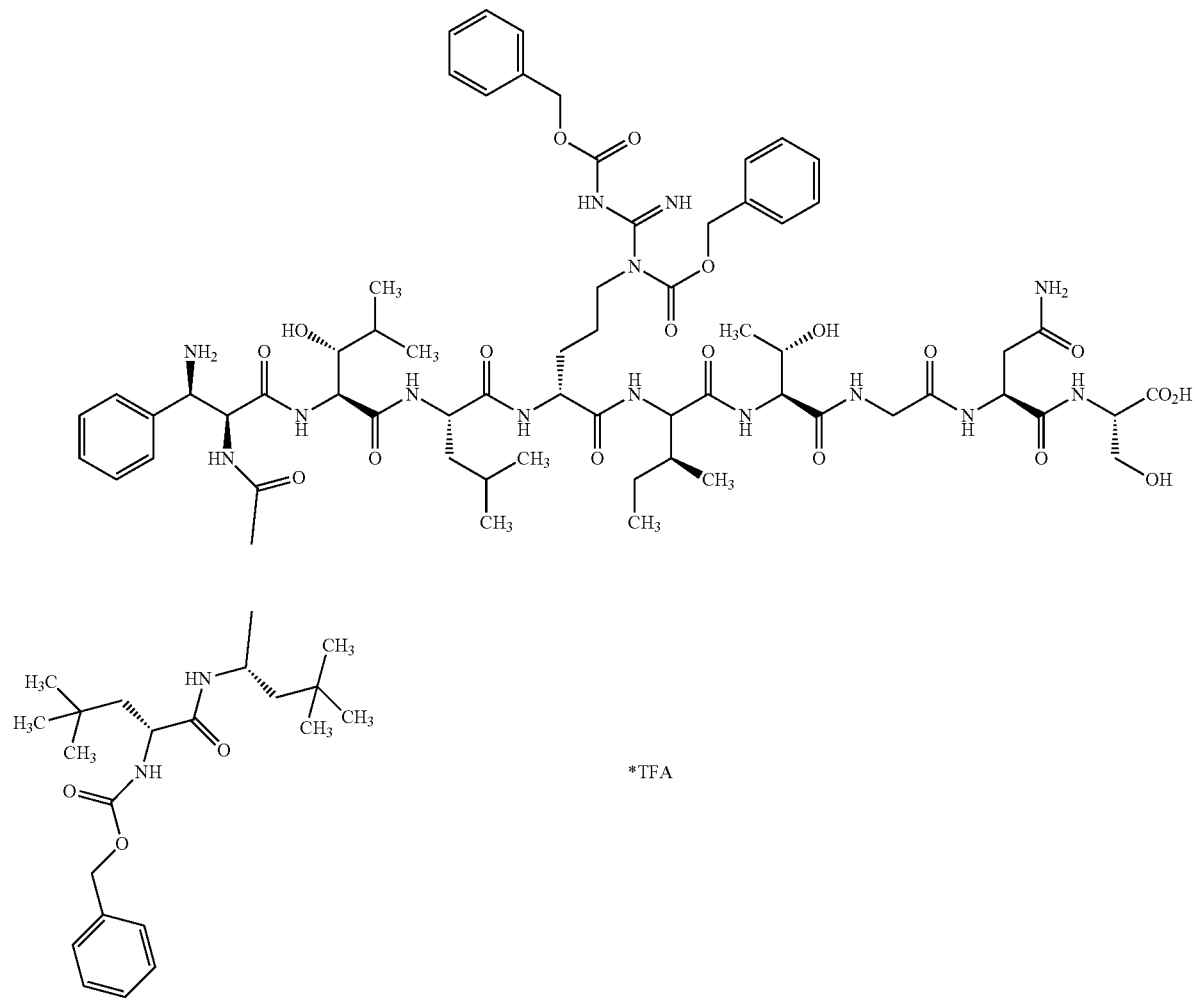

*TFA

The Boc protecting group is removed from exemplary compound 51A (2.5 mg, 1.38 μmol) according to general procedure 1. After fine purification by preparative HPLC (method 26) 2.2 mg (87.3% of theory) of product are obtained.

HPLC (Method 9) $R_t$=24.14 min

LC-MS (Method 18): $R_t$=2.63 min; MS (ESIpos): m/z (%)=854 (100) $[M+2H]^{2+}$; MS (ESIneg.): m/z (%)=1706 (100) $[M-H]^-$.

HR-TOF-MS (Method 24): $C_{84}H_{123}N_{16}O_{22}$ $[M+H]^+$ found 1707.8989, calc. 1707.8993.

Example 53A

[N²-(Benzyloxycarbonyl)-3-tert-butyl-D-alanyl]-[3-tert-butyl-L-alanyl]-{(3R)-3-amino-L-phenylalanyl}-{(3R)-3-hydroxy-L-leucyl}-L-leucyl-{N⁵-[benzyloxycarbonyl]-N⁵-[{[benzyloxycarbonyl]amino}(imino)methyl]-D-ornithyl}-L-isoleucyl-L-allothreonyl-glycyl-L-asparaginyl-L-serine Trifluoroacetate $C^{1.11}$-$N^{3.3}$-lactam

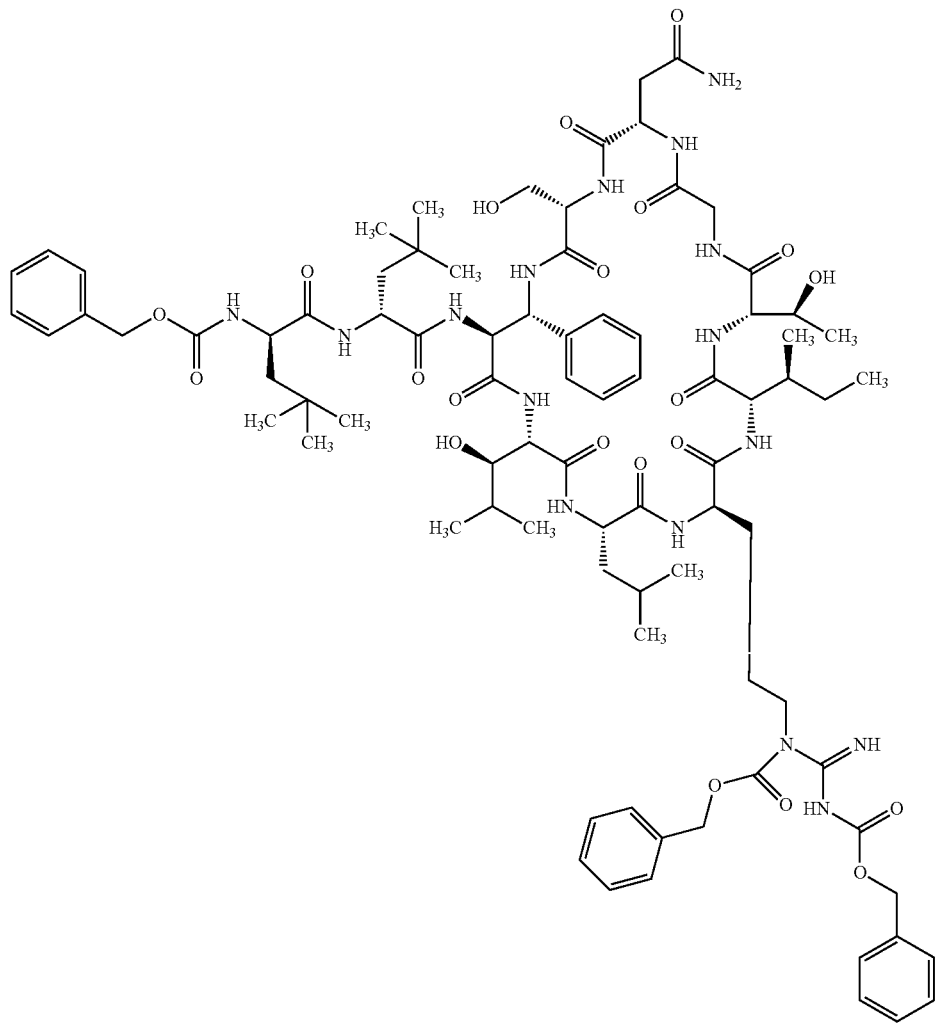

Under an argon protective gas atmosphere, the deprotected amine (example 52A, 2.0 mg, 1.10 μmol) is provided in DMF (1 ml), the solution is cooled to 0° C., HATU (1.3 mg, 3.29 μmol, 3 eq.) and NMM (0.7 μl, 0.7 mg, 6.58 μmol, 6 eq.) are added, and the reaction is slowly brought to RT and stirred at this temperature overnight. For the workup, the solution is purified by preparative HPLC (method 26). 1.9 mg (90.1% of theory) of the target compound are obtained.

HPLC (Method 10) $R_f$=10.70 min.

LC-MS (Method 18): $R_f$=3.25 min; MS (ESIpos): m/z (%)=1691 (53) [M+H]⁺, 846 (100) [M+2H]²⁺; MS (ESIneg.): m/z (%)=1688 (100) [M−H]⁻.

HR-TOF-MS (Method 24): $C_{84}H_{121}N_{16}O_{21}$ [M+H]⁺ found 1689.8929, calc. 1689.8887.

Example 54A

{(3R)-N²-(tert-Butoxycarbonyl)-3-hydroxy-L-leucyl}-L-leucyl-D-arginyl-L-isoleucyl-{O³-(tert-butyl)-L-allothreonyl}-glycyl-{N⁴-trityl-L-asparaginyl}-[O³-(tert-butyl)-L-serine]

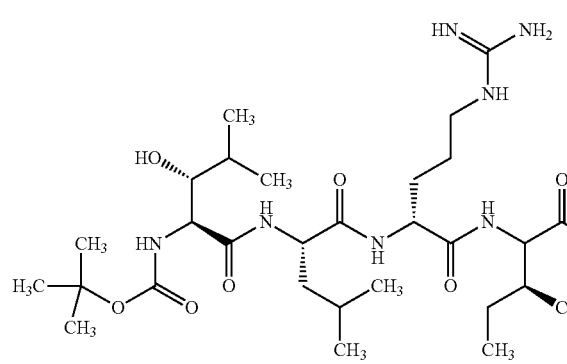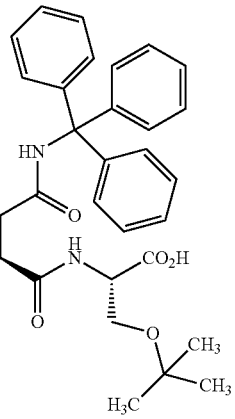

*2 TFA

The benzyl ester-protected compound (example 49A, 62.0 mg, 38.46 µmol) is converted into the product by hydrogenolysis in methanol (20 ml) in 1 h. After chromatography by preparative HPLC (method 26) the target compound (34.3 mg, 61.2% of theory) is obtained.

HPLC (Method 1) $R_t$=2.51 min.

LC-MS (Method 20): $R_t$=2.36 min; MS (ESIpos): m/z (%)=1343 (38) [M+H]⁺, 243 (100); MS (ESIneg.): m/z (%)=1341 (100) [M−H]⁻.

Example 55A

[(3R)-3-Hydroxy-L-leucyl]-L-leucyl-D-arginyl-L-isoleucyl-L-allothreonyl-glycyl-L-asparaginyl-L-serine bistrifluoroacetate Exemplary compound 54A (32.0 mg, 21.95 µmol) is stirred in a solution of TFA (7.3 ml), water (250 µl) and triisopropylsilane (323 µl) at RT for 2 h. For the workup, the solvent is removed on a rotary evaporator at a bath temperature of 30° C., and the residue is concentrated in vacuo once with toluene and once with methylene chloride at a bath temperature of 30° C. After drying under high vacuum, the crude product is dissolved in 0.1% aq. TFA and extracted with MTBE and the separated aq. phase is concentrated in vacuo and subsequently fine purified by preparative HPLC (method 27). 22.5 mg (91.8% of theory) of the title compound are obtained.

HPLC (Method 9) $R_t$=8.38 min.

LC-MS (Method 22): $R_t$=2.30 min; MS (ESIpos): m/z (%)=889 (12) [M+H]⁺, 445 (100) [M+2H]²⁺; MS (ESIneg.): m/z (%)=887 (100) [M−H]⁻.

HR-TOF-MS (Method 24): $C_{37}H_{69}N_{12}O_{13}$ [M+H]⁺ found 889.5102, calc. 889.5102.

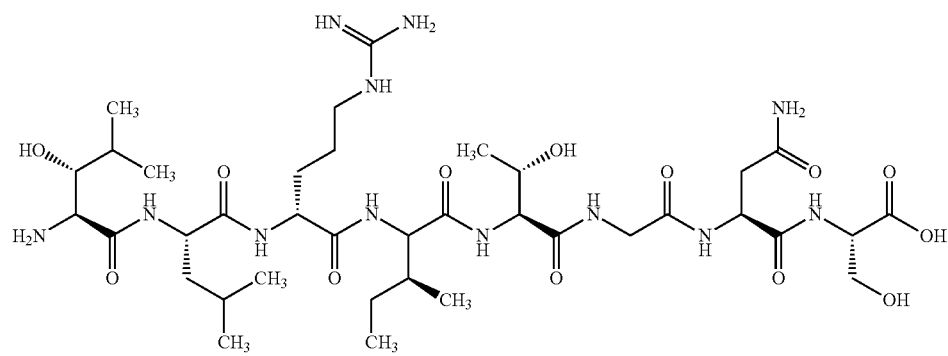

*2 TFA

Example 56A

[N²-(Benzyloxycarbonyl)-3-tert-butyl-D-alanyl]-[3-tert-butyl-L-alanyl]-{(3R)-3-[(tert-butoxycarbonyl)amino]-L-phenylalanyl}-{(3R)-3-hydroxy-L-leucyl}-L-leucyl-D-arginyl-L-isoleucyl-L-allothreonyl-glycyl-L-asparaginyl-L-serine trifluoroacetate

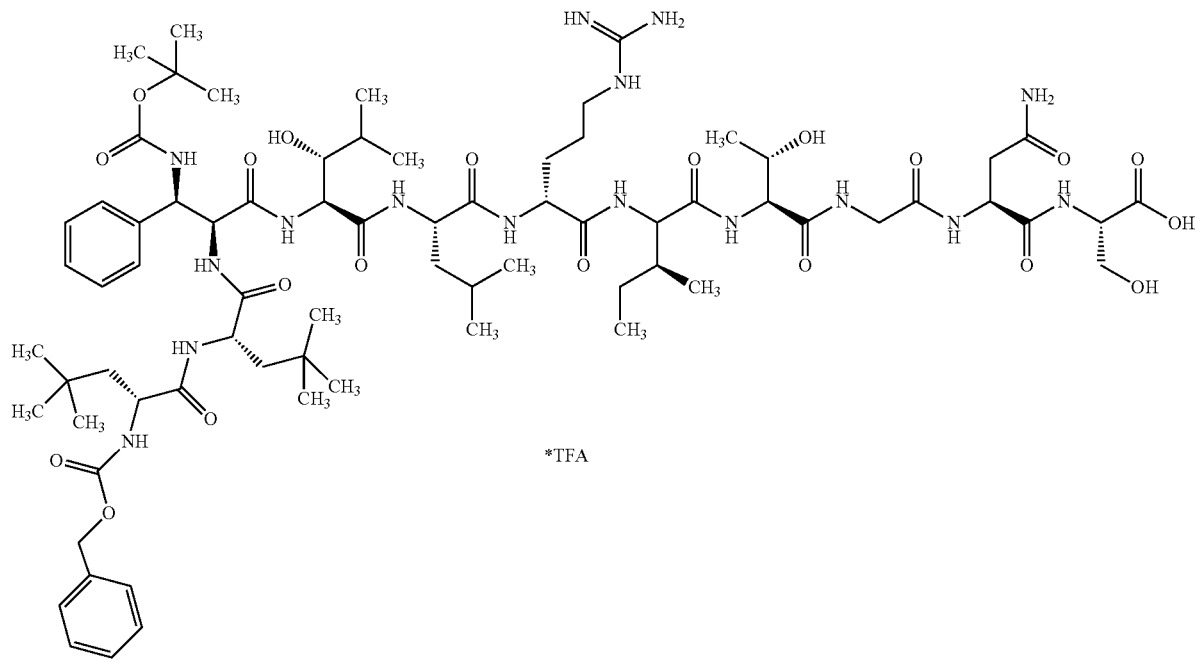

*TFA

Exemplary compound 55A (19.0 mg, 17.00 µmol) and 40A (15.6 mg, 18.70 µmol) are provided in DMF (1 ml), N,N-diisopropylamine (18 µl, 13.2 mg, 102.00 mmol, 6 eq.) is added at 0° C., and the mixture is stirred at this temperature for 2 h. The reaction is warmed to RT and then stirred overnight. For the workup, the solution is concentrated in vacuo and finally fine purified by preparative HPLC (method 26). 24.4 mg (86.7% of theory) of the target compound are obtained.

HPLC (Method 9) $R_t$=23.17 min.

LC-MS (Method 18): $R_t$=2.37 min; MS (ESIpos): m/z (%)=720 (100) $[M-C_4H_8-CO_2+2H]^{2+}$; MS (ESIneg.): m/z (%)=1438 (100) $[M-C_4H_8-CO_2-H]^-$.

HR-TOF-MS (Method 24): $C_{73}H_{119}N_{16}O_{20}$ $[M+H]^+$ found 1539.8772, calc. 1539.8782.

Example 57A

[N²-(Benzyloxycarbonyl)-3-tert-butyl-D-alanyl]-[3-tert-butyl-L-alanyl]-{(3R)-3-amino-L-phenylalanyl}-{(3R)-3-hydroxy-L-leucyl}-L-leucyl-D-arginyl-L-isoleucyl-L-allothreonyl-glycyl-L-asparaginyl-L-serine bistrifluoroacetate

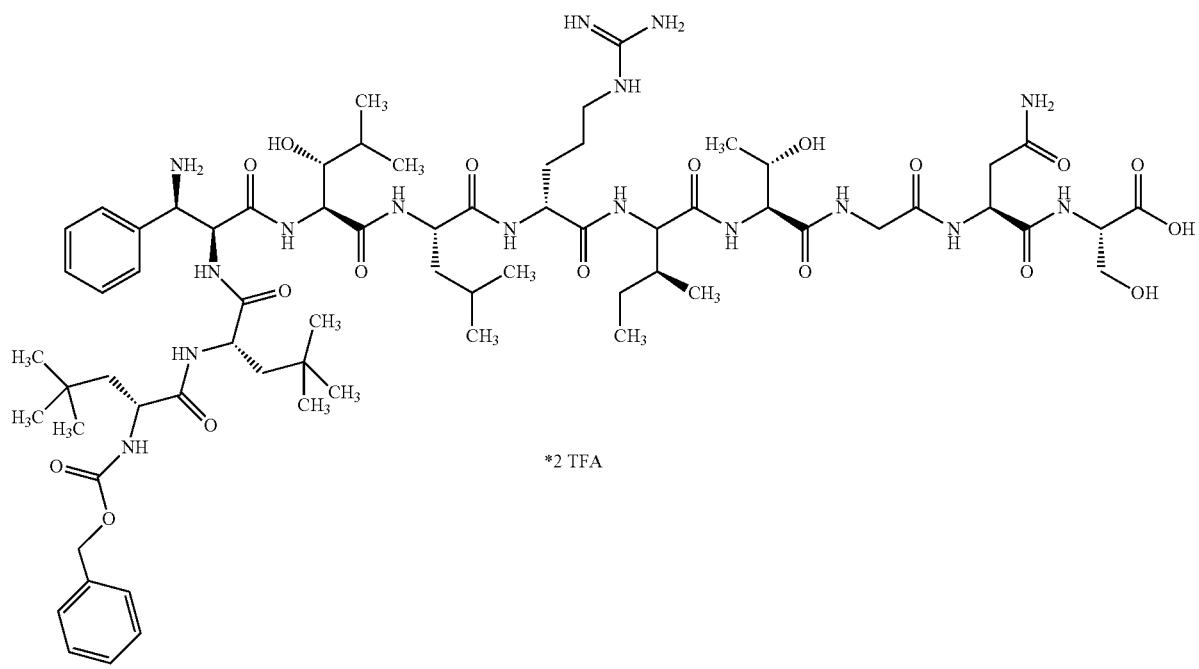

*2 TFA

Exemplary compound 56A (23.0 mg, 13.91 μmol) is converted into the deprotected amine according to procedure 1. After fine purification (method 26) 19.9 mg (85.8% of theory) of the title compound are obtained.

HPLC (Method 9) $R_t$=17.05 min.

LC-MS (Method 18): $R_t$=1.98 min; MS (ESIpos): m/z (%)=1441 (3) [M+H]⁺, 720 (100) [M+2H]²⁺; MS (ESIneg.): m/z (%)=1438 (100) [M−H]⁻.

HR-TOF-MS (Method 24): $C_{68}H_{111}N_{16}O_{18}$ [M+H]⁺ found 1439.8271, calc. 1439.8257.

Example 58A

[$N^2$-(Benzyloxycarbonyl)-3-tert-butyl-D-alanyl]-[3-tert-butyl-L-alanyl]-{(3R)-3-amino-L-phenylalanyl}-{(3R)-3-hydroxy-L-leucyl}-L-leucyl-D-arginyl-L-isoleucyl-L-allothreonyl-glycyl-L-asparaginyl-L-serine $C^{1.11}$-$N^{3.3}$-lactam trifluoroacetate

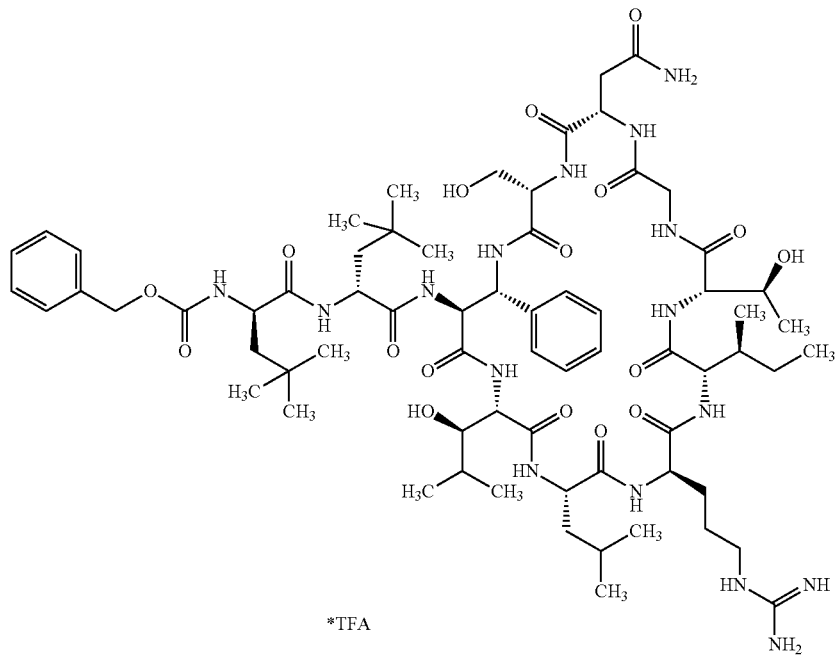

*TFA

Under an argon protective gas atmosphere, the deprotected amine (example 57A, 19.0 mg, 11.39 μmol) is provided in DMF (10 ml), the solution is cooled to 0° C., HATU (13.0 mg, 34.18 μmol, 3 eq.) and NMM (8 μl, 6.9 mg, 68.35 μmol) are added, and the reaction is left to stand at 4° C. for 3 days. For the workup, methanol is added to the mixture at 0° C., and the mixture is concentrated in vacuo at a max. bath temperature of 30° C., and finally fine purified by preparative HPLC (method 26). 14.0 mg (80.0% of theory) of the title compound are obtained.

HPLC (Method 9) $R_t$=22.44 min.

LC-MS (Method 18): $R_t$=2.30 min; MS (ESIpos): m/z (%)=1422 (12) [M+H]$^+$, 711 (100) [M+2H]$^{2+}$; MS (ESIneg.): m/z (%)=1420 (28) [M−H]$^-$, 710 (100) [M−2H]$^{2-}$.

HR-TOF-MS (Method 24): $C_{68}H_{109}N_{16}O_{17}$ [M+H]$^+$ found 1421.8165, calc. 1421.8152.

Example 59A (3R)-3-[(tert-Butyloxycarbonyl)amino]-L-phenylalanine

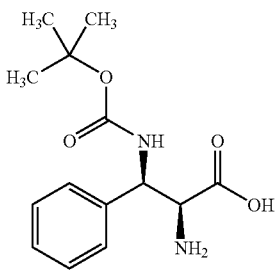

According to procedure 5 the exemplary compound 16A (1000.0 mg, 2.41 mmol) is converted with 10% palladium/carbon (100 mg, 93.98 μmol, 4 mol %) in methanol (100 ml) into the title compound in 1 h. After removing the catalyst by filtration through kieselguhr and concentrating 624.0 mg (92.3%) of crude product are obtained.

HPLC (Method 9) $R_t$=10.27 min.

LC-MS (Method 18): $R_t$=1.52 min; MS (ESIpos.): m/z (%)=281 (82) [M+H]$^+$, 561 (10) [2M+H]$^+$, 225 (100); MS (ESIneg.): m/z (%)=279 (70) [M−H]$^-$, 559 (5) [2M−H]$^-$, 205 (100).

$^1$H NMR (500 MHz, $d_6$-DMSO): δ=1.34 (s, 9H, OC(CH$_3$)$_3$), 3.51 (d, J=4.8 Hz, 1H, H$^\alpha$), 4.88 (dd, J=8.6 Hz, 4.8 Hz, 1H, H$^{\beta)}$, 7.21-7.35 (m, 7H, ArH, NH$_2$), 8.04 (d, J=8.6 Hz, NH).

$^{13}$C NMR (126 MHz, $d_6$-DMSO): δ=28.04 (3C), 53.81, 56.27, 78.06, 127.24, 127.42 (2C), 128.07 (2C), 138.99, 154.12, 167.93.

HR-TOF-MS (Method 24): $C_{14}H_{21}N_2O_4$ [M+H]$^+$ found 281.1506, calc. 281.1496.

Example 60A

Methyl [$N^2$-(benzyloxycarbonyl)-D-leucyl]-L-leucinate

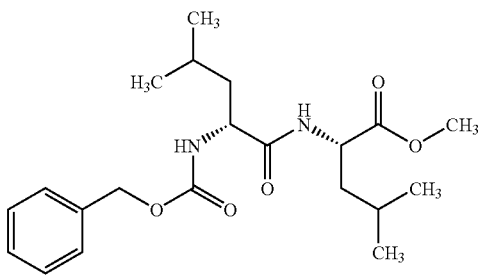

$N^2$-(Benzyloxycarbonyl)-L)-leucine (BACHEM Cat No z13351.) (6.37 g, 24 mmol)) and methyl L-leucinate (3.49 g, 24 mmol, 1 eq.) are dissolved in DMF (75 ml) at 0° C., and NMM (5.28 ml, 48 mmol, 2 eq.) and HATU (13.69 g, 36 mmol, 1.5 eq.) are then added. The mixture is stirred at room temperature for three hours. MTBE and a saturated sodium bicarbonate solution are added, and extraction is carried out. The aqueous phase is back-extracted with a second portion of MTBE, and the combined organic phases are then washed with 1 M citric acid as well as again with a saturated sodium bicarbonate solution, dried over sodium sulfate and concentrated in vacuo. The residue is purified by chromatography in two portions (Biotage 40M, cyclohexane/ethyl acetate 3+1). Yield: 7.85 g (80% of theory).

HPLC (Method 5): $R_t$=4.82 min.

LCMS (Method 18): $R_t$=2.65 min; MS (ESIpos.): m/z (%)=393 (100) [M+H]$^+$.

[α]$^{20}_{Na}$=−5.2° (c=0.52, MeOH).

$^1$H NMR (400 MHz, d$_6$-DMSO) δ (ppm)=0.77-0.92 (m, 12H), 1.31-1.66 (m, 6H), 3.60 (s, 3H), 4.10 (m, 1H), 4.28 (m, 1H), 5.02 (s, 2H), 7.25-7.38 (m, 6H), 8.23 (d, 1H).

$^{13}$C-NMR (126 MHz, d$_6$-DMSO) δ (ppm)=21.1 (CH$_3$), 21.5 (CH$_3$), 22.8 (CH$_3$), 22.9 (CH$_3$), 24.2 (CH), 41.0 (CH$_2$), 50.0 (CH), 51.8 (CH$_3$, OCH$_3$), 52.9 (CH), 65.3 (CH$_2$, OCH$_2$Ph), 127.6 (CH, ar-C), 127.7 (CH, ar-C), 128.3 (CH, ar-C), 137.1 ((C quat, ar-C), 155.8 (C quat, NCOC(CH$_3$)$_3$), 172.4 (C quat, C═O), 172.9 (C quat, C═O).

Example 61A

[$N^2$-(Benzyloxycarbonyl)-D-leucyl]-L-leucine

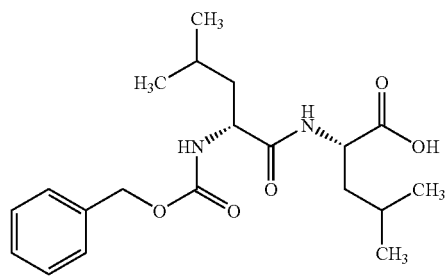

Compound 60A (7.70 g, 19.62 mmol) is taken up in 200 ml of THF/water (3+1), cooled to 0° C. and lithium hydroxide monohydrate (1.65 g, 39.24 mmol, 2 eq.) is added. The mixture is stirred at 0° C. until according to HPLC monitoring the reaction has proceeded to completion (about 45 min). Most of the THF is distilled off in vacuo, the pH is then adjusted to about 4 by adding citric acid, and the mixture is extracted with 2 portions of ethyl acetate. The combined org. phases are dried over sodium sulfate, filtered and concentrated. The product is obtained as an amorphous substance in a yield of 6.87 g (89% of theory).

HPLC (Method 5): $R_t$=4.45 min.

LCMS (Method 18): $R_t$=2.39 min, MS (ESIpos.) m/z (%)=379 (100) [M+H]$^+$, 757 (40) [2M+H]$^+$.

[α]$^{20}_{Na}$=+4.7° (c=0.50, MeOH).

$^1$H NMR (300 MHz, d$_6$-DMSO) δ (ppm)=0.77-0.92 (m, 12H), 1.34-1.68 (m, 6H), 4.04-4.26 (m, 2H), 5.02 (s, 2H), 7.25-7.38 (m, 6H), 8.12 (d, 1H), 12.50 (br. s, 1H).

HR-TOF-MS (Method 24): C$_{20}$H$_{31}$N$_2$O$_5$ [M+H]$^+$ calc. 379.2228, found 379.2216.

Example 62A

Pentafluorophenyl N-[benzyloxycarbonyl]-D-leucyl-L-leucinate

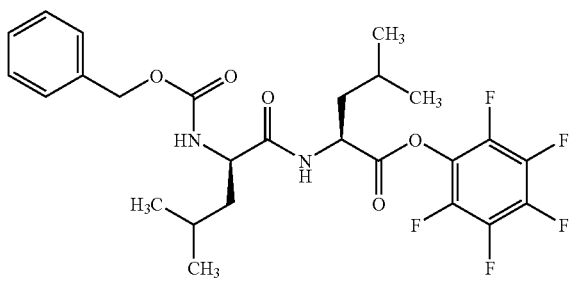

According to the preparation method (example 17A) exemplary compound 61A (1000.0 mg, 2.64 mmol), pentafluorophenol (2431.7 mg, 13.21 mmol, 5 eq.) and EDC (759.8 mg, 3.96 mmol, 1.5 eq.) are converted into the title compound. After fine purification (method 28) 1.3 g (93.0% of theory) of product are obtained which is stored at −25° C. until further use.

HPLC (Method 1) $R_t$=3.08 min.

LC-MS (Method 18): $R_t$=3.26 min; MS (ESIpos.): m/z (%)=545 (100) [M+H]$^+$, 1089 (43) [2M+H]$^+$.

$^1$H NMR (400 MHz, d$_6$-DMSO): δ=0.78-0.99 (m, 12H, 2[CH(CH$_3$)$_2$]), 1.30-1.88 (m, 6H), 4.16 (m, 1H, H$^α$), 4.38-

4.55 (2m, 1H, H^α), 4.95-5.11 (m, 2H, PhCH$_2$), 7.21-7.38 (m, 5H, ArH), 7.41 (d, J=7.4 Hz, 1H, NH), 8.69 (d, J=7.0 Hz, 1H, NH).

Example 63A

{N$^2$-(Benzyloxycarbonyl)-D-leucyl}-L-leucyl-[(3R)-3-[(tert-butoxycarbonyl)amino]-L-phenylalanine]

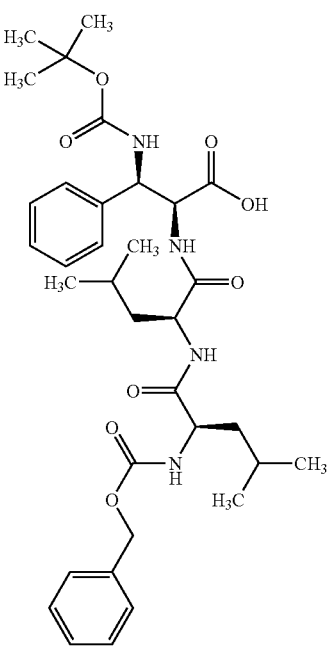

Under an argon protective gas atmosphere, the amino acid (example 59A, 493.0 mg, 1.76 mmol and the carboxylic acid-activated dipeptide (example 62A, 1197.0 mg, 1.76 mmol) are provided in DMF (50 ml), and DIEA (2.4 ml, 1818.4 mg, 14.07 mmol, 8 eq.) is subsequently added to the solution at 0° C. After the addition of the base, the reaction is slowly brought to RT and stirred at this until conversion is complete (3 h). For the workup, potassium dihydrogen phosphate (2.4 g, 17.59 mmol, 10 eq.) is added to the reaction and the mixture is stirred for 10 min, the solid is filtered off, and the filtrate is concentrated in vacuo at a bath temperature of 30° C. 750.0 mg (66.6% of theory) of the title compound are isolated after fine purification (method 28).

HPLC (Method 1) R$_t$=2.72 min.

LC-MS (Method 18): R$_t$=2.86 min; MS (ESIpos.): m/z (%)=641 (100) [M+H]$^+$, 541 (76) [M−C$_4$H$_8$−CO$_2$+H]$^+$, 1281 (42) [2M+H]$^+$; MS (ESIneg.): m/z (%)=639 (100) [M−H]$^-$, 1280 (92) [2M−H]$^-$.

Example 64A

Pentafluorophenyl N-[(benzyloxy)carbonyl]-D-leucyl-L-leucyl-[(3R)-3-[(tert-butoxycarbonyl)amino]-L-phenylalaninate]

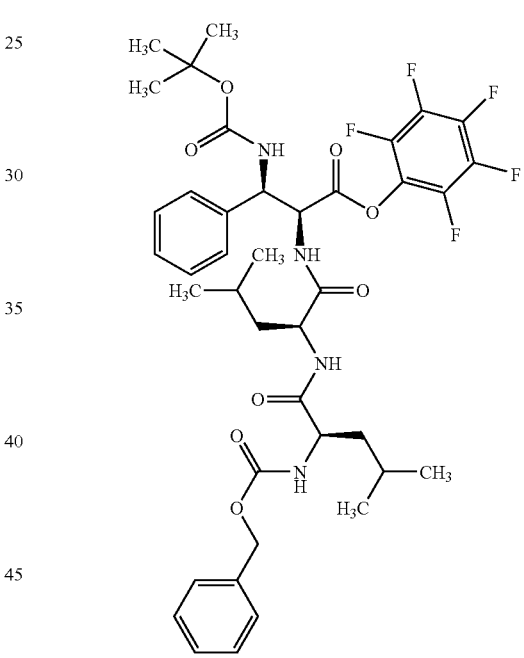

The title compound is prepared according to the example method (example 17A) from the tripeptide (example 63A, 200 mg, 0.31 mmol) and pentafluorophenol (287.3 mg, 1.56 mmol, 5 eq.) in dichloromethane (10 ml) using EDC (89.8 mg, 0.49 mmol, 1.5 eq.). Complete conversion is achieved by stirring the reaction at 0° C. for 2 h and leaving to stand in a refrigerator at 4° C. overnight. After fine purification (method 32) 211.0 mg (83.8% of theory) of product are obtained.

HPLC (Method 1) R$_t$=3.23 min.

LC-MS (Method 21): R$_t$=3.22 min; MS (ESIpos.): m/z (%)=807 (30) [M+H]$^+$, 707 (100) [M−C$_4$H$_8$−CO$_2$+H]$^+$; MS (ESIneg.): m/z (%)=805 (10) [M−H]$^-$, 183 (100).

Example 65A

Chlorotrityl-resin-bound {O³-[tert-butyl]-N²-[(9H-fluoren-9-ylmethoxy)carbonyl]-L-threonyl-glycyl-(N³-trityl-L-asparaginyl)-[O³-(tert-butyl)-L-serine]

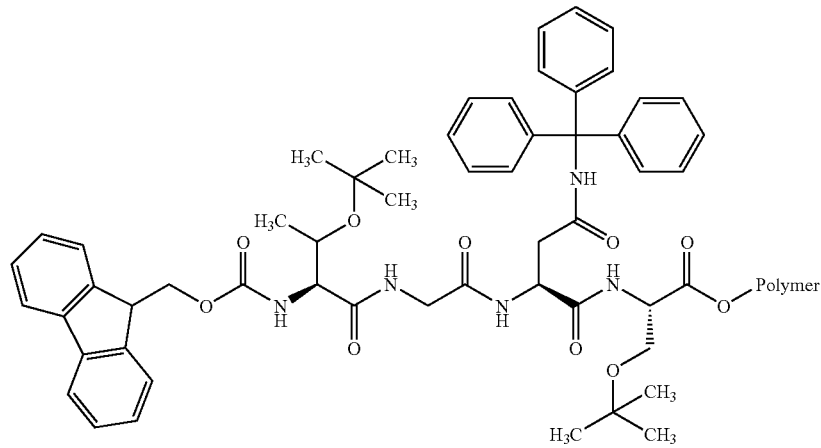

The Fmoc protecting group is removed from the polymer (example 43A, 1000.0 mg, 1.49 mmol) as described in procedure 7. The deprotected tripeptide bound to the resin is subsequently reacted with O-(tert-butyl)-N-[(9H-fluoren-9-ylmethoxy)carbonyl]-L-threonine [Echner, Hartmut; Voelter, Wolfgang; Liebigs Ann. Chem.; GE; 1988; 1095-1098] (1184.5 mg, 2.98 mmol, 2 eq.), DIEA (779 µl, 577.7 mg, 4.47 mmol, 3 eq.) and TBTU (956.6 mg, 2.98 mmol, 2 eq.) overnight to give the F-moc-protected tetrapeptide. The workup of the polymer takes place in analogy to procedure 7. The corresponding side chain-protected peptide is confirmed after a sample removal.

LC-MS (Method 20): $R_t$=3.07 min; MS (ESIpos): m/z (%)=955 (80) [M+H]⁺, 243 (100); MS (ESIneg): m/z (%)=953 (100) [M−H]⁻.

HR-TOF-MS (Method 24): $C_{55}H_{64}N_5O_{10}$ [M+H]⁺ found 954.4636, calc. 954.4648.

Example 66A

Chlorotrityl-resin-bound {N²-[(9H-fluoren-9-ylmethoxy)carbonyl]-L-isoleucyl}-{[O³-(tert-butyl)]-L-threonyl}-glycyl-(N³-trityl-L-asparaginyl)-[O³-(tert-butyl)-L-serine]

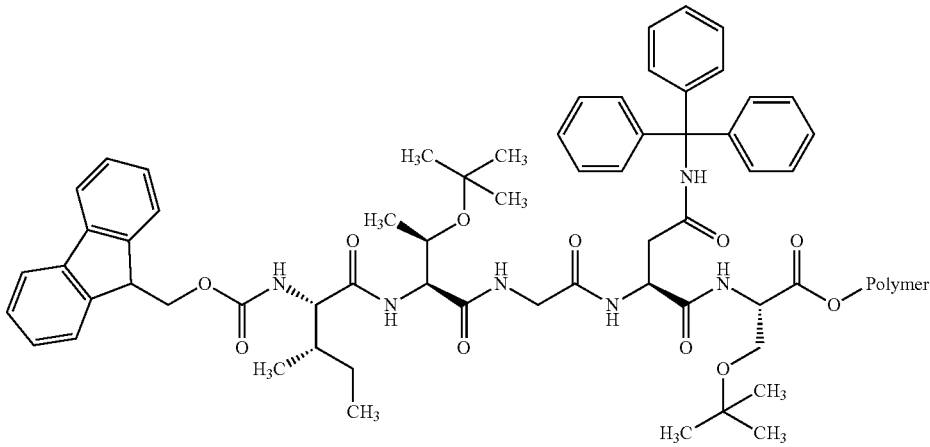

The Fmoc protecting group is removed from the polymer (example 65A, 1000.0 mg, 1.49 mmol) as described in procedure 7. The deprotected tetrapeptide bound to the resin is subsequently reacted with N-[(9H-fluoren-9-ylmethoxy)carbonyl]-L-isoleucine (1053.2 mg, 2.98 mmol, 2 eq.) (H. Echner et al., Liebigs Ann. Chem. 1988, 1095-1098), DIEA (779 µl, 577.7 mg, 4.47 mmol, 3 eq.) and TBTU (956.6 mg, 2.98 mmol, 2 eq.) overnight to give the F-moc-protected pentapeptide. The workup of the polymer takes place in analogy to procedure 7. The corresponding side chain-protected peptide is confirmed after a sample removal.

HPLC (Method 13) $R_t$=2.61 min.

LC-MS (Method 21): $R_t$=3.26 min; MS (ESIpos): m/z (%)=1068 (15) [M+H]$^+$, 243 (100); MS (ESIneg): m/z (%)=1066 (100) [M–H]$^-$.

HR-TOF-MS (Method 24): $C_{61}H_{75}N_6O_{11}$ [M+H]$^+$ found 1067.5503, calc. 1067.5489.

Example 67A

Chlorotrityl-resin-bound {$N^2$-[(9H-fluoren-9-yl-methoxy)carbonyl]-[$N^5$-(imino-{[(2,2,5,7,8-pentamethyl-3,4-dihydro-2H-chromen-6-yl) sulfonyl]amino}methyl)-D-ornithyl]}-L-isoleucyl-[$O^3$-(tert-butyl)-L-threonyl]-glycyl-($N^3$-trityl-L-asparaginyl)-[$O^3$-(tert-butyl)-L-serine]

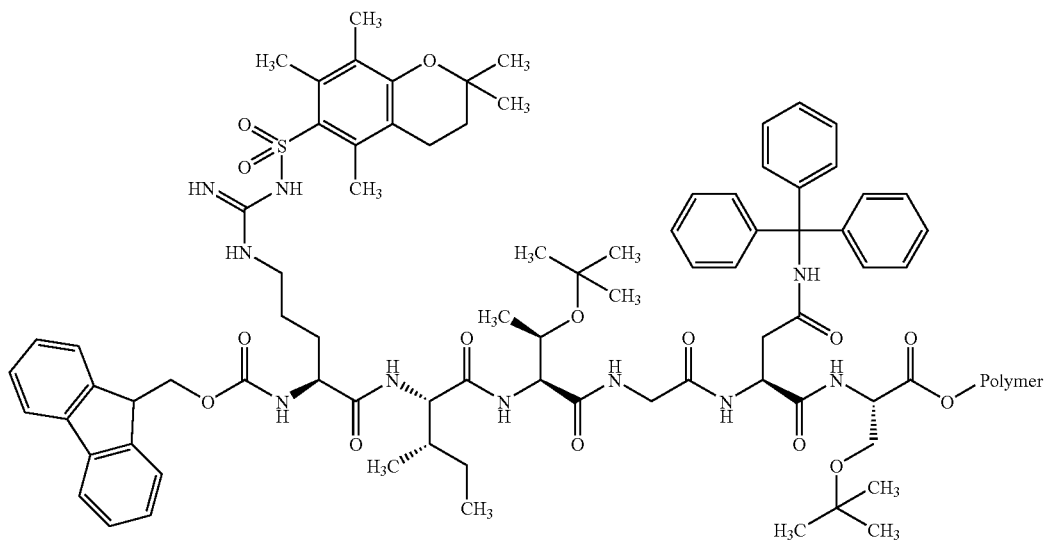

The Fmoc protecting group is removed from the polymer (example 66A, 1000.0 mg, 1.49 mmol) as described in procedure 7. The deprotected pentapeptide bound to the resin is subsequently reacted with $N^2$-[(9H-fluoren-9-ylmethoxy)carbonyl]-$N^5$-(imino{[(2,2,5,7,8-pentamethyl-3,4-dihydro-2H-chromen-6-yl) sulfonyl]amino}methyl)-L-ornithine (1283.9 mg, 1.94 mmol, 1.3 eq.), DIEA (779 µl, 577.7 mg, 4.47 mmol, 3 eq.) and TBTU (956.6 mg, 2.98 mmol, 2 eq.) overnight to give the Fmoc-protected hexapeptide. The workup of the polymer takes place in analogy to procedure 7. The corresponding side chain-protected peptide is confirmed after a sample removal.

LC-MS (Method 20): $R_t$=3.24 min; MS (ESIpos): m/z (%)=1490 (85) [M+H]$^+$, 282 (100); MS (ESIpos): m/z (%)=1488 (100) [M+H]$^+$.

HR-TOF-MS (Method 24): $C_{81}H_{105}N_{10}O_{15}S$ [M+H]$^+$ found 1489.7456, calc. 1489.7477.

Example 68A

Chlorotrityl-resin-bound {N²-[(9H-Fluoren-9-yl-methoxy)carbonyl]-L-leucyl}-[N-5-(imino{[(2,2,5,7,8-pentamethyl-3,4-dihydro-2H-chromen-6-yl)sulfonyl]amino}methyl)-D-ornithyl]-L-isoleucyl-[O³-(tert-butyl)-L-threonyl]-glycyl-(N³-trityl-L-asparaginyl)-[O³-(tert-butyl)-L-serine]

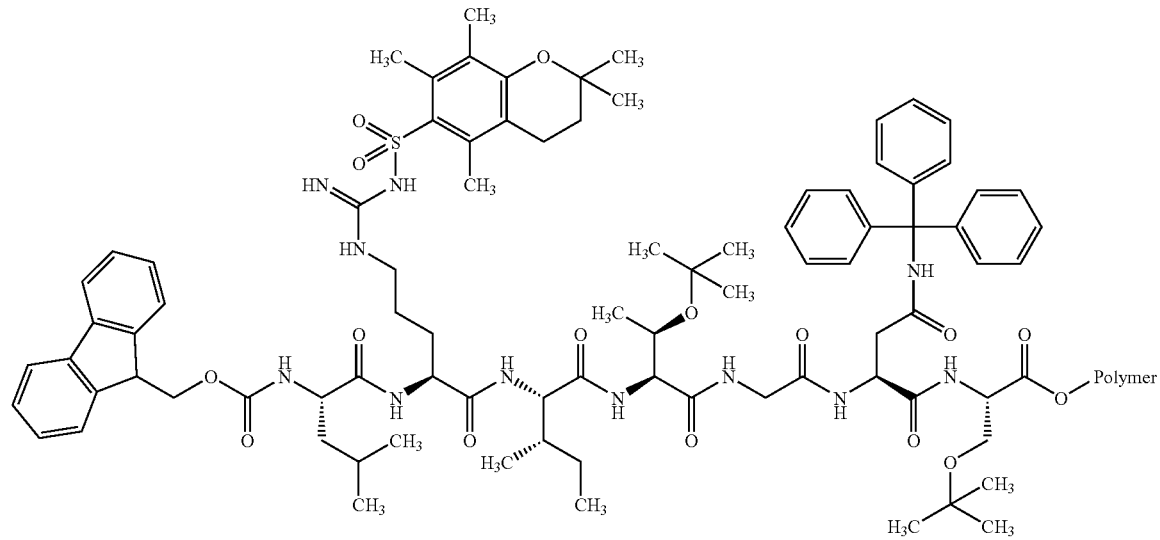

The Fmoc protecting group is removed from the polymer (example 67A, 1000.0 mg, 1.49 mmol) as described in procedure 7. The deprotected hexapeptide bound to the resin is subsequently reacted with N-[(9H-fluoren-9-ylmethoxy)carbonyl]-L-leucine (1053.2 mg, 2.98 mmol, 2 eq.), DIEA (779 µl, 577.7 mg, 4.47 mmol, 3 eq.) and TBTU (956.6 mg, 2.98 mmol, 2 eq.) overnight to give the F-moc-protected heptapeptide. The workup of the polymer takes place in analogy to procedure 7. The corresponding side chain-protected peptide is confirmed after a sample removal.

LC-MS (Method 18): $R_t$=3.54 min; MS (ESIpos): m/z (%)=1602 (100) [M+H]⁺; MS (ESIpos): m/z (%)=1600 (100) [M−H]⁻.

Example 69A

[(3R)-N²-(tert-Butoxycarbonyl)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-[O³-(tert-butyl)-L-threonyl]-glycyl-(N³-trityl-L-asparaginyl)-[O³-(tert-butyl)-L-serine]

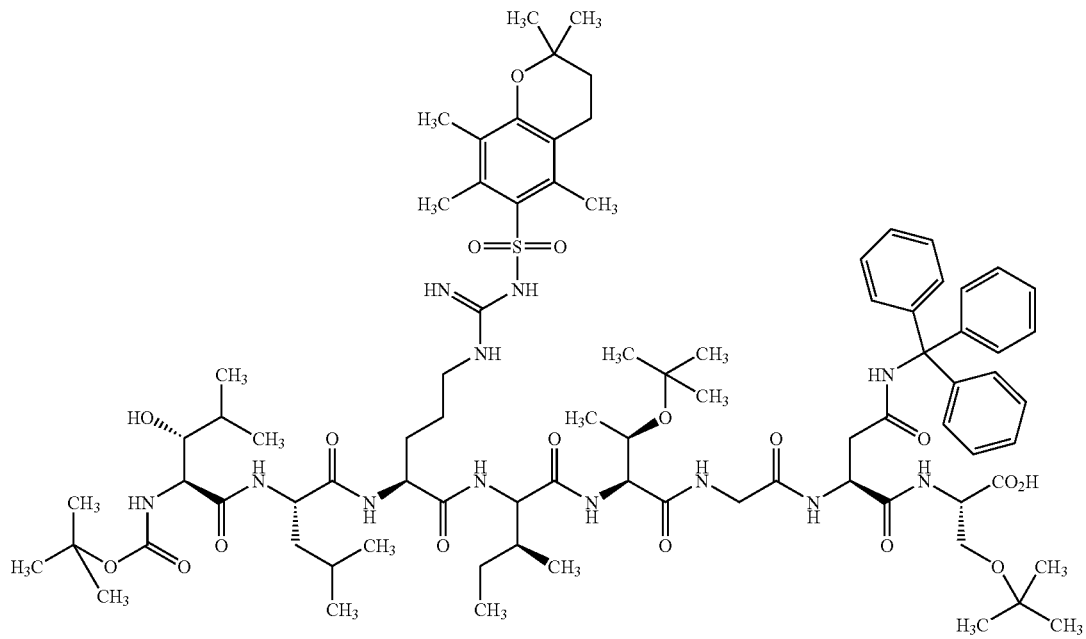

The Fmoc protecting group is removed from the polymer (example 68A, 1000.0 mg, 1.49 mmol) as described in procedure 7. The deprotected heptapeptide bound to the resin is subsequently reacted with (3R)-3-hydroxy-N-(tert-butoxycarbonyl)-L-leucine (552.7 mg, 2.24 mmol, 1.5 eq.), DIEA (597 µl, 442.9 mg, 3.43 mmol, 2.3 eq.) and TBTU (717.6 mg, 2.24 mmol, 1.5 eq.) overnight to give the Fmoc-protected octapeptide. The workup of the polymer takes place in analogy to procedure 7.

The octapeptide bound to the resin is completely removed from the polymer in a solution of acetic acid, trifluoroethanol and dichloromethane (1:1:3). For the workup, the resin is filtered through a frit, and the filtrate is concentrated in vacuo and finally purified by chromatography (method 28). 418.0 mg (17.4% of theory) of the title compound are obtained.

HPLC (Method 13) $R_t$=2.85 min.
HPLC (Method 1) $R_t$=3.32 min.
LC-MS (Method 18): $R_t$=3.39 min; MS (ESIpos.): m/z (%)=1610 (40) [M+H]$^+$, 806 (100) [M+2H]$^{2+}$; MS (ESIneg.): m/z (%)=1608 (100) [M−H]$^−$.
HR-TOF-MS (Method 24): $C_{83}H_{125}N_{12}O_{18}S$ [M+H]$^+$ found 1609.8971, calc. 1609.8951.

Example 70A

[(3R)-3-Hydroxy-L-leucyl]-L-leucyl-D-arginyl-L-isoleucyl-L-threonyl-glycyl-L-asparaginyl-L-serine bistrifluoroacetate

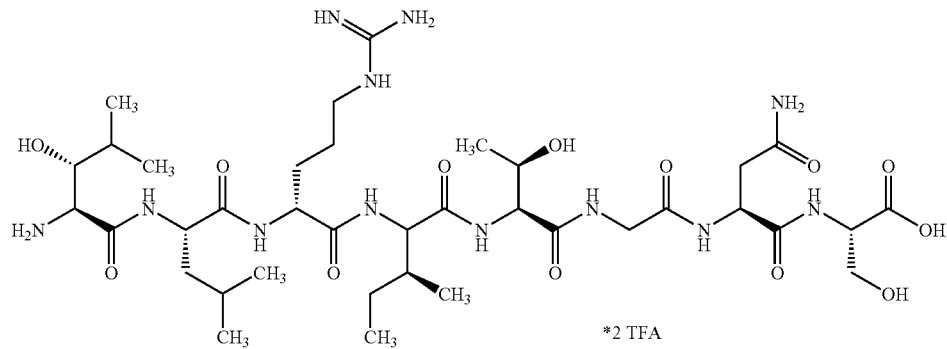

Under an argon protective gas atmosphere, exemplary compound 69A (200.0 mg, 0.12 mmol) is stirred in a solution of TFA (25.3 ml), water (667 µl) and triisopropylsilane (667 µl) at RT for 1 h. For the workup, the solvent is removed on a rotary evaporator at a bath temperature of 30° C., and the residue is concentrated in vacuo once with toluene and once with methylene chloride at a bath temperature of 30° C. The residue is dissolved in 0.1% aq. TFA and extracted once with MTBE, and the separated aq. phase is concentrated in vacuo and subsequently fine purified by preparative HPLC (method 26). 138.0 mg (99.5% of theory) of the title compound are obtained.

HPLC (Method 9) $R_t$=8.60 min.
LC-MS (Method 22): $R_t$=2.43 min; MS (ESIpos): m/z (%)=889 (15) [M+H]$^+$, 445 (100) [M+2H]$^{2+}$; MS (ESIneg.): m/z (%)=887 (100) [M−H]$^−$.

Example 71A

[N²-(Benzyloxycarbonyl)-D-leucyl]-L-leucyl-[(3R)-
N³-(tert-butoxycarbonyl)-3-amino-L-phenylalanyl]-
{(3R)-3-hydroxy-L-leucyl}-L-leucyl-D-arginyl-L-
isoleucyl-L-threonyl-glycyl-L-asparaginyl-L-serine
trifluoroacetate

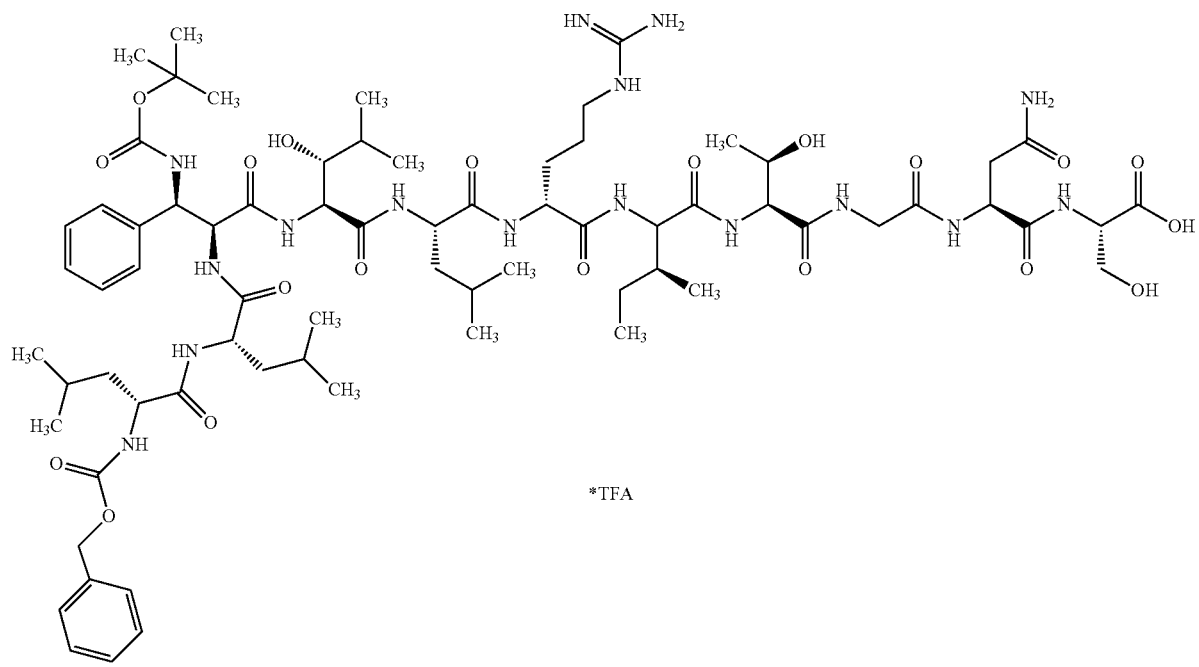

*TFA

The title compound is prepared from the octapeptide (example 70A, 70.0 mg, 62.66 μmol), the carboxylic acid-activated tripeptide (example 64A, 60.7 mg, 75.19 μmol, 1.2 eq.) using N,N-diisopropylamine (65 μl, 48.6 mg, 375.96 μmol, 6 eq.) as indicated in the preparation method for exemplary compound 56A. The reaction is brought to almost complete conversion at RT overnight. After chromatography (method 26) 73.9 mg (72.5% of theory) of product are obtained.

HPLC (Method 9) $R_t$=22.16 min.

LC-MS (Method 20): $R_t$=2.07 min; MS (ESIpos): m/z (%)=1512 (25) [M+H]⁺, 706 (100) [M+2H]²⁺; MS (ESIneg.): m/z (%)=1510 (18) [M−H]⁻, 700 (100).

HR-TOF-MS (Method 24): $C_{71}H_{115}N_{16}O_{20}$ [M+H]⁺ found 1511.8474, calc. 1511.8469.

Example 72A

[N²-(Benzyloxycarbonyl)-D-leucyl]-L-leucyl-[(3R)-3-amino-L-phenylalanyl]-[(3R)-3-hydroxy-L-leucyl]-L-leucyl-D-arginyl-L-isoleucyl-L-threonyl-glycyl-L-asparaginyl-L-serine bistrifluoroacetate

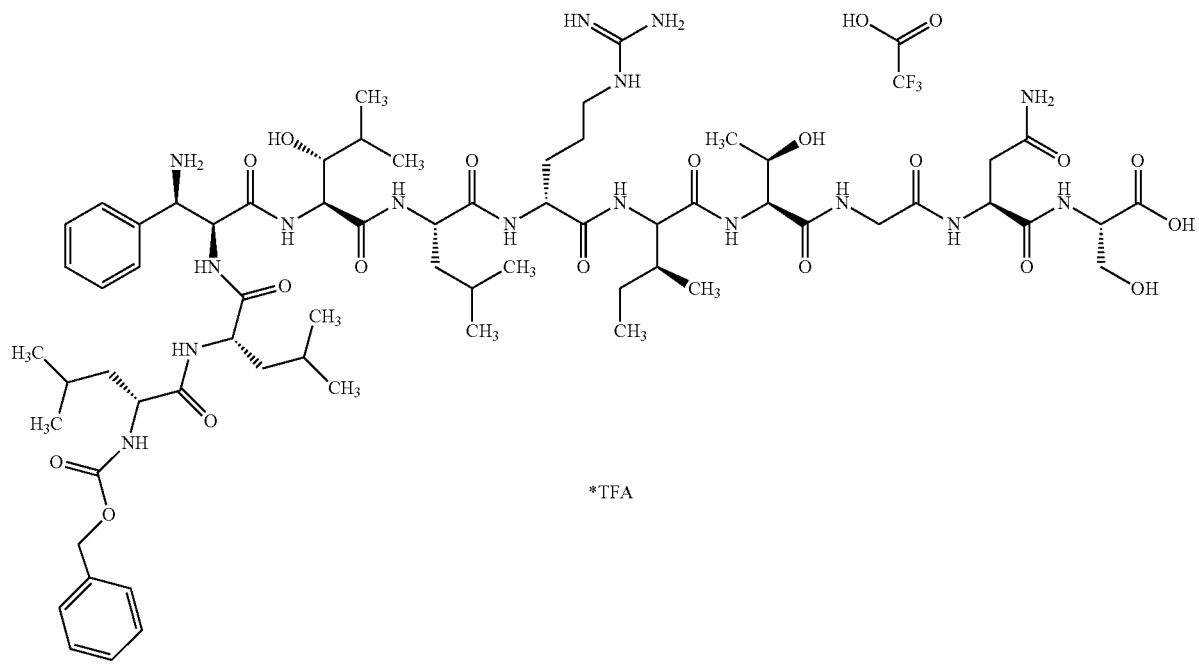

*TFA

Exemplary compound 71A (70.0 mg, 43.06 μmol) is converted into the deprotected amine according to procedure 1. After fine purification (method 26) 45.0 mg (63.7% of theory) of the title compound are obtained.

HPLC (Method 9) R$_t$=16.77 min.

LC-MS (Method 18): R$_t$=1.85 min; MS (ESIpos): m/z (%)=1412 (10) [M+H]$^+$, 706 (100) [M+2H]$^{2+}$; MS (ESIneg.): m/z (%)=1410 (90) [M–H]$^-$, 650 (100).

HR-TOF-MS (Method 24): C$_{66}$H$_{107}$N$_{16}$O$_{18}$ [M+H]$^+$ found 1411.7958, calc. 1411.7944.

Example 73A

[N²-(Benzyloxycarbonyl)-D-leucyl]-L-leucyl-[(3R)-3-amino-L-phenylalanyl]-[(3R)-3-hydroxy-L-leucyl]-L-leucyl-D-arginyl-L-isoleucyl-L-threonyl-glycyl-L-asparaginyl-L-serine C N$^{3,3}$-lactam trifluoroacetate The title compound is prepared according to the preparation method (example 58A) from exemplary compound 73A (42.0 mg, 25.61 µmol), HATU (29.2 mg, 76.83 µmol, 3 eq.) and NMM (17 µl, 15.5 mg, 153.66 µmol). Complete conversion is achieved by stirring at RT in 3 h. 34.1 mg (88.3% of theory) of product are isolated after fine purification (method 26).

HPLC (Method 9) $R_t$=20.29 min.

LC-MS (Method 18): $R_t$=2.06 min; MS (ESIpos): m/z (%)=1393 (32) [M+H]$^+$, 797 (100) [M+2H]$^{2+}$; MS (ESIneg.): m/z (%)=1391 (100) [M−H]$^-$, 695 (32) [M−2H]$^{2-}$.

HR-TOF-MS (Method 24): $C_{66}H_{105}N_{16}O_{17}$ [M+H]$^+$ found 1393.7848, calc. 1393.7839.

1999; 1787-1796] is provided in dichloromethane (190 ml), DIEA (2.4 ml, 1.8 g, 17.27 mmol, 1 eq.) and chlorotrimethylsilane (3.6 ml, 3.1 g, 28.53 mmol, 2 eq.) are added, and the mixture is stirred under reflux overnight. The reaction is cooled (0° C.) and DIEA (4.7 ml, 3.7 g, 28.54 mmol, 2 eq.) again and (9-fluorenylmethyl) chloroformate (3.7 g, 14.27 mmol, 1 eq.) are added, and the mixture is warmed to RT and stirred at this temperature overnight. For the workup, the reaction is diluted with dichloromethane and washed with a 10% aq. citric acid solution, the organic phase is dried over sodium sulfate, the solvent is removed on a rotary evaporator and the mixture is dried in vacuo. 6.5 g (93.2% of theory) of the title compound are obtained.

LC-MS (Method 18): $R_t$=2.57 min; MS (ESIpos): m/z (%)=489 (100) [M+H]$^+$, 977 (100) [2M+H]$^+$; MS (ESIneg.): m/z (%)=487 (80) [M−H]$^-$, 975 (100) [2M−H]$^-$.

Example 75A

Chlorotrityl-resin-bound {$N^5$-[benzyloxycarbonyl]-$N^2$-[(9H-fluoren-9-ylmethoxy)-carbonyl]-D-ornithyl}-L-isoleucyl-[$O^3$-(tert-butyl)-L-allothreonyl]-glycyl-($N^4$-trityl-L-asparaginyl)-[$O^3$-(tert-butyl)-L-serine]

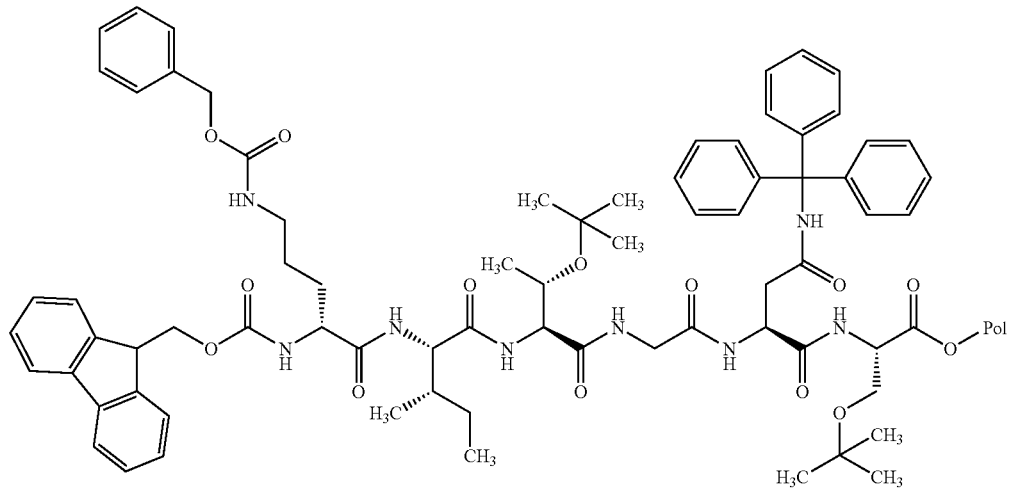

Example 74A $N^5$-[Benzyloxycarbonyl]-$N^2$-[(9H-fluoren-9-yl-methoxy)carbonyl]-D-ornithine

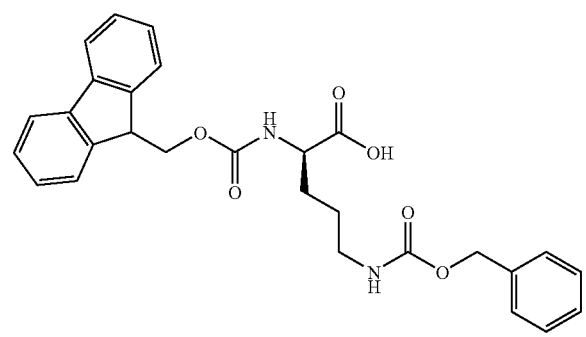

$N^5$-[(Benzyloxy)carbonyl]-D-ornithine (3.8 g, 14.27 mmol) [Ulhaq, Saraj et al.; Bioorg. Med. Chem.; EN; 7; 9;

The Fmoc protecting group is removed from the polymer (example 45A, 1000.0 mg, 1.49 mmol), as described in procedure 7. The deprotected pentapeptide bound to the resin is subsequently reacted with the Fmoc-protected amino acid (example 74A, 1455.9 mg, 2.98 mmol, 2 eq.), DIEA (779 µl, 577.7 mg, 4.47 mmol, 3 eq.) and TBTU (956.8 mg, 2.98 mmol, 2 eq.) overnight to give the F-moc-protected hexapeptide. The workup of the polymer takes place in analogy to procedure 7. The corresponding side chain-protected peptide is confirmed after a sample removal.

HPLC (Method 13) $R_t$=2.73 min.

LC-MS (Method 18): $R_t$=3.27 min; MS (ESIpos): m/z (%)=1316 (100) [M+H]$^+$; MS (ESIneg): m/z (%)=1314 (100) [M+H]$^+$.

Example 76A

Chlorotrityl-Resin-Bound Bound {$N^2$-[(9H-fluoren-9-ylmethoxy)carbonyl]-L-leucyl}-{$N^5$-[(benzyloxy)carbonyl]-D-ornithyl}-L-isoleucyl-[$O^3$-(tert-butyl)-L-allothreonyl]-glycyl-($N^4$-trityl-L-asparaginyl)-[$O^3$-(tert-butyl)-L-serine]

HPLC (Method 13) $R_t$=2.84 min.

LC-MS (Method 18): $R_t$=3.36 min; MS (ESIpos): m/z (%)=1429 (95) [M+H]$^+$, 1430 (100); MS (ESIpos): m/z (%)=1427 (80) [M–H]$^-$, 1428 (100).

HR-TOF-MS (Method 24): $C_{61}H_{75}N_6O_{11}$ [M+H]$^+$ found 1067.5488, calc. 1067.5489.

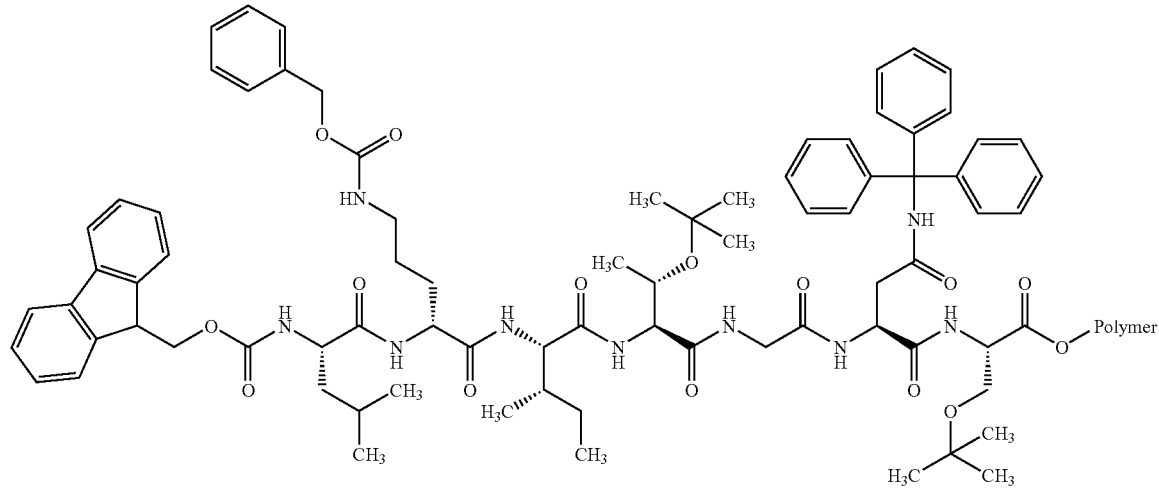

The Fmoc protecting group is removed from the polymer (example 75A, 1000.0 mg, 1.49 mmol) as described in procedure 7. The deprotected hexapeptide bound to the resin is subsequently reacted with N-[(9H-fluoren-9-ylmethoxy)carbonyl]-L-leucine (1053.2 mg, 2.98 mmol, 2 eq.), DIEA (779 µl, 577.7 mg, 4.47 mmol, 3 eq.) and TBTU (956.8 mg, 2.98 mmol, 2 eq.) overnight to give the F-moc-protected heptapeptide. The workup of the polymer takes place in analogy to procedure 7. The corresponding side chain-protected peptide is confirmed after a sample removal.

Example 77A

[(3R)-$N^2$-(tert-Butoxycarbonyl)-3-hydroxy-L-leucyl]-L-leucyl-[$N^5$-(benzyloxycarbonyl)-D-ornithyl]-L-isoleucyl-[$O^3$-(tert-butyl)-L-allothreonyl]-glycyl-[$N^4$-trityl-L-asparaginyl]-[$O^3$-(tert-butyl)-L-serine]

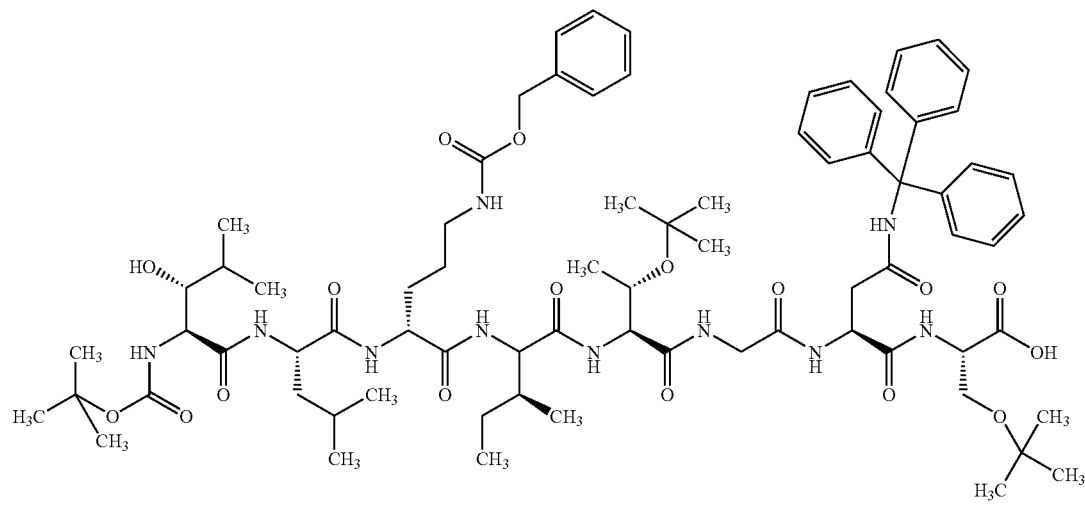

The Fmoc protecting group is removed from the polymer (example 76A, 1000.0 mg, 1.49 mmol) as described in procedure 7. The deprotected heptapeptide bound to the resin is then reacted with (3R)-3-hydroxy-N-(tert-butoxycarbonyl)-L-leucine [Oliyai, Reza, Siahaan, Teruna J., Stella, Valentino J.; Pharm. Res.; EN; 12; 3; 1995; 323-328] (552.7 mg, 2.24 mmol, 1.5 eq.), DIEA (597 µl, 442.9 mg, 3.43 mmol, 2.3 eq.) and TBTU (717.6 mg, 2.24 mmol, 1.5 eq.) overnight to give the Fmoc-protected octapeptide. The workup of the polymer takes place in analogy to procedure 7.

The octapeptide bound to the resin is completely removed from the polymer in a solution of acetic acid, trifluoroethanol and dichloromethane (1:1:3). For the workup, the resin is filtered through a frit, and the filtrate is concentrated in vacuo and finally purified by chromatography (method 28). 604.0 mg (28.3% of theory) of the title compound are obtained.

HPLC (Method 13) $R_t$=2.68 min.
HPLC (Method 1) $R_t$=3.15 min.
LC-MS (Method 18): $R_t$=3.26 min; MS (ESIpos.): m/z (%)=1437 (100) $[M+H]^+$; MS (ESIneg.): m/z (%)=1435 (100) $[M-H]^-$.

Example 78A

[(3R)-3-Hydroxy-L-leucyl]-L-leucyl-[$N^5$-(benzyloxycarbonyl)-D-ornithyl]-L-isoleucyl-L-allothreonyl-glycyl-L-asparaginyl-L-serine Trifluoroacetate

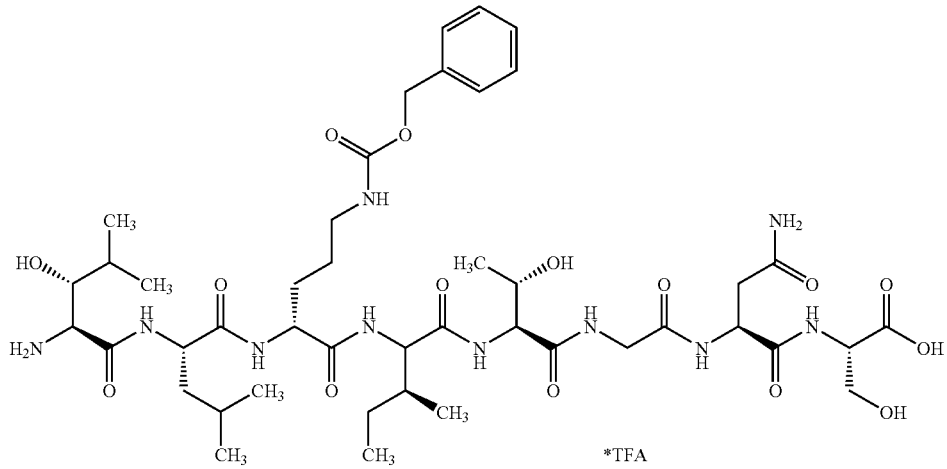

The title compound is prepared from exemplary compound 77A (200.0 mg, 0.14 mmol), as described in the exemplary method (example 70A). After complete conversion at RT (1 h), the solution is concentrated in vacuo at a bath temperature of 30° C., concentrated once with toluene and once with methylene chloride in vacuo at a bath temperature of 30° C., and finally fine purified by preparative RP-HPLC (method 26). 121.0 mg (79.3% of theory) of product are obtained.

HPLC (Method 9) $R_t$=13.26 min.
LC-MS (Method 22): $R_t$=3.04 min; MS (ESIpos): m/z (%)=981 (100) $[M+H]^+$, 491 (10) $[M+2H]^{2+}$; MS (ESIneg.): m/z (%)=979 (100) $[M-H]^-$.

Example 79A

[N²-(Benzyloxycarbonyl)-3-tert-butyl-D-alanyl]-[3-tert-butyl-L-alanyl]-{(3R)-N³-(tert-butoxycarbonyl)-3-amino-L-phenylalanyl}-{(3R)-3-hydroxy-L-leucyl}-L-leucyl-[N5-benzyloxycarbonyl-D-ornityl]-L-isoleucyl-L-allothreonyl-glycyl-L-asparaginyl-L-serine

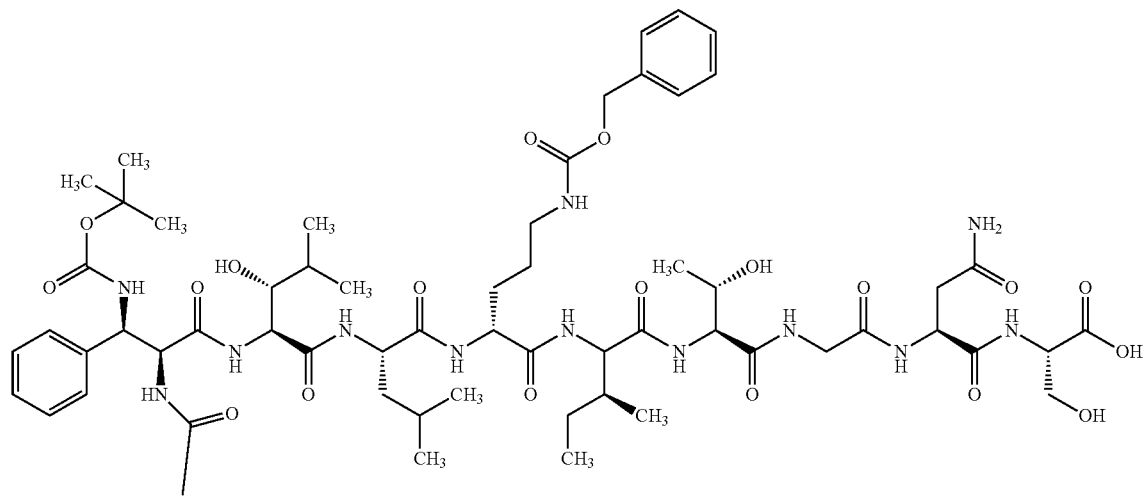

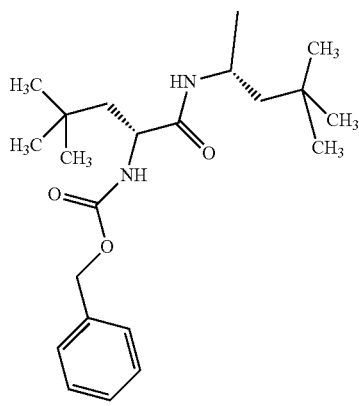

The title compound is prepared from the octapeptide (example 78A, 59.6 mg, 54.44 μmol), the carboxylic acid-activated tripeptide (example 40A, 50.0 mg, 59.89 μmol, 1.1 eq.) and using N,N-diisopropylamine (57 μl, 42.2 mg, 326.7 μmol, 6 eq.) as described in the exemplary method 56A). The reaction is brought to complete conversion at RT overnight. After fine purification (method 26) 52.9 mg (59.5% of theory) of product are obtained.

HPLC (Method 10) $R_t$=10.32 min.

LC-MS (Method 18): $R_t$=3.07 min; MS (ESIpos): m/z (%)=1633 (40) [M+H]⁺, 817 (90) [M+2H]²⁺, 767 (100); MS (ESIneg.): m/z (%)=1631 (65) [M−H]⁻, 761 (100).

HR-TOF-MS (Method 24): $C_{80}H_{123}N_{14}O_{22}$ [M+H]⁺ found 1631.8898, calc. 1631.8931.

Example 80A

[N²-(Benzyloxycarbonyl)-3-tert-butyl-D-alanyl]-[3-tert-butyl-L-alanyl]-{(3R)-3-amino-L-phenylalanyl}-{(3R)-3-hydroxy-L-leucyl}-L-leucyl-[N⁵-(benzyloxycarbonyl)-D-ornityl]-L-isoleucyl-L-allothreonyl-glycyl-L-asparaginyl-L-serine trifluoroacetate

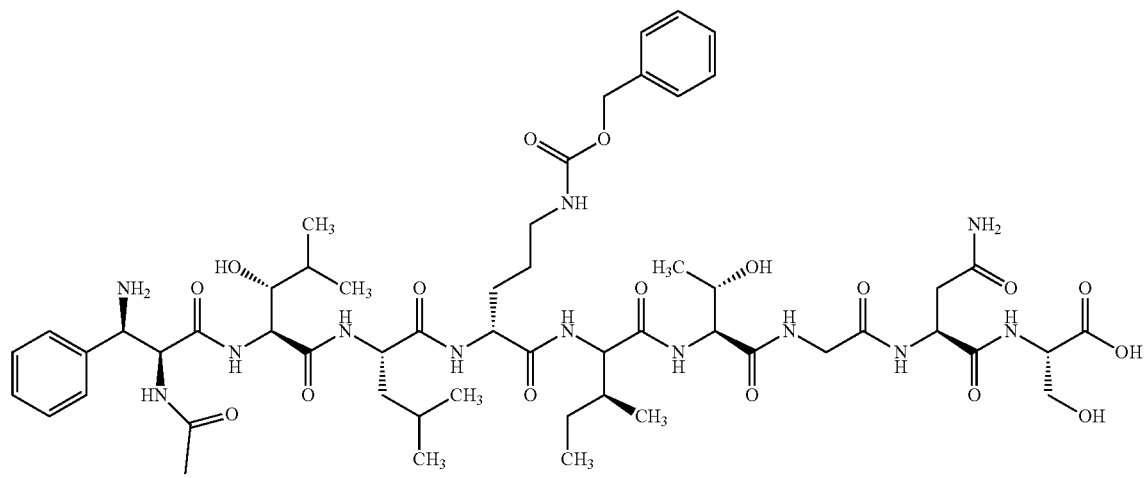

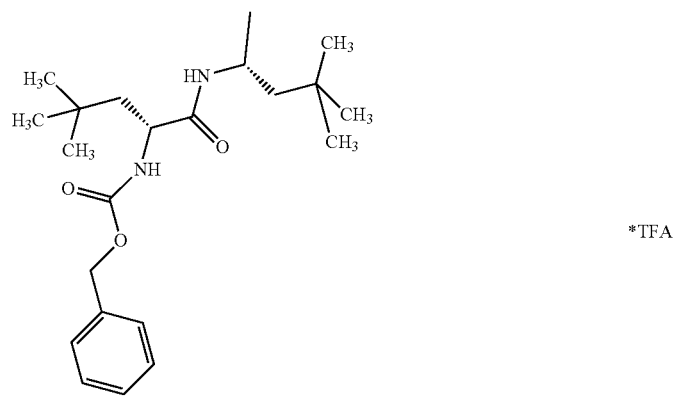

*TFA

Exemplary compound 79A (50.0 mg, 30.64 μmol) is converted into the deprotected amine according to procedure 1. After fine purification (method 26) 27.5 mg (54.5% of theory) of the title compound are obtained.

HPLC (Method 9) $R_t$=21.85 min.

LC-MS (Method 20): $R_t$=2.18 min; MS (ESIpos): m/z (%)=1533 (20) [M+H]⁺, 766 (100) [M+2H]²⁺; MS (ESIneg.): m/z (%)=1531 (58) [M−H]⁻, 764 (12) [M−2H]²⁻, 710 (100).

HR-TOF-MS (Method 24): $C_{75}H_{114}N_{14}O_{20}$ [M+H]⁺ found 1531.8385, calc. 1531.8407.

Example 81A

[N²-(Benzyloxycarbonyl)-3-tert-butyl-D-alanyl]-[3-tert-butyl-L-alanyl]-{(3R)-3-amino-L-phenylalanyl}-[(3R)-3-hydroxy-L-leucyl]-L-leucyl-[N⁵-(benzyloxycarbonyl)-D-ornityl]-L-iso-leucyl-L-allothreonyl-glycyl-L-asparaginyl-L-serine $C^{1.11}$-$N^{3.3}$-lactam

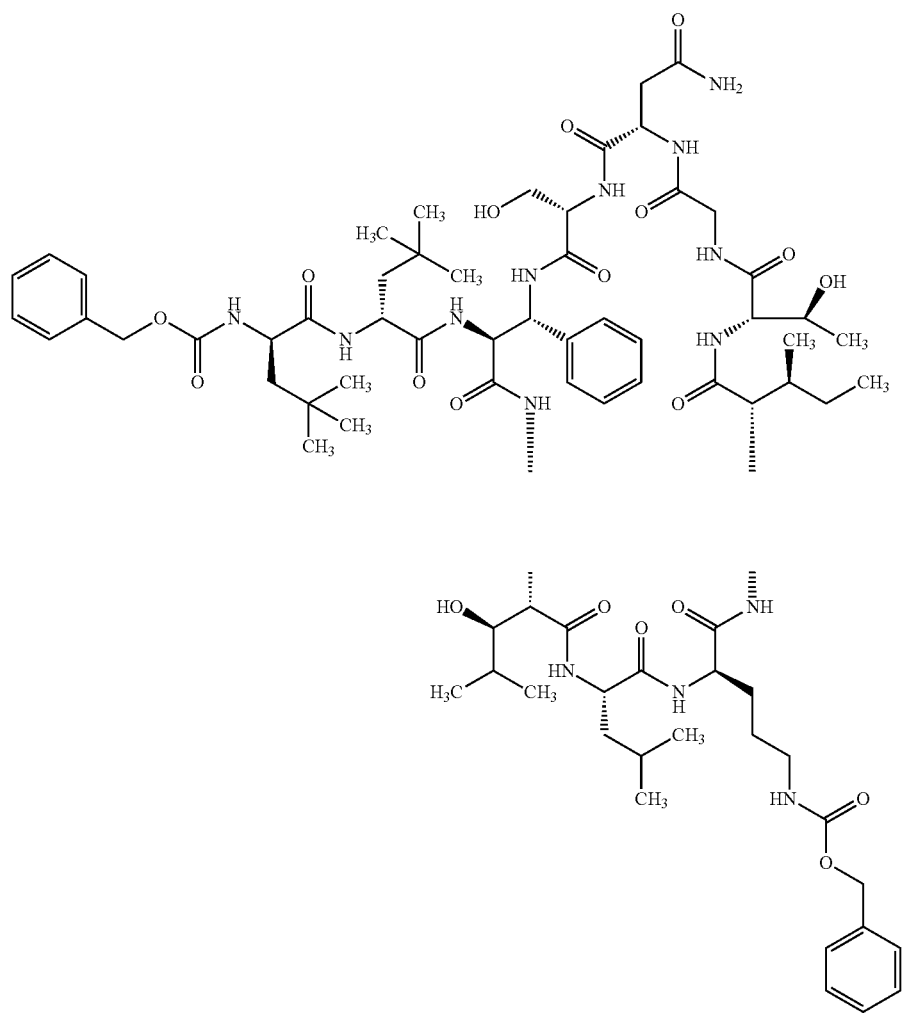

The title compound is prepared according to the preparation method (example 58A) from exemplary compound 80A (25.0 mg, 15.19 µmol), HATU (17.3 mg, 45.57 µmol, 3 eq.) and NMM (10 µl, 9.2 mg, 91.14 µmol). Complete conversion is achieved after 3 days at 4° C. 21.0 mg (91.3% of theory) of the product are isolated after fine purification (method 26).

HPLC (Method 9) $R_t$=26.28 min.

LC-MS (Method 18): $R_t$=2.98 min; MS (ESIpos): m/z (%)=1514 (20) [M+H]⁺, 758 (100) [M+2H]²⁺.

HR-TOF-MS (Method 24): $C_{75}H_{113}N_{14}O_{19}$ $[M+H]^+$ found 1513.8298, calc. 1513.8301.

Example 82A

Methyl (2R*,3R*)-$N^2$-[(benzyloxy)carbonyl]-$N^2$-[(benzyloxy)carbonylamino]-3-[(tert-butoxycarbonyl)amino]-O-methyltyrosinate

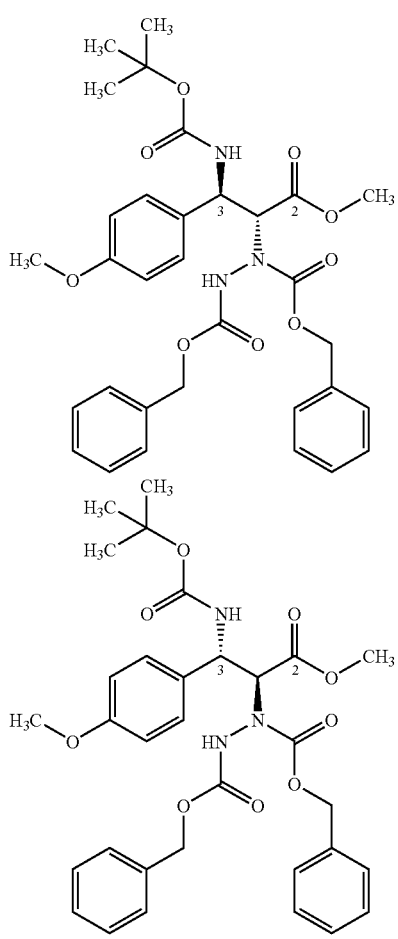

Under an argon protective gas atmosphere, a 1 M LHMDS solution (213.3 mmol, 213.3 ml, 2.2 eq.) in THF is provided in the reaction solvent THF (1.35 l). At −78° C., a solution of methyl (rac)-3-[(tert-butoxycarbonyl)amino]-3-(4-methoxyphenyl)propanoate (D. M. Kalvin, R. W. Woodard, J. Org. Chem., 50, 13, 1985, 2259-2263) (30 g, 96.9 mmol) is slowly added dropwise. The mixture is stirred at −25° C. for 10 min and then cooled again to −78° C. Dibenzyl azadicarboxylate (46.3 g, 155.2 mmol, 1.6 eq.) is added in one portion to the reaction mixture. The mixture is stirred at −60 to −45° C. for 2 h. In order to stop the reaction, the mixture is again cooled to −78° C. and acetic acid (29.1 ml, 484.9 mmol, 5 eq.) is added, and the mixture is then warmed to 0° C. and finally RT. The reaction mixture is evaporated in vacuo and taken up in ethyl acetate (1000 ml). The suspension is washed twice with a sat. aq. sodium bicarbonate solution, twice with water, twice with 5% aq. citric acid and once with a sat. aq. sodium chloride solution. All the aq. phases are re-extracted separately with ethyl acetate. All the org. phases are evaporated in vacuo and again taken up in dichloromethane (2000 ml), filtered, dried over magnesium sulfate, again filtered and evaporated in vacuo. The residue is stirred with cyclohexane, collected by filtration and dried under high vacuum. 25.7 g (44% of theory) of the title compound are obtained as a solid.

HPLC/UV-Vis (Method 5): $R_t$=4.97 min.
HPLC/UV-Vis (Method 3): $R_t$=5.00 min.
LC-MS (Method 18): $R_t$=2.87 min, MS (ESIpos.): m/z (%)=508 (100), 608 (20) $[M+H]^+$; MS (ESIneg.): m/z (%)=532 (50), 606 (100) $[M-H]^-$.

Example 83A

Methyl (2S*,3R*)-$N^2$-[benzyloxycarbonyl]-$N^2$-[(benzyloxycarbonyl)amino]-3-[(tert-butoxycarbonyl)amino]-O-methyltyrosinate

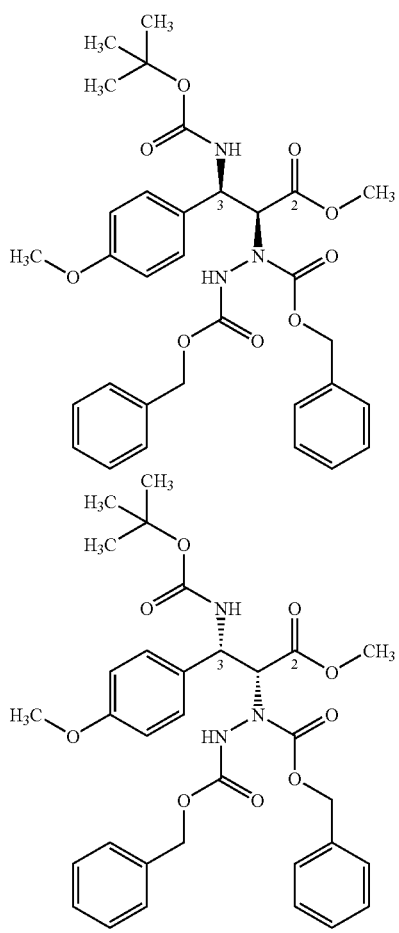

Under an argon protective gas atmosphere, TMG (5.78 ml, 46.1 mmol, 11.2 eq.) is added to a solution of example 82A (2.5 g, 4.1 mmol) in dry DMF p.a. (87 ml) at 0° C. The reaction mixture is allowed to thaw and is stirred until the HPLC chromatogram (method 5) indicates complete conversion (about 70% product) (about 24 h), in order to then stop the reaction by adding acetic acid (pH 4-6). The reaction mixture is evaporated in vacuo at RT and taken up in ethyl acetate. The organic phase is washed twice with water, twice with 5% citric acid, once with a sat. aq. sodium bicarbonate solution, once with a sat. aq. sodium chloride solution, dried over magnesium sulfate, filtered, evaporated in vacuo and dried under high vacuum. The crude product is purified by flash chromatography (silica gel, toluene/ethyl acetate 20:1). 1.89 g (73% of theory) of the title compound are obtained.

HPLC/UV-Vis (Method 5): $R_t$=5.11 min.

HPLC/UV-Vis (Method 4): $R_t$=5.37 min.

LC-MS (Method 18): $R_t$=3.07 min, MS (ESIpos.): m/z (%)=508 (100), 608 (20) [M+H]$^+$; MS (ESIneg.): m/z (%)=532 (100), 606 (30) [M–H]$^-$.

IR $v_{max}$ (NaCl, cm$^{-1}$): 3281, 2974, 1755, 1740, 1686, 1508, 1457, 1416, 1323, 1288, 1267, 1208, 1168, 1137, 1043, 1027.

$^1$H NMR (300 MHz, d$_6$-DMSO): δ=1.29 (s, 9H, tBu), 3.29 (s, 3H, OCH$_3$), 3.72 (s, 3H, COOCH$_3$), 4.80-5.20 (m, 6H), 6.84 (d, J=8.5 Hz, 1H), 7.20-7.40 (m, 12H, ArH), 7.50-7.65 (m, 1H, NH).

HR-TOF-MS (Method 24): $C_{32}H_{38}N_3O_9$ [M+H]$^+$ calc. 608.2603, found 608.2588.

Example 84A

Methyl (+)-(2R,3S)-N$^2$-[benzyloxycarbonyl]-N$^2$-[(benzyloxycarbonyl)amino]-3-[(tert-butoxycarbonyl)amino]-O-methyltyrosinate

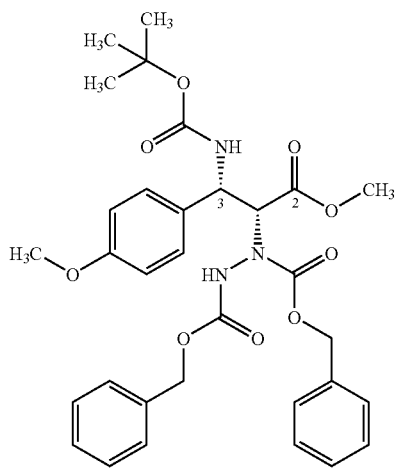

The mixture of enantiomers of example 83A (10.6 g, 17.44 mmol) is separated by preparative HPLC (method 39). 4.18 g (99.5% ee, 79% of theory) of the title compound and 5.2 g (99.5% ee, 98% of theory) of the (–) enantiomer (example 85A) are obtained.

Determination of enantiomers by method 15.

HPLC/UV-Vis (Method 15): $R_t$=3.86 min.

[α]$^{20}_{Na}$=+54° (c=0.24 in MeOH).

HPLC/UV-Vis (Method 5): $R_t$=5.11 min.

HPLC/UV-Vis (Method 4): $R_t$=5.23 min.

LC-MS (Method 18): $R_t$=3.07 min, MS (ESIpos.): m/z (%)=508 (100), 608 (20) [M+H]$^+$; MS (ESIneg.): m/z (%)=532 (100), 606 (30) [M–H]$^-$.

HR-TOF-MS (Method 24): $C_{32}H_{38}N_3O_9$ [M+H]$^+$ calc. 608.2603, found 608.2592.

Example 85A

Methyl (–)-(2S,3R)-N$^2$-[benzyloxycarbonyl]-N$^2$-[(benzyloxycarbonyl)amino]-3-[(tert-butoxycarbonyl)amino]-O-methyltyrosinate

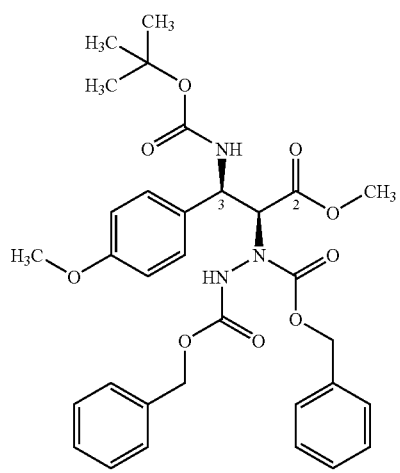

Preparation takes place in analogy to example 84A.

Determination of enantiomers by method 15.

HPLC/UV-Vis (Method 15): $R_t$=7.20 min.

[α]$^{20}_{Na}$=–34° (c=0.27 in MeOH).

HPLC/UV-Vis (Method 5): $R_t$=5.11 min.

HPLC/UV-Vis (Method 4): $R_t$=5.21 min.

LC-MS (Method 23): $R_t$=2.87 min, MS (ESIpos.): m/z (%) 508 (100), 608 (90) [M+H]$^+$; MS (ESIneg.): m/z (%)=532 (60), 606 (100) [M–H]$^-$.

HR-TOF-MS (Method 24): $C_{32}H_{38}N_3O_9$ [M+H]$^+$ calc. 608.2603, found 608.2594.

Example 86A

Methyl (2S*,3R*)-3-[(tert-butoxycarbonyl)amino]-O-methyltyrosinate

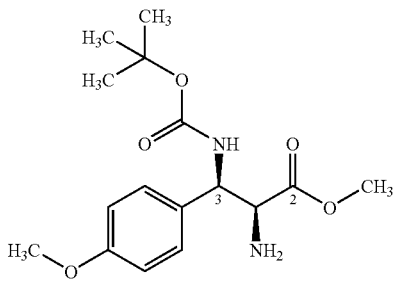

-continued

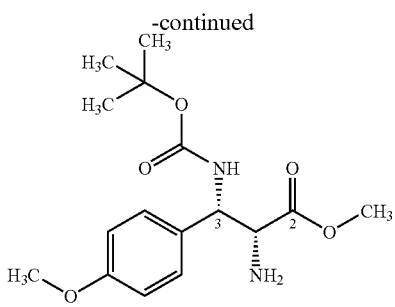

Under an argon protective gas atmosphere, Raney nickel (about 1 g) is added to a solution of example 83A (2.81 g, 4.62 mmol) in methanol/dichloromethane 1:1 (100 ml). The reaction mixture is hydrogenated in a pressurized autoclave under a hydrogen pressure of 80 bar and at RT (12 h). The HPLC chromatogram (method 8) shows complete conversion. The reaction mixture is filtered under an argon protective gas atmosphere through a glass frit/kieselguhr layer, and the glass frit is washed several times with methanol. The filtrate is evaporated in vacuo and dried under high vacuum. The product obtained is a solid (1.50 g, quant.) which is reacted further without fine purification.

HPLC/UV-Vis (Method 8): $R_t$=3.66 min.

Example 87A

Methyl (+)-(2R,3S)-3-[(tert-butoxycarbonyl)amino]-O-methyltyrosinate

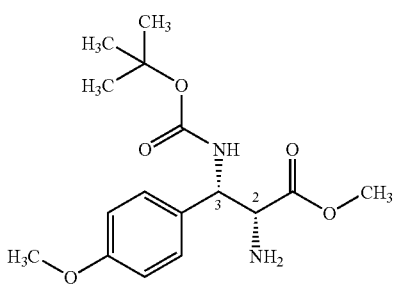

Under an argon protective gas atmosphere, Raney nickel (about 0.8 g) is added to a solution of example 84A (4.00 g, 6.58 mmol) in methanol/dichloromethane 1:1 (100 ml). The reaction mixture is hydrogenated in a pressurized autoclave under a hydrogen pressure of 80 bar and at RT (72 h). The reaction mixture is filtered under an argon protective gas atmosphere through a glass frit/kieselguhr layer, and the glass frit is washed several times with methanol. The filtrate is evaporated in vacuo and taken up in ethyl acetate. A solution of EDTA (2 g) in a 50% aq. sodium bicarbonate solution (700 ml) is added to the solution. The aqueous phase is extracted 5× with ethyl acetate (100 ml). The combined organic phases are then washed twice with a sat. aq. sodium bicarbonate solution and twice with a sat. aq. sodium chloride solution. All the aq. phases are re-extracted separately with ethyl acetate. The combined org. phases are then dried over magnesium sulfate, filtered and dried under high vacuum. The product obtained is a solid (1.04 g, 49% of theory, 96% ee).

HPLC/UV-Vis (Method 16): $R_t$=7.8 min.

$[\alpha]^{20}_{Na}$=+7.7° (c=0.34 in MeOH).

HPLC/UV-Vis (Method 5): $R_t$=3.69 min.

HPLC/UV-Vis (Method 4): $R_t$=3.87 min.

LC-MS (Method 20): $R_t$=1.17 min; MS (ESIpos.): m/z (%)=208 (90), 269 (100), 325 (40) [M+H]$^+$.

IR $\nu_{max}$ (NaCl, cm$^{-1}$): 2933,1737,1709,1611, 1511,1365, 1243,1164, 1030.

Example 88A

Methyl (−)-(2S,3R)-3-[(tert-butoxycarbonyl)amino]-O-methyltyrosinate

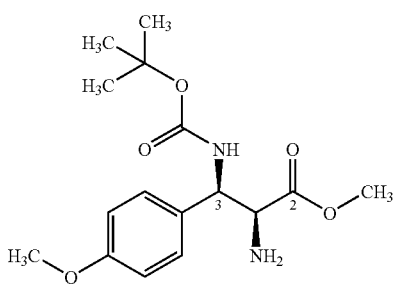

Under an argon protective gas atmosphere, Raney nickel (about 0.7 g) is added to a solution of example 85A (5.20 g, 8.56 mmol) in methanol/dichloromethane 1:1 (140 ml). The reaction mixture is hydrogenated in a pressurized autoclave under a hydrogen pressure of 80 bar and at RT (72 h). The reaction mixture is filtered under an argon protective gas atmosphere through a glass frit/kieselguhr layer, and the glass frit is washed several times with methanol. The filtrate is evaporated in vacuo and taken up in ethyl acetate. The mixture is prepurified by silica gel chromatography (cyclohexane/ethyl acetate 3:1→1:3) and separated by preparative HPLC (method 31). The title compound (324 mg, 91% ee, 8% of theory) is obtained.

HPLC/UV-Vis (Method 16): $R_t$=9.3 min.

HPLC/UV-Vis (Method 5): $R_t$=3.69 min.

HPLC/UV-Vis (Method 4): $R_t$=3.84 min.

LC-MS (Method 20): $R_t$=1.17 min; MS (ESIpos.): m/z (%)=208 (90), 269 (100), 325 (40) [M+H]$^+$.

$^1$H NMR (500 MHz, d$_6$-DMSO): δ=1.37 (s, 9H, C(CH$_3$)$_3$), 3.53 (s, 3H, OCH$_3$), 3.74 (s, 3H, OCH$_3$), 4.26 (m, 1H, β-CH), 5.00 (t, J=9.0 Hz, 1H, β-CH), 6.93 (d, J=8.0 Hz, 2H, ArH), 7.23 (d, J=8.0 Hz, 2H, ArH), 7.52 (d, J=10.0 Hz, 1H, NH), 8.45 (br. s, 2H, NH$_2$).

Example 89A

Methyl (2S*,3R*)-N²-[benzyloxycarbonyl]-3-[(tert-butoxycarbonyl)amino]-O-methyl-tyrosinate

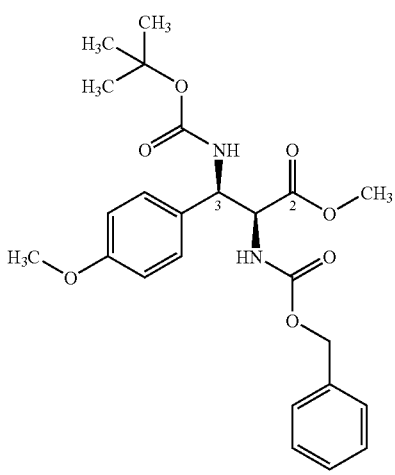

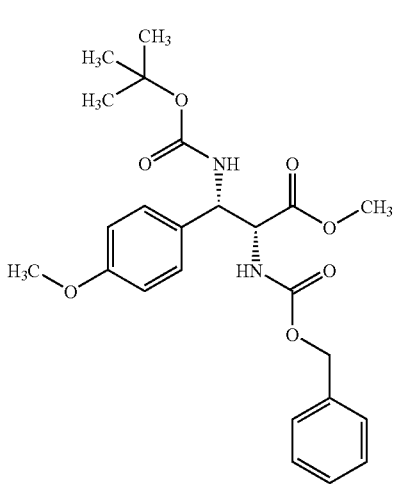

Under an argon protective gas atmosphere, NaHCO₃ (0.58 g, 6.94 mmol, 1.5 eq.) and tetra-N-butylammonium iodide (0.17 g, 0.47 mmol, 0.1 eq.) are added to a solution of example 86A (1.5 g, 4.62 mmol) and N-benzyloxycarbonyloxysuccinimide ester (1268 mg, 5.09 mmol, 1.1 eq.) in dichloromethane/water (1:2, 150 ml) at 0° C. The reaction mixture slowly warms up (12 h), whereby complete conversion is observed by HPLC (method 1). A solution of citric acid (5%) is added to the solution. The aq. phase is extracted three times with dichloromethane (100 ml). The combined organic phases are then washed twice with a sat. aq. sodium bicarbonate solution and twice with a sat. aq. sodium chloride solution. The combined org. phases are then dried over magnesium sulfate, filtered and dried under high vacuum. The product obtained is the title compound as a solid (2.1 g, 99% of theory).

HPLC/UV-Vis (Method 5): $R_t$=4.73 min.

HPLC/UV-Vis (Method 4): $R_t$=4.68 min.

IR $\nu_{max}$ (NaCl, cm⁻¹): 3356, 1737, 1680, 1514, 1242, 1161, 1026, 1004.

¹H NMR (500 MHz, d₆-DMSO): δ=1.36 (s, 9H, C(CH₃)₃), 3.61 (s, 3H, OCH₃), 3.73 (s, 3H, OCH₃), 4.51 (dd, J=9.5, 4.0 Hz, 1H, α-H/β-H), 4.94 (m, 2H, PhCH₂O), 5.20 (dd, J=10.0, 4.0 Hz, 1H, α-H/β-H), 6.87 (d, J=8.5 Hz, 2H, ArH), 7.15-7.22 (m, 4H, ArH), 7.29-7.37 (m, 3H, ArH), 7.50 (d, J=10.0 Hz, 1H, NH), 7.57 (d, J=10.0 Hz, 1H, NH).

¹³C NMR (126 MHz, d₆-DMSO): δ=27.9, 51.9, 53.8, 54.9, 58.9, 65.4, 78.3, 113.5, 126.8, 127.3, 127.5, 127.7, 128.2, 130.9, 136.6, 154.6, 155.9, 158.2, 170.6.

HR-TOF-MS (Method 24): $C_{25}H_{30}N_2O_7$ [M+H]⁺ found 459.2140, calc. 459.2126.

Example 90A

Methyl (+)-(2R,3S)-N²-[benzyloxycarbonyl]-3-[(tert-butoxycarbonyl)amino]-O-methyl-tyrosinate

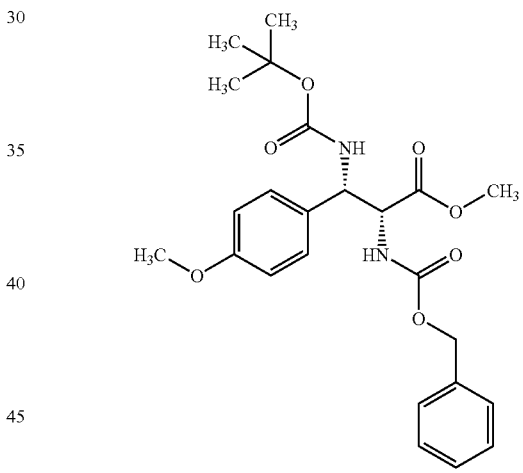

Example 87A (1.0 g, 3.08 mmol) is reacted in analogy to the preparation method for example 89A (reaction time: 12 h). The crude product is purified by preparative HPLC (method 32). 1.4 g (61% of theory, 96% ee) of the title compound are obtained.

HPLC/UV-Vis (Method 16): $R_t$=7.3 min.

$[\alpha]^{20}_{Na}$=+4.0° (c=0.17 in MeOH).

HPLC/UV-Vis (Method 5): $R_t$=4.73 min.

HPLC/UV-Vis (Method 4): $R_t$=4.81 min.

IR $\nu_{max}$ (NaCl, cm⁻¹): 3346, 1741, 1707, 1680, 1517, 1270, 1248, 1160, 1028, 1007.

LC-MS (Method 23): $R_t$=2.63 min; MS (ESIpos.): m/z (%)=298 (100), 459 (30) [M+H]⁺; MS (ESIneg.): m/z (%)=383 (100), 457 (10) [M−H]⁻.

HR-TOF-MS (Method 24): $C_{25}H_{30}N_2O_7$ [M+H]$^+$ found 459.2128, calc. 459.2126.

Example 91A

Methyl (−)-(2S,3R)-N$^2$-[benzyloxycarbonyl]-3-[(tert-butoxycarbonyl)amino]-O-methyl-tyrosinate

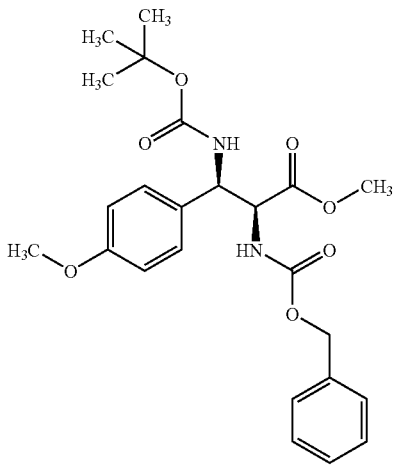

Example 88A (0.32 g, 0.98 mmol) is reacted in analogy to the preparation method for example 89A (reaction time: 12 h). The product obtained is the title product as a solid (0.38 g, 85% of theory).

HPLC/UV-Vis (Method 16): R$_t$=6.3 min.
HPLC/UV-Vis (Method 5): R$_t$=4.73 min.
HPLC/UV-Vis (Method 4): R$_t$=4.81 min.
LC-MS (Method 23): R$_t$=2.60 min; MS (ESIpos.): m/z (%)=298 (100), 459 (70) [M+H]$^+$; MS (ESIneg.): m/z (%)=383 (100), 457 (10) [M−H]$^-$.

Example 92A (2S*,3R*)-N$^2$-[Benzyloxycarbonyl]-3-[(tert-butoxycarbonyl)amino]-O-methyltyrosine

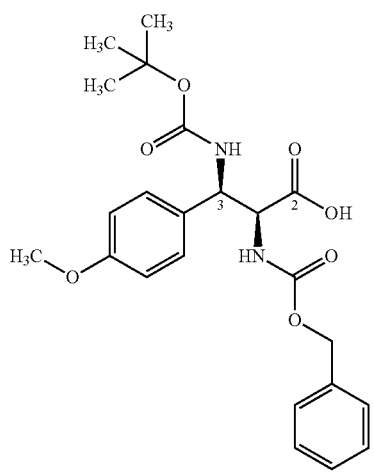

-continued

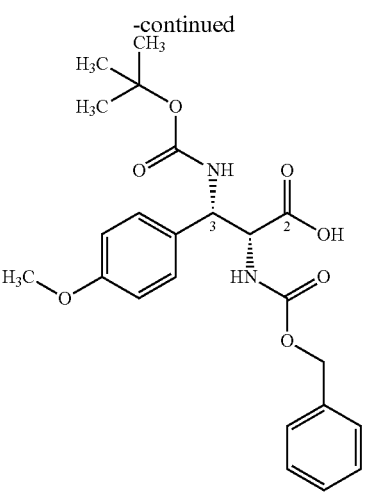

Under an argon protective gas atmosphere, a solution of example 89A (759 mg, 1.69 mmol) is provided in THF/water 2:1 (12 ml). At 0° C., while stirring vigorously, an aq. solution of lithium hydroxide monohydrate (81 mg, 3.39 mmol, 2.05 eq.) is slowly added dropwise. The mixture is stirred at RT until the HPLC chromatogram (method 5) indicates complete conversion (about 3 h). Potassium hydrogen phosphate (225 mg) is subsequently added, and the reaction mixture is concentrated in vacuo and covered with a layer of ethyl acetate (100 ml). The aq. phase is then acidified with 5% citric acid (pH 2-3) and then extracted three times with ethyl acetate (50 ml). The combined org. phases are washed twice with a sat. aq. sodium chloride solution (20 ml), dried over sodium sulfate, filtered, concentrated in vacuo and dried under high vacuum. The title compound is obtained (735 mg quant.).

HPLC/UV-Vis (Method 5): R$_t$=4.45 min.
LC-MS (Method 21): R$_t$=2.33 min; MS (ESIpos.): m/z (%)=389 (100), 445 (90) [M+H]$^+$; MS (ESIneg.): m/z (%)=335 (60), 443 (100) [M−H]$^-$.
$^1$H NMR (400 MHz, d$_6$-DMSO): δ=1.35 (s, 9H, C(CH$_3$)$_3$), 3.72 (s, 3H, OMe), 4.35-4.40 (m, 1H, α-H), 4.94 (s, 2H, PhCH$_2$O), 5.19 (dd, J=10.0, 4.0 Hz, 1H, β-H), 6.86 (d, J=9.0 Hz, 2H), 7.17-7.34 (m, 7H, ArH), 7.44-7.48 (m, 2H, 2 NH), 12.9 (s, br, 1H, CO$_2$H).

Example 93A (+)-(3S)-N$^2$-[Benzyloxycarbonyl]-3-[(tert-butoxycarbonyl)amino]-O-methyl-D-tyrosine

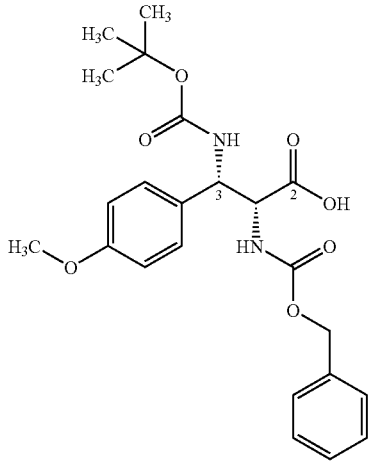

Method A: The mixture of enantiomers of example 92A (735 mg, 2.83 mmol) is separated by preparative HPLC (method 40). 319 mg (99.5% ee, 43% of theory) of the title compound and 307 mg (99.5% ee, 42% of theory) of the other enantiomer (example 94A) are obtained.

Determination of enantiomers by method 16.
HPLC/UV-Vis (Method 16): $R_t$=10.9 min.
$[α]^{20}_{Na}$=+8° (c=0.04 in MeOH).
HPLC/UV-Vis (Method 5): $R_t$=4.45 min.
LC-MS (Method 21): $R_t$=2.33 min; MS (ESIpos.): m/z (%)=389 (100), 445 (90) [M+H]$^+$; MS (ESIneg.): m/z (%)=335 (60), 443 (100) [M−H]$^−$.
IR $ν_{max}$(NaCl, cm$^{−1}$): 3358, 2978, 1705, 1683, 1615, 1515, 1245, 1167, 1027.
HR-TOF-MS (Method 24): $C_{23}H_{29}N_2O_7$ [M+H]$^+$ found 445.1976, calc. 445.1970.

Method B: Example 93A (1.30 g, 2.83 mmol) is reacted in analogy to the preparation method for example 92A (reaction time: 2 h). As product the title compound is obtained as a solid product (0.61 g, 48% of theory, 95% ee).
HPLC/UV-Vis (Method 16): $R_t$=10.9 min.
$[α]^{20}_{Na}$=+15° (c=0.23 in MeOH).
HPLC/UV-Vis (Method 5): $R_t$=4.41 min.
HPLC/UV-Vis (Method 4): $R_t$=4.54 min.
HR-TOF-MS (Method 24): $C_{23}H_{28}N_2O_7Na$ [M+Na]$^+$ found 467.1788, calc. 467.1794.

Example 94A (−)-(3R)-$N^2$-[Benzyloxycarbonyl]-3-[(tert-butoxy-carbonyl)amino]-O-methyl-L-tyrosine

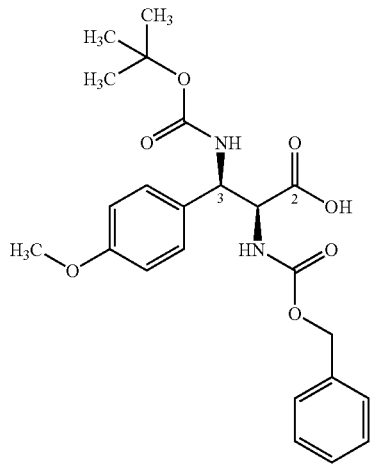

Method A: Preparation method under example 93A (method A)
HPLC/UV-Vis (Method 16): $R_t$=13.3 min.
$[α]^{20}_{Na}$=−10° (c=0.12 in MeOH).
HPLC/UV-Vis (Method 5): $R_t$=4.45 min.
LC-MS (Method 21): $R_t$=2.33 min; MS (ESIpos.): m/z (%)=389 (100), 445 (90) [M+H]$^+$; MS (ESIneg.): m/z (%)=335 (60), 443 (100) [M−H]$^−$.
HR-TOF-MS (Method 24): $C_{23}H_{29}N_2O_7$ [M+H]$^+$ found 445.1976, calc. 445.1970.

Method B: Example 90A (0.38 g, 0.84 mmol) is reacted in analogy to the preparation method for example 92A (reaction time: 2 h). As product the title compound is obtained as a solid (0.132 g, 35% of theory, 94% ee).

HPLC/UV-Vis (Method 16): $R_t$=13.3 min.
$[α]^{20}_{Na}$=−5 (c=0.1 in MeOH).
HPLC/UV-Vis (Method 5): $R_t$=4.41 min.
HPLC/UV-Vis (Method 4): $R_t$=4.49 min.
LC-MS (Method 18): $R_t$=2.38 min; MS (ESIpos.): m/z (%)=389 (100), 445 (100) [M+H]$^+$; MS (ESIneg.): m/z (%)=335 (60), 443 (100) [M−H]$^−$.
$^{13}$C NMR (126 MHz, $d_6$-DMSO): δ=28.0, 53.9, 54.9, 58.8, 65.2, 78.2, 113.4, 127.2, 127.3, 127.6, 128.1, 128.2, 131.7, 136.8, 154.7, 156.0, 158.1, 171.4.
HR-TOF-MS (Method 24): $C_{23}H_{29}N_2O_7$ [M+H]$^+$ found 445.1966, calc. 445.1970.

Example 95A

2-Isopropyl-5-methylcyclohexyl (1S,2R,5R)-[(3S)-$N^2$-[benzyloxycarbonyl]-3-[(tert-butoxy-carbonyl)amino]]-O-methyl-D-tyrosinate

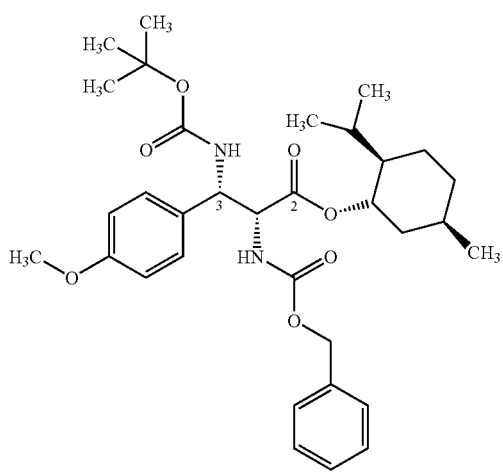

Under an argon protective gas atmosphere, a solution of example 93A (34 mg, 76 μmol, 1 eq.) and (1S,2R,5S)-(+)-menthol (12 mg, 76 μmol, 1 eq.) in dichloromethane is provided. At 0° C., DMAP (17.3 mg, 84 μmol, 1.1 eq.) is added, and a solution of DCC (17.3 mg, 84 μmol, 1.1 eq.) in dichloromethane (0.5 ml) is slowly added dropwise. The mixture is stirred at RT until the HPLC chromatogram (method 5) indicates complete conversion (about 2 h). The reaction mixture is subsequently filtered through kieselguhr and concentrated in vacuo, and ethyl acetate/petroleum ether 3:1 is added. A white solid precipitates and is removed by filtration. The filtrate is concentrated and prepurified by silica gel chromatography (petroleum ether/ethyl acetate 3:1). Purification is by preparative HPLC (method 43). The title compound (17 mg, 38% of theory) is obtained.

HPLC/UV-Vis (Method 5): $R_t$=5.74 min.
HPLC/UV-Vis (Method 4): $R_t$=5.72 min.
LC-MS (Method 18): $R_t$=3.46 min; MS (ESIpos.): m/z (%)=483 (100), 527 (80), 583 (40) [M+H]$^+$.
$^1$H NMR (500 MHz, $d_6$-DMSO): δ=0.71 (d, 3H, J=7 Hz, $CH_3$), 0.81 (d, 3H, J=7 Hz, $CH_3$), 0.81-0.84 (m, 3H), 0.87 (d, 3H, J=7 Hz, CH$_3$), 1.00-1.06 (m, 1H), 1.22-1.28 (m, 1H), 1.35 (s, 9H, C(CH$_3$)$_3$), 1.61-1.70 (m, 3H), 1.89-1.92 (m, 1H), 3.72 (s, 3H, OMe), 4.49 (dd, 1H, J=4.5, 9.5 Hz, β-H), 4.59 (dt, J=4.0, 11.0 Hz, 1H, O—CH), 4.91 (d, J=12.0 Hz, 1H, PhCH$_2$O), 4.97 (d, J=12.0 Hz, 1H, PhCH$_2$O), 5.17 (dd, J=4.5, 9.5 Hz, 1H, β-H), 6.86 (d, 2H, J=9.0 Hz, ArH), 7.16-7.24 (m, 4H, ArH), 7.28-7.34 (m, 3H, ArH), 7.46 (d, 1H, J=8.0 Hz, NH), 7.55 (d, 1H, J=8.0 Hz, NH).

Example 96A 2-(Trimethylsilyl)ethyl (+)-(3S)-N$^2$-[benzyloxycarbonyl]-3-[(tert-butoxycarbonyl)amino]-O-methyl-D-tyrosinate

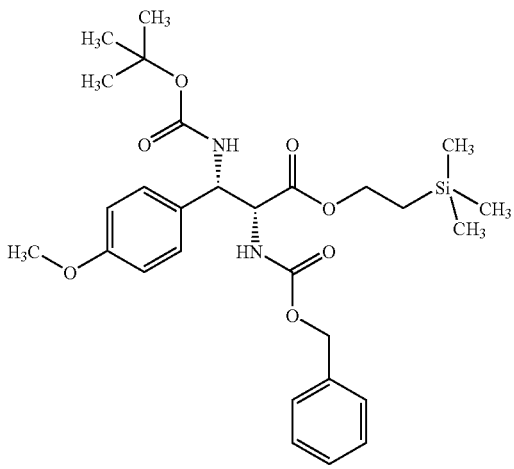

A mixture of example 93A (261 mg, 0.59 mmol), 2-(trimethylsilyl)ethanol (694 mg, 5.87 mmol, 10 eq.) and 4 Å molecular sieves (about 20 mg) in dry dichloromethane p.a. (10 ml) is stirred under an argon protective gas atmosphere at RT for 10 min. Subsequently, at −30° C., DCC (244 mg, 1.17 mmol, 2 eq.) and DMAP (71 mg, 0.59 mmol, 1 eq.) are added. The reaction mixture is allowed to thaw (about 12 h) and is stirred at RT until the HPLC chromatogram (method 5) indicates complete conversion (12 h). The reaction mixture is evaporated in vacuo at RT and purified by silica gel chromatography (petroleum ether/ethyl acetate 3:1). 244 mg (76% of theory, 99% ee) of the title compound are obtained.

HPLC/UV-Vis (Method 16): R$_t$=8.2 min.

[α]$^{20}_{Na}$=+10° (c=0.1 in MeOH).

HPLC/UV-Vis (Method 5): R$_t$=5.34 min.

HPLC/UV-Vis (Method 4): R$_t$=5.42 min.

IR ν$_{max}$ (NaCl, cm$^{-1}$): 3361, 2931, 2118, 1735, 1706, 1681, 1515, 1247, 1165, 1019.

LC-MS (Method 21): R$_t$=3.16 min; MS (ESIpos.): m/z (%)=166 (100), 545 (15) [M+H]$^+$.

HR-TOF-MS (Method 24): C$_{28}$H$_{41}$N$_2$O$_7$Si [M+H]$^+$ found 545.2678, calc. 545.2678.

Example 97A 2-(Trimethylsilyl)ethyl (−)-(3R)-N$^2$-[benzyloxycarbonyl]-3-[(tert-butoxycarbonyl)amino]-O-methyl-L-tyrosinate

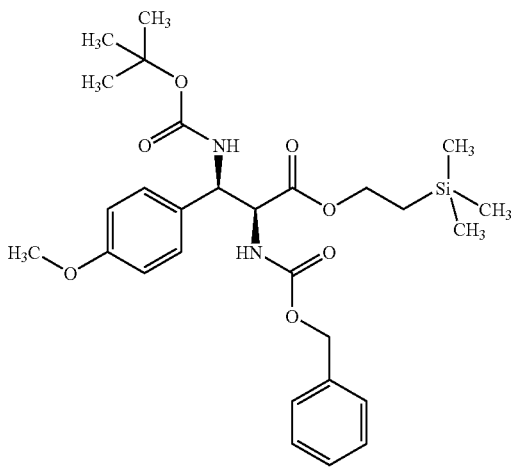

Example 94A (130 mg, 0.29 mmol) is reacted in analogy to the preparation method for example 96A (reaction time: 12 h). As product the title compound is obtained as a solid (149 mg, 94% of theory, >99.5% ee).

HPLC/UV-Vis (Method 16): R$_t$=7.2 min.

[α]$^{20}_{Na}$=−9° (c=0.1 in MeOH).

HPLC/UV-Vis (Method 5): R$_t$=5.34 min.

HPLC/UV-Vis (Method 4): R$_t$=5.32 min.

LC-MS (Method 18): R$_t$=3.24 min; MS (ESIpos.): m/z (%)=545 (100) [M+H]$^+$.

Example 98A 2-(Trimethylsilyl)ethyl (+)-(3S)-3-amino-N$^2$-[benzyloxycarbonyl]-O-methyl-D-tyrosinate trifluoroacetate

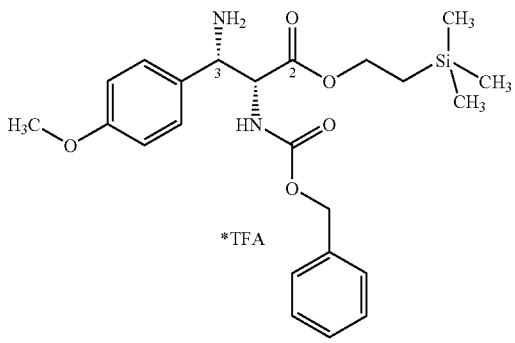

Example 96A (222 mg, 0.41 mmol, 1 eq.) is suspended in dichloromethane (3 ml) and subsequently, under an argon protective gas atmosphere, trifluoroacetic acid (9 ml) is added and the mixture is stirred at RT for 15 min until the HPLC chromatogram shows complete conversion (method 5). The solvent is then distilled off in vacuo, during which the bath temperature should not exceed 30° C. The crude product is purified by preparative HPLC (method 43). 179 mg (79% of theory, >99.5% ee) of the title compound are obtained.

HPLC/UV-Vis (Method 16): $R_t$=8.66 min.

$[\alpha]^{20}_{Na}$=+20° (c=0.22 in MeOH).

HPLC/UV-Vis (Method 5): $R_t$=4.33 min.

HPLC/UV-Vis (Method 4): $R_t$=4.55 min.

IR $\nu_{max}$ (NaCl, cm$^{-1}$): 2956, 1672, 1613, 1518, 1251, 1181, 1138, 1029.

LC-MS (Method 18): $R_t$=2.18 min; MS (ESIpos.): m/z (%)=225 (100), 549 (100) [M+H]$^+$.

$^1$H NMR (500 MHz, d$_6$-DMSO): δ=−0.07 (s, 9H, Si(CH$_3$)$_3$), 0.43-0.52 (m, 2H, CH$_2$Si), 3.75 (s, 3H, OMe), 3.74-3.78 (m, 1H, CH$_2$CH$_2$Si), 3.82-3.88 (m, 1H, CH$_2$CH$_2$Si), 4.38-4.42 (m, 1H, β-H), 4.58 (t$_{app}$, J=approx. 9.0 Hz, 1H, α-H), 5.08 (s, 2H, PhCH$_2$O), 6.98 (d, 2H, J=8.5 Hz, ArH), 7.34-7.40 (m, 8H, ArH), 8.07 (d, 1H, J=8.0 Hz, NH), 8.49 (s, br, 2H, 2 NH).

$^{13}$C NMR (125 MHz, d$_6$-DMSO): δ=−1.8 (3C, (Si(CH$_3$)$_3$)), 16.3 (CH$_2$Si), 54.5 (C$^\beta$), 55.1 (C$^\alpha$), 57.7 (OMe), 62.9 (CH$_2$CH$_2$Si), 66.0 (PhCH$_2$O), 113.9 (2C), 125.3, 127.8 (2C), 127.9, 128.3 (2C), 129.4 (2C), 136.4, 155.8 (CO$_2$Bn), 159.9, 168.9 (CO$_2$TMSE).

HR-TOF-MS (Method 24): C$_{23}$H$_{33}$N$_2$O$_5$Si [M+H]$^+$ found 445.2168, calc. 445.2154.

Example 99A 2-(Trimethylsilyl)ethyl (−)-(3R)-3-amino-N$^2$-[benzyloxycarbonyl]-O-methyl-L-tyrosinate-trifluoroacetate

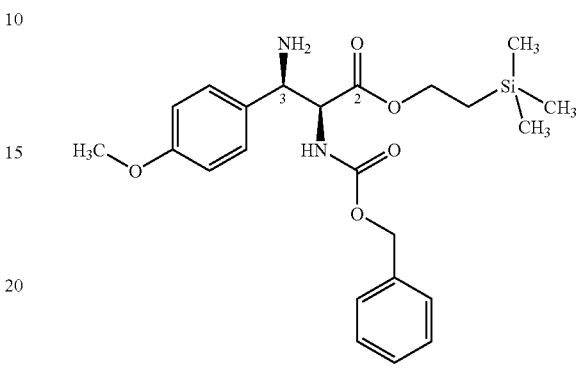

Example 96A (120 mg, 0.22 mmol) is reacted in analogy to the preparation method for example 98A (reaction time: 50 min). As product the title compound is obtained as a solid (71 mg, 56% of theory, >99.5% ee).

HPLC/UV-Vis (Method 16): $R_t$=7.49 min.
HPLC/UV-Vis (Method 5): $R_t$=4.33 min.
HPLC/UV-Vis (Method 4): $R_t$=4.50 min.
IR $\nu_{max}$ (NaCl, cm$^{-1}$): 2956, 1672, 1613, 1518, 1251, 1181, 1138, 1029. HR-TOF-MS (Method 24): C$_{23}$H$_{33}$N$_2$O$_5$Si [M+H]$^+$ found 445.2151, calc. 445.2154.

Example 100A

[(3R)-N$^2$-(tert-Butoxycarbonyl)-3-hydroxy-L-leucyl]-L-leucyl-D-arginyl-L-isoleucyl-L-allothreonyl-glycyl-[(3S)-3-hydroxy-L-asparaginyl]-L-serine trifluoroacetate

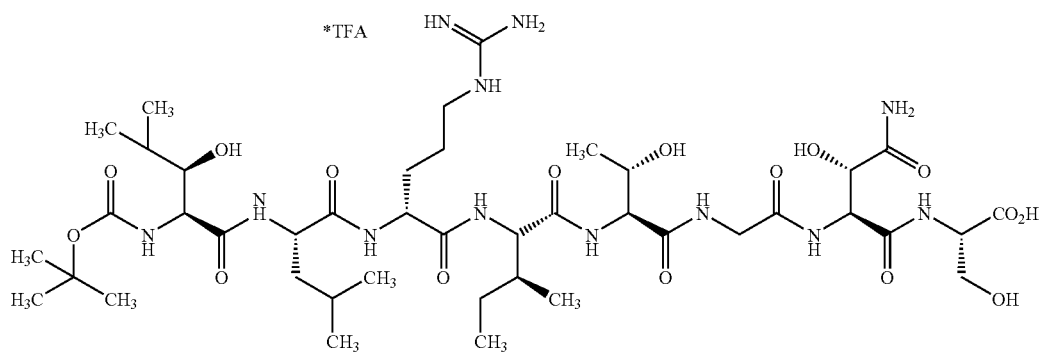

Method A: Under an argon protective gas atmosphere, di-tert-butyldicarbonate (369 mg, 1.69 mmol, 2.5 eq.) and N-methylmorpholine (68 mg, 680 µmol, 1 eq.) are added to a solution of the degradation product from example 3A (690 mg, 680 µmol) in water-dioxane 1:2 (30 ml). The reaction mixture is stirred until the HPLC chromatogram (method 1) shows complete conversion (about 48 h). Potassium dihydrogen phosphate (5 eq.) is added to the reaction mixture and the mixture is concentrated in vacuo and purified by preparative HPLC (method 43 or method 30 followed by a subsequent salt metathesis of the chromatography product by adding TFA (2000 µmol, as a 0.05% solution in acetonitile-water 1:1)). 531 mg (70% of theory) of the title compound are obtained.

Method B: Edman[3.0] precursor trifluoroacetate (100 mg, 0.1 mmol, 1 eq.) is firstly gel chromatographed (method 45, MeOH, 0.2% TFA). Di-tert-butyl dicarbonate (43 mg, 0.2 mmol, 2 eq.) is added to a solution of this material in water (1 ml) and dioxane (2 ml) at RT, and NMM (21.6 µL, 0.2 mmol, 2 eq.) is added dropwise. The reaction mixture is stirred at RT until (about 12 h) the analytical HPLC monitoring (method 8) indicates sufficient conversion (>99%). Potassium dihydrogen phosphate (67 mg, 0.49 mmol, 5 eq.) is added, the reaction mixture is concentrated on a rotary evaporator and then fine purified by preparative HPLC (method 26). 83 mg (76% of theory) of the title compound are obtained.

$[\alpha]^{20}_{Na}$=−18.0° (c=0.19 in methanol).

HPLC/UV-Vis (Method 2): $R_t$=1.7 min.
HPLC/UV-Vis (Method 5): $R_t$=3.57 min.
HPLC/UV-Vis (Method 4): $R_t$=3.79 min.
LC-MS (Method 18): $R_t$=1.70 min; MS (ESIpos.): m/z (%)=453 (100), 1005 (80) [M+H]$^+$; MS (ESIneg.): m/z (%)=1003 (100) [M−H]$^-$.
LC-MS (Method 23): $R_t$=4.6 min; MS (ESIpos.): m/z (%)=453.5 (60) [M−C$_4$H$_8$—CO$_2$+2H]$^{2+}$, 1006 (100) [M+H]$^+$; MS (ESIneg.): m/z (%)=1004 (100) [M−H]$^-$.

IR $\nu_{max}$ (NaCl, cm$^{-1}$): 3288, 2966, 2359, 2341, 1645, 1520, 1368, 1160, 1137, 1054.

$^1$H NMR (500 MHz, d$_5$-pyridine) δ=9.72 (br. s, 1H, NH-Glu$^6$), 9.31 (br d, J=approx. 7.0 Hz, 1H, NH-Arg$^3$), 9.23 (d, J=6.0 Hz, 1H, NH-Leu$^2$), 9.19 (br. s, 1H, εNH-Arg$^3$), 9.00 (d, J=9.0 Hz, 1H, NH-βOH-Asn$^7$), 8.88 (d, J=7.0 Hz, 1H, NH-Thr$^5$), 8.78 (d, J=7.0 Hz, 1H, NH-Ile$^4$), 8.64 (d, J=7.5 Hz, 1H, NH-Ser$^8$), 8.40 (br. s, 1H, NH$_2$-βOH-Asn$^7$), 8.34 (br. s, 1H, NH$_2$-βOH-Asn$^7$), 5.96 (d, J=8.0 Hz, 1H, αCH-βOH-Asn$^7$), 5.51 (s, 1H, δCH-βOH-Asn$^7$), 5.11-5.09 (m, 1H, αCH-Ser$^8$), 5.04 (t, J=7.5 Hz, 1H, αCH-Thr$^5$), 4.95-4.91 (m, 3H, αCH-Arg$^3$ and αCH-βOH-Leu$^1$ and αCH-Leu$^2$), 4.82 (t, J=7.0 Hz, 1H, αCH-Ile$^4$), 4.71-4.66 (m, 1H, ⊕CH-Thr$^5$), 4.44 (dd, J=4.5 and 10.5 Hz, 1H, βCH-Ser$^8$), 4.31-4.26 (m, 3H, βCH-Ser$^8$ and βCH-βOH-Leu$^1$ and αCH-Gly$^6$), 4.20 (dd, J=6.0 and 16.5 Hz, 1H, αCH-Gly$^6$), 3.43 (br d, J=approx. 6.0 Hz, 2H, δCH-Arg$^3$), 2.39-2.36 (m, 2H, βCH-Arg$^3$ and βCH-Ile$^4$), 2.27-2.20 (m, 1H, βCH-Arg$^3$), 2.10-2.05 (m, 2H, γCH-βOH-Leu$^1$ and γCH-Arg$^3$), 1.93-1.79 (m, 4H, βCH-Leu$^2$, γCH-Leu$^2$, γCH-Arg$^3$ and γCH-Ile$^4$), 1.55 (d, J=6.0 Hz, 3H, γCH$_3$-Thr$^5$), 1.45 (s, 9H, O-tBu), approx. 1.47 (hidden, 1H, γCH-Ile$^4$), 1.17-1.15 (m, 4H, γCH$_3$-βOH-Leu$^1$ and γCH-Ile$^4$), 1.05 (d, J=6.0 Hz, 3H, γCH$_3$-βOH-Leu$^1$), 1.05 (t, J=7.0 Hz, 3H, δCH$_3$-Ile$^4$), 0.80 (d, J=6.0 Hz, 3H, δCH$_3$-Leu$^2$), 0.78 (d, J=6.0 Hz, 3H, δCH$_3$-Leu$^2$).

$^{13}$C NMR (125 MHz, d$_5$-pyridine) δ=175.58 (γCO-βOH-Asn$^7$), 174.23 (CO-βOH-Leu$^1$), 173.97 (CO-Arg$^3$), 173.89 (CO-Ser$^8$ or CO-Leu$^2$), 173.69 (CO-Thr$^5$), 173.55 (CO-Ser$^8$ or CO-Leu$^2$), 172.48 (CO-Ile$^4$), 170.90 (CO-βOH-Asn$^7$), 170.50 (CO-Gly$^6$), 158.67 (ζC-Arg$^3$), 157.06 (CO-Boc), 79.13 (C-Boc), 77.09 (βCH-βOH-Leu$^1$), 72.29 (βCH-βOH-Asn$^7$), 68.32 (βCH-Thr$^5$), 63.24 (δCH-Ser$^8$), 59.79 (αCH-Ile$^4$), 59.60 (αCH-Thr$^5$), 58.35 (αCH-βOH-Leu$^1$), 57.11 (αCH-βOH-Asn$^7$), 56.94 (αCH-Ser$^8$), 54.06 (αCH-Arg$^3$), 53.60 (αCH-Leu$^2$), 44.32 (αCH$_2$-Gly$^6$), 41.75 (δCH$_2$-Arg$^3$), 40.41 (βCH$_2$-Leu$^2$), 36.70 (δCH-Ile$^4$), 31.56 (γCH-βOH-Leu$^1$), 29.47 (δCH$_2$-Arg$^3$), 28.48 (Me$_3$-Boc), 26.11 (γCH-Arg$^3$), 25.74 (γCH$_2$-Ile$^4$), 24.93 (γCH-Leu$^2$), 22.94 (δCH$_3$-Leu$^2$), 21.71 (δCH$_3$-Leu$^2$), 21.20 (γCH-Thr$^5$), 19.48 (δCH$_3$-βOH-Leu$^1$), 19.43 (δCH$_3$-βOH-Leu$^1$), 16.02 (γCH-Ile$^4$), 11.20 (δCH$_3$-Ile$^4$).

HR-TOF-MS (Method 24): C$_{42}$H$_{77}$N$_{12}$O$_{16}$ [M+H]$^+$ found 1005.5560, calc. 1005.5576.

Example 101A

N$^2$-(Benzyloxycarbonyl)-N$^3$-{N$^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3S)-3-amino-O-methyl-D-tyrosine (2-(trimethylsilyl)ethyl) ester trifluoroacetate

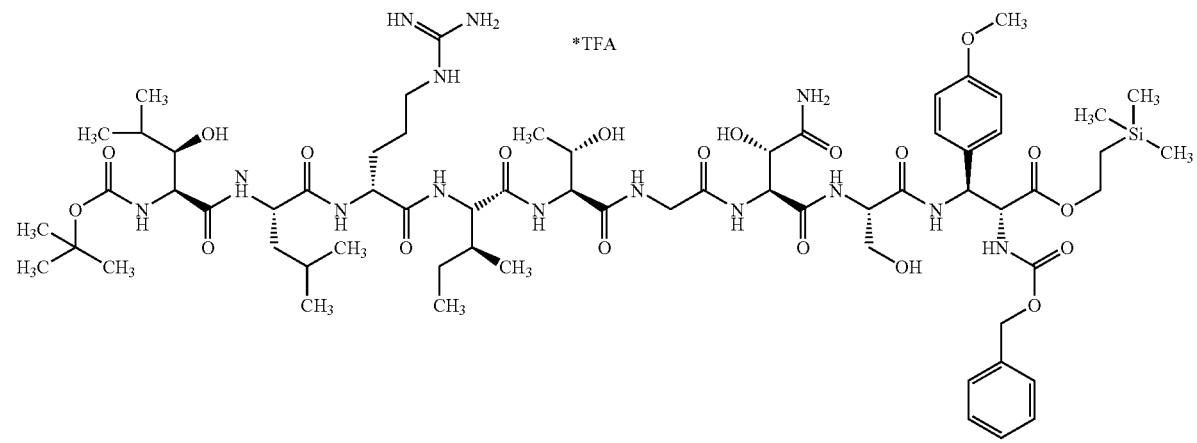

Under an argon protective gas atmosphere, firstly HATU (2.5 eq., 71 mg, 186 µmol) is added to a solution of example 98A (1.2 eq., 50 mg, 89 µmol), of the octapeptide acid (example 10A, 1.0 eq., 83 mg, 75 µmol) and N-methylmorpholine (3.5 eq., 29 µmol) in dry dimethylformamide (0.5 ml) at 0° C. The reaction mixture is stirred at 0° C. (about 3 h). The reaction mixture then shows complete conversion of the amine component (HPLC monitoring, method 5). Solid potassium dihydrogen phosphate (101 mg, 746 μmol, 10 eq.) is added to the reaction mixture and the mixture is filtered and then evaporated under high vacuum and purified by chromatography (method 43). 96.5 mg (84% of theory) of product are obtained.

$[\alpha]^{20}_{Na}$=−6 (c=0.04 in methanol).

HPLC/UV-Vis (Method 5): $R_t$=4.47 min.

HPLC/UV-Vis (Method 4): $R_t$=4.88 min.

LC-MS (Method 18): $R_t$=2.26 min; MS (ESIpos.): m/z (%)=652 (100), 1432 (50) [M+H]$^+$; MS (ESIneg.): m/z (%)=1430 (100) [M−H]$^-$.

HR-TOF-MS (Method 24): $C_{65}H_{107}N_{14}O_{20}Si$ [M+H]$^+$ found 1431.7570, calc. 1431.7550.

Example 102A

N$^2$-(Benzyloxycarbonyl)-N$^3$-{N$^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-O-methyl-L-tyrosine (2-(trimethylsilyl)ethyl) ester trifluoroacetate

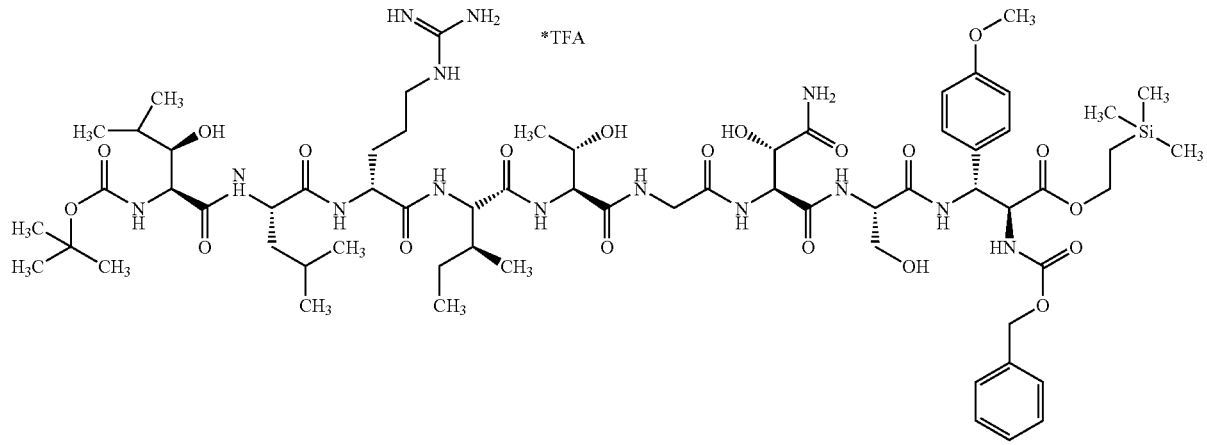

Example 99A (65 mg, 0.116 mmol) is reacted in analogy to the preparation method for example 101A (reaction time: 150 min). As product the title compound is obtained as a solid (111 mg, 74% of theory).

$[\alpha]^{20}_{Na}$=−17° (c=0.09 in methanol).

HPLC/UV-Vis (Method 5): $R_t$=4.47 min.

HPLC/UV-Vis (Method 4): $R_t$=4.87 min.

LC-MS (Method 18): $R_t$=2.16 min; MS (ESIpos.): m/z (%)=652 (100), 1432 (60) [M+H]$^+$; MS (ESIneg.): m/z (%)=1430 (100) [M−H]$^-$.

HR-TOF-MS (Method 24): $C_{65}H_{107}N_{14}O_{20}Si$ [M+H]$^+$ found 1431.7509, calc. 1431.7550.

Example 103A

N²-(Benzyloxycarbonyl)-N³-{N²·¹-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3S)-3-amino-O-methyl-D-tyrosine trifluoroacetate HPLC/UV-Vis (Method 5): $R_t$=3.93 min.

HPLC/UV-Vis (Method 4): $R_t$=4.27 min.

LC-MS (Method 18): $R_t$=2.00 min; MS (ESIpos.): m/z (%)=616 (100), 1332 (20) [M+H]⁺; MS (ESIneg.): m/z (%)=1330 (100) [M−H]⁻.

HR-TOF-MS (Method 24): $C_{60}H_{95}N_{14}O_{20}$ [M+H]⁺ found 1331.6844, calc. 1331.6842.

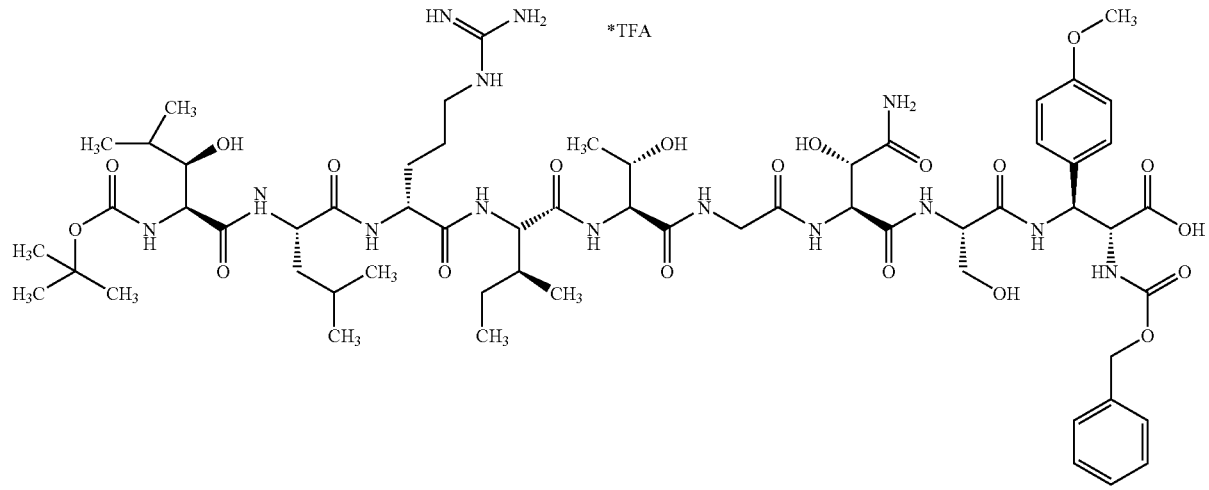

Example 101A (96 mg, 62 µmol) is provided in dry THF (4 ml) under an argon protective gas atmosphere. While stirring vigorously at RT, a 1 N TBAF-THF solution (310 µl, 5 eq.) is added dropwise. Further portions of TBAF (each 5 eq.) are added at regular intervals of 30 min. After about 45 eq., the HPLC chromatogram (method 5) shows complete conversion. The reaction mixture is then neutralized with potassium dihydrogen phosphate (253 mg, about 30 eq.). The reaction mixture is filtered, evaporated in vacuo and purified by preparative HPLC (method 43). 83 mg (93% of theory) of the title compound are obtained.

Example 104A

N²-(Benzyloxycarbonyl)-N³-{N²·¹-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-O-methyl-L-tyrosine trifluoroacetate

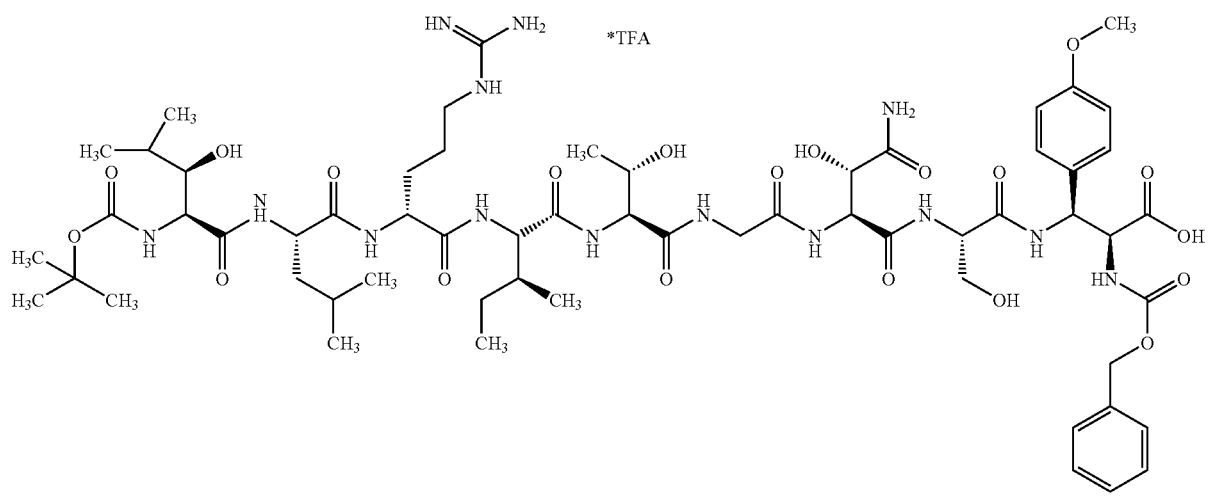

Example 102A (105 mg, 0.068 mmol) is reacted in analogy to the preparation method for example 103A (total of 45 eq. of TBAF). As product the title compound is obtained as a solid (90 mg, 99% of theory).

$[\alpha]^{20}_{Na}=-9°$ (c=0.135 in methanol).

HPLC/UV-Vis (Method 5): $R_t$=3.93 min.

HPLC/UV-Vis (Method 4): $R_t$=4.15 min.

LC-MS (Method 20): $R_t$=1.80 min; MS (ESIpos.): m/z (%)=616 (100), 1332 (40) [M+H]$^+$; MS (ESIneg.): m/z (%)=664 (60), 1330 (100) [M−H]$^-$.

HR-TOF-MS (Method 24): $C_{60}H_{95}N_{14}O_{20}$ [M+H]$^+$ found 1331.6840, calc. 1331.6842.

Example 105A

N$^2$-(Benzyloxycarbonyl)-N$^3$-{[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3S)-3-amino-O-methyl-D-tyrosine trifluoroacetate According to method 1 example 103A (10 mg, 7 μmol) is reacted under an argon protective gas atmosphere. 9.3 mg (99.9% of theory) of the title compound are obtained after freeze-drying.

HPLC/UV-Vis (Method 5): $R_t$=3.47 min.

LC-MS (Method 18): $R_t$=1.50 min; MS (ESIpos.): m/z (%)=616 (100), 1232 (5) [M+H]$^+$; MS (ESIneg.): m/z (%)=1230 (100) [M−H]$^-$.

HR-TOF-MS (Method 24): $C_{55}H_{87}N_{14}O_{18}$ [M+H]$^+$ found 1231.6300, calc. 1231.6318.

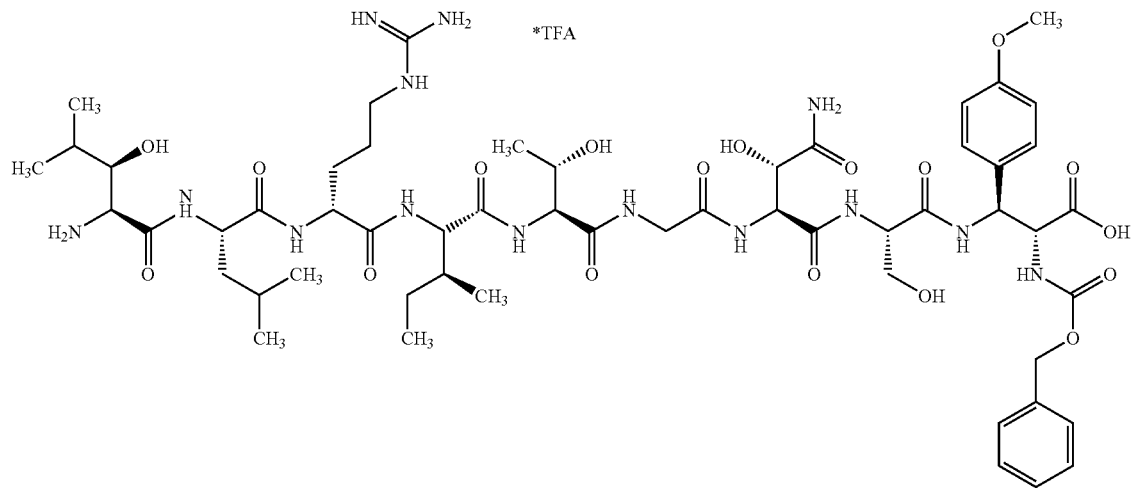

Example 106A

N$^2$-(Benzyloxycarbonyl)-N$^3$-{N$^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-O-methyl-L-tyrosine

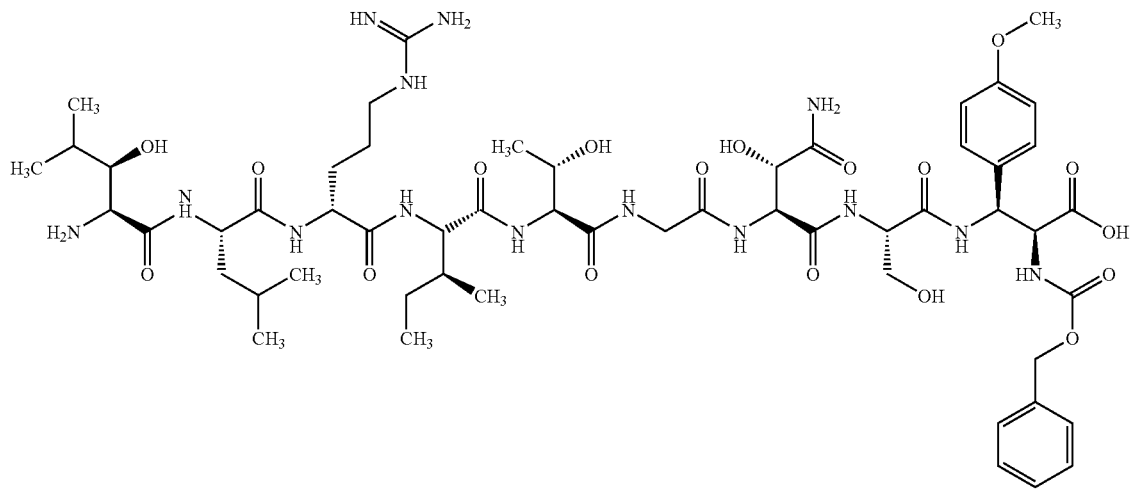

According to procedure 1 example 104A (240 mg, 166 µmol) is reacted under an argon protective gas atmosphere 116 mg (57% of theory) of the title compound are obtained after freeze drying.

$[\alpha]^{20}_{Na}$=−24° (c=0.07 in methanol).

HPLC/UV-Vis (Method 5): $R_t$=3.47 min.

HPLC/UV-Vis (Method 4): $R_t$=3.83 min.

LC-MS (Method 18): $R_t$=1.51 min; MS (ESIpos.): m/z (%)=616 (100), 1232 (5) [M+H]$^+$; MS (ESIneg.): m/z (%)=1230 (100) [M−H]$^-$.

HR-TOF-MS (Method 24): $C_{55}H_{87}N_{14}O_{18}$ [M+H]$^+$ found 1231.6361, calc. 1231.6318.

Example 107A $N^{2.1}$-(Benzyloxycarbonyl)-[(3S)-3-amino-O-methyl-D-tyrosyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam trifluoroacetate

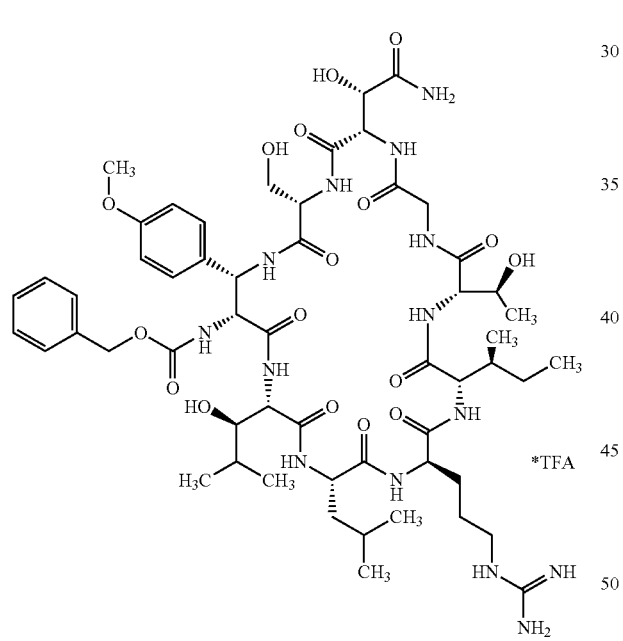

HATU (1.5 mg, 8 µmol, 5 eq.) is firstly added to a solution of example 105A (1.9 mg, 2 µmol, 1 eq.) and NMM (1.7 µL, 15 µmol, 10 eq.) in dry DMF (200 µl) at 0° C. under an argon protective gas atmosphere. The reaction mixture is stirred at 0° C. (about 90 min). The reaction mixture then shows complete conversion of the amine component (HPLC monitoring, method 5). Solid potassium dihydrogen phosphate (20 eq., 4.2 mg, 31 µmol) is added, and the reaction mixture is filtered and then evaporated under high vacuum and purified by chromatography (method 45). 1.8 mg (96% of theory) of product are obtained.

HPLC/UV-Vis (Method 5): $R_t$=3.65 min.

HPLC/UV-Vis (Method 4): $R_t$=3.91 min.

LC-MS (Method 18): $R_t$=1.67 min; MS (ESIpos.): m/z (%)=1214 (100) [M+H]$^+$.

HR-TOF-MS (Method 24): $C_{55}H_{85}N_{14}O_{17}$ [M+H]$^+$ found 1213.6232, calc. 1213.6312.

Example 108A $N^{2.1}$-(Benzyloxycarbonyl)-[(3R)-3-amino-O-methyl-L-tyrosyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam trifluoroacetate

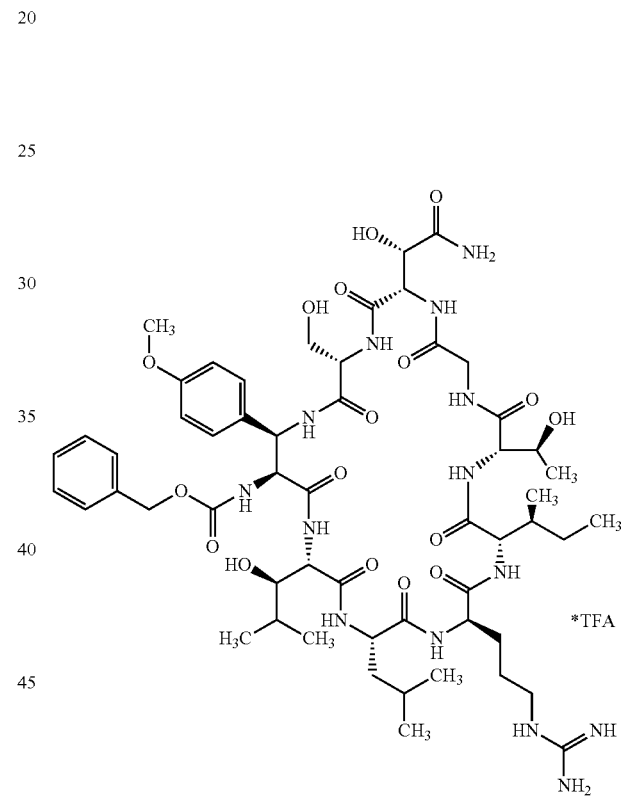

Example 106A (120 mg, 0.097 mmol) is reacted in analogy to the preparation method for example 107A (reaction time 1 h). The title compound is obtained as a solid (39 mg, 33% of theory).

$[\alpha]^{20}_{Na}$=−58° (c=0.07 in methanol).

HPLC/UV-Vis (Method 5): $R_t$=3.71 min.

HPLC/UV-Vis (Method 4): $R_t$=3.98 min.

LC-MS (Method 18): $R_t$=1.74 min; MS (ESIpos.): m/z (%)=1214 (100) [M+H]$^+$; MS (ESIneg.): m/z (%)=1212 (100) [M−H]$^-$.

HR-TOF-MS (Method 24): $C_{55}H_{85}N_{14}O_{17}$ [M+H]$^+$ found 1213.6227, calc. 1213.6312.

Example 109A

[(3S)-3-Amino-O-methyl-D-tyrosyl)]-[(3R)-3-hydroxy-L-leucyl]-L-leucyl-D-arginyl-L-iso-leucyl-L-allothreonyl-glycyl-[(3S)-3-hydroxy-L-asparaginyl]-L-serine $C^{1.9}$-$N^{3.1}$-lactam bistrifluoroacetate

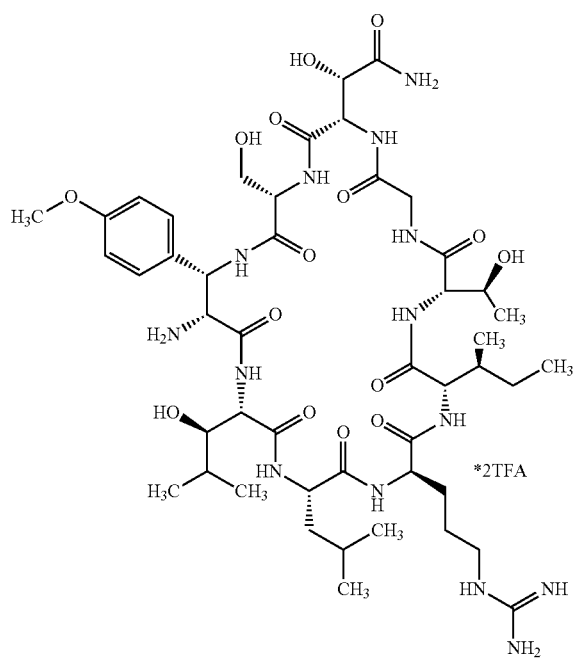

Example 107A (65 mg, 49 μmol) is dissolved in methanol (5 ml) and, under an argon protective gas atmosphere, 10 percent palladium-carbon (10 mg) as well as aqueous 1 N hydrochloric acid (250 μl) are added. Hydrogenation is carried out at RT and under atmospheric pressure until (about 90 min) the analytical HPLC (method 5) indicates complete conversion. The reaction mixture is filtered (through kieselguhr, Celite® or a syringe filter, Biotage, PTFE), concentrated in vacuo and purified by chromatography (method 43). 40.6 mg (63% of theory) of the title compound are obtained.

$[\alpha]^{20}_{Na}$=−21° (c=0.06 in methanol).

HPLC/UV-Vis (Method 5): $R_t$=3.28 min.

HPLC/UV-Vis (Method 4): $R_t$=3.55 min.

LC-MS (Method 18): $R_t$=1.20 min; MS (ESIpos.): m/z (%)=540 (100), 1079 (20) [M+H]$^+$; MS (ESIneg.): m/z (%)=1077 (100) [M−H]$^-$.

HR-TOF-MS (Method 24): $C_{47}H_{78}N_{14}O_{15}$ [M+H]$^+$ found 1079.5835, calc. 1079.5844.

Example 110A

[(3R)-3-Amino-O-methyl-L-tyrosyl)]-[(3R)-3-hydroxy-L-leucyl]-L-leucyl-D-arginyl-L-iso-leucyl-L-allothreonyl-glycyl-[(3S)-3-hydroxy-L-asparaginyl]-L-serine $C^{1.9}$-$N^{3.1}$-lactam bistrifluoroacetate

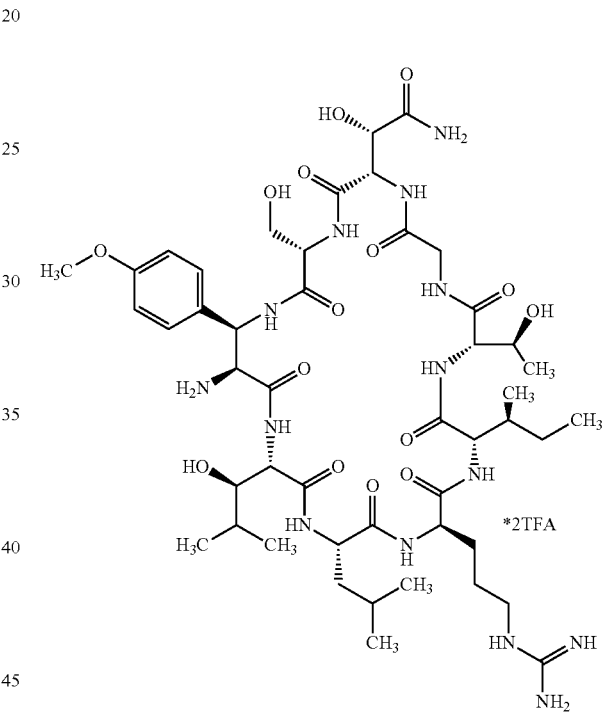

Example 108A (12 mg, 9 μmol) is reacted in analogy to the preparation method for example 109A (reaction time 90 min). As product the title compound is obtained as a solid (10.3 mg, 87% of theory).

$[\alpha]^{20}_{Na}$=−52° (c=0.03 in methanol).

HPLC/UV-Vis (Method 5): $R_t$=3.18 min.

HPLC/UV-Vis (Method 4): $R_t$=3.52 min.

LC-MS (Method 18): $R_t$=1.25 min; MS (ESIpos.): m/z (%)=540 (100), 1079 (5) [M+H]$^+$; MS (ESIneg.): m/z (%)=1077 (100) [M−H]$^-$.

Example 111A

[N²-(Benzyloxycarbonyl)-3-tert-butyl-D-alanyl]-[3-tert-butyl-L-alanyl]-[(3S)-3-amino-O-methyl-D-tyrosyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam trifluoroacetate

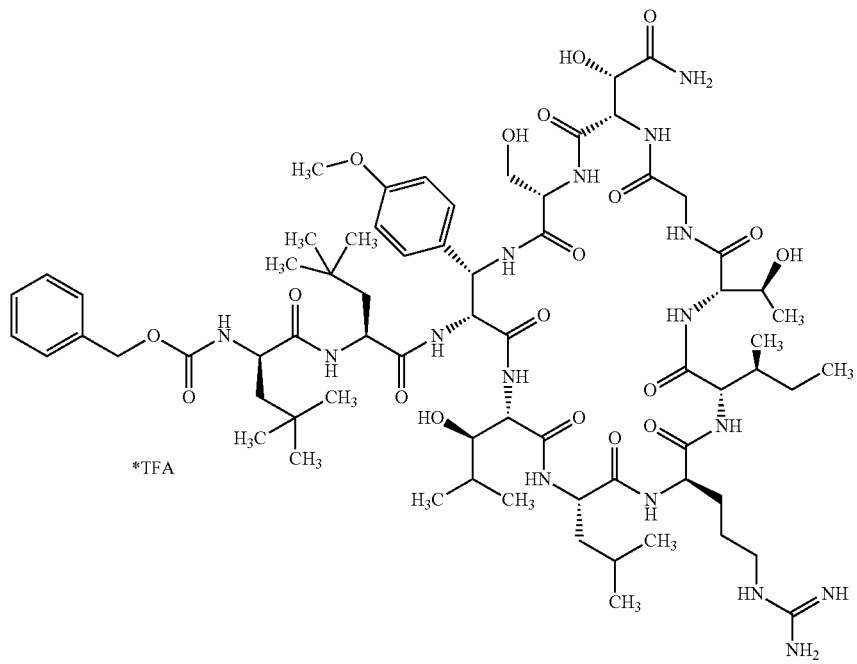

HATU (2.2 mg, 6 µmol, 2.5 eq.) is firstly added to a solution of example 109A (3.0 mg, 2 µmol, 1.0 eq.), the dipeptide acid (example 10A, 2.3 mg, 6 µmol, 2.5 eq.) and NMM (11 µmol, 5 eq.) in dry DMF (1 ml) at −30° C. under an argon protective gas atmosphere. The reaction mixture is stirred and slowly warms (about 1 h) to 0° C. NMM (6 µmol, 2.5 eq. each time) and HATU (6 µmol, 2.5 eq. each time) are added to the reaction mixture at regular intervals (30 min) until the HPLC monitoring (method 5) indicates complete conversion of the amine component. In total, about 20 eq. of NMM and HATU are required for this. Solid potassium dihydrogen phosphate (9.4 mg, 69 µmol, 30 eq.) is added, and the reaction mixture is filtered and then evaporated under high vacuum and purified by chromatography (method 43). 2 mg (55% of theory) of product are obtained.

HPLC/UV-Vis (Method 5): $R_t$=4.2 min.

HPLC/UV-Vis (Method 4): $R_t$=4.49 min.

LC-MS (Method 18): $R_t$=2.07 min; MS (ESIpos.): m/z (%)=734 (100) [M+2H]$^{2+}$, 1468 (20) [M+H]$^+$; MS (ESIneg.): m/z (%)=678 (100), 732 (5) [M−2H]$^{2-}$, 1466 (10) [M−H]$^-$.

HR-TOF-MS (Method 24): $C_{69}H_{111}N_{16}O_{19}$ [M+H]$^+$ found 1467.8228, calc. 1467.8206.

Example 112A

[N²-(Benzyloxycarbonyl)-3-tert-butyl-D-alanyl]-[3-tert-butyl-L-alanyl]-[(3R)-3-amino-O-methyl-L-tyrosyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam trifluoroacetate

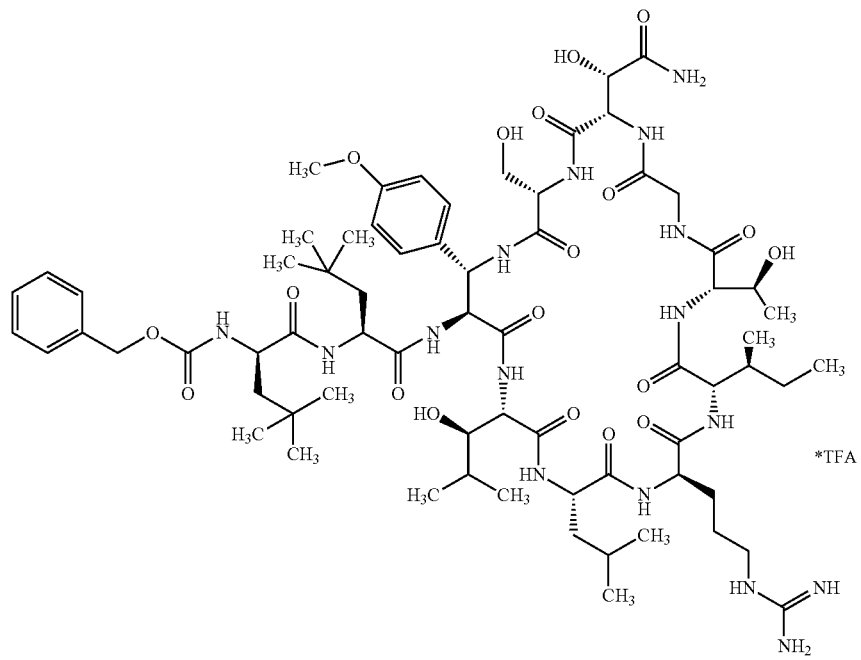

Preparation in analogy to example 111A from the compound of example 109A (30 mg, 23 µmol) and exemplary compound 10A (23.3 mg, 57 µmol, 2.5 eq.). The crude product is purified by chromatography (method 43), whereby after freeze drying 25 mg (69% of theory) of product are obtained as a solid.

$[\alpha]^{20}_{Na}$=−62° (c=0.06 in methanol).
HPLC/UV-Vis (Method 5): $R_t$=4.4 min.
LC-MS (Method 18): $R_t$=2.31 min.
MS (ESIpos.): m/z (%)=734 (100) $[M+2H]^{2+}$, 1468 (20) $[M+H]^+$;
MS (ESIneg.): m/z (%)=678 (70), 733 (100) $[M-2H]^{2-}$, $^{1466}$ (10) $[M-H]^-$.
HR-TOF-MS (Method 24): $C_{69}H_{111}N_{16}O_{19}$ $[M+H]^+$ found 1467.8206, calc. 1467.8206.

Example 113A

3-Amino-3-(4-bromophenyl)propionic acid

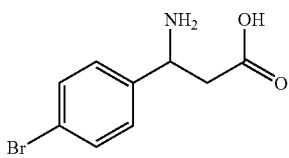

4-Bromobenzaldehyde (50.0 g, 270 mmol), malonic acid (28.1 g, 270 mmol) and ammonium acetate (27.7 g, 359 mmol, 1.3 eq.) are dissolved in ethanol (400 ml). The mixture is heated at reflux for 16 h. The resulting solid is collected on a glass filter funnel, collected with suction filtration and washed with ethanol. The residue is then recrystallized from methanol (80 ml). It is subsequently triturated with ethyl acetate and collected by suction filtration. 41.0 g (0.16 mmol, 62% of theory) of the title compound are obtained as a colorless crystalline solid.

HPLC (Method 5): $R_t$=3.13 min.
LC-MS (Method 20): $R_t$=0.97 min, MS (ESIneg.): m/z (%)=242.0 (100) and 244.0 (80) $[M-H]^-$.
¹H NMR (300 MHz, $d_6$-DMSO) δ=2.36-2.38 (m, 2H, 2-H), 4.25 ("t", J=6.8, 7.6 Hz, 2H, 3-H), 6.56 (d, J=16.1 Hz, 1H, N—H), 7.38 (d, J=8.5 Hz, 1H, N—H), 7.52-7.71 (m, 4H, arom. H).
¹³C-NMR (126 MHz, DCOOD) δ=36.5 ($CH_2$, C-2), 51.9 (CH, C-3), 123.7 (C quat), 129.2 (CH), 132.4 (CH), 133.5 (C quat), 174.0 (C quat, C-1).
HR-TOF-MS (Method 24): $C_9H_{11}NO_2Br$ $[M+H]^+$ calc. 243.9968, found 243.9980.

Example 114A

Methyl 3-amino-3-(4-bromophenyl)propionate hydrochloride

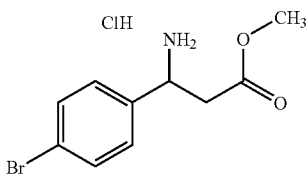

41.0 g (157 mmol) of compound 113A are suspended in methanol (1000 ml) under an argon protective gas atmosphere. 102 ml (410 mmol, 2.6 eq.) of 4 M hydrochloric acid in 1,4-dioxane are added. The starting material dissolves spontaneously on the addition of the hydrochloric acid, and the mixture is stirred at RT overnight. The mixture is then concentrated to dryness in vacuo. The product (51.8 g, purity about 69%, yield 77% of theory) is obtained as a solid and employed without further purification in the next step.

HPLC (Method 5): $R_t$=3.35 min.

LC-MS (Method 20): $R_t$=1.24 min, MS (ESIpos.): m/z (%)=240.9 (20) and 242.8 (20) $[M-NH_2+H]^+$.

$^1$H NMR (300 MHz, $d_6$-DMSO) δ=2.99 (dd, $J_{2,3}$=8.7 Hz, $J_{2,2}$=16.4 Hz, 1H, 2-$H_A$), 3.16 (dd, $J_{2,3}$=4.0 Hz, $J_{2,2}$=16.4 Hz, 1H, 2-$H_B$), 3.56 (s, 3H, $OCH_3$), 4.62 (br. s, 1H, 3-H), 7.49 (d, J=8.5 Hz, 2H, 2'-H), 7.65 (d, J=8.5 Hz, 2H, 2'-H), 8.64 (br. s, 2H, $NH_2$).

$^{13}$C-NMR (126 MHz, $CDCl_3$) δ=43.8 ($CH_2$, C-2), 51.8 ($CH_3$, $OCH_3$), 52.1 (CH, C-3), 121.2 (C quat, C-4'), 128.0 (CH, C-arom.), 131.7 (CH, C-arom.), 143.6 (C quat, C-1'), 172.2 (C quat, C-1).

HR-TOF-MS (Method 24): $C_{10}H_{13}NO_2Br$ $[M+H]^+$ calc. 258.0125, found 258.0119.

Example 115A

Methyl N-butoxycarbonyl-3-amino-3-(4-bromophenyl)propionate

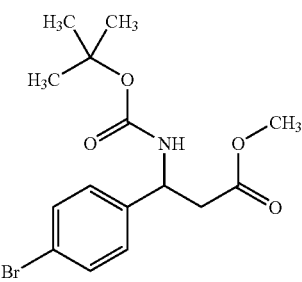

Compound 114A (51.8 g, 121 mmol, 69% purity) is dissolved in 1,4-dioxane/water (2:1, 540 ml). Di-tert-butyl dicarbonate (29.1 g, 133 mmol, 1.1 eq.) and triethylamine (38.8 ml, 28.22 g, 2.3 eq.) are added, and the mixture is stirred at RT for 150 min. The dioxane is distilled off in vacuo, and 150 ml of ethyl acetate and 200 ml of a sat. aq. sodium bicarbonate solution are added. Part of the product 115A precipitates spontaneously and is isolated by filtration. The phases of the filtrate are separated, and the organic phase is washed with 0.5 M citric acid, dried over sodium sulfate and concentrated. A further fraction 115A is obtained from the residue by trituration with methanol. Total yield: 32.9 g (92 mmol, 76% of theory) of the title compound as solid.

HPLC (Method 5): $R_t$=4.80 min.

LC-MS (Method 20): $R_t$=2.37 min, MS (ESIpos.): m/z (%)=358.0 (15) and 360.0 (15) $[M+H]^+$.

$^1$H NMR (300 MHz, $d_6$-DMSO)=1.34 (s, 9H, $COC(CH_3)_3$), 2.62-2.79 (m, 2H, 2-H), 3.55 (s, 3H, $OCH_3$), 4.87 (dd, J=7.9 Hz, $J_2$=15.1 Hz, 1H, 3-H), 7.26 (d, $J_{2',3'}$=8.3 Hz, 2H, 2'-H), 7.51 (d, $J_{2',3'}$=8.3 Hz, 2H, 3'-H).

$^{13}$C-NMR (126 MHz, $CDCl_3$) δ=28.3 ($CH_3$, $COC(CH_3)_3$), 40.4 ($CH_2$, C-2), 50.6 (CH, C-3), 51.9 ($CH_3$, $OCH_3$), 79.9 (C quat, $COC(CH_3)_3$), 121.4 (C quat, C-4'), 127.9 (CH, C-arom.), 131.7 (CH, C-arom.), 140.3 (C quat, C-1'), 155.0 (C quat, $COC(CH_3)_3$, 171.2 (C quat, C-1).

HR-TOF-MS (Method 24): $C_{15}H_{21}NO_4Br$ $[M+H]^+$ calc. 358.0649, found 358.0659.

Example 116A

Methyl (S)-N-butoxycarbonyl-3-amino-3-(4-bromophenyl)propionate

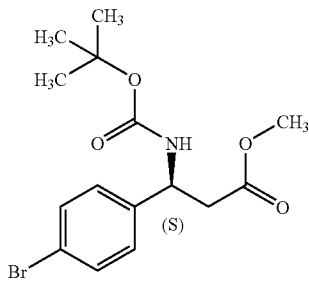

The racemic compound 115A is separated into the title compound (96% ee) and the other enantiomer (>99% ee) by chiral HPLC (method 42). 750 mg of 115A are loaded per run. The (S) enantiomer (example 116A) and the (R) enantiomer are isolated quantitatively in 50% of theory in each case.

Determination of enantiomers by method 17.

HPLC/UV-VIS (Method 17): $R_t$=4.31 min. (title compound)

$[α]^{20}_{Na}$=−38.6 (c=1.0, MeOH). (title compound)

HPLC/UV-VIS (Method 17): $R_t$=3.82 min. (further enantiomer)

$[α]^{20}_{Na}$=+36.8 (c=1.0, MeOH). (further enantiomer)

Example 117A

Methyl (S)-N-butoxycarbonyl-3-amino-3-(4-dimethylaminophenyl)propionate

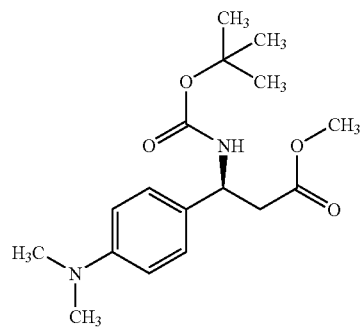

When carrying out this reaction, care must be taken that oxygen and moisture are strictly excluded and the reagents are kept under a dry argon protective gas atmosphere, because otherwise only inadequate conversion takes place. Because the size of the microwave limits the batch size, larger amounts are divided into portions of about 7 mmol of example 116A and processed sequentially.

Example 116A (2.5 g, 6.98 mmol), dimethylamine (1 M in THF, 16 ml, 32 mmol, 4.6 eq.), XPHOS (0.4 g, 0.84 mmol, 0.12 eq.), cesium carbonate (3.2 g, 9.75 mmol, 1.4 eq.) and bis(dibenzylideneacetone)palladium(0) (0.20 g, 0.35 mmol, 0.05 eq.) are mixed under an argon protective gas atmosphere in a 20 ml microwave reaction vessel and crimp-sealed. The mixture is heated in a microwave reactor (Emrys Optimizer Single-Mode laboratory microwave reactor) at 170° C. for 1 h. After cooling, extraction is carried out with water and ethyl acetate, and the organic phase is dried over sodium sulfate. The solvent is removed, the residue is dissolved in methanol, the solution is filtered and the filtrate is concentrated. 117A is obtained in a yield of 2.0 g (6.19 mmol, 89% of theory) and in a purity sufficient for further reaction.

For analytical purposes, a sample of example 117A is fine purified by preparative HPLC (method 33).

HPLC (Method 5): $R_t$=3.60 min.

LC-MS (Method 20): $R_t$=1.84 min, MS (ESIpos.): m/z (%)=323.3 (100) [M+H]$^+$.

$[\alpha]^{20}_{Na}$=−31.0 (c=1.0, MeOH).

$^1$H NMR (400 MHz, d$_6$-DMSO) δ=1.35 (s, 9H, COC(CH$_3$)$_3$), 2.63 (dd, J$_{2,3}$=6.6 Hz, J$_{gem}$=15.5 Hz, 1H, 2-H$_A$), 2.72 (dd, J$_{2,3}$=8.8 Hz, J$_{gem}$=15.5 Hz, 1H, 2-H$_B$), 2.93 (s, 6H, N(CH$_3$)$_2$), 3.54 (s, 3H, OCH$_3$), 4.84 (m, 1H, 3-H), 6.88 (br. s, 2H, 2'-H), 7.20 (d, J$_{2',3'}$=8.3 Hz, 2H, 3'-H), 7.36 (d, J=8.8 Hz, 1H, N—H).

$^{13}$C-NMR (126 MHz, CDCl$_3$) δ=28.3 (CH$_3$, COC(CH$_3$)$_3$), 40.3 (CH$_2$, C-2), 44.9 (CH$_3$, N(CH$_3$)$_2$), 50.3 (CH, C-3), 52.0 (CH$_3$, OCH$_3$), 80.1 (COC(CH$_3$)$_3$), 119.1 (CH, C-3'), 128.0 (CH, C-2'), 140.3 (C quat, C-1'), 144.1 (C quat, C-4'), 155.1 (C quat, COC(CH$_3$)$_3$), 171.2 (C quat, C-1).

HR-TOF-MS (Method 24): C$_{17}$H$_{27}$N$_2$O$_4$ [M+H]$^+$ calc. 322.1893, found 322.1890.

Example 118A

Methyl (3R)-N$^2$-[(benzyloxy)carbonyl]-N$^2$-[(benzyloxy)carbonylamino]-3-[(tert-butoxy-carbonyl)amino]-3-(4-dimethylaminophenyl)-D-alaninate mixed with methyl (3R)-N$^2$-[(benzyloxy)-carbonyl]-N$^2$-[(benzyloxy)carbonylamino]-3-[(tert-butoxycarbonyl)amino]-3-(4-dimethylaminophenyl)-L-alaninate

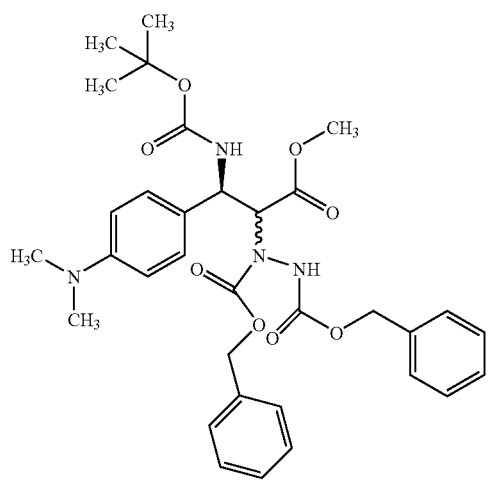

A 1 M LHMDS-solution in THF (21.3 ml, 21.29 mmol, 2.2 eq.) is added to 70 ml of abs. THF under an argon protective gas atmosphere and cooled to −78° C. A solution of compound 117A (3.1 g, 9.68 mmol) in THF (35 ml) is added and the solution is warmed to −25° C., at which temperature it is then stirred for a further 10 min. The mixture is then cooled again to −78° C., dibenzyl azadicarboxylate (3.2 g, 10.65 mmol, 1.1 eq.) is added all at once, and the mixture is stirred for 3 h. At the end the reaction is stopped with acetic acid (2.8 ml, 48.39 mmol, 5 eq.) at −78° C. and stirred for a further 15 min. at this temperature. After warming to RT, an aqueous conc. sodium bicarbonate solution is added and extraction is carried out with several portions of ethyl acetate. The combined organic extracts are washed with an aq. sat. sodium chloride solution, dried over sodium sulfate and concentrated. The amorphous orange-brown residue is covered with a layer of diethyl ether and left to stand for some hours. Part of the product of example 118A separates out in the form of crystals during this time. The remaining product of example 118A can be isolated from the filtrate by flash chromatography (Biotage 40M silica gel, cyclohexane/ethyl acetate 3:1) and renewed crystallization in the presence of diethyl ether, the product being mixed with the diastereomer of example 119A. Total yield of all stereoisomers and mixtures: 1.5 g (2.48 mmol, 18% of theory).

For analytical purposes, a sample of pure diastereomer of example 118A is fine purified by preparative HPLC (method 33).

HPLC (Method 5): $R_t$=4.52 min.

LC-MS (Method 20): $R_t$=2.87 min, MS (ESIpos.): m/z (%)=621.5 (50) [M+H]$^+$.

$[\alpha]^{20}_{Na}$=−22.8 (c=1.0, MeOH).

$^1$H NMR (400 MHz, d$_6$-DMSO) δ=1.30 (s, 9H, COC(CH$_3$)$_3$), 2.86 (s, 6H, N(CH$_3$)$_2$), 3.30 (s, 3H, OCH$_3$), 4.74-5.11 (m, 6H), 6.62 (d, J=8.8 Hz, 2H), 7.15-7.51 (m, 12H, arom. H).

Example 119A

Methyl (3R)-N$^2$-[(benzyloxy)carbonyl]-N$^2$-[(benzyloxy)carbonylamino]-3-[(tert-butoxy-carbonyl)amino]-3-(4-dimethylaminophenyl)-L-alaninate

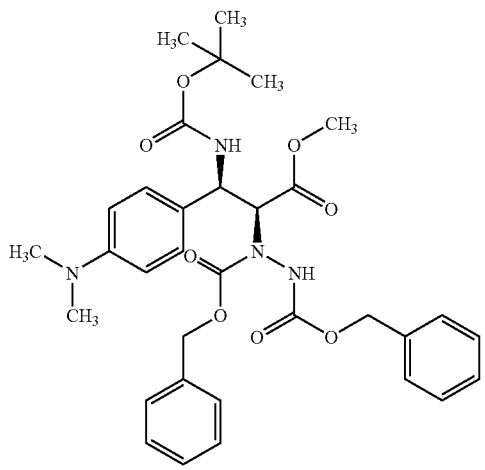

The compound of example 118A (1.6 g, 1.90 mmol) is dissolved in dichloromethane (60 ml). At 0° C., TMG (2.6 ml, 20.93 mmol, 11 eq.) is added and the reaction is stirred at RT overnight. To stop the reaction, the mixture is first cooled to 0° C. and acetic acid (1.3 ml, 22.83 mmol, 12 eq.) is then added. The mixture is diluted with water and extracted with 3 portions of dichloromethane, and the combined organic extracts are concentrated. The residue is triturated with an ethyl acetate/diethyl ether mixture. The compound of example 119A crystallizes, and the compound of example 118A remains predominantly in the supernatant. The latter is concentrated and again subjected to the isomerization with 2 ml of TMG and dichloromethane (40 ml). A second portion of the title compound of example 119A is obtained thereby. The supernatant of the crystallization is chromatographed (method 33) and reisomerized, and a third portion of example 119A is obtained. Total yield: 1.1 g (1.72 mmol, 90% of theory) of example 119A in the form of crystals.

HPLC (Method 5): R$_t$=4.76 min.

LC-MS (Method 20): R$_t$=3.12 min, MS (ESIpos.): m/z (%)=621.5 (90) [M+H]$^+$; MS (ESIneg): m/z (%) 619.5 (60) [M-H]$^-$.

[α]$^{20}_{Na}$=-118 (c=1.0, CHCl$_3$).

$^1$H NMR (400 MHz, d$_6$-DMSO) δ=1.30 (s, 9H, COC(CH$_3$)$_3$), 2.86 (s, 6H, N(CH$_3$)$_2$), 3.30 (s, 3H, OCH$_3$), 4.75-5.23 (m, 4H), 6.62 (d, J=8.8 Hz, 2H), 7.15-7.61 (m, 12H), 8.29 (br. s, 1H, N—H), 8.72 (br. s, 1H, N—H).

$^{13}$C-NMR (126 MHz,) δ=27.94 and 28.07 (CH$_3$, C(CH$_3$)$_3$), 51.31 (CH$_3$), 51.62 (CH$_3$), 51.98 (CH, C-7), 61.81 (CH, C-6), 66.18 and 66.32 and 66.50 (CH$_2$, OCH$_2$Ph), 67.49 and 67.65 (CH$_2$, OCH$_2$Ph), 78.68 and 78.90 (C quat, C-11), 111.74 (CH, C-3'), 123.54 (CH), 124.06 (CH), 126.76 (CH), 127.18 (CH), 127.30 (CH), 127.55 (CH), 127.76 (CH), 127.83 (CH), 127.98 (CH), 128.24 (CH), 128.30 (CH), 128.79 (CH), 135.59 (C quat), 135.77 (C quat), 135.99 (C quat), 136.11 (C quat), 149.74 (C quat), 154.21 (C quat), 154.68 (C quat), 154.92 (C quat), 155.03 (C quat), 155.14 (C quat), 156.09 (C quat), 156.24 (C quat), 166.97 (C quat, C=O).

HR-TOF-MS (Method 24): C$_{33}$H$_{41}$N$_4$O$_8$ [M+H]$^+$ calc. 621.2919, found 621.2922.

Example 120A

Methyl (3R)-3-[(tert-butoxycarbonyl)amino]-4-(dimethylaminophenyl)-L-alaninate

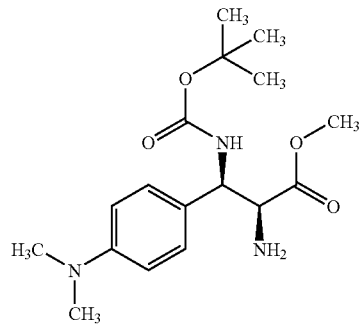

The compound of example 119A (938 mg, 1.51 mmol) is dissolved in dichloromethane-methanol 1:1 (30 ml). Raney nickel (about 200 mg) is added under an argon protective gas atmosphere, and the mixture is hydrogenated under 80 bar for 4 d. When no starting material is detectable any longer by HPLC (method 5), the catalyst is removed by filtration. The filtrate is concentrated. 0.6 g of crude product (purity about 70%) are obtained and are employed without further purification in the next step. For analytical purposes, a sample of the pure compound from example 120A is fine purified by preparative HPLC (method 27).

HPLC (Method 5): R$_t$=3.25 min.

LC-MS (Method 20): R$_t$=1.34 min, MS (ESIpos.): m/z (%)=338.2 (30) [M+H]$^+$.

[α]$^{20}_{Na}$=-11.5° (c=1.0, MeOH).

$^1$H NMR (500 MHz, d$_6$-DMSO) δ=1.37 (s, 9H, COC(CH$_3$)$_3$), 2.90 (s, 6H, N(CH$_3$)$_2$), 3.54 (s, 3H, OCH$_3$), 4.24 (d, J=5.4 Hz, 1H, β-H), 4.96 (dd, J=8.4 Hz, J=8.0 Hz, 1H, α-H), 6.73 (d, J$_{2',3'}$=8.0 Hz, 2H, 3'-H), 7.13 (d, J$_{2',3'}$=8.0 Hz, 2H, 2'-H), 7.46 (d, J=9.6 Hz, H, NH), 8.470 (br. s, 2H, NH$_2$).

$^{13}$C-NMR (126 MHz, d$_6$-DMSO) δ=28.07 (CH$_3$, COC(CH$_3$)$_3$), 40.19 (CH$_3$, N(CH$_3$)$_2$), 52.68 (CH$_3$, OCH$_3$), 54.11 (CH, C-β), 56.79 (CH, C-α), 78.87 (C quat, COC(CH$_3$)$_3$), 112.53 (CH, C-3'), 127.65 (CH, C-2'), 149.87 (C quat), 154.61 (C quat, COC(CH$_3$)$_3$), 167.96 (C quat, CO$_2$CH$_3$).

HR-TOF-MS (Method 24): $C_{17}H_{28}N_3O_4$ [M+H]$^+$ calc. 338.2075, found 338.2064.

Example 121A

Methyl (3R)-N$^2$-(benzyloxy)carbonyl)-3-[(tert-butoxycarbonyl)amino]-4-(dimethyl-aminophenyl)-L-alaninate

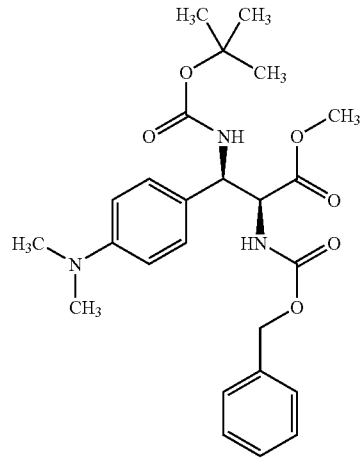

550 mg (1.14 mmol, 70% purity) of the compound of example 120A are dissolved in dioxane/water 8:2.8. Sodium bicarbonate (479 mg, 5.71 mmol, 5 eq.) and benzyl chlorformate (212 µl, 1.48 mmol, 1.3 eq.) are added and the mixture is stirred at RT for 2.5 h. The mixture is then extracted with water and ethyl acetate, and the organic phase is dried over sodium sulfate and concentrated. The title compound of example 121A can be obtained as crystals from the residue by trituration with diethyl ether. Yield: 490 mg (1.04 mmol, 91% of theory).

HPLC (Method 5): $R_t$=4.14 min.

LC-MS (Method 20): $R_t$=2.52 min, MS (ESIpos.): m/z (%)=472.3 (100) [M+H]$^+$.

$[\alpha]^{20}_{Na}$=−13.4° (c=1.0, MeOH).

$^1$H NMR (400 MHz, d$_6$-DMSO) δ=1.36 (s, 9H, COC(CH$_3$)$_3$), 2.86 (s, 6H, N(CH$_3$)$_2$), 3.30 (s, 3H, OCH$_3$), 4.45 (dd, $J_{\alpha,\beta\beta}$=4.2 Hz, J=9.3 Hz, 1H, β-H), 4.94 (d, $J_{gem}$=12.5 Hz, 1H, OCH$_2$Ph), 4.99 (d, $J_{gem}$=12.5 Hz, 1H, OCH$_2$Ph), 5.15 (dd, $J_{\alpha,\beta\beta}$=4.2 Hz, J=10.3 Hz, 1H, α-H), 6.65 (d, $J_{2',3'}$=8.8 Hz, 2H, 3'-H), 7.10 (d, $J_{2',3'}$=8.8 Hz, 2H, 2'-H), 7.23-7.37 (m, 5H), 7.54 (d, J=9.3 Hz, 1H, NH).

$^{13}$C-NMR—(126 MHz, d$_6$-DMSO) δ=28.0 (CH$_3$, COC(CH$_3$)$_3$), 41.1 (CH$_3$, N(CH$_3$)$_2$), 52.0 (CH$_3$, OCH$_3$), 53.8 (CH, C-β), 59.0 (CH, C-α), 65.4 (CH$_2$, OCH$_2$Ph), 78.3 (C quat, COC(CH$_3$)$_3$), 113.7 (CH), 126.9 (C quat), 127.3 (CH), 127.5 (CH), 127.8 (CH), 128.2 (C quat), 128.3 (CH), 136.6 (C quat), 154.6 (C quat, NCO$_2$), 156.0 (NCO$_2$), 170.7 (CO$_2$CH$_3$).

HR-TOF-MS: $C_{25}H_{34}N_3O_6$ [M+H]$^+$ calc. 472.2443, found 472.2460.

Example 122A (3R)-N$^2$-[(Benzyloxy)carbonyl]-3-[(tert-butoxycarbonyl)amino]-4-(dimethylaminophenyl)-L-alanine

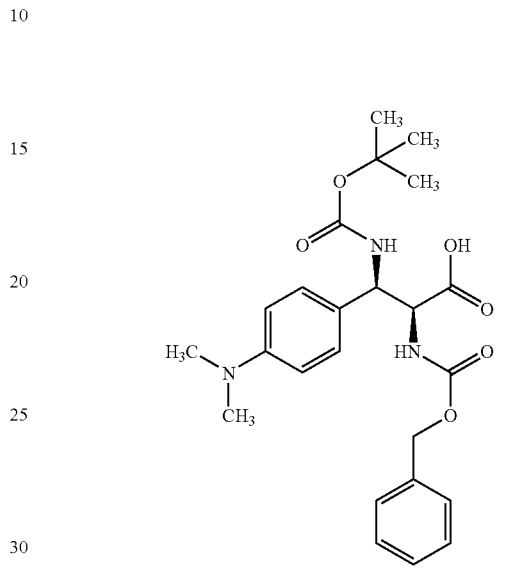

Compound 121A (444 mg, 0.94 mmol) is dissolved in a mixture of 5 ml of THF and 830 µl of water. At 0° C., 99 mg (2.35 mmol, 2.5 eq.) of lithium hydroxide monohydrate are added. The reaction is carried out at 0° C. for about 2 h until no starting material 121A is detectable any more (HPLC, method 5). The reaction is then stopped with acetic acid (620 µl, 2.83 mmol, 3 eq.). The mixture is diluted with water and extracted with ethyl acetate. The organic phase is dried over sodium sulfate and the solvent is distilled off. Yield: 430 mg (quant.).

HPLC (Method 5): $R_t$=3.80 min.

LC-MS (Method 20): $R_t$=2.21 min, MS (ESIpos.): m/z (%)=458.2 (100) [M+H]$^+$; MS (ESIneg): m/z (%)=456.3 (100) [M−H]$^-$.

$[\alpha]^{20}_{Na}$=−16.5 (c=1.0, MeOH).

$^1$H NMR (500 MHz, d$_6$-DMSO) δ=4.39 (dd, $J_{\alpha,\beta}$=3.5 Hz, J=9.6 Hz, 1H, β-H), 4.92 (d, $J_{gem}$=12.8 Hz, 1H, OCH$_2$Ph), 4.97 (d, $J_{gem}$=12.8 Hz, 1H, OCH$_2$Ph), 5.19 (dd, $J_{\alpha,\beta}$=3.5 Hz, J=10.0 Hz, 1H, α-H), 6.86 (br. s, 2H), 7.17 (d, J=8.1 Hz, 2H), 7.24 (d, J=7.0 Hz, 2H), 7.23-7.29 (m, 2H), 7.41 (d, J=10.1 Hz, 1H, NH), 7.48 (d, J=1 Hz, 1H, NH), 13.0 (br. s, 1H, COOH).

$^{13}$C-NMR (126 MHz, d$_6$-DMSO) δ=28.0 (CH$_3$, COC(CH$_3$)$_3$), 41.2 (CH$_3$, N(CH$_3$)$_2$), 53.9 (CH, C-β), 58.8 (CH, C-α), 65.3 (CH$_2$, OCH$_2$Ph), 78.1 (C quat, COC(CH$_3$)$_3$), 113.7 (CH), 126.7 (C quat), 127.1 (CH), 127.3 (CH), 127.6 (CH), 128.1 (C quat), 128.2 (CH), 136.9 (C quat), 154.7 (C quat, NCO$_2$), 156.1 (NCO$_2$), 171.4 (CO$_2$H).

HR-TOF-MS (Method 24): $C_{24}H_{32}N_3O_6$ [M+H]$^+$ calc. 458.2286, found 458.2277.

Example 123A

Pentafluorophenyl (3R)-N-[(benzyloxy)carbonyl]-3-[(tert-butoxycarbonyl)amino]-4-(dimethylaminophenyl)-L-alaninate

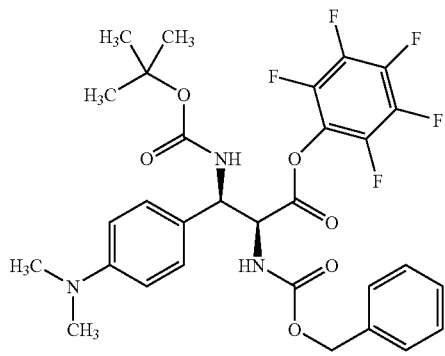

Compound 122A (408 mg, 0.89 mmol) is dissolved in dry THF (11 ml) at 0° C. under an argon protective gas atmosphere. Pentafluorophenyl diphenylphosphinate (514 mg, 1.34 mmol, 1.5 eq.) and NMM (360 mg, 3.57 mmol, 4 eq.) are added, and the reaction mixture is stirred at RT for 16 h. The solvent is then removed and the residue is purified by chromatography (method 33: modified gradient: 0-10 min 10% B, ramp, 30 min 65% B, 36-38 min 10% B). Besides 123A (250 mg, 0.40 mmol, 45% of theory), unreacted starting material (example 122A, 41 mg, 9 μmol, 10% of theory) was isolated.

HPLC (Method 5): $R_t$=3.66 min.

LC-MS (Method 20): $R_t$=3.23 min, MS (ESIpos.): m/z (%)=624.4 (100) [M+H]$^+$.

$[\alpha]^{20}_{Na}$=−19.8° (c=0.5, $CH_2Cl_2$).

$^1$H NMR (400 MHz, $d_6$-DMSO) δ=1.36 (s, 9H, COC(CH$_3$)$_3$), 2.90 (s, 6H, N(CH$_3$)$_2$), 4.96-5.04 (m, 3H, β-H and OCH$_2$Ph), 5.39 (dd, $J_{\alpha,\beta}$=4.4 Hz, J=10.2 Hz, 1H, α-H), 6.75 (br. s, 2H), 7.21-7.33 (m, 7H), 7.57 (d, J=10.3 Hz, 1H, NH), 7.89 (d, J=9.3 Hz, 1H, NH).

$^{13}$C-NMR (126 MHz, $d_6$-DMSO) δ=28.2 (CH$_3$, COC (CH$_3$)$_3$), 43.8. (CH$_3$, N(CH$_3$)$_2$), 55.6 (CH, C-β), 59.1 (CH, C-α), 67.5 (CH$_2$, OCH$_2$Ph), 80.9 (C quat, COC(CH$_3$)$_3$), 117.8 (CH), 124.4 (C quat, m), 128.1 (CH), 128.4 (CH), 128.6 (CH), 128.7 (CH), 132.9 (C quat, m), 136.8 (C quat, m), 138.9 (C quat, m), 139.9 (C quat, m), 141.9 (C quat, m), 155.7 (C quat, NCO$_2$), 156.2 (NCO$_2$), 166.2 (CO$_2$H).

Example 124A

{(3R)-N-[(Benzyloxy)carbonyl]-3-[(tert-butoxycarbonyl)amino]-4-(dimethylamino-phenyl)-L-alanyl}-[(3R)-3-hydroxy-L-leucyl]-L-leucyl-D-arginyl-L-isoleucyl-L-allothreonyl-glycyl-[(3S)-3-hydroxy-L-asparaginyl]-L-serine bistrifluoroacetate

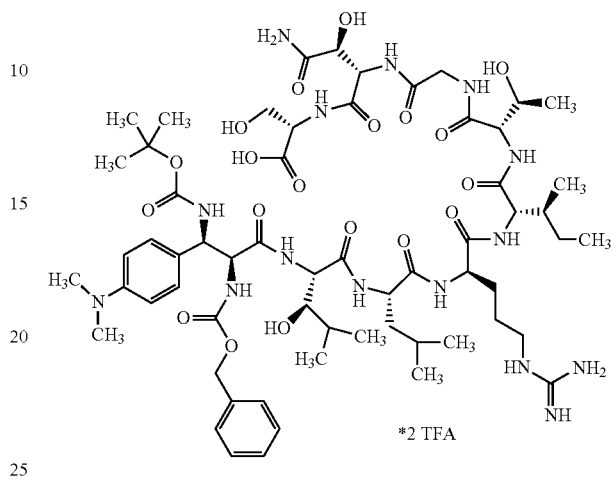

Compound 123A (237 mg, 0.38 mmol) and compound Edman$^{3.0}$ (exemplary compound 3, 465 mg, 0.46 mmol, 1.2 eq.) are dissolved in DMF (40 ml) at 0° C., and DIEA (0.40 ml, 2.28 mmol, 6 eq.) is added. The reaction mixture is stirred further overnight, during which it slowly warms to RT. The DMF is then removed on a rotary evaporator, and the residue is purified by chromatography (method 44). Yield: 550 mg (92% of theory).

HPLC (Method 5): $R_t$=3.62 min.

LC-MS (Method 20): $R_t$=2.01 min, MS (ESIpos.): m/z (%)=673.3 (100) [M+2H]$^{2+}$, MS (ESIneg) m/z (%)=1343 [M−H]$^-$.

HR-TOF-MS (Method 24): $C_{61}H_{98}N_{15}O_{19}$ [M+H]$^+$ calc. 1344.7158, found 1344.7155.

Example 125A

{(3R)-3-Amino-N-[(benzyloxy)carbonyl]-4-(dimethylaminophenyl)-L-alanyl}-[(3R)-3-hydroxy-L-leucyl]-L-leucyl-D-arginyl-L-isoleucyl-L-allothreonyl-glycyl-[(3S)-3-hydroxy-L-asparaginyl]-L-serine bistrifluoroacetate tristrifluoroacetate

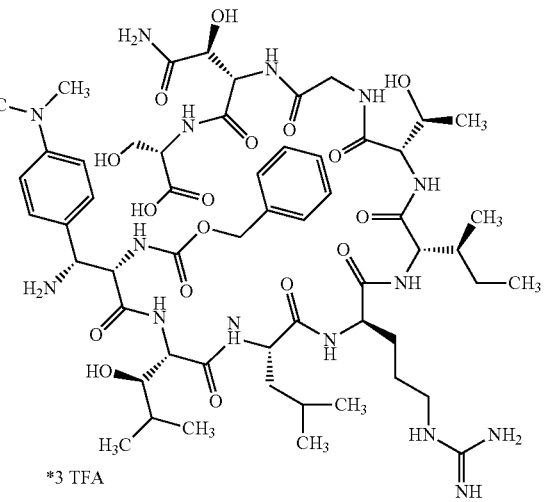

550 mg (0.35 mmol) of the compound of example 124A are dissolved in dichloromethane (2 ml) and then 14 ml of 30% TFA in dichloromethane are added. The mixture is stirred at RT for 15 min and then concentrated and dried under oil pump vacuum. The crude product (644 mg, about 70% pure, 0.28 mmol, 80% of theory) is reacted further without purification.

HPLC (Method 7): $R_t$=3.46 min.

LC-MS (Method 20): $R_t$=1.56 min, MS (ESIpos.): m/z (%)=622.9 (100), [M+2H]$^{2+}$, MS (ESIneg.): m/z (%)=1242.6 [M–H]$^-$.

Example 126A $N^{2.1}$-(Benzyloxycarbonyl)-[(3R)-3-amino-4-(dimethylamino)-L-phenylalanyl]-[(3R)-3-hydroxy-L-leucyl]-L-leucyl-D-arginyl-L-isoleucyl-L-allothreonyl-glycyl-[(3S)-3-hydro-xy-L-asparaginyl]-L-serine $C^{1.9}$-$N^{3.1}$-lactam bistrifluoroacetate

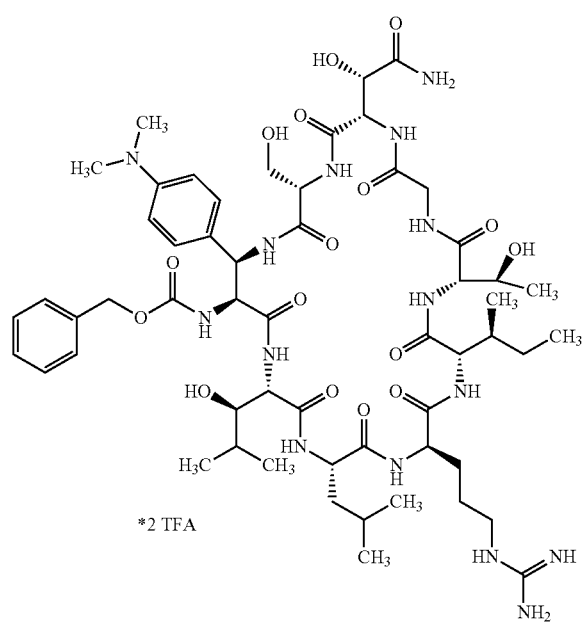

*2 TFA

The crude product from example 125A (644 mg, 0.28 mmol) is dissolved in DMF (30 ml) and cooled to 0° C. HATU (349 mg, 0.92 mmol, 3 eq.) is added, followed by NMM (200 μl, 1.84 mmol, 6 eq.). After 5 min, the ice bath is removed and the mixture is stirred at RT for 3 h. The reaction is stopped by adding methanol and the mixture is initially prepurified by gel chromatography (method 45, eluent: methanol). The product-containing fractions are combined and fine purified by preparative HPLC (method 33). Yield: 211 mg (52% of theory).

HPLC (Method 5): $R_t$=3.64 min.

LC-MS (Method 20): $R_t$=1.70 min, MS (ESIpos.): m/z (%)=614 (100) [M+2H]$^{2+}$, 1226.8 (20) [M+H]$^+$; MS (ESIneg.): m/z (%)=1224.9 (100) [M–H]$^-$.

HR-TOF-MS (Method 24): $C_{56}H_{88}N_{15}O_{16}$ [M+H]$^+$ calc. 1226.6528, found 1226.6534.

Example 127A

[(3R)-3-Amino-4-(dimethylaminophenyl)-L-alanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam trishydrochloride

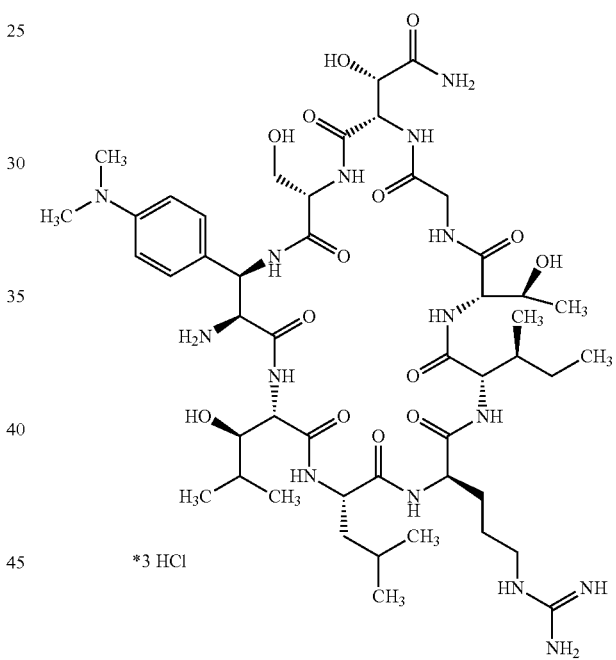

*3 HCl

The compound of example 126A (209 mg, 0.14 mmol) is dissolved in methanol (50 ml), and 1 M aq. hydrochloric acid (860 μl, 6 eq.) as well as 10% palladium-carbon are added. Hydrogenation is carried out under ambient pressure and at RT for 90 min. The mixture is then filtered to remove the catalyst and concentrated. The residue is taken up in water and lyophilized. 170 mg (98% of theory) of the title compound are obtained.

HPLC (Method 7): $R_t$=3.19 min.

LC-MS (Method 20): $R_t$=1.26 min, MS (ESIpos.): m/z (%)=547.1 (100) [M+2H]$^{2+}$, 1092.8 (5) [M+H]$^+$.

HR-TOF-MS (Method 24): $C_{48}H_{82}N_{15}O_{14}$ [M+H]$^+$ calc. 1092.6161, found 1092.6133.

Example 128A $N^{2.1}$-(tert-Butoxycarbonyl)-[3-tert-butyl-D-alanyl]-[3-tert-butyl-L-alanyl]-[(3R)-3-amino-4-(dimethylaminophenyl)-L-alanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam bishydrochloride

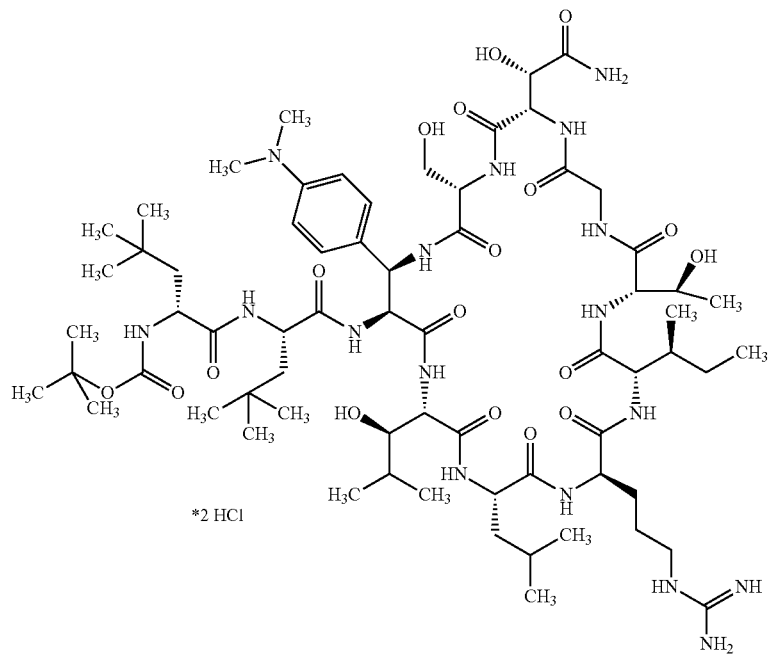

*2 HCl

The compound of example 127A (85 mg, 71 µmol) and the dipeptide (example 9A, 40 mg, 106 µmol, 1.5 eq.) are dissolved in DMF (4 ml) and cooled to 0° C. NMM (31 µl, 281 µmol, 4 eq.) and HATU (43 mg, 113 µmol, 1.6 eq.) are then added and the ice bath is then removed. The mixture slowly warms to ambient temperature. After 1 h, the reaction is stopped by adding methanol, and chromatography is carried out using methanol as mobile phase (method 45). The eluate is checked by HPLC (method 7), and the product-containing fractions are combined and concentrated. 105 mg of the title compound about 66% pure (65% of theory) are obtained. This material is employed in the next stage without further purification.

HPLC (Method 7): $R_t$=4.47 min.

LC-MS (Method 20): $R_t$=2.24 min, MS (ESIpos.): m/z (%)=724.3 (100) [M+2H]$^{2+}$, 1448.3 (5) [M+H]$^+$.

Example 129A (2S)-N-(tert-Butoxycarbonyl)-3-(trimethylsilyl)alanine and

Example 130A (2R)-N-(tert-Butoxycarbonyl)-3-(trimethylsilyl)alanine

The target compound is prepared according to M. Merget, K. Günther, M. Bernd, E. Günther, R. Tacke, *J. Organomet. Chem.* 2001628, 183-194. The separation of the enantiomers is achieved by preparative HPLC (method 41) on a chiral phase and the isomers are assigned by HPLC comparison with an authentic sample of N-(tert-butoxycarbonyl)-L-3-trimethylsilylalanine (2R isomer, Mercachem AMR 39.260).

Example 129A

N-(tert-Butoxycarbonyl)-3-(trimethylsilyl)-D-alanine

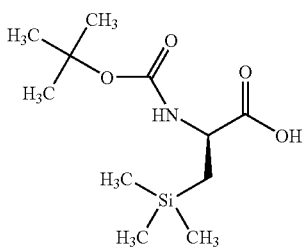

Chiral HPLC (Method 41): $R_t$=4.16 min, e.e.>99%.
$[\alpha]_D^{20}$=+1.1 (c=0.83, methanol)

Example 130A

N-(tert-Butoxycarbonyl)-3-(trimethylsilyl)-L-alanine

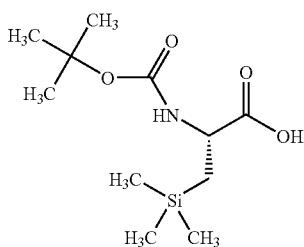

Chiral HPLC (Method 41): $R_t$=9.27 min, e.e.>99%
$[\alpha]_D^{20}$=−1.6 (c=0.66, methanol)

Example 131A

Methyl [$N^2$-(tert-butoxycarbonyl)-3-(trimethylsilyl)-D-alanyl]-2-tert-butyl-L-alaninate

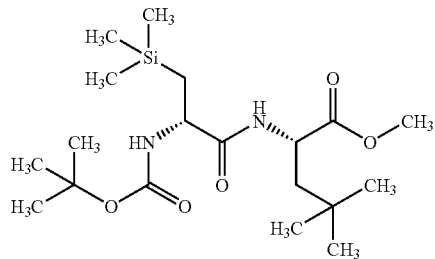

Methyl 2-tert-butyl-L-alaninate trifluoroacetate (215 mg, 0.82 mmol) [S. D. Bull, S. G. Davies, A. C. Garner, M. D. O'Shea, *J. Chem. Soc. Perkin Trans.* 1, 2001, 3281-3287] and example 129A (225 mg, 0.82 mmol, 1 eq.) are dissolved in DMF (5 ml) at 0° C. NMM (360 µl, 3.29 mmol, 4 eq.) and HATU (470 mg, 1.24 mmol, 1.5 eq.) are then added, and the mixture is stirred at RT for 2 h. Extraction is carried out twice with MTBE and a sat. aq. sodium bicarbonate solution, and the combined organic phases are washed with 1 M citric acid and again with a sat. aq. sodium bicarbonate solution, dried over sodium sulfate and concentrated. After purification by chromatography (method 33) 290 mg (0.72 mmol, 88% of theory) of the title compound are obtained.

HPLC (Method 7): $R_t$=5.37 min.

LC-MS (Method 18): $R_t$=3.02 min, MS (ESIpos.): m/z (%)=403.5 (100) [M+H]$^+$.

$^1$H NMR (400 MHz, $d_6$-DMSO) δ=0.01 (s, 9H, Si(CH$_3$)$_3$), 0.89 (m, 1H), 1.37 (s, 9H, COC(CH$_3$)$_3$), 1.55 (dd, J=8.8 Hz, 14.2 Hz, 1H), 1.63 (dd, J=3.4 Hz, 14.2 Hz, 1H), 3.62 (s, 3H, OCH$_3$), 4.04 (m, 1H), 4.27 (m, 1H), 6.70 (d, J=9.0 Hz, 1H, NH), 7.96 (d, J=8.1 Hz, 1H, NH).

Example 132A

[$N^2$-(tert-Butoxycarbonyl)-3-(trimethylsilyl)-D-alanyl]-2-tert-butyl-L-alanine

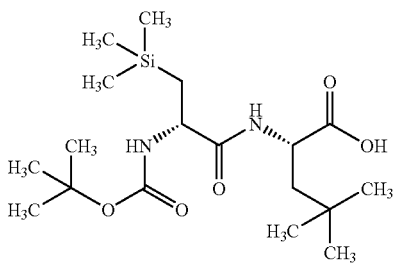

Example 131A (274 mg, 0.68 mmol) is taken up in THF/water (3:1, 21 ml) and cooled to 0° C. Lithium hydroxide monohydrate (57 mg, 1.36 mmol, 2 eq.) is added and the mixture is stirred at 0° C. for 1 h. Most of the THF is removed in vacuo, the pH is adjusted to 4 by adding 1 M citric acid, and the mixture is extracted twice with ethyl acetate. The combined organic phases are dried over sodium sulfate and concentrated. After purification by chromatography (method 33 with modified gradient: 0-2 min 30% B, ramp, 30-35 min-90% B) 237 mg (0.61 mmol, 90% of theory) of the title compound are obtained as a colorless solid.

HPLC (Method 7): $R_t$=4.93 min.

LC-MS (Method 18): $R_t$=2.76 min, MS (ESIpos.): m/z (%)=389.4 (100) [M+H]$^+$.

$^1$H NMR (400 MHz, $d_6$-DMSO) δ=0.00 (s, 9H, Si(CH$_3$)$_3$), 0.88 (m, 1H), 1.36 (s, 9H, COC(CH$_3$)$_3$), 1.51 (dd, J=9.3 Hz, 14.2 Hz, 1H), 1.64 (dd, J=3.0 Hz, 14.2 Hz, 1H), 4.02 (m, 1H), 4.20 (m, 1H), 6.71 (d, J=9.3 Hz, 1H, NH), 7.80 (d, J=8.1 Hz, 1H, NH), 12.49 (br s, 1H, COOH).

Example 133A $N^{2.1}$-(tert-Butoxycarbonyl)-[3-trimethylsilyl-D-alanyl]-[3-tert-butyl-L-alanyl]-[(3R)-3-amino-4-(dimethylaminophenyl)-L-alanyl]-[(3R)-3-hydroxy-L-leucyl]-L-leucyl-D-arginyl-L-iso-leucyl-L-allothreonyl-glycyl-[(3S)-3-hydroxy-L-asparaginyl]-L-serine $C^{1.11}$-$N^{3.3}$-lactam bishydrochloride

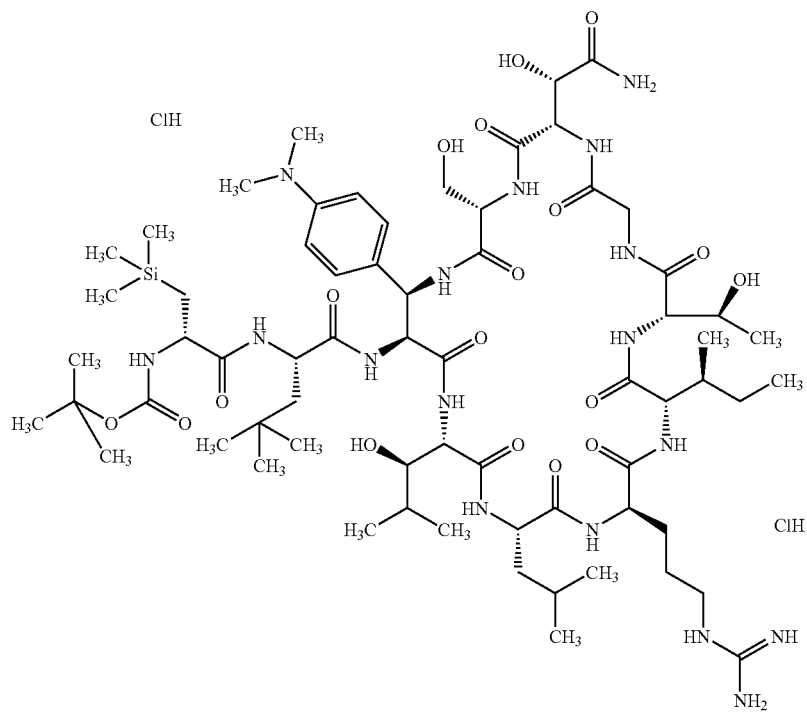

The compound of example 127A (102 mg, 85 µmol) and the dipeptide (example 132A, 50 mg, 127 µmol, 1.5 eq.) are dissolved in DMF (4 ml) and cooled to 0° C. NMM (37 µl, 340 µmol, 4 eq.) and HATU (65 mg, 170 µmol, 2.0 eq.) are then added and the ice bath is then removed. The mixture slowly warms to ambient temperature. After 1 h, the reaction is stopped by adding methanol, and chromatography is carried out on Sephadex LH20 using methanol as mobile phase (method 45). The eluate is checked by HPLC (method 7), and the product-containing fractions are combined and concentrated. 126 mg (82 µmol, 96% of theory) of the title compound are obtained.

HPLC (Method 7): $R_t$=4.55 min.

Example 134A

Benzyl $N^2$-(tert-butoxycarbonyl)-D-phenylalanyl-L-phenylalaninate

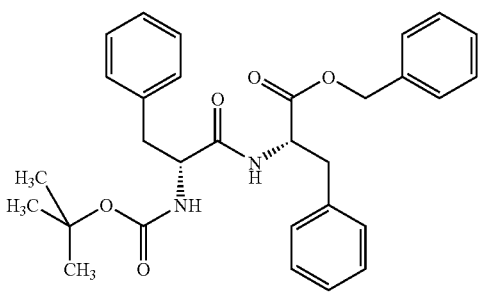

HOBt (2.0 g, 15.08 mmol, 4 eq.), NMM (1.2 ml, 1.1 g, 11.31 mmol, 3 eq.), N-(tert-butoxycarbonyl)-D-phenylalanine (1.0 g, 3.77 mmol, 1 eq.) [Anderson, McGregor; J. Am.

Chem. Soc.; 79; 1957; 6180,6181], EDC (1.4 g, 7.54 mmol, 2 eq.) and again NMM (0.8 ml, 0.8 g, 7.54 mmol, 2 eq.) are successively added to a solution of benzyl L-phenylalaninate hydrochloride (1.1 g, 4.15 mmol, 1.1 eq.) in dichloromethane p.a. (365 ml) at −10° C. The reaction mixture slowly warms to RT and is stirred at this temperature overnight. The solvent is completely removed, and the residue is mixed with ethyl acetate and the mixture is subsequently washed with a sat. aq. sodium bicarbonate solution, 5% aq. citric acid, a sat. aq. sodium bicarbonate solution (500 ml) and a sat. aq. sodium chloride solution. The mixture is dried over sodium sulfate and filtered. The mixture is evaporated to dryness in vacuo and then dried under high vacuum. 1.8 g (96% of theory) of the title compound are obtained and are reacted without further purification.

HPLC (Method 12): $R_t$=9.16 min.
HPLC (Method 4): $R_t$=5.16 min.
$^1$H NMR (400 MHz, $d_6$-DMSO): δ=1.18/1.27 (2s, 9H, OtBu), 2.47-2.57 (m underneath the H-DMSO-Signal, 1H, β-H), 2.66 (dd, J=13.8, 3.7 Hz, 1H, β-CH), 2.91 (dd, J=13.8, 9.4 Hz, 1H, β-CH), 3.09 (dd, J=13.8, 3.1 Hz, 1H, β-CH), 4.19 (td, J=9.3, 4.2 Hz, 1H, α-CH), 4.57 (td, J=8.8, 5.9 Hz, 1H, α-CH), 5.12 (s, 2H, OCH$_2$Ph), 6.76 (d, J=9.2 Hz, 1H, NH), 7.08-7.43 (m, 15H, Aryl-H), 8.48 (d, J=8.1 Hz, 1H, NH).

HR-TOF-MS (Method 24): $C_{30}H_{36}N_2O_5$ [M+H]$^+$ found 503.2566, calc. 503.2546.

Example 135A

N$^2$-(tert-Butoxycarbonyl)-D-phenylalanyl-L-phenylalanine

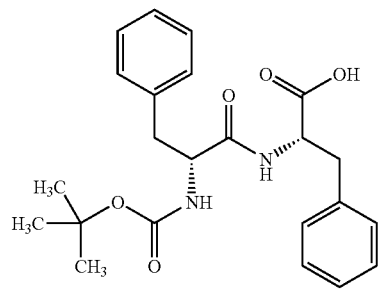

The title compound is prepared from the compound of example 134A (563.0 mg, 1.12 mmol) according to procedure 5. After stirring under a hydrogen atmosphere under atmospheric pressure and at RT for 3 h, a complete conversion is achieved according to the reaction monitoring (method 12). 452.2 mg (97.9% of theory) of product are obtained.

[α]$^{20}_{Na}$=+33.2° (c=0.57 in CH$_2$Cl$_2$).
HPLC (Method 12): $R_t$=7.64 min.
HPLC (Method 4): $R_t$=4.45 min.
$^1$H NMR (400 MHz, $d_6$-DMSO): δ=1.19/1.26 (2s, 9H, OtBu), 2.44-2.56 (m underneath the H-DMSO-Signal, 1H, β-H), 2.69 (dd, J=14.0, 3.8 Hz, 1H, β-CH), 2.86 (dd, J=14.0, 9.5 Hz, 1H, β-CH), 3.08 (dd, J=14.0, 4.6 Hz, 1H, β-CH), 4.18 (td, J=9.7, 3.57 Hz, 1H, α-CH), 4.48 (td, J=9.3, 4.5 Hz, 1H, α-CH), 6.71 (d, J=8.7 Hz, 1H, NH), 7.08-7.32 (m, 10H, Aryl-H), 8.27 (d, J=8.0 Hz, 1H, NH), 12.77 (s br., 1H, COOH).

HR-TOF-MS (Method 24): $C_{23}H_{30}N_2O_5$ [M+H]$^+$ found 413.2082, calc. 413.2076.

Example 136A 2-(Trimethylsilyl)ethyl N$^2$-[(benzyloxy)carbonyl]-3-[(tert-butoxycarbonyl)amino]-L-alaninate

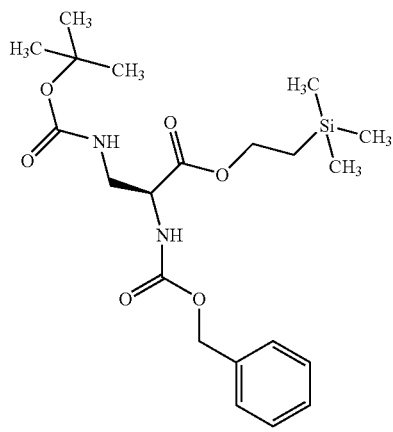

N-[(Benzyloxy)carbonyl]-3-[(tert-butoxycarbonyl)amino]-L-alanine (1000.0 mg, 2.96 mmol) [Rane, F. Dinanath et al.; Tetrahedron Lett.; EN; 34; 20; 1993; 3201-3204] is dissolved in dichloromethane (20 ml), and trimethylsilylethanol (4.2 ml, 3.5 g, 29.55 mmol, 10 eq.), DCC (1.22 g, 5.91 mmol, 2 eq.) and DMAP (361.1 mg, 2.96 mmol, 1 eq.) are successively added to the solution at −20° C. The reaction is warmed to RT and stirred at this temperature overnight and brought to complete conversion. For the workup, the mixture is concentrated, and the residue is taken up in diethyl ether and subsequently extracted twice with water and once with a sat. aq. sodium chloride solution. The etheric phase is dried over sodium sulfate, the desiccant is removed by filtration through silica gel, and most of the solvent is removed from the filtrate on a rotary evaporator. If a precipitate separates out during the concentration, this can be removed again where appropriate through silica gel. The residue obtained is then fine purified by chromatography (method 31) and 1.1 g (86.4% of theory) of the title compound are obtained.

HPLC (Method 12): $R_t$=9.31 min.
LC-MS (Method 18): $R_t$=2.97 min, MS (ESIpos.): m/z (%)=439 (100) [M+H]$^+$.

Example 137A 2-(Trimethylsilyl)ethyl 3-amino-$N^2$-(benzyloxycarbonyl)-L-alaninate trifluoroacetate

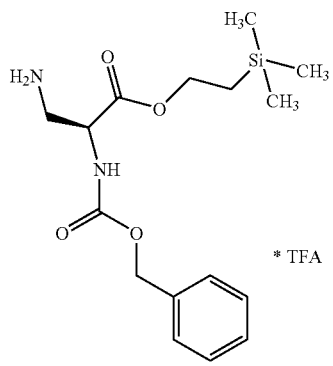

The title compound is prepared from the compound of example 136A (100.0 mg, 0.23 mmol) as described in procedure 1.41 mg (39.7% of theory) of the product are isolated from the crude product after the fine purification (method 35).

HPLC (Method 12): $R_t$=6.33 min.

LC-MS (Method 23): $R_t$=4.83 min, MS (ESIpos.): m/z (%)=339 (15) [M+H]$^+$, 311 (100).

Example 138A $N^2$-(Benzyloxycarbonyl)-$N^3$-{$N^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-alanine 2-(trimethylsilyl)ethyl ester trifluoroacetate The octapeptide (example 100A, 9.0 mg, 8.04 μmol) and exemplary compound 137A (17.0 mg, 39.95 μmol, 5 equivalents) are provided in DMF (900 μl) under an argon protective gas atmosphere at 0° C. Subsequently, base (9 μl, 0.8 mg, 8.04 μmol, 1 eq.) from an NMM stock solution (0.91 mmol/ml in DMF), HATU (6.1 mg, 16.08 μmol, 2 eq.) and again NMM-solution (9 μl, 0.8 mg, 8.04 μmol, 1 eq.) are successively added to the mixture. After stirring for 15 min, finally NMM stock solution (22 μl, 2 mg, 20.10 μmol, 2.5 eq.) is added, and the mixture is slowly warmed to RT and stirred at this temperature overnight. The solution is prepurified by preparative HPLC (method 36) and fine purified by gel chromatography (method 45, eluent: methanol with 0.25% glacial acetic acid). 8.0 mg (69.1% of theory) of the title compound are obtained.

HPLC (Method 12): $R_t$=7.21 min.

LC-MS (Method 23): $R_t$=5.30 min, MS (ESIpos.): m/z (%)=1325 (75) [M+H]$^+$; MS (ESIneg.): m/z (%)=1323 (100) [M−H]$^-$.

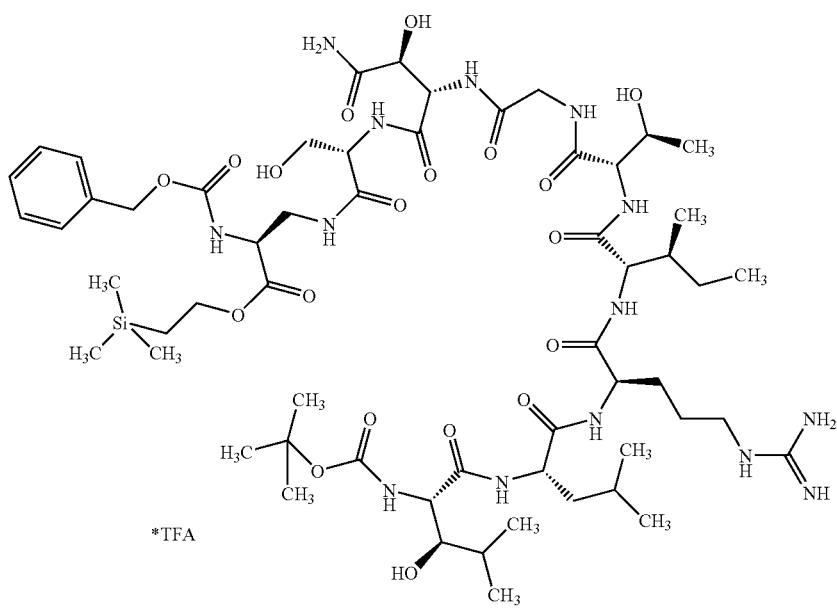

Example 139A

N²-(Benzyloxycarbonyl)-N³-{N²·¹-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-alanine trifluoroacetate

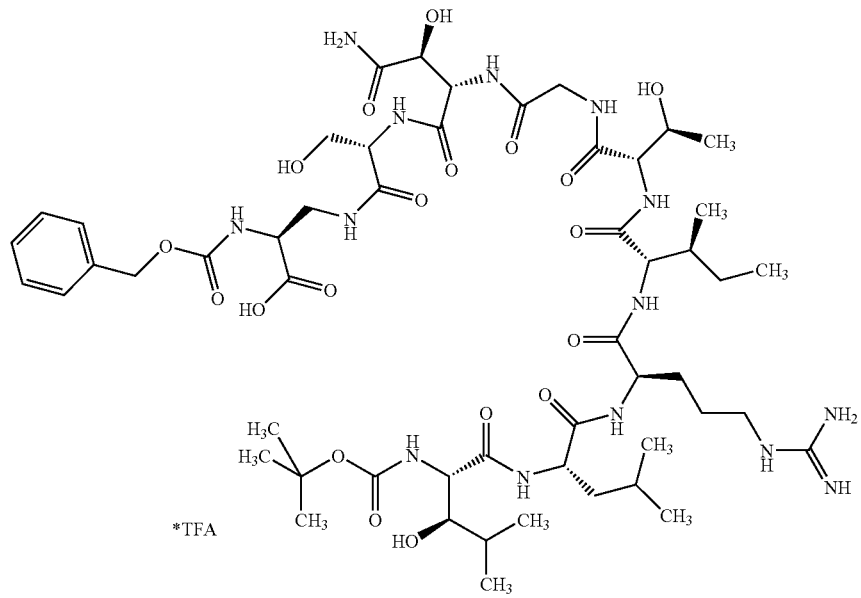

The compound of example 138A (7.5 mg, 5.21 μmol) is provided in 900 μl of THF, and 4 portions of a 1 M TBAF solution in THF (26 μl, 6.8 mg, 26.05 μmol, 5 eq.) are added and, after 15 eq. of base, molecule sieves (4 Å) are also added. The reaction is stirred at RT for 1 h, and complete conversion established by HPLC monitoring (method 12). For the workup, the mixture is neutralized with glacial acetic acid and subsequently concentrated in vacuo and chromatographed by preparative HPLC (method 29). 6.2 mg (88.9% of theory) of the title compound are obtained.

HPLC (Method 12): $R_t$=6.24 min.

LC-MS (Method 23): $R_t$=4.88 min, MS (ESIpos.): m/z (%)=1224 (80) [M+H]⁺, 242 (100); MS (ESIneg.): m/z (%)=1223 (100) [M−H]⁻.

Example 140A

N²-(Benzyloxycarbonyl)-N³-{N²·¹-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-alanine pentafluorophenyl ester trifluoroacetate

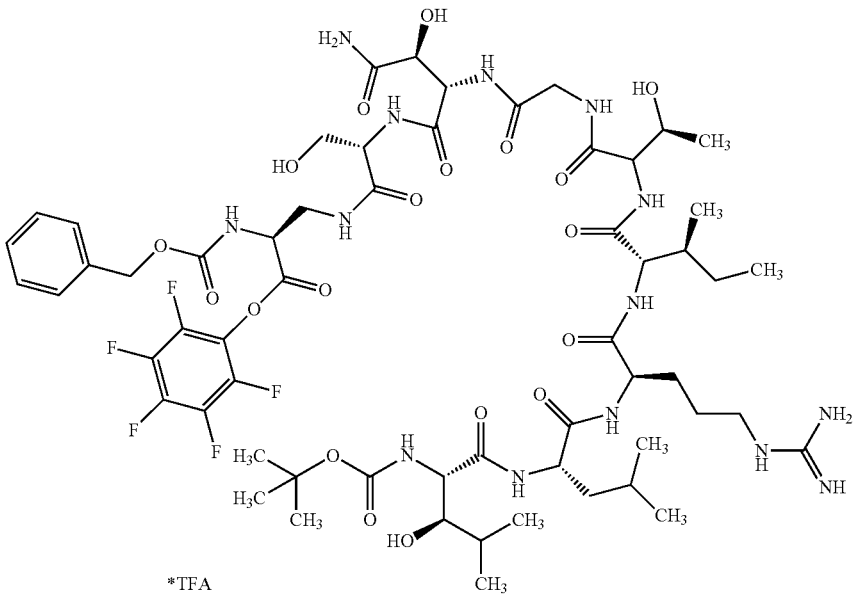

Under an argon protective gas atmosphere, the compound of example 139A (3.1 mg, 2.31 µmol) is provided in dichloromethane (1 ml), and pentafluorophenol (4.3 mg, 23.14 µmol, 10 eq.) is added. The reaction is cooled to −20° C. and finally EDC (1.0 mg, 5.32 µmol, 2.3 eq.) is added, and the mixture is warmed to RT and stirred at this temperature overnight. For the workup, the solvent is completely removed and the residue is freeze dried. The title compound is reacted further as crude product, and a quantitative yield is assumed.

HPLC (Method 12): $R_t$=7.18 min.

LC-MS (Method 23): $R_t$=5.56 min, MS (ESIpos.): m/z (%)=1392 (80) [M+H]$^+$.

Example 141A $N^2$-(Benzyloxycarbonyl)-$N^3$-{[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-alanine pentafluorophenyl ester bishydrochloride

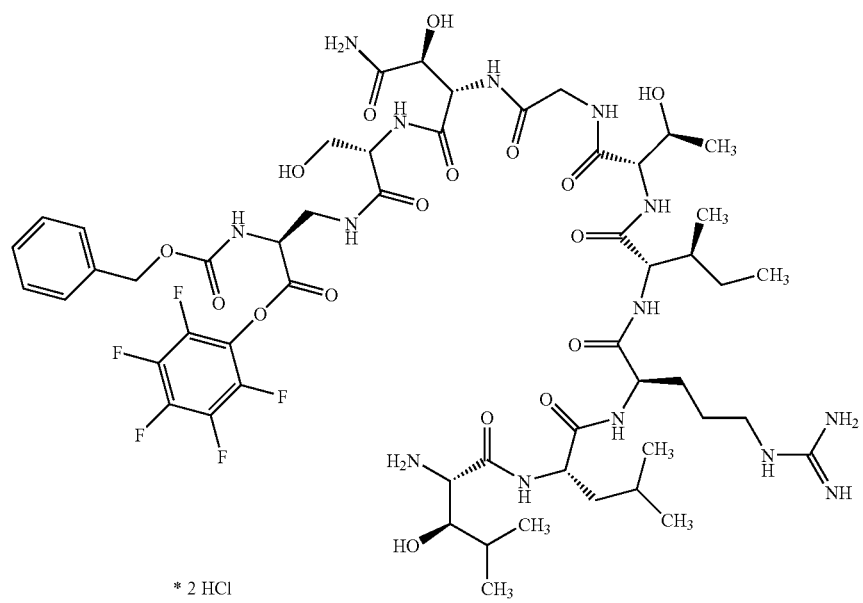

The title compound is prepared from the compound of example 140A (3.0 mg, 1.99 µmol) according to procedure 3. After the addition of hydrochloric acid at 0° C., complete conversion is established by HPLC monitoring (method 12) after 30 min. The title compound is obtained as crude product, assuming a quantitative yield.

LC-MS (Method 23): $R_t$=4.47 min, MS (ESIpos.): m/z (%)=1292 (3) [M+H]$^+$, 646 (100) [M+2H]$^{2+}$, MS (ESIneg.): m/z (%)=1290 (40) [M−H]$^−$, 1106 (100).

Example 142A $N^{2.1}$-(Benzyloxycarbonyl)-[(3R)-3-amino-L-alanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam hydrochloride

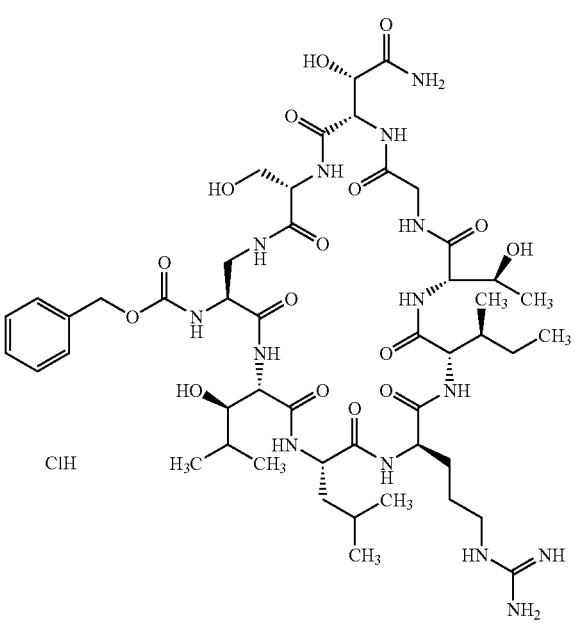

Under an argon protective gas atmosphere, the compound of example 141A (3.0 mg, 2.20 µmol) is provided in chloroform (20 ml). Triethylamin (22 µl, 15.8 mg, 131.94 µmol) is dissolved in chloroform (25 ml) and added dropwise to the solution over the course of 1 h. After the addition is complete, the reaction is stirred at RT overnight. For the workup, the mixture is neutralized with TFA, subsequently concentrated in vacuo and prepurified by gel chromatography (method 45, eluent: methanol with 0.25% glacial acetic acid). 0.4 mg (15.9% of theory) of the product are isolated after fine purification by preparative HPLC (separation phase: Xterra 10 mm, eluent: 0.1% TFA, acetonitrile-water gradient).

HPLC (Method 12): $R_t$=5.96 min.

LC-MS (Method 18): $R_t$=1.72 min, MS (ESIpos.): m/z (%)=1108 (48) [M+H]$^+$, 132 (100); MS (ESIneg.): m/z (%)=1106 (100) [M−H]$^−$.

Example 143A

[(3R)-3-Amino-L-alanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam bishydrochloride

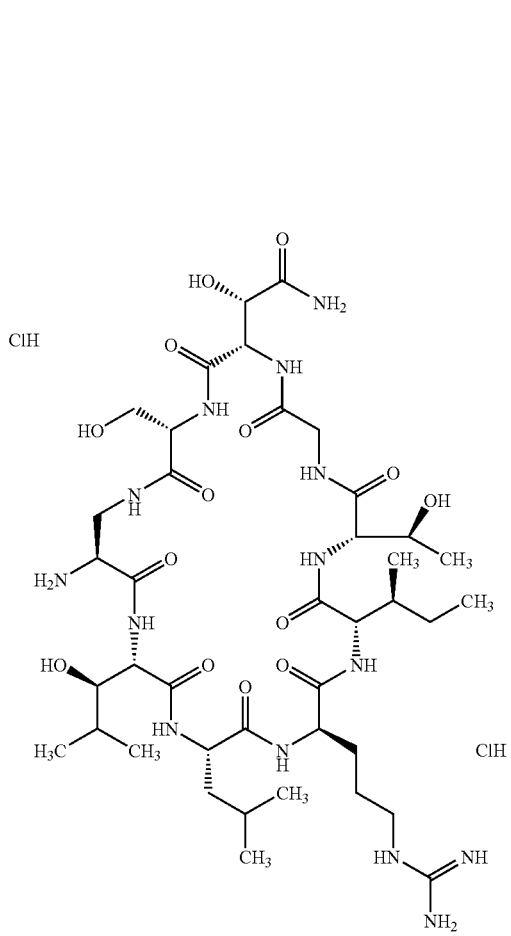

The title compound (0.4 mg, 0.35 µmol) is prepared from the compound of example 142A as described in procedure 4. Complete conversion is achieved after hydrogenation under atmospheric pressure and at RT for 6 h. 0.3 mg (81.9% of theory) of the title compound are obtained as crude product which is reacted further.

Example 144A $N^{2.1}$-(tert-Butoxycarbonyl)-[D-phenylalanyl]-[L-phenylalanyl]-[(3R)-3-amino-L-alanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam trifluoroacetate

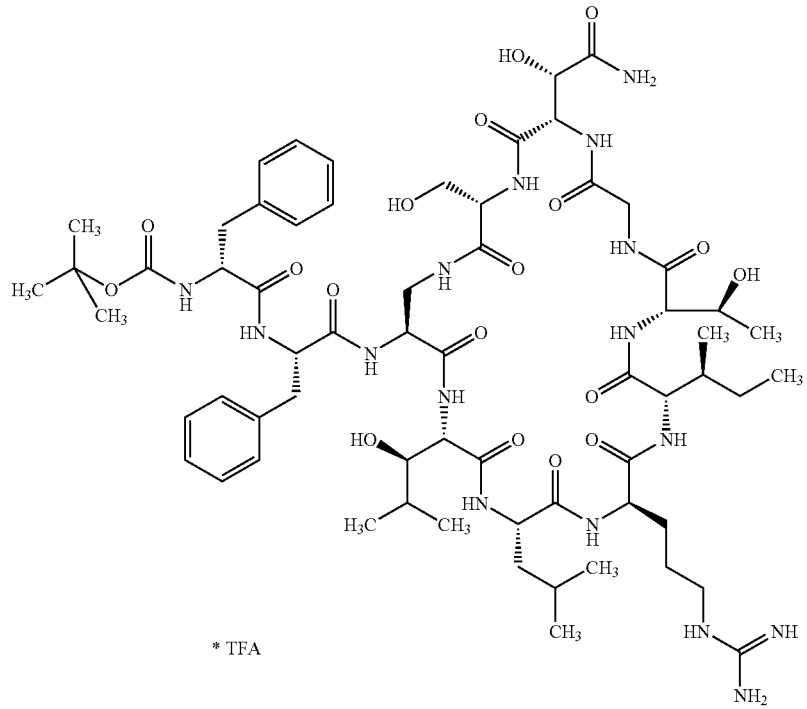

* TFA

The deprotected amine (example 143A, 0.3 mg, 0.29 µmol) and the dipeptide (1.2 mg, 2.86 µmol, 10 eq.) are provided under an argon protective gas atmosphere in DMF (100 µl), and the solution is cooled to 0° C. The base (16 µl, 147 µg, 1.43 µmol, 5 eq.) from the NMM stock solution (90.9 µmol/ml in DMF), HATU (1.1 mg, 2.95 µmol, 10.3 eq.) and further NMM stock solution (16 µl, 147 µg, 1.43 µmol, 5 eq.) are added, and the reaction is stirred for 15 min. Finally, base (40 µl, 367 µg, 3.62 µmol, 12.5 eq.) is again added to the mixture, which is brought to RT while stirring. Stirring is continued at this temperature overnight. For the workup, the mixture is concentrated in vacuo and fine purified by gel chromatography (method 45, eluent: methanol). 0.3 mg (70.6% of theory) of the title compound are obtained.

HPLC (Method 12) $R_t$=7.80 min.

LC-MS (Method 18): $R_t$=2.17 min; MS (ESIpos): m/z (%)=1368 (5) [M+H]$^+$, 634 (100); MS (ESIneg.): m/z (%)=1367 (30) [M−H]$^−$, 683 (100) [M−2H]$^{2-}$.

Example 145A

Polymer-bound [$N^2$-fluorenylmethoxycarbonyl-L-isoleucyl]-$O^3$-(tert-butyl)-L-serine

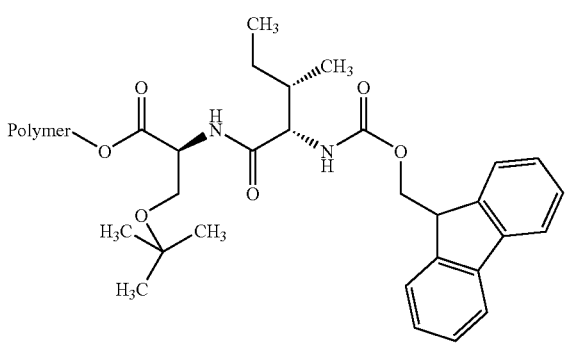

The Fmoc protecting group is removed from the polymer (example 41A, 500 mg, 0.75 mmol) as described in procedure 7. The deprotected amino acid bound to the resin is subsequently reacted with $N^2$-[(9H-fluoren-9-ylmethoxy)carbonyl]-L-isoleucine (1.05 g, 2.98 mmol, 4 eq.), DIEA (0.78 ml, 577 mg, 4.47 mmol, 6 eq.) and TBTU (957 mg, 2.98 mmol, 4 equivalents) overnight to give the Fmoc-protected dipeptide. The workup of the polymer takes place in analogy to procedure 7. The corresponding side chain-protected dipeptide is confirmed after a sample removal.

LC-MS (Method 21): $R_t$=2.68 min; MS (ESIpos): m/z (%)=497.5 (60) [M+H]$^+$, 441.4 (100); MS (ESIneg): m/z (%)=495.5 (5) [M−H]$^−$, 273.4 (100).

Example 146A

Polymer-bound [($N^2$-(9H-fluoren-9-ylmethoxy)carbonyl)-$N^5$-(imino{[(2,2,5,7,8-penta-methyl-3,4-dihydro-2H-chromen-6-yl)sulfonyl]amino}methyl)-D-ornithyl]-L-isoleucyl-$O^3$-(tert-butyl)-L-serine

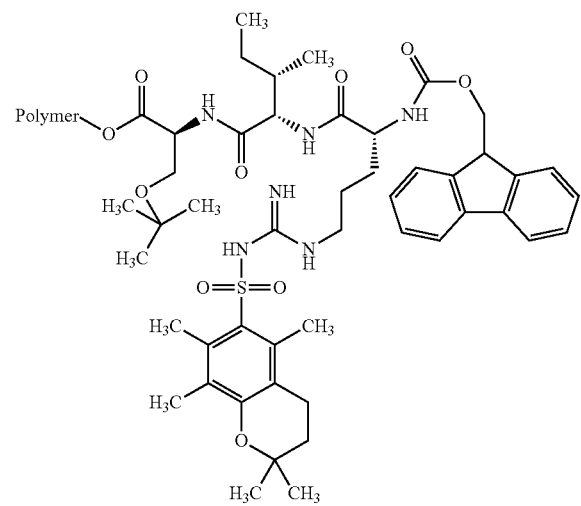

The Fmoc protecting group is removed from the polymer (example 145A, 500 mg, 0.75 mmol) as described in procedure 7. The deprotected amino acid bound to the resin is subsequently reacted with ($N^2$-(9H-fluoren-9-ylmethoxy)carbonyl)-$N^5$-(imino{[(2,2,5,7,8-penta-methyl-3,4-dihydro-2H-chromen-6-yl)sulfonyl]amino}methyl)-D-ornithine (740 mg, 1.12 mmol, 1.5 eq.), DIEA (0.39 ml, 289 mg, 2.24 mmol, 3 eq.) and TBTU (318 mg, 0.99 mmol, 2 equivalents) overnight to give the Fmoc-protected tripeptide. The workup of the polymer takes place in analogy to procedure 7. The corresponding side chain-protected dipeptide is confirmed after a sample removal.

LC-MS (Method 21): $R_t$=2.89 min; MS (ESIpos): m/z (%)=919.5 (100) [M+H]$^+$; MS (ESIneg): m/z (%)=917.7 (100) [M−H]$^−$.

Example 147A

Polymer-bound [($N^2$-(9H-fluoren-9-ylmethoxy)carbonyl)-L-leucyl]-[$N^5$-(imino-{[(2,2,5,7,8-pentamethyl-3,4-dihydro-2H-chromen-6-yl) sulfonyl] amino}methyl)-D-ornithyl]-L-isoleucyl-$O^3$-(tert-butyl)-L-serine

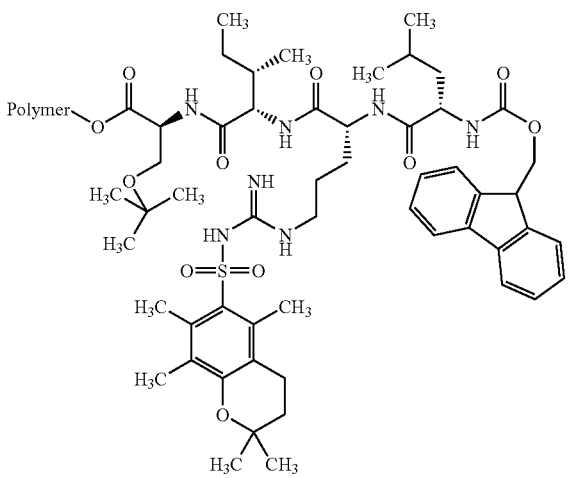

The Fmoc protecting group is removed from the polymer (example 146A, 500 mg, 0.75 mmol) as described in procedure 7. The deprotected amino acid bound to the resin is subsequently reacted with $N^2$-[(9H-fluoren-9-ylmethoxy)carbonyl]-L-leucine (1.05 g, 2.98 mmol, 4 eq.), DIEA (0.78 ml, 577 mg, 4.47 mmol, 6 eq.) and TBTU (956 mg, 2.98 mmol, 4 equivalents) overnight to give the Fmoc-protected tetrapeptide. The workup of the polymer takes place in analogy to procedure 7. The corresponding side chain-protected dipeptide is confirmed after a sample removal.

LC-MS (Method 21): $R_t$=3.27 min; MS (ESIpos): m/z (%)=1033.3 (100) [M+H]$^+$; MS (ESIneg): m/z (%)=1032.2 (100) [M−H]$^−$.

Example 148A

[(3R)-$N^2$-(tert-Butoxycarbonyl)-3-hydroxy-L-leucyl]-L-leucyl-[$N^5$-(imino{[(2,2,5,7,8-pentamethyl-3,4-dihydro-2H-chromen-6-yl)sulfonyl] amino}methyl)-D-ornithyl]}-L-isoleucyl-$O^3$-(tert-butyl)-L-serine

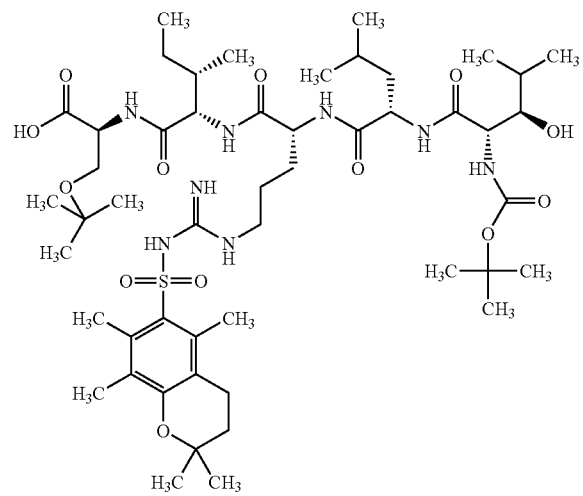

The Fmoc protecting group is removed from the polymer (example 147A, 500 mg, 0.75 mmol) as described in procedure 7. The deprotected amino acid bound to the resin is subsequently reacted with (3R)-N²-(tert-butoxycarbonyl)-3-hydroxy-L-leucine (276 mg, 1.12 mmol, 1.5 eq.), DIEA (0.26 ml, 193 mg, 1.49 mmol, 2 eq.) and TBTU (359 mg, 1.12 mmol, 1.5 equivalents) overnight to give the Boc-protected pentapeptide. It is then washed with DMF, THF and finally dichloromethane and removed from the resin with a mixture of glacial acetic acid, trifluoroethanol and dichloromethane (1+1+3). The crude reaction product is purified by chromatography. The title compound is isolated in a yield of 145 mg (19% of theory).

LC-MS (Method 21): $R_t$=3.17 min; MS (ESIpos): m/z (%)=1040.0 (100) [M+H]⁺; MS (ESIneg): m/z (%)=1038.0 (100) [M−H]⁻.

Example 149A

Benzyl L-serinate trifluoroacetate

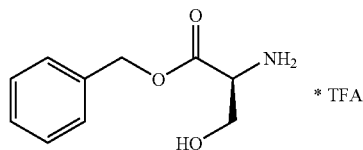

500 mg (1.69 mmol) of benzyl N-tert-butoxycarbonyl-L-serinate are reacted according to procedure 2 in 5.50 ml of the reagent solution. The product is reacted without further purification. Yield: 505 mg (1.63 mmol, 96% of theory).

HPLC (Method 3): $R_t$=3.10 min.

LC-MS (Method 22): $R_t$=1.94 min; MS (ESIpos) m/z (%)=196.0 (100) [M+H]⁺.

Example 150A

Benzyl [N²-(tert-butoxycarbonyl)-L-seryl]-L-serinate

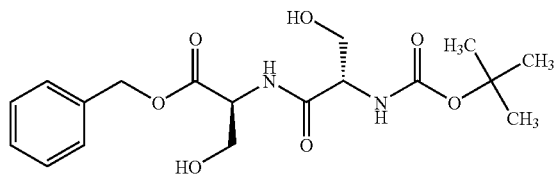

The compound of example 149A (500 mg, 1.62 mmol) and N-tert-butoxycarbonyl-L-serine (332 mg, 1.62 mmol, 1 equivalent) are dissolved in dichloromethane (8.2 ml) and cooled to 0° C. HATU (922 mg, 2.43 mmol, 1.5 equivalents) is added and then, over the course of 15 min, a solution of N,N-diisopropylethylamine (1.41 ml, 8.08 mmol, 5 equivalents) in dichloromethane (5 ml) is added dropwise. The mixture is then stirred at room temperature for 72 h and subsequently washed with sodium bicarbonate, and the organic phase is dried and concentrated. The crude product is purified by chromatography (method 34). Product-containing fractions are combined and lyophilized. Yield: 308 mg (0.81 mmol, 50% of theory) as a colorless solid.

HPLC (Method 4): $R_t$=3.81 min.

LC-MS (Method 18): $R_t$=1.98 min; MS (ESIpos): m/z (%)=283.5 (100) [M-Boc+H]⁺; 383.6 (30) [M+H]⁺.

Example 151A

Benzyl [N²-(tert-butoxycarbonyl)-3-(3-pyridyl)-L-alanyl]-L-serinate

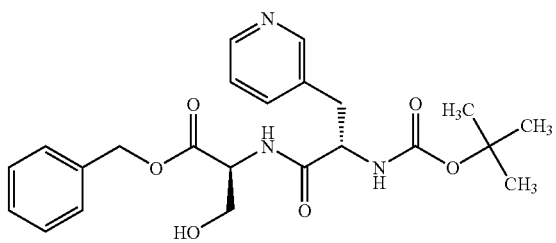

According to the preparation method of the compound of example 150A the title compound is obtained in a yield of 780 mg (69% of theory) from the compound of example 149A (780 mg, 2.52 mmol) and N²-tert-butoxycarbonyl-3-(3-pyridyl)-L-alanine (707 mg, 2.52 mmol).

HPLC (Method 5): $R_t$=3.61 min.

LC-MS (Method 22): $R_t$=2.82 min, MS (ESIpos): m/z (%)=444.2 (100), [M+H]⁺.

Example 152A

Benzyl [N²-(tert-butoxycarbonyl)-L-phenylalanyl]-L-serinate

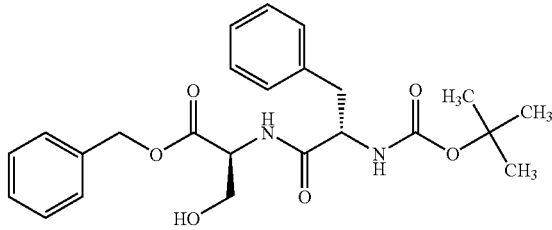

According to the preparation method of the compound of example 150A the title compound is obtained in a yield of 275 mg (55% of theory) from the compound of example 149A (350 mg, 1.13 mmol) and N²-tert-butoxycarbonyl-L-phenylalanine (300 mg, 1.13 mmol).

HPLC (Method 6): $R_t$=4.50 min.

LC-MS (Method 20): $R_t$=2.23 min, MS (ESIpos): m/z (%)=443.2 (100) [M+H]⁺; MS (ESIneg): m/z (%)=441 (50) [M−H]⁻.

HR-TOF-MS (Method 24): $C_{24}H_{31}N_2O_6$ calc. 443.2177, found 443.2180 [M+H]⁺.

Example 153A

Benzyl [N²-(tert-butoxycarbonyl)-L-threonyl]-O³-tert-butyl-L-serinate

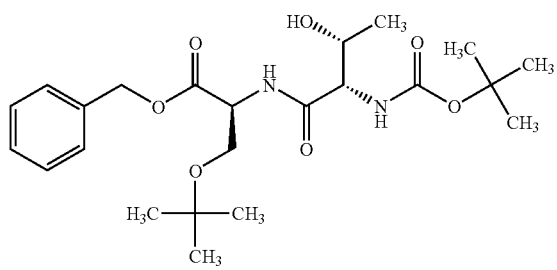

According to the preparation method of the compound of example 150A the title compound is obtained in a yield of 196 mg (49% of theory) from benzyl O³-(tert-butyl)-L-serinate (320 mg, 0.88 mmol) and N²-tert-butoxycarbonylthreonine (192 mg, 0.88 mmol).

HPLC (Method 5): $R_t$=4.73 min.

LC-MS (Method 19): $R_t$=2.56 min, MS (ESIpos): m/z (%)=453.0 (100) [M+H]⁺.

Example 154A

Benzyl [N²-(tert-butoxycarbonyl)-L-allothreonyl]-L-serinate

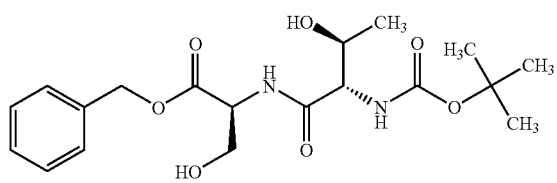

Benzyl L-serinate (314 mg, 1.02 mmol) and NMM (335 µl, 3.05 mmol, 3 equivalents) are provided in DMF at 0° C. Then (N²-tert-butoxycarbonyl)allothreonine (223 mg, 1.02 mmol, 1 equivalent) is added, followed by TCTU (506 mg, 1.42 mmol, 1.4 equivalents). The mixture is stirred overnight and then worked up by chromatography according to method 45. The title compound is obtained in a yield of 298 mg (73% of theory).

HPLC (Method 5): $R_t$=3.89 min.

LC-MS (Method 19): $R_t$=1.91 min, MS (ESIpos): m/z (%)=397.0 (100) [M+H]⁺.

HR-TOF-MS (Method 24): $C_{19}H_{29}N_2O_7$ calc. 397.1970, found 397.1971 [M+H]⁺.

Example 155A

Benzyl [N²-(tert-butoxycarbonyl)-L-alanyl]-L-serinate

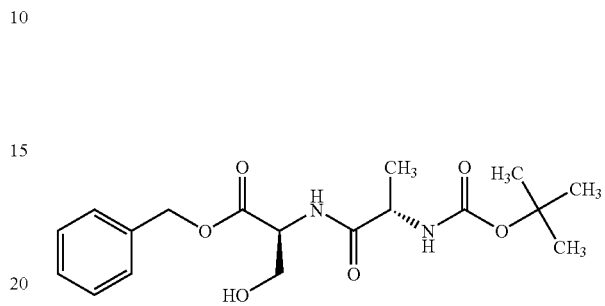

According to the preparation method of the compound of example 150A the title compound is obtained in a yield of 277 mg (78% of theory) from benzyl L-serinate (300 mg, 0.97 mmol) and N²-tert-butoxycarbonylalanine (220 mg, 1.16 mmol).

HPLC (Method 5): $R_t$=4.05 min.

LC-MS (Method 20): $R_t$=1.81 min, MS (ESIpos): m/z (%)=367.2 (50) [M+H]⁺.

Example 156A

Benzyl [N²-(tert-butoxycarbonyl)-L-asparaginyl]-L-serinate

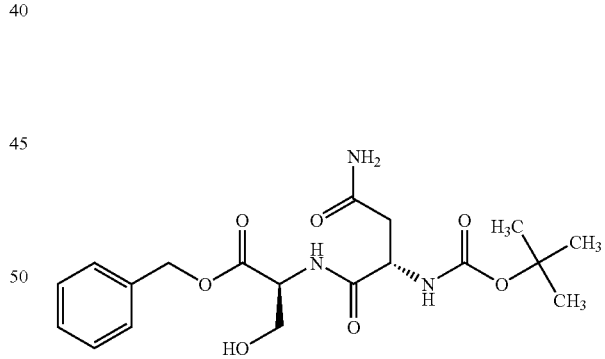

According to the preparation method of the compound of example 150A the title compound is obtained in a yield of 313 mg (39% of theory) from benzyl L-serinate (610 mg, 1.97 mmol) and N²-tert-butoxycarbonylasparagine (458 mg, 1.97 mmol, 1 equivalent).

HPLC (Method 5): $R_t$=3.70 min.

LC-MS (Method 20): $R_t$=1.78 min, MS (ESIpos): m/z (%)=410.1 (100) [M+H]⁺.

HR-TOF-MS (Method 24): $C_{19}H_{27}N_3O_7$ calc. 410.1922, found 410.1914 [M+H]⁺.

Example 157A

Benzyl L-seryl-L-serinate trifluoroacetate

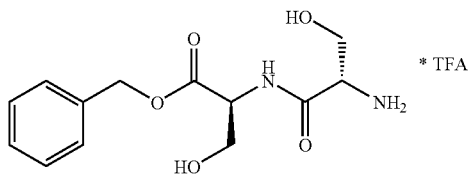

The compound of example 150A (290 mg, 0.76 mmol) is reacted according to procedure 2. 451 mg (quant.) of the crude title compound are obtained and are reacted further without further purification.

LC-MS (Method 22): $R_t$=2.16 min; MS (ESIpos) m/z (%)=283.0 (100) [M+H]$^+$.

Example 158A

Benzyl [3-(3-pyridyl)-L-alanyl]-L-serinate bistrifluoroacetate

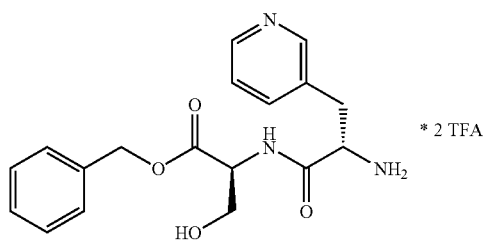

The compound of example 151A (460 mg, 0.99 mmol) is reacted according to procedure 2. 565 mg (quant.) of the crude title compound are obtained and are reacted further without further purification.

HPLC (Method 5): $R_t$=3.03 min.

LC-MS (Method 22): $R_t$=2.23 min, MS (ESIpos): m/z (%) 344.2 (30) [M+H]$^+$.

Example 159A

Benzyl L-phenylalanyl-L-serinat trifluoroacetate

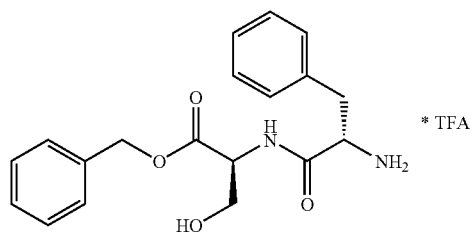

The compound of example 152A (275 mg, 0.62 mmol) is reacted according to procedure 2. 285 mg (93% of theory) of the crude title compound are obtained and are reacted further without further purification.

HPLC (Method 6): $R_t$=3.33 min.

LC-MS (Method 20): $R_t$=1.14 min, MS (ESIpos): m/z (%) 343.3 (100) [M+H]$^+$; MS (ESIneg): m/z (%) 341.3 (100) [M−H]$^-$.

Example 160A

Benzyl L-threonyl-L-serinate trifluoroacetate

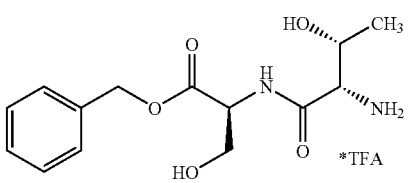

The compound of example 153A (195 mg, 0.43 mmol) is reacted according to procedure 2. 235 mg (quant.) of the crude title compound are obtained and are reacted further without further purification.

HPLC (Method 5): $R_t$=3.20 min.

LC-MS (Method 22): $R_t$=2.32 min, MS (ESIpos): m/z (%) 297 (100) [M+H]$^+$.

Example 161A

Benzyl L-allothreonyl-L-serinate trifluoroacetate

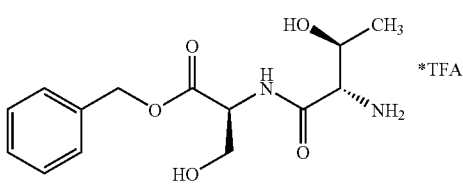

The compound of example 154A (286 mg, 0.72 mmol) is reacted according to procedure 2. 326 mg (quant.) of the crude title compound are obtained and are reacted further without further purification.

HPLC (Method 5): $R_t$=3.16 min.

LC-MS (Method 19): $R_t$=1.38 min, MS (ESIpos): m/z (%) 297 (15) [M+H]$^+$.

HR-TOF-MS (Method 24): $C_{14}H_{21}N_2O_5$ calc. 297.1445, found 297.1436 [M+H]$^+$.

Example 162A

Benzyl L-alanyl-L-serinate trifluoroacetate

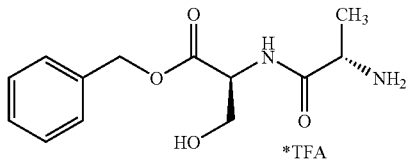

The compound of example 155A (277 mg, 0.76 mmol) is reacted according to procedure 2. 285 mg (quant.) of the crude title compound are obtained and are reacted further without further purification.
HPLC (Method 5): $R_t$=3.20 min.
LC-MS (Method 22): $R_t$=2.35 min, MS (ESIpos): m/z (%) 267 (100) [M+H]$^+$.

Example 163A

Benzyl L-asparaginyl-L-serinate trifluoroacetate

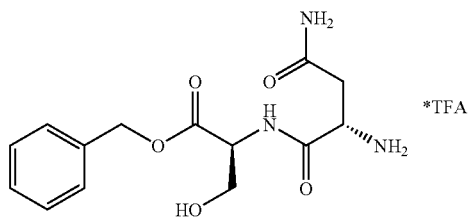

The compound of example 156A (313 mg, 0.76 mmol) is reacted according to procedure 2. 428 mg (quant.) of the crude title compound are obtained and are reacted further without further purification.
HPLC (Method 6): $R_t$=2.96 min.
LC-MS (Method 22): $R_t$=2.07 min, MS (ESIpos): m/z (%) 310 (100) [M+H]$^+$.

Example 164A

Benzyl [N$^2$-(tert-butoxycarbonyl)glycyl]-L-seryl-L-serinate

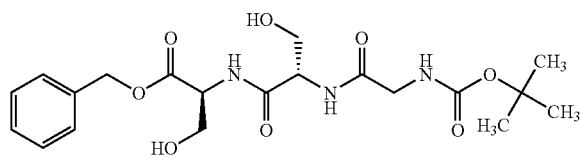

The compound of example 157A (360 mg, 0.85 mmol) and N-tert-butoxycarbonylglycine (149 mg, 0.85 mmol, 1 equivalent) are dissolved in dichloromethane (4.4 ml) and cooled to 0° C. HATU (485 mg, 1.28 mmol, 1.5 equivalents) is added and then, over the course of 15 min, a solution of N,N-diisopropylethylamine (0.74 ml, 4.26 mmol, 5 equivalents) in dichloromethane (3 ml) is added dropwise. The mixture is then stirred at room temp. for 24 h and subsequently washed with sodium bicarbonate, and the organic phase is dried (sodium sulfate) and concentrated. The crude product is purified by chromatography (method 34). Product-containing fractions are combined and lyophilized. Yield: 220 mg (0.50 mmol, 59% of theory) as a colorless solid.
HPLC (Method 3): $R_t$=3.70 min.
LC-MS (Method 1): $R_t$=1.93 min, MS (ESIpos): m/z (%)=440.7 (100).

Example 165A

Benzyl [N$^2$-(tert-butoxycarbonyl)glycyl]-[3-(3-pyridyl)-L-alanyl]-L-serinate

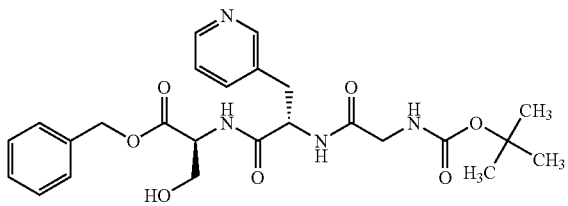

According to the preparation method of the compound of example 164A with DMF (1.8 ml) instead of dichloromethane as solvent the title compound is obtained in a yield of 405 mg (85% of theory) from the compound of example 158A (565 mg, 0.95 mmol) and N-tert-butoxycarbonylglycine (166 mg, 0.95 mmol, 1 equivalent).
HPLC (Method 5): $R_t$=3.52 min.
LC-MS (Method 20): $R_t$=1.49 min, MS (ESIpos): m/z (%)=501.4 (100) [M+H]$^+$.

Example 166A

Benzyl [N$^2$-(tert-butoxycarbonyl)glycyl]-L-phenylalanyl-L-serinate

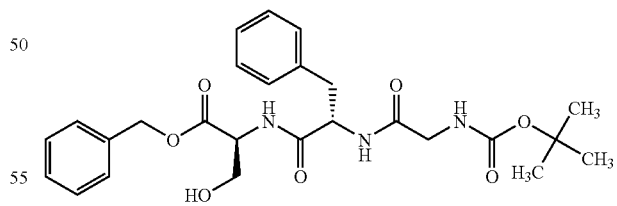

According to the preparation method of the compound of example 164A with DMF (2.0 ml) instead of dichloromethane as solvent the title compound is obtained in a yield of 237 mg (82% of theory) from the compound of example 159A (285 mg, 0.58 mmol) and N-tert-butoxycarbonylglycine (122 mg, 0.70 mmol, 1 equivalent).
HPLC (Method 6): $R_t$=4.28 min.
LC-MS (Method 19): $R_t$=2.29 min, MS (ESIpos): m/z (%)=500.2 (100) [M+H]$^+$.

HR-TOF-MS (Method 24): $C_{26}H_{34}N_3O_7$ calc. 500.2392, found 500.2399 $[M+H]^+$.

Example 167A

Benzyl [$N^2$-tert-butoxycarbonyl-glycyl]-L-threonyl-L-serinate

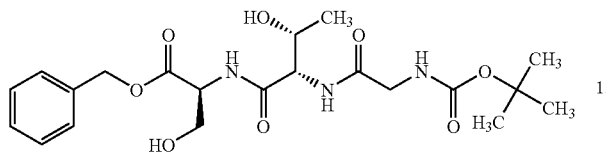

According to the preparation method of the compound of example 164A with DMF (1.8 ml) instead of dichloromethane as solvent the title compound is obtained in a yield of 84 mg (34% of theory) from the compound of example 160A (173 mg, 0.49 mmol) and $N^2$-tert-butoxycarbonylglycine (103 mg, 0.59 mmol, 1.2 equivalent).

HPLC (Method 5): $R_t$=4.45 min.

LC-MS (Method 19): $R_t$=2.38 min, MS (ESIpos): m/z (%)=510.2 (100) $[M+H]^+$.

Example 168A

Benzyl [$N^2$-tert-butoxycarbonyl-glycyl]-L-allothreonyl-L-serinate

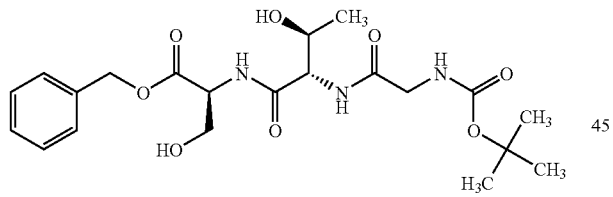

The compound of example 161A (295 mg, 0.72 mmol) and $N^2$-tert-butoxycarbonylglycine (126 mg, 0.72 mmol, 1.0 equivalent) are provided in DMF at 0° C. TCTU (329 mg, 0.87 mmol, 1.2 equivalents) and NMM (238 µl, 2.16 mmol, 3 equivalents) are then added. The mixture is stirred at room temperature overnight and then worked up by chromatography according to method 45. Product-containing fractions are combined and purified by chromatography according to a modified method 32 (gradient: 0-5 min 10% B, 5.01-35 min ramp 85% B, 35.01-40 min 85% B). The title compound is obtained in a yield of 170 mg (52% of theory).

HPLC (Method 5): $R_t$=3.73 min.

LC-MS (Method 19): $R_t$=1.82 min, MS (ESIpos): m/z (%)=454.1 (80) $[M+H]^+$.

HR-TOF-MS (Method 24): $C_{21}H_{32}N_3O_8$ calc. 454.2184, found 454.2177 $[M+H]^+$.

Example 169A

Benzyl [$N^2$-tert-butoxycarbonyl-glycyl]-L-alanyl-L-serinate

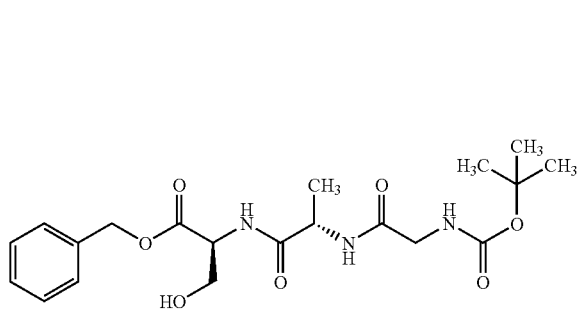

According to the preparation method of the compound of example 164A with DMF (1.8 ml) instead of dichloromethane as solvent the title compound is obtained in a yield of 172 mg (43% of theory) from the compound of example 162A (285 mg, 0.75 mmol) and $N^2$-tert-butoxycarbonylglycine (157 mg, 0.90 mmol, 1.2 equivalents).

HPLC (Method 5): $R_t$=3.83 min.

LC-MS (Method 21): $R_t$=1.85 min, MS (ESIpos): m/z (%)=424.4 (100) $[M+H]^+$.

Example 170A

Benzyl [$N^2$-(tert-butoxycarbonyl)-glycyl]-L-asparaginyl-L-serinate

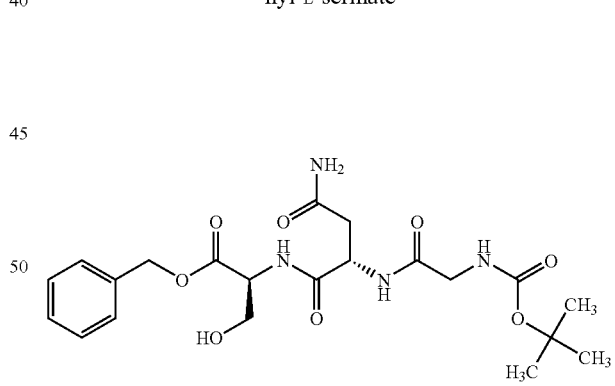

According to the preparation method of the compound of example 164A with DMF (2.0 ml) instead of dichloromethane as solvent the title compound is obtained in a yield of 208 mg (56% of theory) from the compound of example 163A (428 mg, 0.80 mmol) and $N^2$-tert-butoxycarbonylglycine (167 mg, 0.96 mmol, 1.2 equivalents).

HPLC (Method 6): $R_t$=3.60 min.

LC-MS (Method 21): $R_t$=1.75 min, MS (ESIpos): m/z (%)=467.0 (100) $[M+H]^+$.

HR-TOF-MS (Method 24): $C_{21}H_{31}N_4O_8$ calc. 467.2137, found 467.2142 $[M+H]^+$.

Example 171A

Benzyl glycyl-L-seryl-L-serinate trifluoroacetate

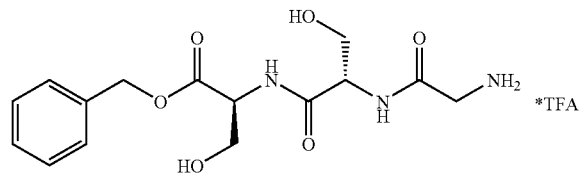

The compound of example 164A (88 mg, 0.20 mmol) is reacted according to procedure 2 in 1.5 ml of the reagent solution. The crude product is reacted further without further purification.
Yield: 118 mg (quant.)
HPLC (Method 3): $R_t$=3.08 min.
LC-MS (Method 22): $R_t$=2.56 min, MS (ESIpos): m/z (%)=340.0 (100) $[M+H]^+$.

Example 172A

Benzyl [glycyl]-[3-(3-pyridyl)-L-alanyl]-L-serinate bistrifluoroacetate

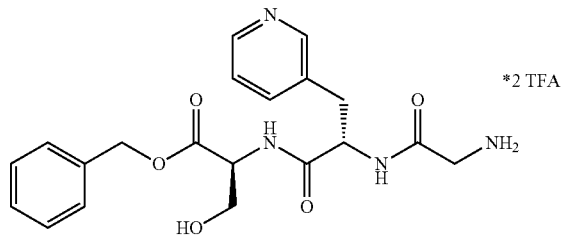

The compound of example 165A (60 mg, 0.12 mmol) is reacted according to procedure 2 in 1.5 ml of the reagent solution. The crude product is reacted further without further purification. Yield: 81 mg (quant.)
HPLC (Method 5): $R_t$=3.05 min.
LC-MS (Method 22): $R_t$=2.36 min, MS (ESIpos): m/z (%) 401.0 (40) $[M+H]^+$.

Example 173A

Benzyl glycyl-L-phenylalanyl-L-serinate trifluoroacetate

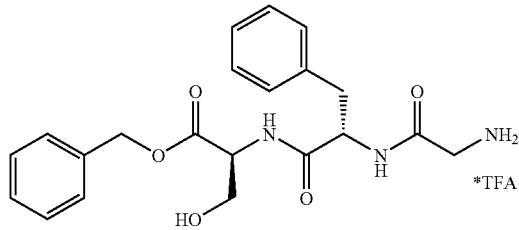

The compound of example 166A (63 mg, 0.13 mmol) is reacted according to procedure 2 in 1.0 ml of the reagent solution. The crude product is reacted further without further purification. Yield: 65 mg (96% of theory).

HPLC (Method 6): $R_t$=3.35 min.
LC-MS (Method 22): $R_t$=1.26 min, MS (ESIpos): m/z (%)=400.1 (90) $[M+H]^+$; MS (ESIneg): m/z (%)=398.1 (100) $[M-H]^-$.
HR-TOF-MS (Method 24): $C_{21}H_{26}N_3O_5$ calc. 400.1867, found 400.1869 $[M+H]^+$.

Example 174A

Benzyl glycyl-L-threonyl-L-serinate trifluoroacetate

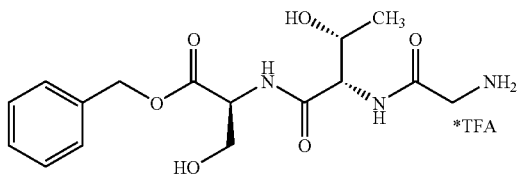

The compound of example 167A (82 mg, 0.16 mmol) is reacted according to procedure 2 in 1.5 ml of the reagent solution. The crude product is purified by chromatography (method 44). Yield: 43 mg (76% of theory).
HPLC (Method 5): $R_t$=3.16 min.
LC-MS (Method 22): $R_t$=2.35 min, MS (ESIpos): m/z (%)=354 (50) $[M+H]^+$.

Example 175A

Benzyl glycyl-L-allothreonyl-L-serinate trifluoroacetate

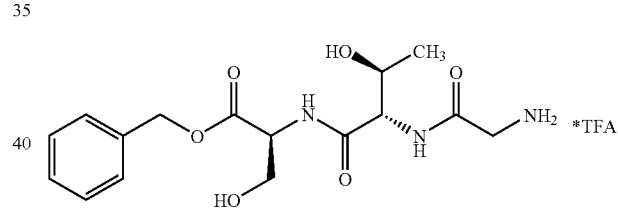

The compound of example 168A (169 mg, 0.37 mmol) is reacted according to procedure 2 in 1.5 ml of the reagent solution. The crude product (194 mg, about quant.) is reacted further without further purification.
HPLC (Method 5): $R_t$=3.16 min.
LC-MS (Method 21): $R_t$=0.78 min, MS (ESIpos): m/z (%)=354.3 (100) $[M+H]^+$.
HR-TOF-MS (Method 24): $C_{16}H_{24}N_4O_6$ calc. 354.1660, found 354.1648 $[M+H]^+$.

Example 176A

Benzyl glycyl-L-alanyl-L-serinate trifluoroacetate

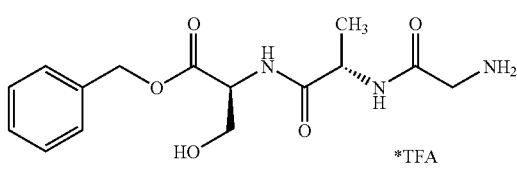

The compound of example 169A (172 mg, 0.32 mmol) is reacted according to procedure 2 in 3.0 ml of the reagent solution. The crude product is reacted further without purification. Yield: 175 mg (99% of theory).

HPLC (Method 5): $R_t$=3.20 min.

LC-MS (Method 22): $R_t$=2.41 min, MS (ESIpos): m/z (%)=324 (40) [M+H]$^+$.

HPLC (Method 6): $R_t$=2.89 min.

LC-MS (Method 22): $R_t$=2.14 min, MS (ESIpos): m/z (%)=367 (100) [M+H]$^+$.

HR-TOF-MS (Method 24): $C_{16}H_{23}N_4O_6$ calc. 367.1613, found 367.1609 [M+H]$^+$.

Example 178A

Benzyl [(3R)-$N^2$-(tert-butoxycarbonyl)-3-hydroxy-L-leucyl]-L-leucyl-D-arginyl-L-isoleucyl-L-allothreonyl-glycyl-L-seryl-L-serinate trifluoroacetate

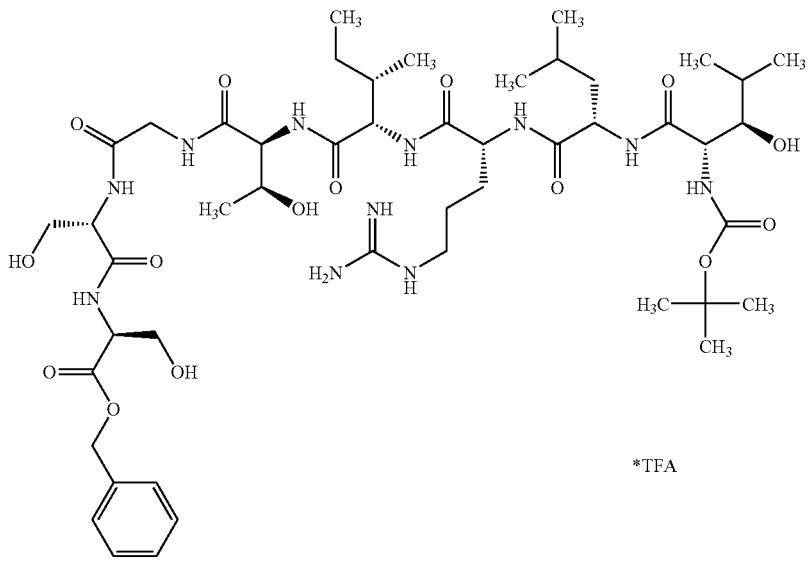

Example 177A

Benzyl glycyl-L-asparaginyl-L-serinate trifluoroacetate

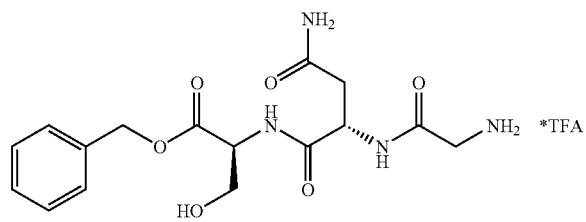

The compound of example 170A (60 mg, 0.13 mmol) is reacted according to procedure 2 in 1.0 ml of the reagent solution. The crude product is reacted further without purification. Yield: 62 mg (quant.).

The compounds of example 32A (75 mg, 38 μmol) and 171A (26 mg, 45 μmol, 1.2 equivalents) are dissolved in DMF (950 μl), and the solution is cooled to −20° C. 4-Methylmorpholine (29 μl, 263 μmol, 7 equivalents) and HATU (23 mg, 60 μmol, 1.6 equivalents) are added, and the mixture is stirred at room temperature for 16 h. The complete mixture is then put onto an HPLC column and purified by chromatography according to method 33. Product-containing fractions are combined and lyophilized. 15 mg (34% of theory) of the title compound are obtained as a colorless solid.

HPLC (Method 5): $R_t$=3.89 min.

LC-MS (Method 19): $R_t$=1.81 min, MS (ESIpos): m/z (%)=1053 (90) [M+H]$^+$.

Example 179A

Benzyl [(3R)-N²-(tert-butoxycarbonyl)-3-hydroxy-L-leucyl]-L-leucyl-D-arginyl-L-isoleucyl-L-allothreonyl-glycyl-[3-(3-pyridyl)-L-alanyl]-L-serinate trifluoroacetate According to the preparation method of the compound of example 178A the title compound is obtained in a yield of 34 mg (33% of theory) from the compound of example 32A (80 mg, 83 μmol) and the compound of example 172A (79 mg, 125 μmol, 1.5 equivalents).

HPLC (Method 5): $R_t$=3.75 min.

LC-MS (Method 18): $R_t$=1.52 min, MS (ESIpos): m/z (%)=557.6 (100) [M+2H]²⁺; 1113.8 (10) [M+H]⁺.

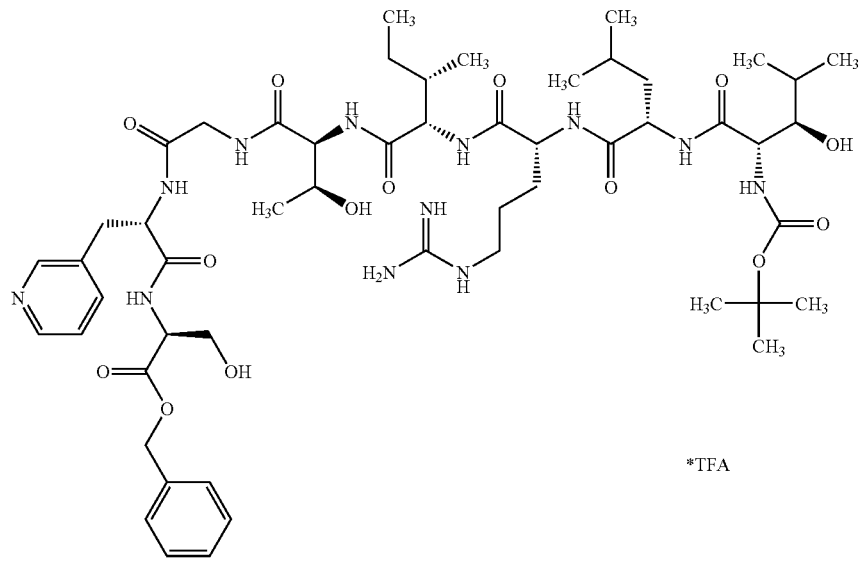

*TFA

Example 180A

Benzyl [(3R)-N²-(tert-butoxycarbonyl)-3-hydroxy-L-leucyl]-L-leucyl-D-arginyl-L-isoleucyl-L-allothreonyl-glycyl-L-phenylalanyl-L-serinate trifluoroacetate

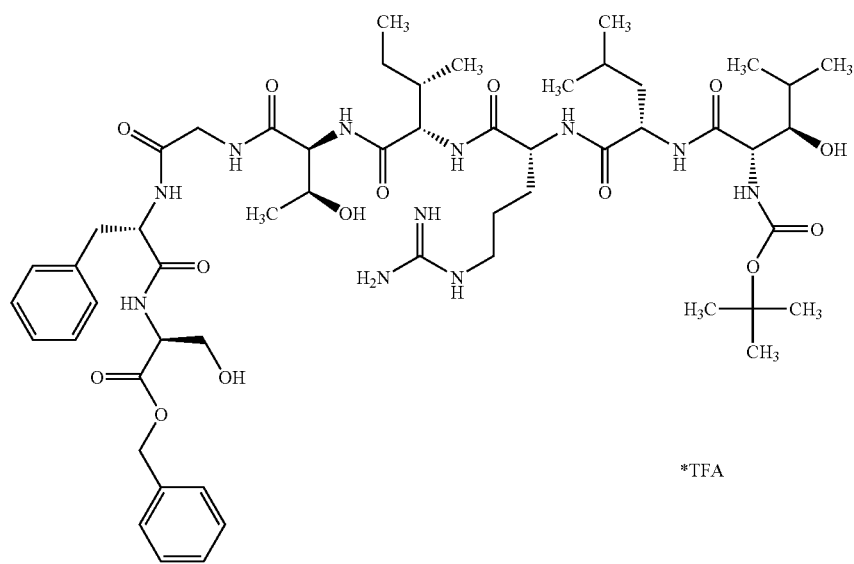

*TFA

According to the preparation method of the compound of example 178A the title compound is obtained in a yield of 39 mg (33% of theory) from the compound of example 32A (82 mg, 97 μmol) and the compound of example 173A (65 mg, 126 μmol, 1.3 equivalents).

HPLC (Method 6): $R_t$=3.96 min.

LC-MS (Method 19): $R_t$=1.87 min, MS (ESIpos): m/z (%)=506.8 (90) $[M+2H]^{2+}$; 1112.5 (100) $[M+H]^+$; MS (ESIneg): m/z (%)=1110.5 (100) $[M-H]^-$.

HR-TOF-MS (Method 24): $C_{54}H_{86}N_{11}O_{14}$ calc. 1112.6351, found 1112.6343 $[M+H]^+$.

Example 181A

Benzyl [(3R)-$N^2$-(tert-Butoxycarbonyl)-3-hydroxy-L-leucyl]-L-leucyl-D-arginyl-L-isoleucyl-L-allothreonyl-glycyl-L-threonyl-L-serinate trifluoroacetate

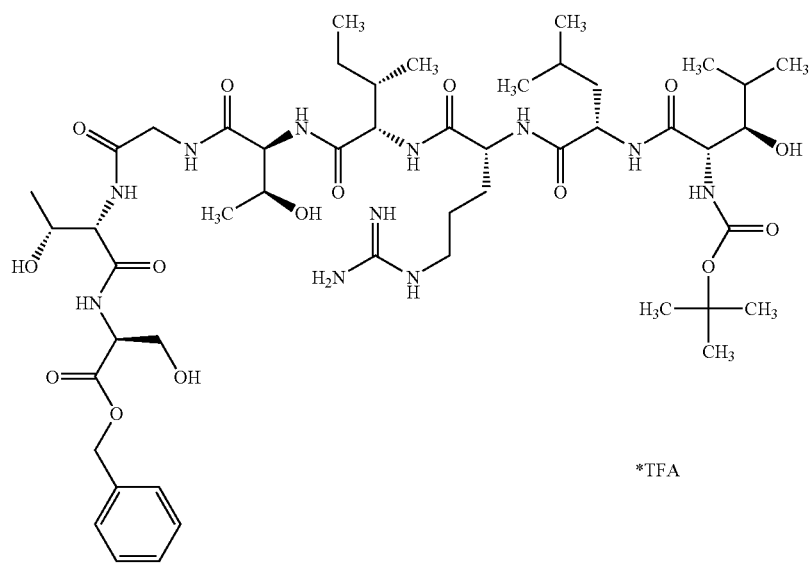

*TFA

The title compound is obtained in a yield of 21 mg (20% of theory) according to the preparation method of the compound of example 178A from the compound of example 32A (67 mg, 80 μmol) and the compound of example 174A (31 mg, 88 μmol, 1.1 equivalents).

HPLC (Method 5): $R_t$=3.89 min.

LC-MS (Method 19): $R_t$=1.71 min, MS (ESIpos): m/z (%)=1066.7 (100) $[M+H]^+$.

HR-TOF-MS (Method 24): $C_{49}H_{84}N_{11}O_{15}$ calc. 1066.6143, found 1066.6130 $[M+H]^+$.

Example 182A

Benzyl [(3R)-N²-(tert-butoxycarbonyl)-3-hydroxy-L-leucyl]-L-leucyl-D-arginyl-L-isoleucyl-L-allothreonyl-glycyl-L-allothreonyl-L-serinate trifluoroacetate

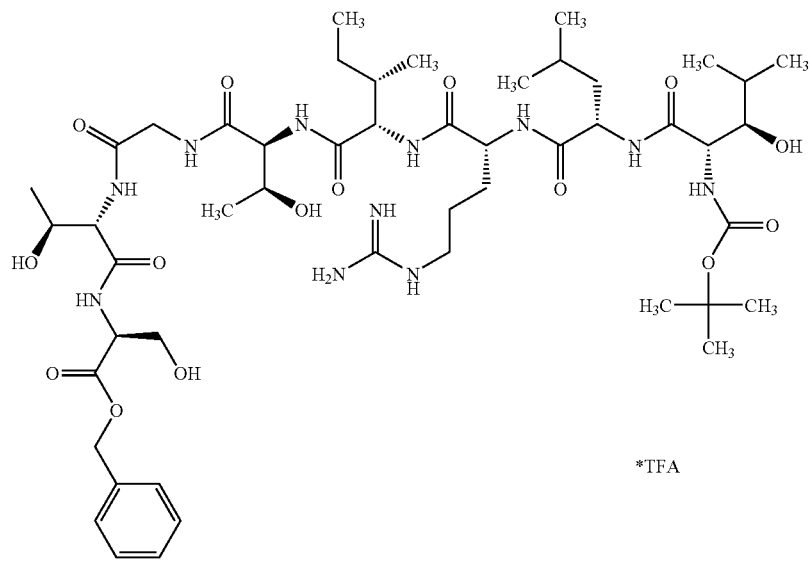

*TFA

The compound of example 32A (57 mg, 59 µmol) and the compound of example 175A (48 mg, 71 µmol, 1.2 equivalents) are reacted according to the preparation method of the compound of example 178A. The workup takes place on Sephadex LH₂O (method 45) followed by chromatography according to a modified method 44 (gradient: 0-5 min 5% B, ramp, 30-35 min 75% B, 35.01-40 min 75% B). The title compound is obtained in a yield of 65 mg (93% of theory).

HPLC (Method 6): $R_t$=3.70 min.

LC-MS (Method 19): $R_t$=1.70 min, MS (ESIpos): m/z (%)=483.9 (100) [M-Boc+2H]²⁺, 1066.6 (70) [M+H]⁺.

HR-TOF-MS (Method 24): $C_{49}H_{84}N_{11}O_{15}$ calc. 1066.6143, found 1066.6134 [M+H]⁺.

Example 183A

Benzyl [(3R)-N²-(tert-butoxycarbonyl)-3-hydroxy-L-leucyl]-L-leucyl-D-arginyl-L-isoleucyl-L-allothreonyl-glycyl-L-alanyl-L-serinate trifluoroacetate

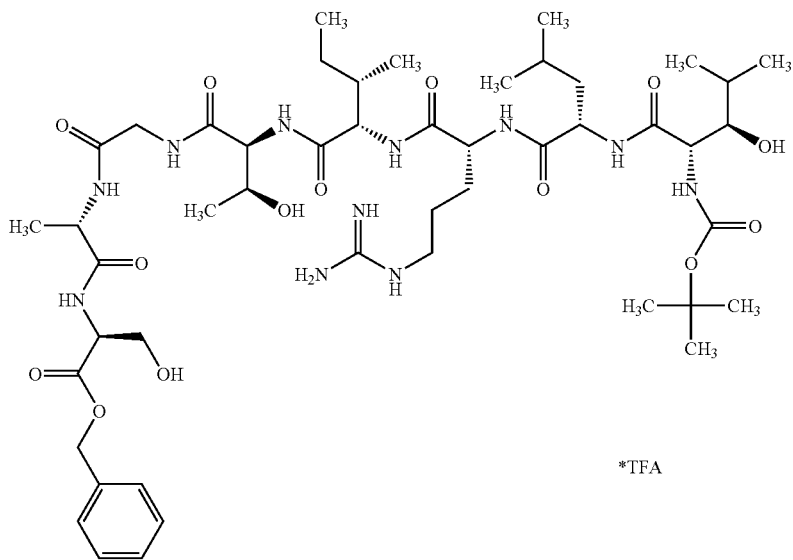

*TFA

According to the preparation method of the compound of example 178A and after an additional purification by chromatography (Kromasil RP-18 5 μm, 100 Å, 250×20 mm; eluent A: water+0.05% TFA, eluent B: acetonitrile+0.05% TFA: flow rate: 10 ml/min; 60% A, 40% β isocratic), the title compound is obtained in a yield of 48 mg (50% of theory) from the compound of example 32A (80 mg, 84 μmol) and the compound of example 176A (60 mg, 109 μmol, 1.3 equivalents).

HPLC (Method 5): $R_t$=3.99 min.

LC-MS (Method 19): $R_t$=1.70 min, MS (ESIpos): m/z (%)=1036.6 (100) [M+H]$^+$.

HR-TOF-MS (Method 24): $C_{48}H_{81}N_{11}O_{14}$ calc. 1036.6038, found 1036.6027 [M+H]$^+$.

Example 184A

Benzyl [(3R)-$N^2$-(tert-butoxycarbonyl)-3-hydroxy-L-leucyl]-L-leucyl-[$N^5$-(imino-{[(2,2,5,7,8-pentamethyl-3,4-dihydro-2H-chromen-6-yl)sulfonyl]amino}methyl)-D-ornithyl]}-L-isoleucyl-[$O^3$-(tert-butyl)-L-seryl]-glycyl-[(3S)-3-hydroxy-L-asparaginyl]-L-serinate

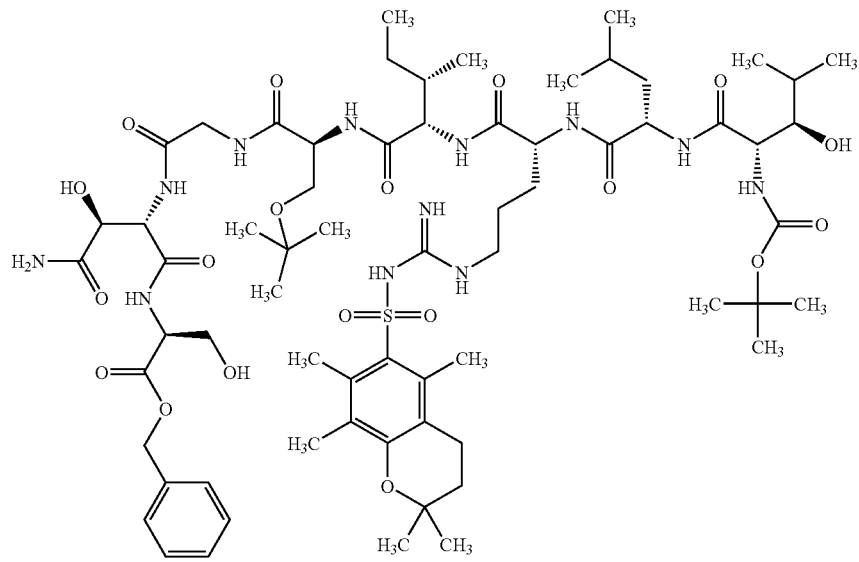

According to the preparation method of the compound of example 178A and after an additional purification by chromatography (Kromasil RP-18 5 μm, 100 Å, 250×20 mm; eluent A: water+0.05% TFA, eluent B: acetonitrile+0.05% TFA: flow rate: 10 ml/min; 60% A, 40% β isocratic), the title compound is obtained in a yield of 62 mg (49% of theory) from the compound of example 148A (87 mg, 84 μmol) and the compound of example 36A (50 mg, 101 μmol, 1.2 equivalents).

HPLC (Method 5): $R_t$=4.40 min.

LC-MS (Method 19): $R_t$=2.97 min, MS (ESIpos): m/z (%)=1403.7 (100) [M+H]$^+$.

HR-TOF-MS (Method 24): $C_{66}H_{107}N_{12}O_{19}S$ calc. 1403.7491, found 1403.7517 [M+H]$^+$.

Example 185A

Benzyl [(3R)-N²-(tert-butoxycarbonyl)-3-hydroxy-L-leucyl]-L-leucyl-D-arginyl-L-isoleucyl-L-allothreonyl-glycyl-L-asparaginyl-L-serinate trifluoroacetate

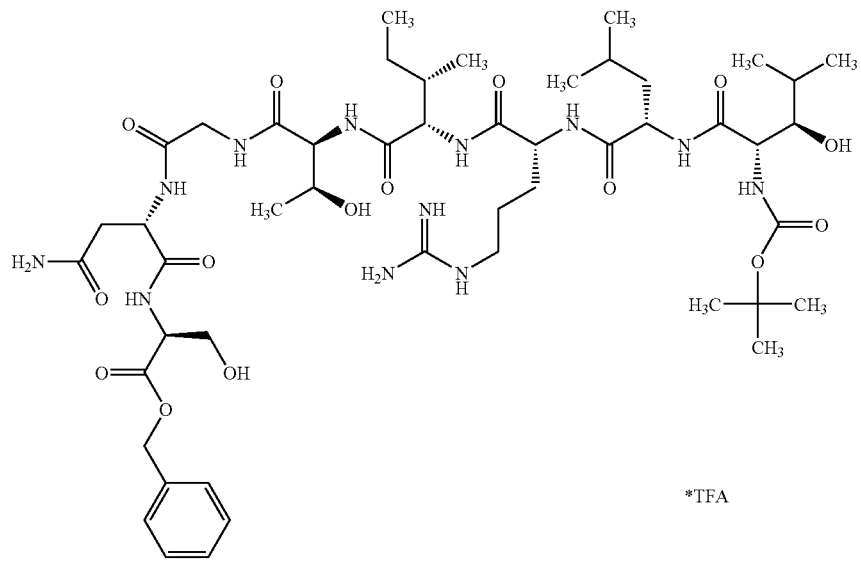

*TFA

According to the preparation method for the compound of example 178A the title compound is obtained in a yield of 48 mg (31% of theory) from the compound of example 32A (100 mg, 118 µmol) and the compound of example 177A (62 mg, 130 µmol, 1.1 equivalents).

HPLC (Method 6): $R_t$=3.66 min.

LC-MS (Method 22): $R_t$=1.66 min, MS (ESIpos): m/z (%) 490.3 (100) [M-Boc+2H]$^{2+}$, 1079.6 (80) [M+H]$^+$.

HR-TOF-MS (Method 24): $C_{49}H_{83}N_{12}O_{15}$ calc. 1079.6096, found 1079.6090 [M+H]$^+$.

Example 186A

[(3R)-N²-(tert-butoxycarbonyl)-3-hydroxy-L-leucyl]-L-leucyl-D-arginyl-L-isoleucyl-L-allothreonyl-glycyl-L-seryl-L-serine trifluoroacetate The compound of example 178A (21 mg, 18 µmol) is hydrogenated in 750 µl of acetic acid in the presence of 5 mg of 10% palladium-carbon at room temperature under atmospheric pressure for 2 h. The mixture is filtered to remove the catalyst and dried to a constant weight under oil pump vacuum. The title compound is obtained in quantitative yield (20 mg) and is reacted further without purification.

HPLC (Method 5): $R_t$=3.56 min.

LC-MS (Method 19): $R_t$=1.72 min, MS (ESIpos): m/z (%)=963.0 (90) [M+H]$^+$.

HR-TOF-MS (Method 24): $C_{41}H_{76}N_{11}O_{15}$ calc. 962.5517, found 962.5537 [M+H]$^+$.

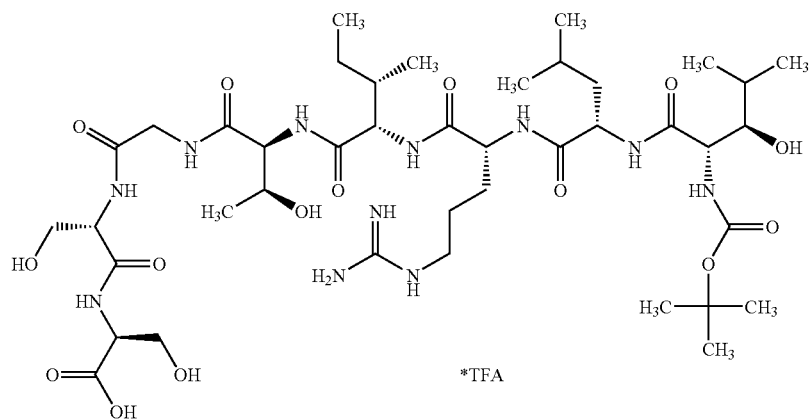

*TFA

Example 187A

[(3R)-N²-(tert-butoxycarbonyl)-3-hydroxy-L-leucyl]-L-leucyl-D-arginyl-L-isoleucyl-L-allothreonyl-glycyl-[3-(3-pyridyl)-L-alanyl]-L-serine bistrifluoroacetate

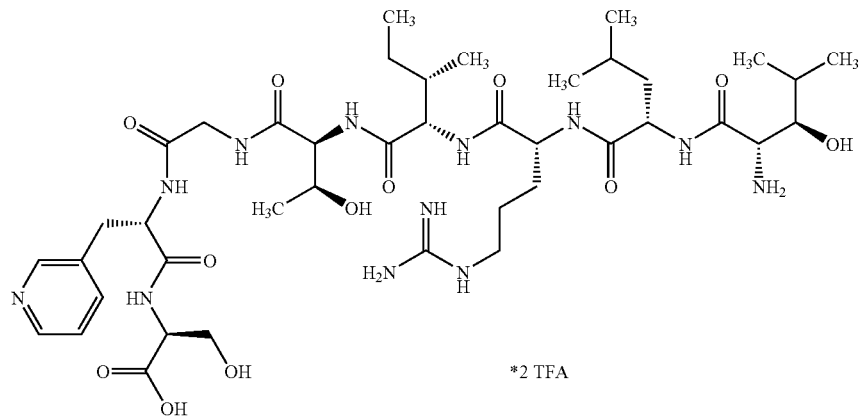

The compound of example 179A (55 mg, 45 μmol) is hydrogenated according to the preparation method of the compound of example 186A. After concentration of the crude product it is directly subjected to a Boc removal according to procedure 2 and again concentrated. 41 mg (88% of theory) of the title compound are obtained and are reacted further without further purification.

HPLC (Method 5): $R_t$=3.56 min.

LC-MS (Method 22): $R_t$=2.19 min, MS (ESIpos): m/z (%)=462 (40) [M+H]⁺; (ESIneg): m/z (%)=[M−H]⁻.

HR-TOF-MS (Method 24): $C_{41}H_{71}N_{12}O_{12}$ calc. 923.5309, found 923.5321 [M+H]⁺.

Example 188A

[(3R)-N²-(tert-Butoxycarbonyl)-3-hydroxy-L-leucyl]-L-leucyl-D-arginyl-L-isoleucyl-L-allothreonyl-glycyl-L-phenylalanyl-L-serine trifluoroacetate The compound of example 180A (39 mg, 32 μmol) is hydrogenated according to the preparation method for preparing the compound of example 186A. 36 mg (quant.) of the title compound are obtained and are reacted further without further purification.

HPLC (Method 6): $R_t$=3.55 min.

LC-MS (Method 18): $R_t$=1.75 min, MS (ESIpos): m/z (%) 462 (100) [M-Boc+2H]²⁺, 1022.1 (10) [M+H]⁺; (ESIneg): m/z (%)=1020.8 [M−H]⁻.

HR-TOF-MS (Method 24): $C_{47}H_{80}N_{11}O_{14}$ calc. 1022.5881, found 1022.5876 [M+H]⁺.

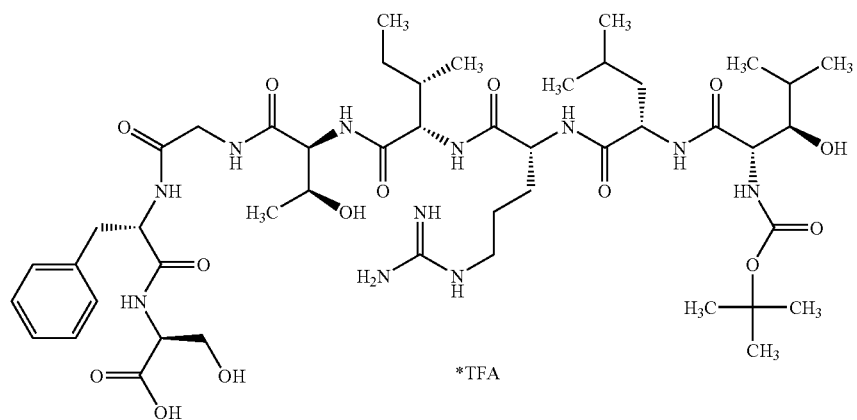

Example 189A

[(3R)-N²-(tert-Butoxycarbonyl)-3-hydroxy-L-leucyl]-L-leucyl-D-arginyl-L-isoleucyl-L-allothreonyl-glycyl-L-threonyl-L-serine bistrifluoroacetate

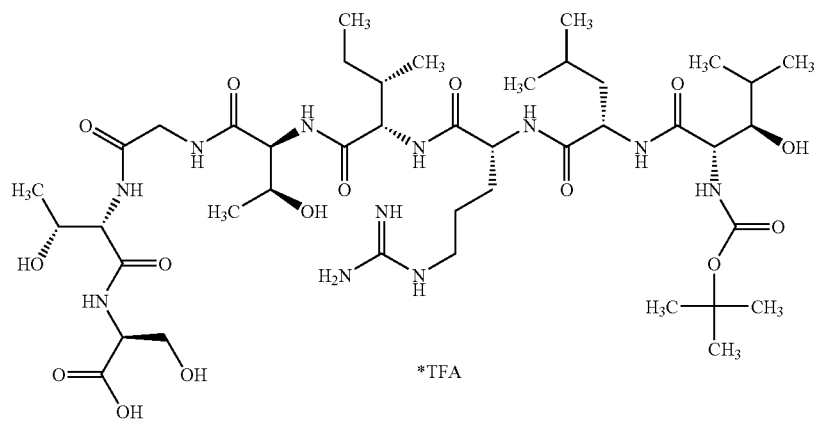

The compound of example 181A (21 mg, 18 μmol) is hydrogenated according to the preparation method of the compound of example 186A. 18 mg (98% of theory) of the title compound are obtained as a colorless solid.

HPLC (Method 5): $R_t$=3.58 min.

LC-MS (Method 19): $R_t$=1.58 min, MS (ESIpos): m/z (%)=976.6 (80) [M+H]⁺.

Example 190A

[(3R)-3-Hydroxy-L-leucyl]-L-leucyl-D-arginyl-L-isoleucyl-L-allothreonyl-glycyl-L-allothreonyl-L-serine bistrifluoroacetate The compound of example 197A (44 mg, 37 μmol) is dissolved in methanol (5.0 ml), 10% Pd/C (20 mg) is added, and the mixture is hydrogenated at room temperature under atmospheric pressure for 2 h. The mixture is filtered to remove the catalyst and the filtrate is concentrated. 42 mg (quant.) of the crude title compound are obtained and are reacted further without purification.

HPLC (Method 5): $R_t$=3.00 min.

LC-MS (Method 22): $R_t$=2.32 min, MS (ESIpos): m/z (%)=439 (100) [M+2H]²⁺; MS (ESIneg): m/z (%)=875 (100) [M−H]⁻.

HR-TOF-MS (Method 24): $C_{37}H_{69}N_{11}O_{13}$ calc. 876.5150, found 876.5146 [M+H]⁺.

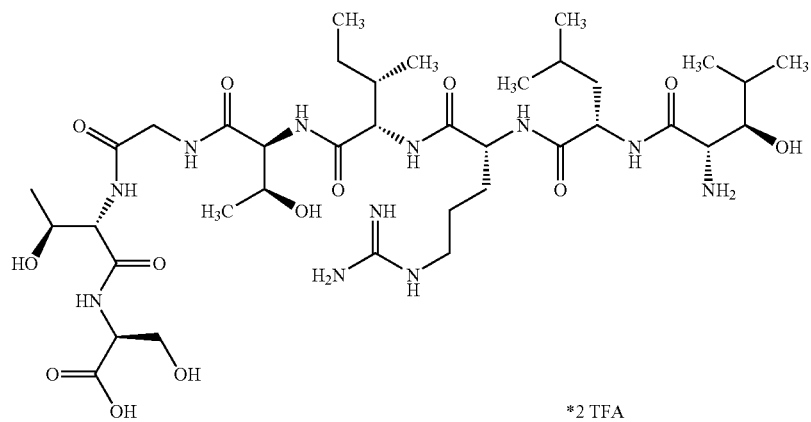

Example 191A

[(3R)-N²-(tert-Butoxycarbonyl)-3-hydroxy-L-leucyl]-L-leucyl-D-arginyl-L-isoleucyl-L-allothreonyl-glycyl-L-alanyl-L-serine trifluoroacetate

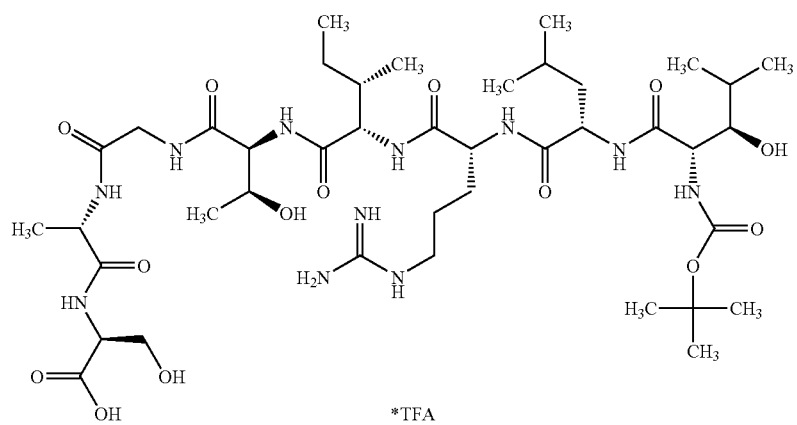

*TFA

Example 192A

[(3R)-N²-(tert-Butoxycarbonyl)-3-hydroxy-L-leucyl]-L-leucyl-[N⁵-(imino{[(2,2,5,7,8-pentamethyl-3,4-dihydro-2H-chromen-6-yl)sulfonyl] amino}methyl)-D-ornithyl]}-L-isoleucyl-[O³-(tert-butyl)-L-seryl]-glycyl-[(3S)-3-hydroxy-L-asparaginyl]-L-serine

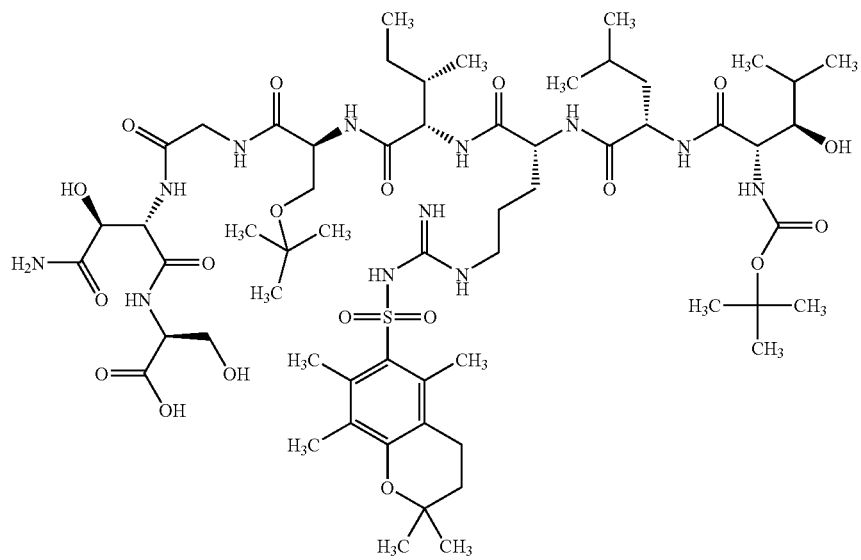

The compound of example 183A (47 mg, 41 μmol) is hydrogenated according to the preparation method of the compound of example 186A. 43 mg (99% of theory) of the title compound are obtained as a solid.

HPLC (Method 5): $R_t$=3.62 min.

LC-MS (Method 19): $R_t$=1.58 min, MS (ESIpos): m/z (%)=946.5 (100) [M+H]⁺.

HR-TOF-MS (Method 24): $C_{41}H_{76}N_{11}O_{14}$ calc. 946.5568, found 946.5569 [M+H]⁺.

The compound of example 184A (62 mg, 41 μmol) is hydrogenated according to the preparation method of the compound of example 186A. 56 mg (96% of theory) of the title compound are obtained as a solid.

HPLC (Method 5): $R_t$=4.57 min.

LC-MS (Method 19): $R_t$=3.06 min, MS (ESIpos): m/z (%)=1313.7 (100) [M+H]⁺.

HR-TOF-MS (Method 24): $C_{59}H_{101}N_{12}O_{19}S$ calc. 1313.7022, found 1313.7020 [M+H]⁺.

Example 193A

[(3R)-N²-(tert-Butoxycarbonyl)-3-hydroxy-L-leucyl]-L-leucyl-D-arginyl-L-isoleucyl-L-allothreonyl-glycyl-L-asparaginyl-L-serine trifluoroacetate

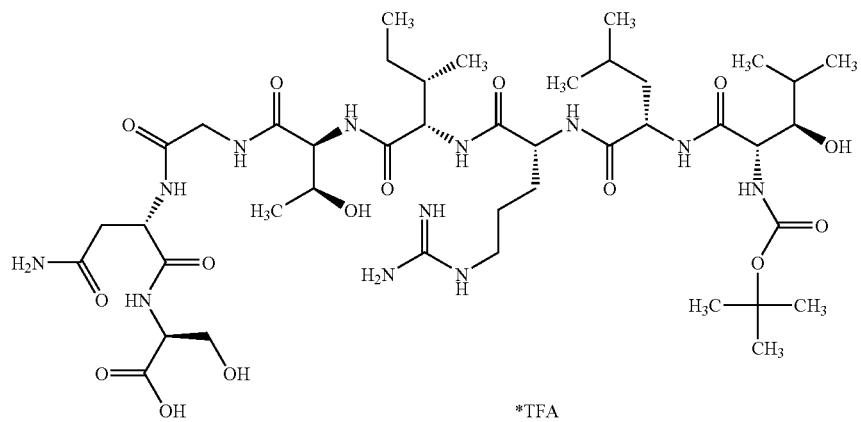

*TFA

The compound of example 185A (48 mg, 40 μmol) is hydrogenated according to the preparation method of the compound of example 186A. 42 mg (99% of theory) of the title compound are obtained as a colorless solid.

HPLC (Method 5): $R_t$=3.40 min.
LC-MS (Method 19): $R_t$=1.57 min, MS (ESIpos): m/z (%)=445.3 (100) $[M+2H]^{2+}$, 9989.6 (70) $[M+H]^+$.
HR-TOF-MS (Method 24): $C_{42}H_{77}N_{12}O_{15}$ calc. 989.5626, found 989.5619 $[M+H]^+$.

Example 194A

[(3R)-3-Hydroxy-L-leucyl]-L-leucyl-D-arginyl-L-isoleucyl-L-allothreonyl-glycyl-L-seryl-L-serine bistrifluoroacetate

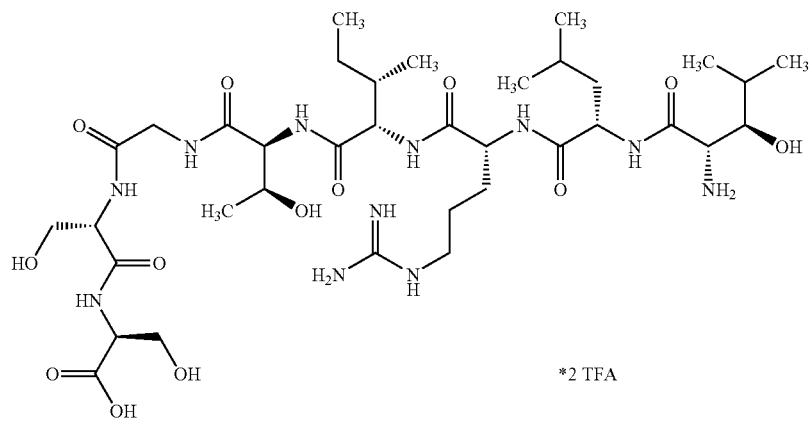

*2 TFA

The compound of example 186A (20 mg, 18 μmol) is reacted according to procedure 2. 20 mg (99% of theory) of the title compound are obtained as a solid.

HPLC (Method 5): $R_t$=2.96 min.
LC-MS (Method 22): $R_t$=2.25 min, MS (ESIpos): m/z (%)=432 (100) $[M+2H]^{2+}$, 862.6 (1) $[M+H]^+$.
HR-TOF-MS (Method 24): $C_{36}H_{68}N_{11}O_{13}$ calc. 862.4993, found 862.5027 $[M+H]^+$.

Example 195A

[(3R)3-Hydroxy-L-leucyl]-L-leucyl-D-arginyl-L-isoleucyl-L-allothreonyl-glycyl-L-phenyl alanyl-L-serine bistrifluoroacetate

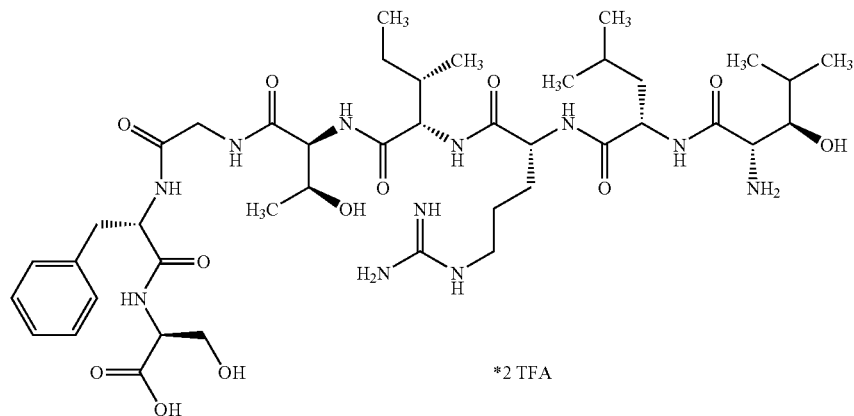

The compound of example 188A (36 mg, 32 µmol) is reacted according to procedure 2. 36 mg (99% of theory) of the title compound are obtained as solid.

HPLC (Method 6): $R_t$=2.98 min.
LC-MS (Method 19): $R_t$=1.11 min, MS (ESIpos): m/z (%)=461.8 (100) $[M+2H]^{2+}$, 922.5 (10) $[M+H]^+$; MS (ESIpos): m/z (%)=920.5 (100) $[M-H]^-$.
HR-TOF-MS (Method 24): $C_{42}H_{72}N_{11}O_{12}$ calc. 922.5357, found 922.5357 $[M+H]^+$.

Example 196A

[(3-R)-3-Hydroxy-L-leucyl]-L-leucyl-D-arginyl-L-isoleucyl-L-allothreonyl-glycyl-L-threonyl-L-serine bistrifluoroacetate

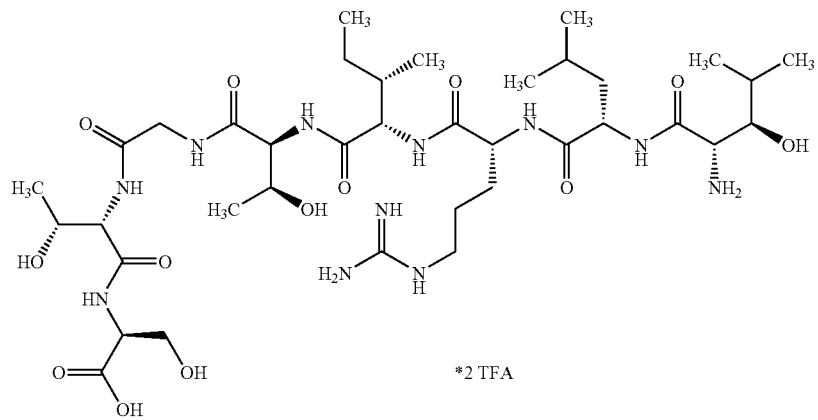

The compound of example 189A (18 mg, 17 µmol) is reacted according to procedure 2. 18 mg (94% of theory) of the title compound are obtained as a solid.

HPLC (Method 5): $R_t$=2.99 min.
LC-MS (Method 22): $R_t$=2.47 min, MS (ESIpos): m/z (%)=439 (100) $[M+2H]^{2+}$.
HR-TOF-MS (Method 24): $C_{37}H_{70}N_{11}O_{13}$ calc. 876.5150, found 876.5161 $[M+H]^+$.

Example 197A

Benzyl [(3R)-3-hydroxy-L-leucyl]-L-leucyl-D-arginyl-L-isoleucyl-L-allothreonyl-glycyl-L-allothreonyl-L-serinate bistrifluoroacetate

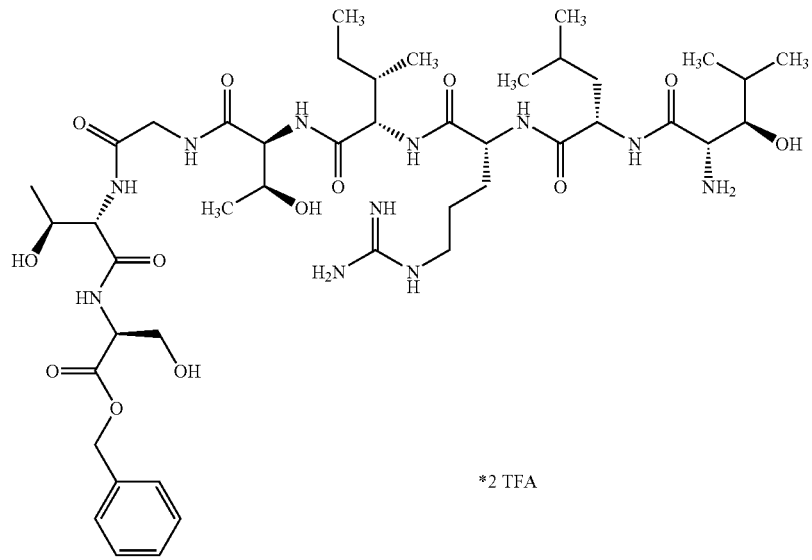

*2 TFA

The compound of example 182A (57 mg, 48 μmol) is reacted according to procedure 2. After purification by chromatography according to a modified method 44 (gradient: 0-5 min 5% B, ramp, 30-35 min 60% B, 35.01-40 min 60% B) 45 mg (78% of theory) of the title compound are obtained.

HPLC (Method 5): $R_t$=3.40 min.

LC-MS (Method 19): $R_t$=1.12 min, MS (ESIpos): m/z (%)=483.9 (100) [M+2H]$^{2+}$, 966.6 (10) [M+H]$^+$.

HR-TOF-MS (Method 24): $C_{44}H_{75}N_{11}O_{13}$ calc. 966.5619, found 966.5643 [M+H]$^+$.

Example 198A

[(3R)-3-Hydroxy-L-leucyl]-L-leucyl-D-arginyl-L-isoleucyl-L-allothreonyl-glycyl-L-alanyl-L-serine bistrifluoroacetate The compound of example 191A (43 mg, 38 μmol) is reacted according to procedure 2 in 2 ml of the reagent solution. 45 mg of the crude title compound are obtained as a solid.

HPLC (Method 5): $R_t$=2.99 min.

LC-MS (Method 22): $R_t$=2.32 min, MS (ESIpos): m/z (%) 424 (100) [M+2H]$^{2+}$.

HR-TOF-MS (Method 24): $C_{36}H_{67}N_{11}O_{12}$ calc. 846.5044, found 846.5029 [M+H]$^+$.

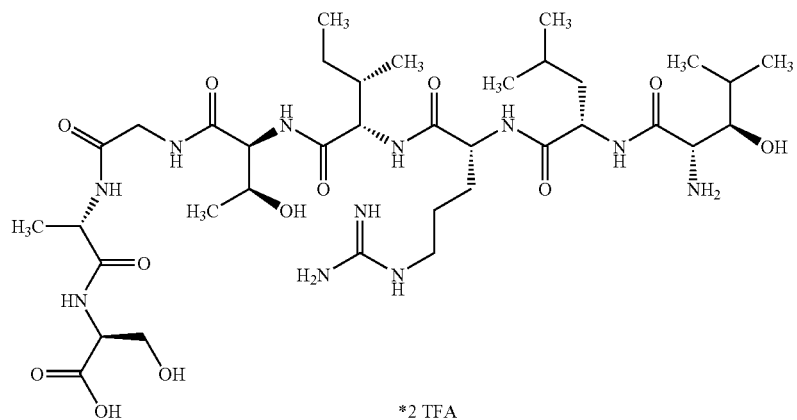

*2 TFA

Example 199A

[(3R)-3-Hydroxy-L-leucyl]-L-leucyl-D-arginyl-L-iso-leucyl-L-seryl-glycyl-[(3S)-3-hydroxy-L-asparaginyl]-L-serinate bistrifluoroacetate

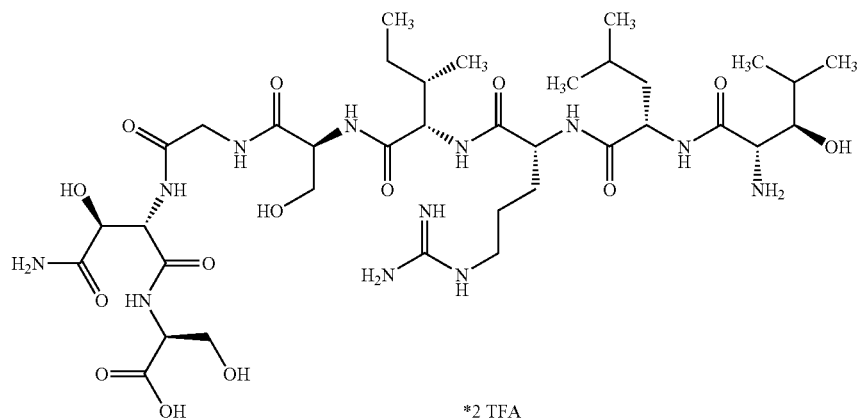

The compound of example 192A (56 mg, 39 µmol), 11 µl of water and 11 µl of triisopropylsilane are taken up in 4.0 ml of TFA. After 2 h, the mixture is concentrated and purified by chromatography (method 45). 40 mg of the title compound (90% of theory) are obtained as a solid.

HPLC (Method 5): $R_t$=2.96 min.

LC-MS (Method 22): $R_t$=2.30 min, MS (ESIpos): m/z (%)=446 (100) [M+2H]$^{2+}$.

Example 200A

[(3R)-3-Hydroxy-L-leucyl]-L-leucyl-D-arginyl-L-iso-leucyl-L-allothreonyl-glycyl-L-asparaginyl-L-serine bistrifluoroacetate The compound of example 193A (42 mg, 38 µmol) is reacted according to procedure 2 in 2 ml of the reagent solution. 42 mg (99% of theory) of the crude title compound are obtained as a solid.

HPLC (Method 5): $R_t$=2.77 min.

LC-MS (Method 22): $R_t$=2.16 min, MS (ESIpos): m/z (%)=446 (100) [M+2H]$^{2+}$, 890 (20) [M+H]$^+$; MS (ESIneg): m/z (%)=888 (100) [M−H]$^-$.

HR-TOF-MS (Method 24): $C_{37}H_{69}N_{12}O_{13}$ calc. 889.5102, found 889.5095 [M+H]$^+$.

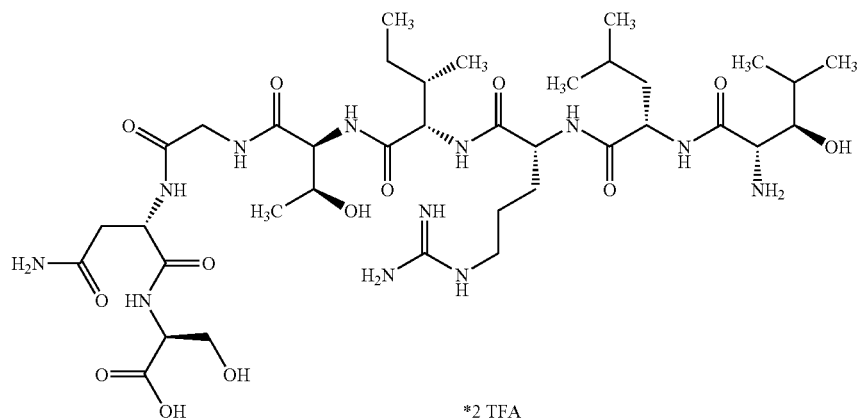

Example 201A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-seryl-L-serine trifluoroacetate

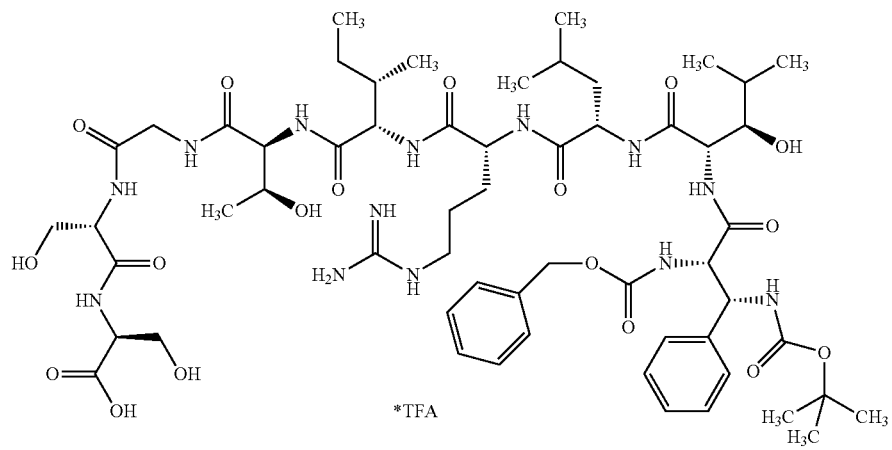

The compound of example 194A (19 mg, 17 μmol) and the compound of example 17A (12 mg, 19 μmol, 1.1 equivalents) are dissolved in DMF (530 μl) at 0° C., and DIEA (15 μl, 87 μmol, 5 eq.) is added. The reaction mixture is stirred further overnight, during which it slowly warms to RT. The mixture is taken up in acetonitrile and purified by chromatography (method 44). Yield: 14 mg, (10 μmol 59% of theory) of the title compound as a solid.

HPLC (Method 5): $R_t$=3.94 min.

LC-MS (Method 19): $R_t$=1.93 min, MS (ESIpos): m/z (%)=1259.1 (50) [M+H]⁺.

HR-TOF-MS (Method 24): $C_{58}H_{92}N_{13}O_{18}$ calc. 1258.6678, found 1258.6675 [M+H]⁺.

Example 202A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-[3-(3-pyridyl)-L-alanyl]-L-serine trifluoroacetate

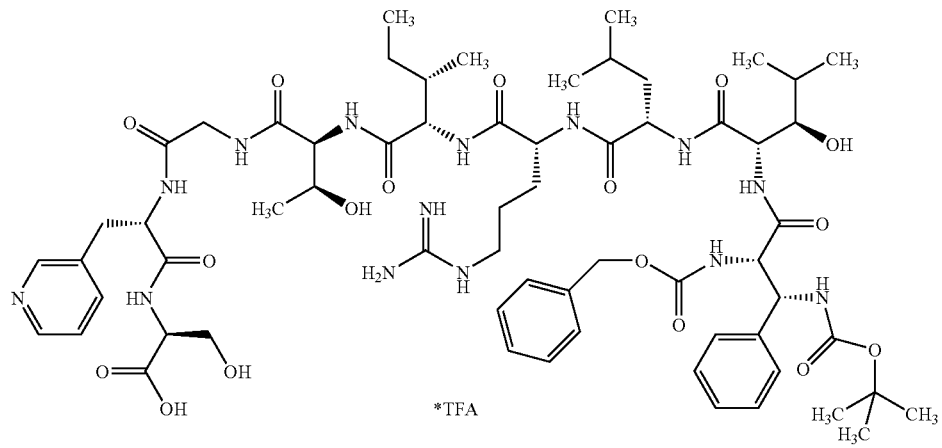

The compound of example 187A (41 mg, 36 μmol) is reacted with the compound of example 17A (23 mg, 39 μmol, 1.1 equivalents) according to the preparation method of the compound of example 201A. 37 mg (73% of theory) of the title compound are obtained.

HPLC (Method 5): $R_t$=3.87 min.

LC-MS (Method 19): $R_t$=1.72 min, MS (ESIpos): m/z (%)=660.5 (100) [M+2H]²⁺, 1319.7 (5) [M+H]⁺; (ESIneg): m/z (%)=1317.5 (100) [M−H]⁻.

HR-TOF-MS (Method 24): $C_{63}H_{95}N_{14}O_{17}$ calc. 1319.6995, found 1319.6978 [M+H]⁺.

Example 203A

[(3R)-$N^2$-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-phenyalanyl-L-serine bistrifluoroacetate

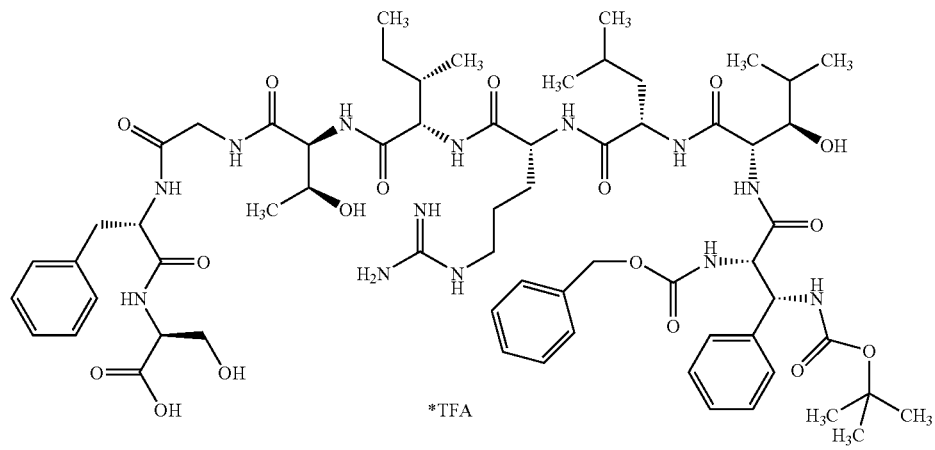

The compound of example 195A (36 mg, 31 μmol) is reacted with the compound of example 17A (22 mg, 39 μmol, 1.2 equivalents) according to the preparation method of the compound of example 201A. 34 mg (70% of theory) of the title compound are obtained.

HPLC (Method 6): $R_t$=3.93 min.

LC-MS (Method 19): $R_t$=2.01 min, MS (ESIpos): m/z (%)=610.1 (100) [M-Boc+2H]$^{2+}$, 1318.8 (20) [M+H]$^+$; (ESIneg): m/z (%)=1316.7 (100) [M−H]$^-$.

HR-TOF-MS (Method 24): $C_{64}H_{96}N_{13}O_{17}$ calc. 1318.7042, found 1318.7036 [M+H]$^+$.

Example 204A

[(3R)-$N^2$-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-threonyl-L-serine trifluoroacetate The compound of example 196A (18 mg, 17 μmol) is reacted with the compound of example 17A (12 mg, 21 μmol, 1.1 equivalents) according to the preparation method of the compound of example 201A. After purification according to method 45, 17 mg (76% of theory) of the title compound are isolated.

HPLC (Method 5): $R_t$=3.96 min.

LC-MS (Method 19): $R_t$=1.97 min, MS (ESIpos): m/z (%)=1272.8 (40) [M+H]+

HR-TOF-MS (Method 24): $C_{59}H_{94}N_{13}O_{18}$ calc. 1272.6835, found 1272.6853 [M+H]$^+$.

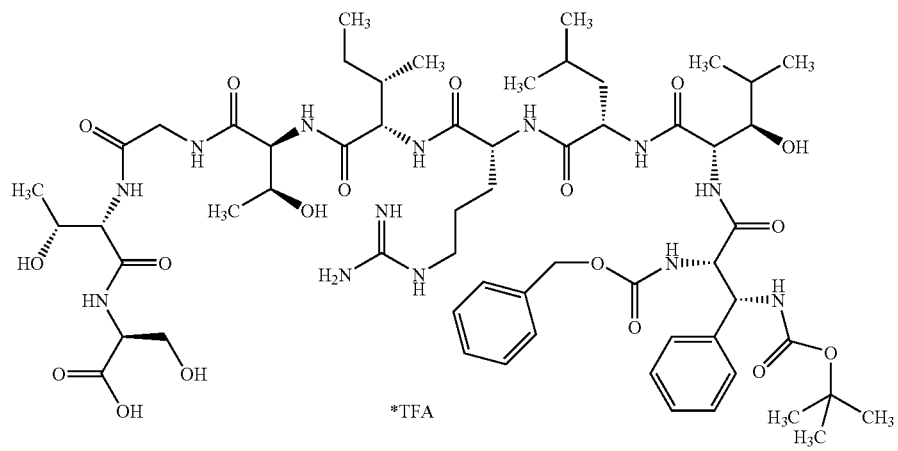

Example 205A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-allothreonyl-L-serinate trifluoroacetate

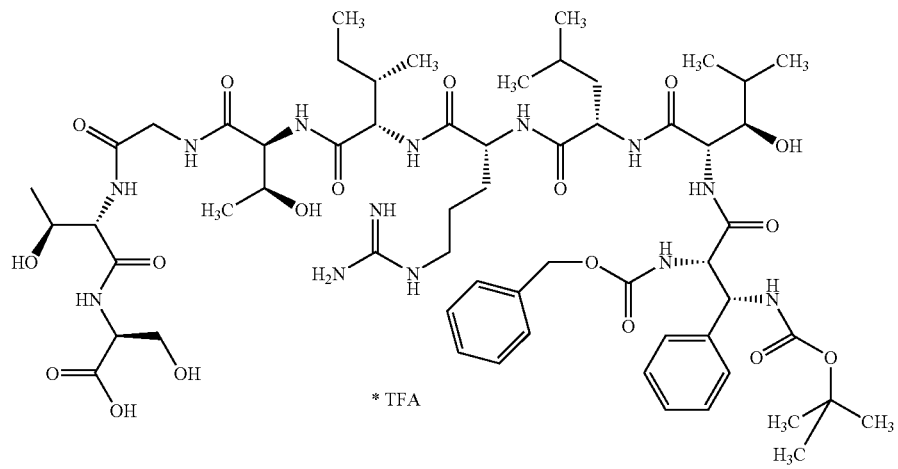

The compound of example 190A (44 mg, 40 µmol) is reacted with the compound of example 17A (25 mg, 44 µmol, 1.1 equivalents) according to the preparation method of the compound of example 201A. After purification according to method 45, 50 mg (90% of theory) of the title compound are isolated.

HPLC (Method 5): $R_t$=3.80 min.

LC-MS (Method 19): $R_t$=1.98 min, MS (ESIpos): m/z (%)=1272.7 (20) [M+H]⁺

HR-TOF-MS (Method 24): $C_{59}H_{94}N_{13}O_{18}$ calc. 1272.6835, found 1272.6846 [M+H]⁺.

Example 206A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-alanyl-L-serine trifluoroacetate The compound of example 198A (45 mg, 42 µmol) is reacted with the compound of example 17A (32 mg, 54 µmol, 1.3 equivalents) according to the preparation method of the compound of example 201A. After purification according to method 45, 38 mg (67% of theory) of the title compound are isolated.

HPLC (Method 5): $R_t$=3.99 min.

LC-MS (Method 19): $R_t$=2.12 min, MS (ESIpos): m/z (%) 571.9 (90) [M-Boc+2H]²⁺; 1242.7 (100) [M+H]⁺.

HR-TOF-MS (Method 24): $C_{58}H_{92}N_{13}O_{17}$ calc. 1242.6729, found 1242.6691 [M+H]⁺.

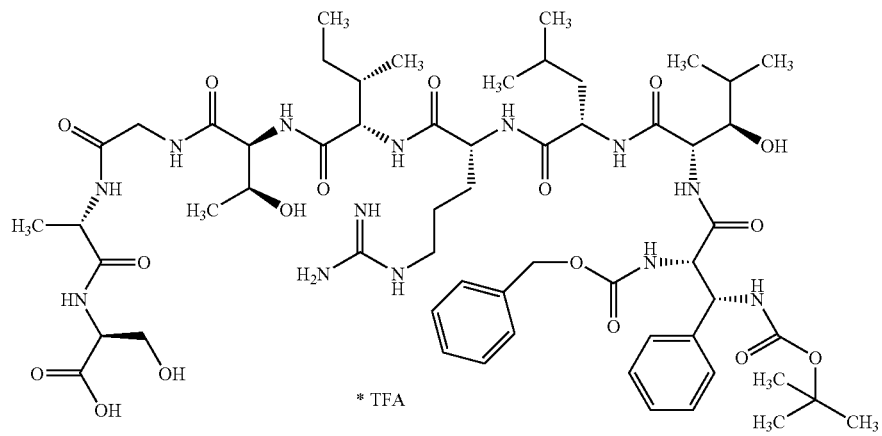

Example 207A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-seryl-glycyl-[(3S)-3-hydroxy-L-asparaginyl]-L-serinate trifluoroacetate

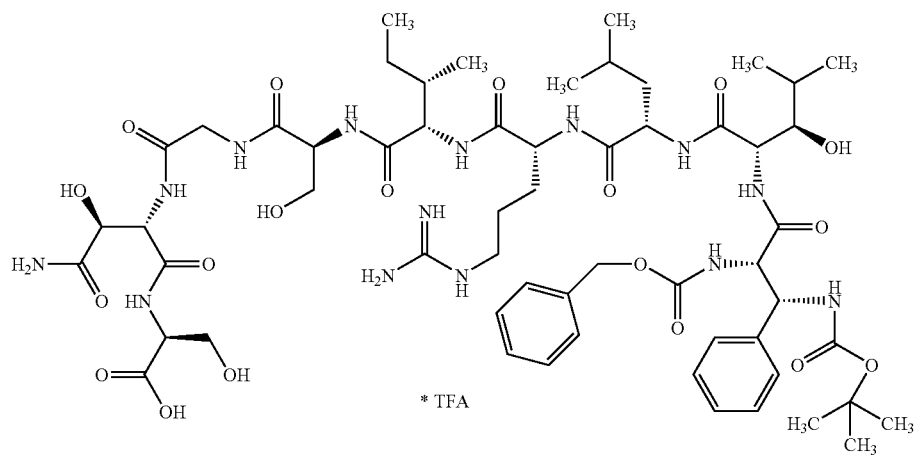

The compound of example 199A (39 mg, 35 µmol) is reacted with the compound of example 17A (24 mg, 42 µmol, 1.2 equivalents) according to the preparation method of the compound of example 201A. After purification according to method 45, 42 mg (80% of theory) of the title compound are isolated.

HPLC (Method 5): $R_t$=3.93 min.

LC-MS (Method 19): $R_t$=1.93 min, MS (ESIpos): m/z (%)=594.4 (100) [M-Boc+2H]$^{2+}$; 1287.7 (30) [M+H]$^+$.

Example 208A

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-L-asparaginyl-L-serine trifluoroacetate The compound of example 200A (42 mg, 38 µmol) is reacted with the compound of example 17A (26 mg, 45 µmol, 1.2 equivalents) according to the preparation method of the compound of example 201A. After purification according to method 45, 46 mg (81% of theory) of the title compound are isolated.

HPLC (Method 5): $R_t$=3.78 min.

LC-MS (Method 19): $R_t$=1.91 min, MS (ESIpos): m/z (%) 1285.7 (40) [M+H]$^+$.

HR-TOF-MS (Method 24): $C_{59}H_{93}N_{14}O_{18}$ calc. 1285.6787, found 1285.6777 [M+H]$^+$.

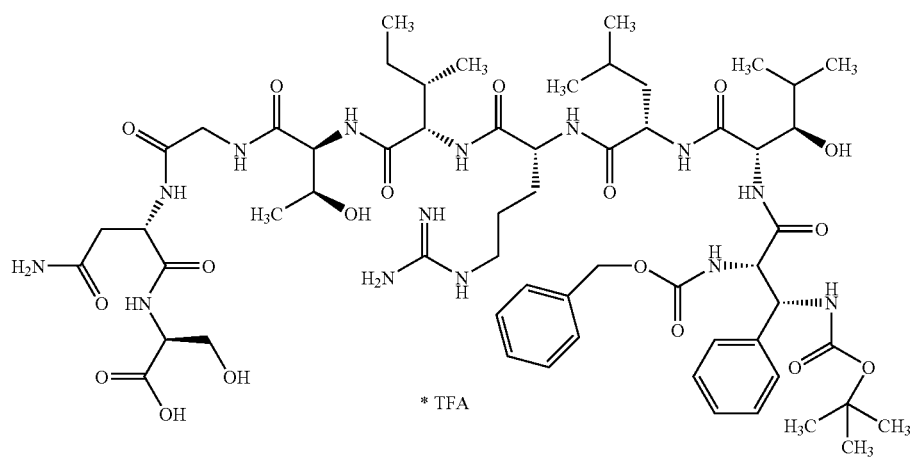

Example 209A

[(3R)-N²-(Benzyloxycarbonyl)-3-amino}-L-phenyla-
lanyl]-[(3R)-3-hydroxy-L-leucyl]-L-leucyl-D-
arginyl-L-isoleucyl-L-allothreonyl-glycyl-L-seryl-L-
serine bistrifluoroacetate

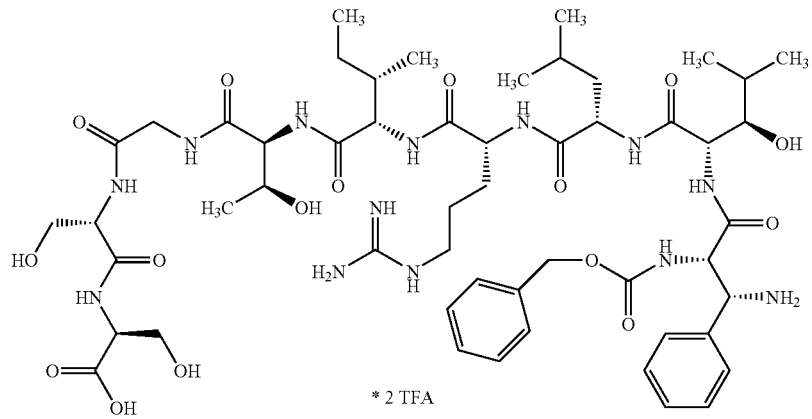

The compound of example 201A (14 mg, 10 µmol) is reacted according to procedure 2 with 0.5 ml of the reagent solution. Without further purification, 13 mg (9.3 µmol, 95% of theory) of the title compound are obtained as a solid.

HPLC (Method 5): $R_t$=3.44 min.

LC-MS (Method 20): $R_t$=1.19 min, MS (ESIpos): m/z (%)=580 (100) [M+2H]$^{2+}$, 1158.6 (5) [M+H]$^+$.

HR-TOF-MS (Method 24): $C_{53}H_{84}N_{13}O_{16}$ calc. 1158.6154, found 1158.6183 [M+H]$^+$.

Example 210A

[(3R)-N²-(Benzyloxycarbonyl)-3-amino}-L-phenyla-
lanyl]-[(3R)-3-hydroxy-L-leucyl]-L-leucyl-D-
arginyl-L-isoleucyl-L-allothreonyl-glycyl-[3-(3-py-
ridyl)-L-alanyl]-L-serine bistrifluoroacetate The compound of example 202A (37 mg, 26 µmol) is reacted according to procedure 2 with 0.5 ml of the reagent solution. Without further purification, 46 mg of the crude title compound are obtained.

HPLC (Method 5): $R_t$=3.39 min.

LC-MS (Method 22): $R_t$=2.67 min, MS (ESIpos): m/z (%) 610 (20) [M+2H]$^{2+}$; (ESIneg m/z (%)=1218 (100) [M−H]$^-$.

HR-TOF-MS (Method 24): $C_{58}H_{87}N_{14}O_{15}$ calc. 1219.6470, found 1219.6472 [M+H]$^+$.

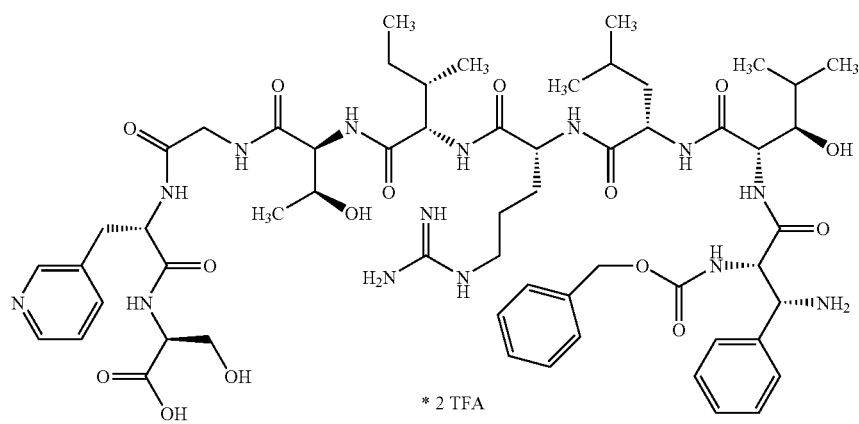

Example 211A

[(3R)-N²-(Benzyloxycarbonyl)-3-amino}-L-phenyla-
lanyl]-[(3R)-3-hydroxy-L-leucyl]-L-leucyl-D-
arginyl-L-isoleucyl-L-allothreonyl-glycyl-L-phenyla-
lanyl-L-serine bistrifluoroacetate

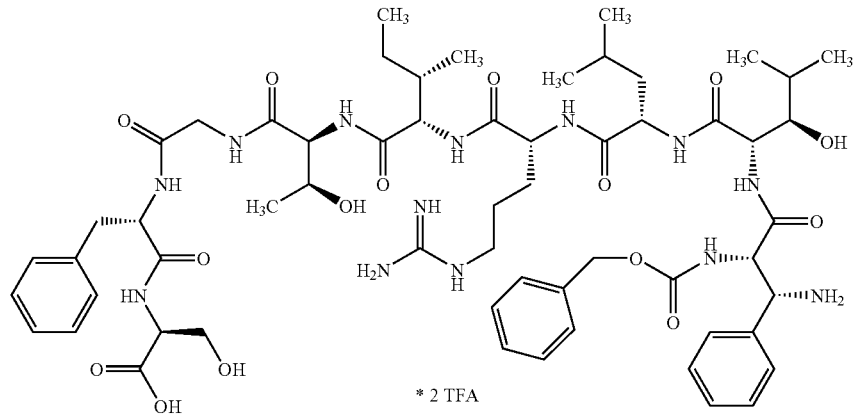

The compound of example 203A (34 mg, 22 μmol) is reacted according to procedure 2 with 2.0 ml of the reagent solution. Without further purification, 34 mg (quant.) of the crude title compound are obtained.

HPLC (Method 5): $R_t$=3.34 min.

LC-MS (Method 20): $R_t$=1.37 min, MS (ESIpos): m/z (%) 610.1 (100) [M+2H]$^{2+}$, 1218.8 (5) [M+H]$^+$; (ESIneg m/z (%)=1216.8 (100) [M–H]$^-$.

HR-TOF-MS (Method 24): $C_{59}H_{88}N_{13}O_{15}$ calc. 1218.6518, found 1218.6539 [M+H]$^+$.

Example 212A

[(3R)-N²-(Benzyloxycarbonyl)-3-amino}-L-phenyla-
lanyl]-[(3R)-3-hydroxy-L-leucyl]-L-leucyl-D-
arginyl-L-isoleucyl-L-allothreonyl-glycyl-L-
threonyl-L-serine bistrifluoroacetate The compound of example 204A (17 mg, 12 μmol) is reacted according to procedure 2 with 1.0 ml of the reagent solution. Without further purification, 17 mg (quant.) of the crude title compound are obtained.

HPLC (Method 5): $R_t$=3.48 min.

LC-MS (Method 21): $R_t$=1.49 min, MS (ESIpos): m/z (%) 587.2 (100) [M+2H]$^{2+}$, 1172.7 (5) [M+H]$^+$.

HR-TOF-MS (Method 24): $C_{54}H_{86}N_{13}O_{16}$ calc. 1172.6310, found 1172.6328 [M+H]$^+$.

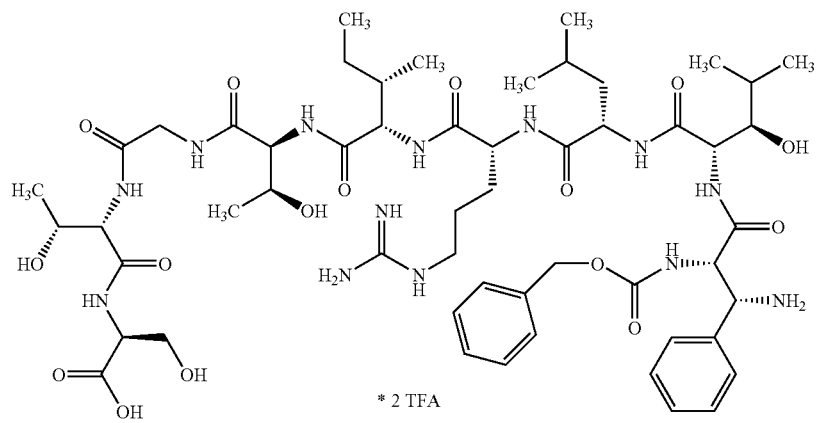

Example 213A

[(3R)-N²-(Benzyloxycarbonyl)-3-amino}-L-phenyla-
lanyl]-[(3R)-3-hydroxy-L-leucyl]-L-leucyl-D-
arginyl-L-isoleucyl-L-allothreonyl-glycyl-L-allothreo-
nyl-L-serinate bistrifluoroacetate

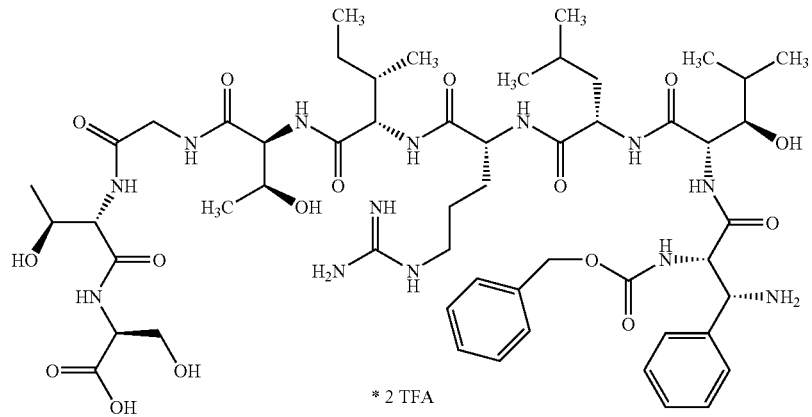

The compound of example 205A (50 mg, 36 μmol) is reacted according to procedure 2 with 4.8 ml of the reagent solution. Without further purification, 56 mg (quant.) of the crude title compound are obtained and are reacted further without purification.

HPLC (Method 6): $R_t$=3.22 min.

LC-MS (Method 19): $R_t$=1.32 min, MS (ESIpos): m/z (%) 586.9 (100) [M+2H]²⁺.

HR-TOF-MS (Method 24): $C_{54}H_{86}N_{13}O_{16}$ calc. 1172.6310, found 1172.6323 [M+H]⁺.

Example 214A

[(3R)-N²-(Benzyloxycarbonyl)-3-amino-L-phenyla-
lanyl]-[(3R)-3-hydroxy-L-leucyl]-L-leucyl-D-
arginyl-L-isoleucyl-L-allothreonyl-glycyl-L-alanyl-L-
serine bistrifluoroacetate The compound of example 206A (49 mg, 36 μmol) is reacted according to procedure 2 with 1.0 ml of the reagent solution for 1 h. Without further purification, 49 mg (quant.) of the crude title compound are obtained.

HPLC (Method 5): $R_t$=3.46 min.

LC-MS (Method 19): $R_t$=1.49 min, MS (ESIpos): m/z (%) 572.0 (100) [M+2H]²⁺, 1142.6 (5) [M+H]⁺.

HR-TOF-MS (Method 24): $C_{53}H_{84}N_{13}O_{15}$ calc. 1142.6205, found 1142.6221 [M+H]⁺.

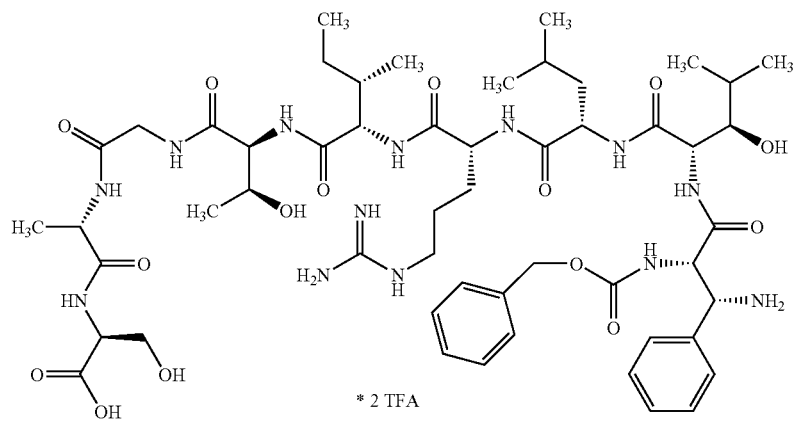

Example 215A

[(3R)-N²-(Benzyloxycarbonyl)-3-amino-L-phenyla-
lanyl]-[(3R)-3-hydroxy-L-leucyl]-L-leucyl-D-
arginyl-L-isoleucyl-L-seryl-glycyl-[(3S)-3-hydroxy-L-
asparaginyl]-L-serinate bistrifluoroacetate

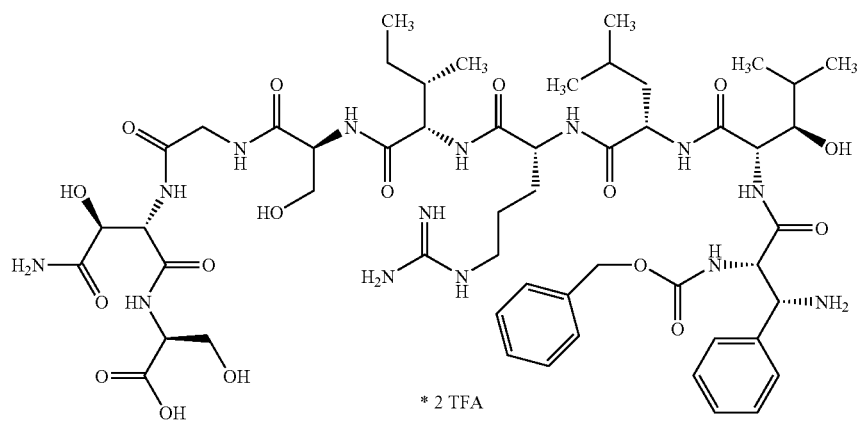

* 2 TFA

The compound of example 207A (42 mg, 28 μmol) is reacted according to procedure 2 with 1.0 ml of the reagent solution for 1 h. Without further purification, 43 mg (quant.) of the crude title compound are obtained.

HPLC (Method 5): $R_t$=3.43 min.

LC-MS (Method 19): $R_t$=1.34 min, MS (ESIpos): m/z (%) 594.5 (100) [M+2H]$^{2+}$, 1187.6 (5) [M+H]$^+$.

HR-TOF-MS (Method 24): $C_{53}H_{83}N_{14}O_{17}$ calc. 1187.6056, found 1187.6074 [M+H]$^+$.

Example 216A

[(3R)-N²-(Benzyloxycarbonyl)-3-amino-L-phenyla-
lanyl]-[(3R)-3-hydroxy-L-leucyl]-L-leucyl-D-
arginyl-L-isoleucyl-L-allothreonyl-glycyl-L-asparagi-
nyl-L-serine bistrifluoroacetate

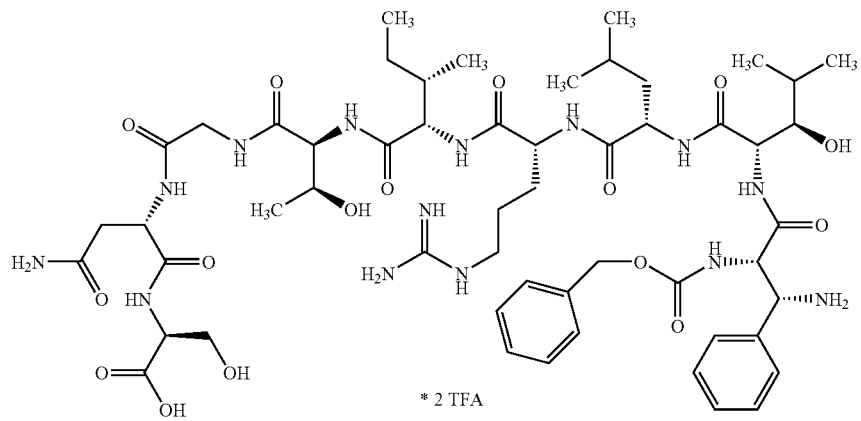

* 2 TFA

The compound of example 208A (46 mg, 30 μmol) is reacted according to procedure 2 with 1.0 ml of the reagent solution for 30 min. Without further purification, 46 mg (quant.) of the crude title compound are obtained.

HPLC (Method 5): $R_t$=3.21 min.

LC-MS (Method 19): $R_t$=1.31 min, MS (ESIpos): m/z (%) 593.5 (100) [M+2H]$^{2+}$, 1185.5 (5) [M+H]$^+$.

HR-TOF-MS (Method 24): $C_{54}H_{85}N_{14}O_{16}$ calc. 1185.6263, found 1185.6241 [M+H]$^+$.

Example 217A

[(3R)-$N^2$-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-L-seryl-L-serine $C^{1.9}$-$N^{3.1}$-lactam Trifluoroacetate

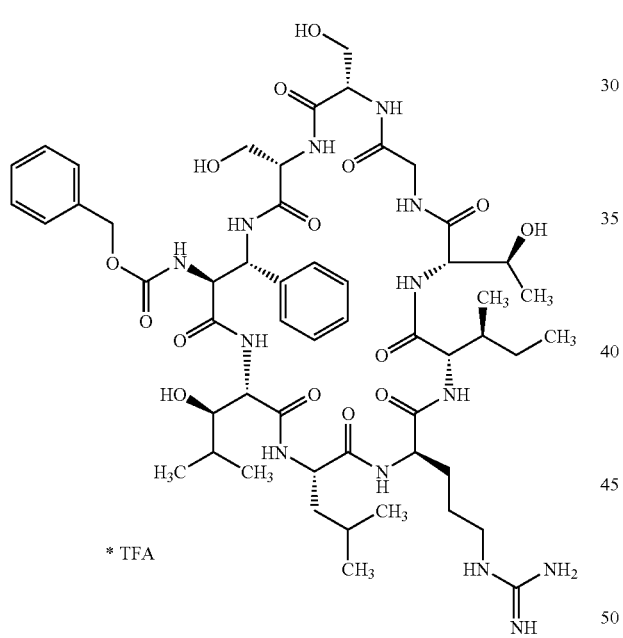

The compound of example 209A (13 mg, 9.3 μmol) is dissolved in DMF (480 μL), and the solution is cooled to 0° C. 4-Methylmorpholine (6 μL, 56 μmol, 6 equivalents) and HATU (11 mg, 28 μmol, 3 equivalents) are added, and the mixture is stirred at 0° C. for 2 h. The complete mixture is then put onto an HPLC column and purified by chromatography according to method 44. Product-containing fractions are combined and lyophilized. 5 mg (4.0 μmol, 43% of theory) of the title compound are obtained as solid.

HPLC (Method 5): $R_t$=3.70 min.

LC-MS (Method 20): $R_t$=1.49 min, MS (ESIpos): m/z (%) 570.9 (80) [M+2H]$^{2+}$, 1140.6 (90) [M+H]$^+$.

HR-TOF-MS (Method 24): $C_{53}H_{82}N_{13}O_{15}$ calc. 1140.6048, found 1140.6066 [M+H]$^+$.

Example 218A

[(3R)-$N^2$-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-[3-(3-pyridyl)-L-alanyl]-L-serine $C^{1.9}$-$N^{3.1}$-lactam trifluoroacetate

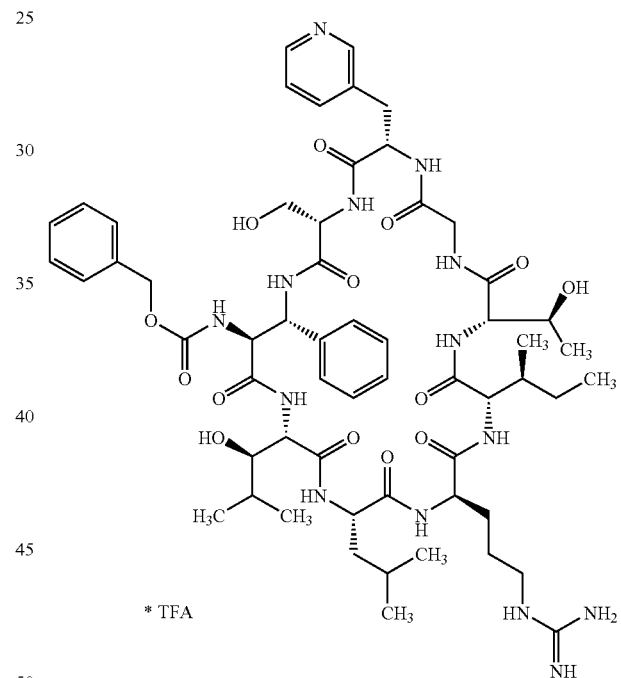

According to the preparation method of the compound of example 217A the title compound is obtained in a yield of 17 mg (51% of theory) from the compound of example 210A (37 mg, 26 μmol).

HPLC (Method 5): $R_t$=3.60 min.

LC-MS (Method 19): $R_t$=1.45 min, MS (ESIpos): m/z (%) 601.5 (100) [M+2H]$^{2+}$, 1201.6 (20) [M+H]$^+$.

HR-TOF-MS (Method 24): $C_{58}H_{85}N_{14}O_{14}$ calc. 1204.6365, found 1201.6338 [M+H]$^+$.

Example 219A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-L-phenylalanyl]-L-serine C¹·⁹-N³·¹-lactam trifluoroacetate

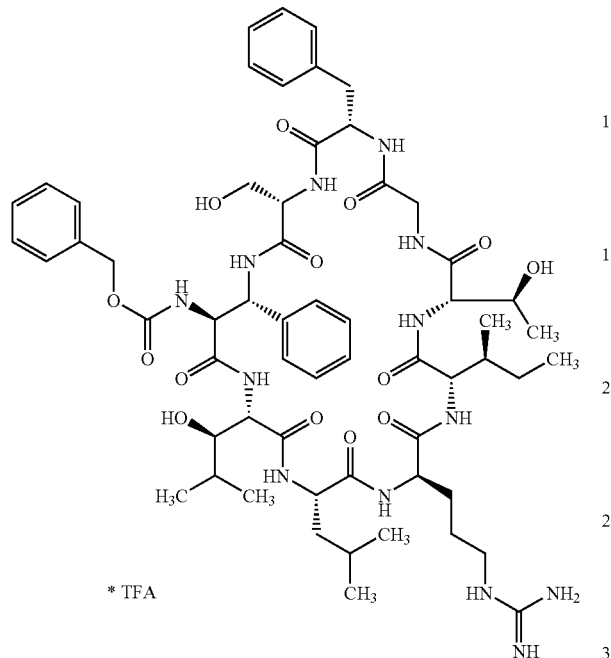

*TFA

According to the preparation method of the compound of example 217A the title compound is obtained in a yield of 28 mg (96% of theory) from the compound of example 211A (34 mg, 22 µmol).

HPLC (Method 6): $R_t$=3.78 min.

LC-MS (Method 20): $R_t$=1.75 min, MS (ESIpos): m/z (%)=601.0 (50) [M+2H]²⁺, 1200.8 (100) [M+H]⁺; MS (ESIneg): m/z (%)=1198.8 (100) [M–H]⁻.

Example 220A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-L-threonyl-L-serine C¹·⁹-N³·¹-lactam trifluoroacetate

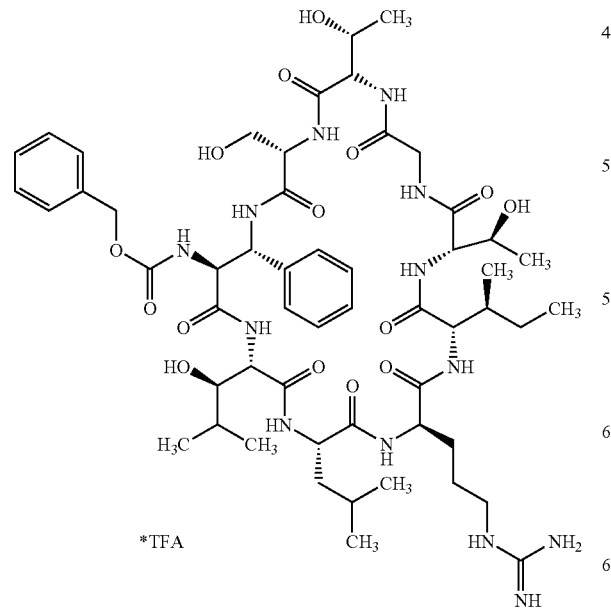

*TFA

According to the preparation method for the compound of example 217A, the title compound is obtained in a yield of 10 mg (65% of theory), from the compound of example 212A (17 mg, 12 µmol).

HPLC (Method 5): $R_t$=3.75 min.

LC-MS (Method 19): $R_t$=1.59 min, MS (ESIpos): m/z (%)=1154.7 (100) [M+H]⁺.

HR-TOF-MS (Method 24): $C_{54}H_{84}N_{13}O_{15}$ calc. 1154.6205, found 1154.6194 [M+H]⁺.

Example 221A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-L-allothreonyl-L-aserinate C¹·⁹-N³·¹-lactam trifluoroacetate

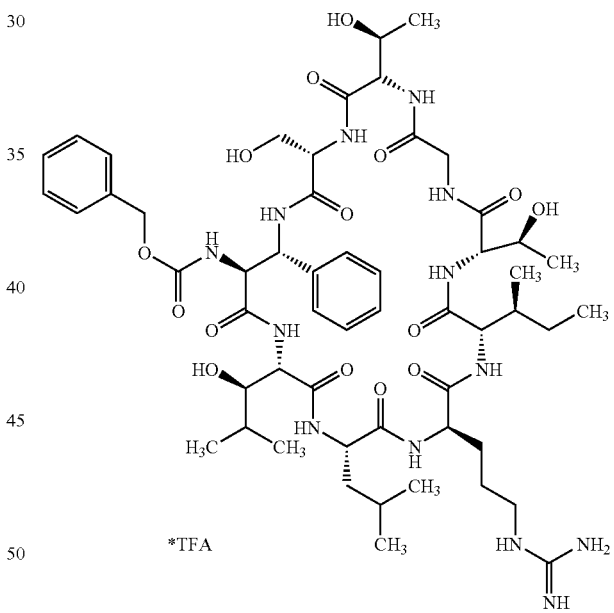

*TFA

The compound of example 213A (50 mg, 36 µmol) is cyclized according to the preparation method of the compound of example 217A. method 45 is then used for chromatography. The title compound is obtained in a crude yield of 52 mg (75% pure, 86% of theory) and is not further purified.

HPLC (Method 6): $R_t$=3.55 min.

LC-MS (Method 19): $R_t$=1.60 min, MS (ESIpos): m/z (%)=1154.7 (100) [M+H]⁺.

HR-TOF-MS (Method 24): $C_{54}H_{84}N_{13}O_{15}$ calc. 1154.6205, found 1154.6171 [M+H]⁺.

Example 222A

[(3R)-$N^2$-(Benzyloxycarbonyl)-3-amino-L-phenyla-lanyl]-[(3R)-3-hydroxy-L-leucyl]-L-leucyl-D-arginyl-L-isoleucyl-L-allothreonyl-glycyl-L-alanyl-L-serine $C^{1.9}$-$N^{3.1}$-lactam trifluoroacetate

Example 223A

[(3R)-$N^2$-(Benzyloxycarbonyl)-3-amino-L-phenyla-lanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam trifluoroacetate

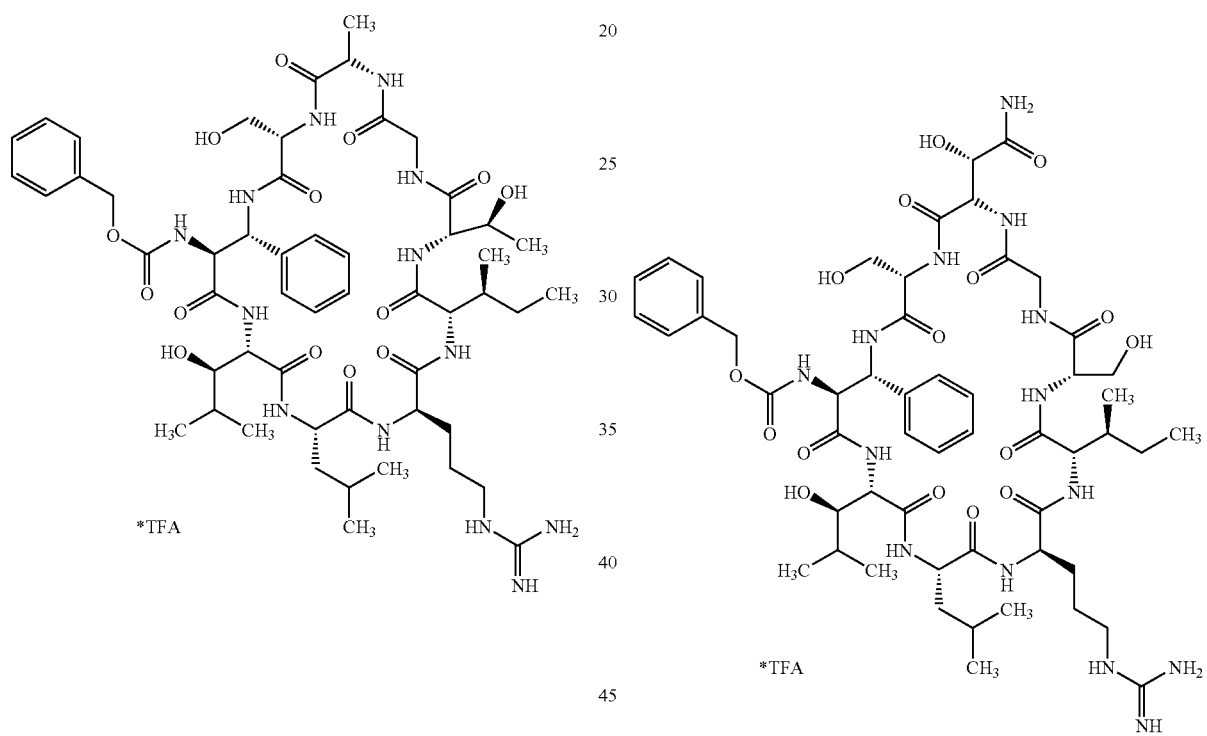

According to the preparation method for the compound of example 217A, whereby purification takes place according to method 45, the title compound is obtained in a yield of 34 mg (77% of theory) from the compound of example 214A (49 mg, 36 µmol).

HPLC (Method 5): $R_t$=3.78 min.

LC-MS (Method 19): $R_t$=1.61 min, MS (ESIpos): m/z (%)=1124.6 (100) [M+H]$^+$.

HR-TOF-MS (Method 24): $C_{53}H_{82}N_{13}O_{14}$ calc. 1154.6099, found 1124.6073 [M+H]$^+$.

According to the preparation method for the compound of example 217A, whereby purification takes place according to method 45, the title compound is obtained in a yield of 28 mg (73% of theory) from the compound of example 215A (42 mg, 27 µmol).

HPLC (Method 5): $R_t$=3.68 min.

LC-MS (Method 19): $R_t$=1.57 min, MS (ESIpos): m/z (%)=1169.6 (100) [M+H]$^+$.

HR-TOF-MS (Method 24): $C_{53}H_{81}N_{14}O_{16}$ calc. 1169.5950, found 1169.5939 [M+H]$^+$.

Example 224A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-L-asparaginyl-L-serine $C^{1.9}$-$N^{3.1}$-lactam trifluoroacetate

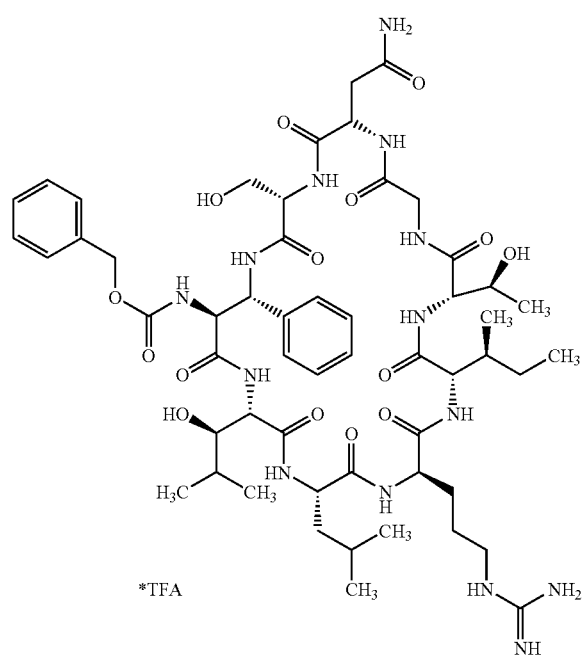

According to the preparation method for the compound of example 217A, whereby purification takes place according to method 45, the title compound is obtained in a yield of 29 mg (75% of theory) from the compound of example 216A (45 mg, 30 µmol).

HPLC (Method 5): $R_t$=3.52 min.

LC-MS (Method 19): $R_t$=1.56 min, MS (ESIpos): m/z (%)=1167.5 (100) [M+H]⁺.

HR-TOF-MS (Method 24): $C_{54}H_{83}N_{14}O_{15}$ calc. 1167.6157, found 1167.6152 [M+H]⁺.

Example 225A

[(3R)-3-Amino-L-phenylalanyl]-[(3R)-3-hydroxy-L-leucyl]-L-leucyl-D-arginyl-L-iso-leucyl-L-allothreonyl-glycyl-L-seryl-L-serine $C^{1.9}$-$N^{3.1}$-lactam bishydrochloride

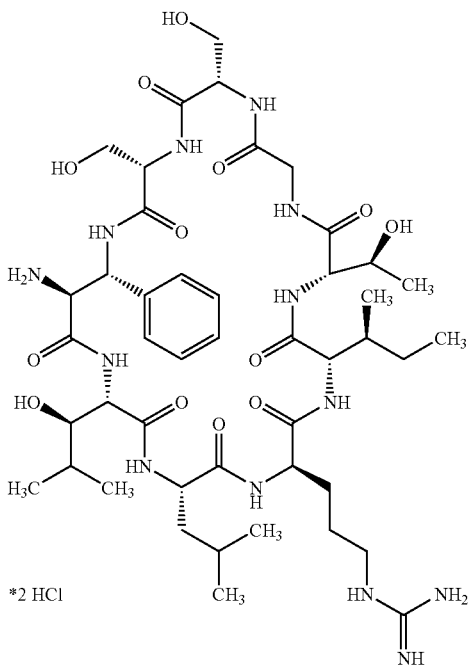

The compound of example 217A is dissolved in methanol (750 µL) in the presence of 1 M hydrochloric acid (24 µL, 6 equivalents) and hydrogenated in the presence of 3 mg of 10% palladium-carbon under atmospheric pressure at room temperature for 1.5 h. The solution is filtered to remove the catalyst and concentrated. The title compound is obtained in a yield of 4.3 mg (quant.) as a solid.

HPLC (Method 5): $R_t$=3.21 min.

LC-MS (Method 20): $R_t$=0.90 min, MS (ESIpos): m/z (%)=503.9 (100) [M+2H]²⁺, 1006.6 (3) [M+H]⁺.

HR-TOF-MS (Method 24): $C_{45}H_{76}N_{13}O_{13}$ calc. 1006.5681, found 1006.5670 [M+H]⁺.

Example 226A

[(3R)-3-Amino-L-phenylalanyl]-[(3R)-3-hydroxy-L-leucyl]-L-leucyl-D-arginyl-L-iso-leucyl-L-allothreonyl-glycyl-[3-(3-pyridyl)-L-alanyl]-L-serine $C^{1.9}$-$N^{3.1}$-lactam Bishydrochloride

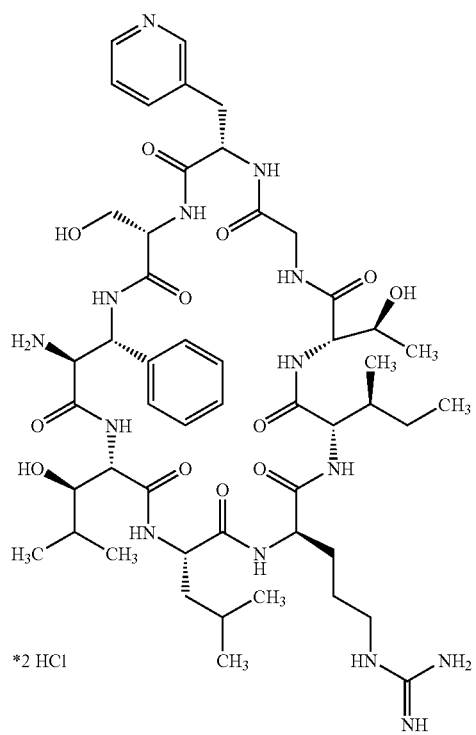

Example 227A

[(3R)-3-Amino-L-phenylalanyl]-[(3R)-3-hydroxy-L-leucyl]-L-leucyl-D-arginyl-L-iso-leucyl-L-allothreonyl-glycyl-L-phenylalanyl-L-serine $C^{1.9}$-$N^{3.1}$-lactam bishydrochloride

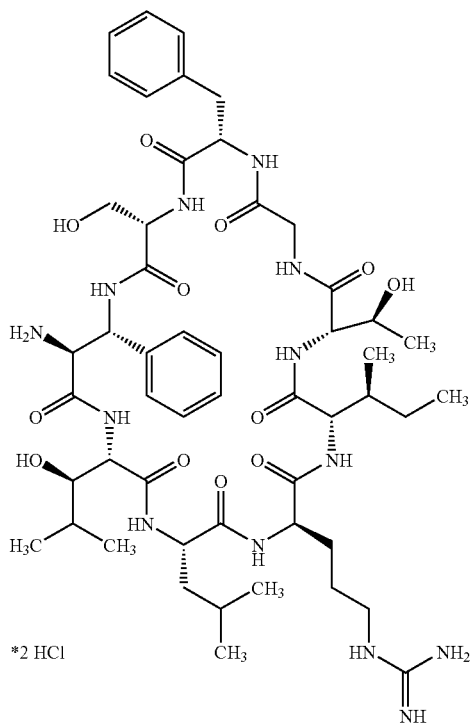

According to the preparation method of the compound of example 225A, the title compound is obtained in a yield of 17 mg (quant.) from the compound of example 218A (17 mg, 13 μmol).

HPLC (Method 5): $R_t$=3.17 min.

LC-MS (Method 22): $R_t$=2.34 min, MS (ESIpos): m/z (%) 534 (20) [M+2H]$^{2+}$; (ESIneg): m/z (%)=1065 (100) [M−H]$^-$.

HR-TOF-MS (Method 24): $C_{50}H_{79}N_{14}O_{12}$ calc. 1067.5997, found 1067.6006 [M+H]$^+$.

According to the preparation method of the compound of example 225A, the title compound is obtained in a yield of 24 mg (99% of theory) from the compound of example 219A (28 mg, 21 μmol).

HPLC (Method 5): $R_t$=3.17 min.

LC-MS (Method 21): $R_t$=1.15 min, MS (ESIpos): m/z (%)=534 (100) [M+2H]$^{2+}$; (ESIneg): m/z (%)=1064.8 (50) [M−H]$^-$.

HR-TOF-MS (Method 24): $C_{51}H_{80}N_{13}O_{12}$ calc. 1066.6044, found 1066.6013 [M+H]$^+$.

249
Example 228A

[(3R)-3-Amino-L-phenylalanyl]-[(3R)-3-hydroxy-L-leucyl]-L-leucyl-D-arginyl-L-isoleucyl-L-allothreonyl-glycyl-L-threonyl-L-serine $C^{1.9}$-$N^{3.3}$-lactam bishydrochloride

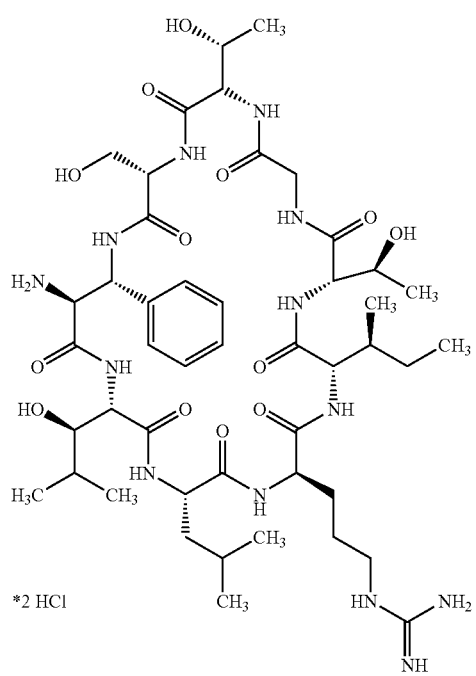

*2 HCl

According to the preparation method of the compound of example 225A, the title compound is obtained in a yield of 8.5 mg (99% of theory) from the compound of example 220A (10 mg, 8 μmol).

HPLC (Method 5): $R_t$=3.25 min.

LC-MS (Method 22): $R_t$=2.49 min, MS (ESIpos): m/z (%)=511 (100) $[M+2H]^{2+}$

HR-TOF-MS (Method 24): $C_{46}H_{78}N_{13}O_{13}$ calc. 1020.5837, found 1020.5831 $[M+H]^+$.

250
Example 229A

[(3R)-3-Amino-L-phenylalanyl]-[(3R)-3-hydroxy-L-leucyl]-L-leucyl-D-arginyl-L-isoleucyl-L-allothreonyl-glycyl-L-allothreonyl-L-serinate $C^{1.9}$-$N^{3.1}$-lactam bishydrochloride

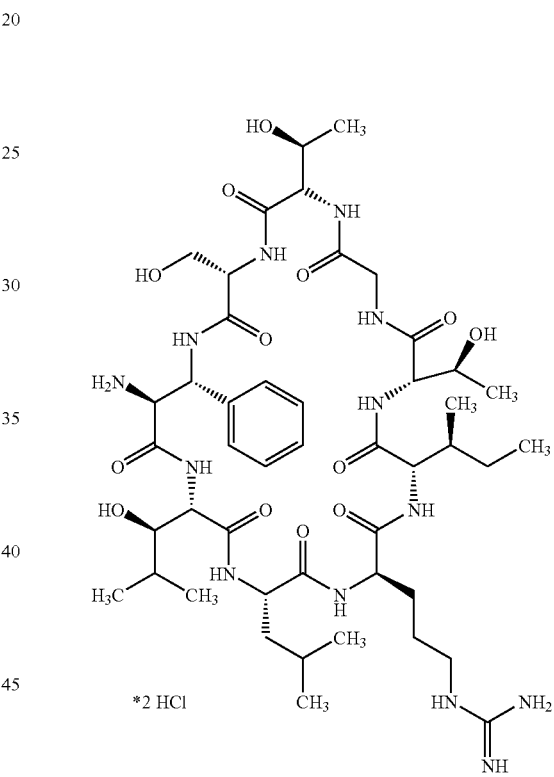

*2 HCl

According to the preparation method of the compound of example 225A, the title compound is obtained in a yield of 40 mg (86% of theory) from the compound of example 221A (52 mg, 41 μmol).

HPLC (Method 6): $R_t$=2.93 min.

Example 230A

[(3R)-3-Amino-L-phenylalanyl]-[(3R)-3-hydroxy-L-leucyl]-L-leucyl-D-arginyl-L-isoleucyl-L-allothreonyl-glycyl-L-alanyl-L-serine $C^{1.9}$-$N^{3.1}$-lactam bishydrochloride

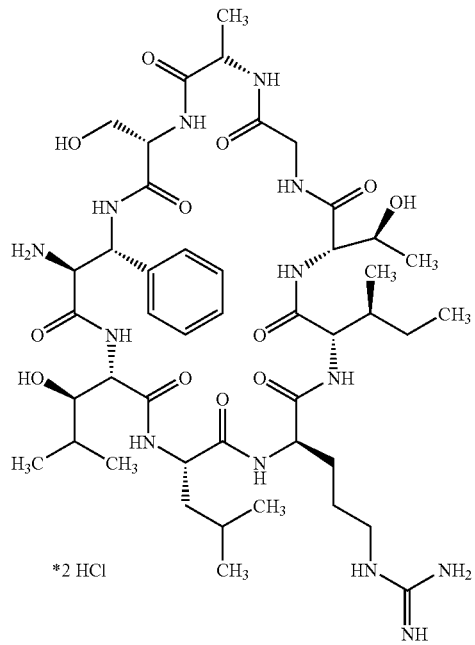

According to the preparation method of the compound of example 225A, the title compound is obtained in a yield of 29 mg (99% of theory) from the compound of example 222A (34 mg, 27 µmol).

HPLC (Method 5): $R_t$=3.24 min.

LC-MS (Method 22): $R_t$=2.48 min, MS (ESIpos): m/z (%)=496 (100) $[M+2H]^{2+}$.

HR-TOF-MS (Method 24): $C_{45}H_{76}N_{13}O_{12}$ calc. 990.5731, found 990.5726 $[M+H]^+$.

Example 231A

[(3R)-3-Amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$-$N^{3.1}$-lactam bishydrochloride

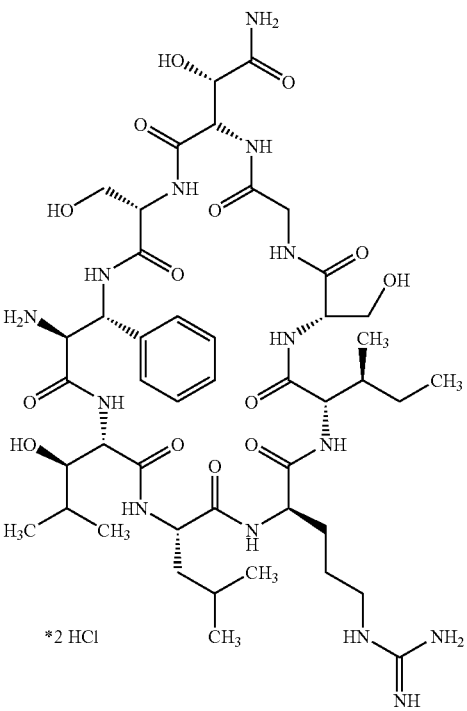

According to the preparation method of the compound of example 225A, the title compound is obtained in a yield of 21 mg (95% of theory) from the compound of example 223A (28 mg, 20 µmol).

HPLC (Method 5): $R_t$=3.16 min.

LC-MS (Method 22): $R_t$=2.43 min, MS (ESIpos): m/z (%)=519 (100) $[M+2H]^{2+}$.

HR-TOF-MS (Method 24): $C_{45}H_{75}N_{14}O_{14}$ calc. 1035.5582, found 1035.5585 $[M+H]^+$.

Example 232A

[(3R)-3-Amino-L-phenylalanyl]-[(3R)-3-hydroxy-L-leucyl]-L-leucyl-D-arginyl-L-isoleucyl-L-allothreonyl-glycyl-L-asparaginyl-L-serine $C^{1.9}$-$N^{3.1}$-lactam bishydrochloride

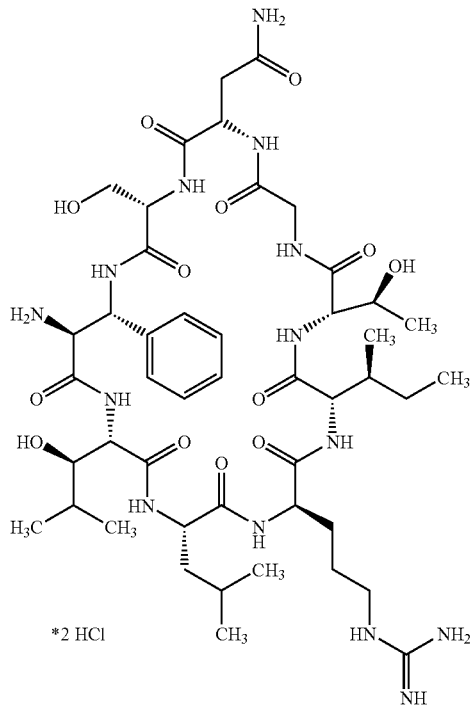

According to the preparation method of the compound of example 225A, the title compound is obtained in a yield of 24 mg (96% of theory) from the compound of example 224A (29 mg, 23 μmol).

HPLC (Method 5): $R_t$=2.90 min.

LC-MS (Method 22): $R_t$=2.32 min, MS (ESIpos): m/z (%)=517 (100) $[M+2H]^{2+}$, 1033 (5) $[M+H]^{+}$.

HR-TOF-MS (Method 24): $C_{46}H_{76}N_{14}O_{13}$ calc. 1033.5790, found 1033.5773 $[M+H]^{+}$.

Example 233A

[$N^2$-(Benzyloxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-seryl-L-serine $C^{1.11}$-$N^{3.3}$-lactam hydrochloride

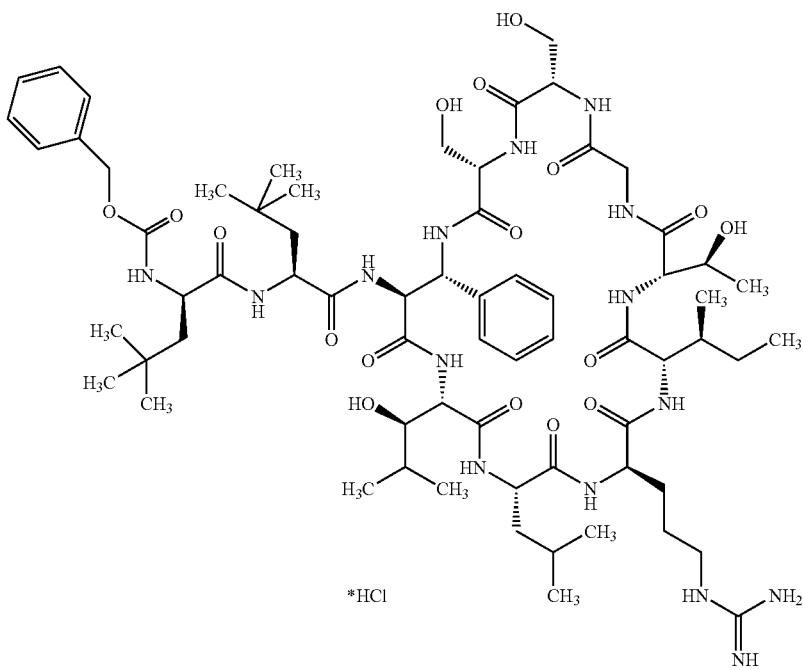

The compound of example 225A (4.3 mg, 4 µmol) and the compound of example 10A (2.5 mg, 6 µmol, 1.5 equivalents) are dissolved in DMF (300 µl) and the solution is cooled to 0° C. 4-Methylmorpholine (20 µl, 16 µmol, 4 equivalents) and HATU (2.4 mg, 6 µmol, 1.6 equivalents) are added and the mixture is stirred at room temperature for 2 h. The reaction is then stopped with 3 ml of methanol and purified by chromatography according to method 45. Product-containing fractions are combined and concentrated. 4 mg (2.8 µmol, 70% of theory) of the title compound are obtained as a solid.

HPLC (Method 5): $R_t$=4.45 min.

LC-MS (Method 19): $R_t$=2.08 min, MS (ESIpos): m/z (%)=698.6 (100) $[M+2H]^{2+}$, 1395.4 (30) $[M+H]^+$.

HR-TOF-MS (Method 24): $C_{67}H_{109}N_{15}O_{17}$ calc. 1394.8043, found 1394.8070 $[M+H]^+$.

Example 234A

[$N^2$-(Benzyloxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[3-(3-pyridyl)-L-alanyl]-L-serine $C^{1.11}$-$N^{3.3}$-lactam hydrochloride

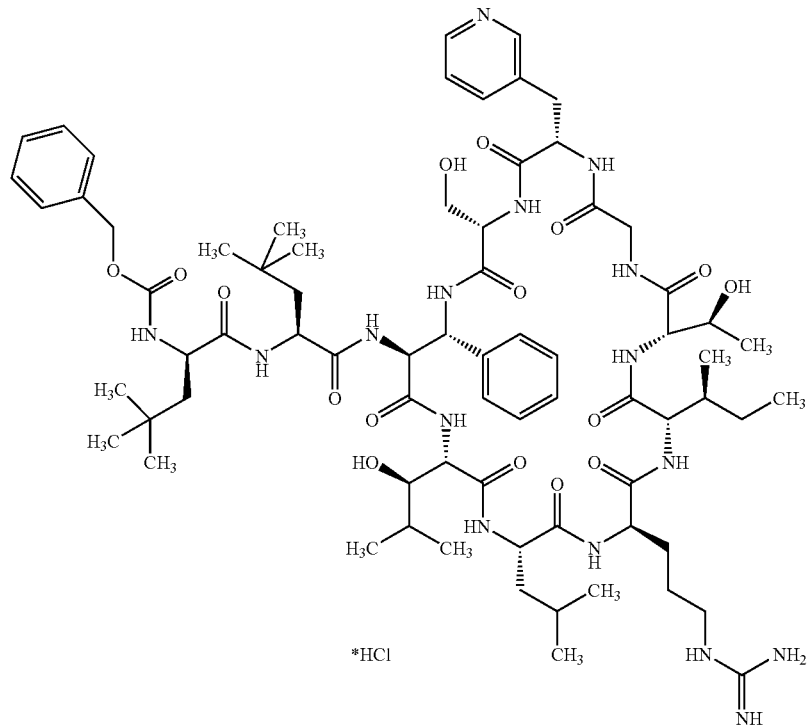

According to the preparation method for preparing exemplary compound 233A, the title compound is obtained in a yield of 12 mg (54% of theory) from exemplary compound 226A (17 mg, 13 µmol).

HPLC (Method 5): $R_t$=4.25 min.

LC-MS (Method 22): $R_t$=3.61 min, MS (ESIpos): m/z (%)=729 (100) $[M+2H]^{2+}$; (ESIneg): m/z (%)=1454 (100) $[M-H]^-$.

HR-TOF-MS (Method 24): $C_{72}H_{111}N_{16}O_{16}$ calc. 1455.8359, found 1455.8347 $[M+H]^+$.

Example 235A

[N²-(tert-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-phenylalanyl-L-serine $C^{1.11}$-$N^{3.3}$-lactam Hydrochloride

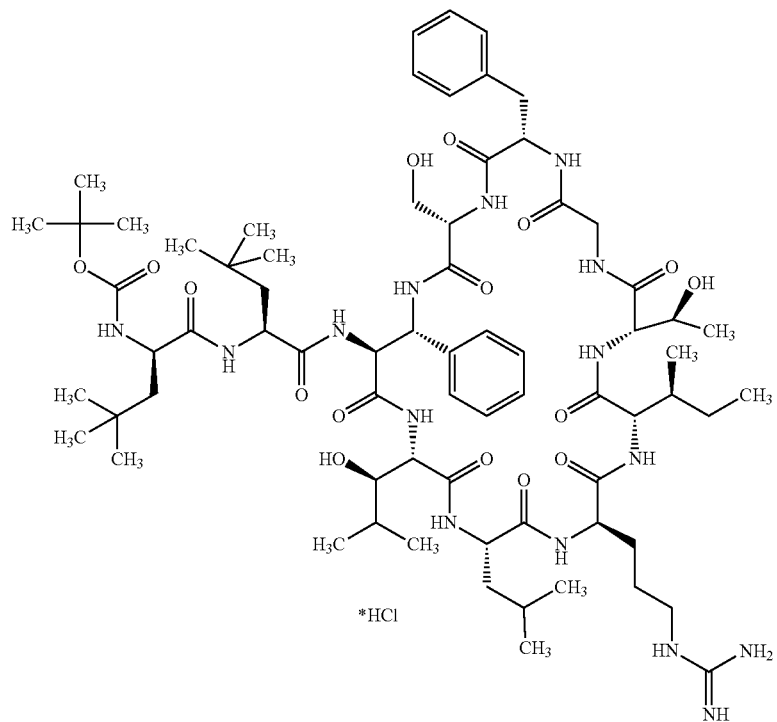

According to the preparation method of the compound of example 233A, the title compound is obtained in a yield of 19 mg (62% of theory) from the compound of example 227A (24 mg, 21 μmol) and the dipeptide of example 8A (10 mg, 27 μmol, 1.3 equivalents).

HPLC (Method 6): $R_t$=4.57 min.

LC-MS (Method 20): $R_t$=2.291 min, MS (ESIpos): m/z (%)=661.2 (100) [M-Boc+2H]$^{2+}$, 1421.0 (30) [M+H]$^+$; (ESIneg): m/z (%)=1419.1 (20) [M−H]$^−$.

HR-TOF-MS (Method 24): $C_{70}H_{113}N_{15}O_{16}$ calc. 1420.8563, found 1420.8558 [M+H]$^+$.

Example 236A

[N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[L-threonyl]-L-serine $C^{1.11}$-$N^{3.3}$-lactam hydrochloride

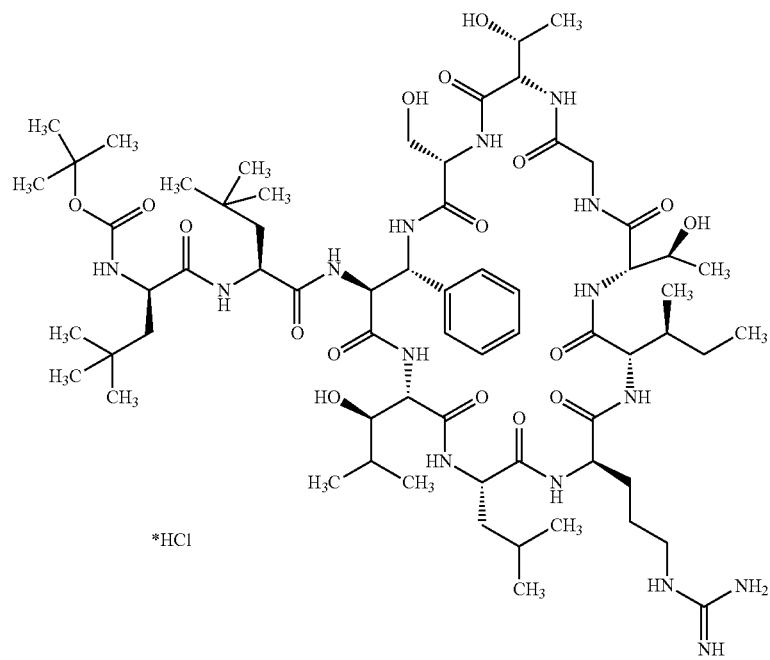

According to the preparation method of the compound of example 233A the title compound is obtained in a yield of 10 mg (91% of theory) from the compound of example 228A (8.5 mg, 8 µmol) and the dipeptide of example 8A (4 mg, 10 µmol, 1.3 equivalents).

HPLC (Method 5): $R_t$=4.65 min.

LC-MS (Method 19): $R_t$=2.09 min, MS (ESIpos): m/z (%) 1374.8 (30) [M+H]⁺

HR-TOF-MS (Method 24): $C_{65}H_{112}N_{15}O_{17}$ calc. 1374.8356, found 1374.8376 [M+H]⁺.

Example 237A

[N²-(tert.-Butoxycarbonyl)-3-tert-butyl-D-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-allothreonyl-L-serinate C$^{1.11}$-N$^{3.3}$-lactam hydrochloride

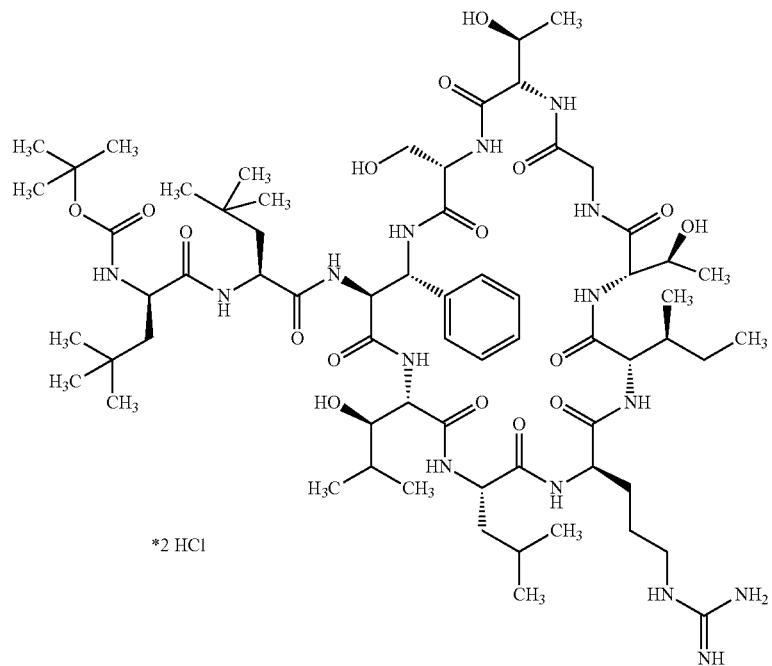

According to the preparation method of the compound of example 233A the title compound is obtained in a yield of 47 mg (purity 77%, 69% of theory) from the compound of example 229A (40 mg, 35 µmol) and the dipeptide of example 8A (17 mg, 46 µmol, 1.5 equivalents).

HPLC (Method 6): R$_t$=4.31 min.

LC-MS (Method 19): R$_t$=2.08 min, MS (ESIpos): m/z (%)=1374.8 (50) [M+H]$^+$

HR-TOF-MS (Method 24): C$_{65}$H$_{112}$N$_{15}$O$_{17}$ calc. 1374.8356, found 1374.8362 [M+H]$^+$.

Example 238A

[N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-alanyl-L-serine C$^{1.11}$-N$^{3.3}$-lactam hydrochloride

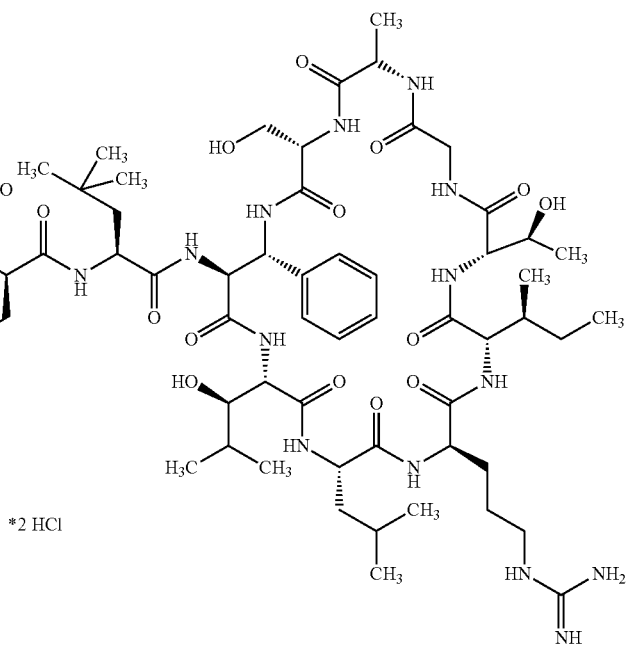

According to the preparation method of the compound of example 233A the title compound is obtained in a yield of 37 mg (98% of theory) from the compound of example 230A (29 mg, 27 µmol) and the dipeptide of example 8A (13 mg, 35 µmol, 1.3 equivalents).

HPLC (Method 5): $R_t$=4.60 min.

LC-MS (Method 19): $R_t$=2.10 min, MS (ESIpos): m/z (%)=623.0 (100) $[M-Boc+2H]^{2+}$; 1344.9 (90) $[M+H]^+$ HR-TOF-MS (Method 24): $C_{64}H_{109}N_{15}O_{16}$ calc. 1344.8250, found 1344.8241 $[M+H]^+$.

Example 239A $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam hydrochloride

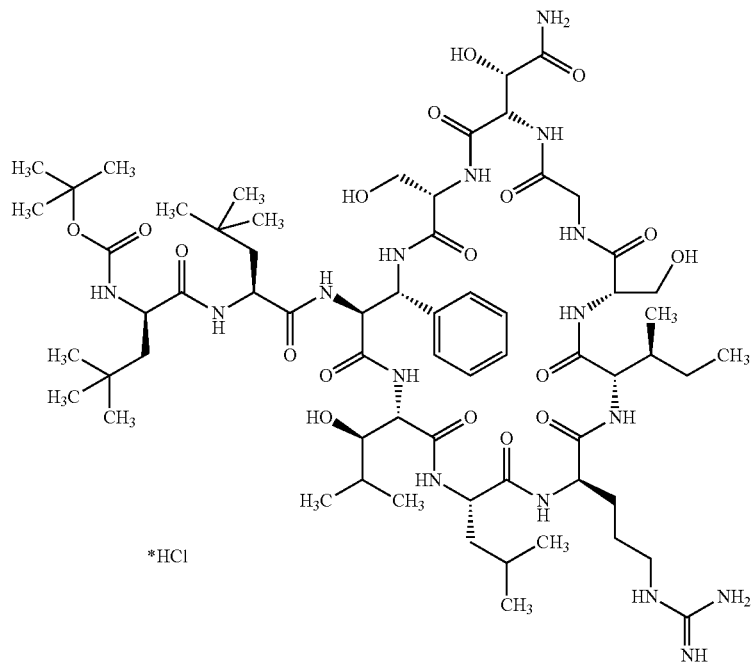

According to the preparation method of the compound of example 233A the title compound is obtained in a yield of 24 mg (89% of theory) from the compound of example 231A (21 mg, 19 µmol) and the dipeptide of example 8A (9 mg, 25 µmol, 1.3 equivalents).

HPLC (Method 5): $R_t$=4.42 min.

LC-MS (Method 19): $R_t$=2.03 min, MS (ESIpos): m/z (%)=645.5 (100) $[M-Boc+2H]^{2+}$; 1389.9 (40) $[M+H]^+$.

HR-TOF-MS (Method 24): $C_{64}H_{108}N_{16}O_{18}$ calc. 1389.8101, found 1389.8105 $[M+H]^+$.

Example 240A

[N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-asparaginyl-L-serine $C^{1.9}$-$N^{3.1}$-lactam hydrochloride

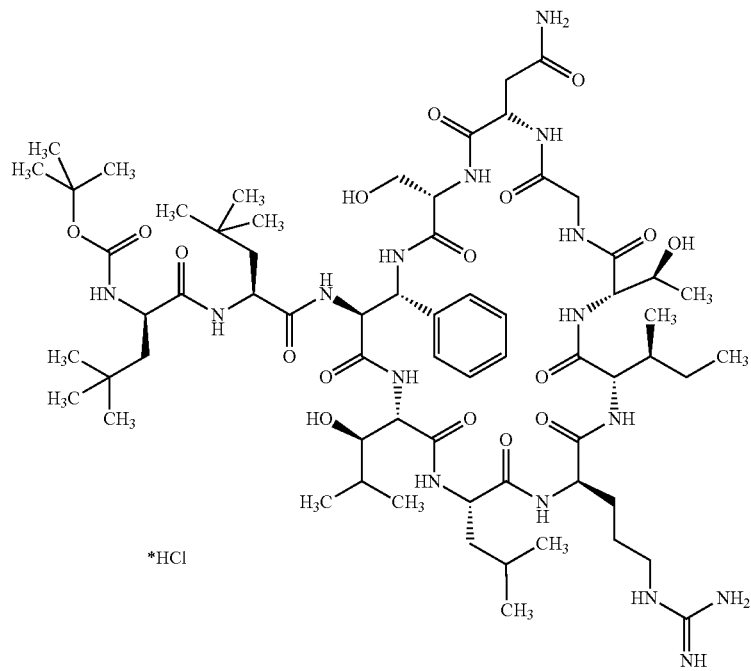

According to the preparation method of the compound of example 233A the title compound is obtained in a yield of 30 mg (97% of theory) from the compound of example 232A (24 mg, 22 μmol) and the dipeptide of example 8A (11 mg, 28 μmol, 1.3 equivalents).

HPLC (Method 5): $R_t$=4.26 min.

LC-MS (Method 21): $R_t$=2.19 min, MS (ESIpos): m/z (%)=644.7 (100) [M−Boc+2H]²⁺.

HR-TOF-MS (Method 24): $C_{65}H_{111}N_{16}O_{17}$ calc. 1387.8308, found 1387.8304 [M+H]⁺.

Example 241A

Benzyl N²-(tert-butoxycarbonyl)-L-alaninate

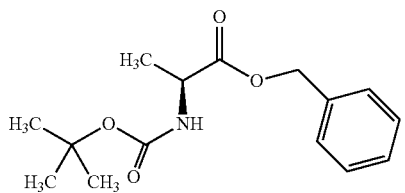

N²-(tert-Butoxycarbonyl)-L-alanine (1.13 g, 5.83 mmol) is dissolved in dry DCM (6 ml), some 3 Å molecular sieves are added, and the mixture is then cooled to 0° C. Benzyl alcohol (1.81 ml, 17.48 mmol, 3 equivalents), EDCI (2.23 g, 11.65 mmol, 2 equivalents), and DMAP (71 mg, 0.58 mmol, 0.1 equivalent) are added. The mixture is stirred for 150 min, during which it is allowed to slowly warm to RT. The mixture is then concentrated to dryness and the residue is worked up by chromatography (Biotage, cyclohexane-ethyl acetate 9:1). Product-containing fractions are combined and concentrated. The title compound is obtained in a yield of 1.03 g (63% of theory).

HPLC (Method 5): $R_t$=4.70 min.

LC-MS (Method 21): $R_t$=2.44 min, MS (ESIpos): m/z (%)=280.3 (30) [M+H]⁺.

Example 242A

Benzyl L-alaninate Trifluoroacetate

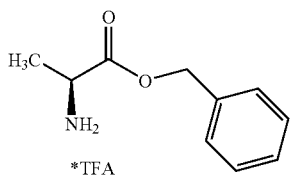

The compound of example 241A (200 mg, 716 μmol) is reacted according to procedure 2 with 2.0 ml of the reagent solution for 60 min. Without further purification, 200 mg (95% of theory) of the crude title compound are obtained.

LC-MS (Method 22): $R_t$=2.30 min, MS (ESIpos): m/z (%)=180 (100) [M+H]⁺.

Example 243A

Benzyl [N²-(tert-butoxycarbonyl)-glycyl]-[(3S)-3-hydroxy-O⁴-methyl-L-aspartyl]-L-alaninate

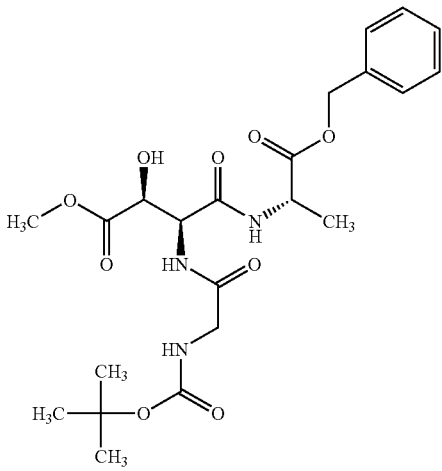

The compound of example 33A (441 mg, 895 µmol) and the compound of example 242A (315 mg, 1.07 mmol, 1.2 equivalents) are dissolved in DMF (4.8 ml) and cooled to −20° C. 4-Methylmorpholine (492 µl, 4.48 mmol, 5 equivalents) and HATU (510 mg, 1.34 mmol, 1.5 equivalents) are then added, and the mixture is slowly warmed to room temperature and stirred for about 16 h. The mixture is then purified by chromatography in two steps (method 45, then method 34). The title compound is obtained in a yield of 277 mg (64% of theory).

HPLC (Method 5): $R_t$=4.06 min.

LC-MS (Method 19): $R_t$=2.13 min, MS (ESIpos): m/z (%)=482.1 (100) [M+H]⁺.

HR-TOF-MS (Method 24): $C_{22}H_{32}N_3O_9$ calc. 482.2134, found 482.2120 [M+H]⁺.

Example 244A

Benzyl [N²-(tert-butoxycarbonyl)-glycyl]-[(3S)-3-hydroxy-L-asparaginyl]-L-alaninate

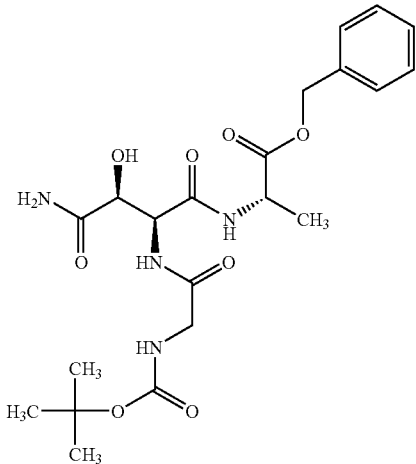

The compound of example 243A (139 mg, 288 µmol) is provided in 5.1 ml of acetonitrile and cooled to 0° C.; 3.1 ml of a conc. aqueous ammonia solution are added, and stirring is continued at 0° C. After 20 min, the reaction is stopped with glacial acetic acid (2.6 ml), diluted with water and extracted with ethyl acetate. The organic extract is washed with conc. brine, dried over sodium sulfate and concentrated. Yield: 122 mg (75% of theory) of the crude title compound which is reacted further without purification.

HPLC (Method 6): $R_t$=3.78 min.

LC-MS (Method 20): $R_t$=1.69 min, MS (ESIpos): m/z (%)=467.1 (100) [M+H]⁺; MS (ESIneg): m/z (%)=465.2 (100) [M−H]⁻.

HR-TOF-MS (Method 24): $C_{21}H_{31}N_4O_8$ calc. 467.2137, found 467.2137 [M+H]⁺.

Example 245A

Benzyl glycyl-[(3S)-3-hydroxy-L-asparaginyl]-L-alaninate trifluoroacetate

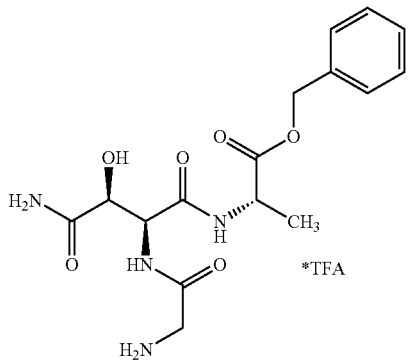

The compound of example 241A (122 mg, 217 µmol) is reacted according to procedure 2 with 2.0 ml of the reagent solution for 60 min. Without further purification, 100 mg (96% of theory) of the crude title compound are obtained.

HPLC (Method 6): $R_t$=3.05 min.

LC-MS (Method 22): $R_t$=2.23 min, MS (ESIpos): m/z (%)=367 (100) [M+H]⁺.

HR-TOF-MS (Method 24): $C_{16}H_{23}N_4O_6$ calc. 367.1613, found 367.1622 [M+H]⁺.

Example 246A

Benzyl [(3R)-N²-(tert-butoxycarbonyl)-3-hydroxy-L-leucyl]-L-leucyl-D-arginyl-L-isoleucyl-L-allothreonyl-glycyl-[(3S)-3-hydroxy-L-asparaginyl]-L-alaninate trifluoroacetate

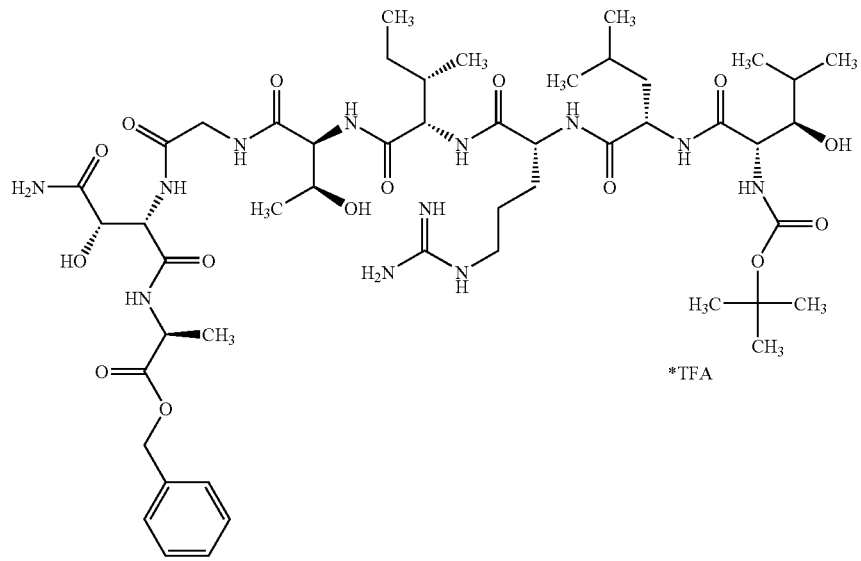

The compound of example 32A (133 mg, 139 μmol) and the compound of example 245A (100 mg, 208 μmol, 1.5 equivalents) are dissolved in DMF (950 μl), and the solution is cooled to −20° C. 4-Methylmorpholine (46 pt, 416 μmol, 3 equivalents) and HATU (84 mg, 222 μmol, 1.6 equivalents) are added, and the mixture is stirred at room temperature for 16 h. The complete mixture is then purified by chromatography according to method 45. Product-containing fractions are combined and lyophilized. 157 mg (95% of theory) of the title compound are obtained as a solid.

HPLC (Method 6): $R_t$=3.66 min.

LC-MS (Method 19): $R_t$=1.71 min, MS (ESIpos): m/z (%)=1079.1 (80) [M+H]⁺.

HR-TOF-MS (Method 24): $C_{49}H_{83}N_{12}O_{15}$ calc. 1079.6096, found 1079.6094 [M+H]⁺.

Example 247A

[(3R)-N²-(tert-Butoxycarbonyl)-3-hydroxy-L-leucyl]-L-leucyl-D-arginyl-L-isoleucyl-L-allothreonyl-glycyl-[(3S)-3-hydroxy-L-asparaginyl]-L-alanine trifluoroacetate

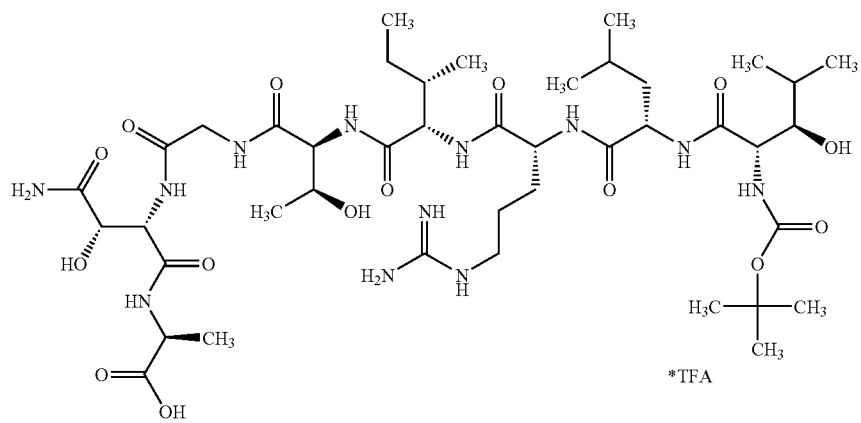

The compound of example 246A (190 mg, 159 µmol) is hydrogenated according to the method for preparing the compound of example 186A. 172 mg (98% of theory) of the title compound are obtained as a solid.

HPLC (Method 6): $R_t$=3.39 min.

LC-MS (Method 19): $R_t$=1.55 min, MS (ESIpos): m/z (%)=445.3 (100) $[M+2H]^{2+}$, 989.5 (60) $[M+H]^+$; MS (ESIneg): m/z (%)=987.5 (100) $[M-H]^-$.

HR-TOF-MS (Method 24): $C_{42}H_{77}N_{12}O_{15}$ calc. 989.5626, found 989.5651 $[M+H]^+$.

Example 248A

[(3R)-3-Hydroxy-L-leucyl]-L-leucyl-D-arginyl-L-isoleucyl-L-allothreonyl-glycyl-[(3S)-3-hydroxy-L-asparaginyl]-L-alanine bistrifluoroacetate

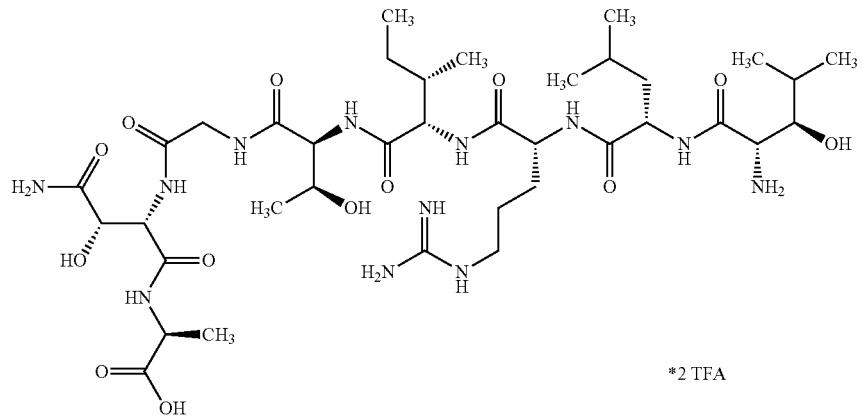

*2 TFA

The compound of example 247A (172 mg, 156 µmol) is reacted according to procedure 2 with 2.0 ml of the reagent solution for 30 min. Without further purification, 174 mg (quant.) of the crude title compound are obtained.

HPLC (Method 6): $R_t$=2.78 min.

LC-MS (Method 22): $R_t$=2.17 min, MS (ESIpos): m/z (%) 889 (80) $[M+H]^+$; MS (ESIneg): m/z (%)=887 (100), $[M-H]^-$.

HR-TOF-MS (Method 24): $C_{37}H_{69}N_{12}O_{13}$ calc. 889.5102, found 889.5096 $[M+H]^+$.

Example 249A

[(3R)-$N^2$-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine trifluoroacetate

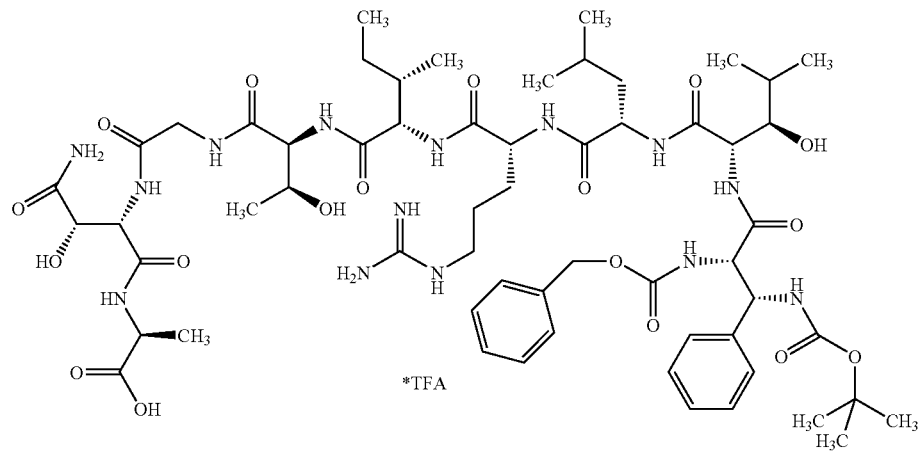

*TFA

According to the method for preparing the compound of example 201A the compound of example 248A (174 mg, 156 µmol) is reacted with the compound of example 17A (99 mg, 171 µmol, 1.1 equivalents). After purification by chromatography (variant of method 36, instead of the gradient and separation is carried out isocratic with eluent A:eluent B=3:2), 81 mg (34% of theory) of the title compound are isolated.

HPLC (Method 6): $R_t$=3.76 min.

LC-MS (Method 19): $R_t$=1.89 min, MS (ESIpos): m/z (%)=593.4 (100) [M-Boc+2H]$^{2+}$, 1285.7 (30) [M+H]$^+$; (ESIneg): m/z (%)=1283.5 (100) [M−H]$^-$.

HR-TOF-MS (Method 24): $C_{59}H_{93}N_{14}O_{18}$ calc. 1285.6787, found 1285.6781 [M+H]$^+$.

Example 250A

[(3R)-$N^2$-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine bistrifluoroacetate

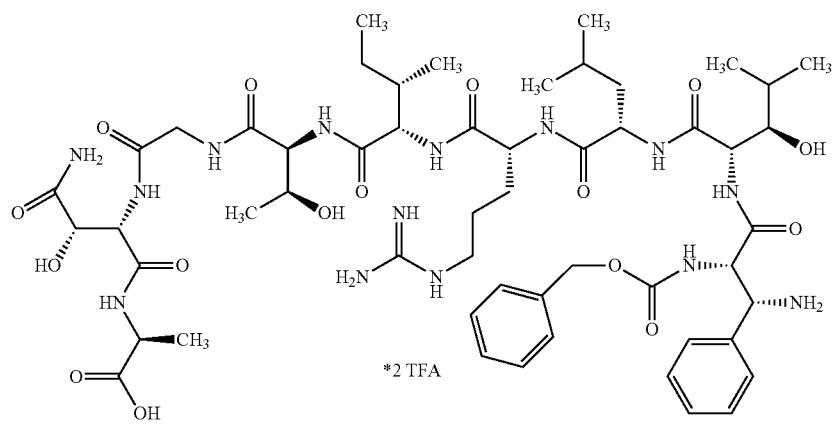

The compound of example 249A (81 mg, 54 µmol) is reacted according to procedure 2 with 2.0 ml of the reagent solution for 60 min. Without further purification, 81 mg (99% of theory) of the crude title compound are obtained.

HPLC (Method 6): $R_t$=3.20 min.

LC-MS (Method 19): $R_t$=1.29 min, MS (ESIpos): m/z (%)=593.7 (100) [M+2H]$^{2+}$, 1185.6 (5) [M+H]$^+$; MS (ESIneg): m/z (%)=1183.7 (100), [M−H]$^-$ HR-TOF-MS (Method 24): $C_{54}H_{85}N_{14}O_{16}$ calc. 1185.6263, found 1185.6249 [M+H]$^+$..

Example 251A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine $C^{1.9}$-$N^{3.1}$-lactam trifluoroacetate

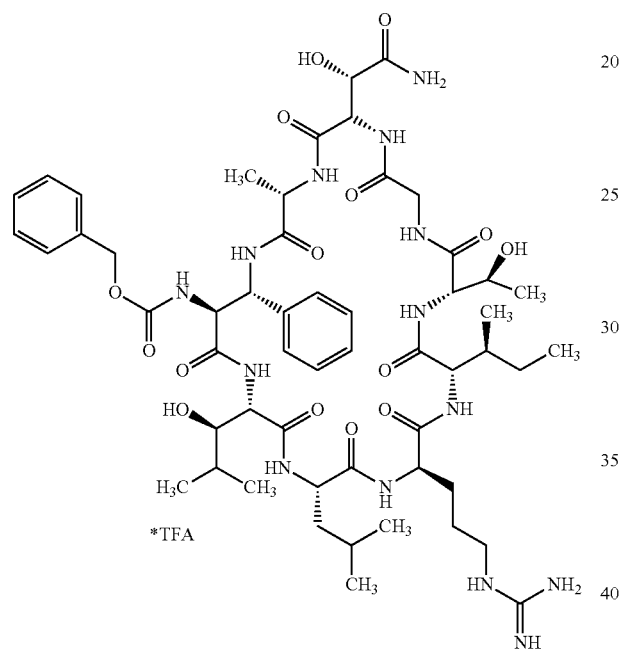

According to the method for preparing the compound of example 217A, whereby purification takes place according to method 45, the title compound is obtained in a yield of 69 mg (93% of theory) from the compound of example 250A (81 mg, 53 µmol).

HPLC (Method 6): $R_t$=3.56 min.

LC-MS (Method 19): $R_t$=1.67 min, MS (ESIpos): m/z (%)=1167.6 (100) [M+H]⁺; MS (ESIneg): m/z (%)=1165.6 (100), [M−H]⁻.

HR-TOF-MS (Method 24): $C_{54}H_{83}N_{14}O_{15}$ calc. 1167.6157, found 1167.6154 [M+H]⁺.

Example 252A

[(3R)-3-Amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine $C^{1.9}$-$N^{3.1}$-lactam bishydrochloride

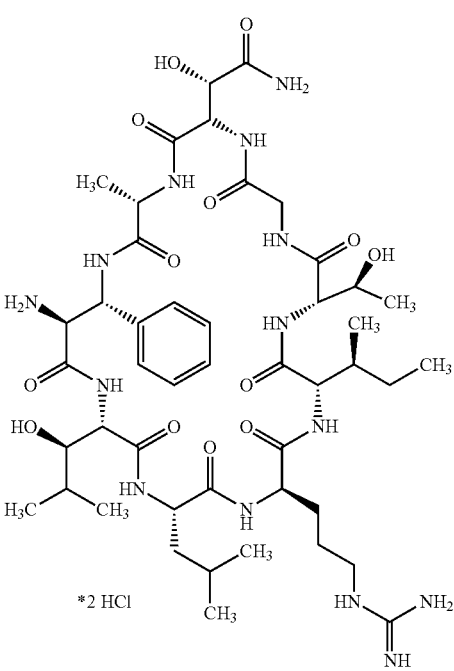

According to the method for preparing the compound of example 225A the title compound is obtained in a yield of 53 mg (97% of theory) from the compound of example 251A (69 mg, 49 µmol).

HPLC (Method 6): $R_t$=2.98 min.

LC-MS (Method 20): $R_t$=0.96 min, MS (ESIpos): m/z (%) 517.5 (100) [M+2H]²⁺, 1033.7 (10) [M+H]⁺; MS (ESIneg): m/z (%)=1031.7 (60) [M−H]⁻, 1077.7 (100) [M+HCOOH−H]⁻.

HR-TOF-MS (Method 24): $C_{46}H_{77}N_{14}O_{13}$ calc. 1033.5790, found 1033.5782 [M+H]⁺.

Example 253A

[N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine $C^{1.11}$-$N^{3.3}$-lactam hydrochloride

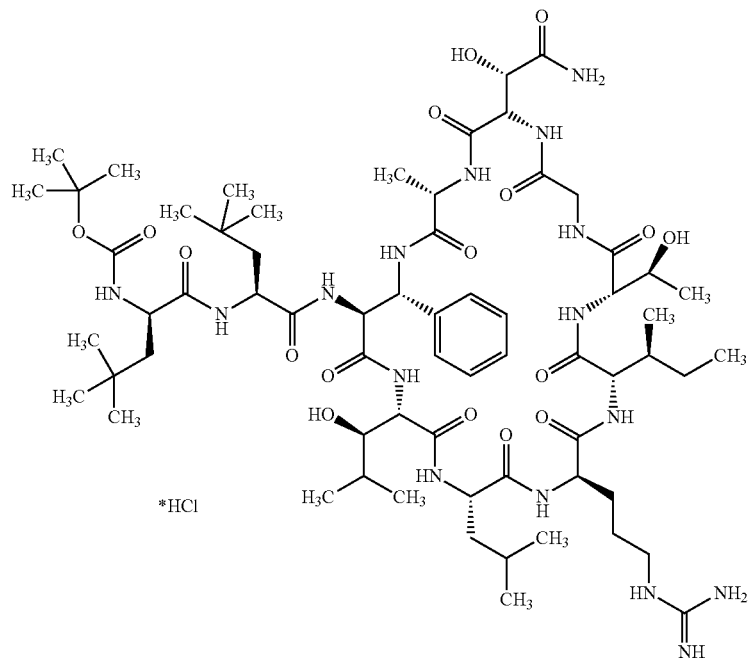

According to the method for preparing the compound of example 233A the title compound is obtained in a yield of 58 mg (85% of theory) from the compound of example 252A (53 mg, 48 µmol) and the dipeptide of example 8A (23 mg, 62 µmol, 1.3 equivalents).

HPLC (Method 6): $R_t$=4.35 min.

LC-MS (Method 19): $R_t$=2.08 min, MS (ESIpos): m/z (%)=1387.9 (100) [M+H]⁺.

HR-TOF-MS (Method 24): $C_{65}H_{111}N_{16}O_{17}$ calc. 1387.8308, found 1387.8314 [M+H]⁺.

Example 254A

Pentafluorophenyl [(3R)-N²-(tert-butoxycarbonyl)-3-hydroxy-L-leucyl]-L-leucyl-D-arginyl-L-isoleucyl-L-allothreoninate trifluoroacetate

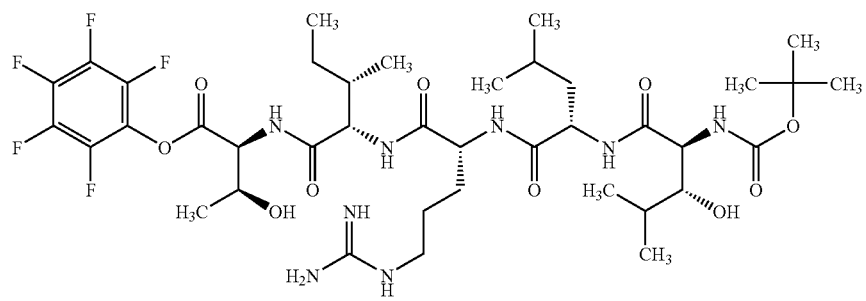

The compound of example 32A (60 mg, 71 μmol), pentafluorophenol (65 mg, 355 μmol, equivalents) and EDCI (20 mg, 107 μmol, 1.5 equivalents) are dissolved in dichloromethane (0.9 ml) at 0° C. under argon and stirred at room temperature overnight. The solvent is removed and the residue is chromatographed (method 34). The title compound is isolated in a yield of 32 mg (45% of theory).

HPLC (Method 6): $R_t$=4.12 min.

LC-MS (Method 19): $R_t$=1.93 min, MS (ESIpos): m/z (%)=897.4 (100) [M+H]$^+$.

Example 255A

Pentafluorophenyl
N$^2$-(tert-butoxycarbonyl)-D-alanine

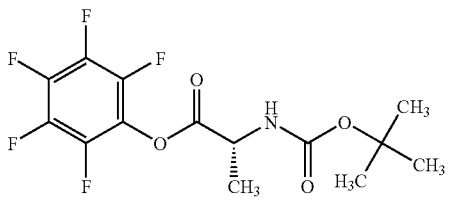

The title compound is isolated in a yield of 471 mg (64% of theory) in analogy to the preparation of the compound of example 254A from N$^2$-(tert-butoxycarbonyl)-D-alanine (390 mg, 2.06 mmol).

HPLC (Method 5): $R_t$=5.00 min.

LC-MS (Method 21): $R_t$=2.74 min, MS (ESIpos): m/z (%)=356 (5) [M+H]$^+$.

Example 256A

[N$^2$-(tert-Butoxycarbonyl)-D-alanyl]-(3S)-O$^4$-methyl-3-hydroxy-L-aspartic acid

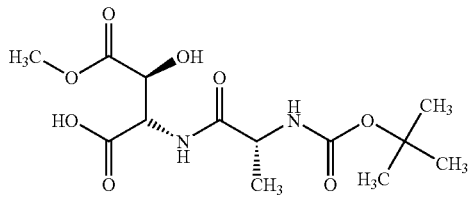

The compound of example 255A (470 mg, 1.32 mmol) and (2S,3S)-2-amino-3-hydroxy-4-methoxy-4-oxobutyric acid hydrochloride (see example 33A for preparation, 407 mg, 2.04 mmol, 1.6 equivalents) are dissolved in DMF (20 ml) at 0° C., and DIPEA (1.78 ml, 10.20 mmol, 7.7 equivalents) are added. The mixture is stirred at room temperature for about 16 h and then chromatographed according to method 45 and fine purified by method 32. Yield: 200 mg (29% of theory).

HPLC (Method 5): $R_t$=3.26 min.

LC-MS (Method 19): $R_t$=1.48 min, MS (ESIpos): m/z (%)=335.2 (90) [M+H]$^+$.

Example 257A

Benzyl [N$^2$-(tert-butoxycarbonyl)-D-alanyl]-[(3S)-O$^4$-methyl-3-hydroxy-L-aspartyl]-L-serinate

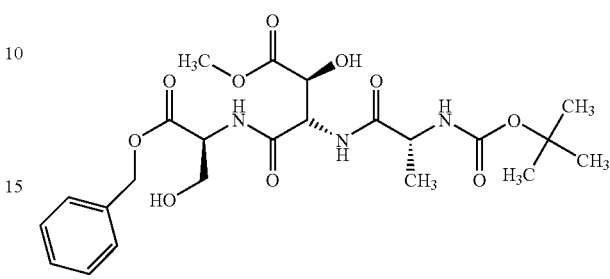

The compound of example 256A (195 mg, 0.58 mmol) and the compound of example 149A (190 mg, 0.61 mmol, 1.1 equivalents) are dissolved in DMF (5.0 ml), and the solution is cooled to 0° C. 4-Methylmorpholine (203 μl, 1.84 mmol, 3 equivalents) and TCTU (326 mg, 0.92 mmol, 1.5 equivalents) are added, and the mixture is stirred at room temperature for 2.5 h. The complete mixture is then chromatographed (method 45) and fine purified by method 32. Product-containing fractions are combined and lyophilized. 146 mg (47% of theory) of the title compound are obtained as a solid.

HPLC (Method 5): $R_t$=3.89 min.

LC-MS (Method 19): $R_t$=1.94 min, MS (ESIpos): m/z (%)=511.1 (100) [M+H]$^+$.

$[\alpha]^{20}_{Na}$+15.9 (c=0.5, MeOH).

Example 258A

[N$^2$-(tert-Butoxycarbonyl)-D-alanyl]-[(3S)-O$^4$-methyl-3-hydroxy-L-aspartyl]-L-serine

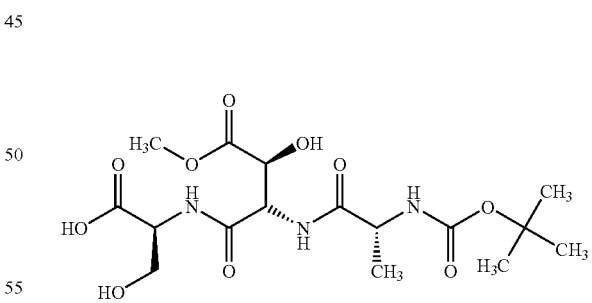

The compound of example 257A (135 mg, 264 μmol) is hydrogenated in the presence of 30 mg of 10% palladium-carbon in methanol (8.0 ml) at room temperature for 2 h. The mixture is filtered to remove the catalyst and concentrated, and the crude product is chromatographed (method 32). Yield: 117 mg (quant.).

HPLC (Method 5): $R_t$=3.11 min.

LC-MS (Method 19): $R_t$=1.40 min, MS (ESIpos): m/z (%)=422.1 (100) [M+H]$^+$.

HR-TOF-MS (Method 24): $C_{16}H_{28}N_3O_{10}$ calc. 422.1770, found 422.1776 $[M+H]^+$.

Example 259A

[$N^2$-(tert-Butoxycarbonyl)-D-alanyl]-[(3S)-3-hydroxy-L-asparaginyl]-L-serine

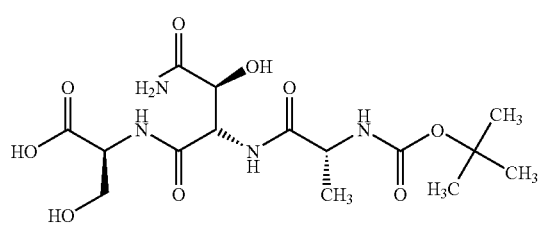

The compound of example 258A (116 mg, 275 µmol) is provided in 5.0 ml of acetonitrile and cooled to 0° C.; 3.0 ml of a conc. aqueous ammonia solution are added and stirring is continued at 0° C. After 5 min, the reaction is stopped with glacial acetic acid (1.2 ml), concentrated and chromatographed (method 32). Yield: 64 mg (57% of theory).

HPLC (Method 6): $R_t$=2.82 min.

LC-MS (Method 19): $R_t$=1.12 min, MS (ESIpos): m/z (%)=407.0 (90) $[M+H]^+$; MS (ESIneg): m/z (%)=405.0 (100) $[M-H]^-$.

HR-TOF-MS (Method 24): $C_{15}H_{27}N_4O_9$ calc. 407.1773, found 407.1781 $[M+H]^+$.

Example 260A

[D-Alanyl]-[(3S)-3-hydroxy-L-aspartyl-L-serine trifluoroacetate

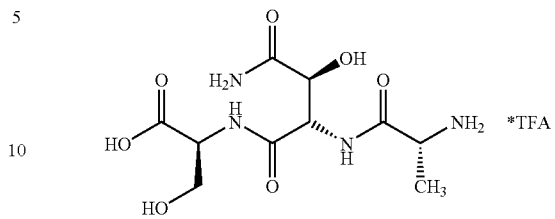

The compound of example 259A (63 mg, 155 µmol) is reacted according to procedure 2 with 2.0 ml of the reagent solution for 30 min. Without further purification, 67 mg (quant.) of the crude title compound are obtained.

HPLC (Method 6): $R_t$=0.72 min.

LC-MS (Method 19): $R_t$=0.52 min, MS (ESIpos): m/z (%)=307 (100) $[M+H]^+$.

HR-TOF-MS (Method 24): $C_{10}H_{19}N_4O_7$ calc. 307.1249, found 307.1245 $[M+H]^+$.

Example 261A

[(3R)-$N^2$-(tert-Butoxycarbonyl)-3-hydroxy-L-leucyl]-L-leucyl-D-arginyl-L-isoleucyl-L-allothreonyl-D-alanyl-[(3S)-3-hydroxy-L-asparaginyl]-L-serinate trifluoroacetate

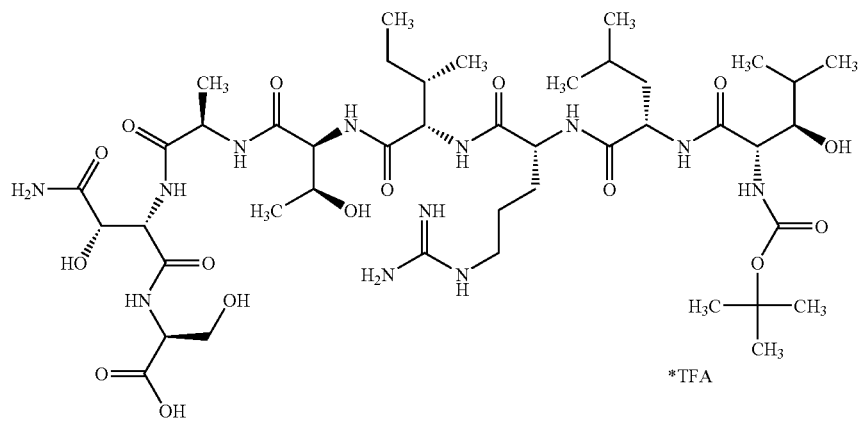

The compound of example 254A (32 mg, 32 µmol) and the compound of example 260A, 13 mg, 32 µmol, 1 equivalent) are dissolved in DMF (1.5 ml) at 0° C., and DIPEA (28 µl, 158 µmol, 5 equivalents) are added. The mixture is stirred at room temperature for about 16 h and then chromatographed according to method 45. Yield: 30 mg (84% of theory).

HPLC (Method 6): $R_t$=3.40 min.

LC-MS (Method 19): $R_t$=1.60 min, MS (ESIpos): m/z (%)=460.3 (100) $[M-Boc+2H]^{2+}$, 1019.6 (60) $[M+H]^+$.

HR-TOF-MS (Method 24): $C_{43}H_{79}N_{12}O_{16}$ calc. 1019.5732, found 1019.5716 $[M+H]^+$.

Example 262A

[(3R)-3-Hydroxy-L-leucyl]-L-leucyl-D-arginyl-L-isoleucyl-L-allothreonyl-D-alanyl-[(3S)-3-hydroxy-L-asparaginyl]-L-serinate bistrifluoroacetate

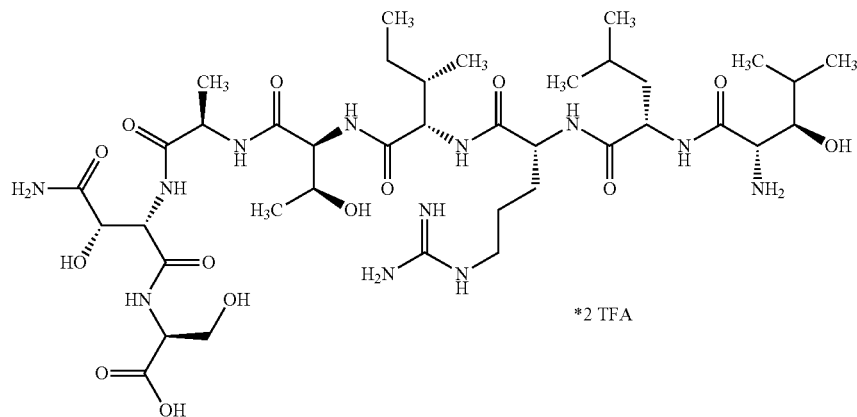

*2 TFA

The compound of example 261A (59 mg, 52 μmol) is reacted according to procedure 2 with 2.0 ml of the reagent solution for 30 min. Without purification, 64 mg (quant.) of the crude title compound are obtained.

HPLC (Method 6): $R_t$=2.91 min.

LC-MS (Method 22): $R_t$=2.20 min, MS (ESIpos): m/z (%) 461 (100) [M+2H]$^{2+}$; MS (ESIneg): m/z (%)=918 (100) [M−H]$^-$.

HR-TOF-MS (Method 24): $C_{38}H_{71}N_{12}O_{14}$ calc. 919.5208, found 919.5212 [M+H]$^+$.

Example 263A

[(3R)-N$^2$-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-D-alanyl-[(3S)-3-hydroxy-L-asparaginyl]-L-serine trifluoroacetate According to the method for preparing the compound of example 201A the compound of example 262A (92 mg, 80 μmol) is reacted with the compound of example 17A (51 mg, 88 μmol, 1.1 equivalents). After purification by chromatography (method 44), 35 mg (31% of theory) of the title compound are isolated.

HPLC (Method 6): $R_t$=3.76 min.

LC-MS (Method 19): $R_t$=1.94 min, MS (ESIpos): m/z (%) 608.4 (100) [M−Boc+2H]$^{2+}$, 1315.6 (30) [M+H]$^+$; MS (ESIneg): m/z (%)=1313.7 (100) [M−H]$^-$.

HR-TOF-MS (Method 24): $C_{60}H_{95}N_{14}O_{19}$ calc. 1315.6893, found 1315.6873 [M+H]$^+$.

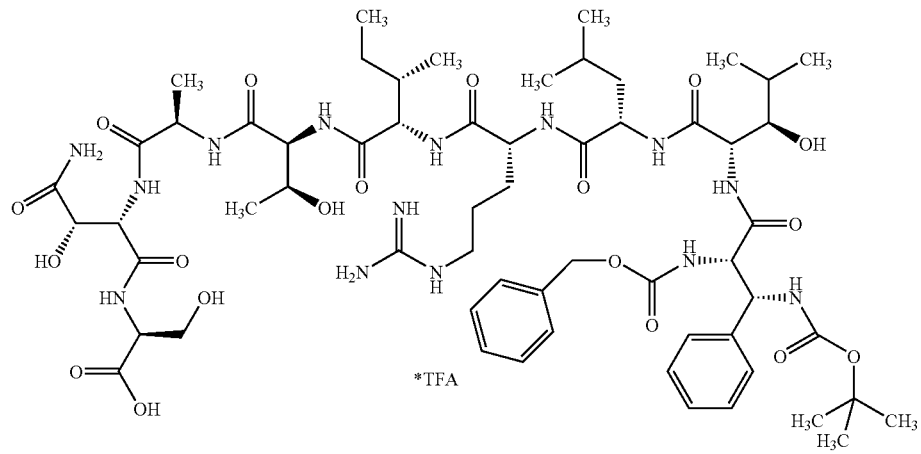

*TFA

Example 264A

[(3R)-N²-(Benzyloxycarbonyl)-3-amino-L-phenyla- lanyl]-[(3R)-3-hydroxy-L-leucyl]-L-leucyl-D- arginyl-L-isoleucyl-L-allothreonyl-D-alanyl-[(3S)-3- hydroxy-L-asparaginyl]-L-serine bistrifluoroacetate

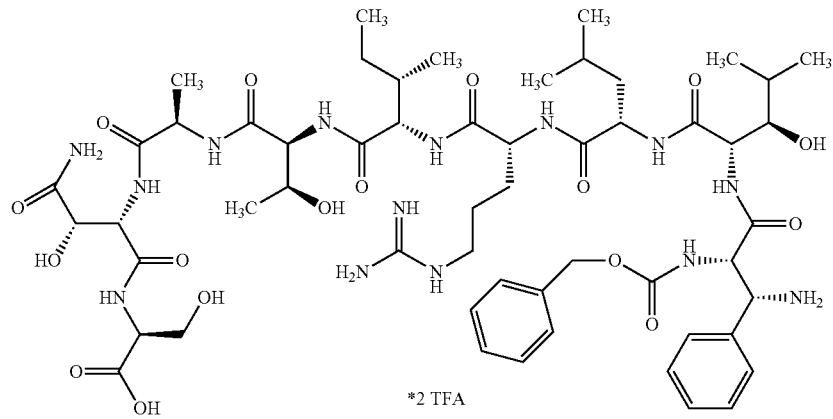
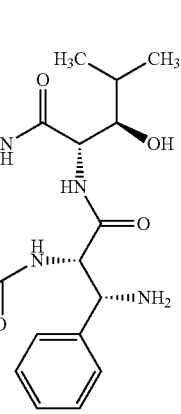

The compound of example 262A (35 mg, 24 µmol) is reacted according to procedure 2 with 2.0 ml of the reagent solution for 30 min. Without further purification, 37 mg (quant.) of the crude title compound are obtained.

HPLC (Method 6): $R_t$=3.20 min.
LC-MS (Method 19): $R_t$=1.36 min, MS (ESIpos): m/z (%) 608.3 (100) [M+2H]$^{2+}$, 1215.7 (5) [M+H]$^+$; MS (ESIneg): m/z (%)=1213.7 (100) [M−H]$^-$.
HR-TOF-MS (Method 24): $C_{55}H_{87}N_{14}O_{17}$ calc. 1215.6369, found 1215.6340 [M+H]$^+$.

Example 265A

[(3R)-N²-(Benzyloxycarbonyl)-3-amino-L-phenyla- lanyl]-[(3R)-3-hydroxy-L-leucyl]-L-leucyl-D- arginyl-L-isoleucyl-L-allothreonyl-D-alanyl-[(3S)-3- hydroxy-L-asparaginyl]-L-serine $C^{1.9}$-$N^{3.1}$-lactam trifluoroacetate

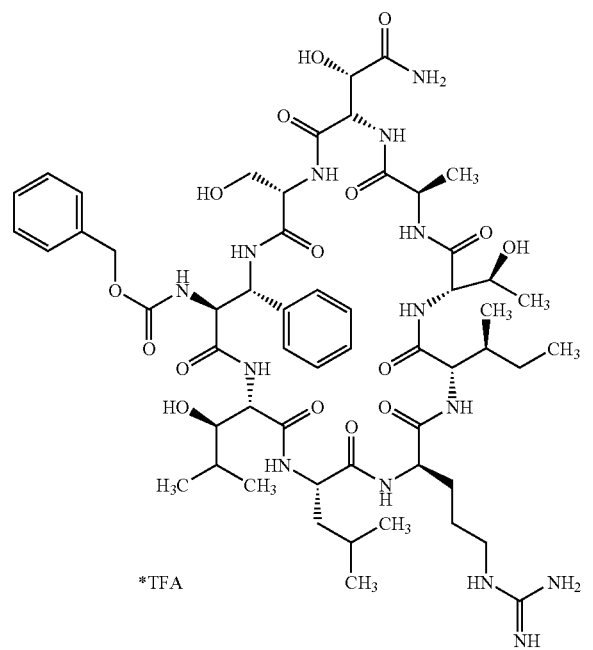

According to the method for preparing the compound of example 217A, whereby purification takes place according to method 45, the title compound is obtained in a yield of 46 mg (48% of theory (approx. 34% pure)) from the compound of example 264A (36 mg, 25 µmol).

HPLC (Method 6): $R_t$=3.55 min.
LC-MS (Method 19): $R_t$=1.61 min, MS (ESIpos): m/z (%)=599.3 (100) [M+2H]$^{2+}$; 1197.6 (30) [M+H]$^+$; MS (ESIneg): m/z (%)=1195.6 (100), [M−H]$^-$.
HR-TOF-MS (Method 24): $C_{55}H_{85}N_{14}O_{16}$ calc. 1197.6263, found 1197.6290 [M+H]$^+$.

Example 266A

[(3R)-3-Amino-L-phenylalanyl]-[(3R)-3-hydroxy-L- leucyl]-L-leucyl-D-arginyl-L-isoleucyl-L- allothreonyl-D-alanyl-[(3S)-3-hydroxy-L-asparagi- nyl]-L-serine $C^{1.9}$-$N^{3.1}$-lactam trifluoroacetate

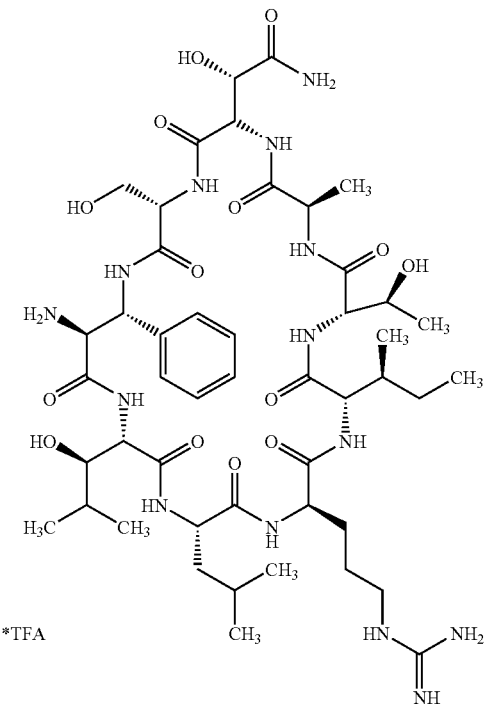

The compound of example 265A (46 mg, purity about 34%, approx. 12 μmol) is hydrogenated in the presence of a spatula tip of 10% palladium on carbon in methanol under atmospheric pressure at room temperature for 1 h. The mixture is filtered to remove the catalyst and concentrated. The crude product (42 g) is reacted further without purification.

HPLC (Method 6): $R_t$=2.98 min.

LC-MS (Method 22): $R_t$=2.33 min, MS (ESIpos): m/z (%)=533 (100) [M+2H]$^{2+}$, 1064 (10) [M+H]$^+$; MS (ESIneg) m/z (%) 1062 (100) [M]$^-$.

HR-TOF-MS (Method 24): $C_{47}H_{79}N_{14}O_{14}$ calc. 1063.5895, found 1063.5869 [M+H]$^+$.

Example 267A

[N$^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-D-alanyl-[(3S)-3-hydroxy-L-asparaginyl]-L-serine $C^{1.11}$-$N^{3.3}$-lactam trifluoroacetate

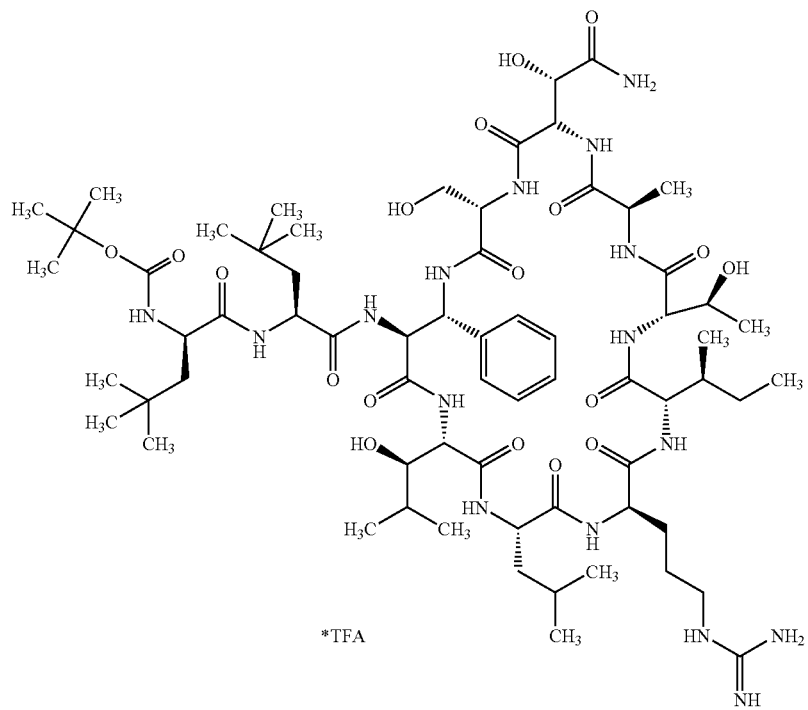

According to the method for preparing the compound of example 233A the title compound is obtained in a crude yield of 28 mg from the compound of example 266A (34 mg of crude product, approx. 12 μmol) and the dipeptide of example 8A (13 mg, 35 μmol, approx. 2.4 equivalents). The product is employed in the next synthesis step without further purification.

HPLC (Method 6): $R_t$=4.27 min.

LC-MS (Method 19): $R_t$=2.12 min, MS (ESIpos): m/z (%) 659.6 (100) [M-Boc+2H]$^{2+}$ 1417.8 (50) [M+H]$^+$.

Example 268A rac N-(tert-Butoxycarbonyl)-3-(trimethylsilyl)alanine

The synthesis takes place according to Merget, K. Günther, M. Bernd, E. Günther, R. Tacke, *J. Organomet. Chem.* 2001 628, 183-194. The enantiomers are separated by preparative HPLC on a chiral phase:

Gilson Abimed HPLC, UV detector 212 nm, column: Daicel Chiralpak AD-H 5 μm; 250×20 mm; flow rate: 15 ml/min; eluent A: isohexane, eluent B: 0.2% acetic acid/1% water/2-propanol; isocratic.

Example 269A (2S compound or N-(tert-butoxycarbonyl)-D-3-trimethylsilylalanine)

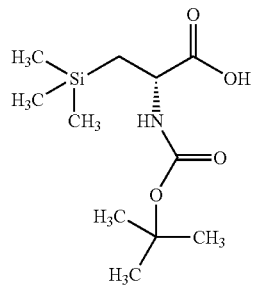

Preparative HPLC: $R_t$=4.16 min
$[\alpha]_D^{20}$+1.1 (c=0.83, Methanol)

Example 270A (2R or N-(tert-butoxycarbonyl)-L-3-trimethylsilylalanine)

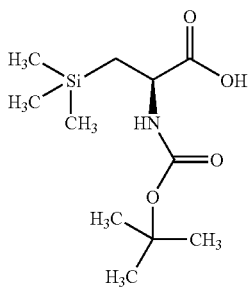

Preparative HPLC: $R_t$=9.27 min
$[\alpha]_D^{20}$=−1.6 (c=0.66, Methanol)

Example 271A

Methyl N-(tert-butoxycarbonyl)-3-pyridin-3-yl-L-alaninate

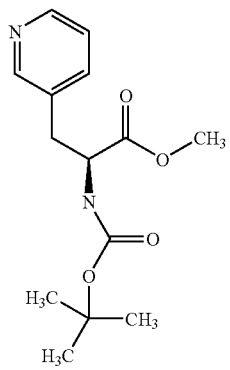

Analogous to B. Neises, W. Steglich, *Org. Synth.* 1985, 63, 183-187.

(2S)-N-(tert-Butoxycarbonyl)-3-(3-pyridyl)alanine (25.00 g, 93.88 mmol) is dissolved in 300 ml of dichloromethane under argon. Methanol (11.4 ml, 9.02 g, 281 mmol, 3 equivalents) and a grain of DMAP are added. The mixture is then cooled to 0° C. EDC (19.80 g, 103 mmol, 1.1 equivalents) is added. After 5 min, the ice bath is removed and the mixture is stirred at room temperature for 1 h. The mixture is then concentrated in vacuo, and the residue is mixed with ethyl acetate and extracted with conc. sodium bicarbonate. The aqueous phase is back-extracted once with ethyl acetate, and the combined organic phases are then washed with 0.5 M citric acid and subsequently once again with conc. sodium bicarbonate. The organic phase is dried over sodium sulfate, filtered and concentrated in vacuo. A clear oil remains which crystallizes on drying under oil pump vacuum. Yield: 23.60 g (84.2 mmol, 90% of theory).

HPLC/UV-Vis (Method 5): $R_t$=3.28 min.

$^1$H NMR (400 MHz, d$_6$-DMSO) δ 1.30 (s, 9 H), 2.86 (m, 1 H), 3.04 (m, 1 H), 3.63 (s, 3 H), 4.22 (m, 1 H), 7.28-7.39 (m, 2 H), 7.69 (d, 1 H), 8.43 (m, 2 H).

LC-MS (Method 18): $R_t$=1.21 min, MS (ESIpos.): m/z (%)=281 (100) [M+H]$^+$.

Example 272A

3-[(2S)-2-Ammonio-3-methoxy-3-oxopropyl]pyridinium bis(trifluoroacetate)

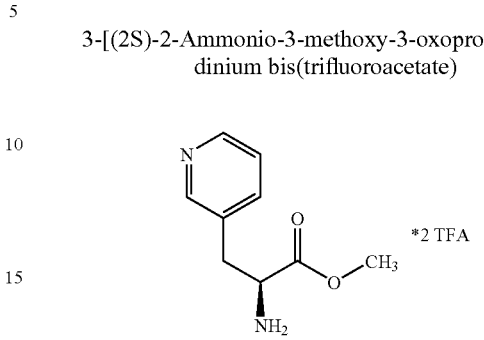

Compound 271A (11.8 g, 42.09 mmol) is dissolved in 30% TFA in dichloromethane (160 ml) and stirred at room temperature for 30 min. The mixture is then concentrated in vacuo. The residue is taken up in a little water and lyophilized. The lyophilizate is then mixed with toluene and concentrated in vacuo. Finally, the product is dried to constant weight under oil pump vacuum. Yield: 17.15 g (quant.).

HPLC/UV-Vis (Method 5): $R_t$=0.88 min.

$^1$H NMR (400 MHz, d$_6$-DMSO) δ 2.79 (dd, 1 H), 2.92 (dd, 1 H), 3.60 (s, 3 H), 3.63 (m, 1 H), 7.30 (m, 1 H), 7.62 (d, 1 H), 8.41 (m, 2 H).

LC-MS (Method 18): $R_t$ 0.46 min, MS (ESIpos.): m/z (%)=181 (100) [M+H]$^+$.

Example 273A

Methyl N-(tert-butoxycarbonyl)-3-(trimethylsilyl)-D-alanyl-3-pyridin-3-yl-L-alaninate

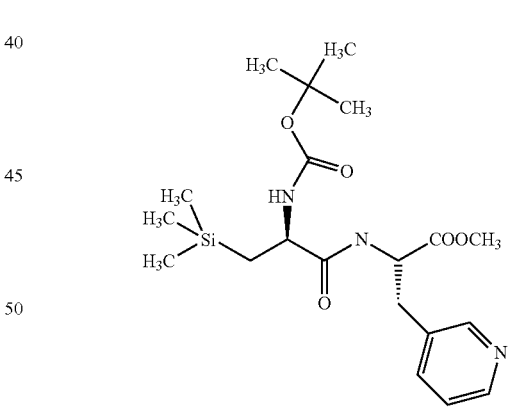

Compound 269A (10.31 g, 39.4 mmol) and compound 272A (16.10 g, 39.4 mmol, 1 equivalent) are dissolved in DMF (186 mL) at 0° C. NMM (17.34 ml, 16.00 g, 4 equivalents) and HATU (22.49 g, 59.16 mmol, 1.5 equivalents) are then added. The mixture is stirred at room temperature for two hours. tert-Butyl methyl ether is added, and the mixture is washed with conc. sodium carbonate. The aqueous phase is back-extracted once with tert-butyl methyl ether, and the combined organic phases are then washed with 1 M aqueous citric acid and again with conc. sodium carbonate, dried over Na$_2$SO$_4$, filtered and concentrated in vacuo. Filtration through silica gel is carried out (cyclohexane/ethyl acetate 2+1). Yield: 14.1 g (84% of theory).

HPLC/UV-Vis (Method 5): $R_t$=3.91 min.

$^1$H NMR (400 MHz, $d_6$-DMSO) δ −0.09 (s, 9 H), 0.56-0.75 (m, 2 H), 1.47 (s, 9 H), 2.90 (dd, 1 H), 3.09 (dd, 1 H), 3.62 (s, 3 H), 3.98 (m, 1 H), 4.49 (m, 1 H), 3.68 (d, 1 H), 7.26 (dd, 1 H), 7.61 (m, 1 H), 8.20 (d, 1 H), 8.40 (m, 2 H).

LC-MS (Method 18): $R_t$ 1.90 min, MS (ESIpos.): m/z (%)=424 (50) [M+H]$^+$.

Example 274A

N-(tert-Butoxycarbonyl)-3-(trimethylsilyl)-D-alanyl-3-pyridin-3-yl-L-alanine

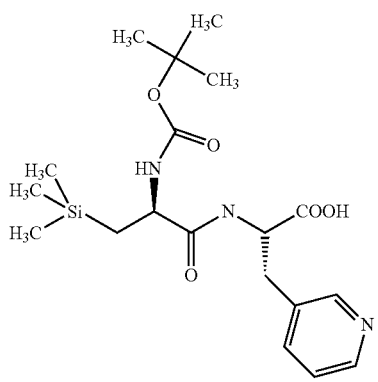

Compound 273A (7.4 g, 17.56 mmol) is taken up in THF/water (6+4), cooled to 0° C., and lithium hydroxide monohydrate (1.47 g, 35.13 mmol, 2 equivalents) is added. The mixture is stirred at 0° C. After one hour, a further equivalent (0.74 g) of lithium hydroxide monohydrate is added, and stirring is continued for one hour. Most of the THF is removed in vacuo, and the pH is then adjusted to 4 by adding citric acid. A solid precipitates. The mixture is extracted with three portions of ethyl acetate, during which the solid dissolves. The combined organic phases are dried over sodium sulfate, filtered and concentrated. The crude product is purified by chromatography on Sephadex LH 20 (Method 45). Yield: 6.67 g (93% of theory).

HPLC/UV-Vis (Method 5): $R_t$=3.73 min.

$^1$H NMR (300 MHz, $d_6$-DMSO) δ −0.09 (s, 9 H), 0.56-0.75 (m, 2 H), 1.35 (s, 9 H), 2.90 (dd, 1 H), 3.09 (dd, 1 H), 3.98 (m, 1 H), 4.41 (m, 1 H), 6.70 (d, 1 H), 7.26 (dd, 1 H), 7.60 (m, 1 H), 8.00 (d, 1 H), 8.37 (m, 2 H).

LC-MS (Method 18): $R_t$ 1.71 min, MS (ESIpos.): m/z (%)=410 (100) [M+H]$^+$.

Example 275A (3R)-3-[(tert-Butoxycarbonyl)amino]-L-phenylalanine

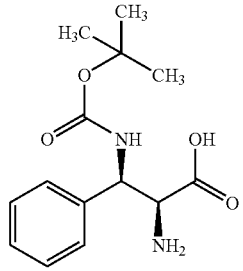

Exemplary compound 16A (3.00 g, 7.24 mmol) is dissolved in methanol (60 ml), 10% palladium on activated carbon (50 mg) are added, and the mixture is stirred under a hydrogen atmosphere at room temperature and under atmospheric pressure for 6 h. The mixture is then filtered to remove the catalyst and concentrated. The crude reaction product (2.20 g, requant.) is employed in the next step without purification.

HPLC (Method 6): $R_t$=3.21 min.

LC-MS (Method 51): $R_t$=1.55 min, MS (ESIpos): m/z (%)=281.3 (30) [M+H]$^+$, MS (ESIneg): m/z (%)=279.1 (100) [M−H]$^-$.

[α]$^{20}_{Na}$=−23.4 (c=1.0, MeOH).

$^1$H-NMR (400 MHz, $d_6$-DMSO) δ (ppm)=1.34 (s, 9H), 3.52 (d, J=4.6 Hz, 1H), 4.88 (dd, J=4.6, J=8.4 Hz, 1H), 7.29 (m, 5H), 8.02 (d, J=8.6 Hz, 1H).

HR-TOF-MS: $C_{14}H_{21}N_2O_4$ calc. 281.1496, found 281.1503 [M+H]$^+$.

Example 276A (βR)-β-[(tert-Butoxycarbonyl)amino]-$N^2$-[(9H-fluoren-9-ylmethoxy)carbonyl]-L-phenylalanine

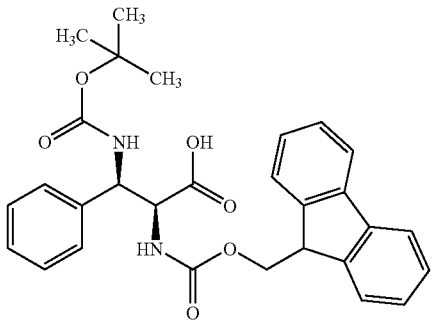

Exemplary compound 275A (2.2 g of crude product, 7.24 mmol) and (9H-fluoren-9-ylmethoxy)carbonylsuccinimide (2.90 g, 8.58 mmol, 1.2 equivalents), as well as sodium carbonate (1.18 g, 11.70 mmol, 1.5 equivalents) are dissolved in 1,4-dioxane-water (7+3) and stirred at room temperature overnight. The reaction is then stopped by adding 5% aqueous citric acid and extracted with two portions of ethyl acetate. The combined organic extracts are dried over sodium sulfate and concentrated, and the residue is triturated with water and acetonitrile. The crystalline crude product is then purified by chromatography according to method 34. Yield: 2.58 g (66% of theory) as a colorless solid.

HPLC (Method 6): $R_t$=4.86 min.

LC-MS (Method 20): $R_t$=2.51 min, MS (ESIpos): m/z (%)=503.2 (70) [M+H]$^+$, MS (ESIneg): m/z (%)=501.3 (100) [M−H]$^-$.

$^1$H NMR (400 MHz, $d_6$-DMSO) δ (ppm)=1.38 (s, 9H), 4.75 (dd, J=3.9, J=9.8 Hz, 1H), 5.29 (dd, J=3.9, J=10.0 Hz 1H), 7.21-7.60 (m, 13H), 7.87 (d, J=7.4 Hz, 1H).

HR-TOF-MS: $C_{29}H_{31}N_2O_6$ calc. 503.2177, found 503.2158 $[M+H]^+$.

Example 277A

Pentafluorophenyl (3R)-3-[(tert-butoxycarbonyl)amino]-$N^2$-[(9H-fluoren-9-ylmethoxy)-carbonyl]-L-phenylalaninate

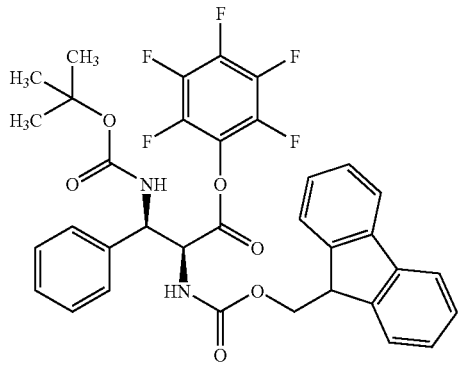

Exemplary compound 276A (2.58 g, 5.14 mmol) and pentafluorophenol (4.72 g, 25.68 mmol, 5 equivalents) are dissolved in dichloromethane (350 ml), and cooled to 0° C. EDCI (1.48 g, 7.70 mmol, 1.5 equivalents) is added, and the mixture is stirred for 6 h while slowly warming to room temperature. The solvent is then distilled off and the residue is purified in several portions by chromatography according to method 34. Yield: 2.80 g (81% of theory) of the title compound as a colorless solid.

HPLC (Method 54) $R_t$=5.09 min.

LC-MS (Method 19): $R_t$=3.34 min, MS (ESIpos): m/z (%)=6693.0 (20) $[M+H]^+$.

$^1$H NMR (400 MHz, $d_6$-DMSO) δ (ppm)=1.39 (s, 9H), 4.11-4.26 (m, 3H), 5.16 (dd, J=4.4, J=9.5 Hz, 1H), 5.52 (dd, J=4.4, J=10.0 Hz, 1H), 7.27-7.57 (m, 9H), 7.56 (t, J=6.6 Hz, 2H), 7.73 (d, J=10.3 Hz, 1H), 7.87 (d, J=7.4 Hz, 2H), 7.93 (d, J=9.6 Hz, 1H).

HR-TOF-MS: $C_{35}H_{30}N_2O_6$ calc. 669.2019, found 669.1996 $[M+H]^+$.

Example 278A

Ethyl (3R)-3-[(tert-butoxycarbonyl)amino]-$N^2$-(diphenylmethylene)-L-leucinate

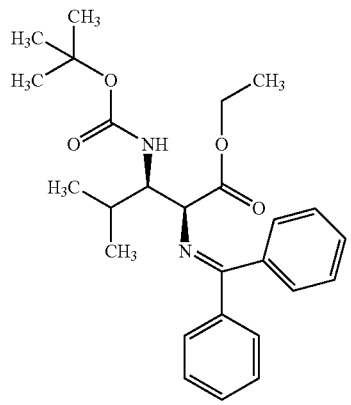

The Mannich reaction is based on a method for the addition of copper enolates onto sulfonylimines: L. Bernardi, A. Gothelf, R. G. Hazell, K. A. Jørgensen, J. Org. Chem. 2003, 68, 2583-2591. tert-Butyl [(1E)-phenylmethylene]carbamate can be prepared according to the literature: A. Klepacz, A. Zwierzak, Tetrahedron Lett. 2002 43; 1079-1080.

Freshly activated 3 Å molecular sieves, tetrakis(acetonitrile)copper(I) hexafluorophosphate (293 mg, 0.79 mmol, 0.035 equivalents) and (R)-(+)-2-(2-(diphenylphosphino)phenyl)-4-isopropyl-2-oxazoline (335 mg, 0.90 mmol, 0.04 equivalents) are provided under argon and abs. THF (228 ml) is added. Triethylamine (109 μl, 80 mg, 0.79 mmol, 0.035 equivalent) is then pipetted in. The mixture is cooled to −20° C. and, as soon as this temperature is reached, ethyl N-(diphenylmethylene)glycinate (6.00 g, 22.44 mmol) and tert-butyl [(1E)-phenylmethylene]carbamate (6.92 g, 40.4 mmol, 1.8 equivalents) are added. The mixture is stirred for 16 h, during which it is allowed to slowly reach room temperature. Silica gel (about 15 g) is then added and the solvent is distilled off in vacuo. The residue is loaded onto a glass column packed with silica gel and eluted with cyclohexane-ethyl acetate 9+1. The title compound ($R_f$=0.22, CyHex-EtOAc 9+1) contains the enantiomer with the D-threo configuration and a smaller amount (about 36%) of the two enantiomers with erythro configurations, which are removed at a later stage. The product is very sensitive to acids, and investigations by HPLC (method 6) and LC-MS (method 19) always show a proportion of benzophenone eliminated under the chromatography conditions. Yield: 2.66 g (27% of theory).

LC-MS (Method 19): $R_t$=3.23 min (21%, erythro), MS (ESIpos): m/z (%)=439.4 (100) $[M+H]^+$ and 3.23 min (48%, threo), MS (ESIpos): m/z (%)=439.3 (100) $[M+H]^+$.

$^1$H NMR (400 MHz, $d_6$-DMSO) δ (ppm)=0.62 (d, J=6.6 Hz, 3H), 0.83 (d, J=6.6 Hz, 3H), 1.13 (t, J=7.1 Hz, 3H), 1.38 (s, 9H), 1.61 (m, 1H), 3.74 (ddd, $J_1$=2.7, $J_2$=$J_3$=9.6 Hz, 1H), 3.96 (d, J=2.7 Hz, 1H), 3.99-4.06 (m, 2H), 6.51 (d, J=10.0 Hz, 1H), 7.07 (m, 2H), 7.38-7.52 (m, 6H), 7.67-7.77 (m, 2H).

HR-TOF-MS: $C_{26}H_{35}N_2O_4$ calc. 439.2592, found 439.2606 $[M+H]^+$.

Example 279A

Ethyl (3R)-3-[(tert-butoxycarbonyl)amino]-L-leucinate trifluoroacetate

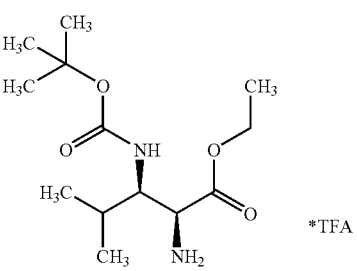

The title compound of example 278A (4.44 g, 10.12 mmol) is dissolved in dichloromethane (87 ml), 857 µl of TFA (11.13 mmol, 1.1 equivalents) and water (273 µl, 15.18 µmol, 1.5 equivalents) are added, and the mixture is stirred at room temperature for 1 h. All the volatile constituents of the reaction mixture are distilled off in vacuo, and the residue (5.97 g) is employed in the next stage without purification.

HPLC (Method 6): $R_t$=3.41 min.

LC-MS (Method 19): $R_t$=1.31 min, MS (ESIpos): m/z (%)=275.2 (50) $[M+H]^+$.

Example 280A

Ethyl (3R)-$N^2$-(benzyloxy)carbonyl-3-[(tert-butoxycarbonyl)amino]-L-leucinate

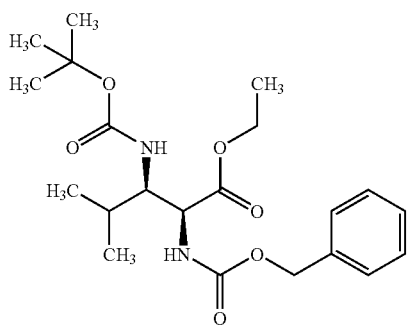

Exemplary compound 279A (5.97 g of crude product, approx. 10.11 mmol) and benzyloxycarbonylsuccinimide (3.02 g, 12.13 mmol, 1.2 equivalents) are dissolved in dichloromethane-water (4+1), and the mixture is cooled to 0° C. While stirring vigorously, sodium bicarbonate (2.55 g, 30.33 mmol, 3 equivalents) and tetrabutylammonium iodide (373 mg, 1.01 mmol, 0.1 equivalent) are added, and the mixture is stirred vigorously at room temperature for 16 h. The organic phase is separated off, washed with conc. NaCl, dried over sodium sulfate and concentrated. The crude product is isolated in several portions according to method 34, removing the benzophenone and part of the erythro diastereomer. In total, 1.65 g (4.03 mmol, 40% of theory) of the title compound are obtained.

$R_f$=0.076 (CyHex-EtOAc 9+1).

HPLC (Method 54): $R_t$=4.33 min (erythro diastereomer) and 4.52 min (threo diastereomer).

LC-MS (Method 19): $R_t$=2.71 min, MS (ESIpos): m/z (%)=409.3 (30) $[M+H]^+$, erythro isomer and $R_t$=2.75 min, MS (ESIpos): m/z (%)=409.0 (70) $[M+H]^+$ threo isomer).

$^1$H NMR (400 MHz, $d_6$-DMSO) δ (ppm)=0.71-0.86 (m, 6H), 1.16 (t, J=7.1 Hz, 3H), 1.34 (s, 9H), 1.59 (m, 1H), 3.70 (ddd, J=3.4, $J^1$=$J^2$=10.3 Hz, 1H), 3.99-4.08 (m, 2H), 4.32 (dd, J=3.4, J=9.5 Hz, 1H), 5.03 (d, J=12.4 Hz, 1H), 5.10 (d, J=12.4 Hz, 1H), 6.62 (d, J=10.5 Hz, 1H), 7.31-7.40 (m, 5H), 7.44 (d, J=9.3 Hz, 1H).

HR-TOF-MS: $C_{21}H_{33}N_2O_6$ calc. 409.2334, found 409.2329 $[M+H]^+$.

Example 281A (3R)-3-[(tert-Butoxycarbonyl)amino]-$N^2$-(benzyloxy)carbonyl-L-leucine

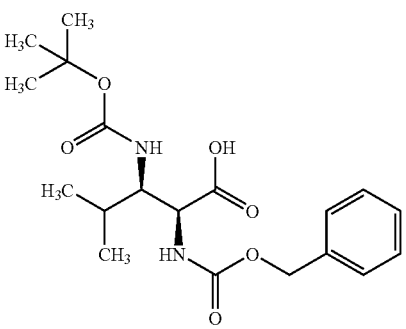

The title compound of example 280A (2.78 g, 6.82 mmol) is dissolved in a THF-water mixture (1+1, 40 ml) at 0° C., lithium hydroxide monohydrate (629 mg, 15.0 mmol, 2.2 equivalents) is added, and the mixture is stirred at 0° C. for 3 h. The THF is then distilled off, and the aqueous residue is acidified with 1 M citric acid and extracted with two portions of ethyl acetate. The combined organic extracts are dried over sodium sulfate and concentrated. The crude residue (2.42 g, 93% of theory) is separated by chromatography on a chiral phase according to method 55. In this case, the enantiomers of the threo diastereomer and those of the minor erythro diastereomer are each obtained separately. The e.e. of the main isomer (title compound) after the chiral chromatography is determined according to method 56 and is 100%. The yield of the title compound is 780 mg (30% of theory based on the starting compound 280A).

HPLC (Method 6): $R_t$=4.51 min.

LC-MS (Method 19): $R_t$=2.44 min, MS (ESIpos): m/z (%)=381.1 (30) $[M+H]^+$, MS (ESIneg): m/z (%)=379.2 (100) $[M-H]^-$.

$^1$H NMR (400 MHz, $d_6$-DMSO) δ (ppm)=0.82 (d, J=9.3 Hz, 3H), 0.85 (d, J=6.6 Hz, 3H), 1.35 (s, 9H), 3.72 (ddd, $J^1$=3.2, $J^2$=$J^3$=10.0 Hz, 1H), 4.26 (dd, J=3.2, J=9.6 Hz, 1H), 5.03 (d, J=12.7 Hz, 1H), 5.08 (d, J=12.4 Hz, 1H), 6.63 (d, J=10.5 Hz, 1H), 7.31-7.40 (m, 6H), 12.62 (br s, 1H).

HR-TOF-MS: $C_{19}H_{28}N_2O_6Na$ calc. 403.1845, found 403.1832 $[M+Na]^+$.

Chirale HPLC (Method 56): $R_t$=8.97 min.

Example 282A

Pentafluorphenyl (3R)-3-[(tert-butoxycarbonyl)amino]-N²-(benzyloxy)carbonylamino-L-leucinate

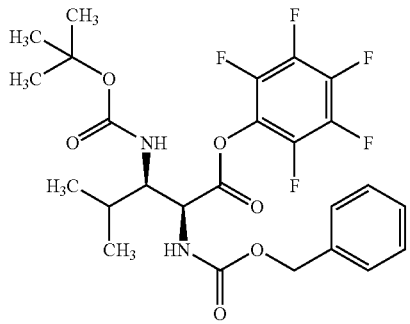

Exemplary compound 281A (100 mg, 263 µmol) and pentafluorophenol (242 mg, 1.31 mmol, 5 equivalents) are dissolved in dichloromethane (20 ml) at room temperature, EDCI (76 mg, 394 µmol, 1.5 equivalents) is then added, and the mixture is left to stand in a refrigerator for about 12 h. The solvent is subsequently distilled off in vacuo, and the residue is purified by chromatography (method 32). The title compound is obtained in a yield of 132 mg (92% of theory) as a colorless solid.

HPLC (Method 54): $R_t$=4.89 min.

LC-MS (Method 19): $R_t$=3.19 min, MS (ESIpos): m/z (%)=547.2 (40) [M+H]⁺.

Example 283A

Benzyl N²-(tert-butoxycarbonyl)-3-{[(9H-fluoren-9-ylmethoxy)carbonyl]amino}-L-ala-nyl-L-serinate

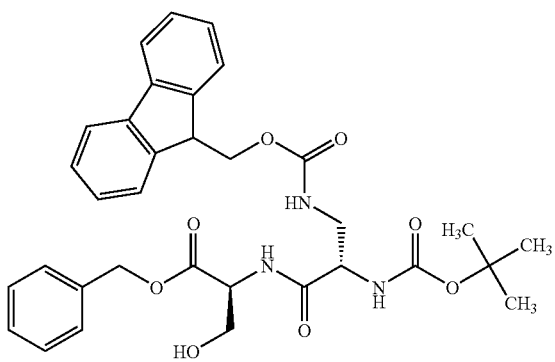

The compound of example 149A (2.08 g, 6.73 mmol) and N-(tert-butoxycarbonyl)-3-{[(9H-fluoren-9-ylmethoxy)carbonyl]amino}-L-alanine (22.73 g, 6.39 mmol, 0.95 equivalents) are dissolved in DMF (32 mL) and cooled to 0° C. HATU (3.84 g, 10.09 mmol, 1.5 equivalents) and 4-methylmorpholine (2.22 mL, 20.18 mmol, 3 equivalents) are added. The mixture is then stirred at room temperature for 2.5 h. The complete mixture is subsequently loaded onto a Sephadex LH20 column and chromatographed according to method 45. Product-containing fractions are combined and purified according to method 34. Yield: 2.41 g (59% of theory) as a colorless solid.

HPLC (Method 6): $R_t$=4.81 min.

LC-MS (Method 51): $R_t$=3.94 min, MS (ESIpos): m/z (%)=504.4 (100) [M-BOC+H⁺¹]⁺, 604.4 (40) [M+H]⁺.

[α]²⁰_{Na}=+1.5 (c=0.5, MeOH).

¹H NMR (400 MHz, d₆-DMSO) δ (ppm) 1.36 (s, 9H), 3.18 (m, 1H), 3.66 (m, 1H), 3.75 (m, 1H), 4.15-4.28 (m, 4H), 4.42 (m, 1H), 5.90 (t, J=5.6 Hz, 1H), 5.20 (s, 2H), 6.82 (d, J=8.04 Hz, 1H), 7.21 (m, 1H), 7.31-7.43 (m, 10H), 7.67 (d, J=7.8 Hz, 1H), 7.89 (d, J=7.6 Hz, 1H), 8.14 (d, J=7.6 Hz, 1H).

HR-TOF-MS: $C_{33}H_{38}N_3O_8$ calc. 604.2654, found 604.2646 [M+H]⁺.

Example 284A

Benzyl 3-{[(9H-fluoren-9-ylmethoxy)carbonyl]amino}-L-alanyl-L-serinate trifluoroacetate

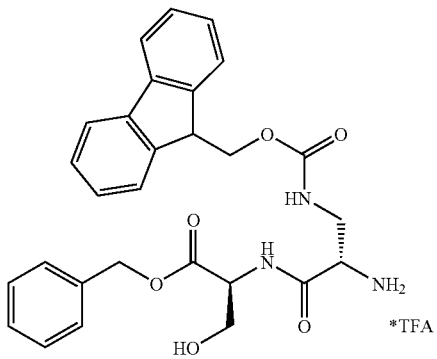

Exemplary compound 283A (2.39 g, 3.96 mmol) is reacted according to procedure 2. 2.96 g (quant.) of the crude title compound are obtained and are reacted further without further purification.

HPLC (Method 6): $R_t$=3.84 min.

LC-MS (Method 22): $R_t$=3.14 min; MS (ESIpos) m/z (%) 504.0 (100) [M+H]⁺.

[α]²⁰_{Na}=−0.5 (c=1.0, MeOH).

HR-TOF-MS: $C_{28}H_{30}N_3O_6$ calc. 504.2130, found 504.2140 [M+H]⁺.

Example 285A

Benzyl [N-(tert-butoxycarbonyl)glycyl]-[3-{[(9H-fluoren-9-ylmethoxy)carbonyl]amino}-L-alanyl]-L-serinate

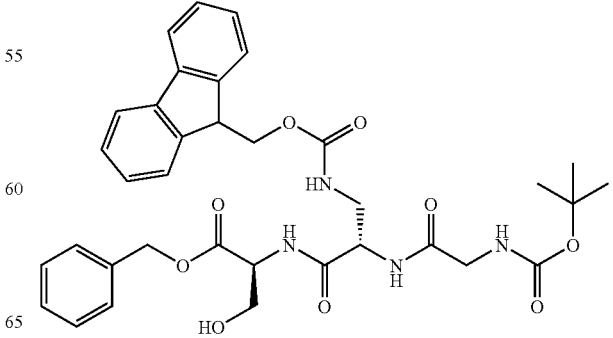

Exemplary compound 284A (2.90 g, ~83% pure, 3.89 mmol) and N-tert-butoxycarbonyl-glycine (751 mg, 4.29 mmol, 1 equivalent) are dissolved in DMF (20 ml) and cooled to 0° C. HATU (2.22 g, 5.85 mmol, 1.5 equivalents) and 4-methylmorpholine (2.14 ml, 19.49 mmol, 5 equivalents) are added. The reaction mixture is stirred at 0° C. for 2.5 h and the reaction is then stopped by adding a 5% aqueous citric acid solution and extracted with 5 portions of MTBE. The combined organic extracts are dried (sodium sulfate) and concentrated. The crude product is purified by chromatography (method 34). Product-containing fractions are combined and lyophilized. Yield: 1.54 g (60% of theory) as a colorless solid.

HPLC (Method 3) $R_f$=4.64 min.

LC-MS (Method 19): $R_f$=2.65 min, MS (ESIpos): m/z (%)=661.2 (100) [M+H]$^+$.

$[\alpha]^{20}_{Na}$=−8.7 (c=0.5, MeOH).

The title compound of example 285A (88 mg, 0.20 mmol) is reacted according to procedure 2. The crude product is reacted further without further purification. Yield: 1.84 g (quant.)

HPLC (Method 3): $R_f$=3.78 min.

LC-MS (Method 19): $R_f$=1.74 min, MS (ESIpos): m/z (%)=561.2 (100) [M+H]$^+$.

$[\alpha]^{20}_{Na}$=0.0 (c=1.0, MeOH).

HR-TOF-MS: $C_{30}H_{33}N_4O_7$ calc. 561.2344, found 561.2343 [M+H]$^+$.

Example 287A

Benzyl [(3R)-N$^2$-(tert-butoxycarbonyl)-3-hydroxy-L-leucyl]-L-leucyl-D-arginyl-L-isoleucyl-L-allothreonyl-glycyl-[3-{[(9H-fluoren-9-ylmethoxy)carbonyl]amino}-L-alanyl]-L-serinate trifluoroacetate

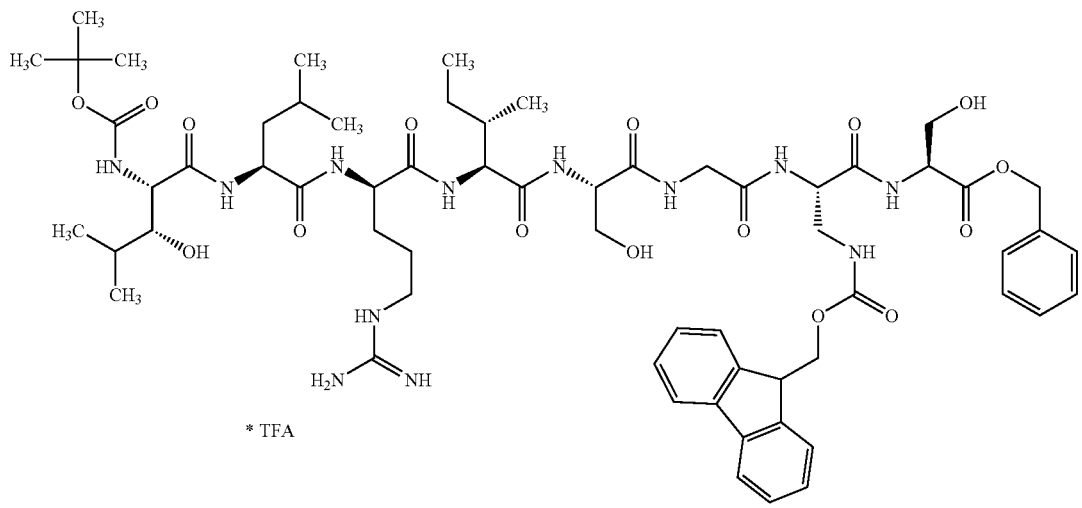

HR-TOF-MS: $C_{35}H_{41}N_4O_9$ calc. 661.2869, found 661.2864 [M+H]$^+$.

Example 286A

Benzyl glycyl]-[3-{[(9H-fluoren-9-ylmethoxy)carbonyl]amino}-L-alanyl]-L-serinate trifluoroacetate

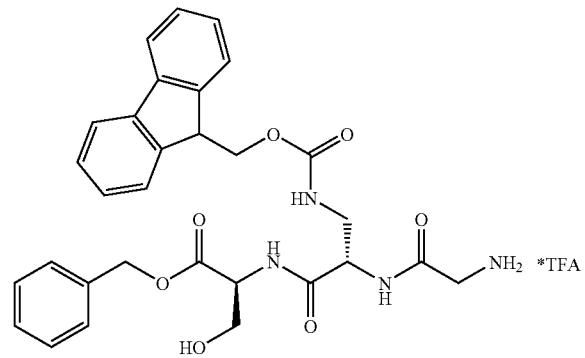

Exemplary compound 32A (701 mg, 830 μmol) and 286A (700 mg, 830 μmol, 1 equivalent) are dissolved in DMF (11.2 ml), and the solution is cooled to 0° C. 4-Methylmorpholine (274 μl, 2.49 mmol, 3 equivalents) and HATU (473 mg, 1.25 mmol, 1.5 equivalents) are added, and the mixture is stirred at 0° C. for 3 h. The complete mixture is then put onto a Sephadex LH-20 column and chromatographed according to method 45. Product-containing fractions are combined, concentrated and purified according to method 34. Product-containing fractions are combined and lyophilized. 643 mg (56% of theory) of the title compound are obtained as a colorless solid.

HPLC (Method 6): $R_f$=4.27 min.

LC-MS (Method 19): $R_f$=2.13 min, MS (ESIpos): m/z (%)=1273.9 (30) [M+H]$^+$, MS (ESIneg) m/z (%)=1317.9 (100) [M+HCOO$^-$]$^-$.

HR-TOF-MS: $C_{63}H_{93}N_{12}O_{16}$ calc. 1273.6826, found 1273.6851 [M+H]$^+$.

Example 288A

Benzyl [(3R)-3-hydroxy-L-leucyl]-L-leucyl-D-arginyl-L-isoleucyl-L-allothreonyl-glycyl-[3-{[(9H-fluoren-9-ylmethoxy)carbonyl]amino}-L-alanyl]-L-serinate bistrifluoroacetate

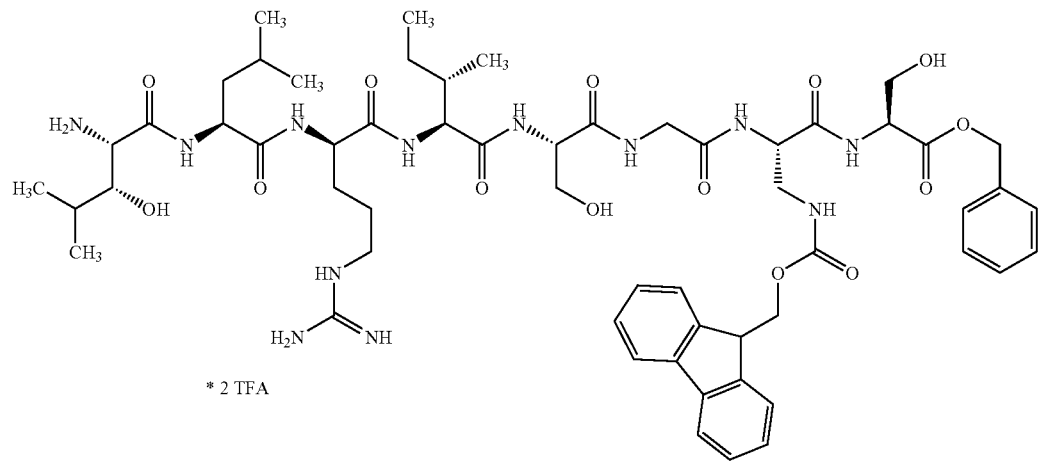

* 2 TFA

Compound 287A (643 mg, 463 µmol) is reacted according to procedure 2. The title compound is obtained crude in approximately quantitative yield (783 mg) and reacted further without purification.

HPLC (Method 5): $R_t$=3.61 min.

LC-MS (Method 51): $R_t$=2.53 min, MS (ESIpos): m/z (%)=588.1 (100) [M+2H]$^{2+}$.

HR-TOF-MS: $C_{58}H_{85}N_{12}O_{14}$ calc. 1173.6306, found 1173.6304 [M+H]$^+$.

Polymer-Bound Peptides

Example 289A

Polymer-bound N-(tert.-butoxycarbonyl)-O-tert-butyl-L-threonyl-L-leucyl-N$^5$-(imino{[(2,2,5,7,8-pentamethyl-3,4-dihydro-2H-chromen-6-yl)sulfonyl]amino}methyl)-D-ornithyl-L-isoleucyl-O-tert-butyl-L-allothreonyl-glycyl-O-tert-butyl-L-seryl-O-tert-butyl-L-serine

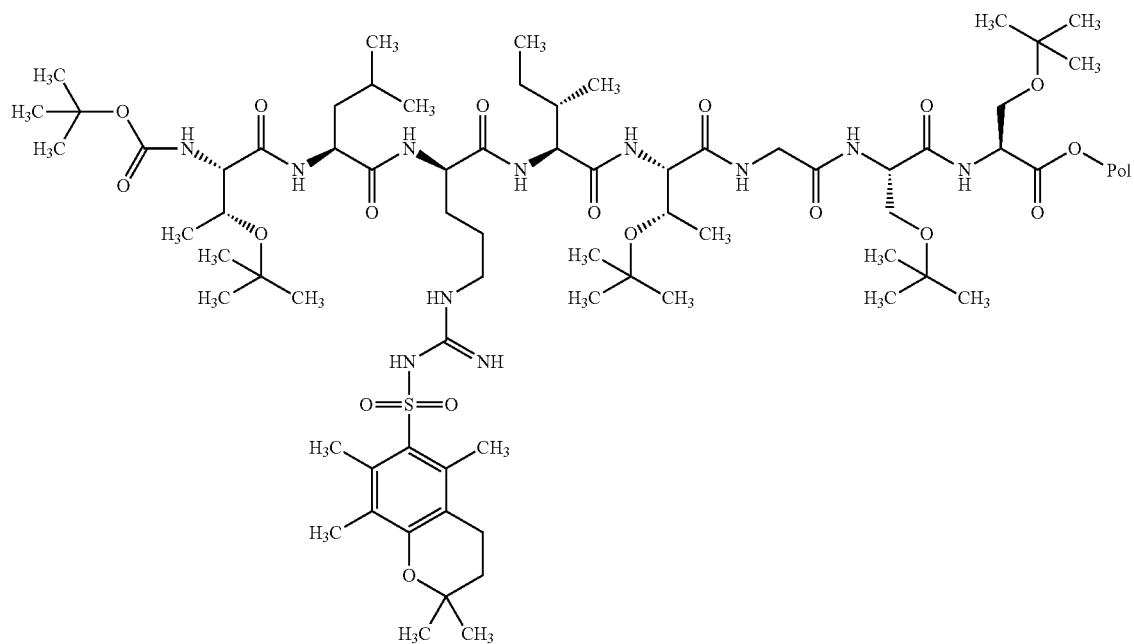

34.00 g (50.66 mmol) of 2-chlorotrityl-resin (Iris Biotech, CAS No 42074-68-0, loading 1.49 mmol/g) are provided in 400 ml of dichloromethane, and 67.989 g (177.31 mmol) of O-tert.-butyl-N-[(9H-fluoren-9-ylmethoxy)carbonyl]-L-serine and 65.476 g (506.60 mmol) of N-ethyl-N-isopropylpropan-2-amine (DIEA) are added. The mixture is shaken at RT overnight. 5 ml of methanol are added, and the mixture is shaken at RT for 30 min. The solid is collected by suction filtration, washed three times each with 400 ml of dimethylformamide, methanol and dichloromethane and collected by suction filtration. The solid is subsequently treated twice in succession with piperidine as follows: the resin is mixed with 400 ml of a 20% piperidine solution in dimethylformamide, shaken for 30 min and collected by suction filtration.

The resin obtained in this way is provided in 400 ml of dimethylformamide, and 48.564 g (126.65 mmol) of O-tert.-butyl-N-[(9H-fluoren-9-ylmethoxy)carbonyl]-L-serine, 40.665 g (126.65 mmol) of N-[(1H-benzotriazol-1-yloxy)(dimethylamino)-methylene]-N-methylmethanaminium tetrafluoroborate (TBTU) and 24.553 g (189.975 mmol) of N-ethyl-N-isopropylpropan-2-amine (DIEA) are added. The mixture is shaken at RT overnight. The solid is collected by suction filtration, washed three times each with 400 ml of dimethylformamide, methanol and dichloromethane and collected by suction filtration. The solid is subsequently treated twice in succession with piperidine as follows: the resin is mixed with 400 ml of a 20% piperidine solution in dimethylformamide, shaken for 30 min and collected by suction filtration.

The resin obtained in this way is provided in 400 ml of dimethylformamide, and 37.665 g (126.65 mmol) of N-[(9H-fluoren-9-ylmethoxy)carbonyl]-glycine, 40.665 g (126.65 mmol) of N-[(1H-benzotriazol-1-yloxy)(dimethylamino)methylene]-N-methylmethanaminium tetrafluoroborate (TBTU) and 24.553 g (189.975 mmol) of N-ethyl-N-isopropylpropan-2-amine (DIEA) are added. The mixture is shaken at RT overnight. The solid is collected by suction filtration, washed three times each with 400 ml of dimethylformamide, methanol and dichloromethane and collected by suction filtration. The solid is subsequently treated twice in succession with piperidine as follows: the resin is mixed with 400 ml of a 20% piperidine solution in dimethylformamide, shaken for 30 min and collected by suction filtration.

The resin obtained in this way is provided in 400 ml of dimethylformamide, and 50.340 g (126.65 mmol) of O-tert.-butyl-N-[(9H-fluoren-9-ylmethoxy)carbonyl]-L-allothreonine, 40.665 g (126.65 mmol) of N-[(1H-benzotriazol-1-yloxy)(dimethylamino)methylene]-N-methylmethanaminium tetrafluoroborate (TBTU) and 24.553 g (189.975 mmol) of N-ethyl-N-isopropylpropan-2-amine (DIEA) are added. The mixture is shaken at RT overnight. The solid is collected by suction filtration, washed three times each with 400 ml of dimethylformamide, methanol and dichloromethane and collected by suction filtration. The solid is subsequently treated twice in succession with piperidine as follows: the resin is mixed with 400 ml of a 20% piperidine solution in dimethylformamide, shaken for 30 min and collected by suction filtration.

32 g (47.68 mmol; assumed: 1.49 mmol/g loading) of the resin obtained in this way are provided in 400 ml of dimethylformamide, and 42.128 g (119.20 mmol) of N-[(9H-fluoren-9-ylmethoxy)carbonyl]-L-isoleucine, 38.273 g (119.20 mmol) of N-[(1H-benzotriazol-1-yloxy)(dimethylamino)methylene]-N-methylmethanaminium tetrafluoroborate (TBTU) and 23.109 g (178.80 mmol) of N-ethyl-N-isopropylpropan-2-amine (DIEA) are added. The mixture is shaken at RT overnight. The solid is collected by suction filtration, washed three times each with 400 ml of dimethylformamide, methanol and dichloromethane and collected by suction filtration. Because coupling was incomplete (according to HPLC), 400 ml of dimethylformamide, 25.277 g (71.52 mmol) of N-[(9H-fluoren-9-ylmethoxy)carbonyl]-L-isoleucine, 22.964 g (71.52 mmol) of N-[(1H-benzotriazol-1-yloxy)(dimethylamino)methylene]-N-methylmethanaminium tetrafluoroborate (TBTU) and 13.865 g (107.28 mmol) of N-ethyl-N-isopropylpropan-2-amine (DIEA) were again added, and the mixture was shaken overnight. The solid is collected by suction filtration, washed three times each with 400 ml of dimethylformamide, methanol and dichloromethane and collected by suction filtration. The solid is subsequently treated twice in succession with piperidine as follows: the resin is mixed with 400 ml of a 20% piperidine solution in dimethylformamide, shaken for 30 min, collected by suction filtration and dried in vacuo.

14 g (20.86 mmol; assumed: 1.49 mmol/g loading) of the resin obtained in this way are provided in 200 ml of dimethylformamide, and 34.566 g (52.15 mmol) of $N^2$— [(9H-fluoren-9-ylmethoxy)carbonyl]-$N^5$-(imino{[(2,2,5,7,8-pentamethyl-3,4-dihydro-2H-chromen-6-yl)-sulfonyl]amino}methyl)-D-ornithine, 16.745 g (52.15 mmol) N-[(1H-benzotriazol-1-yl-oxy)(dimethylamino)methylene]-N-methylmethanaminium tetrafluoroborate (TBTU) and 13.48 g (104.30 mmol) of N-ethyl-N-isopropylpropan-2-amine (DIEA) are added. The mixture is shaken at RT overnight. The solid is collected by suction filtration, washed three times each with 200 ml of dimethylformamide, methanol and dichloromethane and collected by suction filtration. The solid is subsequently treated twice in succession with piperidine as follows: the resin is mixed with 200 ml of a 20% piperidine solution in dimethylformamide, shaken for 30 min, collected by suction filtration and dried in vacuo.

The resin obtained in this way is provided in 200 ml of dimethylformamide, and 18.431 g (52.15 mmol) of N-[(9H-fluoren-9-ylmethoxy)carbonyl]-L-leucine, 16.745 g (52.15 mmol) of N-[(1H-benzotriazol-1-yloxy)(dimethylamino)methylene]-N-methylmethanaminium tetrafluoroborate (TBTU) and 13.480 g (104.30 mmol) of N-ethyl-N-isopropylpropan-2-amine (DIEA) are added. The mixture is shaken at RT overnight. The solid is collected by suction filtration, washed three times each with 200 ml of dimethylformamide, methanol and dichloromethane and collected by suction filtration. The solid is subsequently treated twice in succession with piperidine as follows: the resin is mixed with 200 ml of a 20% piperidine solution in dimethylformamide, shaken for 30 min, collected by suction filtration and dried in vacuo.

2.0 g (2.98 mmol; assumed: 1.49 mmol/g loading) of the resin obtained in this way are provided in 20 ml of dimethylformamide, and 2.462 g (8.94 mmol) of N-(tert-butoxycarbonyl)-O-tert.-butyl-L-threonine, 2.870 g (8.94 mmol) of N-[(1H-benzotriazol-1-yloxy)(dimethylamino)methylene]-N-methylmethanaminium tetrafluoroborate (TBTU) and 2.311 g (17.88 mmol) of N-ethyl-N-isopropylpropan-2-amine (DIEA) are added. The mixture is shaken at RT overnight. The solid is collected by suction filtration, washed three times each with 20 ml of dimethylformamide, methanol and dichloromethane and collected by suction filtration.

Example 290A

N-[(9H-Fluoren-9-ylmethoxy)carbonyl]glycyl-L-serine

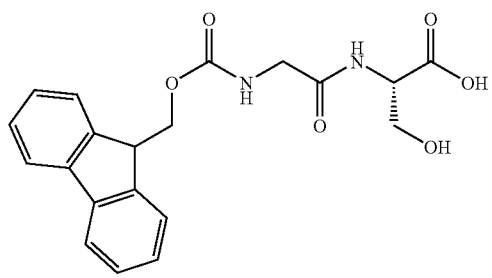

1 g (0.62 mmol) of a Wang resin (Merck Biosciences; loading: 0.62 mmol/g) preloaded with O-tert.-butyl-N-[(9H-fluoren-9-ylmethoxy)carbonyl]-L-serine is treated twice in succession with piperidine as follows: the resin is mixed with 10 ml of a 20% piperidine solution in dimethylformamide, shaken for 30 min and collected by suction filtration. The resin obtained in this way is provided in 10 ml of dimethylformamide, and 369 mg (1.24 mmol) of N-[(9H-fluoren-9-ylmethoxy)carbonyl]glycine, 398 mg (1.24 mmol) of N-[(1H-benzotriazol-1-yloxy)(dimethyl-amino)methylene]-N-methylmethanaminium tetrafluoroborate (TBTU) and 240 mg (1.86 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. 20 ml of a 50% trifluoroacetic acid solution in dichloromethane are added and left to act for 60 min, the resin is removed by filtration on a frit and the resin is washed three times with 10 ml of dichloromethane. The filtrate is concentrated and the target compound is obtained as crude product.

LC-MS (Method: LC-MS (Method 19): $R_t$=2.10 min, MS (ESIpos): m/z (%)=): 385.0 [M+H]$^+$.

Example 291A

Polymer-bound [N-tertbutoxycarbonyl-(3R)-3-hydroxy-L-leucyl]-[3-tertbutyl-L-alanyl]-[N$^5$-(imino{[(2,2,5,7,8-pentamethyl-3,4-dihydro-2H-chromen-6-yl)sulfonyl]amino}-methyl)-D-ornithyl]-L-isoleucyl-L-allothreonyl-glycyl-[O$^3$-tertbutyl-L-seryl]-O$^3$-tertbutyl-L-serine

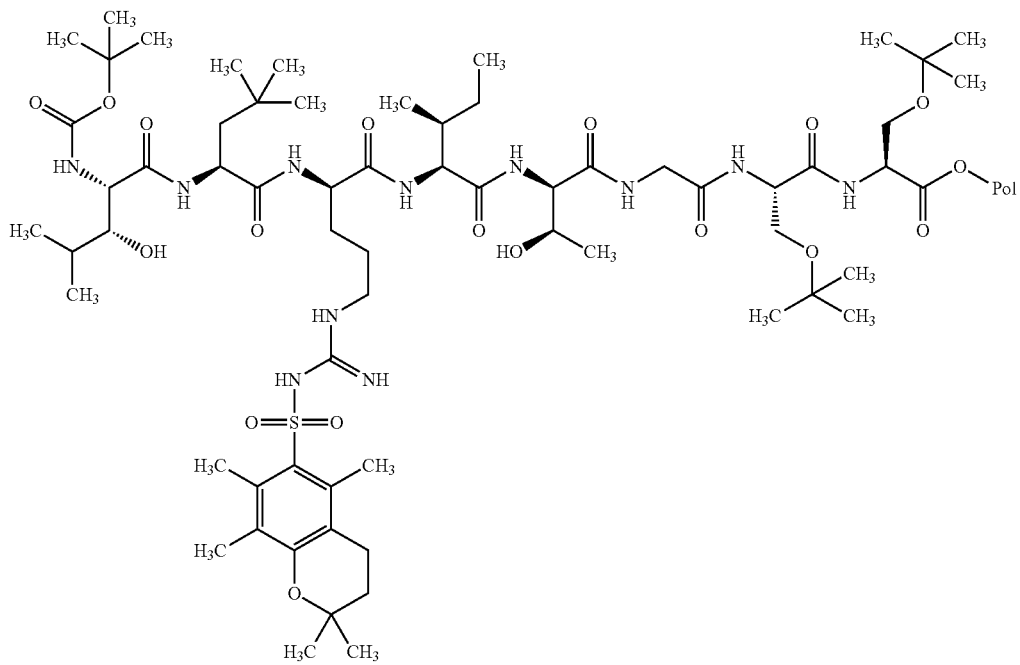

1 g (0.62 mmol) of a Wang resin (Merck Biosciences; loading: 0.62 mmol/g) preloaded with O-tert.-butyl-N-[(9H-fluoren-9-ylmethoxy)carbonyl]-L-serine is treated twice in succession with piperidine as follows: the resin is mixed with 10 ml of a 20% piperidine solution in dimethylformamide, shaken for 30 min and collected by suction filtration. The resin obtained in this way is provided in 10 ml of dimethylformamide, and 477 mg (1.24 mmol) of exemplary compound 290A, 398 mg (1.24 mmol) of N-[(1H-benzotriazol-1-yloxy)(dimethylamino)methylene]-N-methylmethanaminium tetrafluoroborate (TBTU) and 320 mg (2.48 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 423 mg (1.24 mmol) of N-[(9H-fluoren-9-ylmethoxy)carbonyl]-D-allothreonine, 399 mg (1.24 mmol) of N-[(1H-benzotriazol-1-yloxy)(dimethylamino)methylene]-N-methylmethanaminium tetrafluoroborate (TBTU) and 320 mg (2.48 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 438 mg (1.24 mmol) of N-[(9H-fluoren-9-ylmethoxy)carbonyl]-L-isoleucine, 399 mg (1.24 mmol) of N-[(1H-benzotriazol-1-yloxy)(dimethylamino)methylene]-N-methylmethanaminium tetrafluoroborate (TBTU) and 240 mg (1.86 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 821 mg (1.24 mmol) of $N^2$-[(9H-fluoren-9-ylmethoxy)carbonyl]-$N^5$-(imino{[(2,2,5,7,8-pentamethyl-3,4-dihydro-2H-chromen-6-yl)sulfonyl]amino}methyl)-D-ornithine, 399 mg (1.24 mmol) of N-[(1H-benzotriazol-1-yloxy)(dimethylamino)methylene]-N-methylmethanaminium tetrafluoroborate (TBTU) and 240 mg (1.86 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

812 mg (0.503 mmol) of the resin obtained in this way are provided in 10 ml of dimethylformamide, and 370 mg (1.01 mmol) of N-[(9H-fluoren-9-ylmethoxy)-carbonyl]-4-methyl-L-leucine, 323 mg (1.01 mmol) of N-[(1H-benzotriazol-1-yloxy)-(dimethylamino)methylene]-N-methylmethanaminium tetrafluoroborate (TBTU) and 195 mg (1.51 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 157 mg (0.633 mmol) of N-(tert-butoxycarbonyl)-(3R)-3-hydroxy-L-leucine, 203 mg (0.633 mmol) of N-[(1H-benzotriazol-1-yloxy)(dimethylamino)methylene]-N-methylmethanaminium tetrafluoroborate (TBTU) and 196 mg (1.52 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

Example 292A

Polymer-bound [N-tertbutoxycarbonyl-(3R)-3-hydroxy-L-leucyl]-[3-trimethylsilyl-L-alanyl]-[$N^5$-(imino{[(2,2,5,7,8-pentamethyl-3,4-dihydro-2H-chromen-6-yl)sulfonyl]amino}methyl)-D-ornithyl]-L-isoleucyl-[O-tertbutyl-L-allothreonyl]-glycyl-[$O^3$-tertbutyl-L-seryl]-$O^3$-tertbutyl-L-serine

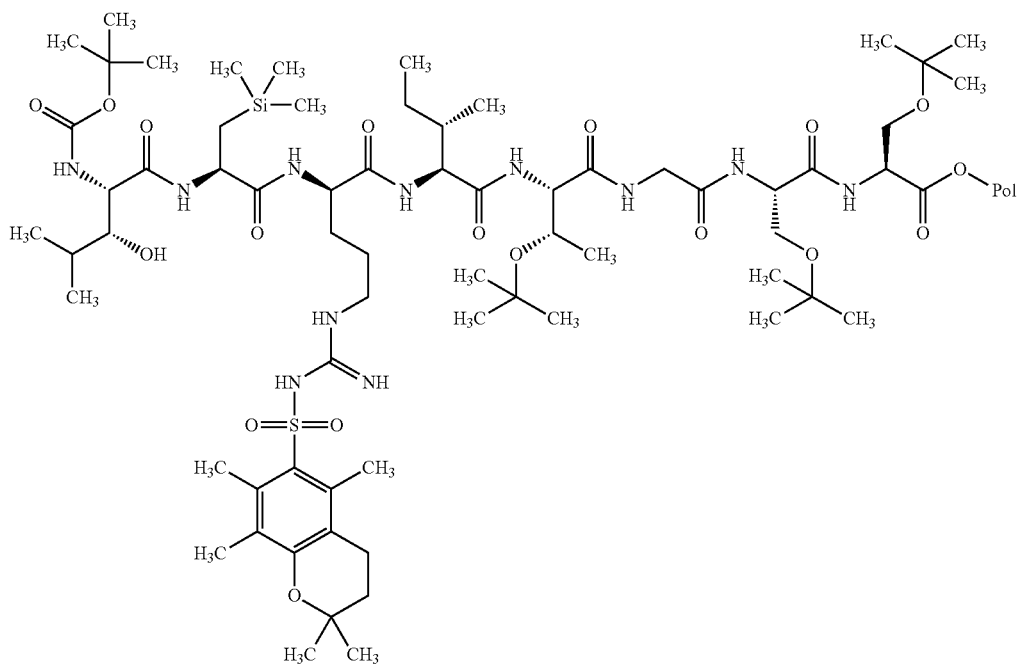

1 g of Wang resin (Rapp Polymer; loading: 1.28 mmol/g) is introduced into 10 ml of dimethylformamide. 982 mg (2.56 mmol) of O-tert.-butyl-N-[(9H-fluoren-9-ylmethoxy)carbonyl]-L-serine, 910 mg (2.56 mmol) of N-{[(6-chloro-1H-benzotriazol-1-yl)oxy](dimethylamino)methylene}-N-methylmethanaminium tetrafluoroborate (TCTU) and 496 mg (3.84 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

A further coupling with O-tert.-butyl-N-[(9H-fluoren-9-ylmethoxy)carbonyl]-L-serine is carried out using the same ratios of amounts and under the described conditions (see directly above).

The resin obtained in this way is provided in 10 ml of dimethylformamide, and 761 mg (2.56 mmol) of N-[(9H-fluoren-9-ylmethoxy)carbonyl]glycine, 910 mg (2.56 mmol) of N-{[(6-chloro-1H-benzotriazol-1-yl)oxy](dimethylamino)methylene}-N-methylmethanaminium tetrafluoroborate (TCTU) and 496 mg (3.84 mmol) of N-ethyl-N-isopropylpropan-2-amine (DIEA) are added. The mixture is shaken at RT for 5 hours. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 1.017 g (2.56 mmol) of O-tert-butyl-N-[(9H-fluoren-9-ylmethoxy)carbonyl]-D-allothreonine, 910 mg (2.56 mmol) of N-{[(6-chloro-1H-benzotriazol-1-yl)oxy](dimethylamino)methylene}-N-methylmethanaminium tetrafluoroborate (TCTU) and 496 mg (3.84 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 904 mg (2.56 mmol) of N-[(9H-fluoren-9-ylmethoxy)carbonyl]-L-isoleucine, 822 mg (2.56 mmol) of N-{[(1H-benzotriazol-1-yl)oxy](dimethylamino)methylene}-N-methylmethanaminium tetrafluoroborate (TBTU) and 496 mg (3.84 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 1.697 g (2.56 mmol) of $N^2$-[(9H-fluoren-9-ylmethoxy)carbonyl]-$N^5$-(imino{[(2,2,5,7,8-pentamethyl-3,4-dihydro-2H-chromen-6-yl)sulfonyl]amino}methyl)-D-ornithine, 822 mg (2.56 mmol) of N-[(1H-benzotriazol-1-yloxy)(dimethylamino)methylene]-N-methylmethanaminium tetrafluoroborate (TBTU) and 662 mg (5.12 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 982 mg (2.56 mmol) of N-[(9H-fluoren-9-ylmethoxy)carbonyl]-3-(trimethylsilyl)-L-alanine, 822 mg (2.56 mmol) of N-[(1H-benzotriazol-1-yloxy(dimethylamino)-methylene]-N-methylmethanaminium tetrafluoroborate (TBTU) and 662 mg (5.12 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration. The solid is subsequently treated twice in succession with piperidine as follows: the resin is mixed with 10 ml of a 20% piperidine solution in dimethylformamide, shaken for 30 min and collected by suction filtration.

The resin obtained in this way is provided in 10 ml of dimethylformamide, and 261 mg (0.705 mmol) of threo N-(tert-butoxycarbonyl)-(3R)-3-hydroxy-L-leucine, 339 mg (1.057 mmol) of N-[(1H-benzotriazol-1-yloxy)(dimethylamino)methylene]-N-methylmethanaminium tetrafluoroborate (TBTU) and 273 mg (2.114 mmol) of N-ethyl-N-isopropylpropan-2-amine (DIEA) are added. The mixture is shaken at RT overnight. The solid is collected by suction filtration, washed three times each with 10 ml of dimethylformamide, methanol and dichloromethane and collected by suction filtration.

Compounds 293A-458A depicted in the following tables were prepared according to the indicated procedures from the indicated starting materials.

| No. | Name | Structure | Synthesis Method |
|---|---|---|---|
| 293A | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-[O³-tertbutyl-L-seryl]-glycyl-[O³-tertbutyl-l-seryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 294A | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H- | | Prepared according to procedure 8 from 1.75 g of 2- |

-continued

| No. | Name | Structure | Synthesis Method |
|---|---|---|---|
| | chromen-6-yl)sulfonyl]amino}methyl)-D-ornithyl]-L-valyl-L-allothreonyl-glycyl-[O³-tertbutyl-L-seryl]-O³-tertbutyl-L-serine | | chlorotrityl chloride-resin loaded with 0.85 mmol of O³-tertbutyl-N-[(9H-fluoren-9-ylmethoxy)carbonyl]-L-serine per gram |
| 295A | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-leucyl-L-allothreonyl-glycyl-[O³-tertbutyl-L-seryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 296A | | | |

-continued

| No. | Name | Synthesis Method |
|---|---|---|
| | Polymer-bound [N-tertbutoxycarbonyl-(3R)-3-hydroxy-L-leucyl]-L-leucyl-[N$^5$-(imino{[(2,2,5,7,8-pentamethyl-3,4-dihydro-2H-chromen-6-yl)sulfonyl]amino}methyl)-D-ornithyl]-[3-trimethylsilyl]-L-alanyl-L-allothreonyl-glycyl-[O$^3$-tertbutyl-L-seryl]-O$^3$-tertbutyl-L-serine | Prepared according to procedure 8 from 1.75 g of 2-chlorotrityl chloride-resin loaded with 0.85 mmol of O$^3$-tertbutyl-N-[(9H-fluoren-9-ylmethoxy)carbonyl]-L-serine per gram |
| 297A | 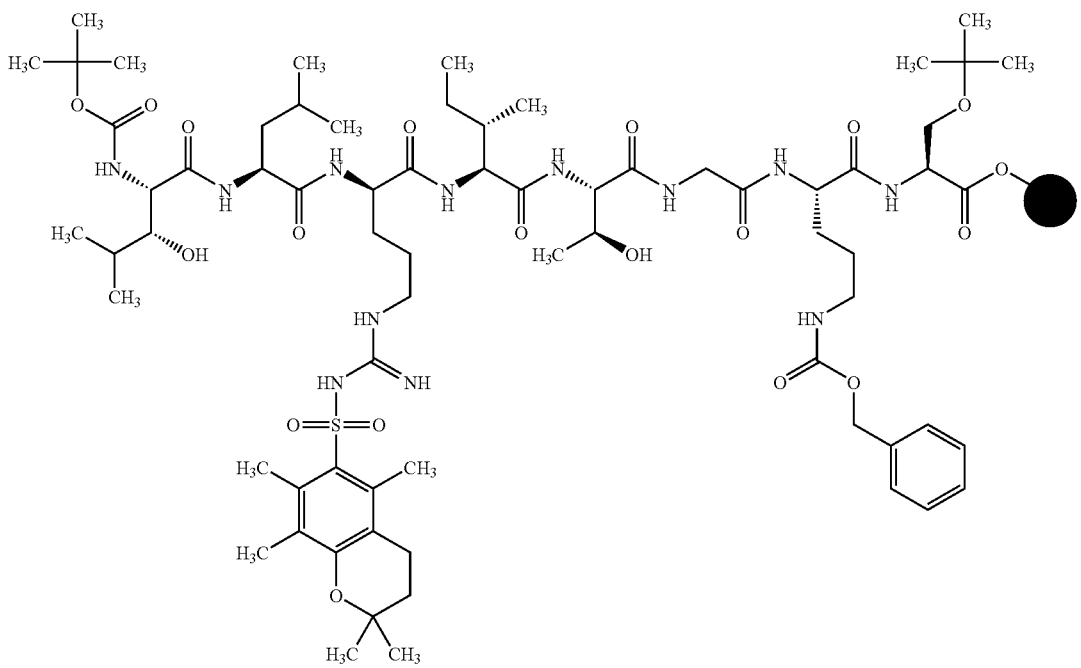 | |
| | Polymer-bound [N-tertbutoxycarbonyl-(3R)-3-hydroxy-L-leucyl]-L-leucyl-[N$^5$-(imino{[(2,2,5,7,8-pentamethyl-3,4-dihydro-2H-chromen-6-yl)sulfonyl]amino}methyl)-D-ornithyl]-L-phenylalanyl-L-allothreonyl-glycyl-[N$^5$-benzyloxycarbonyl-L-ornithyl]-O$^3$-tertbutyl-L-serine | Prepared according to procedure 8 from 1.75 g of 2-chlorotrityl chloride-resin loaded with 0.85 mmol of O$^3$-tertbutyl-N-[(9H-fluoren-9-ylmethoxy)carbonyl]-L-serine per gram |
| 298A | 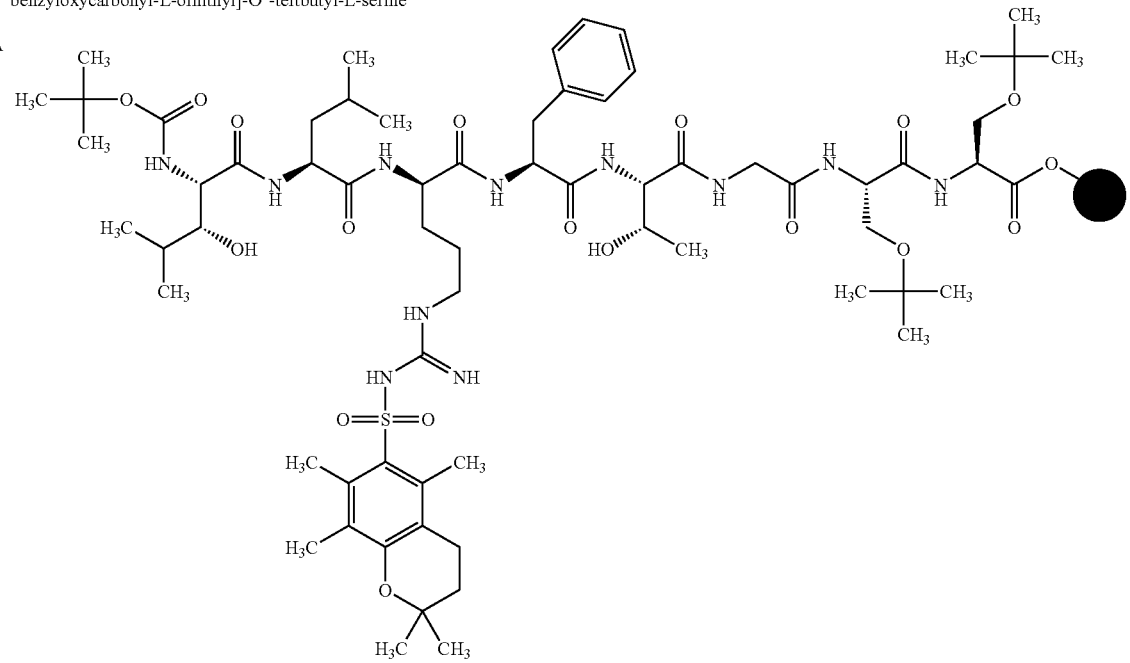 | |

| No. | Name | Structure | Synthesis Method |
|---|---|---|---|
| | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-phenylalanyl-L-allothreonyl-glycyl-[O³-tertbutyl-L-seryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 299A | | 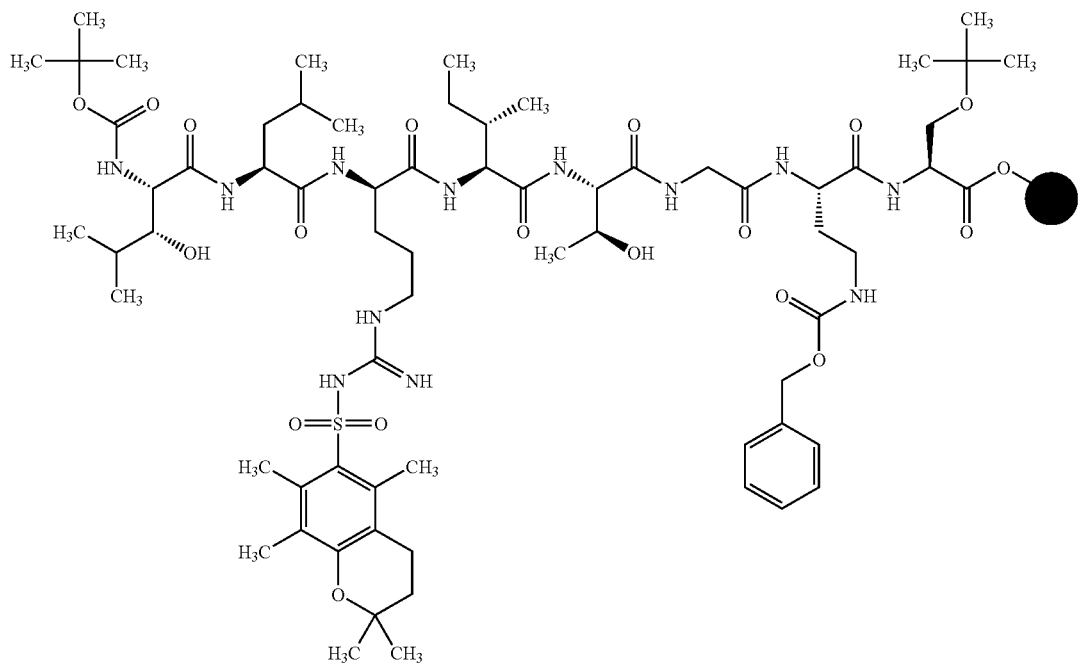 | |
| | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-[(2S)-2-amino-4-benzyloxycarbonylamino-butyryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |

-continued

| No. | Name | Structure Synthesis Method |
|---|---|---|

300A

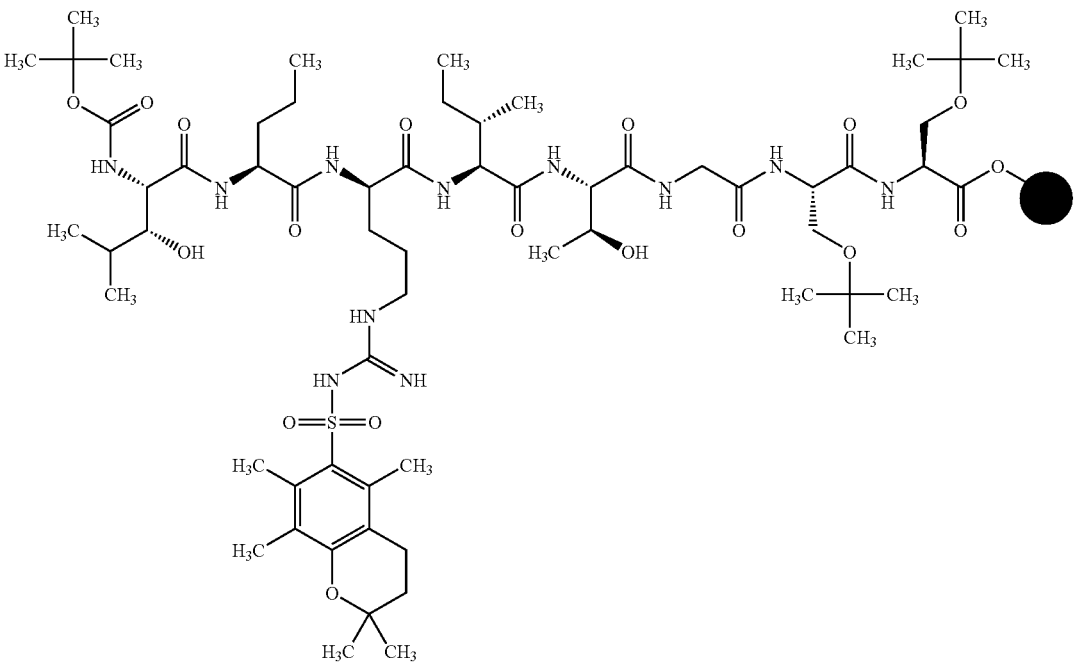

Polymer-bound [N-tertbutoxycarbonyl-(3R)-3-hydroxy-L-leucyl]-L-norvalyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-[O³-tertbutyl-L-seryl]-O³-tertbutyl-L-serine Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram

301A

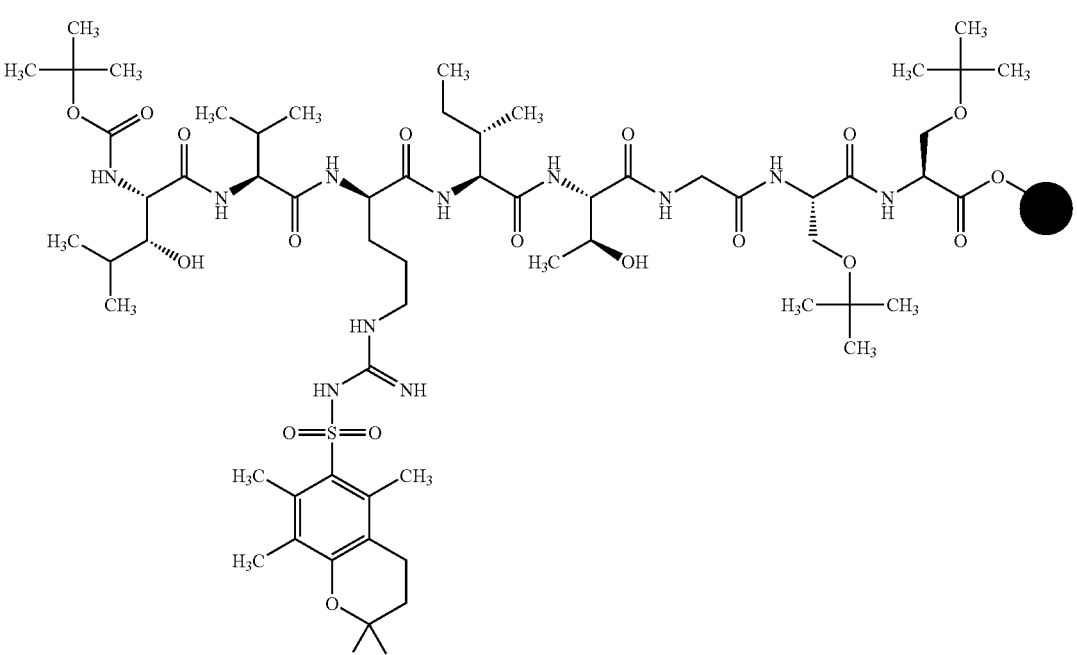

Polymer-bound [N-tertbutoxycarbonyl-(3R)-3-hydroxy-L-leucyl]-L-valyl-[N⁵-(imino{[(2,2,5,7,8-pentamethyl-3,4-dihydro- Prepared according to procedure 8 from 1.75 g of 2-chlorotrityl chloride-resin loaded with 0.85 mmol of O³-tertbutyl-N-

-continued

| No. | Name | Structure | Synthesis Method |
|---|---|---|---|
| 302A | 2H-chromen-6-yl)sulfonyl]amino}methyl)-D-ornithyl]-L-isoleucyl-L-allothreonyl-glycyl-[O³-tertbutyl-L-seryl]-O³-tertbutyl-L-serine | 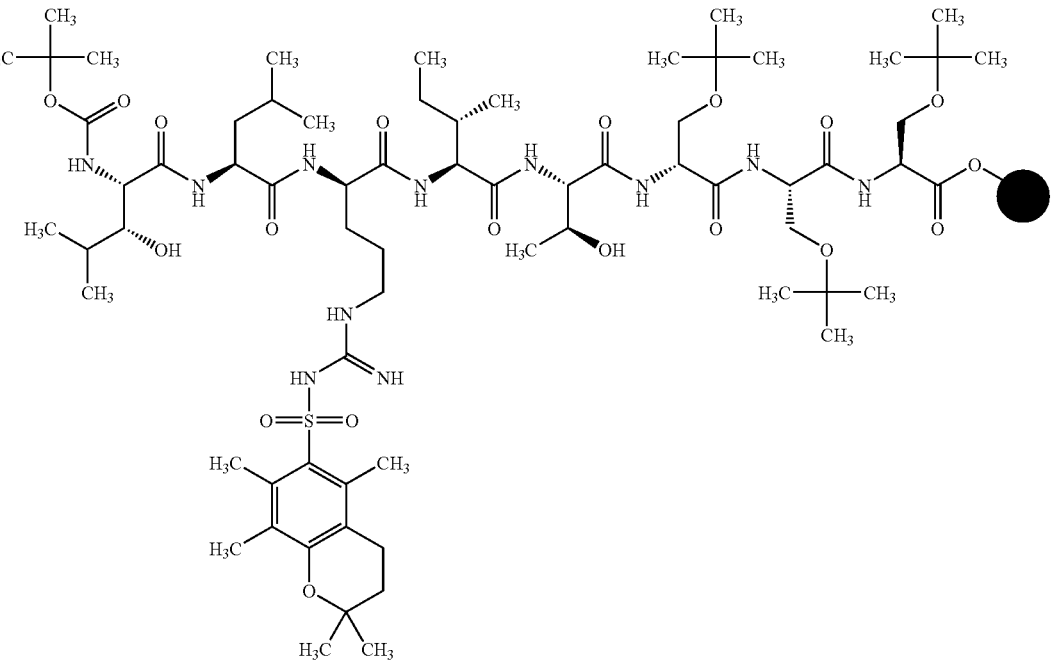 | [(9H-fluoren-9-ylmethoxy)carbonyl]-L-serine per gram |
| | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-[O³-tertbutyl-D-seryl]-[O³-tertbutyl-L-seryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 303A | | 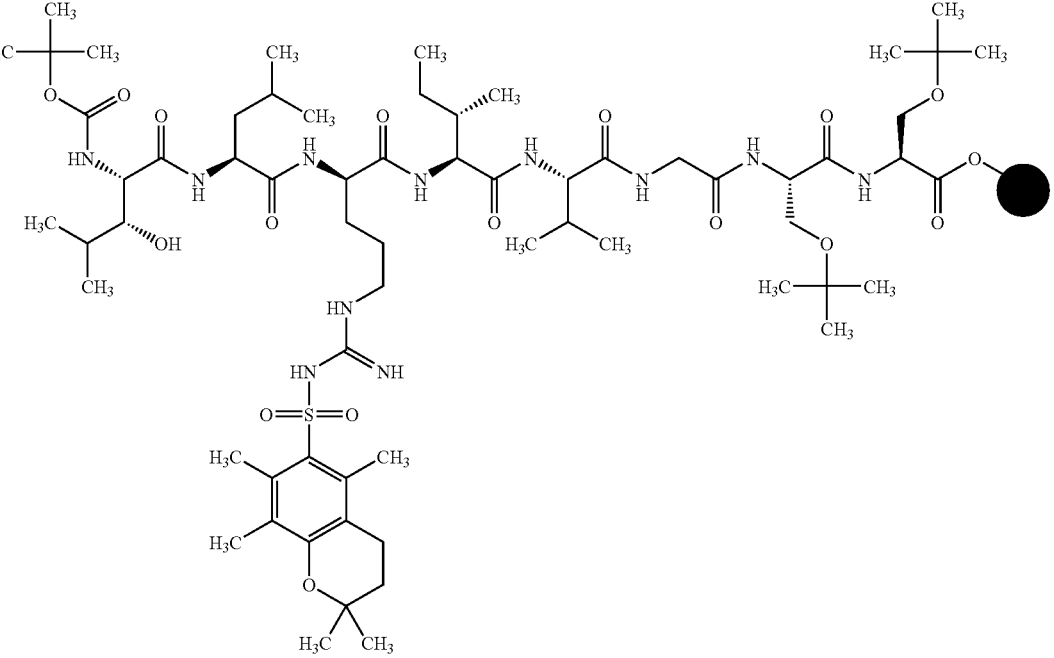 | |
| | Polymer-bound [N-tertbutoxycarbonyl-(3R)-3-hydroxy-L-leucyl]-L-leucyl-[N⁵-(imino{[(2,2,5,7,8-pentamethyl-3,4-dihydro- | | Prepared according to procedure 8 from 1.75 g of 2-chlorotrityl chloride-resin loaded with 0.85 mmol of O³-tertbutyl-N- |

| No. | Name | Synthesis Method |
|---|---|---|
| | 2H-chromen-6-yl)sulfonyl]amino}methyl)-D-ornithyl]-L-isoleucyl-L-valyl-glycyl-[O³-tertbutyl-L-seryl]-O³-tertbutyl-L-serine | [(9H-fluoren-9-ylmethoxy)carbonyl]-L-serine per gram |
| 304A | 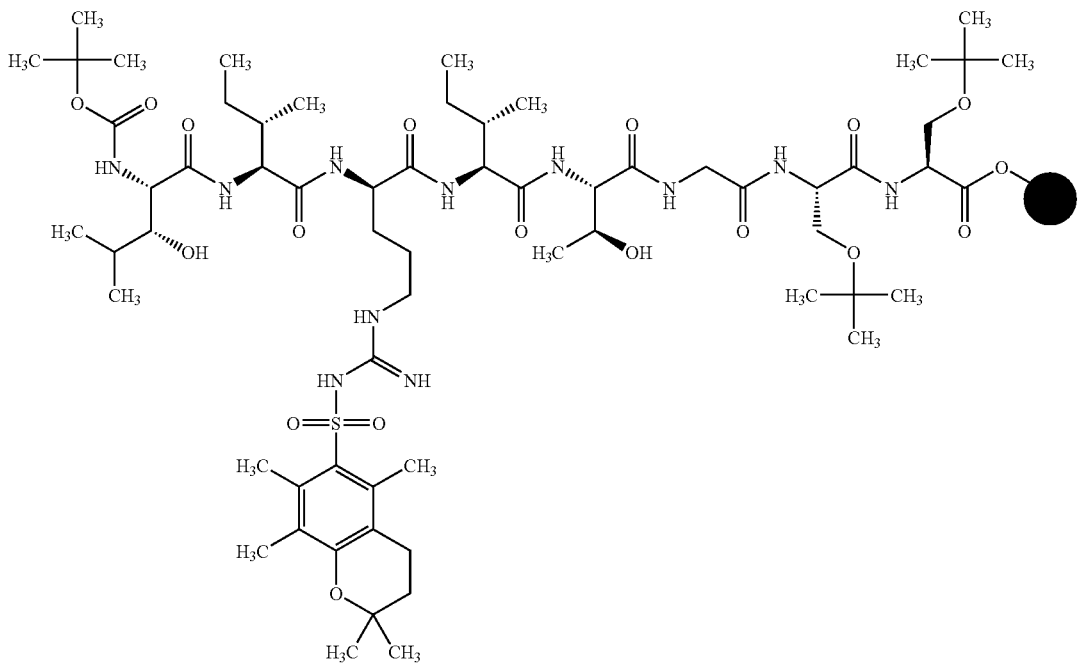 Polymer-bound [N-tertbutoxycarbonyl-(3R)-3-hydroxy-L-leucyl]-L-isoleucyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-[O³-tertbutyl-L-seryl]-O³-tertbutyl-L-serine | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 305A | 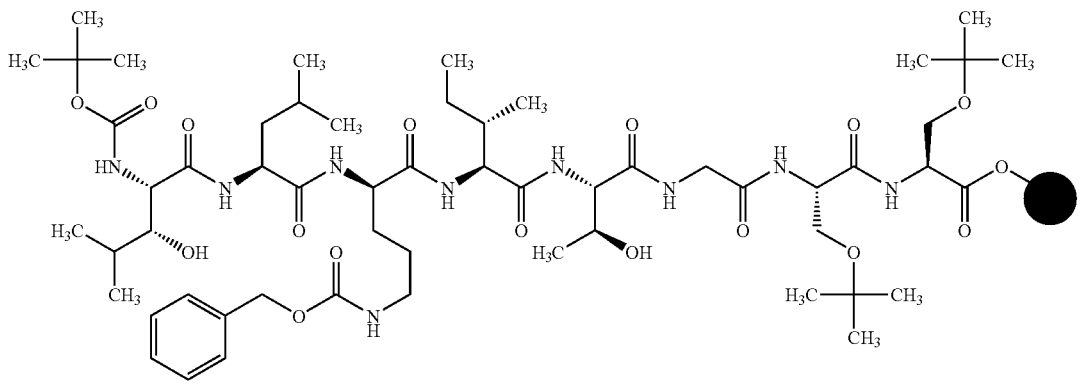 Polymer-bound [N-tertbutoxycarbonyl-(3R)-3-hydroxy-L-leucyl]-L-leucyl-[N⁵-benzyloxycarbonyl-D-ornithyl]-L-isoleucyl-L-allothreonyl-glycyl-[O³-tertbutyl-L-seryl]-O³-tertbutyl-L-serine | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |

| No. | Name | Structure | Synthesis Method |
|---|---|---|---|
| 306A | Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-L-leucyl-glycyl-[O³-tertbutyl-L-seryl]-O³-tertbutyl-L-serine | 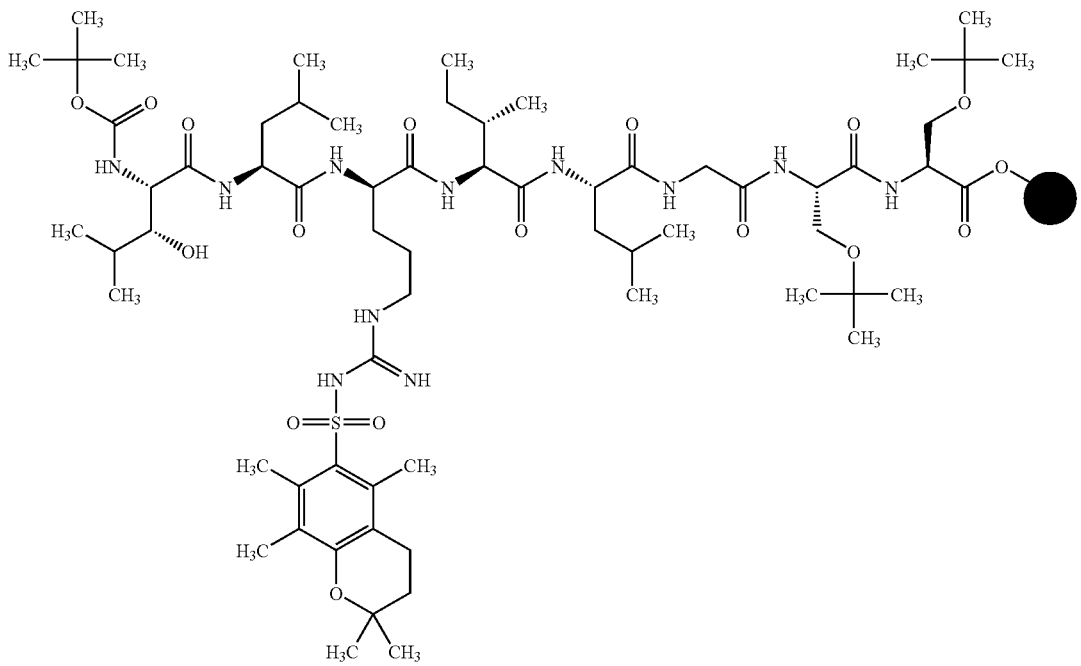 | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 307A | Polymer-bound [N-tertbutoxycarbonyl-(3R)-3-hydroxy-L-leucyl]-L-leucyl-[(2R)-2-amino-4-benzyloxycarbonylaminobutyryl]-L-isoleucyl-L-allothreonyl-glycyl-[O³-tertbutyl-L-seryl]-tertbutyl-L-serine | 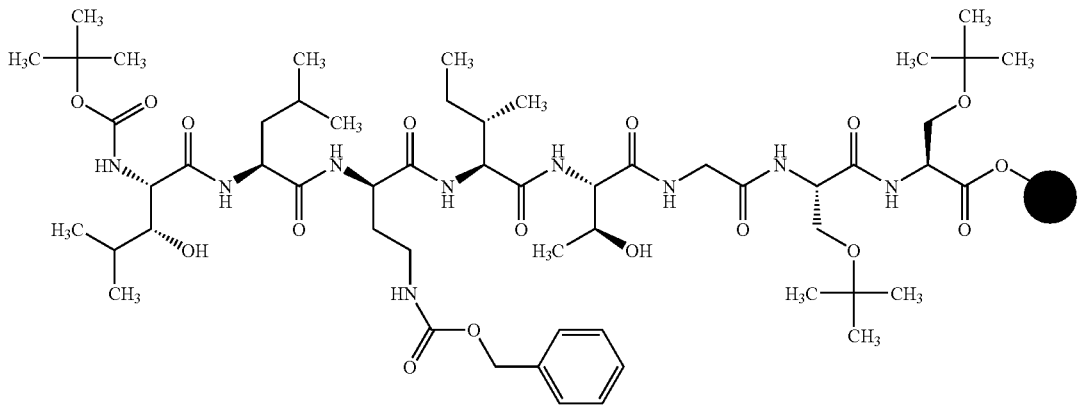 | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |

| No. | Name | Structure | Synthesis Method |
|---|---|---|---|
| 308A | 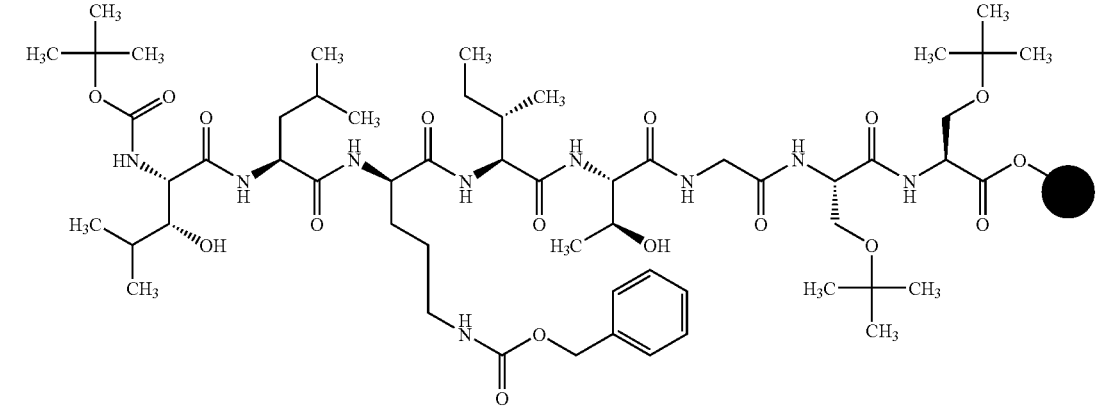 Polymer-bound [N-tertbutoxycarbonyl-(3R)-3-hydroxy-L-leucyl]-L-leucyl-[N6-benyloxycarbonyl-L-lysyl]-L-isoleucyl-L-allothreonyl-glycyl-[O³-tertbutyl-L-seryl]-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 309A | 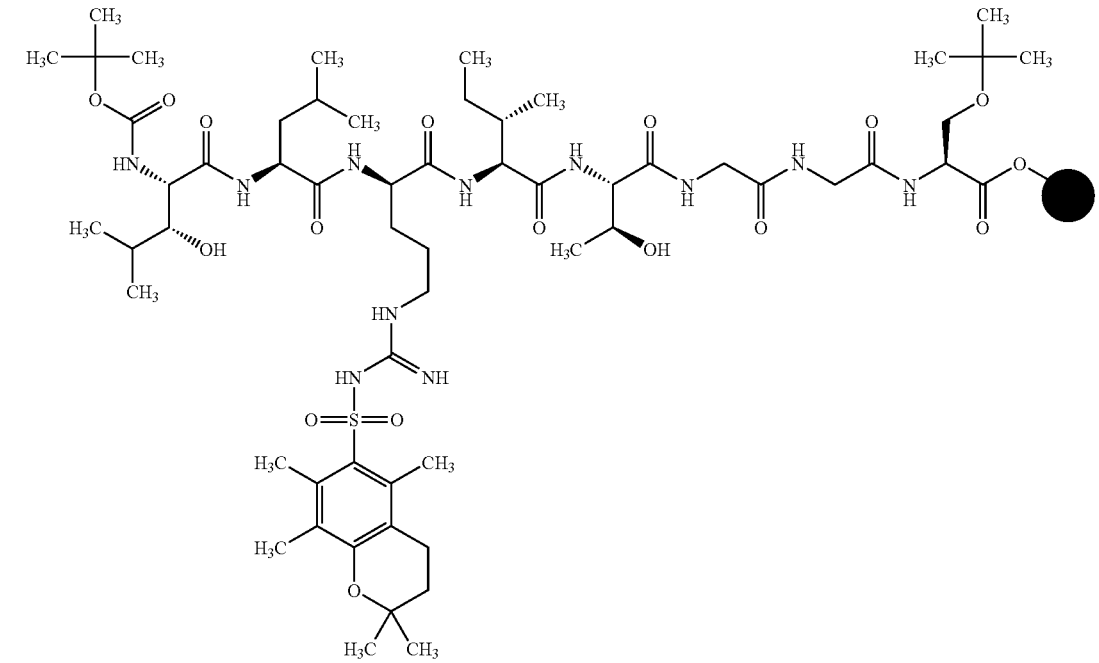 Polymer-bound [N-tertbutoxycarbonyl-(3R)-3-hydroxy-L-leucyl]-L-leucyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-glycyl-O³-tertbutyl-L-serine | | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |

| No. | Name | Structure / Synthesis Method |
|---|---|---|
| 310A | 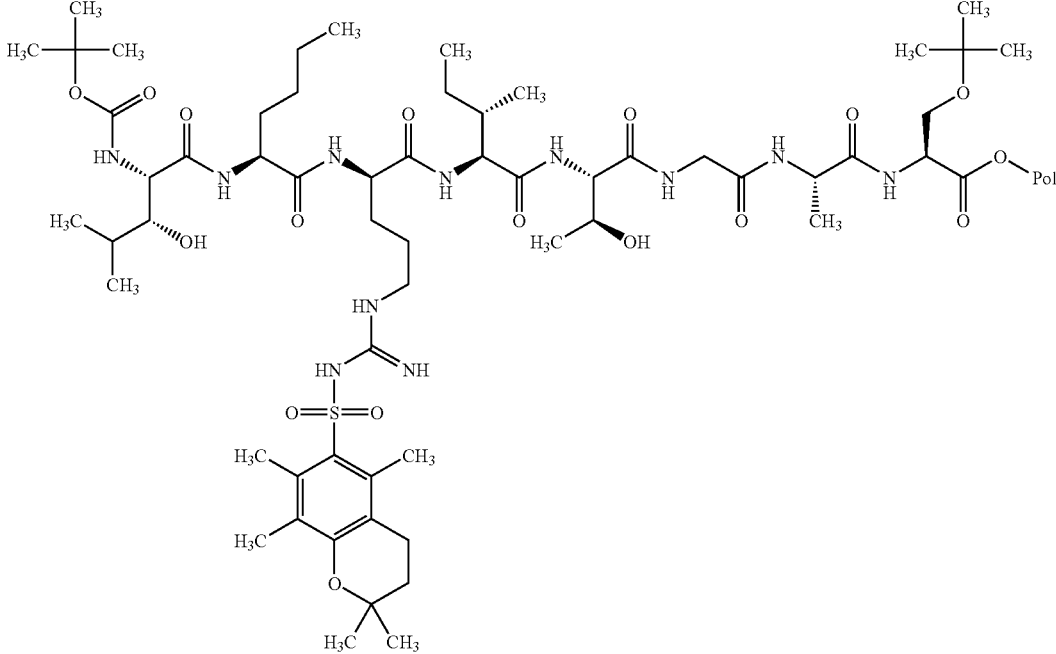 Polymer-bound [N-tertbutoxycarbonyl-(3R)-3-hydroxy-L-leucyl]-L-norleucyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-L-alanyl-O³-tertbutyl-L-serine | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |
| 311A | 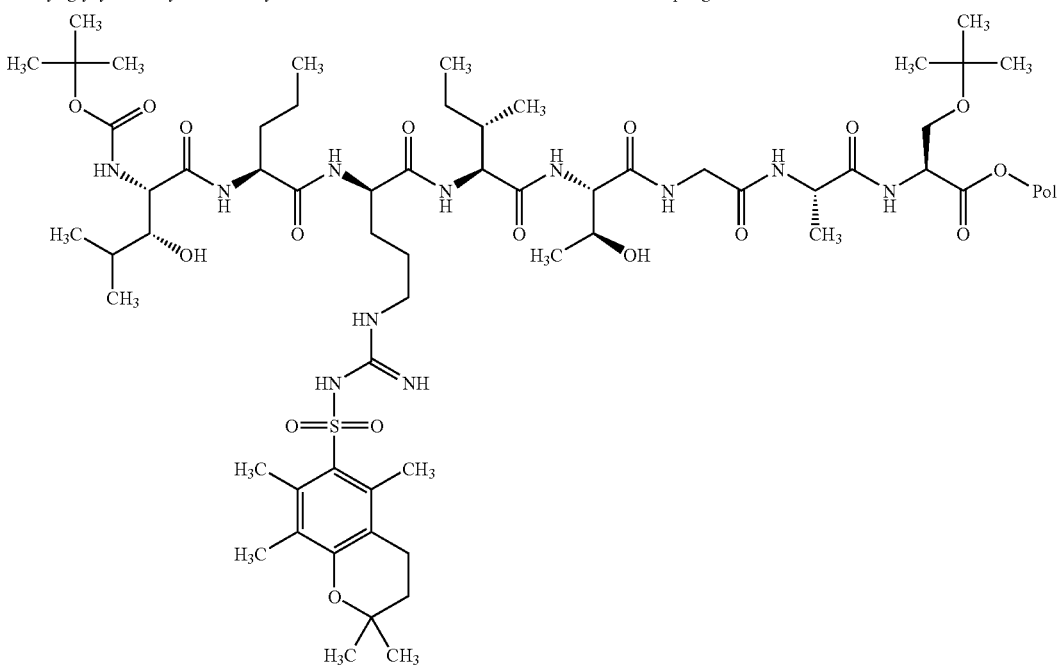 Polymer-bound [N-tertbutoxycarbonyl-(3R)-3-hydroxy-L-leucyl]-L-norvalyl-[N⁵-(imino{[(2,2,5,7,8-pentamethyl-3,4-dihydro-2H-chromen-6-yl)sulfonyl]amino}methyl)-D-ornithyl]-L-isoleucyl-L-allothreonyl-glycyl-L-alanyl-O³-tertbutyl-L-serine | Prepared according to procedure 8 from 1.75 g of 2-chlorotrityl chloride-resin loaded with 0.85 mmol of O³-tertbutyl-N-[(9H-fluoren-9-ylmethoxy)carbonyl]-L-serine per gram |

| Deprotected octapeptides |
|---|
| Structure |

| No. | Name Yield, Synthesis Method | Analysis |
|---|---|---|

312A

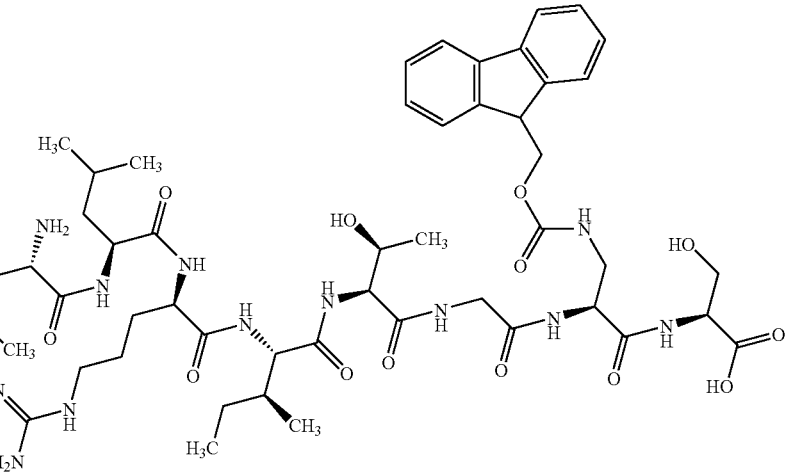

[(3R)-3-Hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine bistrifluoroacetate
647 mg (98% of theory) from 701 mg (0.50 mmol) of compound 288A according to procedure 5

HPLC (Method 6): $R_t$ = 3.35 min; LC-MS (Method 19): $R_t$ = 1.50 min, MS (ESIpos): m/z (%) = 543 (100) [M + 2 H]$^{2+}$, 1083 (20) [M + H]$^+$, MS (ESIneg): m/z (%) = 1081 (100) [M − H]−;
R-TOF-MS: $C_{51}H_{79}N_{12}O_{14}$ calc. 1083.5834, found 1083.5815 [M + H]$^+$.

313A

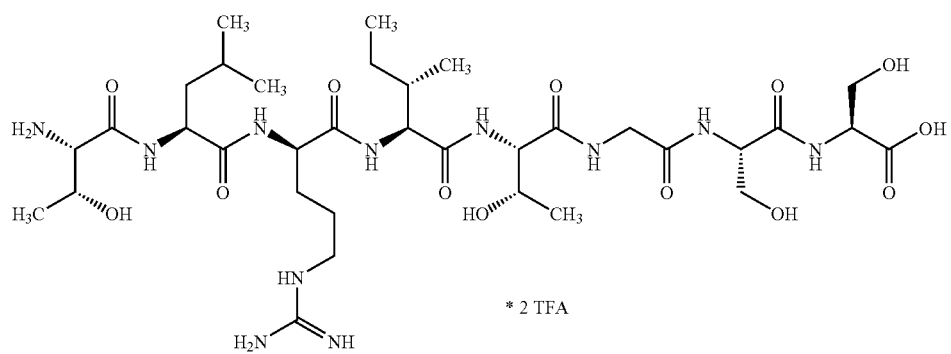

* 2 TFA

L-Threonyl-L-leucyl-D-arginyl-L-isoleucyl-L-allothreonyl-glycyl-L-seryl-L-serine bistrifluoroacetate
31 mg from 40 mg of 289A according to procedure 9

(LC-MS (Method 22): $R_t$ = 2.08 min, MS (ESIpos): m/z (%) = 418 (100) [M + 2 H]$^{2+}$.
HR-TOF-MS: $C_{34}H_{64}N_{11}O_{13}$ calc. 834.4680, found 834.4653 [M + H]$^+$.

314A

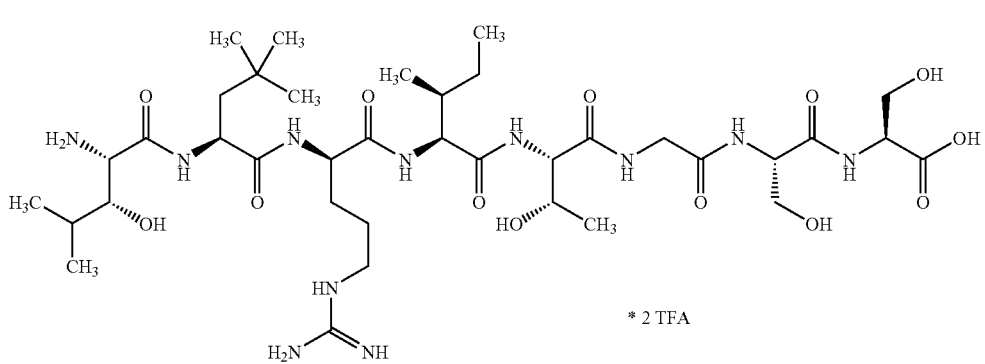

* 2 TFA

[(3R)-3-Hydroxy-L-leucyl]-[3-tertbutyl-L-alanyl]-D-arginyl-L-isoleucyl-L-allothreonyl-glycyl-L-seryl-L-

| | Deprotected octapeptides | |
|---|---|---|
| | Structure | |
| No. | Name<br>Yield, Synthesis Method | Analysis |
| | serine bistrifluoroacetate<br>250 mg crude yield from the mixture described in<br>example 291A according to general procedure 9 | |
| 315A | [(3R)-3-Hydroxy-L-leucyl]-[3-trimethylsilyl-L-alanyl]-<br>D-arginyl-L-isoleucyl-L-allothreonyl-glycyl-L-seryl-L-<br>serine bistrifluoroacetate<br>53 mg crude yield from the mixture described in<br>example 292A according to general procedure 9 | LC-MS (Method 22): $R_t$ = 2.29 min, MS<br>(ESIpos): m/z = 892.0 [M + H]$^+$. |
| 316A | [(3R)-3-Hydroxy-L-leucyl]-L-leucyl-D-arginyl-L-<br>isoleucyl-L-seryl-glycyl-L-seryl-L-serine<br>bistrifluoroacetate<br>900 mg from exemplary compound 293A according to<br>procedure 9 | HPLC (Method 6): $R_t$ = 2.79 min; LC-MS<br>(Method 22): $R_t$ = 2.10 min, MS (ESIpos):<br>m/z (%) = 425 (100) [M + 2 H]$^{2+}$; MS<br>(ESIneg): m/z (%) = 846 (100) [M − H]$^-$;<br>HR-TOF-MS: $C_{35}H_{66}N_{11}O_{13}$ calc. 848.4837,<br>found 848.4806 [M + H]$^+$. |
| 317A | [(3R)-3-Hydroxy-L-leucyl]-L-leucyl-D-arginyl-L-valyl-<br>L-allothreonyl-glycyl-L-seryl-L-serine | HPLC (Method 6): $R_t$ = 2.70 min; LC-MS<br>(Method 22): $R_t$ = 2.05 min, MS (ESIpos): |

-continued

Deprotected octapeptides

Structure

| No. | Name Yield, Synthesis Method | Analysis |
|---|---|---|
| | bistrifluoroacetate 1.01 g from exemplary compound 294A according to procedure 9 | m/z (%) = 425 (100) [M + 2 H]$^{2+}$, MS (ESIneg): m/z (%) = 846 (100) [M − H]$^-$; HR-TOF-MS: $C_{35}H_{66}N_{11}O_{13}$ calc. 848.4837, found 848.4810 [M + H]$^+$. |

318A

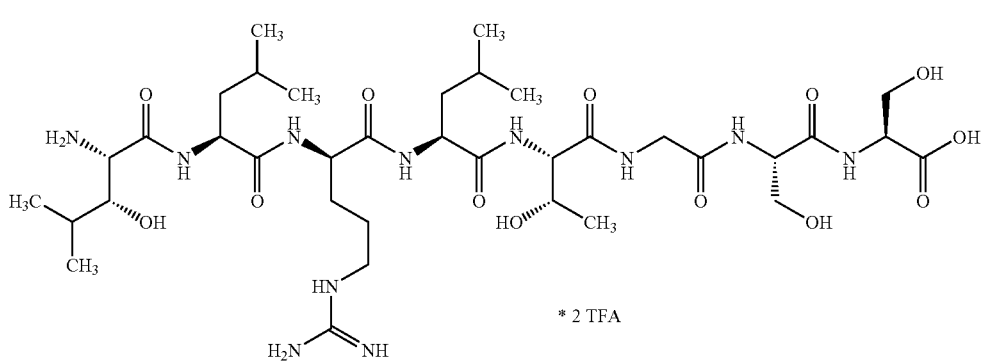

\* 2 TFA

[(3R)-3-Hydroxy-L-leucyl]-L-leucyl-D-arginyl-L-leucyl-L-allothreonyl-glycyl-L-seryl-L-serine bistrifluoroacetate
1.11 g (40% pure) from exemplary compound 295A according to procedure 9

HPLC (Method 6): $R_t$ = 2.84 min; LC-MS (Method 22): $R_t$ = 2.20 min, MS (ESIpos): m/z (%) = 432 (100) [M + 2 H]$^{2+}$, MS (ESIneg): m/z (%) = 861 (5) [M − H]$^-$; HR-TOF-MS: $C_{36}H_{68}N_{11}O_{13}$ calc. 862.4993, found 862.4977 [M + H]$^+$.

319A

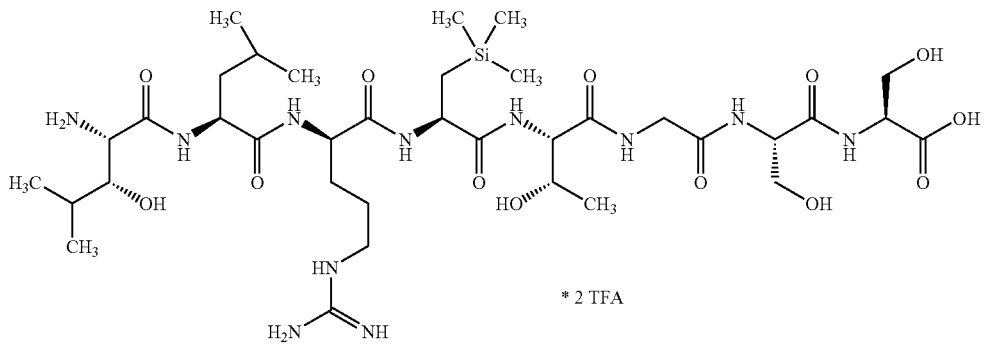

\* 2 TFA

[(3R)-3-Hydroxy-L-leucyl]-L-leucyl-D-arginyl-[3-trimethylsilyl-L-alanlyl]-L-allothreonyl-glycyl-L-seryl-L-serine bistrifluoroacetate
1.50 g (64% pure) from exemplary compound 296A according to procedure 9, purification according to method 45.

HPLC (Method 6): $R_t$ = 2.96 min; LC-MS (Method 22): $R_t$ = 2.31 min, MS (ESIpos): m/z (%) = 447 (100) [M + 2 H]$^{2+}$, MS (ESIneg): m/z (%) = 890 (100) [M − H]$^-$; HR-TOF-MS: $C_{36}H_{70}N_{11}O_{13}$Si calc. 892.4919, found 892.4955 [M + H]$^+$.

320A

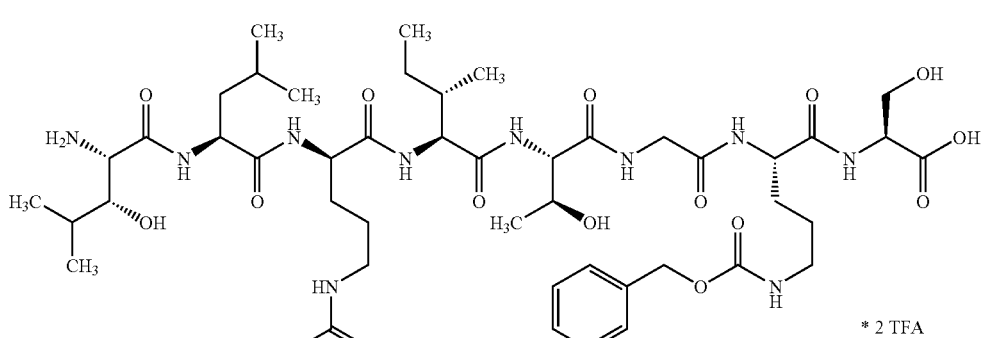

\* 2 TFA

[(3R)-3-Hydroxy-L-leucyl]-L-leucyl-D-arginyl-L-isoleucyl-L-allothreonyl-glycyl-(N$^5$-

HPLC (Method 6): $R_t$ = 3.17 min; LC-MS (Method 19): $R_t$ = 1.30 min, MS (ESIpos):

-continued

Deprotected octapeptides

Structure

| No. | Name<br>Yield, Synthesis Method | Analysis |
|---|---|---| benzyloxycarbonyl-L-ornithyl-L-serine bistrifluoroacetate
1.27 g (45% pure) from exemplary compound 297A according to procedure 9, purification according to method 45.

m/z (%) = 512.4 (100) [M + 2 H]$^{2+}$, MS (ESIneg): m/z (%) = 1021.7 (100) [M − H]$^-$; HR-TOF-MS: C$_{46}$H$_{79}$N$_{12}$O$_{14}$ calc. 1023.5834, found 1023.5842 [M + H]$^+$.

321A

[(3R)-3-Hydroxy-L-leucyl]-L-leucyl-D-arginyl-L-phenylalanlyl-L-allothreonyl-glycyl-L-seryl-L-serine bistrifluoroacetate
943 mg (66% pure) from exemplary compound 298A according to procedure 9, purification according to method 45

HPLC (Method 6): R$_t$ = 2.86 min; LC-MS (Method 22): R$_t$ = 2.19 min, MS (ESIpos): m/z (%) = 449 (100) [M + 2 H]$^{2+}$, MS (ESIneg): m/z (%) = 894 (100) [M − H]$^-$; HR-TOF-MS: C$_{39}$H$_{66}$N$_{11}$O$_{13}$ calc. 896.4837, found 896.4849 [M + H]$^+$.

322A

[(3R)-3-Hydroxy-L-leucyl]-L-leucyl-D-arginyl-L-isoleucyl-L-allothreonyl-glycyl-[(2S)-2-amino-4-benzyloxycarbonylaminobutyryl]-L-serine bistrifluoroacetate
980 mg (67% pure) from exemplary compound 299A according to procedure 9, purification according to method 45

HPLC (Method 6): R$_t$ = 3.13 min; LC-MS (Method 19): R$_t$ = 1.26 min, MS (ESIpos): m/z (%) = 505 (100) [M + 2 H]$^{2+}$, MS (ESIneg): m/z (%) = 1007.8 (100) [M − H]$^-$; HR-TOF-MS: C$_{45}$H$_{77}$N$_{12}$O$_{14}$ calc. 1009.5677, found 1009.5704 [M + H]$^+$.

-continued

Deprotected octapeptides

| No. | Name<br>Yield, Synthesis Method | Structure | Analysis |
|---|---|---|---|
| 323A | 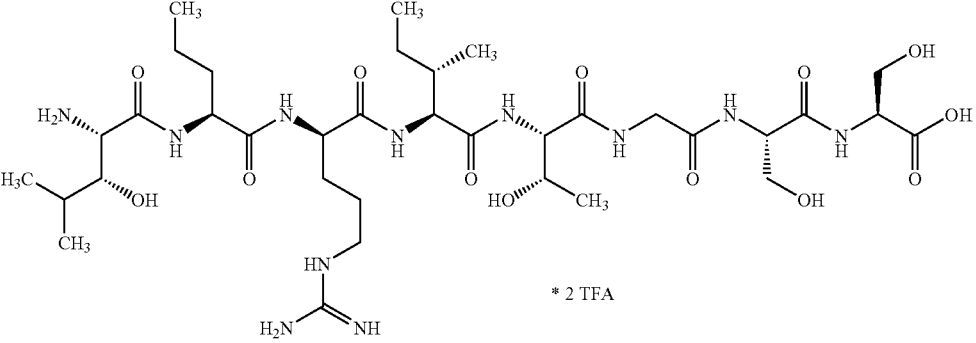<br>[(3R)-3-Hydroxy-L-leucyl]-L-norvalyl-D-arginyl-L-isoleucyl-L-allothreonyl-glycyl-L-seryl-L-serine bistrifluoroacetate<br>1320 mg (35% pure) from exemplary compound 300A according to procedure 9, purification according to method 45 | * 2 TFA | HPLC (Method 6): $R_t$ = 2.69 min; LC-MS (Method 22): $R_t$ = 2.03 min, MS (ESIpos): m/z (%) = 848.5 (60) $[M + H]^+$, MS (ESIneg): m/z (%) = 846.5 (100) $[M - H]^-$. |
| 324A | 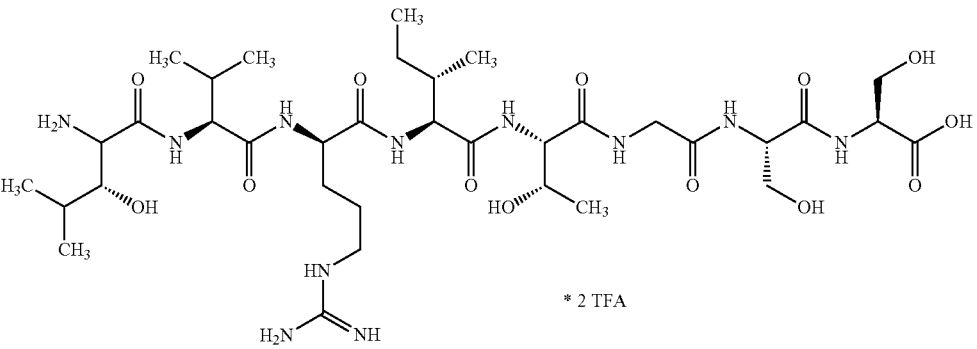<br>[(3R)-3-Hydroxy-L-leucyl]-L-valyl-D-arginyl-L-isoleucyl-L-allothreonyl-glycyl-L-seryl-L-serine bistrifluoroacetate<br>843 mg (50% pure) from exemplary compound 301A according to procedure 9, purification according to method 45 | * 2 TFA | HPLC (Method 6): $R_t$ = 2.74 min; LC-MS (Method 22): $R_t$ = 2.01 min, MS (ESIpos): m/z (%) = 424.8 (100) $[M + 2H]^{2+}$, MS (ESIneg): m/z (%) = 846.4 (100) $[M - H]^-$. |
| 325A | 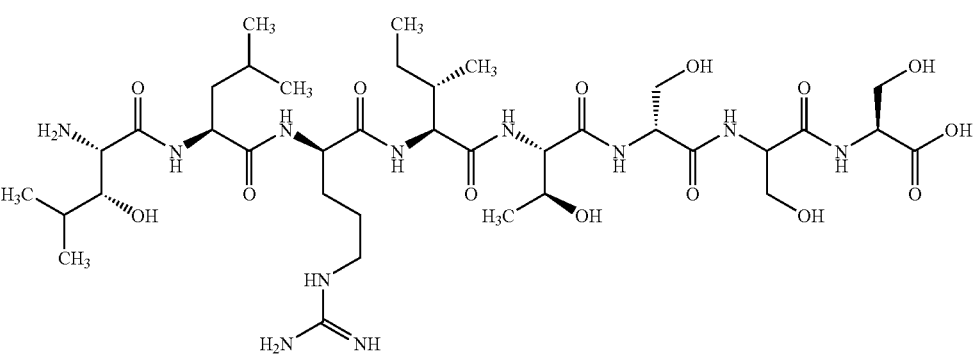<br>[(3R)-3-Hydroxy-L-leucyl]-L-leucyl-D-arginyl-L-isoleucyl-L-allothreonyl-D-seryl-L-seryl-L-serine bistrifluoroacetate<br>900 mg (33% pure) from exemplary compound 302A according to procedure 9, purification according to method 45 | | HPLC (Method 6): $R_t$ = 2.81 min; LC-MS (Method 22): $R_t$ = 2.19 min, MS (ESIpos): m/z (%) = 447 (100) $[M + 2H]^{2+}$, 892 (50) $[M + H]^+$, MS (ESIneg): m/z (%) = 890 (100) $[M - H]^-$; HR-TOF-MS: $C_{37}H_{70}N_{11}O_{14}$ calc. 892.5099, found 892.5120 $[M + H]^+$. |

-continued

Deprotected octapeptides

Structure

No. | Name Yield, Synthesis Method | Analysis

326A

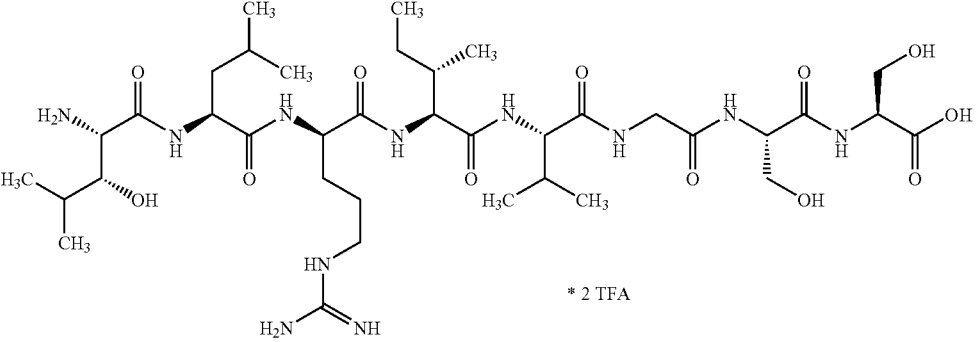

* 2 TFA

[(3R)-3-Hydroxy-L-leucyl]-L-leucyl-D-arginyl-L-isoleucyl-L-valyl-glycyl-L-seryl-L-serine bistrifluoroacetate
720 mg (72% pure) from exemplary compound 303A according to procedure 9, purification according to method 45

HPLC (Method 6): $R_t$ = 2.92 min; LC-MS (Method 22): $R_t$ = 2.26 min, MS (ESIpos): m/z (%) = 430.9 (100) $[M + 2 H]^{2+}$, MS (ESIneg): m/z (%) = 858.4 (100) $[M - H]^-$; HR-TOF-MS: $C_{37}H_{70}N_{11}O_{12}$ calc. 860.5200, found 860.5173 $[M + H]^+$.

327A

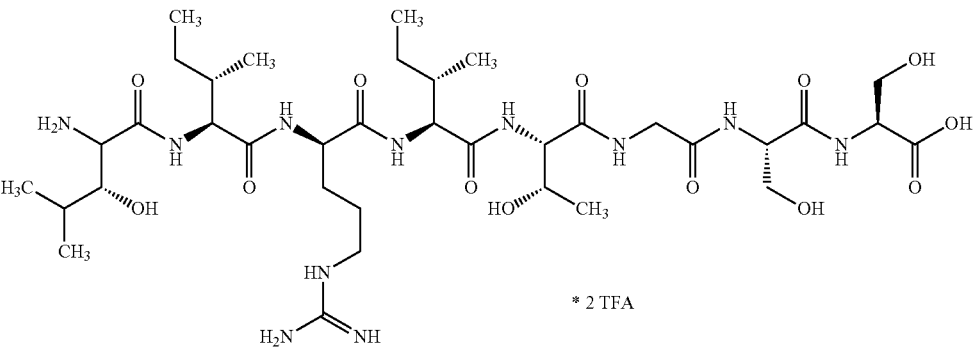

* 2 TFA

[(3R)-3-Hydroxy-L-leucyl]-L-isoleucyl-D-arginyl-L-isoleucyl-L-allothreonyl-glycyl-L-seryl-L-serine bistrifluoroacetate
1030 mg (45% pure) from exemplary compound 304A according to procedure 9, purification according to method 45

HPLC (Method 6): $R_t$ = 2.73 min; LC-MS (Method 22): $R_t$ = 2.08 min, MS (ESIpos): m/z (%) = 862.2 (100) $[M + H]^+$, MS (ESIneg): m/z (%) = 860.2 (100) $[M - H]^-$; HR-TOF-MS: $C_{36}H_{68}N_{11}O_{13}$ calc. 862.4993, found 862.5002 $[M + H]^+$.

328A

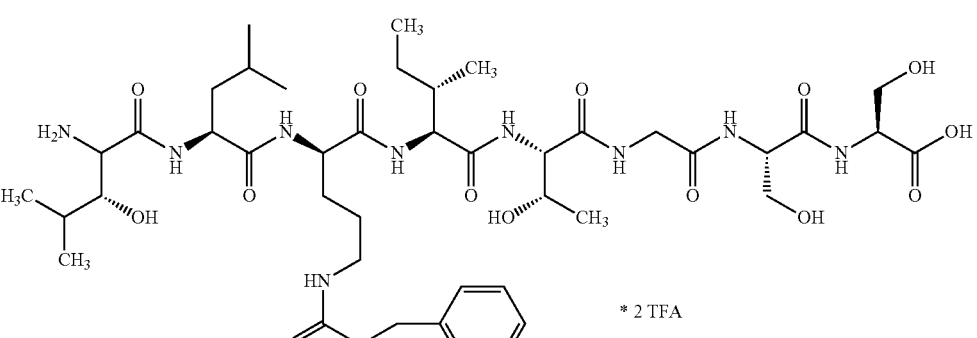

* 2 TFA

[(3R)-3-Hydroxy-L-leucyl]-L-leucyl-($N^5$-benzyloxycarbonyl-D-ornithyl)-L-isoleucyl-L-allothreonyl-glycyl-L-seryl-L-serine bistrifluoroacetate
1090 mg (28% pure) from exemplary compound 305A according to procedure 9, purification according to method 45

HPLC (Method 6): $R_t$ = 3.45 min; LC-MS (Method 19): $R_t$ = 1.66 min, MS (ESIpos): m/z (%) = 954.6 (100) $[M + H]^+$, MS (ESIneg): m/z (%) = 952.5 (100) $[M - H]^-$; HR-TOF-MS: $C_{43}H_{72}N_9O_{15}$ calc. 954.5143, found 954.5155 $[M + H]^+$.

Deprotected octapeptides

| No. | Name, Yield, Synthesis Method | Analysis |
|---|---|---|
| 329A | [(3R)-3-Hydroxy-L-leucyl]-L-leucyl-D-arginyl-L-isoleucyl-L-leucyl-glycyl-L-seryl-L-serine bistrifluoroacetate<br>680 mg (36% pure) from exemplary compound 306A according to procedure 9, purification according to method 45 | HPLC (Method 6): $R_t$ = 3.03 min; LC-MS (Method 19): $R_t$ = 1.17 min, MS (ESIpos): m/z (%) = 438.0 (100) $[M + 2 H]^{2+}$, MS (ESIneg): m/z (%) = 954.5 (100) $[M - H]^-$; HR-TOF-MS: $C_{38}H_{72}N_{11}O_{12}$ calc. 874.5357, found 874.5373 $[M + H]^+$. |
| 330A | [(3R)-3-Hydroxy-L-leucyl]-L-leucyl-[(2R)-2-amino-4-benzyloxycarbonylaminobutyryl]-L-isoleucyl-L-allothreonyl-glycyl-L-seryl-L-serine bistrifluoroacetate<br>1120 mg (64% pure) from exemplary compound 307A according to procedure 9, purification according to method 45 | HPLC (Method 6): $R_t$ = 3.43 min; LC-MS (Method 19): $R_t$ = 1.64 min, MS (ESIpos): m/z (%) = 940.5 (100) $[M + H]^+$, MS (ESIneg): m/z (%) = 938.6 (100) $[M - H]^-$; HR-TOF-MS: $C_{42}H_{70}N_9O_{15}$ calc. 940.4986, found 940.4999 $[M + H]^+$. |
| 331A | [(3R)-3-Hydroxy-L-leucyl]-L-leucyl-($N^6$-benzyloxycarbonyl-D-lysyl)-L-isoleucyl-L-allothreonyl-glycyl-L-seryl-L-serine bistrifluoroacetate<br>930 mg (58% pure) from exemplary compound 308A according to procedure 9 | HPLC (Method 6): $R_t$ = 3.46 min; LC-MS (Method 19): $R_t$ = 1.70 min, MS (ESIpos): m/z (%) = 968.6 (100) $[M + H]^+$, MS (ESIneg): m/z (%) = 966.6 (100) $[M - H]^-$; HR-TOF-MS: $C_{44}H_{74}N_9O_{15}$ calc. 968.5255, found 968.5272 $[M + H]^+$. |

-continued

Deprotected octapeptides

Structure

No. | Name Yield, Synthesis Method | Analysis

332A

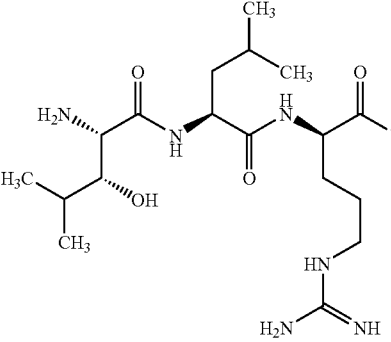

[(3R)-3-Hydroxy-L-leucyl]-L-leucyl-D-arginyl-L-isoleucyl-L-allothreonyl-glycyl-glycyl-L-serine bistrifluoroacetate
1.37 g (60% pure) from exemplary compound 310A according to procedure 9, purification according to method 45

HPLC (Method 6): $R_t$ = 2.82 min; LC-MS (Method 22): $R_t$ = 2.12 min, MS (ESIpos): m/z (%) = 417 (100) [M + 2 H]$^{2+}$, MS (ESIneg): m/z (%) = 830 (100) [M − H]$^-$; HR-TOF-MS: $C_{35}H_{66}N_{11}O_{12}$ calc. 832.4887, found 832.4868 [M + H]$^+$.

333A

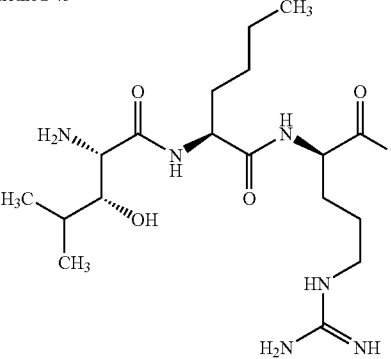

[(3R)-3-Hydroxy-L-leucyl]-L-norleucyl-D-arginyl-L-isoleucyl-L-allothreonyl-glycyl-L-alanyl-L-serine bistrifluoroacetate
984 mg (60% pure) from exemplary compound 309A according to procedure 9, purification according to method 45.

HPLC (Method 6): $R_t$ = 2.84 min; LC-MS (Method 22): $R_t$ = 2.16 min, MS (ESIpos): m/z (%) = 423.9 (100) [M + 2 H]$^{2+}$, MS (ESIneg): m/z (%) = 844.3 (100) [M − H]$^-$; HR-TOF-MS: $C_{36}H_{68}N_{11}O_{12}$ calc. 846.5044, found 846.5025 [M + H]$^+$.

334A

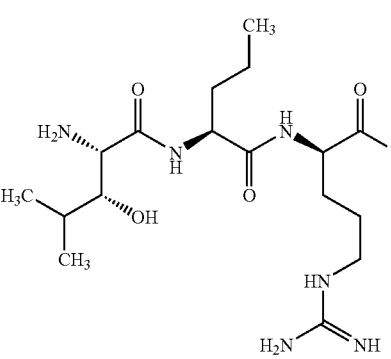

[(3R)-3-Hydroxy-L-leucyl]-L-norvalyl-D-arginyl-L-isoleucyl-L-allothreonyl-glycyl-L-alanyl-L-serine bistrifluoroacetate
1.21 g (41% pure) from exemplary compound 311A according to procedure 9, purification according to method 45

HPLC (Method 6): $R_t$ = 2.73 min; LC-MS (Method 22): $R_t$ = 2.04 min, MS (ESIpos): m/z (%) = 417 (100) [M + 2 H]$^{2+}$, MS (ESIneg): m/z (%) = 830.4 (100) [M − H]$^-$; HR-TOF-MS: $C_{35}H_{66}N_{11}O_{12}$ calc. 832.4887, found 832.4899 [M + H]$^+$.

Protected nonapeptides

| No. | Name Yield, Synthesis Method | Structure Analysis |
|---|---|---|

335A

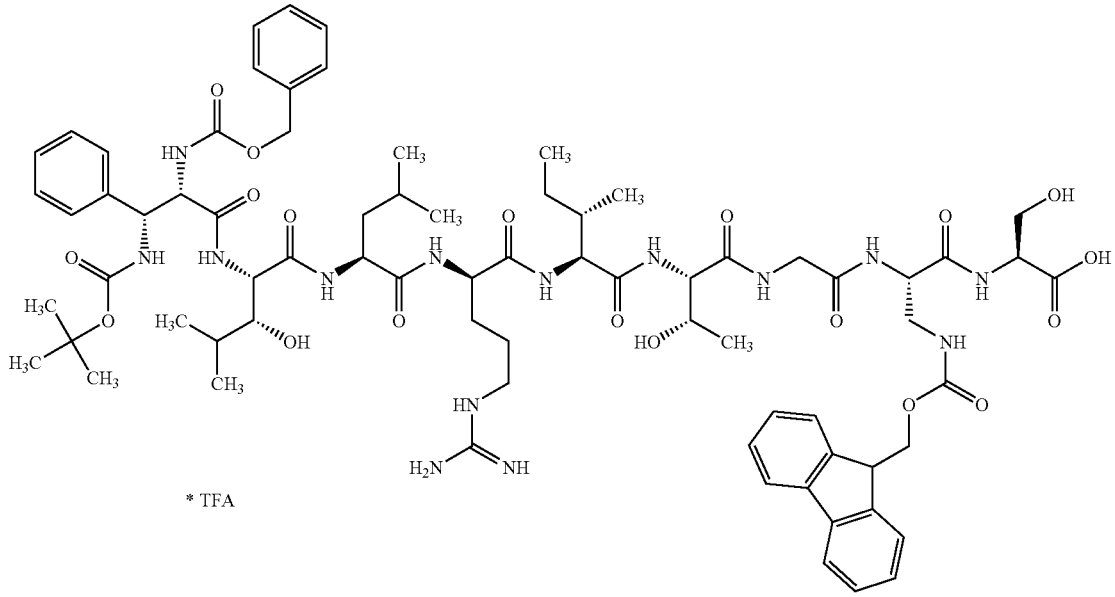

* TFA (3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine trifluoroacetate
Yield: 1008 mg (83% pure, ~quant) as a colorless solid from 647 mg of exemplary compound 312A and exemplary compound 17A according to procedure 10, purification according to method 45 and method 44

HPLC (Method 6): $R_t$ = 4.17 min; LC-MS (Method 19): $R_t$ = 2.27 min, MS (ESIpos): m/z (%) = 1481 (20) [M + H]⁺, MS (ESIneg): m/z (%) = 1478 (20) [M − H]⁻; HR-TOF-MS: $C_{48}H_{81}N_{14}O_{17}$ calc. 1125.5899, found 1125.5891 [M + H]⁺.

336A

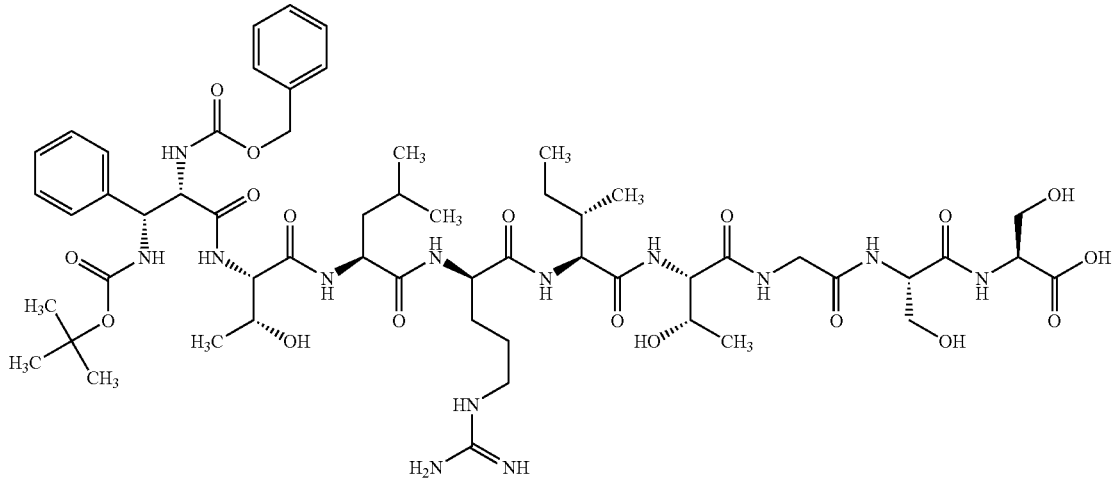

* TFA

[(3R)-N²-(Benzyloxycarbonyl)-3-{(tert-butoxycarbonyl)amino}-L-phenylalanyl]-L-threonyl-L-leucyl-D-arginyl-l-isoleucyl-L-allothreonyl-glycyl-L-seryl-L-serine trifluoroacetate
Yield: 21 mg (64% of theory) from exemplary compound 313A (26 mg, 24 μmol) and 17A according to procedure 10, purification according to method 45.

HPLC (Method 6): $R_t$ = 3.71 min; LC-MS (Method 19): $R_t$ = 1.89 min, MS (ESIpos): m/z (%) = 1230 (30) [M + H]⁺, MS (ESIneg): m/z (%) = 1228.7 (100) [M − H]⁻.

| | Protected nonapeptides |
|---|---|
| No. | Name<br>Yield, Synthesis Method |  Structure  Analysis |

337A

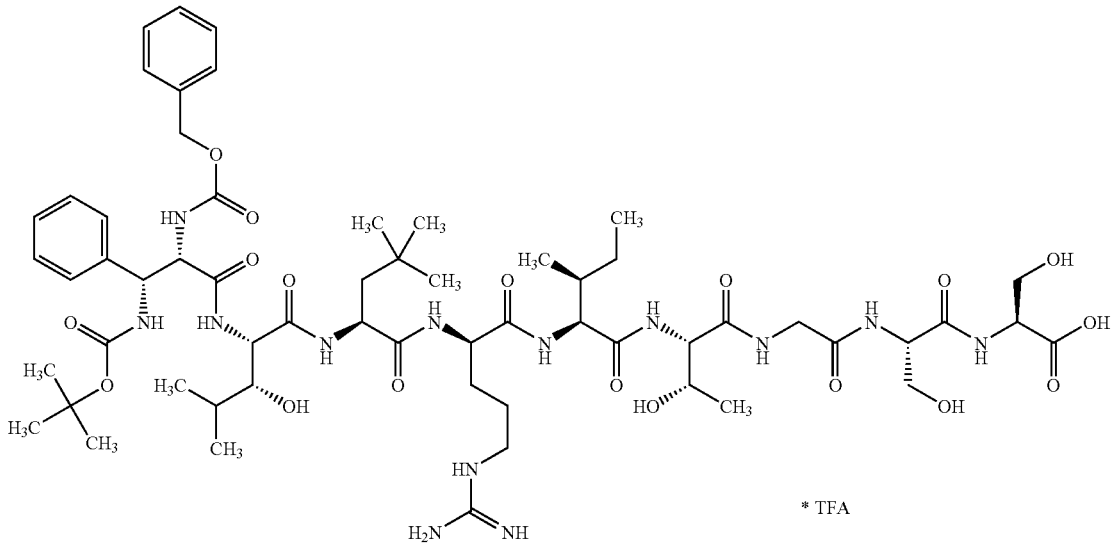

[(3R)-N²-(Benzyloxycarbonyl)-3-{(tert-butoxycarbonyl)amino}-L-phenylalanyl]-[(3R)-3-hydroxy-L-leucyl]-[3-tertbutyl-L-alanyl]-D-arginyl-L-isoleucyl-L-allothreonyl-glycyl-L-seryl-L-serine trifluoroacetate
Yield: 37 mg (74% of theory) from exemplary compound 314A (40 mg, 36 µmol) and 17A according to procedure 10, purification according to method 45.

HPLC (Method 6): $R_t$ = 3.85 min; LC-MS (Method 19): $R_t$ = 1.93 min, MS (ESIpos): m/z (%) = 1272.8 (100) [M + H]⁺, MS (ESIneg) m/z (%) = 1270.9 (100) [M − H]⁻; HR-TOF-MS: $C_{59}H_{94}N_{13}O_{18}$ calc. 1272.6835, found 1272.6824 [M + H]⁺.

338A

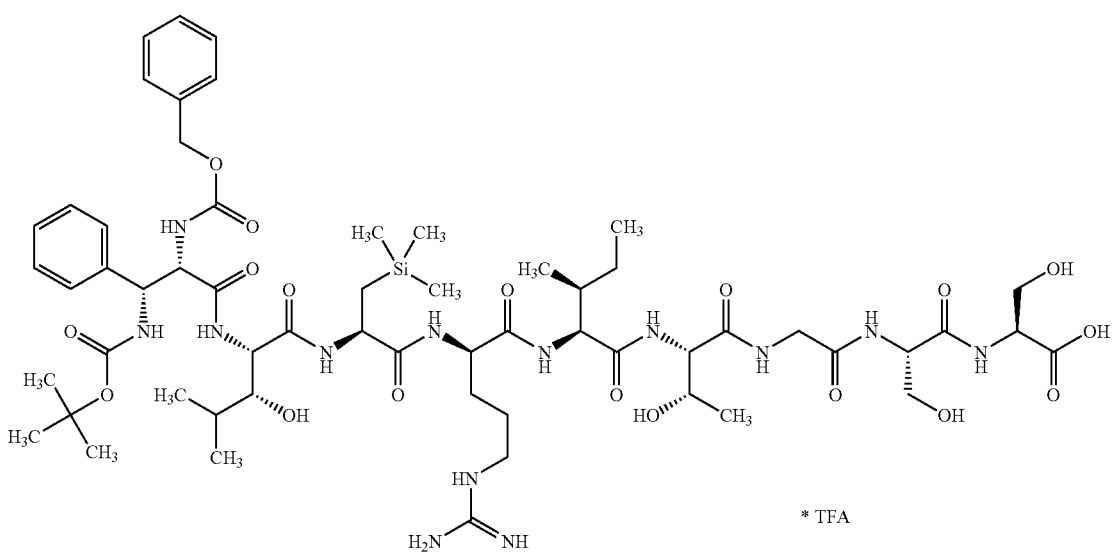

[(3R)-N²-(Benzyloxycarbonyl)-3-{(tert-butoxycarbonyl)amino}-L-phenylalanyl]-[(3R)-3-hydroxy-L-leucyl]-(3-trimethylsilyl-L-alanyl)-D-arginyl-L-isoleucyl-L-allothreonyl-glycyl-L-seryl-L-serine trifluoroacetate
Yield: 56 mg (85% of theory) from exemplary compound 315A (53 mg, 47 µmol) and 17A according to procedure 10, purification according to method 45

HPLC (Method 6): $R_t$ = 3.90 min; LC-MS (Method 19): $R_t$ = 1.99 min, MS (ESIpos): m/z (%) = 1288.9 (40) [M + H]⁺; HR-TOF-MS: $C_{58}H_{94}N_{13}O_{19}Si$ calc. 1288.6604, found 1288.6608 [M + H]⁺.

-continued

Protected nonapeptides

| No. | Name Yield, Synthesis Method | Structure | Analysis |
|---|---|---|---|

339A

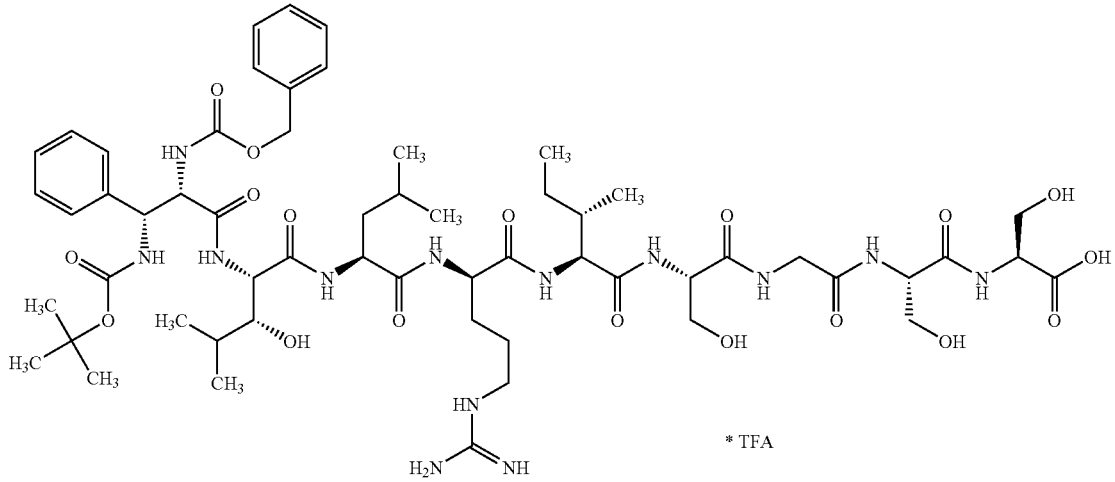

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-seryl-glycyl-L-seryl-L-serine trifluoroacetate
Yield: 42 mg (30% of theory) from exemplary compound 316A (108 mg, 100 μmol) and 17A according to procedure 10, purification according to method 45 and method 32

HPLC (Method 6): $R_t$ = 3.78 min; LC-MS (Method 19): $R_t$ = 1.95 min, MS (ESIpos): m/z (%) = 1244.8 (30) [M + H]⁺, MS (ESIneg): m/z (%) = 1242.8 (100) [M − H]⁻; HR-TOF-MS: $C_{57}H_{90}N_{13}O_{18}$ calc. 1244.6522, found 1244.6544 [M + H]⁺.

340A

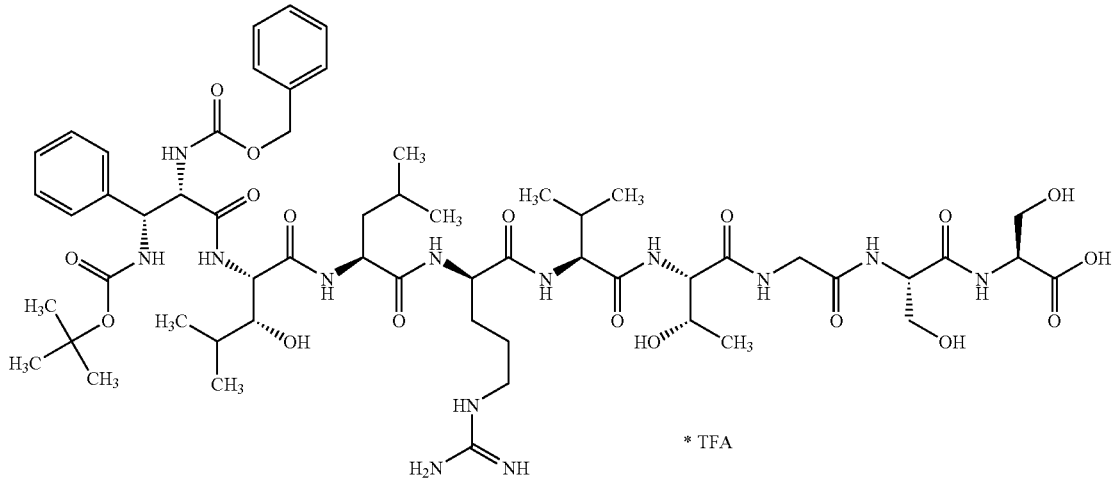

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-valyl-L-allothreonyl-glycyl-L-seryl-L-serine trifluoroacetate
Yield: 48 mg (42% of theory) from exemplary compound 317A (90 mg, 84 μmol) and 17A according to procedure 10, purification according to method 44

HPLC (Method 6): $R_t$ = 3.75 min; LC-MS (Method 19): $R_t$ = 1.93 min, MS (ESIpos): m/z (%) = 1244.7 (30) [M + H]⁺, MS (ESIneg): m/z (%) = 1242.8 (100) [M − H]⁻; HR-TOF-MS: $C_{57}H_{90}N_{13}O_{18}$ calc. 1244.6522, found 1244.6490 [M + H]⁺.

| Protected nonapeptides | |
|---|---|
| No. Name Yield, Synthesis Method | Structure Analysis |
| 341A | 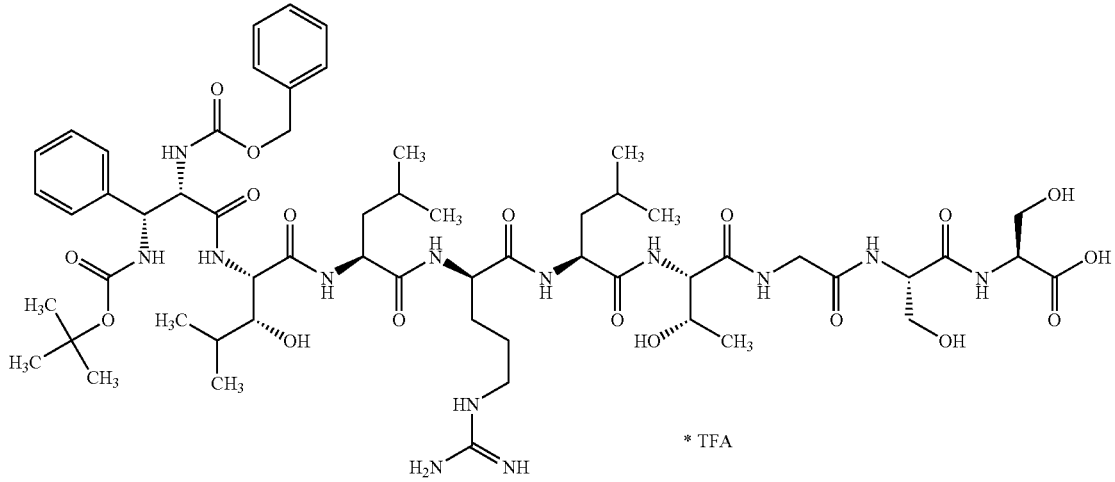 |
| [(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-leucyl-L-allothreonyl-glycyl-L-seryl-L-serine trifluoroacetate Yield: 49 mg (43% of theory) from exemplary compound 318A (90 mg, 83 µmol) and 17A according to procedure 10, purification according to method 44 | HPLC (Method 6): $R_t$ = 3.81 min; LC-MS (Method 19): $R_t$ = 1.98 min, MS (ESIpos): m/z (%) = 1258.8 (50) [M + H]⁺, MS (ESIneg): m/z (%) = 1256.8 (90) [M − H]⁻; HR-TOF-MS: $C_{58}H_{92}N_{13}O_{18}$ calc. 1258.6678, found 1258.6677 [M + H]⁺. |
| 342A | 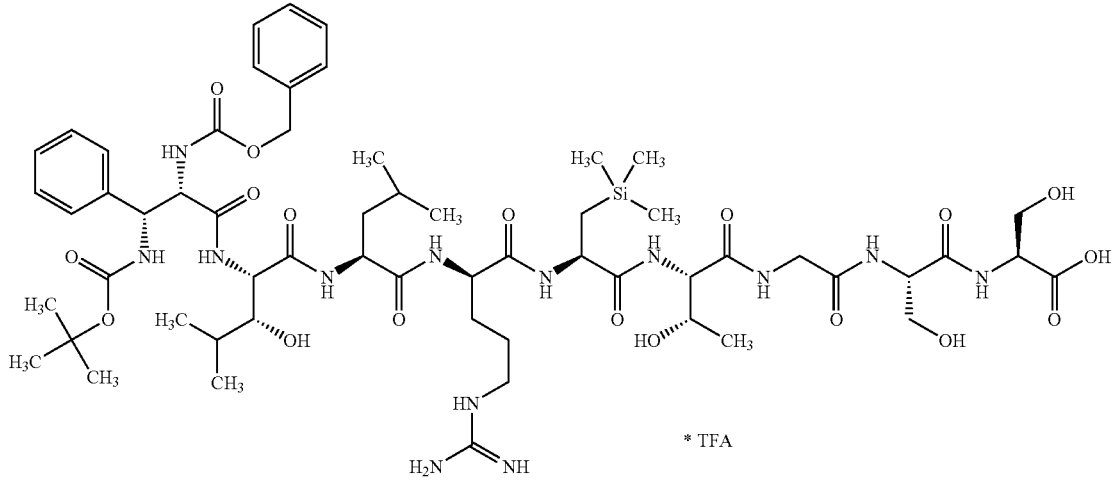 |
| [(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-[3-trimethylsilyl-L-alanlyl]-L-allothreonyl-glycyl-L-seryl-L-serine trifluoroacetate Yield: 42 mg (33% of theory) from exemplary compound 319A (90 mg, 80 µmol) and 17A according to procedure 10, purification according to method 44 | HPLC (Method 6): $R_t$ = 3.89 min; LC-MS (Method 19): $R_t$ = 2.06 min, MS (ESIpos): m/z (%) = 1288.7 (40) [M + H]⁺, MS (ESIneg): m/z (%) = 1286.7 (100) [M − H]⁻; HR-TOF-MS: $C_{58}H_{94}N_{13}O_{18}Si$ calc. 1288.6604, found 1288.6587 [M + H]⁺. |

| Protected nonapeptides |
|---|
| Structure |
| Name |
| No. Yield, Synthesis Method     Analysis |

343A

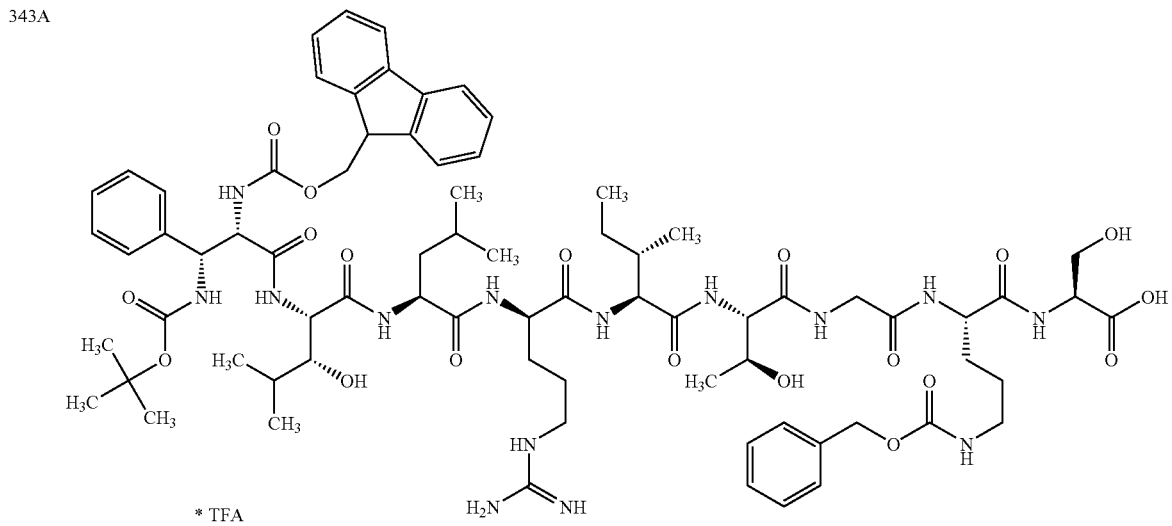

{(3R)-N²-[(9H-Fluoren-9-ylmethoxy)carbonyl]-3-
[(tert-butoxycarbonyl)amino]-L-phenylalanyl}-[(3R)-
3-hydroxy-L-leucyl]-L-leucyl-D-arginyl-L-isoleucyl-L-
allothreonyl-glycyl-(N⁵-benzyloxycarbonyl-L-ornithyl-
L-serine trifluoroacetate
Yield: 42 mg (33% of theory) from exemplary
compound 320A (90 mg, 80 μmol) and 277A
according to procedure 10, purification according to
method 44

HPLC (Method 6): $R_t$ = 4.21 min.

344A

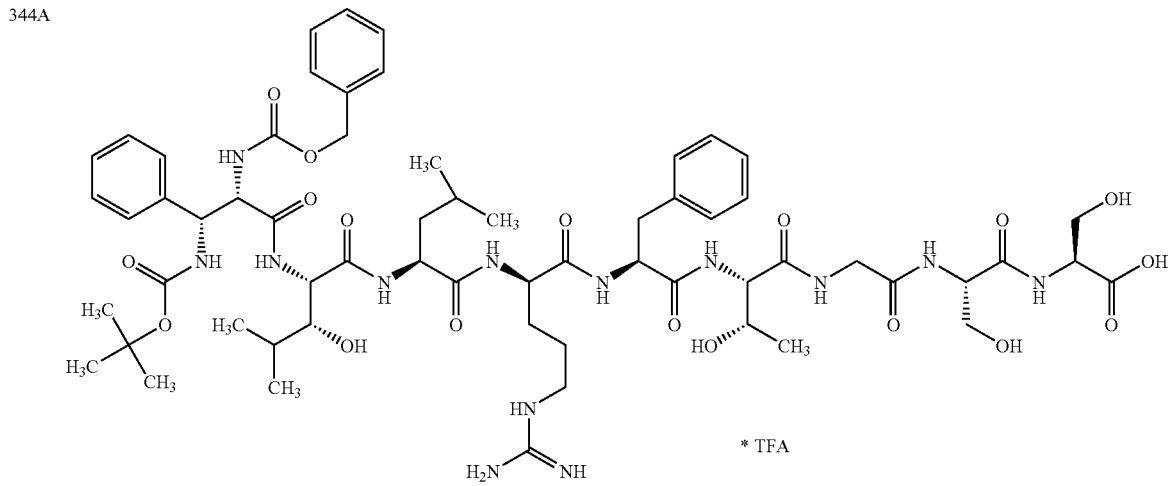

[(3R)-N²-(Benzyloxycarbonyl)-3-{(tert-
butoxycarbonyl)amino}-L-phenylalanyl]-[(3R)-3-
hydroxy-L-leucyl]-L-leucyl-D-arginyl-L-phenylalanlyl-
L-allothreonyl-glycyl-L-seryl-L-serine trifluoroacetate
Yield: 55 mg (49% of theory) from exemplary
compound 321A (90 mg, 80 μmol) and 17A according
to procedure 10, purification according to method 44

HPLC (Method 6): $R_t$ = 3.80 min; LC-MS
(Method 19): $R_t$ = 1.97 min, MS (ESIpos):
m/z (%) = 1292.7 (30) [M + H]⁺, MS
(ESIneg): m/z (%) = 1290.7 (80) [M − H]⁻.

| Protected nonapeptides |
|---|

| No. | Name Yield, Synthesis Method | Structure Analysis |
|---|---|---|

345A

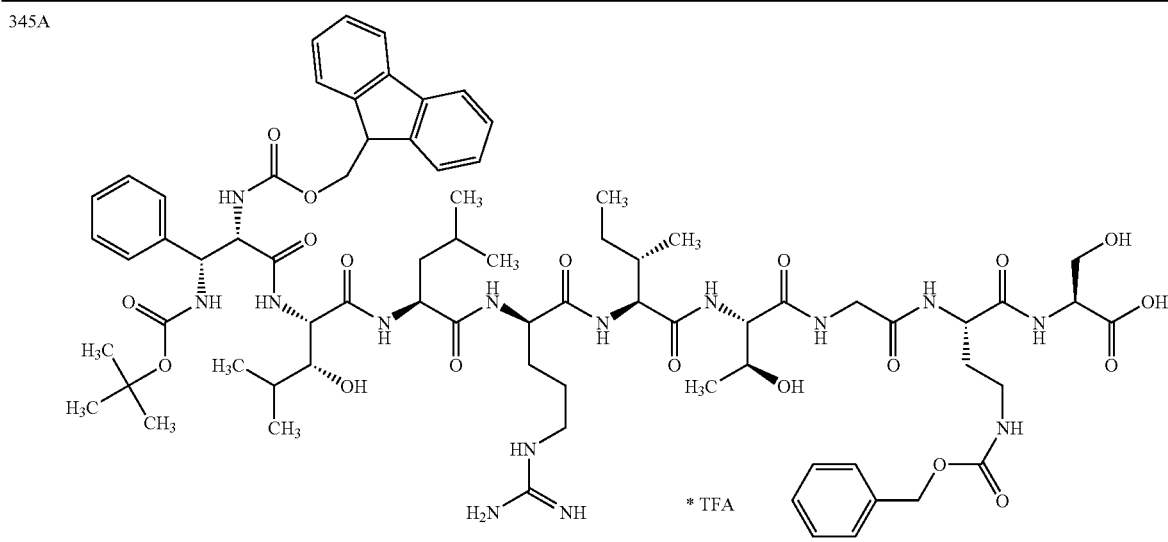

{(3R)-N²-[(9H-Fluoren-9-ylmethoxy)carbonyl]-3-[(tert-butoxycarbonyl)amino]-L-phenylalanyl}-[(3R)-3-hydroxy-L-leucyl]-L-leucyl-D-arginyl-L-isoleucyl-L-allothreonyl-glycyl-[(2S)-2-amino-4-benzyloxycarbonylaminobutyryl]-L-serine trifluoroacetate
Yield: 57 mg (27% of theory) from exemplary compound 322A (100 mg, 81 μmol) and 277A according to procedure 10, purification according to method 44

HPLC (Method 6): $R_t$ = 4.20 min; LC-MS (Method 19): $R_t$ = 2.28 min, MS (ESIpos): m/z (%) = 1494.7 (20) [M + H]⁺, MS (ESIneg): m/z (%) = 1493.1 (50) [M − H]⁻; HR-TOF-MS: $C_{74}H_{105}N_{14}O_{19}$ calc. 1493.7675, found 1493.7666 [M + H]⁺.

346A

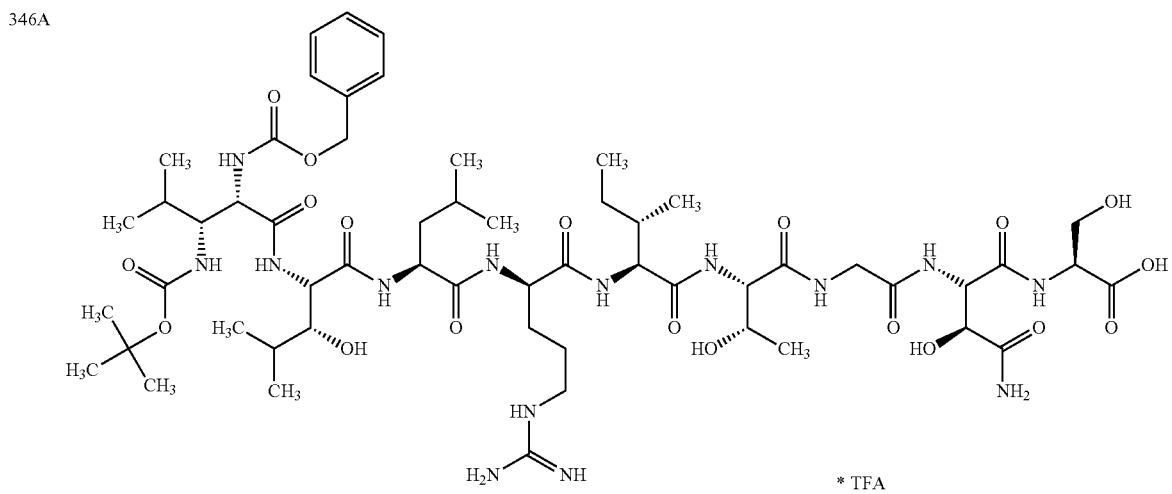

[(3R)-N²-(Benzyloxycarbonyl)-3-{(tert-butoxycarbonyl)amino}-L-leucyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine trifluoroacetate
Yield: 311 mg (94% of theory) from exemplary compound 3A (272 mg, 240 μmol) and 282A according to procedure 10, purification according to method 45

HPLC (Method 6): $R_t$ = 3.76 min; LC-MS (Method 19): $R_t$ = 1.95 min, MS (ESIpos): m/z (%) = 1267.8 (20) [M + H]⁺, MS (ESIneg): m/z (%) = 1265.9 (100) [M − H]⁻; HR-TOF-MS: $C_{56}H_{95}N_{14}O_{19}$ calc. 1267.6893, found 1267.6907 [M + H]⁺.

| Protected nonapeptides |
|---|
| Structure |

| No. | Name Yield, Synthesis Method | Analysis |
|---|---|---|

347A

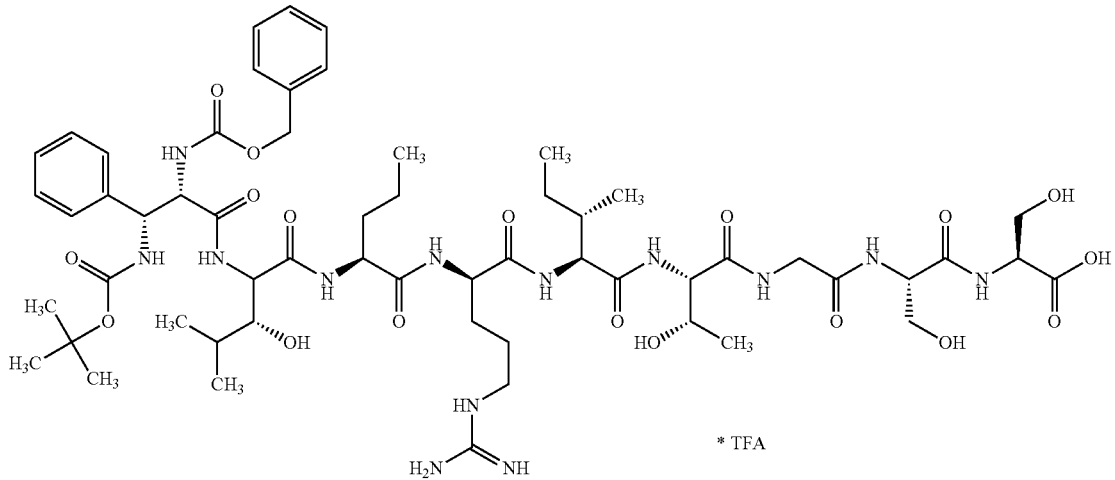

[(3R)-N²-(Benzyloxycarbonyl)-3-{(tert-butoxycarbonyl)amino}-L-phenylalanyl]-[(3R)-3-hydroxy-L-leucyl]-L-norvalyl-D-arginyl-L-isoleucyl-L-allothreonyl-glycyl-L-seryl-L-serine trifluoroacetate
Yield: 173 mg (91% of theory) from exemplary compound 323A (150 mg, 139 μmol) and 17A according to procedure 10, purification according to method 44

HPLC (Method 6): $R_t$ = 3.75 min; LC-MS (Method 19): $R_t$ = 1.94 min, MS (ESIpos): m/z (%) = 1244.7 (30) [M + H]⁺, MS (ESIneg): m/z (%) = 1242.8 (100) [M − H]⁻; HR-TOF-MS: $C_{57}H_{90}N_{13}O_{18}$ calc. 1244.6522, found 1244.6555 [M + H]⁺.

348A

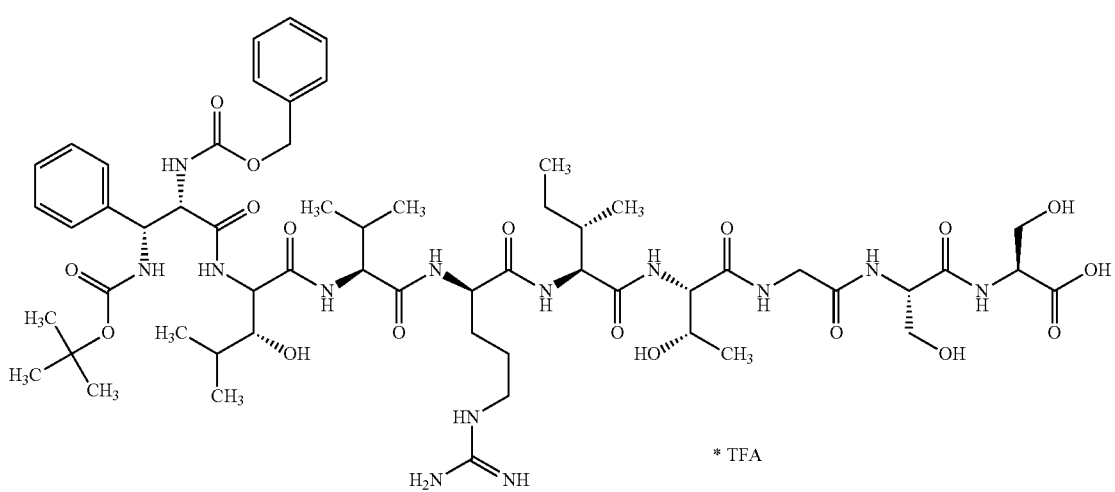

[(3R)-N²-(Benzyloxycarbonyl)-3-{(tert-butoxycarbonyl)amino}-L-phenylalanyl]-[(3R)-3-hydroxy-L-leucyl]-L-valyl-D-arginyl-L-isoleucyl-L-allothreonyl-glycyl-L-seryl-L-serine trifluoroacetate
Yield: 61 mg (32% of theory) from exemplary compound 324A (150 mg, 139 μmol) and 17A according to procedure 10, purification according to method 34.

HPLC (Method 6): $R_t$ = 3.74 min; LC-MS (Method 19): $R_t$ = 1.94 min, MS (ESIpos): m/z (%) = 1244.7 (30) [M + H]⁺, MS (ESIneg): m/z (%) = 1243.7 (40) [M − H]⁻; HR-TOF-MS: $C_{57}H_{90}N_{13}O_{18}$ calc. 1244.6522, found 1244.6528 [M + H]⁺.

-continued

Protected nonapeptides

| No. | Name Yield, Synthesis Method | Structure Analysis |
|---|---|---|

349A

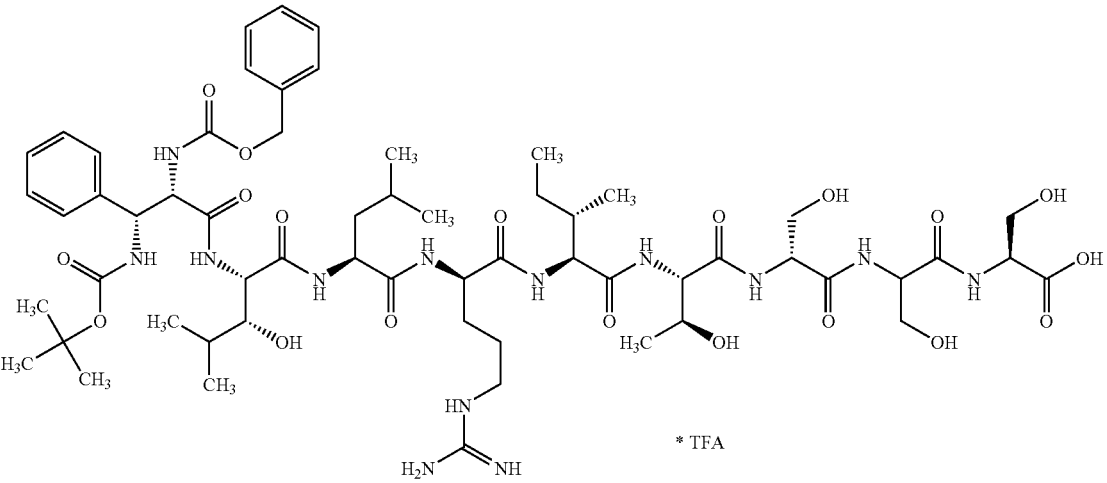

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-D-seryl-L-seryl-L-serine trifluoroacetate
Yield: 73 mg (29% of theory) from exemplary compound 325A (200 mg, 179 µmol) and 17A according to procedure 10, purification according to method 44.

HPLC (Method 6): $R_t$ = 3.78 min; LC-MS (Method 19): $R_t$ = 1.97 min, MS (ESIpos): m/z (%) = 1288.7 (40) [M + H]⁺, MS (ESIneg): m/z (%) = 1286.6 (100) [M − H]⁻; HR-TOF-MS: $C_{59}H_{94}N_{13}O_{19}$ calc. 1288.6784, found 1288.6792 [M + H]⁺.

350A

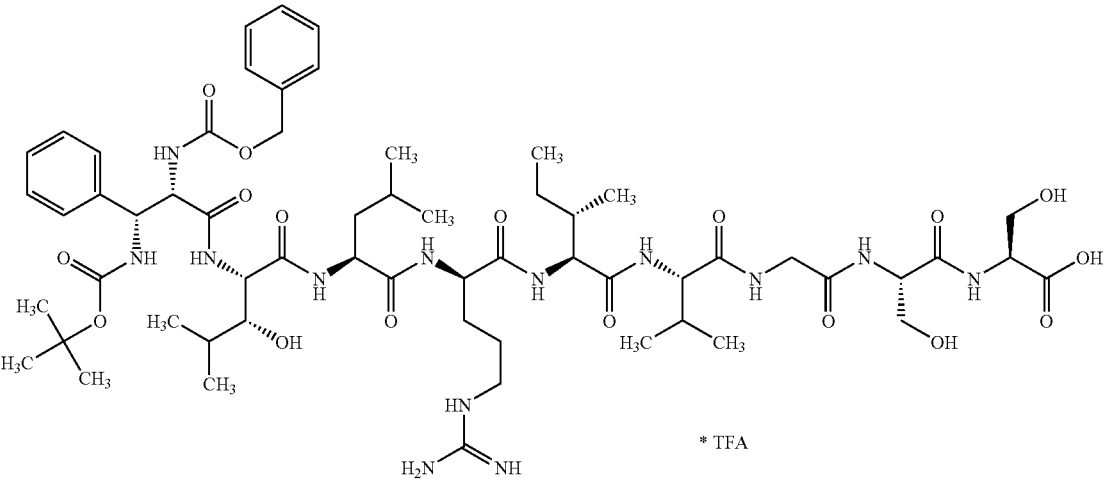

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-valyl-glycyl-L-seryl-L-serine trifluoroacetate
Yield: 44 mg (24% of theory) from exemplary compound 326A (200 mg, 132 µmol) and 17A according to procedure 10, purification according to method 44.

HPLC (Method 6): $R_t$ = 3.88 min; LC-MS (Method 19): $R_t$ = 2.02 min, MS (ESIpos): m/z (%) = 1256.8 (20) [M + H]⁺, MS (ESIneg): m/z (%) = 1254.8 (100) [M − H]⁻.

-continued

Protected nonapeptides

| No. | Name<br>Yield, Synthesis Method | Structure<br>Analysis |
|---|---|---|

351A

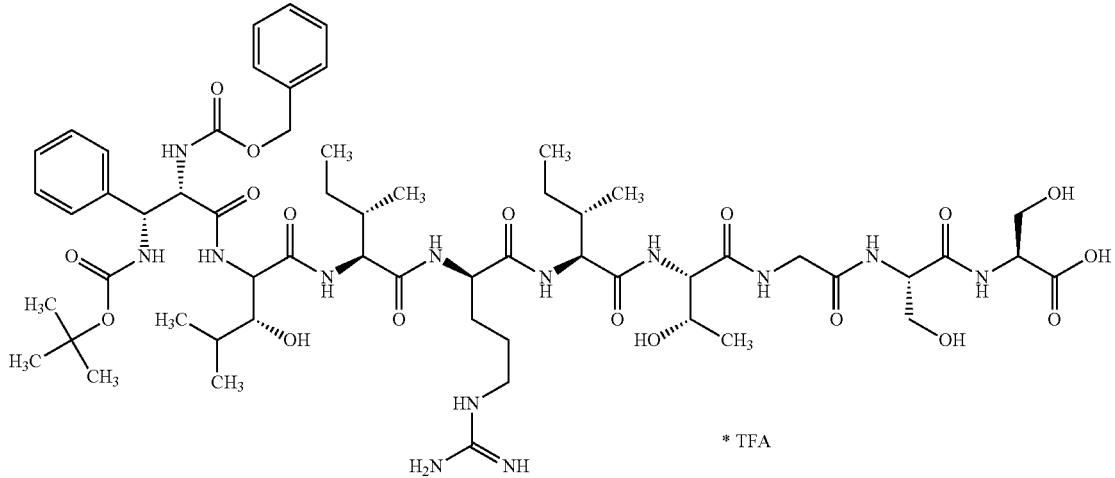

[(3R)-N²-(Benzyloxycarbonyl)-3-{(tert-butoxycarbonyl)amino}-L-phenylalanyl]-[(3R)-3-hydroxy-L-leucyl]-L-isoleucyl-D-arginyl-L-isoleucyl-L-allothreonyl-glycyl-L-seryl-L-serine trifluoroacetate
Yield: 39 mg (18% of theory) from exemplary compound 327A (175 mg, 161 µmol) and 17A according procedure 10, purification according to method 32.

HPLC (Method 6): $R_t$ = 3.79 min; LC-MS (Method 51): $R_t$ = 2.98 min, MS (ESIpos): m/z (%) = 1258.9 (10) [M + H]⁺, MS (ESIneg): m/z (%) = 1257.3 (5) [M − H]⁻; HR-TOF-MS: $C_{58}H_{92}N_{13}O_{18}$ calc. 1258.6678, found 1258.6698 [M + H]⁺.

352A

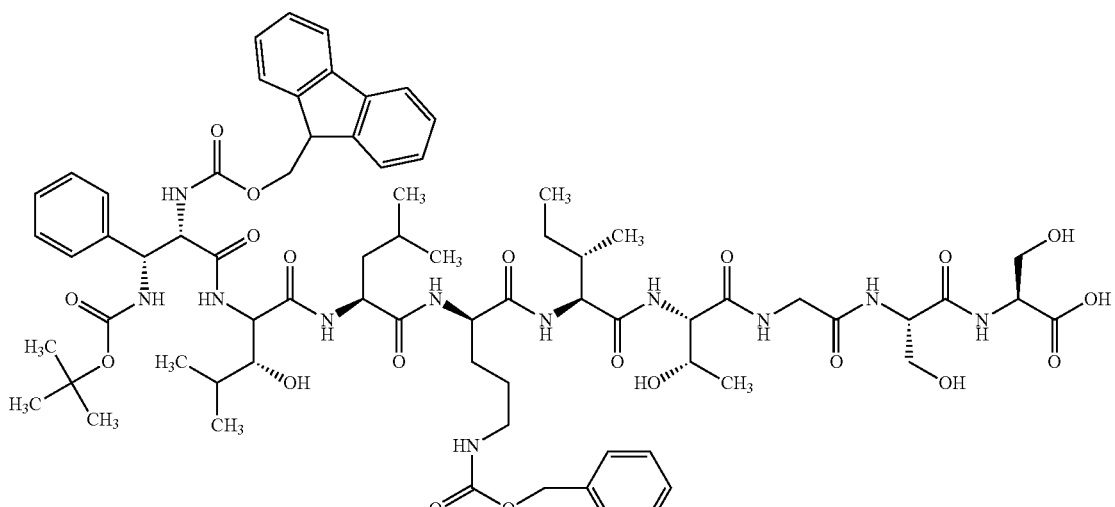

(3R)-N²-[(9H-Fluoren-9-ylmethoxy)carbonyl]-3-[(tert-butoxycarbonyl)amino]-L-phenylalanyl 1-[(3R)-3-hydroxy-L-leucyl]-L-leucyl-(N⁵-benzyloxycarbonyl-D-orrnthyl)-L-isoleucyl-L-allothreonyl-glycyl-L-seryl-L-serine trifluoroacetate
Yield: 103 mg (33% pure, 17% of theory) from exemplary compound 328A (150 mg, 140 µmol) and 277A according to procedure 10, purification according to method 34.

HPLC (Method 6): $R_t$ = 4.70 min; LC-MS (Method 19): $R_t$ = 3.26 min, MS (ESIpos): m/z (%) = 1439.7 (100) [M + H]⁺, MS (ESIneg): m/z (%) = 1437.8 (80) [M − H]⁻; HR-TOF-MS: $C_{72}H_{100}N_{11}O_{20}$ calc. 1438.7148, found 1438.7141 [M + H]⁺.

-continued

| Protected nonapeptides |
|---|
| Structure |
| No. Name Yield, Synthesis Method     Analysis |

353A

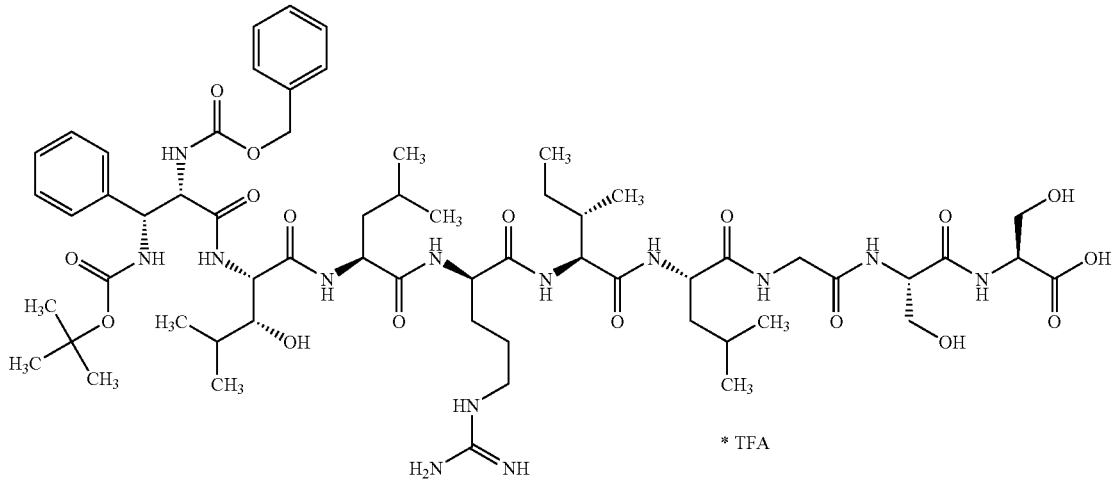

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-leucyl-glycyl-L-seryl-L-serine trifluoroacetate
Yield: 14 mg (14% of theory) from exemplary compound 329A (130 mg, 71 µmol) and 17A according to procedure 10, purification according to method 32.

HPLC (Method 6): $R_t$ = 3.89 min; LC-MS (Method 19): $R_t$ = 2.08 min, MS (ESIpos): m/z (%) = 1270.8 (100) [M + H]$^+$, MS (ESIneg): m/z (%) = 1268.8 (100) [M − H]$^-$; HR-TOF-MS: $C_{60}H_{96}N_{13}O_{17}$ calc. 1270.7042, found 1270.7047 [M + H]$^+$.

354A

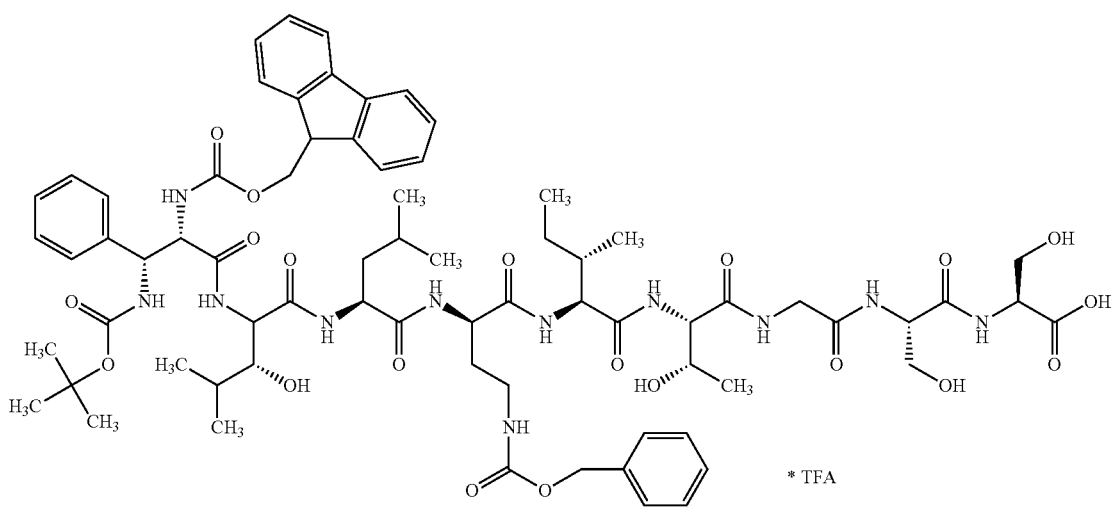

{(3R)-N²-[(9H-Fluoren-9-ylmethoxy)carbonyl]-3-[(tert-butoxycarbonyl)amino]-L-phenylalanyl}-[(3R)-3-hydroxy-L-leucyl]-L-leucyl-[(2R)-2-amino-4-benzyloxycarbonylaminobutyryl]-L-isoleucyl-L-allothreonyl-glycyl-L-seryl-L-serine trifluoroacetate
Yield: 106 mg (60% pure, 31% of theory) from exemplary compound 330A (150 mg, 142 µmol) and 277A according to procedure 10, purification according to method 34.

HPLC (Method 6): $R_t$ = 4.71 min; LC-MS (Method 19): $R_t$ = 3.23 min, MS (ESIpos): m/z (%) = 1425.5 (100) [M + H]$^+$, MS (ESIneg): m/z (%) = 1422.8 (100) [M − H]$^-$; HR-TOF-MS: $C_{71}H_{98}N_{11}O_{20}$ calc. 1424.6985, found 1424.6980 [M + H]$^+$.

Protected nonapeptides

| No. | Name Yield, Synthesis Method | Structure Analysis |
|---|---|---|

355A

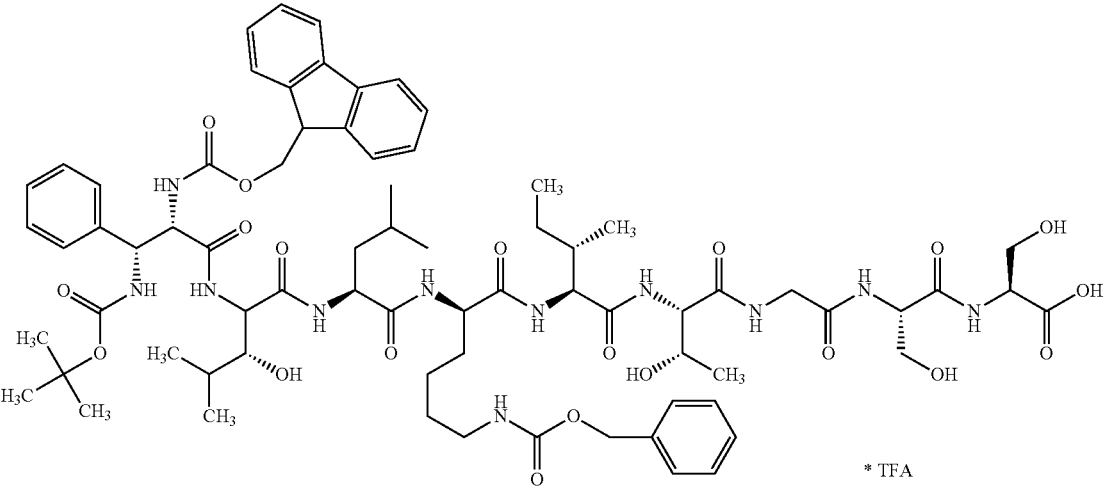

{(3R)-N²-[(9H-Fluoren-9-ylmethoxy)carbonyl]-3-[(tert-butoxycarbonyl)amino]-L-phenylalanyl}-[(3R)-3-hydroxy-L-leucyl]-L-leucyl-(N⁶-benzyloxycarbonyl-D-lysyl)-L-isoleucyl-L-allothreonyl-glycyl-L-seryl-L-serine trifluoroacetate
Yield: 49 mg (21% of theory) from exemplary compound 331A (180 mg, 150 µmol) and 277A according to procedure 10, purification according to method 32.

HPLC (Method 6): $R_t$ = 4.71 min; LC-MS (Method 19): $R_t$ = 3.35 min, MS (ESIpos): m/z (%) = 1452.7 (90) [M + H]⁺, MS (ESIneg): m/z (%) = 1451.7 (100) [M − H]⁻; HR-TOF-MS: $C_{73}H_{102}N_{11}O_{20}$ calc. 1452.7298, found 1452.7283 [M + H]⁺.

356A

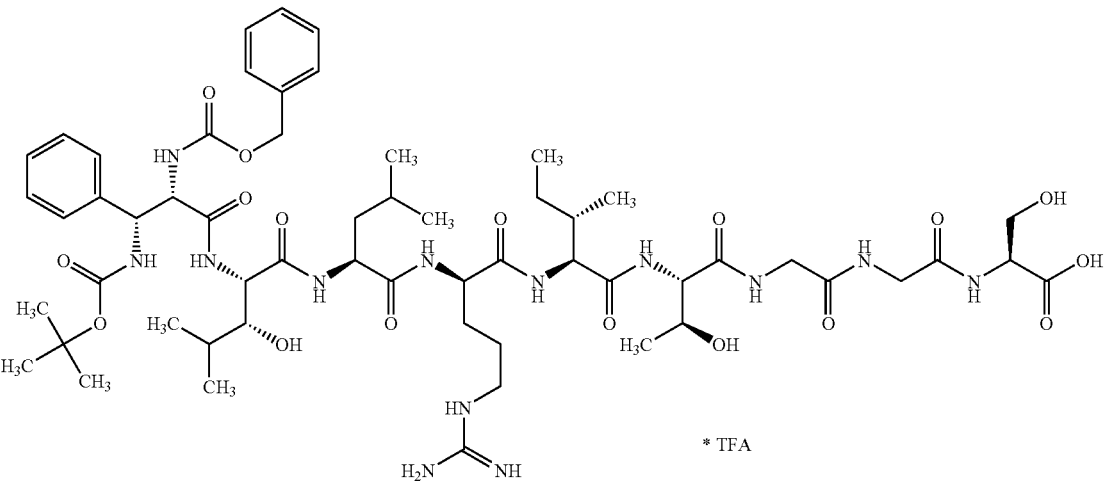

[(3R)-N²-(Benzyloxycarbonyl)-3-{(tert-butoxycarbonyl)amino}-L-phenylalanyl]-[(3R)-3-hydroxy-L-leucyl]-L-leucyl-D-arginyl-L-isoleucyl-L-allothreonyl-glycyl-glycyl-L-serine trifluoroacetate
Yield: 133 mg (60% pure, 84% of theory) from exemplary compound 332A (100 mg, 70 µmol) and 17A according to procedure 10, purification according to method 32.

HPLC (Method 6): $R_t$ = 3.83 min; LC-MS (Method 19): $R_t$ = 1.96 min, MS (ESIpos): m/z (%) = 1228.7 (20) [M + H]⁺, MS (ESIneg): m/z (%) = 1226.8 (100) [M − H]⁻; HR-TOF-MS: $C_{57}H_{90}N_{13}O_{17}$ calc. 1228.6573, found 1228.6533 [M + H]⁺.

-continued

Protected nonapeptides

| No. | Name<br>Yield, Synthesis Method | Structure<br>Analysis |
|---|---|---|

357A

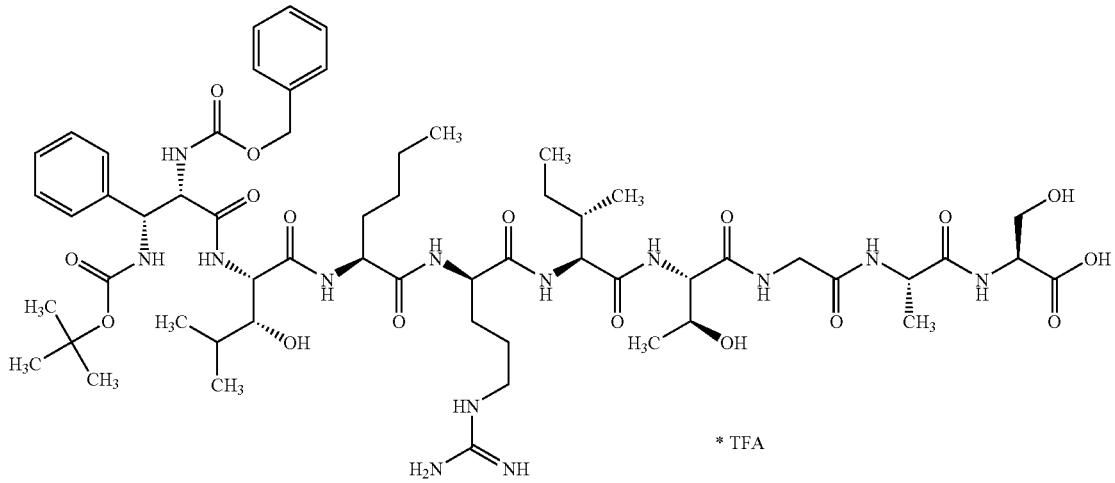

[(3R)-N²-(Benzyloxycarbonyl)-3-{(tert-butoxycarbonyl)amino}-L-phenylalanyl]-[(3R)-3-hydroxy-L-leucyl]-L-norleucyl-D-arginyl-L-isoleucyl-L-allothreonyl-glycyl-L-alanyl-L-serine trifluoroacetate
Yield: 95 mg (25% of theory) from exemplary compound 333A (300 mg, 279 μmol) and 17A according to procedure 10, purification according to method 34.

HPLC (Method 6): $R_t$ = 3.83 min; LC-MS (Method 52): $R_t$ = 1.51 min, MS (ESIpos): m/z (%) = 1242.8 (90) [M + H]⁺, MS (ESIneg): m/z (%) = 1241.8 (100) [M − H]⁻; HR-TOF-MS: $C_{58}H_{92}N_{13}O_{17}$ calc. 1242.6729, found 1242.6741 [M + H]⁺.

358A

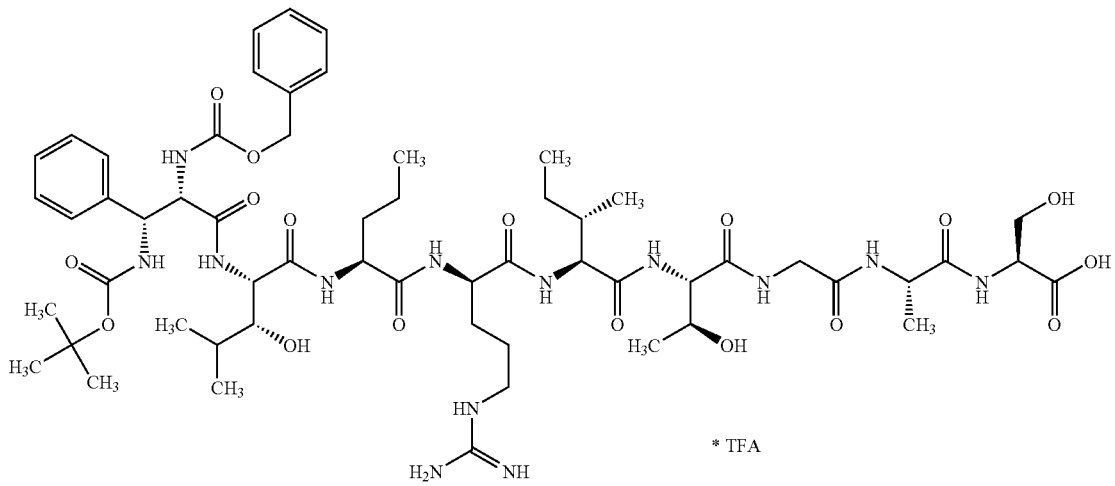

[(3R)-N²-(Benzyloxycarbonyl)-3-{(tert-butoxycarbonyl)amino}-L-phenylalanyl]-[(3R)-3-hydroxy-L-leucyl]-L-norvalyl-D-arginyl-L-isoleucyl-L-allothreonyl-glycyl-L-alanyl-L-serine trifluoroacetate
Yield: 87 mg (23% of theory) from exemplary compound 334A (300 mg, 283 μmol) and 17A according to procedure 10, purification according to method 34.

HPLC (Method 6): $R_t$ = 3.78 min; LC-MS (Method 19): $R_t$ = 1.94 min, MS (ESIpos): m/z (%) = 1228.7 (60) [M + H]⁺, MS (ESIneg): m/z (%) = 1226.7 (100) [M − H]⁻; HR-TOF-MS: $C_{57}H_{90}N_{13}O_{17}$ calc. 1228.6573, found 1228.6592 [M + H]⁺.

| Partially deprotected nonapeptides | |
|---|---|
| Name | Structure |
| No. Yield, Synthesis Method | Analysis |

359A

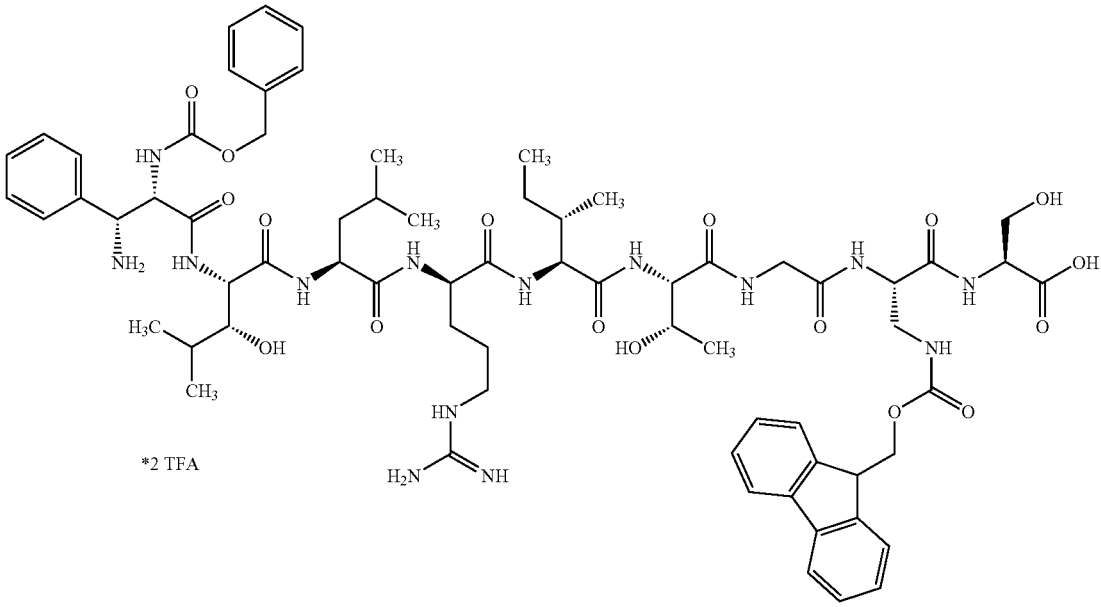

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine bistrifluoroacetate
Yield: 1110 mg (~quant) as a colorless solid from 1070 mg of exemplary compound 335A according to procedure 2, crude product reacted further without purification.

HPLC (Method 6): $R_t$ = 3.60 min; LC-MS (Method 51): $R_t$ = 2.72 min, MS (ESIpos): m/z (%) = 691.2 (100) $[M + 2H]^{2+}$; HR-TOF-MS: $C_{68}H_{95}N_{14}O_{17}$ calc. 1379.6995, found 1379.6998 $[M + H]^+$.

360A

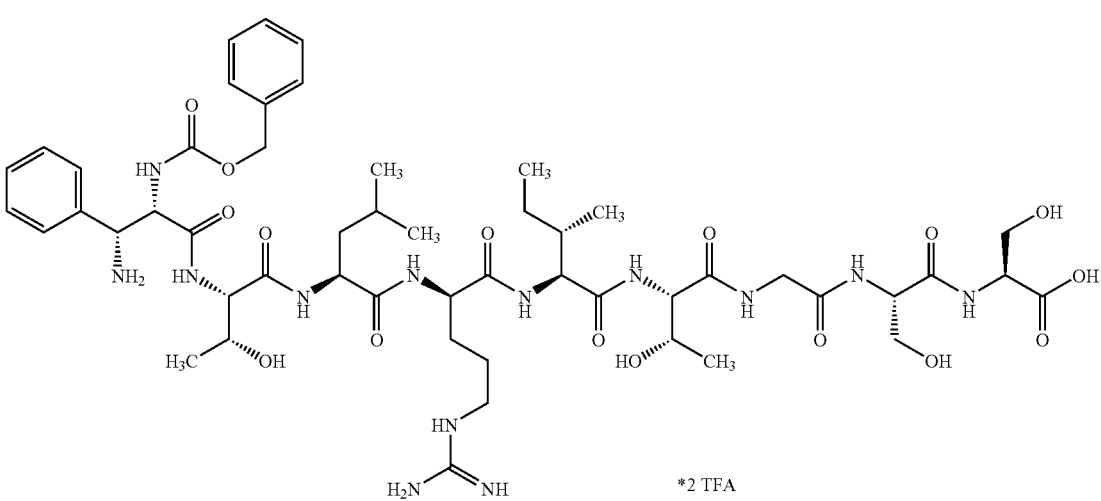

[(3R)-N²-(Benzyloxycarbonyl)-3-amino-L-phenylalanyl]-L-threonyl-L-leucyl-D-arginyl-L-isoleucyl-L-allothreonyl-glycyl-L-seryl-L-serine bistrifluoroacetate
Yield: 21 mg (99% of theory) as a colorless solid from 21 mg of exemplary compound 336A according to procedure 2, crude product reacted further without purification.

HPLC (Method 6): $R_t$ = 3.11 min; LC-MS (Method 20): $R_t$ = 1.13 min, MS (ESIpos): m/z (%) = 566.0 (100) $[M + 2H]^{2+}$; MS (ESIneg) m/z (%) = 1128.8 (100) $[M - H]^-$; HR-TOF-MS: $C_{51}H_{80}N_{13}O_{16}$ calc. 1130.5841, found 1130.5847 $[M + H]^+$.

-continued

Partially deprotected nonapeptides

Structure

No. | Name Yield, Synthesis Method | Analysis

361A

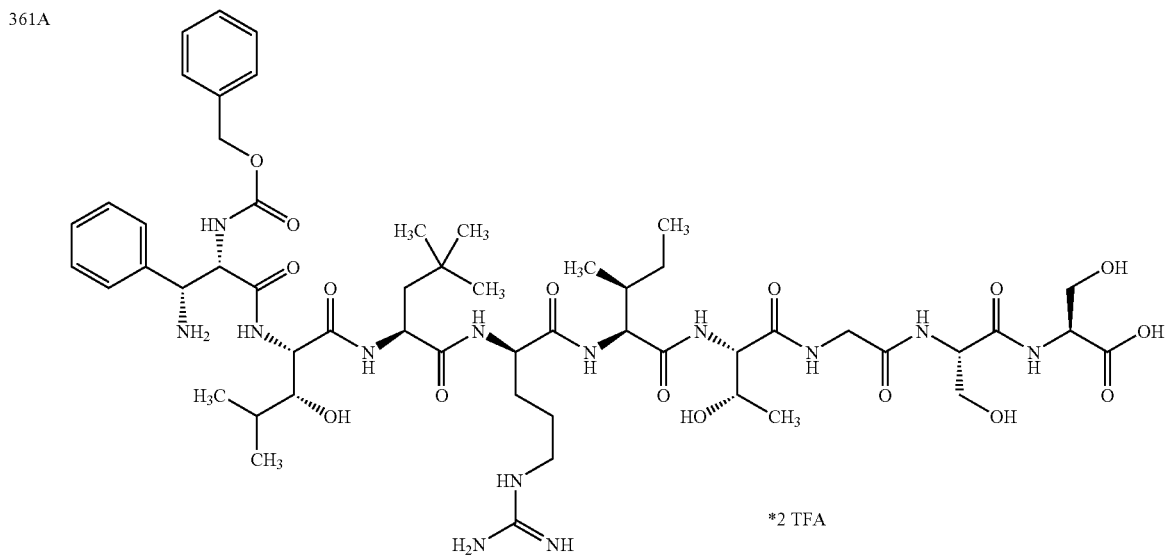

*2 TFA

[(3R)-N²-(Benzyloxycarbonyl)-3-amino-L-phenylalanyl]-[(3R)-3-hydroxy-L-leucyl]-[3-tertbutyl-L-alanyl]-D-arginyl-L-isoleucyl-L-allothreonyl-glycyl-L-seryl-L-serine bistrifluoroacetate
Yield: 37 mg (99% of theory) as a colorless solid from 37 mg of exemplary compound 337A according to procedure 2, crude product reacted further without purification.

HPLC (Method 6): $R_t$ = 3.28 min; LC-MS (Method 19): $R_t$ = 1.34 min, MS (ESIpos): m/z (%) = 587.2 (100) [M + 2H]$^{2+}$, 1172.8 (10) [M + H]$^+$, MS (ESIneg): m/z (%) = 1170.8 (100) [M − H]$^−$; HR-TOF-MS: $C_{54}H_{86}N_{13}O_{16}$ calc. 1172.6310, found 1172.6310 [M + H]$^+$.

362A

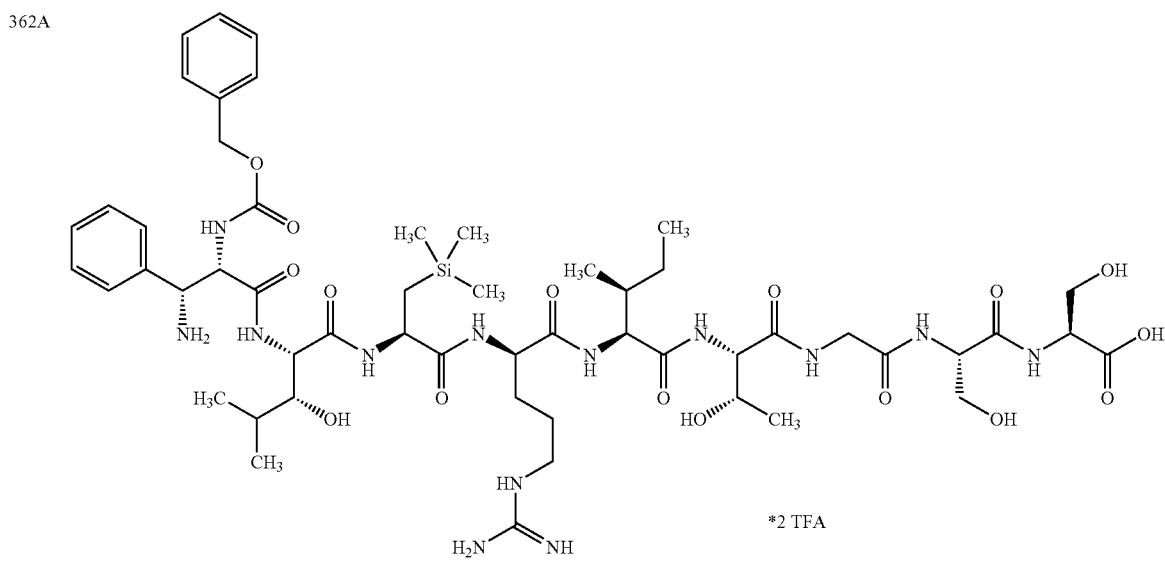

*2 TFA

[(3R)-N²-(Benzyloxycarbonyl)-3-amino-L-phenylalanyl]-[(3R)-3-hydroxy-L-leucyl]-(3-trimethylsilyl-L-alanyl)-D-arginyl-L-isoleucyl-L-allothreonyl-glycyl-L-seryl-L-serine bistrifluoroacetate
Yield: 54 mg (97% of theory) as a colorless solid from 55 mg of exemplary compound 338A according to procedure 2, crude product reacted further without purification.

HPLC (Method 6): $R_t$ = 3.33 min; LC-MS (Method 22): $R_t$ = 2.73 min, MS (ESIpos): m/z (%) = 595.3 (100) [M + 2H]$^{2+}$, 1189.0 (10) [M + H]$^+$, MS (ESIneg): m/z (%) = 1186.9 (100) [M − H]$^−$; HR-TOF-MS: $C_{53}H_{86}N_{13}O_{16}Si$ calc. 1188.6080, found 1188.6074 [M + H]$^+$.

Partially deprotected nonapeptides

| No. | Name<br>Yield, Synthesis Method | Structure<br>Analysis |
|---|---|---|

363A

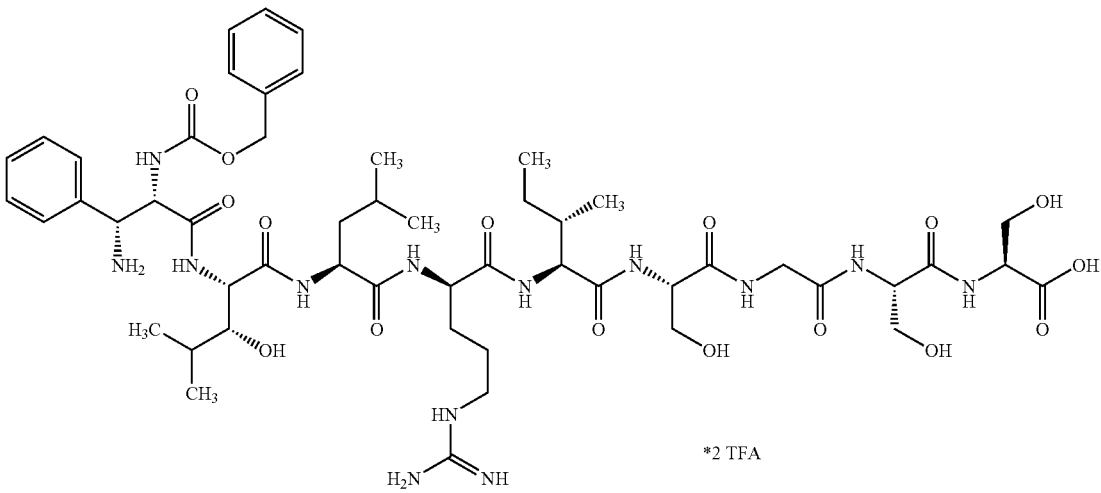

*2 TFA

[(3R)-N²-(Benzyloxycarbonyl)-3-amino-L-phenylalanyl]-[(3R)-3-hydroxy-L-leucyl]-L-leucyl-D-arginyl-L-isoleucyl-L-seryl-glycyl-L-seryl-L-serine bistrifluoroacetate
Yield: 48 mg (94% pure, ~quant.) as a colorless solid from 42 mg of exemplary compound 339A according to procedure 2, crude product reacted further without purification.

HPLC (Method 6): $R_t$ = 3.22 min; LC-MS (Method 19): $R_t$ = 1.35 min, MS (ESIpos): m/z (%) = 573.0 (100) [M + 2H]²⁺, MS (ESIneg): m/z (%) = 1142.8 (100) [M − H]⁻; HR-TOF-MS: $C_{52}H_{82}N_{13}O_{16}$ calc. 1144.5997, found 1144.5963 [M + H]⁺.

364A

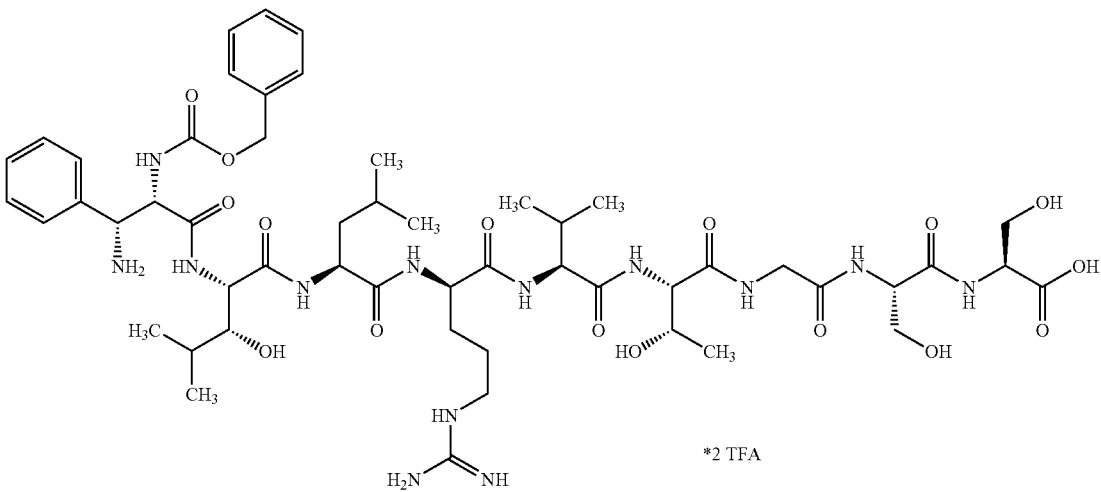

*2 TFA

[(3R)-N²-(Benzyloxycarbonyl)-3-amino-L-phenylalanyl]-[(3R)-3-hydroxy-L-leucyl]-L-leucyl-D-arginyl-L-valyl-L-allothreonyl-glycyl-L-seryl-L-serine bistrifluoroacetate
Yield: 54 mg (70% pure, ~quant.) as a colorless solid from 48 mg of exemplary compound 340A according to procedure 2, crude product reacted further without purification.

HPLC (Method 6): $R_t$ = 3.17 min; LC-MS (Method 19): $R_t$ = 1.30 min, MS (ESIpos): m/z (%) = 573.1 (100) [M + 2H]²⁺, 1144.6 (10) [M + H]⁺, MS (ESIneg): m/z (%) = 1142.8 (100) [M − H]⁻; HR-TOF-MS: $C_{52}H_{82}N_{13}O_{16}$ calc. 1144.5997, found 1144.5988 [M + H]⁺.

-continued

Partially deprotected nonapeptides

Structure

No. | Name Yield, Synthesis Method | Analysis

365A

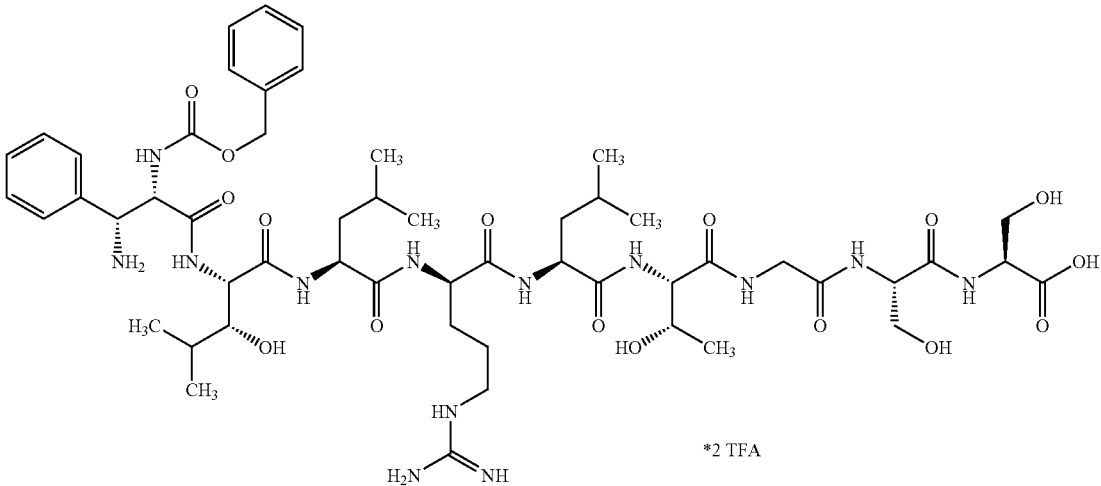

*2 TFA

[(3R)-N²-(Benzyloxycarbonyl)-3-amino-L-phenylalanyl]-[(3R)-3-hydroxy-L-leucyl]-L-leucyl-D-arginyl-L-leucyl-L-allothreonyl-glycyl-L-seryl-L-serine bistrifluoroacetate
Yield: 55 mg (70% pure, ~quant.) as a colorless solid from 49 mg of exemplary compound 341A according to procedure 2, crude product reacted further without purification.

HPLC (Method 6): $R_t$ = 3.23 min; LC-MS (Method 19): $R_t$ = 1.37 min, MS (ESIpos): m/z (%) = 580 (100) $[M + 2H]^{2+}$, 1158.6 (5) $[M + H]^+$, MS (ESIneg): m/z (%) = 1156.8 (100) $[M - H]^-$; HR-TOF-MS: $C_{53}H_{84}N_{13}O_{16}$ calc. 1158.6154, found 1158.6183 $[M + H]^+$.

366A

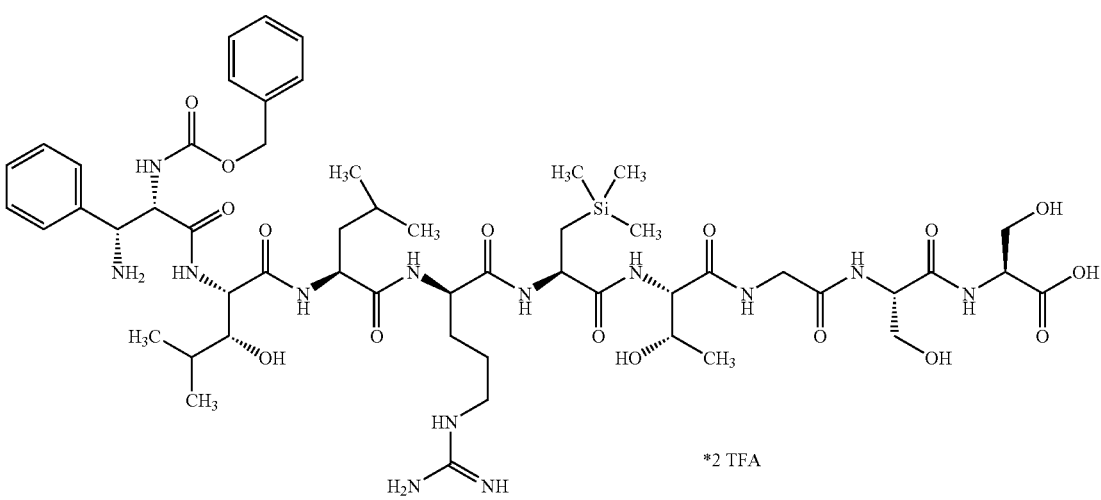

*2 TFA

[(3R)-N²-(Benzyloxycarbonyl)-3-amino-L-phenylalanyl]-[(3R)-3-hydroxy-L-leucyl]-L-leucyl-D-arginyl-[3-trimethylsilyl-L-alanlyl]-L-allothreonyl-glycyl-L-seryl-L-serine bistrifluoroacetate
Yield: 49 mg (~quant.) as a colorless solid from 42 mg of exemplary compound 342A according to procedure 2, crude product reacted further without purification.

HPLC (Method 6): $R_t$ = 3.31 min; LC-MS (Method 19): $R_t$ = 1.47 min, MS (ESIpos): m/z (%) = 595.0 (100) $[M + 2H]^{2+}$, 1188.7 (5) $[M + H]^+$, MS (ESIneg): m/z (%) = 1187.7 (100) $[M - H]^-$; HR-TOF-MS: $C_{53}H_{86}N_{13}O_{16}Si$ calc. 1188.6080, found 1188.6067 $[M + H]^+$.

-continued

Partially deprotected nonapeptides

| No. | Name<br>Yield, Synthesis Method | Structure | Analysis |
|---|---|---|---|

367A

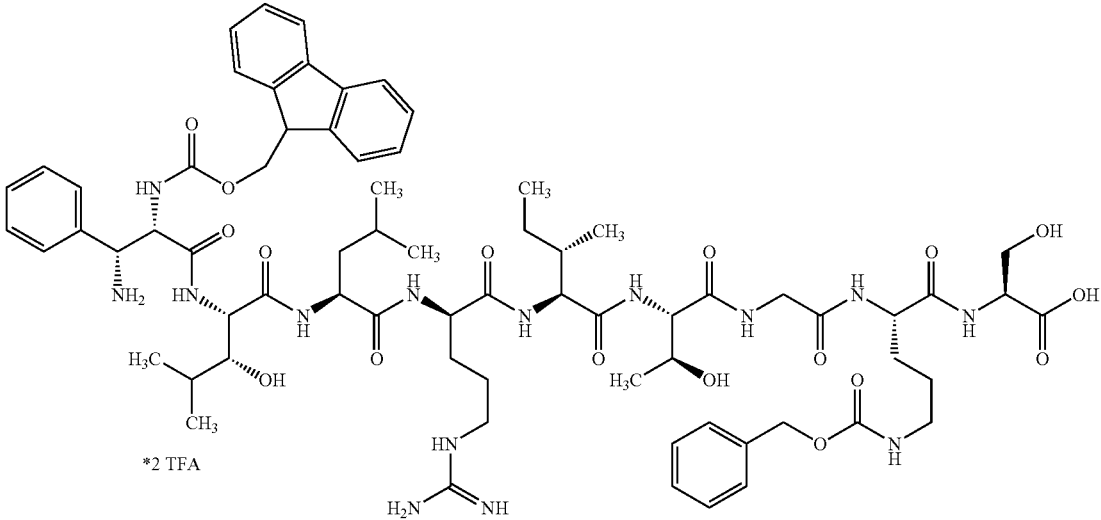

{(3R)-N²-[(9H-Fluoren-9-ylmethoxy)carbonyl]-3-amino-L-phenylalanyl}-[(3R)-3-hydroxy-L-leucyl]-L-leucyl-D-arginyl-L-isoleucyl-L-allothreonyl-glycyl-(N⁵-benzyloxycarbonyl-L-ornithyl-L-serine bistrifluoroacetate
Yield: 42 mg (~quant.) as a colorless solid from 39 mg of exemplary compound 343A according to procedure 2, crude product reacted further without purification.

HPLC (Method 6): $R_t$ = 3.62 min; LC-MS (Method 19): $R_t$ = 1.79 min, MS (ESIpos): m/z (%) = 704.5 (100) [M + 2H]²⁺, MS (ESIneg): m/z (%) = 1406 (100) [M − H]⁻; HR-TOF-MS: $C_{70}H_{99}N_{14}O_{17}$ calc. 1407.7308, found 1407.7306 [M + H]⁺.

368A

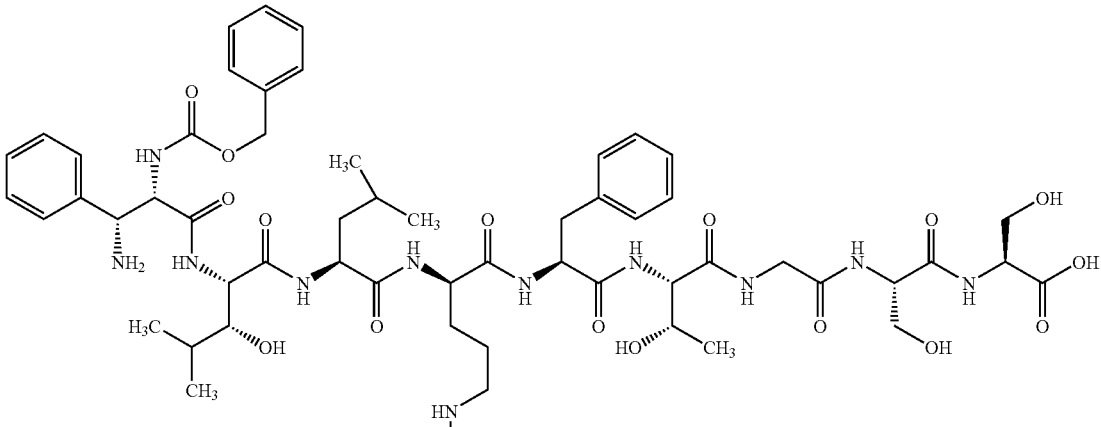

[(3R)-N²-(Benzyloxycarbonyl)-3-amino-L-phenylalanyl]-[(3R)-3-hydroxy-L-leucyl]-L-leucyl-D-arginyl-L-phenylalanlyl-L-allothreonyl-glycyl-L-seryl-L-serine bistrifluoroacetate
Yield: 33 mg (59% of theory) as a colorless solid from 55 mg of exemplary compound 344A according to procedure 2, crude product reacted further without purification.

HPLC (Method 6): $R_t$ = 3.26 min; LC-MS (Method 19): $R_t$ = 1.42 min, MS (ESIpos): m/z (%) = 597.1 (100) [M + 2H]²⁺, MS (ESIneg): m/z (%) = 1190.7 (100) [M − H]⁻.

Partially deprotected nonapeptides

| No. | Name Yield, Synthesis Method | Structure | Analysis |
|---|---|---|---|
| 369A | {(3R)-N²-[(9H-Fluoren-9-ylmethoxy)carbonyl]-3-amino-L-phenylalanyl}-[(3R)-3-hydroxy-L-leucyl]-L-leucyl-D-arginyl-L-isoleucyl-L-allothreonyl-glycyl-[(2S)-2-amino-4-benzyloxycarbonylaminobutyryl]-L-serine bistrifluoroacetate<br>Yield: 87 mg (~quant.) as a colorless solid from 72 mg of exemplary compound 345A according to procedure 2, crude product reacted further without purification. | 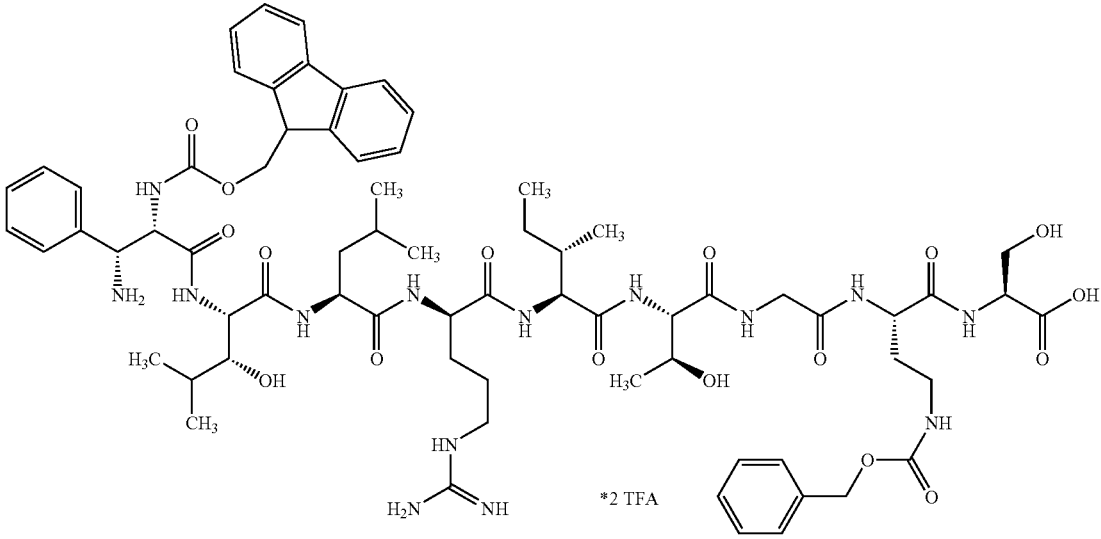 | HPLC (Method 6): $R_t$ = 3.63 min; LC-MS (Method 19): $R_t$ = 1.76 min, MS (ESIpos): m/z (%) = 679.5 (100) [M + 2H]²⁺, MS (ESIneg): m/z (%) = 1391.7 (100) [M − H]⁻; HR-TOF-MS: $C_{69}H_{97}N_{14}O_{17}$ calc. 1393.7151, found 1393.7189 [M + H]⁺. |
| 370A | [(3R)-N²-(Benzyloxycarbonyl)-3-amino-L-leucyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine bistrifluoroacetate<br>Yield: 399 mg (96% pure, ~quant.) as a colorless solid from 311 mg of exemplary compound 346A according to procedure 2, crude product reacted further without purification. | 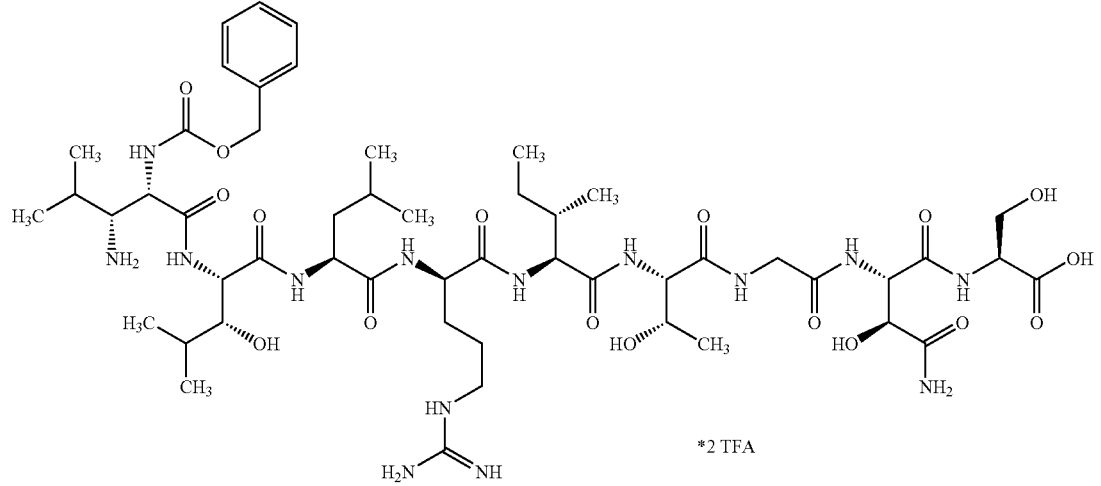 | HPLC (Method 6): $R_t$ = 3.18 min; LC-MS (Method 19): $R_t$ = 1.30 min, MS (ESIpos): m/z (%) = 584.6 (100) [M + 2H]²⁺, MS (ESIneg): m/z (%) = 1165.7 (100) [M − H]⁻. |

| Partially deprotected nonapeptides |
|---|
| Structure |

| No. | Name Yield, Synthesis Method | | Analysis |
|---|---|---|---|

371A

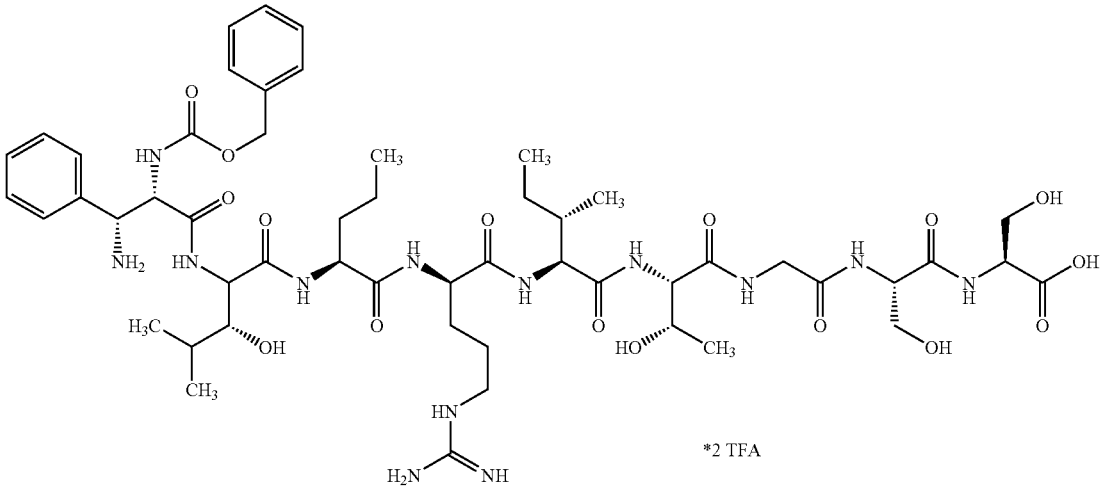

*2 TFA

[(3R)-N²-(Benzyloxycarbonyl)-3-amino-L-phenylalanyl]-[(3R)-3-hydroxy-L-leucyl]-L-norvalyl-D-arginyl-L-isoleucyl-L-allothreonyl-glycyl-L-seryl-L-serine bistrifluoroacetate
Yield: 195 mg (~quant.) as a colorless solid from 173 mg of exemplary compound 347A according to procedure 2, crude product reacted further without purification.

HPLC (Method 6): $R_t$ = 3.18 min; LC-MS (Method 19): $R_t$ = 1.32 min, MS (ESIpos): m/z (%) = 572.9 (100) [M + 2H]²⁺, 1144.7 (5) [M + H]⁺, MS (ESIneg): m/z (%) = 1142.7 (100) [M − H]⁻; HR-TOF-MS: $C_{52}H_{82}N_{13}O_{16}$ calc. 1144.5997, found 1144.6023 [M + H]⁺.

372A

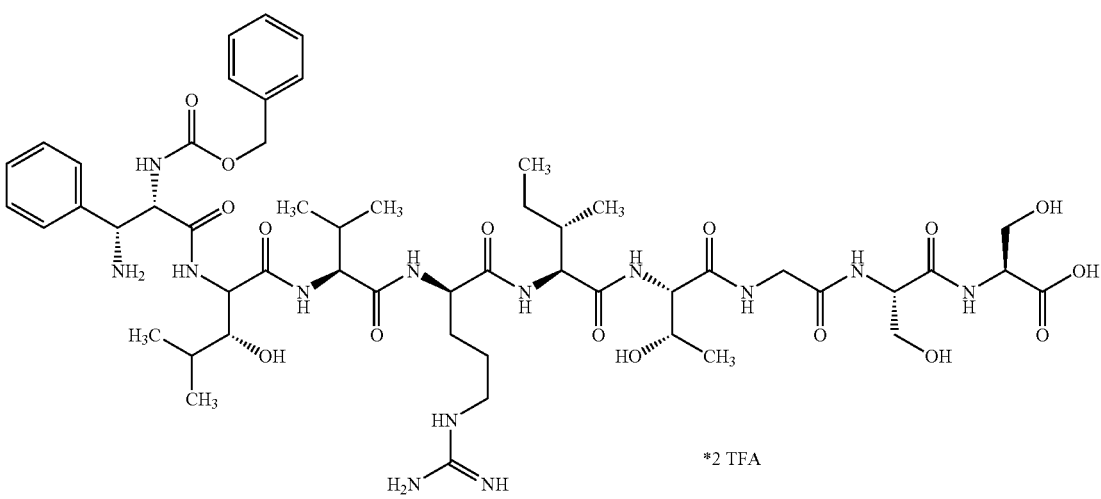

*2 TFA

[(3R)-N²-(Benzyloxycarbonyl)-3-amino-L-phenylalanyl]-[(3R)-3-hydroxy-L-leucyl]-L-valyl-D-arginyl-L-isoleucyl-L-allothreonyl-glycyl-L-seryl-L-serine bistrifluoroacetate
Yield: 67 mg (~quant.) as a colorless solid from 61 mg of exemplary compound 348A according to procedure 2, crude product reacted further without purification.

HPLC (Method 6): $R_t$ = 3.16 min; LC-MS (Method 19): $R_t$ = 1.30 min, MS (ESIpos): m/z (%) = 572.9 (100) [M + 2H]²⁺, 1144.6 (5) [M + H]⁺, MS (ESIneg): m/z (%) = 1142.8 (100) [M − H]⁻; HR-TOF-MS: $C_{52}H_{82}N_{13}O_{16}$ calc. 1144.5997, found 1144.5995 [M + H]⁺.

| Partially deprotected nonapeptides |
| --- |
| Structure |

| No. | Name Yield, Synthesis Method | Analysis |
| --- | --- | --- |
| 373A | 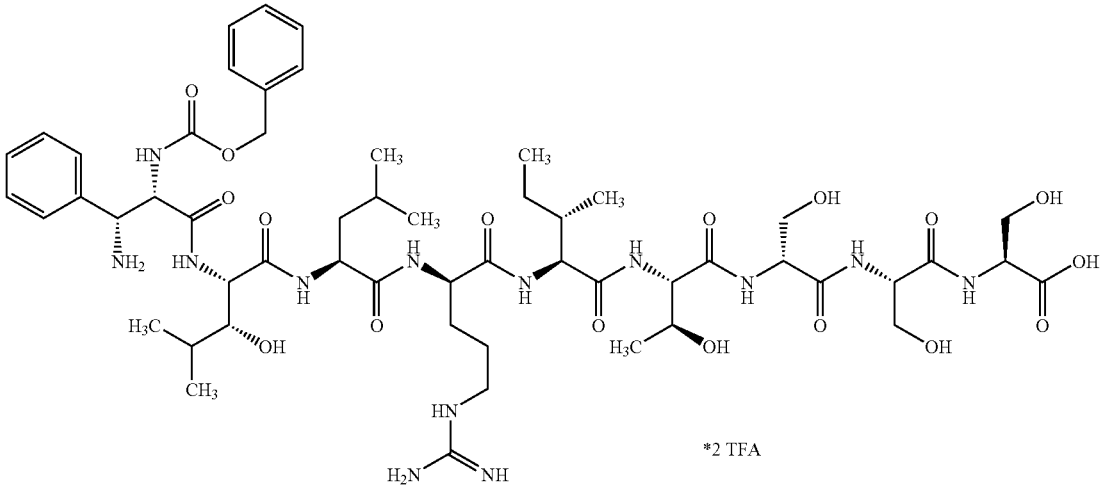 [(3R)-$N^2$-(Benzyloxycarbonyl)-3-amino-L-phenylalanyl]-[(3R)-3-hydroxy-L-leucyl]-L-leucyl-D-arginyl-L-isoleucyl-L-allothreonyl-D-seryl-L-seryl-L-serine bistrifluoroacetate<br>Yield: 89 mg (~quant.) as a colorless solid from 73 mg of exemplary compound 349A according to procedure 2, crude product reacted further without purification. | HPLC (Method 6): $R_t$ = 3.64 min. |
| 374A | 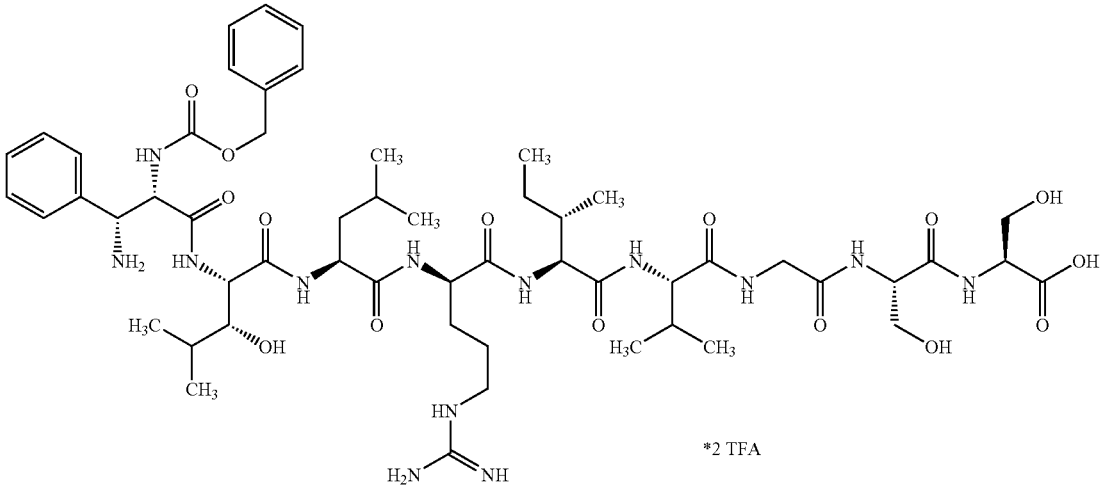 [(3R)-$N^2$-(Benzyloxycarbonyl)-3-amino-L-phenylalanyl]-[(3R)-3-hydroxy-L-leucyl]-L-leucyl-D-arginyl-L-isoleucyl-L-valyl-glycyl-L-seryl-L-serine bistrifluoroacetate<br>Yield: 55 mg (99% of theory) as a colorless solid from 55 mg of exemplary compound 350A according to procedure 2, crude product reacted further without purification. | HPLC (Method 6): $R_t$ = 3.29 min; LC-MS (Method 19): $R_t$ = 1.44 min, MS (ESIpos): m/z (%) = 579.0 (100) [M + 2H]$^{2+}$, 1156.7 (10) [M + H]$^+$, MS (ESIneg): m/z (%) = 1154.8 (100) [M − H]$^-$, HR-TOF-MS: $C_{54}H_{86}N_{13}O_{15}$ calc. 1156.6361, found 1156.6384 [M + H]$^+$. |

Partially deprotected nonapeptides

| No. | Name Yield, Synthesis Method | Structure Analysis |
|---|---|---|
| 375A | [(3R)-N²-(Benzyloxycarbonyl)-3-amino-L-phenylalanyl]-[(3R)-3-hydroxy-L-leucyl]-L-isoleucyl-D-arginyl-L-isoleucyl-L-allothreonyl-glycyl-L-seryl-L-serine bistrifluoroacetate<br>Yield: 39 mg (96% of theory) as a colorless solid from 391 mg of exemplary compound 351A according to procedure 2, crude product reacted further without purification. | HPLC (Method 6): $R_t$ = 3.21 min; LC-MS (Method 19): $R_t$ = 1.35 min, MS (ESIpos): m/z (%) = 580.0 (100) [M + 2H]²⁺, MS (ESIneg): m/z (%) = 1156.7 (100) [M − H]⁻; HR-TOF-MS: $C_{53}H_{84}N_{13}O_{16}$ calc. 1158.6154, found 1158.6184 [M + H]⁺. |
| 376A | {(3R)-N²-[(9H-Fluoren-9-ylmethoxy)carbonyl]-3-amino-L-phenylalanyl}-[(3R)-3-hydroxy-L-leucyl]-L-leucyl-(N⁵-benzyloxycarbonyl-D-ornithyl)-L-isoleucyl-L-allothreonyl-glycyl-L-seryl-L-serine bistrifluoroacetate<br>Yield: 123 mg (~quant.) as a colorless solid from 103 mg of exemplary compound 352A according to procedure 2, crude product reacted further without purification. | HPLC (Method 6): $R_t$ = 3.95 min; LC-MS (Method 19): $R_t$ = 2.15 min, MS (ESIpos): m/z (%) = 1338.7 (100) [M + H]⁺, MS (ESIneg): m/z (%) = 1336.7 (100) [M − H]⁻; HR-TOF-MS: $C_{67}H_{92}N_{11}O_{18}$ calc. 1338.6617, found 1338.6619 [M + H]⁺. |

Partially deprotected nonapeptides

| No. | Name<br>Yield, Synthesis Method | Structure<br>Analysis |
|---|---|---|

377A

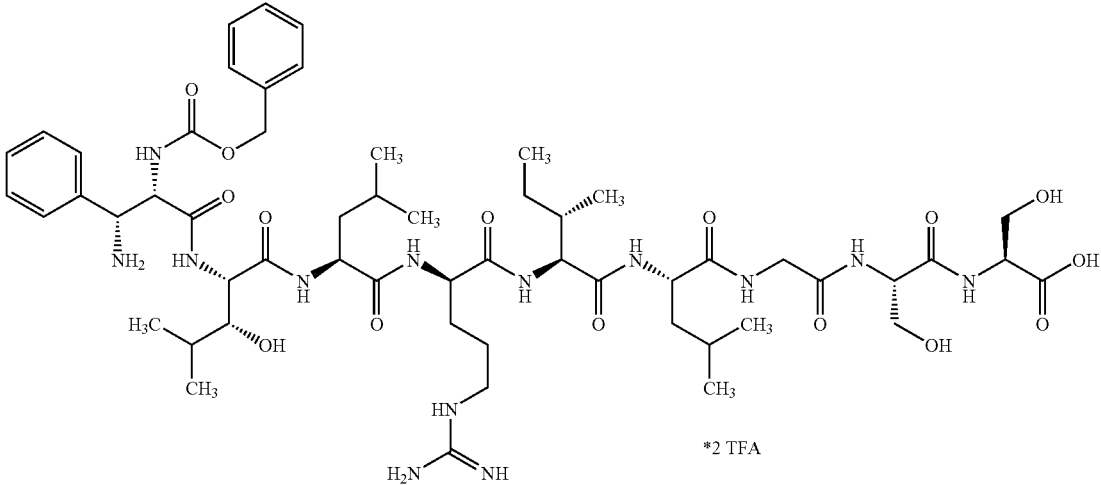

*2 TFA

[(3R)-N²-(Benzyloxycarbonyl)-3-amino-L-phenylalanyl]-[(3R)-3-hydroxy-L-leucyl]-L-leucyl-D-arginyl-L-isoleucyl-L-leucyl-glycyl-L-seryl-L-serine bistrifluoroacetate
Yield: 40 mg (~quant.) as a colorless solid from 40 mg of exemplary compound 353A according to procedure 2, crude product reacted further without purification.

HPLC (Method 6): $R_t$ = 3.32 min, LC-MS (Method 19): $R_t$ = 1.51 min, MS (ESIpos): m/z (%) = 586.0 (100) [M + 2H]$^{2+}$, 1170.0 (5) [M + H]$^+$, MS (ESIneg): m/z (%) = 1168.7 (100) [M − H]$^-$; HR-TOF-MS: $C_{55}H_{88}N_{13}O_{15}$ calc. 1170.6518, found 1170.6501 [M + H]$^+$.

378A

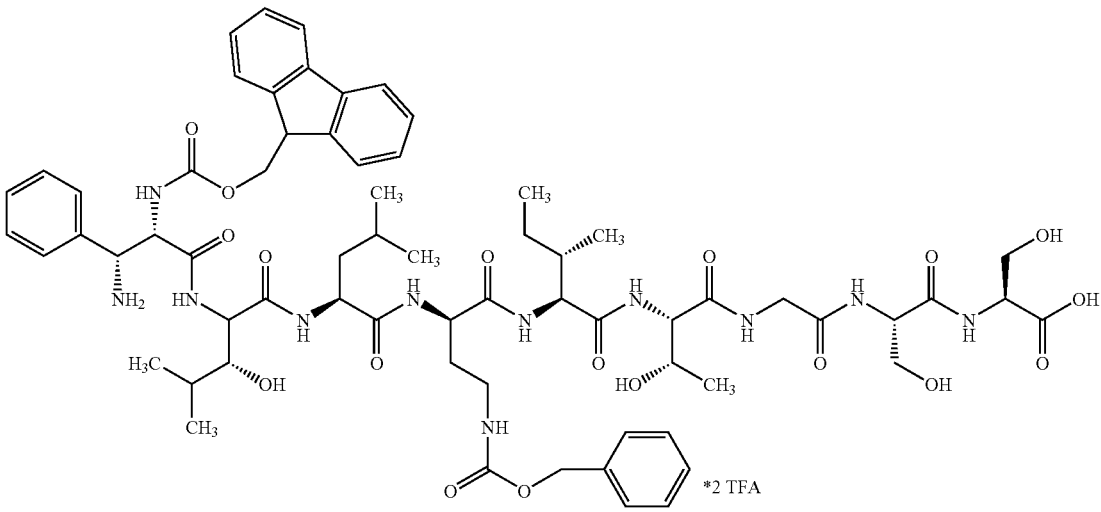

*2 TFA

[(3R)-N²-[(9H-Fluoren-9-ylmethoxy)carbonyl]-3-amino-L-phenylalanyl}-[(3R)-3-hydroxy-L-leucyl]-L-leucyl-[(2R)-2-amino-4-benzyloxycarbonylaminobutyryl]-L-isoleucyl-L-allothreonyl-glycyl-L-seryl-L-serine bistrifluoroacetate
Yield: 131 mg (58% pure, 70% of theory) as a colorless solid from 106 mg of exemplary compound 354A according to procedure 2, crude product reacted further without purification.

HPLC (Method 6): $R_t$ = 3.92 min; LC-MS (Method 19): $R_t$ = 2.14 min, MS (ESIpos): m/z (%) = 1324.6 (100) [M + H]$^+$, MS (ESIneg): m/z (%) = 1322.7 (100) [M − H]$^-$; HR-TOF-MS: $C_{66}H_{90}N_{11}O_{18}$ calc. 1324.6460, found 1324.6471 [M + H]$^+$.

| Partially deprotected nonapeptides |
|---|
| Structure |

| No. | Name Yield, Synthesis Method | Analysis |
|---|---|---|

379A

{(3R)-N²-[(9H-Fluoren-9-ylmethoxy)carbonyl]-3-amino-L-phenylalanyl}-[(3R)-3-hydroxy-L-leucyl]-L-leucyl-(N⁶-benzyloxycarbonyl-D-lysyl)-L-isoleucyl-L-allothreonyl-glycyl-L-seryl L-serine bistrifluoroacetate
Yield: 48 mg (90% of theory) as a colorless solid from 49 mg of exemplary compound 355A according to procedure 2, crude product reacted further without purification.

HPLC (Method 6): $R_t$ = 3.97 min; LC-MS (Method 19): $R_t$ = 2.18 min, MS (ESIpos): m/z (%) = 1352.7 (100) [M + H]⁺, MS (ESIneg): m/z (%) = 1351.7 (100) [M − H]⁻; HR-TOF-MS: $C_{68}H_{94}N_{11}O_{18}$ calc. 1352.6773, found 1352.6771 [M + H]⁺.

380A

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-glycyl-L-serine bistrifluoroacetate
Yield: 167 mg (~quant.) as a colorless solid from 133 mg of exemplary compound 356A according to procedure 2, crude product reacted further without purification.

HPLC (Method 6): $R_t$ = 3.25 min; LC-MS (Method 19): $R_t$ = 1.38 min, MS (ESIpos): m/z (%) = 565.0 (100) [M + 2H]²⁺, MS (ESIneg): m/z (%) = 1126.8 (100) [M − H]⁻; HR-TOF-MS: $C_{52}H_{82}N_{13}O_{15}$ calc. 1128.6048, found 1128.6061 [M + H]⁺.

Partially deprotected nonapeptides

| No. | Name, Yield, Synthesis Method | Structure / Analysis |
|---|---|---|

381A

[(3R)-N²-(Benzyloxycarbonyl)-3-amino-L-phenylalanyl]-[(3R)-3-hydroxy-L-leucyl]-L-norleucyl-D-arginyl-L-isoleucyl-L-allothreonyl-glycyl-L-alanyl-L-serine trifluoroacetate
Yield: 104 mg (quant.) from exemplary compound 357A (95 mg, 70 μmol) according to procedure 2, crude product reacted further without purification.

HPLC (Method 6): $R_t$ = 3.25 min; LC-MS (Method 52): $R_t$ = 1.00 min, MS (ESIpos): m/z (%) = 572.0 (100) [M + 2H]$^{2+}$, MS (ESIneg): m/z (%) = 1140.7 (100) [M − H]$^-$; HR-TOF-MS: $C_{53}H_{84}N_{13}O_{15}$ calc. 1142.6205, found 1142.6184 [M + H]$^+$.

*2 TFA

382A

[(3R)-N²-(Benzyloxycarbonyl)-3-amino-L-phenylalanyl]-[(3R)-3-hydroxy-L-leucyl]-L-norvalyl-D-arginyl-L-isoleucyl-L-allothreonyl-glycyl-L-alanyl-L-serine trifluoroacetate
Yield: 103 mg (quant.) from exemplary compound 358A (87 mg, 65 μmol) according to procedure 2, crude product reacted further without purification.

HPLC (Method 6): $R_t$ = 3.18 min; LC-MS (Method 52): $R_t$ = 0.91 min, MS (ESIpos): m/z (%) = 1128.7 (10) [M + H]$^+$, 565.0 (100) [M + 2H]$^{2+}$, MS (ESIneg): m/z (%) = 1126.7 (100) [M − H]$^-$; HR-TOF-MS: $C_{52}H_{81}N_{13}O_{15}$ calc. 1128.6048, found 1128.6030 [M + H]$^+$.

*2 TFA

| Cyclization |
|---|
| Structure |

| No. | Name<br>Yield, Synthesis Method | Analysis |
|---|---|---|

383A

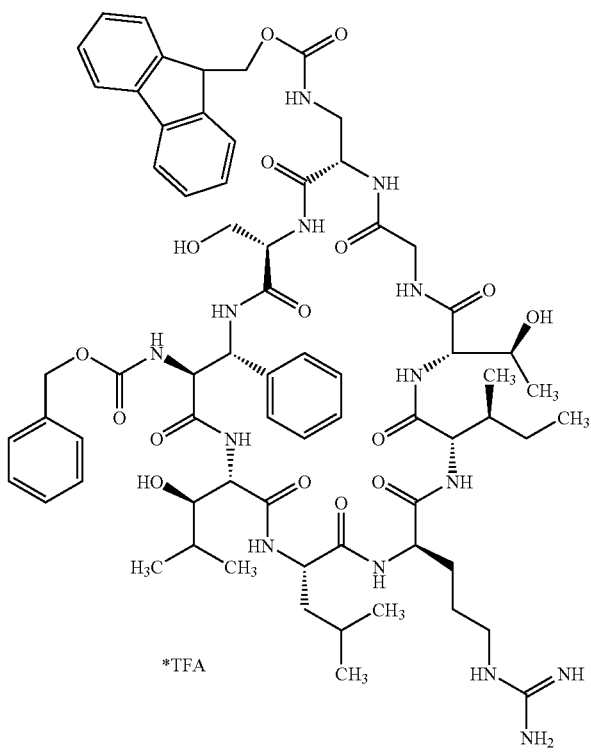

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine $C^{1.9}$-$N^{3.1}$-lactam trifluoroacetate Yield: 590 mg (67% of theory) from exemplary compound 359A (1110 mg, 700 µmol) according to procedure 11, purification according to method 45 and subsequently method 34.

HPLC (Method 6): $R_t$ = 4.07 min; LC-MS (Method 19): $R_t$ = 2.02 min, MS (ESIpos): m/z (%) = 681.6 (100) $[M + 2H]^{2+}$; HR-TOF-MS: $C_{68}H_{93}N_{14}O_{16}$ calc. 1361.6889, found 1361.6866 $[M + H]^+$.

-continued

Cyclization

Structure

| No. | Name Yield, Synthesis Method | Analysis |

384A

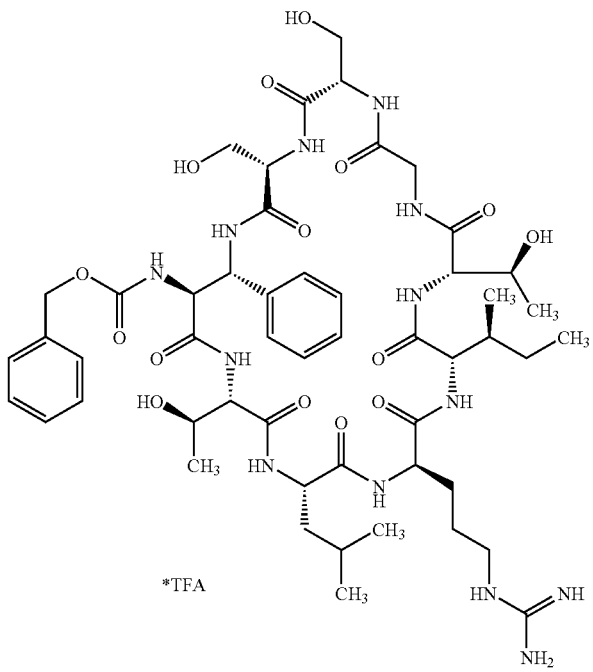

*TFA

[(3R)-N²-(Benzyloxycarbonyl)-3-amino-L-phenylalanyl]-L-threonyl-L-leucyl-D-arginyl-L-isoleucyl-L-allothreonyl-glycyl-L-seryl $C^{1.9}$-$N^{3.1}$-lactam trifluoroacetate
Yield: 14 mg (73% of theory) from exemplary compound 360A (21 mg, 15 μmol) according to procedure 11, purification according to method 45.

HPLC (Method 6): $R_t$ = 3.45 min; LC-MS (Method 19): $R_t$ = 1.56 min, MS (ESIpos): m/z (%) = 1112.6 (50) [M + H]⁺, MS (ESIneg) m/z (%) = 1110.7 (100) [M − H]⁻; HR-TOF-MS: $C_{51}H_{78}N_{13}O_{15}$ calc. 1112.5735, found 1112.5710 [M + H]⁺.

385A

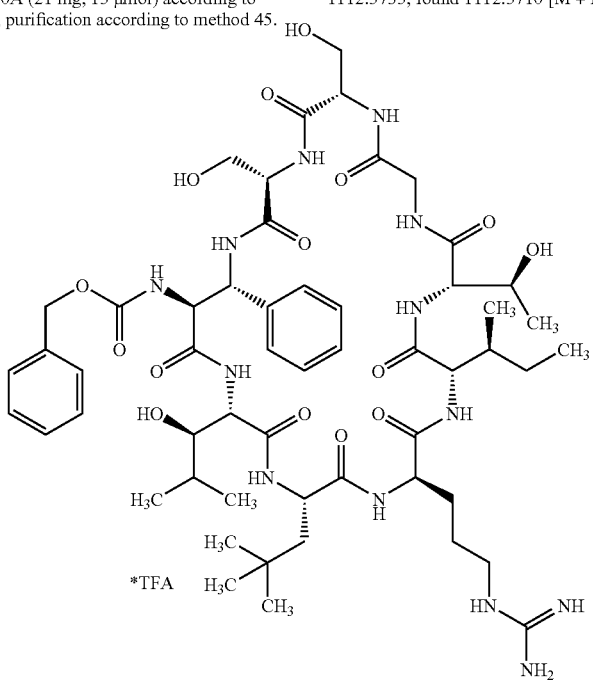

*TFA

[(3R)-N²-(Benzyloxycarbonyl)-3-amino-L-phenylalanyl]-[(3R)-3-hydroxy-L-leucyl]-[3-tertbutyl- HPLC (Method 6): $R_t$ = 3.62 min; LC-MS (Method 19): $R_t$ = 1.58 min, MS (ESIpos):

| Cyclization | |
|---|---|
| Structure | |
| Name<br>No. Yield, Synthesis Method | Analysis |

L-alanyl]-D-arginyl-L-isoleucyl-L-allothreonyl-glycyl-L-seryl-L-serine $C^{1.9}$-$N^{3.1}$-lactam trifluoroacetate
Yield: 30 mg (90% of theory) from exemplary compound 361A (37 mg, 26 μmol) according to procedure 11, purification according to method 45.

m/z (%) = 1154.8 (100) [M + H]$^+$, MS (ESIneg): m/z (%) = 1152.9 (100) [M − H]$^-$; HR-TOF-MS: $C_{54}H_{84}N_{13}O_{15}$ calc. 1154.6205, found 1154.6210 [M + H]$^+$.

386A

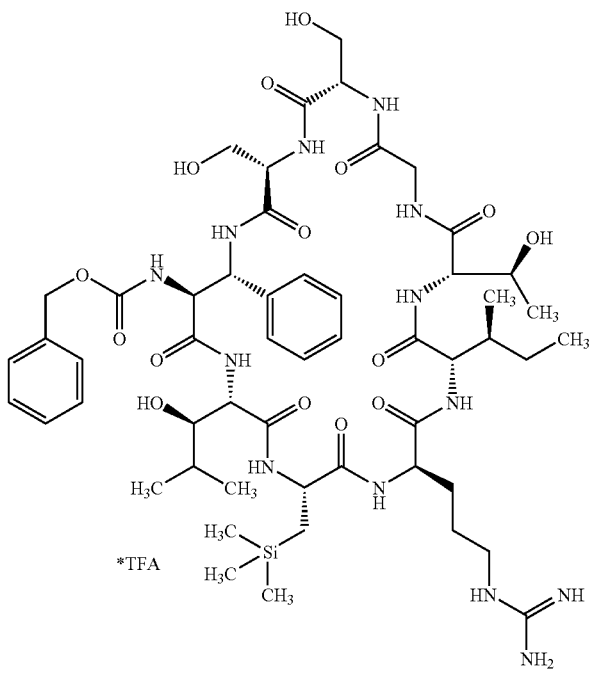

[(3R)-$N^2$-(Benzyloxycarbonyl)-3-amino-L-phenylalanyl]-[(3R)-3-hydroxy-L-leucyl]-(3-trimethylsilyl-L-alanyl)-D-arginyl-L-isoleucyl-L-allothreonyl-glycyl-L-seryl-L-serine $C^{1.9}$-$N^{3.1}$-lactam trifluoroacetate
Yield: 54 mg (98% of theory) from exemplary compound 362A (37 mg, 26 μmol) according to procedure 11, purification according to method 45.

HPLC (Method 6): $R_t$ = 3.68 min; LC-MS (Method 19): $R_t$ = 1.62 min, MS (ESIpos): m/z (%) = 586 (100) [M + 2H]$^{2+}$, 1170.8 (70) [M + H]$^+$, MS (ESIneg) m/z (%) = 1168.8 (100) [M − H]$^-$; HR-TOF-MS: $C_{53}H_{84}N_{13}O_{15}$ calc. 1170.5974, found 1170.5962 [M + H]$^+$.

Cyclization

| No. | Name Yield, Synthesis Method | Structure | Analysis |
|---|---|---|---|

387A

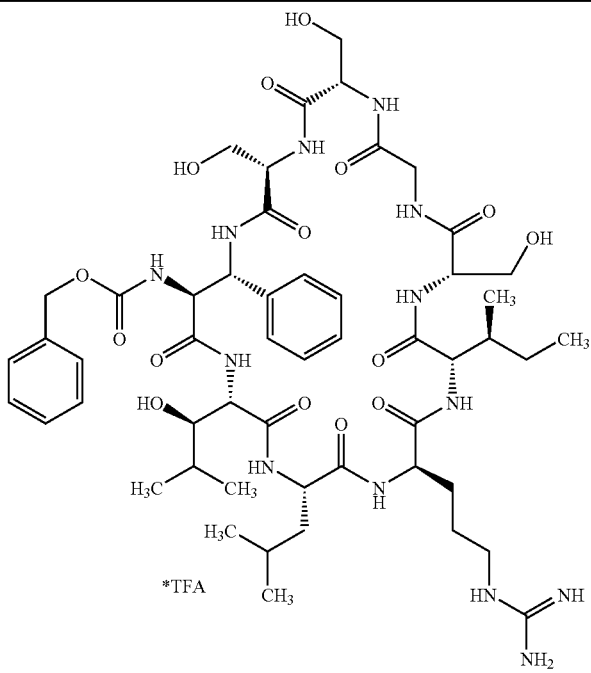

[(3R)-N²-(Benzyloxycarbonyl)-3-amino-L-phenylalanyl]-[(3R)-3-hydroxy-L-leucyl]-L-leucyl-D-arginyl-L-isoleucyl-L-seryl-glycyl-L-seryl-L-serine $C^{1.9}$-$N^{3.1}$-lactam trifluoroacetate
Yield: 31 mg (81% of theory) from exemplary compound 363A (48 mg, 31 μmol) according to procedure 11, purification according to method 45.

HPLC (Method 6): $R_t$ = 3.53 min; LC-MS (Method 19): $R_t$ = 1.56 min, MS (ESIpos): m/z (%) = 1126.6 (100) [M + H]⁺, MS (ESIneg): m/z (%) = 1124.7 (100) [M − H]⁻.

388A

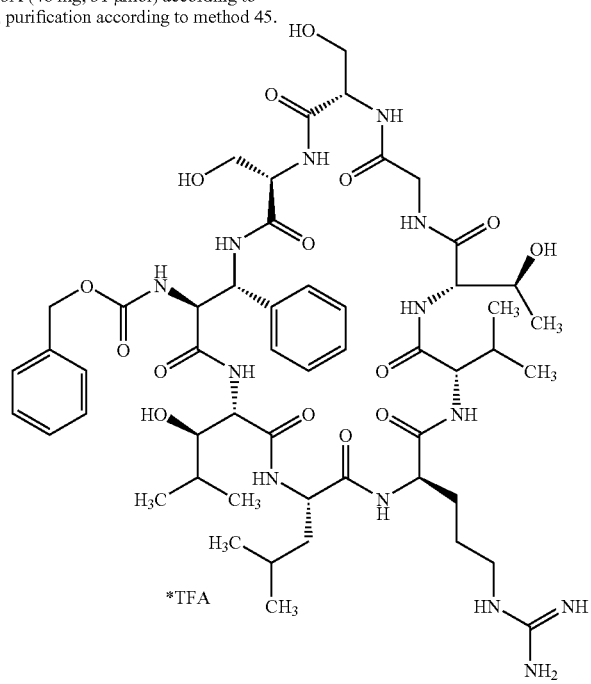

[(3R)-N²-(Benzyloxycarbonyl)-3-amino-L-phenylalanyl]-[(3R)-3-hydroxy-L-leucyl]-L-leucyl-D-

HPLC (Method 6): $R_t$ = 3.48 min; LC-MS (Method 19): $R_t$ = 1.56 min, MS (ESIpos):

-continued

| | Cyclization | |
|---|---|---|
| | Structure | |
| No. | Name<br>Yield, Synthesis Method | Analysis |
| | arginyl-L-valyl-L-allothreonyl-glycyl-L-seryl-L-serine $C^{1.9}$-$N^{3.1}$-lactam trifluoroacetate<br>Yield: 77 mg (41% pure, 91% of theory) from exemplary compound 364A (54 mg, 28 μmol) according to procedure 11, purification according to method 45. | m/z (%) = 564.0 (90) [M + 2H]$^{2+}$, 1126.7 (90) [M + H]$^+$, MS (ESIneg): m/z (%) = 1125.8 (100) [M – H]$^-$; HR-TOF-MS: $C_{52}H_{80}N_{13}O_{15}$ calc. 1126.5892, found 1126.5864 [M + H]$^+$. |

389A

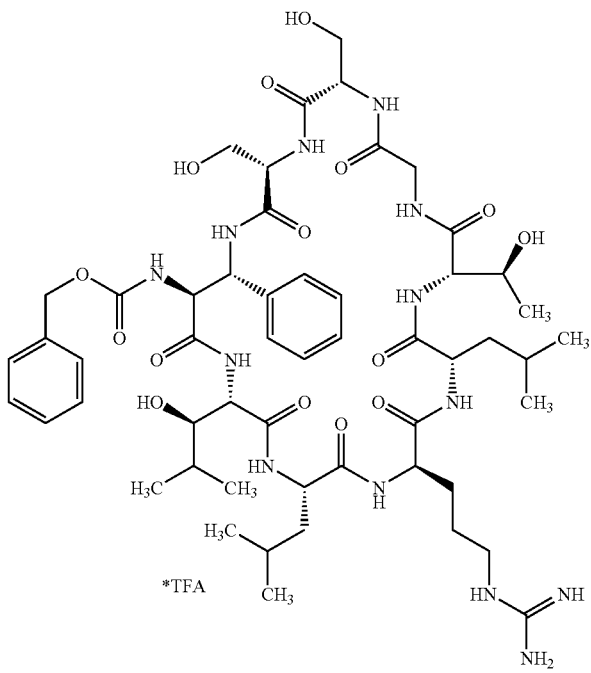

[(3R)-$N^2$-(Benzyloxycarbonyl)-3-amino-L-phenylalanyl]-[(3R)-3-hydroxy-L-leucyl]-L-leucyl-D-arginyl-L-leucyl-L-allothreonyl-glycyl-L-seryl-L-serine $C^{1.9}$-$N^{3.1}$-lactam trifluoroacetate
Yield: 78 mg (39% pure, 87% of theory) from exemplary compound 365A (55 mg, 28 μmol) according to procedure 11, purification according to method 45.

HPLC (Method 6): $R_t$ = 3.58 min; LC-MS (Method 19): $R_t$ = 1.63 min, MS (ESIpos): m/z (%) = 571.6 (30) [M + 2H]$^{2+}$, 1140.8 (100) [M + H]$^+$, MS (ESIneg): m/z (%) = 1138.9 (100) [M – H]$^-$; HR-TOF-MS: $C_{53}H_{82}N_{13}O_{15}$ calc. 1140.6048, found 1140.6014 [M + H]$^+$.

-continued

| Cyclization |
|---|
| Structure |

| No. | Name Yield, Synthesis Method | Analysis |
|---|---|---|

390A

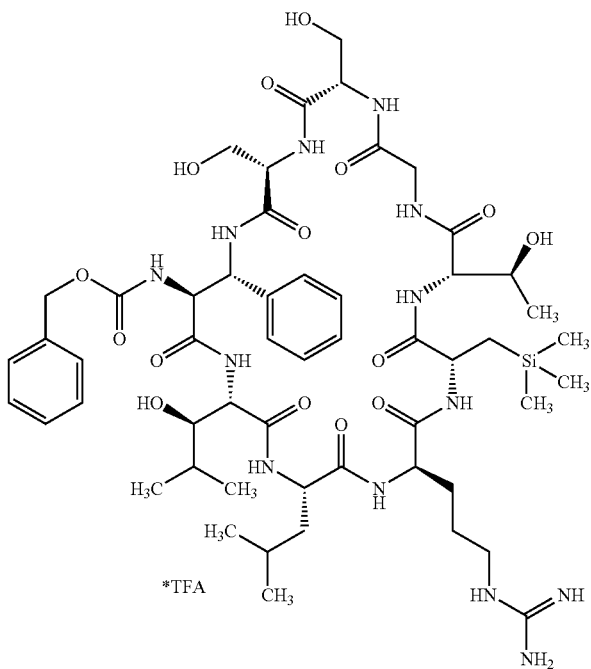

[(3R)-N²-(Benzyloxycarbonyl)-3-amino-L-phenylalanyl]-[(3R)-3-hydroxy-L-leucyl]-L-leucyl-D-arginyl-[3-trimethylsilyl-L-alanlyl]-L-allothreonyl-glycyl-L-seryl-L-serine $C^{1.9}$-$N^{3.1}$-lactam trifluoroacetate
Yield: 55 mg (42% pure, 51% of theory) from exemplary compound 366A (54 mg, 35 µmol) according to procedure 11, purification according to method 45.

HPLC (Method 6): $R_t$ = 3.70 min; LC-MS (Method 19): $R_t$ = 1.73 min, MS (ESIpos): m/z (%) = 586.1 (60) $[M + 2H]^{2+}$, 1170.8 (100) $[M + H]^+$, MS (ESIneg): m/z (%) = 1168.7 (100) $[M - H]^-$; HR-TOF-MS: $C_{53}H_{84}N_{13}O_{15}Si$ calc. 1170.5974, found 1170.5972 $[M + H]^+$.

-continued

Cyclization

Structure

| No. | Name Yield, Synthesis Method | Analysis |
|---|---|---|

391A

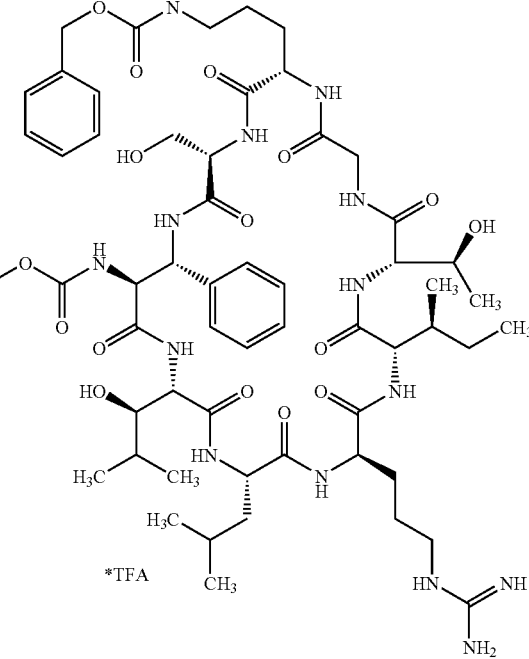

{(3R)-N²-[(9H-Fluoren-9-ylmethoxy)carbonyl]-3-amino-L-phenylalanyl}-[(3R)-3-hydroxy-L-leucyl]-L-leucyl-D-arginyl-L-isoleucyl-L-allothreonyl-glycyl-(N⁵-benzyloxycarbonyl-L-ornithyl-L-serine $C^{1.9}$-$N^{3.1}$-lactam trifluoroacetate Yield: 34 mg (88% of theory) from exemplary compound 367A (42 mg, 26 µmol) according to procedure 11, purification according to method 45.

HPLC (Method 6): $R_t$ = 4.08 min; LC-MS (Method 19): $R_t$ = 2.02 min, MS (ESIpos): m/z (%) = 695.7 (100) [M + 2H]²⁺, 1389.7 (50) [M + H]⁺, MS (ESIneg): m/z (%) = 1387.8 (80) [M − H]⁻; HR-TOF-MS: $C_{70}H_{97}N_{14}O_{16}$ calc. 1389.7202, found 1389.7228 [M + H]⁺.

392A

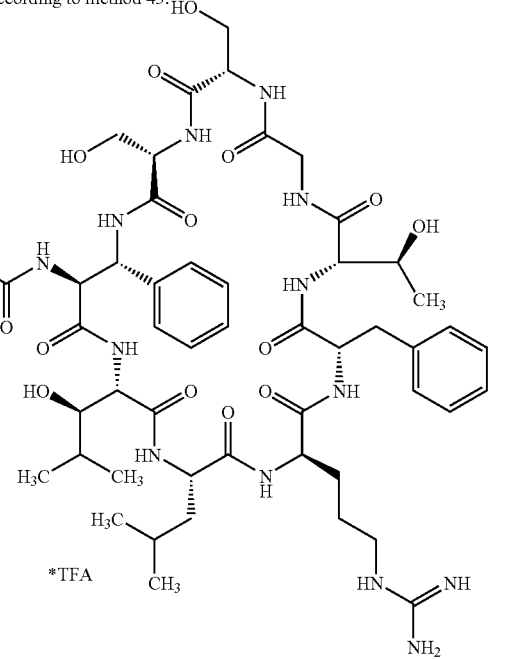

[(3R)-N²-(Benzyloxycarbonyl)-3-amino-L-phenylalanyl]-[(3R)-3-hydroxy-L-leucyl]-L-leucyl-D-

HPLC (Method 6): $R_t$ = 3.61 min; LC-MS (Method 19): $R_t$ = 1.67 min, MS (ESIpos):

-continued

Cyclization

Structure

| No. | Name Yield, Synthesis Method | Analysis |
|---|---|---| arginyl-L-phenylalanlyl-L-allothreonyl-glycyl-L-seryl-L-serine $C^{1.9}$-$N^{3.1}$-lactam trifluoroacetate Yield: 23 mg (76% of theory) from exemplary compound 368A (33 mg, 23 μmol) according to procedure 11, purification according to method 45.

m/z (%) = 1174.7 (80) $[M + H]^+$, MS (ESIneg s): m/z (%) = 1172.7 (100) $[M - H]^-$.

393A

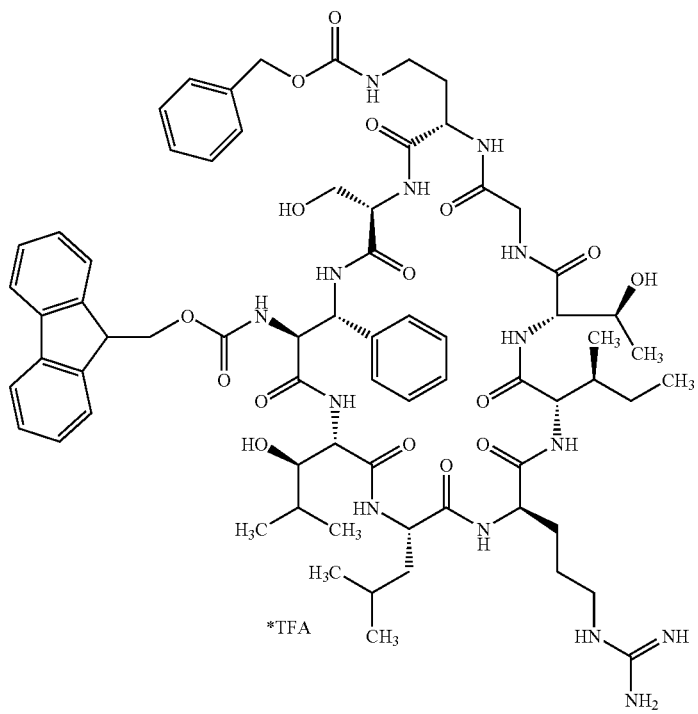

{(3R)-$N^2$-[(9H-Fluoren-9-ylmethoxy)carbonyl]-3-amino-L-phenylalanyl}-[(3R)-3-hydroxy-L-leucyl]-L-leucyl-D-arginyl-L-isoleucyl-L-allothreonyl-glycyl-[(2S)-2-amino-4-benzyloxycarbonylaminobutyryl]-L-serine $C^{1.9}$-$N^{3.1}$-lactam trifluoroacetate Yield: 80 mg (58% pure, 66% of theory) from exemplary compound 369A (77 mg, 47 μmol) according to procedure 11, purification according to method 45.

HPLC (Method 6): $R_t$ = 4.07 min; LC-MS (Method 19): $R_t$ = 2.04 min, MS (ESIpos): m/z (%) = 688.5 (100) $[M + 2H]^{2+}$, 1376.7 (60) $[M + H]^+$, MS (ESIneg): m/z (%) = 1374.7 (60) $[M - H]^-$; HR-TOF-MS: $C_{69}H_{95}N_{14}O_{16}$ calc. 1375.7045, found 1375.7006 $[M + H]^+$.

| | Cyclization |
|---|---|
| | Structure |
| No. | Name Yield, Synthesis Method | Analysis |

394A

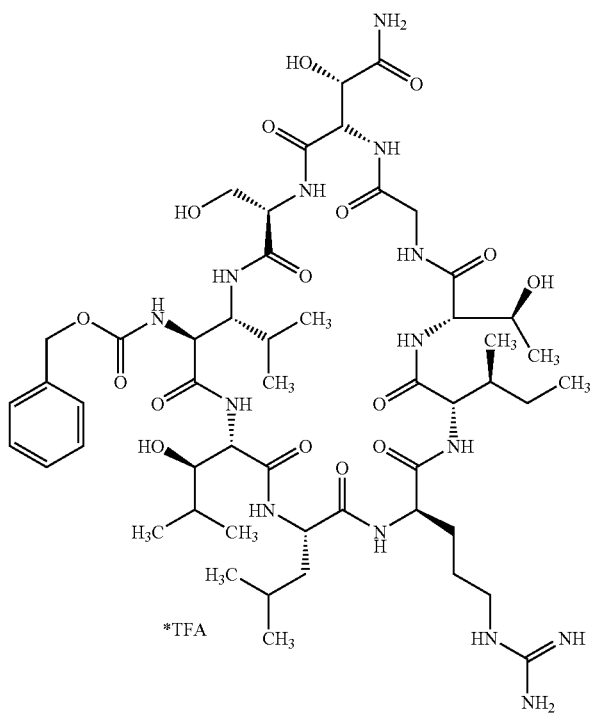

[(3R)-N²-(Benzyloxycarbonyl)-3-amino-L-leucyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine $C^{1.9}$-$N^{3.1}$-lactam trifluoroacetate
Yield: 275 mg (2 isomers, 61% pure, total 53% of theory) from exemplary compound 370A (399 mg, 252 μmol) according to procedure 11, purification according to method 45.

HPLC (Method 6): $R_t$ = 3.48 and 3.57 min; LC-MS (Method 19): $R_t$ = 1.56 and 1.60 min, MS (ESIpos): m/z (%) = 575.7 (80) [M + 2H]²⁺, 1149.8 (100) [M + H]⁺; HR-TOF-MS: $C_{51}H_{85}N_{14}O_{16}$ calc. 1149.6263, found 1149.6283 [M + H]⁺.

| No. | Name Yield, Synthesis Method | Analysis |
|---|---|---|

395A

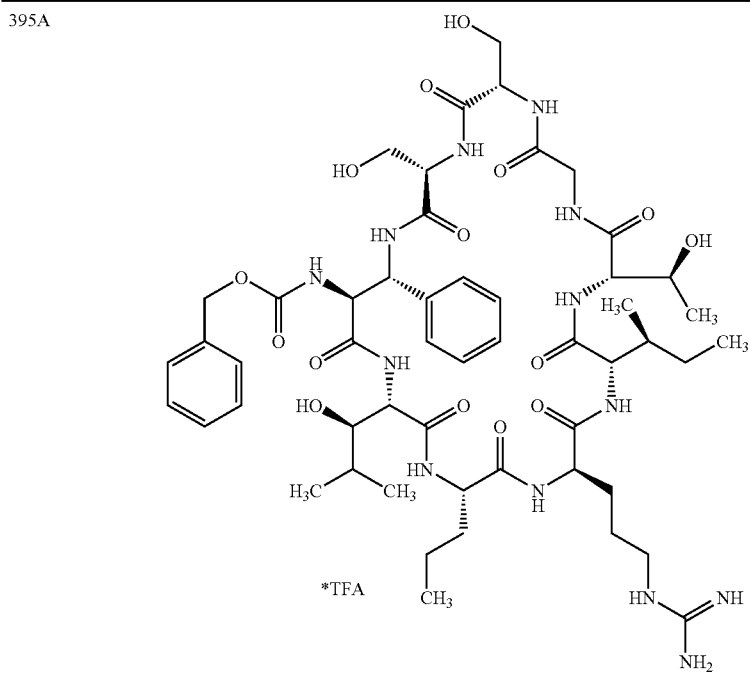

*TFA

[(3R)-N²-(Benzyloxycarbonyl)-3-amino-L-phenylalanyl]-[(3R)-3-hydroxy-L-leucyl]-L-norvalyl-D-arginyl-L-isoleucyl-L-allothreonyl-glycyl-L-seryl-L-serine C$^{1.9}$-N$^{3.1}$-lactam trifluoroacetate
Yield: 135 mg (77% of theory) from exemplary compound 371A (195 mg, 142 µmol) according to procedure 11, purification according to method 45.

HPLC (Method 6): R$_t$ = 3.49 min; LC-MS (Method 19): R$_t$ = 1.57 min, MS (ESIpos): m/z (%) = 1126.6 (100) [M + H]$^+$, MS (ESIneg): m/z (%) = 1124.6 (100) [M − H]$^-$; HR-TOF-MS: C$_{52}$H$_{80}$N$_{13}$O$_{15}$ calc. 1126.5892, found 1126.5864 [M + H]$^+$.

396A

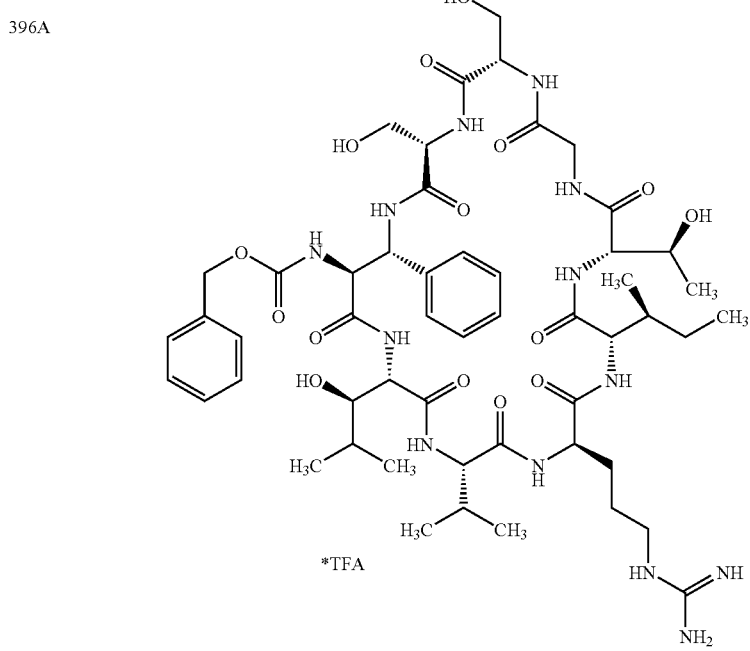

*TFA

[(3R)-N²-(Benzyloxycarbonyl)-3-amino-L-phenylalanyl]-[(3R)-3-hydroxy-L-leucyl]-L-valyl-D-

HPLC (Method 6): R$_t$ = 3.51 min, LC-MS (Method 19): R$_t$ = 1.58 min, MS (ESIpos):

Cyclization

Structure

| No. | Name<br>Yield, Synthesis Method | Analysis |
|---|---|---|
| | arginyl-L-isoleucyl-L-allothreonyl-glycyl-L-seryl-L-serine $C^{1.9}$-$N^{3.1}$-lactam trifluoroacetate<br>Yield: 61 mg (quant.) from exemplary compound 372A (67 mg, 49 μmol) according to procedure 11, purification according to method 45. | m/z (%) = 1126.7 (100) $[M + H]^+$, MS (ESIneg): m/z (%) = 1125.7 (100) $[M - H]^-$; 1170.8 (40) $[M + HCOO^-]^-$; HR-TOF-MS: $C_{52}H_{80}N_{13}O_{15}$ calc. 1126.5892, found 1126.5880 $[M + H]^+$. |

397A

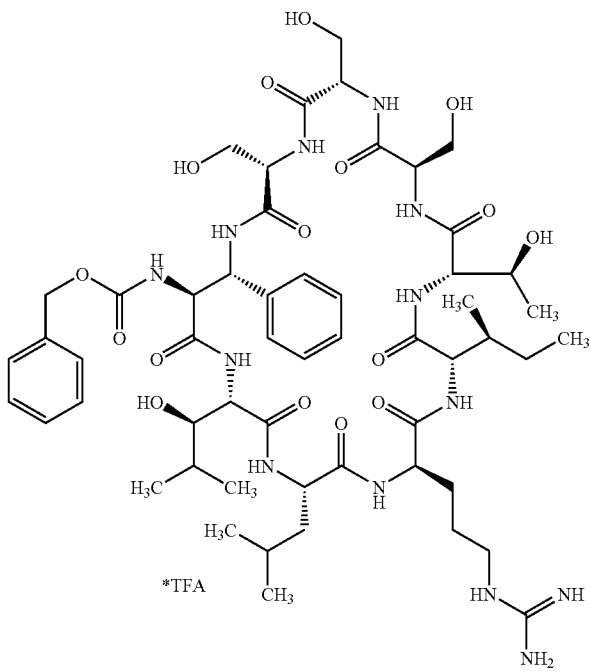

| | [(3R)-$N^2$-(Benzyloxycarbonyl)-3-amino-L-phenylalanyl]-[(3R)-3-hydroxy-L-leucyl]-L-leucyl-D-arginyl-L-isoleucyl-L-allothreonyl-D-seryl-L-seryl-L-serine $C^{1.9}$-$N^{3.1}$-lactam trifluoroacetate<br>Yield: 71 mg (93% of theory) from exemplary compound 373A (84 mg, 59 μmol) according to procedure 11, purification according to method 45. | HPLC (Method 6): $R_t$ = 3.51 min; LC-MS (Method 19): $R_t$ = 1.59 min, MS (ESIpos): m/z (%) = 586.0 (70) $[M + 2H]^{2+}$, 1170.7 (100) $[M + H]^+$, MS (ESIneg): m/z (%) = 1168.7 (100) $[M - H]^-$; HR-TOF-MS: $C_{54}H_{84}N_{13}O_{16}$ calc. 1170.6154, found 1170.6132 $[M + H]^+$. |

-continued

Cyclization

Structure

| No. | Name Yield, Synthesis Method | Analysis |
|---|---|---|

398A

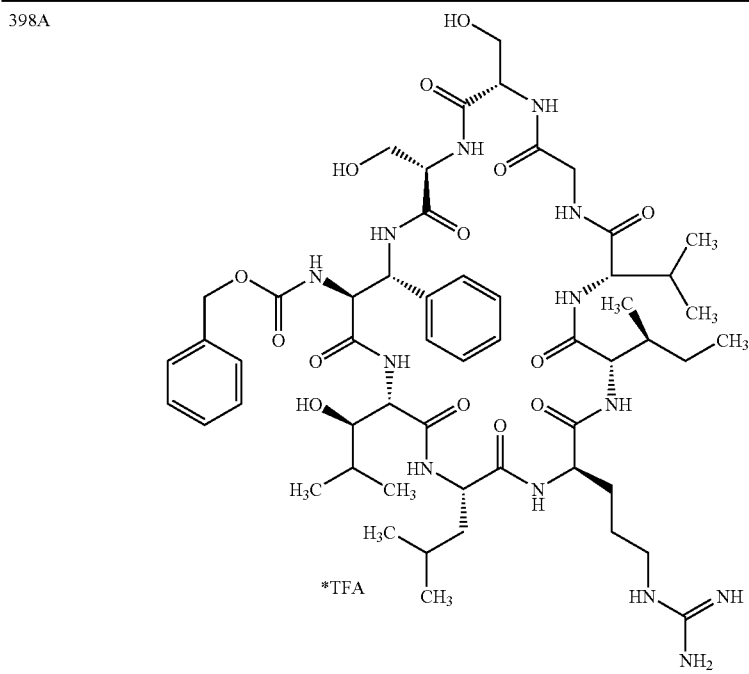

[(3R)-N²-(Benzyloxycarbonyl)-3-amino-L-phenylalanyl]-[(3R)-3-hydroxy-L-leucyl]-L-leucyl-D-arginyl-L-isoleucyl-L-valyl-glycyl-L-seryl-L-serine $C^{1.9}$-$N^{3.1}$-lactam trifluoroacetate
Yield: 31 mg (62% of theory) from exemplary compound 374A (55 mg, 40 µmol) according to procedure 11, purification according to method 45.

HPLC (Method 6): $R_t$ = 3.62 min; LC-MS (Method 19): $R_t$ = 1.65 min, MS (ESIpos): m/z (%) = 1138.6 (100) $[M + H]^+$, MS (ESIneg): m/z (%) = 1136.7 (100) $[M - H]^-$; HR-TOF-MS: $C_{54}H_{84}N_{13}O_{14}$ calc. 1138.6256, found 1138.6219 $[M + H]^+$.

399A

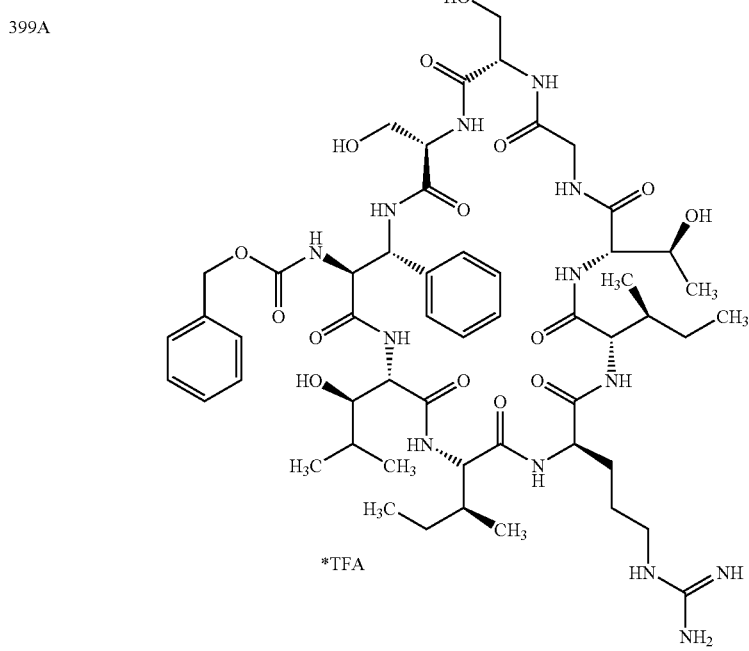

[(3R)-N²-(Benzyloxycarbonyl)-3-amino-L-phenylalanyl]-[(3R)-3-hydroxy-L-leucyl]-L-isoleucyl- HPLC (Method 6): $R_t$ = 3.50 min; LC-MS (Method 19): $R_t$ = 1.62 min, MS (ESIpos):

| Cyclization |
|---|
| Structure |

| No. | Name<br>Yield, Synthesis Method | Analysis |
|---|---|---|
| | D-arginyl-L-isoleucyl-L-allothreonyl-glycyl-L-seryl-L-serine $C^{1.9}$-$N^{3.1}$-lactam trifluoroacetate<br>Yield: 22 mg (95% pure, 62% of theory) from exemplary compound 375A (39 mg, 27 μmol) according to procedure 11, purification according to method 45. | m/z (%) = 1140.7 (100) [M + H]$^+$, MS (ESIneg): m/z (%) = 1138.7 (100) [M − H]$^-$. |

400A

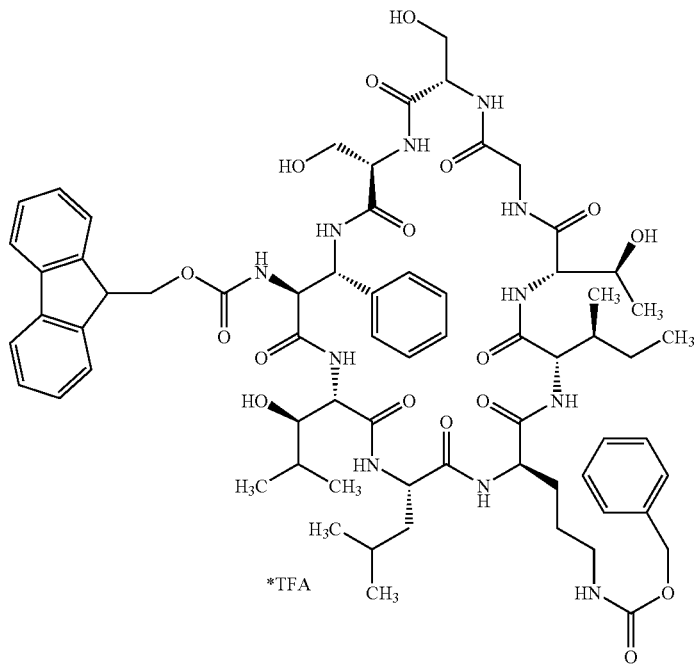

*TFA

{(3R)-$N^2$-[(9H-Fluoren-9-ylmethoxy)carbonyl]-3-amino-L-phenylalanyl}-[(3R)-3-hydroxy-L-leucyl]-L-leucyl-($N^5$-benzyloxycarbonyl-D-ornithyl)-L-isoleucyl-L-allothreonyl-glycyl-L-seryl-L-serine $C^{1.9}$-$N^{3.1}$-lactam trifluoroacetate
Yield: 93 mg (50% pure, 48% of theory) from exemplary compound 376A (107 mg, 74 μmol) according to procedure 11, purification according to method 45.

HPLC (Method 6): $R_t$ = 4.46 min; LC-MS (Method 19): $R_t$ = 2.64 min, MS (ESIpos): m/z (%) = 1320.7 (100) [M + H]$^+$, MS (ESIneg): m/z (%) = 1319.6 (80) [M − H]$^-$; HR-TOF-MS: $C_{67}H_{90}N_{11}O_{17}$ calc. 1320.6511, found 1320.6536 [M + H]$^+$.

-continued

Cyclization

Structure

| No. | Name Yield, Synthesis Method | Analysis |
|---|---|---|

401A

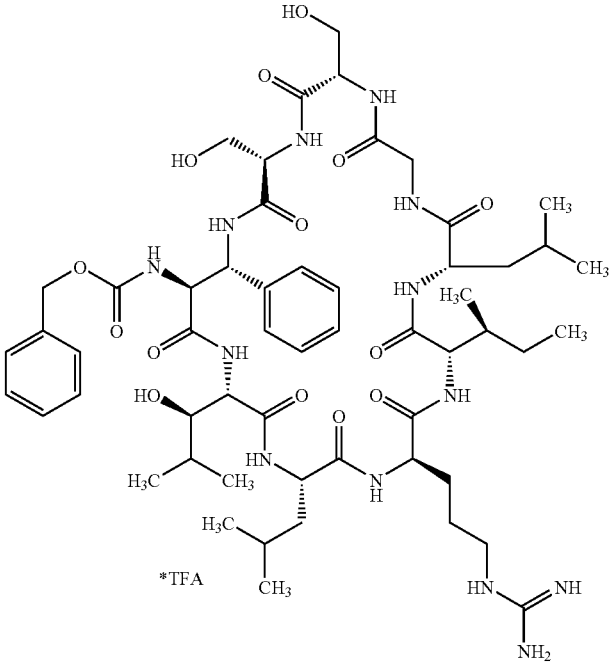

[(3R)-N²-(Benzyloxycarbonyl)-3-amino-L-phenylalanyl]-[(3R)-3-hydroxy-L-leucyl]-L-leucyl-D-arginyl-L-isoleucyl-L-leucyl-glycyl-L-seryl-L-serine $C^{1.9}$-$N^{3.1}$-lactam trifluoroacetate
Yield: 35 mg (97% of theory) from exemplary compound 377A (40 mg, 29 μmol) according to procedure 11, purification according to method 45.

HPLC (Method 6): $R_t$ = 3.67 min; LC-MS (Method 19): $R_t$ = 1.70 min, MS (ESIpos): m/z (%) = 1152.7 (100) [M + H]⁺, MS (ESIneg): m/z (%) = 1150.7 (100) [M − H]⁻; HR-TOF-MS: $C_{55}H_{86}N_{13}O_{14}$ calc. 1152.6412, found 1152.6426 [M + H]⁺.

402A

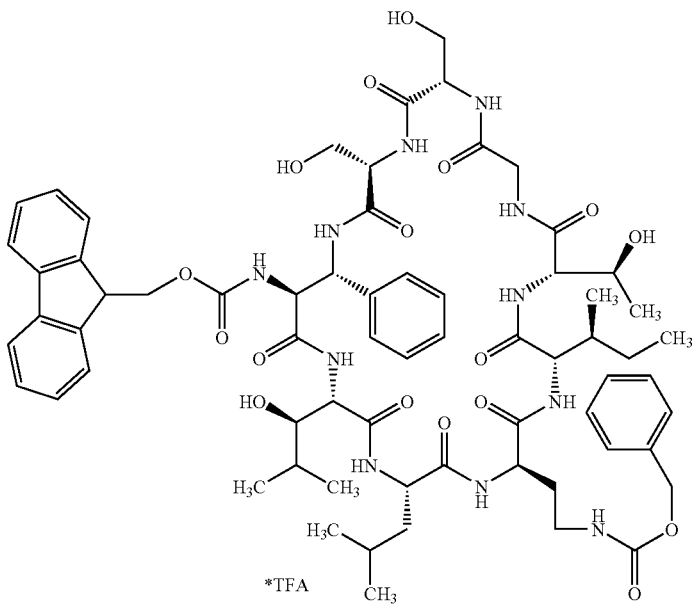

{(3R)-N²-[(9H-Fluoren-9-ylmethoxy)carbonyl]-3-amino-L-phenylalanyl}-[(3R)-3-hydroxy-L-leucyl]-L-leucyl-[(2R)-2-amino-4-

HPLC (Method 6): $R_t$ = 4.45 min; LC-MS (Method 19): $R_t$ = 2.63 min, MS (ESIpos): m/z (%) = 1306.6 (100) [M + H]⁺, MS

Cyclization

Structure

| No. | Name<br>Yield, Synthesis Method | Analysis |
|---|---|---|
| | benzyloxycarbonylaminobutyryl]-L-isoleucyl-L-allothreonyl-glycyl-L-seryl-L-serine $C^{1.9}$-$N^{3.1}$-lactam trifluoroacetate<br>Yield: 96 mg (86% pure, 85% of theory) from exemplary compound 378A (107 mg, 74 µmol) according to procedure 11, purification according to method 45. | (ESIneg): m/z (%) = 1305.5 (60) [M − H]$^-$;<br>HR-TOF-MS: $C_{66}H_{88}N_{11}O_{17}$ calc. 1306.6355, found 1306.6365 [M + H]$^+$. |
| 403A | 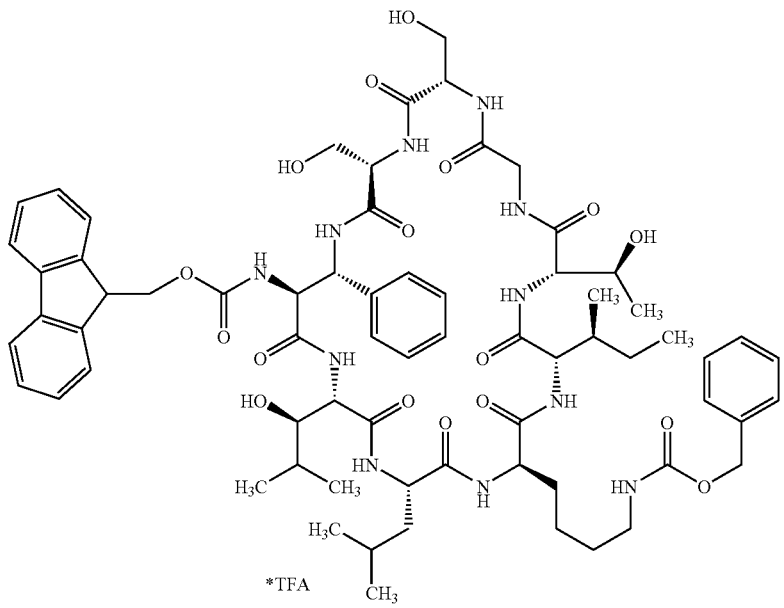<br>*TFA<br><br>{(3R)-$N^2$-[(9H-Fluoren-9-ylmethoxy)carbonyl]-3-amino-L-phenylalanyl}-[(3R)-3-hydroxy-L-leucyl]-L-leucyl-($N^6$-benzyloxycarbonyl-D-lysyl)-L-isoleucyl-L-allothreonyl-glycyl-L-seryl-L-serine $C^{1.9}$-$N^{3.1}$-lactam trifluoroacetate<br>Yield: 46 mg (64% pure, 78% of theory) from exemplary compound 379A (48 mg, 26 µmol) according to procedure 11, purification according to method 45. | HPLC (Method 6): R$_t$ = 4.44 min; LC-MS (Method 19): R$_t$ = 2.64 min, MS (ESIpos): m/z (%) = 1335.6 (100) [M + H]$^+$, MS (ESIneg): m/z (%) = 1333.6 (80) [M − H]$^-$;<br>HR-TOF-MS: $C_{68}H_{92}N_{11}O_{17}$ calc. 1334.6668, found 1334.6653 [M + H]$^+$. |

-continued

Cyclization

Structure

| No. | Name Yield, Synthesis Method | Analysis |
|---|---|---|

404A

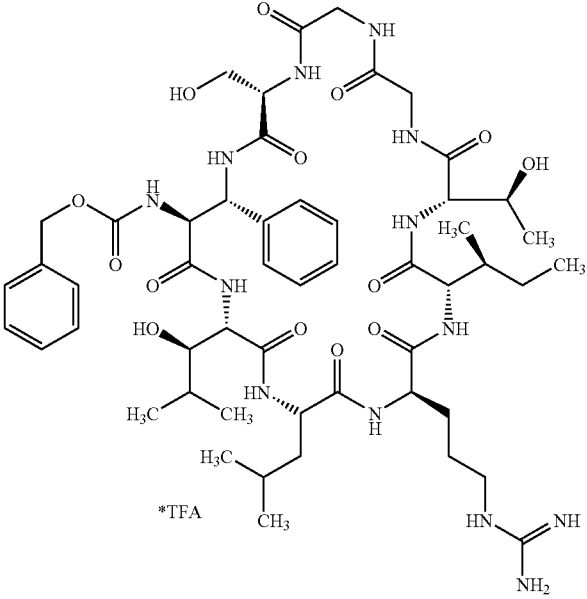

*TFA

[(3R)-N²-(Benzyloxycarbonyl)-3-amino-L-phenylalanyl]-[(3R)-3-hydroxy-L-leucyl]-L-leucyl-D-arginyl-L-isoleucyl-L-allothreonyl-glycyl-glycyl-L-serine $C^{1.9}$-$N^{3.1}$-lactam trifluoroacetate
Yield: 160 mg (25% pure, 38% of theory) from exemplary compound 380A (167 mg, 86 µmol) according to procedure 11, purification according to method 45.

HPLC (Method 6): $R_t$ = 3.61 min; LC-MS (Method 19): $R_t$ = 1.62 min, MS (ESIpos): m/z (%) = 1110.8 (60) [M + H]⁺, MS (ESIneg): m/z (%) = 1108.8 (100) [M − H]⁻; HR-TOF-MS: $C_{52}H_{80}N_{13}O_{14}$ calc. 1110.5943, found 1110.5898 [M + H]⁺.

405A

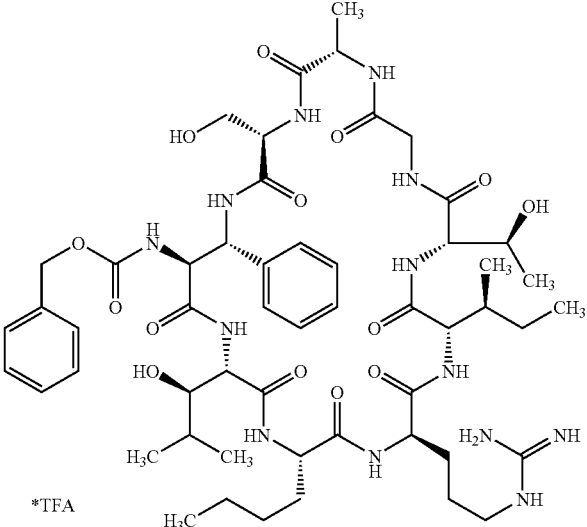

*TFA

[(3R)-N²-(Benzyloxycarbonyl)-3-amino-L-phenylalanyl]-[(3R)-3-hydroxy-L-leucyl]-L-norleucyl-D-arginyl)-L-isoleucyl-L-allothreonyl-glycyl-L-alanyl-L-serine $C^{1.9}$-$N^{3.1}$-lactam trifluoroacetate
Yield: 74 mg (80% of theory) from exemplary compound 381A (103 mg, 75 µmol) according to procedure 11, purification according to method 45.

HPLC (Method 6): $R_t$ = 3.65 min; LC-MS (Method 19): $R_t$ = 1.69 min, MS (ESIpos): m/z (%) = 1124.6 (100) [M + H]⁺, MS (ESIneg): m/z (%) = 1122.7 (100) [M − H]⁻; HR-TOF-MS: $C_{53}H_{82}N_{13}O_{14}$ calc. 1124.6099, found 1124.6068 [M + H]⁺.

| Cyclization |
|---|
| Structure |

| No. | Name Yield, Synthesis Method | Analysis |
|---|---|---|

406A

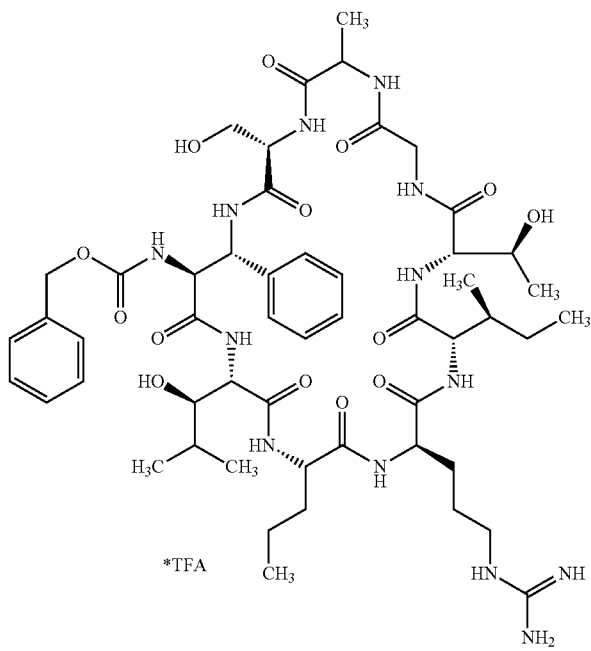

[(3R)-N²-(Benzyloxycarbonyl)-3-amino-L-phenylalanyl]-[(3R)-3-hydroxy-L-leucyl]-L-norvalyl-D-arginyl-L-isoleucyl-L-allothreonyl-glycyl-L-alanyl-L-serine $C^{1.9}$-$N^{3.1}$-lactam trifluoroacetate
Yield: 107 mg (quant.) from exemplary compound 382A (103 mg, 76 µmol) according to procedure 11, purification according to method 45.

HPLC (Method 6): $R_t$ = 3.57 min; LC-MS (Method 19): $R_t$ = 1.62 min, MS (ESIpos): m/z (%) = 1110.7 (100) [M + H]⁺, MS (ESIneg): m/z (%) = 1108.6 (100) [M − H]⁻; HR-TOF-MS: $C_{52}H_{80}N_{13}O_{14}$ calc. 1110.5943, found 1110.5936 [M + H]⁺.

| No. | Name Yield, Synthesis Method | Analysis |
|---|---|---|
| 407A | 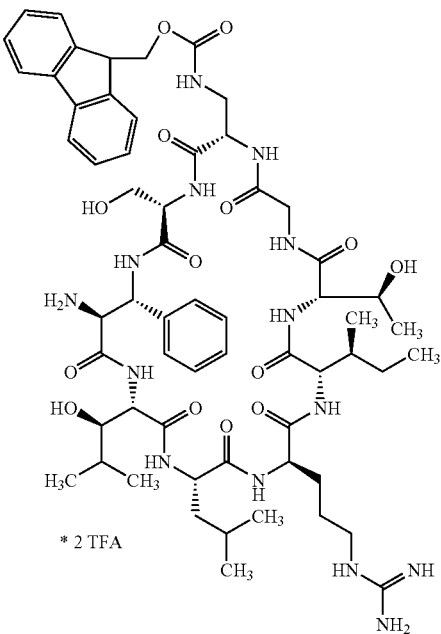 | |
| | [(3R)-3-Amino-L-phenylalanyl]-[(3R)-3-hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine $C^{1.9}$-$N^{3.1}$-lactam bishydrochloride<br>Yield: 368 mg (63% of theory) from exemplary compound 383A (590 mg, 400 µmol) according to procedure 4, purification according to method 34. | HPLC (Method 6): $R_t$ = 3.51 min;<br>LC-MS (Method 19): $R_t$ = 1.73 min,<br>MS (ESIpos): m/z (%) = 614.6 (100) $[M + 2H]^{2+}$, 1227.8 (100) $[M + H]^+$;<br>HR-TOF-MS: $C_{60}H_{87}N_{14}O_{14}$ calc 1227.6521, found 1227.6506 $[M + H]^+$. |
| 408A | 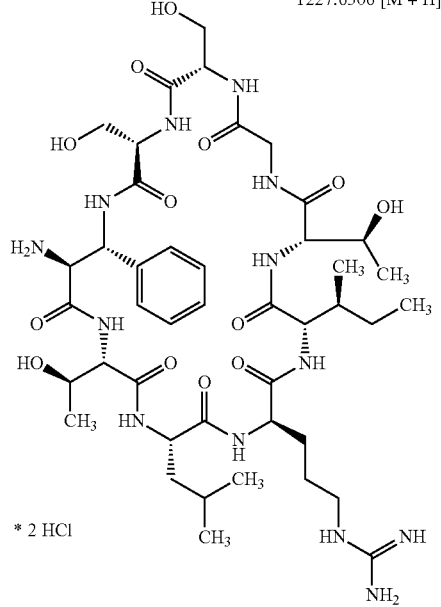 | |
| | [(3R)-3-Amino-L-phenylalanyl]-L-threonyl-L-leucyl-D-arginyl-L- | HPLC (Method 6): $R_t$ = 2.87 min; |

-continued

| | | |
|---|---|---|
| | isoleucyl-L-allothreonyl-glycyl-L-seryl $C^{1.9}$-$N^{3.1}$-lactam bishydrochloride<br>Yield: 10 mg (86% of theory) from exemplary compound 384A (13 mg, 11 µmol) according to procedure 4. | LC-MS (Method 22): $R_t$ = 2.23 min,<br>MS (ESIpos): m/z (%) = 490 (100) $[M + 2H]^{2+}$,<br>MS (ESIneg): m/z (%) = 977 (100) $[M - H]^-$;<br>HR-TOF-MS: $C_{43}H_{72}N_{13}O_{13}$ calc. 978.5368, found 978.5376 $[M + H]^+$. |
| 409A | 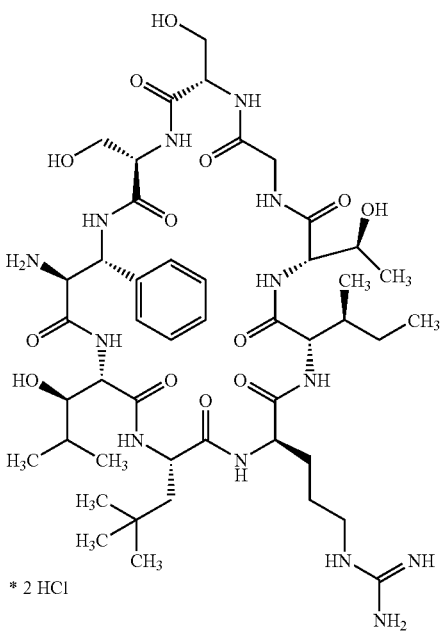 | |
| | [(3R)-3-Amino-L-phenylalanyl]-[(3R)-3-hydroxy-L-leucyl]-[3-tertbutyl-L-alanyl]-D-arginyl-L-isoleucyl-L-allothreonyl-glycyl-L-seryl-L-serine $C^{1.9}$-$N^{3.1}$-lactam bishydrochloride<br>Yield: 25 mg (63% of theory) from exemplary compound 385A (30 mg, 24 µmol) according to procedure 4. | HPLC (Method 6): $R_t$ = 3.07 min;<br>LC-MS (Method 19): $R_t$ = 0.86 min,<br>MS (ESIpos): m/z (%) = 511.0 (100) $[M + 2H]^{2+}$,<br>MS (ESIneg): m/z (%) = 1018.8 (100) $[M - H]^-$;<br>HR-TOF-MS: $C_{46}H_{78}N_{13}O_{13}$ calc. 1020.5837, found 1020.5822 $[M + H]^+$. |

410A

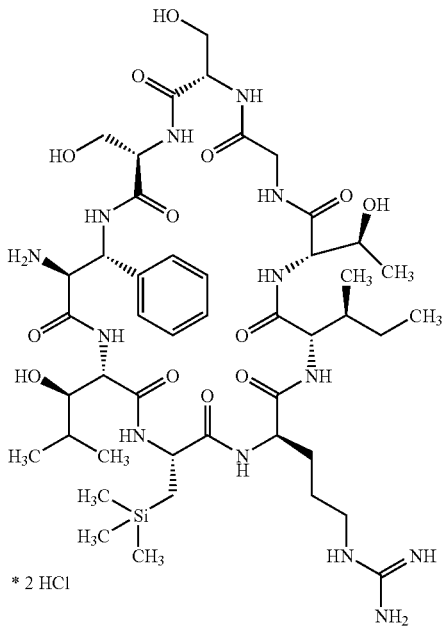

* 2 HCl

[(3R)-3-Amino-L-phenylalanyl]-[(3R)-3-hydroxy-L-leucyl]-(3-trimethylsilyl-L-alanyl)-D-arginyl-L-isoleucyl-L-allothreonyl-glycyl-L-seryl-L-serine $C^{1.9}$-$N^{3.1}$-lactam bishydrochloride
Yield: 41 mg (90% of theory) from exemplary compound 386A (48 mg, 37 µmol) according to procedure 4.

HPLC (Method 6): $R_t$ = 3.12 min;
LC-MS (Method 19): $R_t$ = 1.04 min,
MS (ESIpos):
m/z (%) = 519.2 (100) [M +H]$^+$, 1036.8 (10) [M + H]$^+$, MS (ESIneg): m/z (%) = 1034.8 (100) [M − H]$^−$;
HR-TOF-MS:
$C_{45}H_{78}N_{13}O_{13}Si$ calc. 1036.5606, found 1036.5598 [M + H]$^+$.

411A

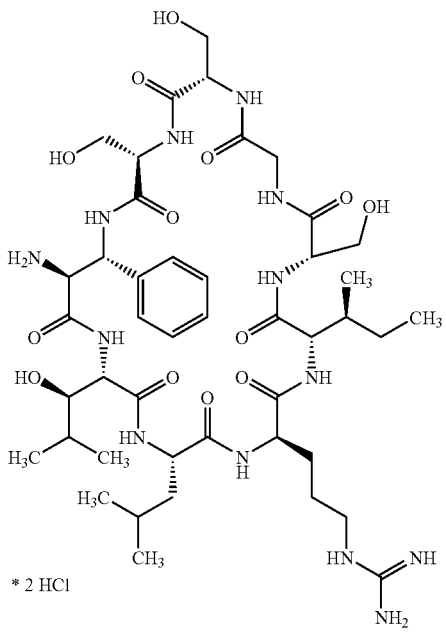

* 2 HCl

[(3R)-3-Amino-L-phenylalanyl]-[(3R)-3-hydroxy-L-leucyl]-L-leucyl-D-L-arginyl-isoleucyl-L-seryl-glycyl-L-seryl-L-serine $C^{1.9}$-$N^{3.1}$-lactam HPLC (Method 6): $R_t$ = 2.96 min;
LC-MS (Method 22): $R_t$ = 2.29 min, bishydrochloride
Yield: 26 mg (98% of theory) from exemplary compound 387A (31 mg, 37 µmol) according to procedure 4.

MS (ESIpos):
m/z (%) = 497 (100) [M + 2H]$^{2+}$,
MS (ESIneg):
m/z (%) = 990.6 (100) [M − H]$^−$;
HR-TOF-MS:
$C_{44}H_{74}N_{13}O_{13}$ calc. 992.5524, found 992.5505 [M + H]$^+$.

412A

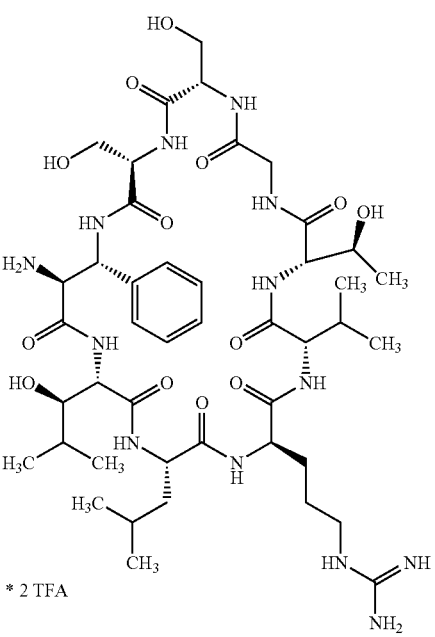

* 2 TFA

[(3R)-3-Amino-L-phenylalanyl]-[(3R)-3-hydroxy-L-leucyl]-L-leucyl-D-arginyl-L-valyl-L-allothreonyl-glycyl-L-seryl-L-serine $C^{1.9}$-$N^{3.1}$-lactam bistrifluoroacetate
Yield: 57 mg of crude product (~quant.) from exemplary compound 388A (54 mg, 37 µmol) according to procedure 4 as a yellowish amorphous powder.

HPLC (Method 6): $R_t$ = 2.91 min;
LC-MS (Method 19): $R_t$ = 0.78 min,
MS (ESIpos):
m/z (%) = 496.9 (100) [M + 2H]$^{2+}$, 992.6 (10) [M + H]$^+$;
HR-TOF-MS:
$C_{44}H_{74}N_{13}O_{13}$ calc. 992.5524, found 992.5518 [M + H]$^+$.

413A

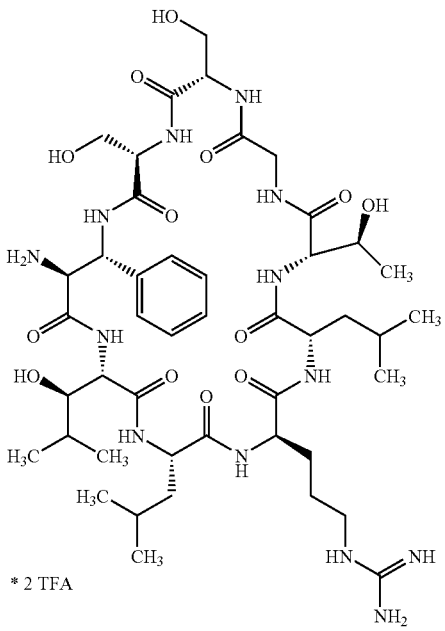

* 2 TFA

[(3R)-3-Amino-L-phenylalanyl]-[(3R)-3-hydroxy-L-leucyl]-L-leucyl-D-arginyl-L-leucyl-L-allothreonyl-glycyl-L-seryl-L-serine $C^{1.9}$-$N^{3.1}$-lactam bistrifluoroacetate
Yield: 57 mg (85% pure, 89% of theory) from exemplary compound 389A (55 mg, 44 μmol) according to procedure 4 as a yellowish amorphous powder.

HPLC (Method 6): $R_t$ = 2.97 min;
LC-MS (Method 19): $R_t$ = 0.95 min,
MS (ESIpos):
m/z (%) = 504.0 (100) $[M + 2H]^{2+}$,
MS (ESIneg):
m/z (%) = 1004.7 (10) $[M - H]^-$;
HR-TOF-MS:
$C_{45}H_{75}N_{13}O_{13}$ calc. 1006.5681, found 1006.5715 $[M + H]^+$.

414A

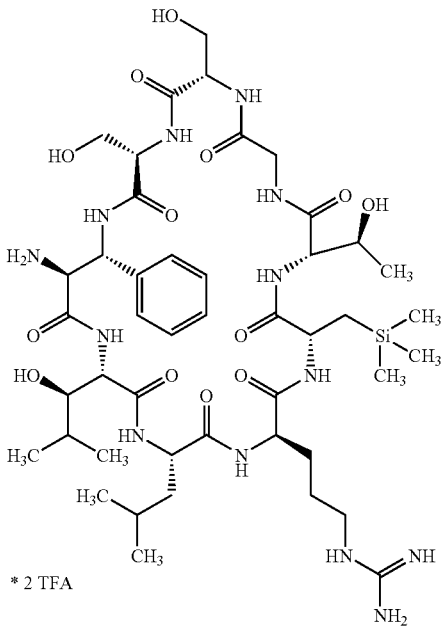

* 2 TFA

[(3R)-3-Amino-L-phenylalanyl]-[(3R)-3-hydroxy-L-leucyl]-L-leucyl-D-arginyl-[3-trimethylsilyl-L-alanlyl]-L-allothreonyl-glycyl-L-seryl-L-serine HPLC (Method 6): $R_t$ = 3.10 min;
LC-MS (Method 19): $R_t$ = 1.13 min, $C^{1.9}$-$N^{3.1}$-lactam bistrifluoroacetate
Yield: 74 mg of crude product from exemplary compound 390A (55 mg, 60% pure, 26 μmol) according to procedure 4 as a yellowish amorphous powder.

MS (ESIpos):
m/z (%) = 519.1 (100) $[M + 2H]^{2+}$, 1036.7 (10) $[M + H]^+$;
MS (ESIneg):
m/z (%) = 1034.6 (100) $[M - H]^-$;
HR-TOF-MS:
$C_{45}H_{78}N_{13}O_{13}Si$ calc. 1036.5606, found 1036.5604 $[M + H]^+$.

415A

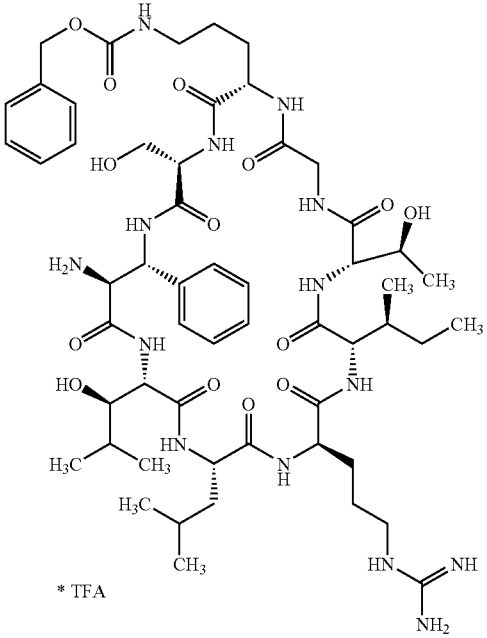

* TFA

{(3R)-3-Amino-L-phenylalanyl}-[(3R)-3-hydroxy-L-leucyl]-L-leucyl-D-arginyl-L-isoleucyl-L-allothreonyl-glycyl-($N^5$-benzyloxycarbonyl-L-ornithyl-L-serine $C^{1.9}$-$N^{3.1}$-lactam bishydrochloride
Yield: 39 mg (70% pure, 76% of theory) from exemplary compound 391A (42 mg, 28 μmol) according to procedure 12, purification according to method 45.

HPLC (Method 6): $R_t$ = 3.32 min,
LC-MS (Method 19): $R_t$ = 1.36 min,
MS (ESIpos):
m/z (%) = 584.5 (100) $[M + 2H]^{2+}$, 1167.7 (10) $[M + H]^+$;
MS (ESIneg):
m/z (%) = 1165.7 (100) $[M - H]^-$;
HR-TOF-MS:
$C_{55}H_{87}N_{14}O_{14}$ calc. 1167.6521, found 1167.6541 $[M + H]^+$.

416A

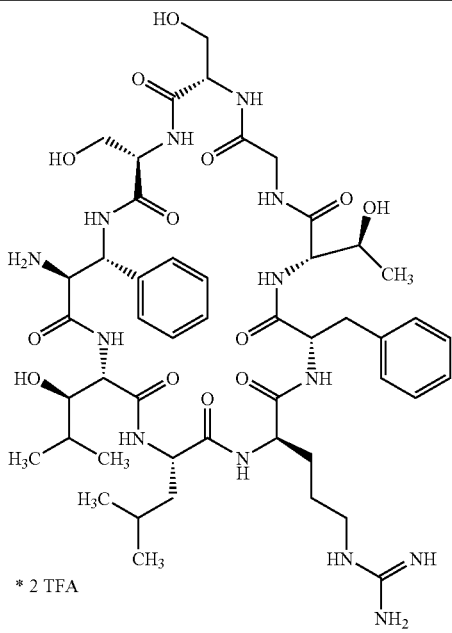

* 2 TFA

[(3R)-3-Amino-L-phenylalanyl]-[(3R)-
3-hydroxy-L-leucyl]-L-leucyl-D-
arginyl-L-phenylalanyl-L-allothreonyl-
glycyl-L-seryl-L-serine $C^{1.9}$-$N^{3.1}$-lactam
bistrifluoroacetate
Yield: 24 mg (71% pure, 77% of
theory) from exemplary compound
392A (55 mg, 44 μmol) according to
procedure 4 as a yellowish amorphous
powder.

HPLC (Method 6):
$R_t$ = 3.01 min;
LC-MS (Method 19):
$R_t$ = 1.07 min,
MS (ESIpos):
m/z (%) = 521.0 (100)
$[M + 2H]^{2+}$,
MS (ESIneg):
m/z (%) = 1038.7 (100)
$[M - H]^-$;
HR-TOF-MS:
$C_{48}H_{74}N_{13}O_{13}$ calc.
1040.5524, found
1040.5537 $[M + H]^+$.

417A

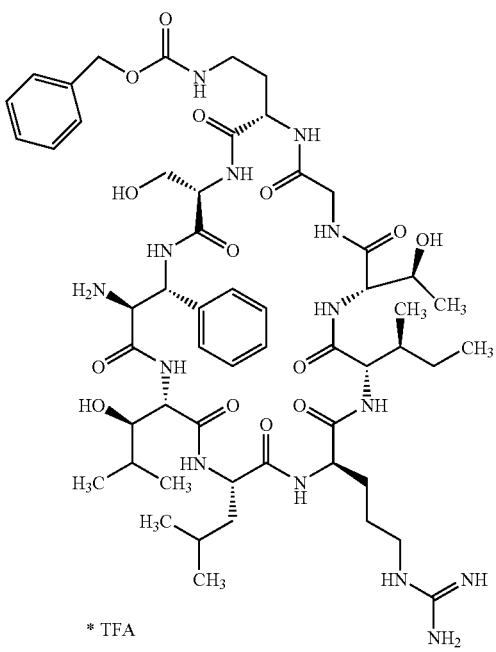

* TFA

{(3R)-3-Amino-L-phenylalanyl}-[(3R)-
3-hydroxy-L-leucyl]-L-leucyl-D-
arginyl-L-isoleucyl-L-allothreonyl-
glycyl-[(2S)-2-amino-4-
benzyloxycarbonylaminobutyryl]-
L-serine $C^{1.9}$-$N^{3.1}$-lactam
trifluoroacetate
Yield: 50 mg (76% of
theory) from exemplary compound
393A (77 mg, 52 μmol) according to
procedure 12, purification according to
method 45.

HPLC (Method 6):
$R_t$ = 3.27 min;
LC-MS (Method 19):
$R_t$ = 1.34 min,
MS (ESIpos):
m/z (%) = 577.6 (100)
$[M + 2H]^{2+}$,
HR-TOF-MS:
$C_{54}H_{85}N_{14}O_{14}$ calc.
1153.6365, found
1153.6338 $[M + H]^+$.

418A

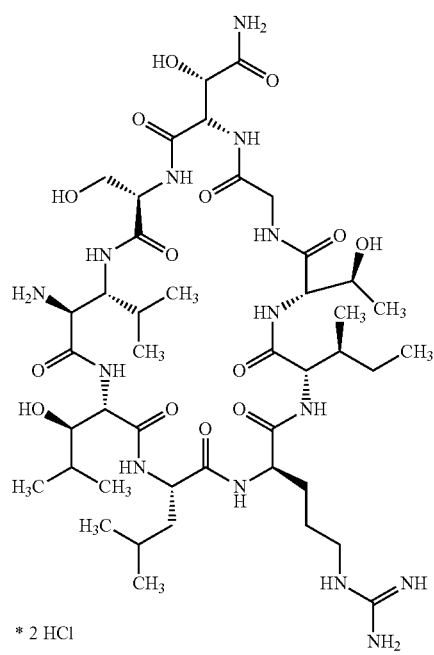

* 2 HCl

[(3R)-3-Amino-L-leucyl]-[(3R)-
3-hydroxy-L-leucyl]-L-leucyl-D-
arginyl-L-isoleucyl-L-allothreonyl-
glycyl-[(3R)-3-hydroxy-L-asparaginyl]-
L-serine $C^{1.9}$-$N^{3.1}$-lactam
bishydrochloride
Yield: 228 mg (96% of
theory) from exemplary compound
394A (275 mg, 218 μmol) according to
procedure 4.

HPLC (Method 6):
$R_t$ = 2.90 min;
LC-MS (Method 19):
$R_t$ = 0.56 min,
MS (ESIpos):
m/z (%) = 508.3 (100)
$[M + 2H]^{2+}$, 1015.6
(20) $[M + H]^+$;
HR-TOF-MS:
$C_{43}H_{79}N_{14}O_{14}$ calc.
1015.5895, found
1015.5869 $[M + H]^+$.

419A

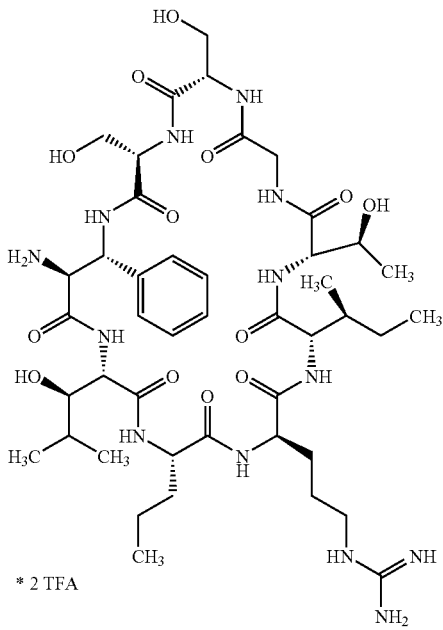

* 2 TFA

[(3R)-3-Amino-L-phenylalanyl]-[(3R)-3-hydroxy-L-leucyl]-L-norvalyl-D-arginyl-L-isoleucyl-L-allothreonyl-glycyl-L-seryl-L-serine $C^{1.9}$-$N^{3.1}$-lactam bistrifluoroacetate
Yield: 90 mg (68% of theory) from exemplary compound 395A (135 mg, 109 μmol) according to procedure 4 as a yellowish amorphous solid.

HPLC (Method 6): $R_t$ = 2.90 min;
LC-MS (Method 51): $R_t$ = 0.95 min,
MS (ESIpos):
m/z (%) = 497.4 (100) $[M + 2H]^{2+}$, 992.6 (10) $[M + H]^+$;
HR-TOF-MS:
$C_{44}H_{73}N_{13}O_{13}$ calc. 992.5524, found 992.5522 $[M + H]^+$.

420A

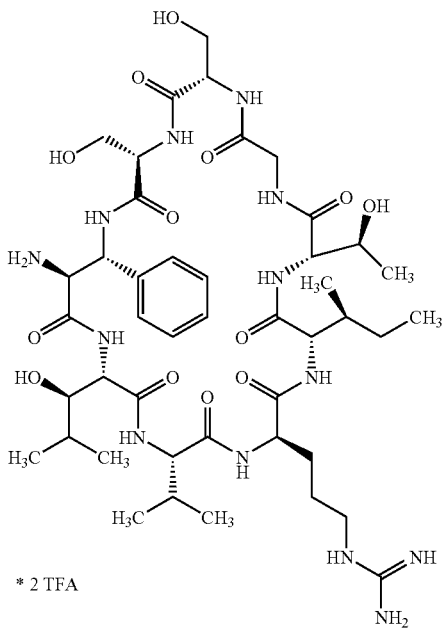

* 2 TFA

[(3R)-3-Amino-L-phenylalanyl]-[(3R)-3-hydroxy-L-leucyl]-L-valyl-D-arginyl-L-isoleucyl-L-allothreonyl-glycyl-L-seryl-L-serine $C^{1.9}$-$N^{3.1}$-lactam bistrifluoroacetate
Yield: 65 mg (crude product) from exemplary compound 396A (61 mg, 49 μmol) according to procedure 4.

HPLC (Method 6): $R_t$ = 2.90 min;
LC-MS (Method 22): $R_t$ = 2.20 min,
MS (ESIpos):
m/z (%) = 497.0 (100) $[M + 2H]^{2+}$, 992.4 (20) $[M + H]^+$,
MS (ESIneg):
m/z (%) = 990.5 (100) $[M - H]^-$;
HR-TOF-MS:
$C_{44}H_{74}N_{13}O_{13}$ calc. 992.5524, found 992.5540 $[M + H]^+$.

421A

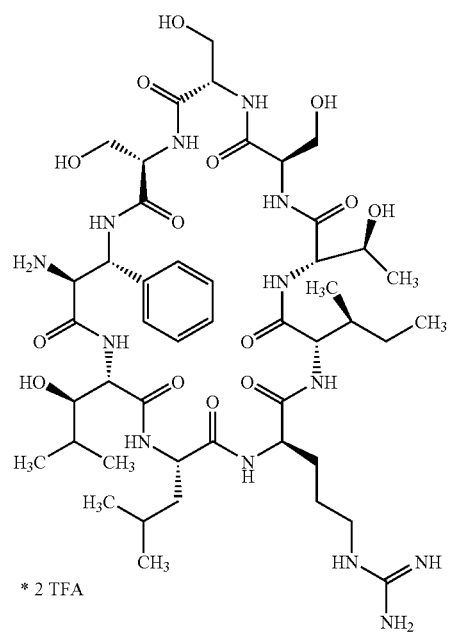

* 2 TFA

[(3R)-3-Amino-L-phenylalanyl]-[(3R)-3-hydroxy-L-leucyl]-L-leucyl-D-arginyl-L-isoleucyl-L-allothreonyl-D-seryl-L-seryl-L-serine $C^{1.9}$-$N^{3.1}$-lactam bistrifluoroacetate
Yield: 65 mg (93% of theory) from exemplary compound 397A (71 mg, 55 μmol) according to procedure 4 as a yellowish solid.

HPLC (Method 6): $R_t$ = 2.96 min;
LC-MS (Method 22): $R_t$ = 2.39 min,
MS (ESIpos):
m/z (%) = 519.1 (100), 1036.6 (10) $[M + H]^+$,
MS (ESIneg):
m/z (%) = 1034.6 (100) $[M - H]^-$;
HR-TOF-MS:
$C_{46}H_{78}N_{13}O_{14}$ calc. 1036.5786, found 1036.5795 $[M + H]^+$.

439

422A

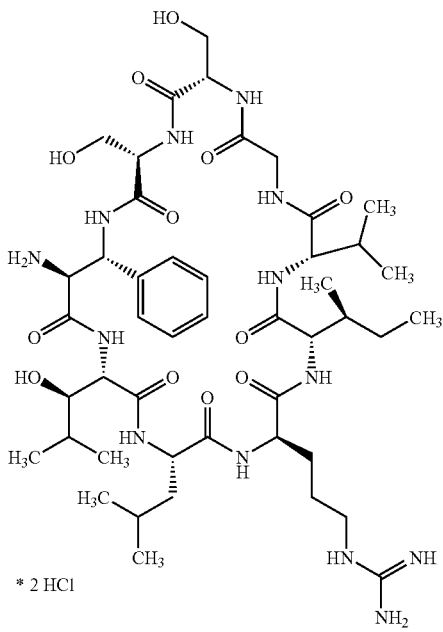

* 2 HCl

[(3R)-3-Amino-L-phenylalanyl]-[(3R)-3-hydroxy-L-leucyl]-L-leucyl-D-arginyl-L-isoleucyl-L-valyl-glycyl-L-seryl-L-serine $C^{1.9}$-$N^{3.1}$-lactam bishydrochloride
Yield: 22 mg (83% of theory) from exemplary compound 398A (31 mg, 25 μmol) according to procedure 4.

HPLC (Method 6):
$R_t$ = 3.07 min;
LC-MS (Method 51):
$R_t$ = 1.41 min,
MS (ESIpos):
m/z (%) = 503.6 (100)
$[M + 2H]^{2+}$,
MS (ESIneg):
m/z (%) = 1002.8 (100)
$[M - H]^-$;
HR-TOF-MS:
$C_{46}H_{78}N_{13}O_{12}$ calc.
1004.5888, found
1004.5897 $[M + H]^+$.

423A

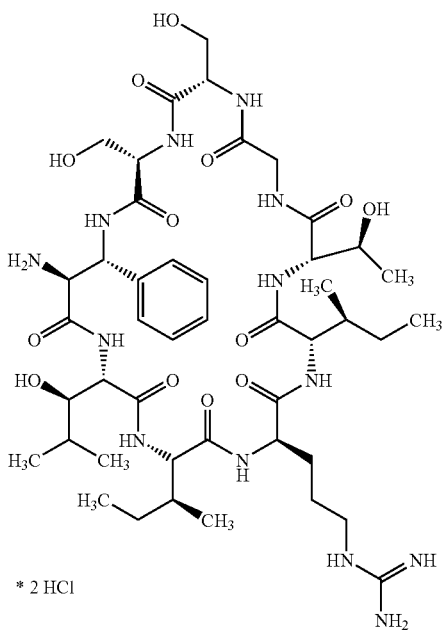

* 2 HCl

[(3R)-3-Amino-L-phenylalanyl]-[(3R)-3-hydroxy-L-leucyl]-L-isoleucyl-D-

HPLC (Method 6):
$R_t$ = 2.93 min;

440 arginyl-L-isoleucyl-L-allothreonyl-glycyl-L-seryl-L-serine $C^{1.9}$-$N^{3.1}$-lactam bishydrochloride
Yield: 19 mg (93% pure, 93% of theory) from exemplary compound 399A (22 mg, 18 μmol) according to procedure 4

LC-MS (Method 22):
$R_t$ = 2.23 min,
MS (ESIpos):
m/z (%) = 1006.2 (50)
$[M + H]^+$,
MS (ESIneg):
m/z (%) = 1004.6 (100)
$[M - H]^-$;
HR-TOF-MS:
$C_{45}H_{76}N_{13}O_{13}$ calc.
1006.5681, found
1006.5696 $[M + H]^+$.

424A

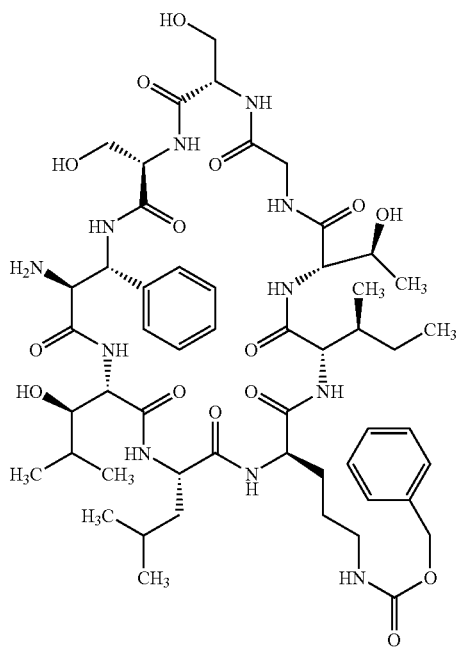

{(3R)-3-Amino-L-phenylalanyl}-[(3R)-3-hydroxy-L-leucyl]-L-leucyl-($N^5$-benzyloxycarbonyl-D-ornithyl)-L-isoleucyl-L-allothreonyl-glycyl-L-seryl-L-serine $C^{1.9}$-$N^{3.1}$-lactam
Yield: 95 mg (80% pure, 71% of theory) from exemplary compound 400A (130 mg, 98 μmol) according to procedure 12.

HPLC (Method 6):
$R_t$ = 3.63 min;
LC-MS (Method 19):
$R_t$ = 1.72 min,
MS (ESIpos):
m/z (%) = 1098.7 (100)
$[M + H]^+$,
MS (ESIneg):
m/z (%) = 1096.7 (100)
$[M - H]^-$;
HR-TOF-MS:
$C_{52}H_{80}N_{11}O_{15}$ calc.
1098.5830, found
1098.5825 $[M + H]^+$.

425A

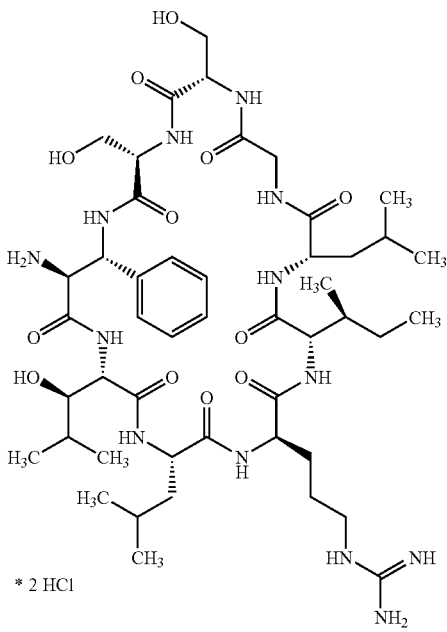

* 2 HCl

[(3R)-3-Amino-L-phenylalanyl]-[(3R)-3-hydroxy-L-leucyl]-L-leucyl-D-arginyl-L-isoleucyl-L-leucyl-glycyl-L-seryl-L-serine $C^{1.9}$-$N^{3.1}$-lactam bishydrochloride
Yield: 35 mg (84% pure, 97% of theory) from exemplary compound 401A (35 mg, 28 μmol) according to procedure 4.

HPLC (Method 6):
$R_t$ = 3.14 min;
LC-MS (Method 19):
$R_t$ = 1.25 min,
MS (ESIpos):
m/z (%) = 509.9 (100) [M + 2H]$^{2+}$, 1018.6 (10) [M + H]$^+$,
MS (ESIneg):
m/z (%) = 1016.7 (100) [M − H]$^-$;
HR-TOF-MS:
$C_{47}H_{80}N_{13}O_{12}$ calc. 1018.6044, found 1018.6025 [M + H]$^+$.

426A

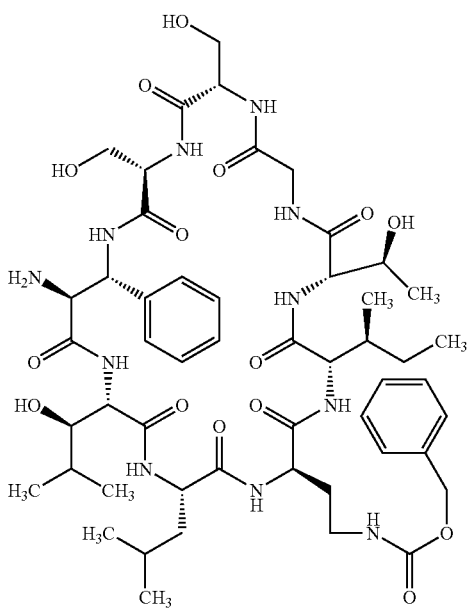

{(3R)-3-Amino-L-phenylalanyl}-[(3R)-3-hydroxy-L-leucyl]-L-leucyl-[(2R)-2-amino-4-benzyloxycarbonylaminobutyryl]-L-isoleucyl-L-allothreonyl-glycyl-L-seryl-L-serine $C^{1.9}$-$N^{3.1}$-lactam
Yield: 112 mg (60% pure, 62% of theory) from exemplary compound 402A (130 mg, 100 μmol) according to procedure 12.

HPLC (Method 6):
$R_t$ = 3.63 min;
LC-MS (Method 19):
$R_t$ = 1.70 min,
MS (ESIpos):
m/z (%) = 1084.6 (100) [M + H]$^+$,
MS (ESIneg):
m/z (%) = 1082.6 (100) [M − H]$^-$;
HR-TOF-MS:
$C_{51}H_{78}N_{11}O_{15}$ calc. 1084.5674, found 1084.5679 [M + H]$^+$.

427A

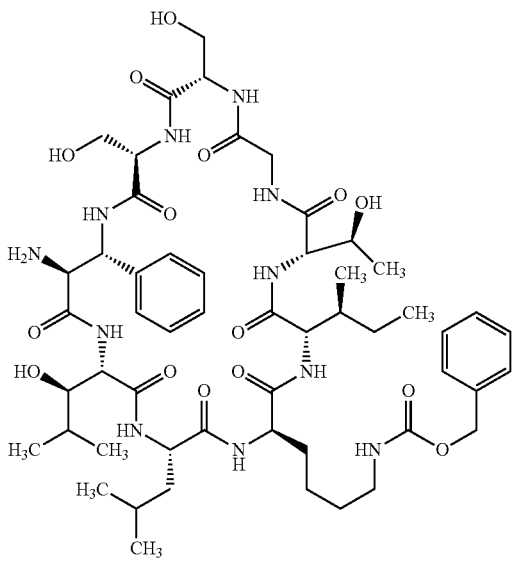

{(3R)-3-Amino-L-phenylalanyl}-[(3R)-3-hydroxy-L-leucyl]-L-leucyl-(N$^6$-benzyloxycarbonyl-D-lysyl)-L-isoleucyl-L-allothreonyl-glycyl-L-seryl-L-serine $C^{1.9}$-$N^{3.1}$-lactam
Yield: 21 mg (92% of theory) from exemplary compound 403A (46 mg, 20 μmol) according to procedure 12.

HPLC (Method 6):
$R_t$ = 3.67 min;
LC-MS (Method 19):
$R_t$ = 1.77 min,
MS (ESIpos):
m/z (%) = 1112.6 (100) [M + H]$^+$,
MS (ESIneg):
m/z (%) = 1110.6 (100) [M − H]$^-$;
HR-TOF-MS:
$C_{53}H_{82}N_{11}O_{15}$ calc. 1112.5987, found 1112.5979 [M + H]$^+$.

428A

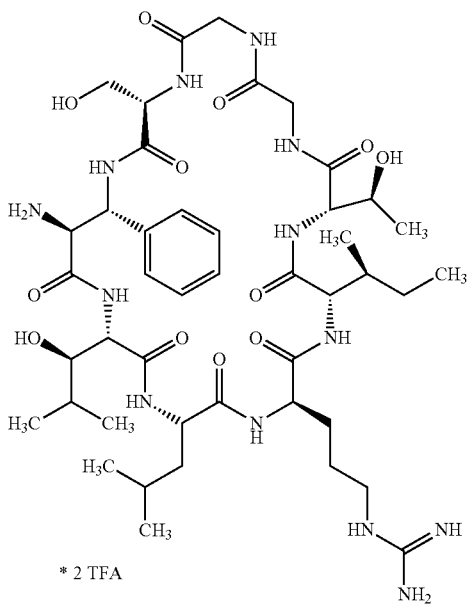

* 2 TFA

[(3R)-3-Amino-L-phenylalanyl]-[(3R)-3-hydroxy-L-leucyl]-L-leucyl-D-arginyl-L-isoleucyl-L-allothreonyl-glycyl-glycyl-L-serine $C^{1.9}$-$N^{3.1}$-lactam bistrifluoroacetate
Yield: 160 mg (97% of theory) from exemplary compound 404A (167 mg, 136 μmol) according to procedure 4 as an amorphous solid.

HPLC (Method 6): $R_t$ = 3.00 min;
LC-MS (Method 22): $R_t$ = 2.29 min,
MS (ESIpos):
m/z (%) = 489 (100) [M + 2H]$^{2+}$,
MS (ESIneg):
m/z (%) = 975 (100) [M − H]$^-$;
HR-TOF-MS:
$C_{44}H_{74}N_{13}O_{12}$ calc. 976.5575, found 976.5537 [M + H]$^+$.

429A

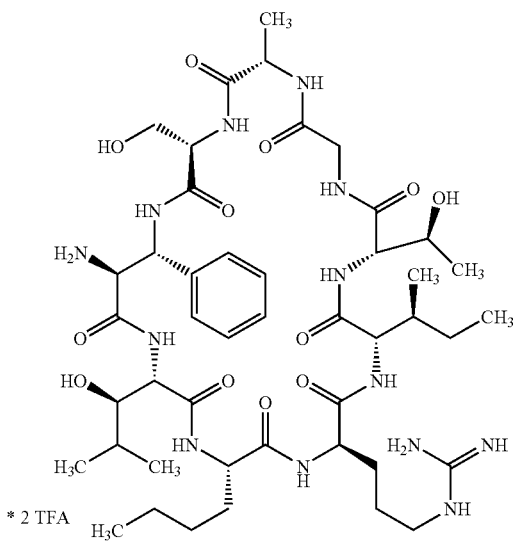

* 2 TFA

[(3R)-3-Amino-L-phenylalanyl]-[(3R)-3-hydroxy-L-leucyl]-L-norleucyl-D-arginyl)-L-isoleucyl-L-allothreonyl-glycyl-L-alanyl-L-serine $C^{1.9}$-$N^{3.1}$-lactam bistrifluoroacetate
Yield: 77 mg (55% pure, 56% of theory) from exemplary compound 405A (74 mg, 60 μmol) according to procedure 4, purification according to method 45.

HPLC (Method 6): $R_t$ = 3.02 min;
LC-MS (Method 19):
$R_t$ = 1.04 min,
MS (ESIpos):
m/z (%) = 990.6 (100) [M + H]$^+$,
MS (ESIneg):
m/z (%) = 988.6 (100) [M − H]$^-$;
HR-TOF-MS:
$C_{45}H_{76}N_{13}O_{12}$ calc. 990.5731, found 990.5715 [M + H]$^+$.

430A

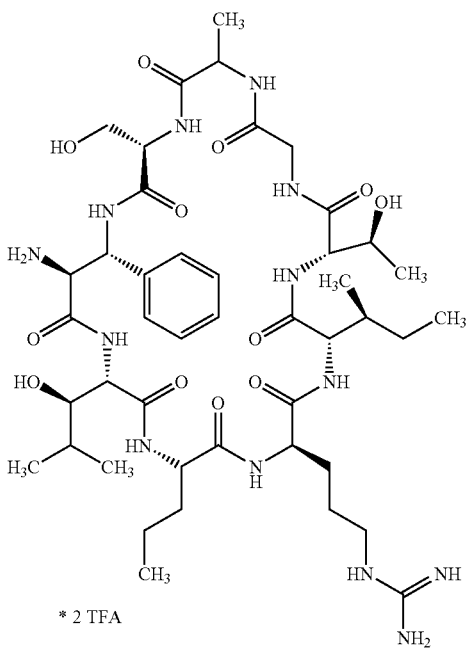

* 2 TFA

[(3R)-3-Amino-L-phenylalanyl]-[(3R)-3-hydroxy-L-leucyl]-L-norvalyl-D-arginyl-L-isoleucyl-L-allothreonyl-glycyl-L-alanyl-L-serine $C^{1.9}$-$N^{3.1}$-lactam bistrifluoroacetate
Yield: 111 mg (quant.) from exemplary compound 406A (107 mg, 87 μmol) according to procedure 4, purification according to method 45.

HPLC (Method 6): $R_t$ = 2.96 min;
LC-MS (Method 22): $R_t$ = 2.21 min,
MS (ESIpos):
m/z (%) = 976.5 (80) [M + H]$^+$,
MS (ESIneg):
m/z (%) = 975.5 (100) [M − H]$^-$;
HR-TOF-MS:
$C_{44}H_{74}N_{13}O_{12}$ calc. 976.5575, found 976.5552 [M + H]$^+$.

| Attachment of the N-terminal dipeptide fragment | | |
|---|---|---|
| Structure | | |
| Example No. | Name Yield, Synthesis Method | Analysis |

431A

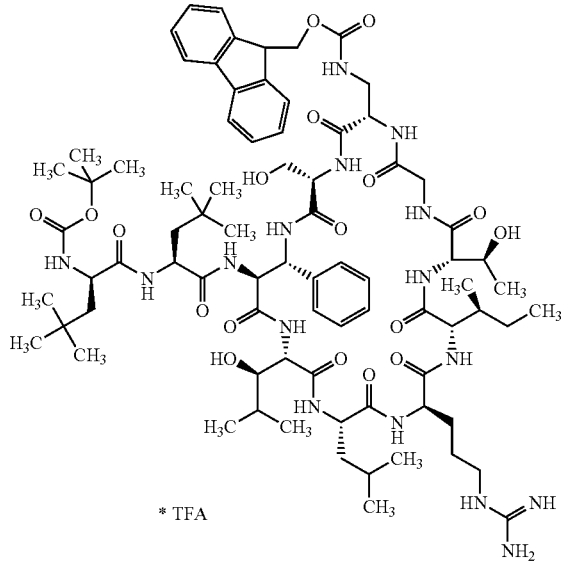

* TFA

| [N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(2S)-2-amino-3-(9H-fluoren-9-ylmethoxycarbonyl)aminobutyryl]-L-serine $C^{1.11}$-$N^{3.3}$-lactam trifluoroacetate<br>Yield: 310 mg (78% of theory) from exemplary compound 407A (343 mg, 236 μmol) and exemplary compound 8A according to procedure 13. | HPLC (Method 6):<br>$R_t$ = 4.89 min;<br>LC-MS (Method 19):<br>$R_t$ = 2.46 min,<br>MS (ESIpos):<br>m/z (%) = 1582.8 (100)<br>$[M + H]^+$;<br>HR-TOF-MS:<br>$C_{79}H_{121}N_{16}O_{18}$ calc.<br>1581.9040, found<br>1581.9067 $[M + H]^+$. |

432A

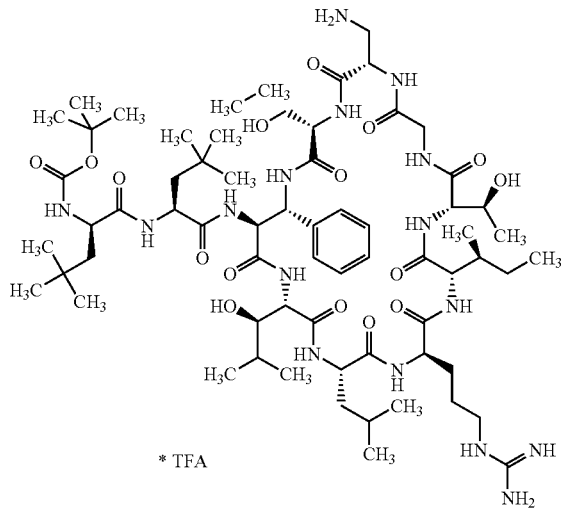

* TFA

| [N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl- | HPLC (Method 6):<br>$R_t$ = 3.99 min;<br>LC-MS (Method 19):<br>$R_t$ = 2.20 min, |

-continued

| L-isoleucyl-L-allothreonyl-glycyl-[(2S)-2,3-diaminobutyryl]-L-serine $C^{1.11}$-$N^{3.3}$-lactam trifluoroacetate<br>Yield: 273 mg (quant.) from exemplary compound 431A (310 mg, 183 μmol) according to procedure 12, purification according to method 45. | MS (ESIpos):<br>m/z (%) = 680.8 (100)<br>$[M + 2H]^{2+}$;<br>HR-TOF-MS:<br>$C_{64}H_{111}N_{16}O_{16}$ calc.<br>1359.8359, found<br>1359.8328 $[M + H]^+$. |

433A

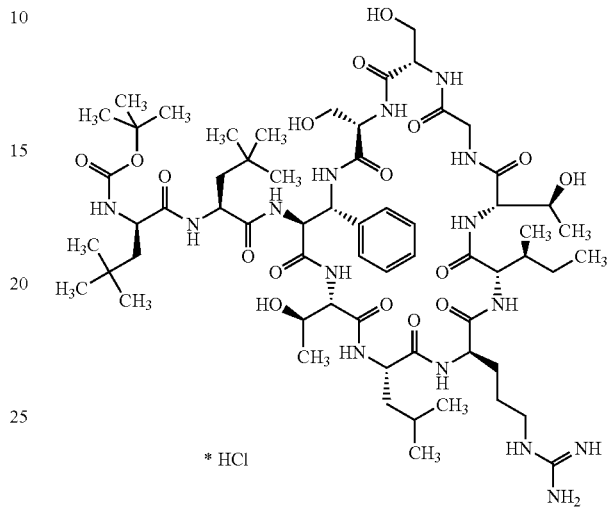

* HCl

| [N²-(tert.-Butoxycarbonyl)-3-tert-butyl-D-alanyl]-[3-tert-butyl-L-alanyl]-[(3R)-3-amino-L-phenylalanyl]-L-threonyl-L-leucyl-D-arginyl-L-isoleucyl-L-allothreonyl-glycyl-L-serine $C^{1.11}$-$N^{3.3}$-lactam hydrochloride<br>Yield: 6.5 mg (50% of theory) from exemplary compound 408A (10 mg, 10 μmol) and exemplary compound 8A according to procedure 13. | HPLC (Method 6):<br>$R_t$ = 4.21 min;<br>LC-MS (Method 22):<br>$R_t$ = 3.59 min,<br>MS (ESIpos):<br>m/z (%) = 617 (100)<br>$[M + 2H]^{2+}$, 1333 (20)<br>$[M + H]^+$;<br>MS (ESIneg):<br>m/z (%) = 1331 (100)<br>$[M - H]^-$;<br>HR-TOF-MS:<br>$C_{60}H_{102}N_{17}O_{17}$ calc.<br>1332.7635, found<br>1332.7664 $[M + H]^+$. |

434A

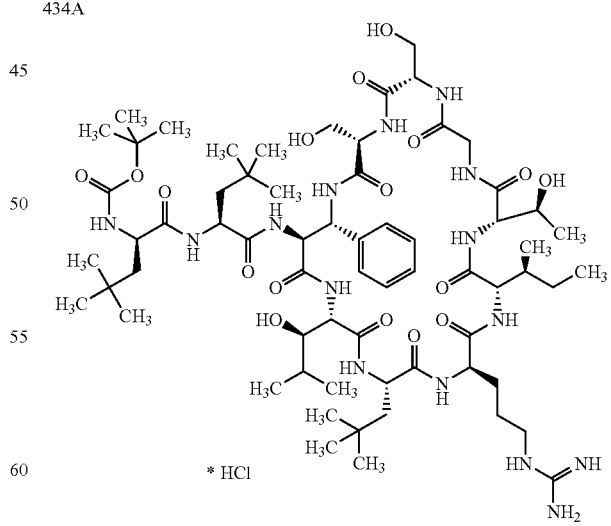

* HCl

| [N²-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-[3-tert-butyl-L- | HPLC (Method 6):<br>$R_t$ = 4.46 min;<br>LC-MS (Method 19):<br>$R_t$ = 2.15 min, |

| | | | |
|---|---|---|---|
| alanyl]-D-arginyl-L-isoleucyl-L-allothreonyl-glycyl-L-seryl-L-serine $C^{1.11}$-$N^{3.3}$-lactam hydrochloride Yield: 22 mg (68% of theory) from exemplary compound 409A (25 mg, 23 µmol) and exemplary compound 8A according to procedure 13. | MS (ESIpos): m/z (%) = 638.2 (100) $[M + 2H]^{2+}$, 1375 (40) $[M + H]^{+}$, HR-TOF-MS: $C_{65}H_{112}N_{15}O_{17}$ calc. 1374.8356, found 1374.8351 $[M + H]^{+}$. | hydroxy-L-leucyl]-L-leucyl-D-arginyl-L-isoleucyl-L-seryl-glycyl-L-seryl-L-serine $C^{1.11}$-$N^{3.3}$-lactam hydrochloride Yield: 23 mg (66% of theory) from exemplary compound 411A (26 mg, 24 µmol) and exemplary compound 8A according to procedure 13. | $R_t$ = 2.08 min, MS (ESIpos): m/z (%) = 1346.9 (40) $[M + H]^{+}$, MS (ESIneg): m/z (%) = 1344.9 (40) $[M - H]^{-}$; HR-TOF-MS: $C_{63}H_{108}N_{15}O_{17}$ calc. 1346.8043, found 1346.8036 $[M + H]^{+}$. |

435A

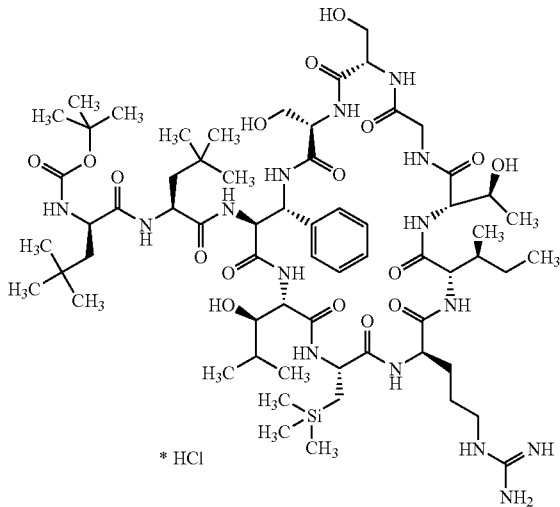

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-[3-trimethylsilyl-L-alanyl]-D-arginyl-L-isoleucyl-L-allothreonyl-glycyl-L-seryl-L-serine $C^{1.11}$-$N^{3.3}$-lactam hydrochloride Yield: 29 mg (56% of theory) from exemplary compound 410A (40 mg, 36 µmol) and exemplary compound 8A according to procedure 13. | HPLC (Method 6): $R_t$ = 4.53 min; LC-MS (Method 19): $R_t$ = 2.19 min, MS (ESIpos): m/z (%) = 646.3 (100) $[M + 2H]^{2+}$, 1392.1 (20) $[M + H]^{+}$, MS (ESIneg): m/z (%) = 1389.3 (50) $[M - H]^{-}$; HR-TOF-MS: $C_{64}H_{112}N_{15}O_{17}Si$ calc. 1380.8125, found 1390.8101 $[M + H]^{+}$. |

437A

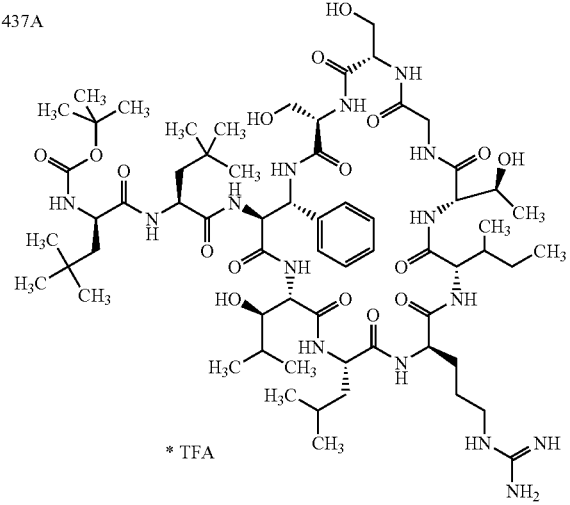

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-valyl-L-allothreonyl-glycyl-L-seryl-L-serine $C^{1.11}$-$N^{3.3}$-lactam trifluoroacetate Yield: 75 mg (71% pure, 78% of theory) from exemplary compound 412A (57 mg, 47 µmol) and exemplary compound 8A according to procedure 13. | HPLC (Method 6): $R_t$ = 4.23 min; LC-MS (Method 19): $R_t$ = 2.06 min, MS (ESIpos): m/z (%) = 1346.8 (40) $[M + H]^{+}$, MS (ESIneg): m/z (%) = 1344.9 (60) $[M - H]^{-}$; HR-TOF-MS: $C_{63}H_{108}N_{15}O_{17}$ calc. 1346.8043, found 1346.8047 $[M + H]^{+}$. |

436A

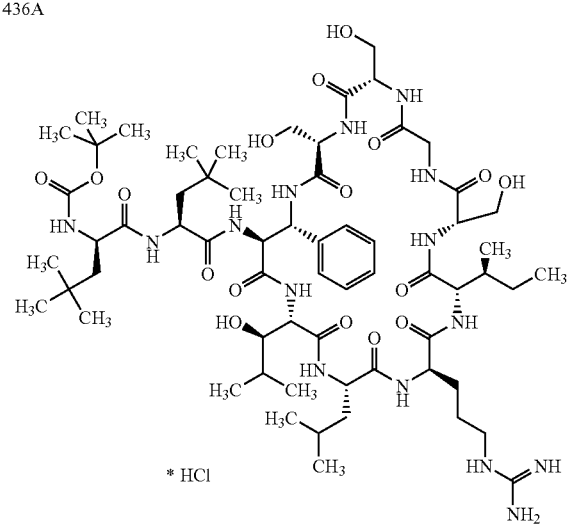

438A

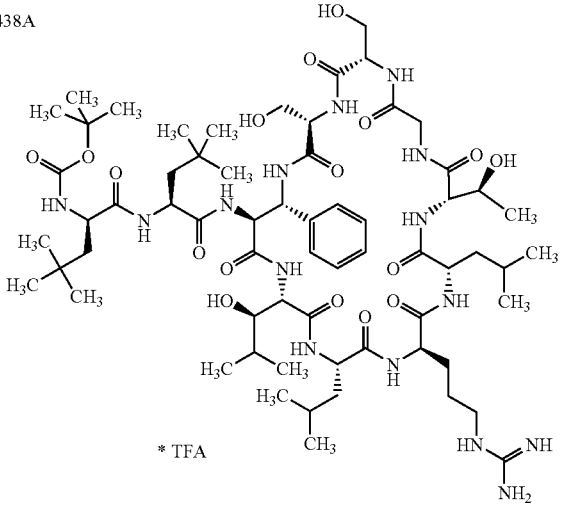

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3- | HPLC (Method 6): $R_t$ = 4.20 min; LC-MS (Method 19): |

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl- | HPLC (Method 6): $R_t$ = 4.39 min; LC-MS (Method 19): $R_t$ = 2.14 min, |

449
-continued

L-leucyl-L-allothreonyl-glycyl-L-seryl-L-serine C[1.11]-N[3.3]-lactam trifluoroacetate
Yield: 72 mg (quant.) from exemplary compound 413A (60 mg, 49 µmol) and exemplary compound 8A according to procedure 13.

MS (ESIpos): m/z (%) = 1360.0 (40) [M + H]+, MS (ESIneg): HR-TOF-MS: C$_{64}$H$_{110}$N$_{15}$O$_{17}$ calc. 1360.8199, found 1360.8199 [M + H]+.

439A

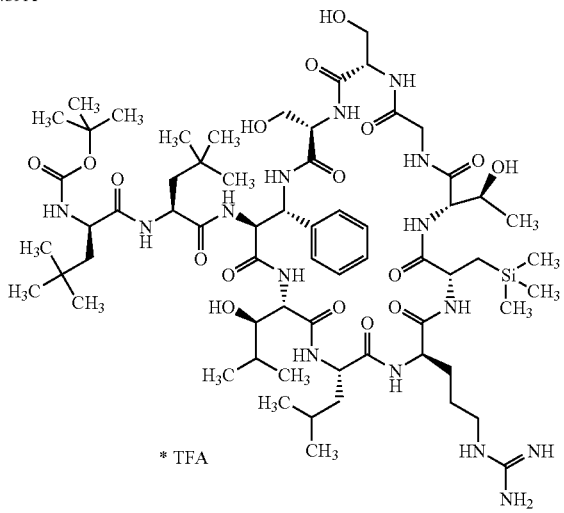

* TFA

[N$^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-[3-trimethylsilyl-L-alanlyl]-L-allothreonyl-glycyl-L-seryl-L-serine C[1.11]-N[3.3]-lactam trifluoroacetate
Yield: 62 mg (54% pure, 63% of theory) from exemplary compound 414A (74 mg, 35 µmol) and exemplary compound 8A according to procedure 13.

HPLC (Method 6): R$_t$ = 4.53 min; LC-MS (Method 19): R$_t$ = 2.18 min, MS (ESIpos): m/z (%) = 1391.8 (40) [M + H]+, MS (ESIneg): m/z (%) = 1388.8 (30) [M − H]−; HR-TOF-MS: C$_{64}$H$_{112}$N$_{15}$O$_{17}$Si calc. 1390.8125, found 1390.8092 [M + H]+.

440A

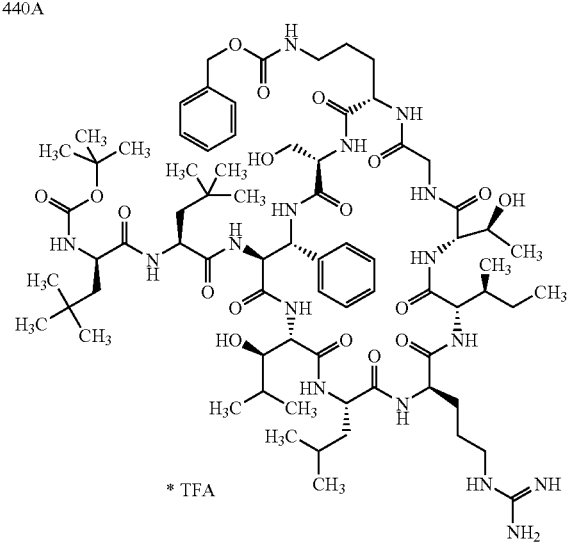

* TFA

[N$^2$-(tert.-Butoxycarbonyl)-3-tert-butyl-D-alanyl]-[3-tert-butyl-L-alanyl]-[(3R)-3-amino-L-phenylalanyl]-[(3R)-3-

HPLC (Method 6): R$_t$ = 5.17 min; LC-MS (Method 19):

450
-continued hydroxy-L-leucyl]-L-leucyl-D-arginyl-L-isoleucyl-L-allothreonyl-glycyl-(N$^5$-benzyloxycarbonyl-L-ornithyl)-L-serine C[1.11]-N[3.3]-lactam trifluoroacetate
Yield: 39 mg (79% of theory) from exemplary compound 415A (39 mg, 30 µmol) and exemplary compound 8A according to procedure 13.

R$_t$ = 2.33 min, MS (ESIpos): m/z (%) = 1522.9 (30) [M + H]+, MS (ESIneg): m/z (%) = 1520.0 (30) [M − H]−; HR-TOF-MS: C$_{74}$H$_{121}$N$_{16}$O$_{18}$ calc. 1521.9040, found 1521.9021 [M + H]+.

441A

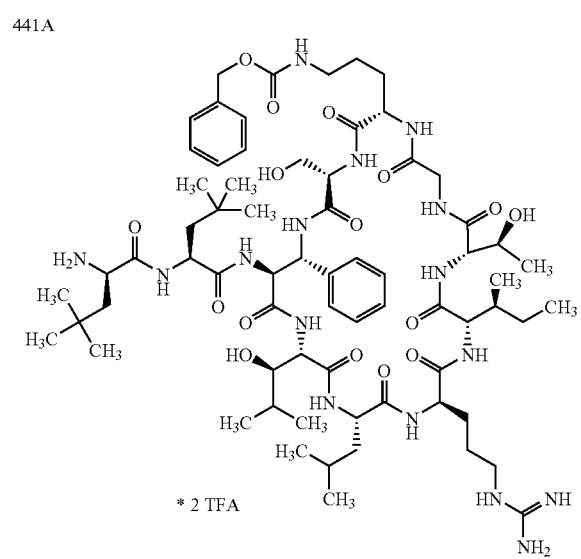

* 2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-(N$^5$-benzyloxycarbonyl-L-ornithyl)-L-serine C[1.11]-N[3.3]-lactam bistrifluoroacetate
Yield: 65 mg of crude product from exemplary compound 440A (39 mg, 24 µmol) according to procedure 2.

HPLC (Method 6): R$_t$ = 3.72 min.

442A

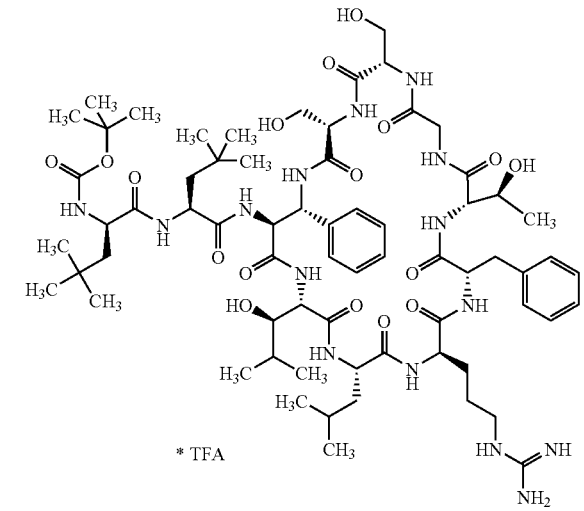

* TFA

[N$^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl- HPLC (Method 6): R$_t$ = 4.32 min; LC-MS (Method 19): R$_t$ = 1394.8 (30)

| | |
|---|---|
| L-phenylalanlyl-L-allothreonyl-glycyl-L-seryl-L-serine $C^{1.11}$-$N^{3.3}$-lactam trifluoroacetate<br>Yield: 12 mg (40% of theory) from exemplary compound 416A (24 mg, 19 µmol) and exemplary compound 8A according to procedure 13. | $[M + H]^+$ min,<br>MS (ESIpos):<br>m/z (%) = ,<br>MS (ESIneg):<br>m/z (%) = 1392.9<br>$[M − H]^−$;<br>HR-TOF-MS:<br>$C_{67}H_{108}N_{15}O_{17}$ calc.<br>1394.8043, found<br>1394.8065 $[M + H]^+$. |

443A

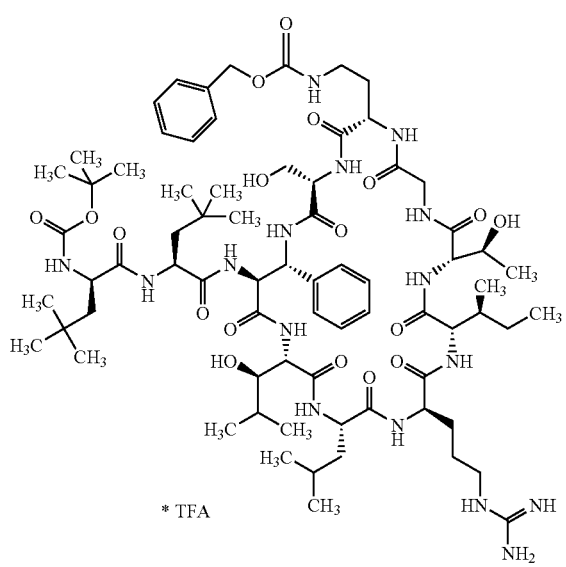

* TFA

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(2S)-2-amino-4-benzyloxycarbonylaminobutyryl]-L-serine $C^{1.11}$-$N^{3.3}$-lactam-trifluoroacetate<br>Yield: 61 mg (95% of theory) from exemplary compound 417A (50 mg, 39 µmol) and exemplary compound 8A according to procedure 13. | HPLC (Method 6):<br>$R_t$ = 4.65 min;<br>LC-MS (Method 19):<br>$R_t$ = 2.32 min,<br>MS (ESIpos):<br>m/z (%) = 1508.8 (10)<br>$[M + H]^+$,<br>MS (ESIneg):<br>m/z (%) = 1506.7 (60)<br>$[M − H]^−$;<br>HR-TOF-MS:<br>$C_{73}H_{119}N_{16}O_{18}$ calc.<br>1507.8883, found<br>1507.8895 $[M + H]^+$. |

444A

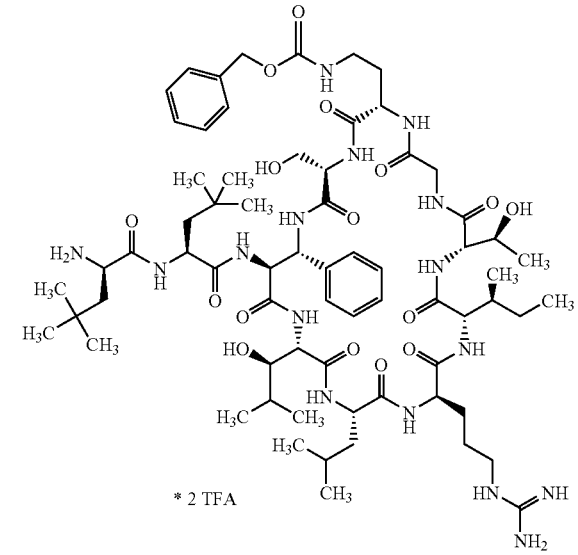

* 2 TFA

| | |
|---|---|
| [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(2S)-2-amino-4-benzyloxycarbonylaminobutyryl]-L-serine $C^{1.11}$-$N^{3.3}$-lactam-trifluoroacetate<br>Yield: 75 mg (crude product) from exemplary compound 443A (61 mg, 46 µmol) according to procedure 2. | HPLC (Method 6):<br>$R_t$ = 3.65 min;<br>LC-MS (Method 19):<br>$R_t$ = 1.96 min,<br>MS (ESIpos):<br>m/z (%) = 704.7 (100)<br>$[M + 2H]^{2+}$, 1407 (1)<br>$[M + H]^+$,<br>MS (ESIneg):<br>m/z (%) = 1405.9 (100)<br>$[M − H]^−$. |

445A

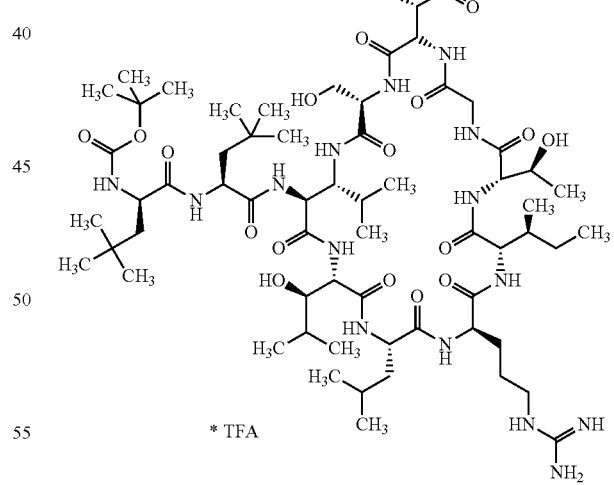

* TFA

| | |
|---|---|
| $[N^2$-(tert.-Butoxycarbonyl)-3-tert-butyl-D-alanyl]-[3-tert-butyl-L-alanyl]-[(3R)-3-amino-L-leucyl]-L-leucyl-D-arginyl-L-isoleucyl-L-allothreonyl-glycyl-[(3R)-3-hydroxy -L-asparaginyl]-L-serine $C^{1.11}$-$N^{3.3}$-lactam trifluoroacetate<br>Yield: 53 mg (17% of theory) from exemplary compound 445A (228 mg, 30 µmol) according to procedure 13, separation | HPLC (Method 6):<br>$R_t$ = 4.29 min;<br>LC-MS (Method 19):<br>$R_t$ = 2.11 min,<br>MS (ESIpos):<br>m/z (%) = 1369.8 (50)<br>$[M + H]^+$,<br>MS (ESIneg):<br>m/z (%) = 1367.9 (40)<br>$[M − H]^−$; |

| | |
|---|---|
| from other diastereomer according to method 44. | HR-TOF-MS: $C_{62}H_{113}N_{16}O_{18}$ calc. 1369.8414, found 1369.8396 $[M + H]^+$. |

446A

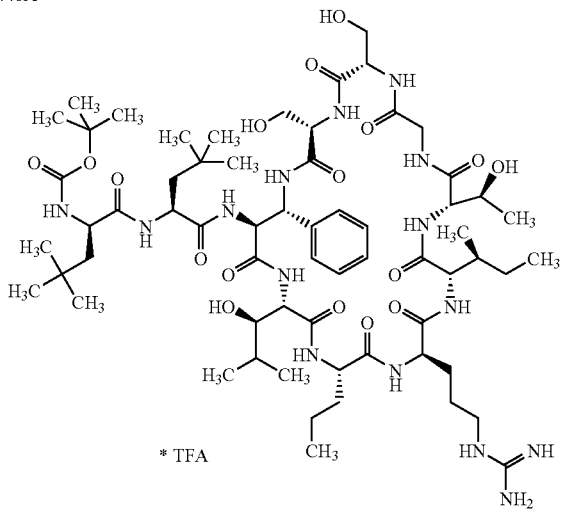

*TFA

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-norvalyl-D-arginyl-L-isoleucyl-L-allothreonyl-glycyl-L-seryl-L-serine $C^{1.9}$-$N^{3.1}$-lactam-$C^{1.11}$-$N^{3.3}$-lactam trifluoroacetate<br>Yield: 54 mg (50% of theory) from exemplary compound 419A (90 mg, 74 μmol) and exemplary compound 8A according to procedure 13. | HPLC (Method 6): $R_t = 4.23$ min;<br>LC-MS (Method 19): $R_t = 2.05$ min,<br>MS (ESIpos): m/z (%) = 1346.9 (60) $[M + H]^+$,<br>MS (ESIneg): m/z (%) = 1344.8 (60) $[M - H]^-$;<br>HR-TOF-MS: $C_{63}H_{108}N_{15}O_{17}$ calc. 1346.8043, found 1346.8088 $[M + H]^+$. |

447A

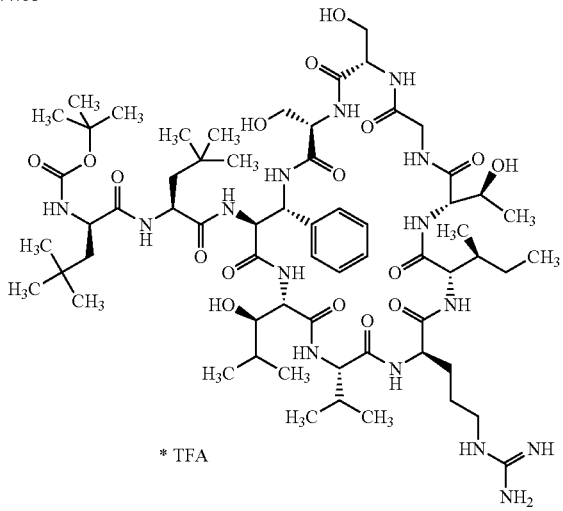

*TFA

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-valyl-D-arginyl-L-isoleucyl-L-allothreonyl-glycyl-L-seryl-L-serine $C^{1.11}$-$N^{3.3}$-lactam trifluoroacetate<br>Yield: 54 mg (65% of theory) from | HPLC (Method 6): $R_t = 4.28$ min;<br>LC-MS (Method 19): $R_t = 3.32$ min,<br>MS (ESIpos): m/z (%) = 1347.8 (60) $[M + H]^+$,<br>MS (ESIneg): |

| | |
|---|---|
| exemplary compound 420A (65 mg, 53 μmol) and exemplary compound 8A according to procedure 13. | m/z (%) = 1344.7 (1) $[M - H]^-$;<br>HR-TOF-MS: $C_{63}H_{108}N_{15}O_{17}$ calc. 1346.8043, found 1346.8046 $[M + H]^+$. |

448A

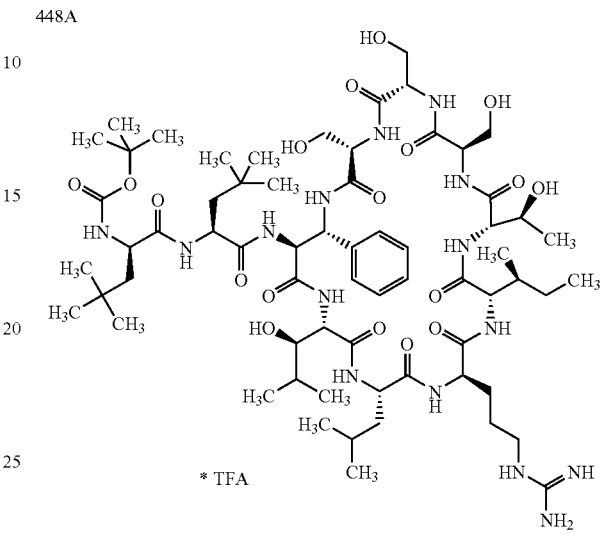

*TFA

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-D-seryl-L-seryl-L-serine $C^{1.11}$-$N^{3.3}$-lactam trifluoroacetate<br>Yield: 64 mg (83% of theory) from exemplary compound 421A (65 mg, 51 μmol) and exemplary compound 8A according to procedure 13. | HPLC (Method 6): $R_t = 4.23$ min;<br>LC-MS (Method 51): $R_t = 2.08$ min,<br>MS (ESIpos): m/z (%) = 1390.8 (60) $[M + H]^+$,<br>MS (ESIneg): m/z (%) = 1388.8 (60) $[M - H]^-$;<br>HR-TOF-MS: $C_{65}H_{112}N_{15}O_{18}$ calc. 1390.8305, found 1390.8306 $[M + H]^+$. |

449A

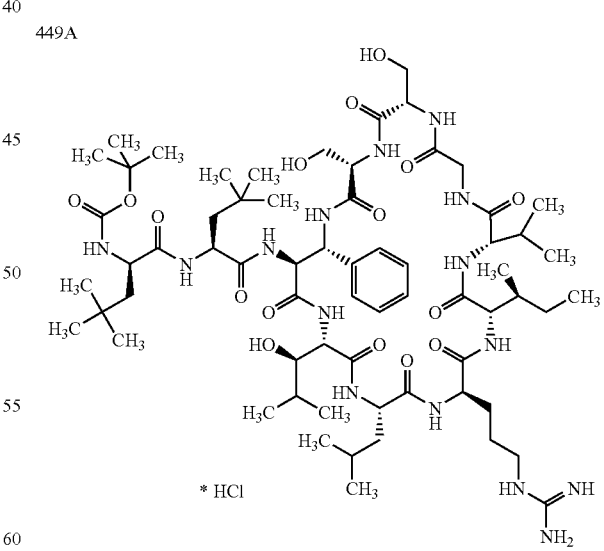

*HCl

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-valyl-glycyl-L-seryl-L-serine $C^{1.11}$-$N^{3.3}$-lactam | HPLC (Method 6): $R_t = 4.29$ min;<br>LC-MS (Method 19): $R_t = 2.10$ min,<br>MS (ESIpos): m/z (%) = 1358.8 (30) |

-continued

| | |
|---|---|
| hydrochloride<br>Yield: 33 mg (75% of theory) from exemplary compound 422A (22 mg, 20 µmol) and exemplary compound 8A according to procedure 13. | [M + H]+,<br>MS (ESIneg):<br>m/z (%) = 1356.0 (60) [M − H]−; +[M + H]+;<br>HR-TOF-MS:<br>C65H112N15O16 calc. 1358.8406, found 1358.8383 [M + H]+. |

450A

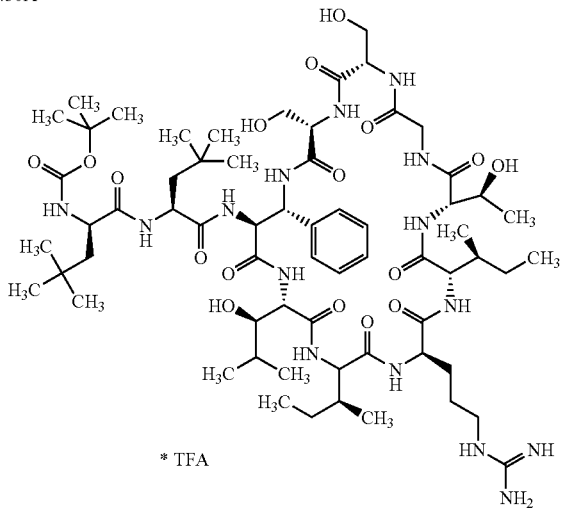

* TFA

| | |
|---|---|
| [N2-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-isoleucyl-D-arginyl-L-isoleucyl-L-allothreonyl-glycyl-L-seryl-L-serine C1.11-N3.3-lactam hydrochloride<br>Yield: 15 mg (78% pure, 50% of theory) from exemplary compound 423A (19 mg, 16 µmol) and exemplary compound 8A according to procedure 13. | HPLC (Method 6):<br>Rt = 4.30 min;<br>LC-MS (Method 19):<br>Rt = 2.14 min,<br>MS (ESIpos):<br>m/z (%) = 1360.8 (50) [M + H]+,<br>MS (ESIneg):<br>m/z (%) = 1358.8 (100) [M − H]−;<br>HR-TOF-MS:<br>C64H110N15O17 calc. 1360.8199, found 1360.8233 [M + H]+. |

451A

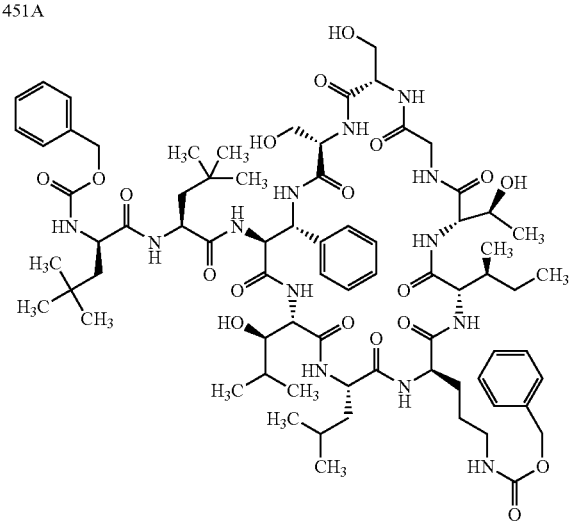

| | |
|---|---|
| [N2-(Benzyloxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-(N5-benzyloxycarbonyl-D-ornithyl)-L- | HPLC (Method 6):<br>Rt = 4.97 min;<br>LC-MS (Method 19):<br>Rt = 3.04 min,<br>MS (ESIpos): |

-continued

| | |
|---|---|
| isoleucyl-L-allothreonyl-glycyl-L-seryl-L-serine C1.11-N3.3-lactam<br>Yield: 15 mg (74% pure, 59% of theory) from exemplary compound 424A (49 mg, 45 µmol) and exemplary compound 10A according to procedure 13. | m/z (%) = 744.2 (100) [M + 2H]2+,<br>1487.8 (90) [M + H]+,<br>MS (ESIneg):<br>m/z (%) = 1485.9 (100) [M − H]−;<br>HR-TOF-MS:<br>C74H112N13O19 calc. 1486.8192, found 1486.8167 [M + H]+. |

452A

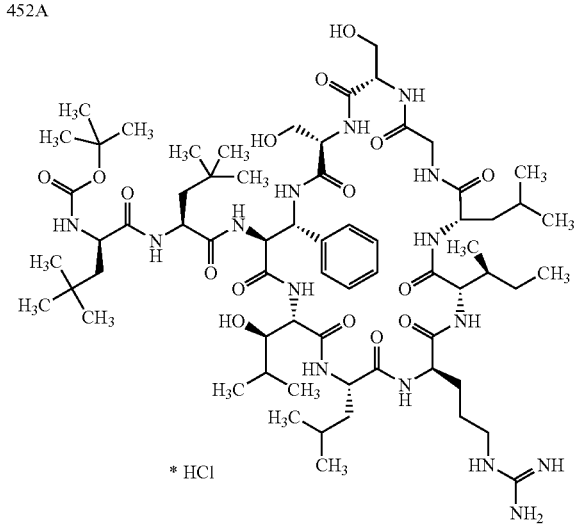

* HCl

| | |
|---|---|
| [N2-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-leucyl-glycyl-L-seryl-L-serine C1.11-N3.3-lactam hydrochloride<br>Yield: 42 mg (75% pure, 80% of theory) from exemplary compound 425A (35 mg, 27 µmol) and exemplary compound 8A according to procedure 13. | HPLC (Method 6):<br>Rt = 4.31 min;<br>LC-MS (Method 19):<br>Rt = 2.16 min,<br>MS (ESIpos):<br>m/z (%) = 1372.9 (50) [M + H]+,<br>MS (ESIneg):<br>m/z (%) = 1370.8 (100) [M − H]−;<br>HR-TOF-MS:<br>C66H114N15O16 calc. 1372.8563, found 1372.8544 [M + H]+. |

453A

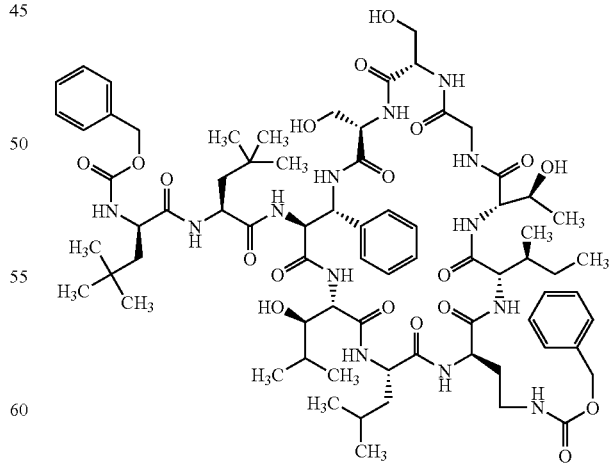

| | |
|---|---|
| [N2-(Benzyloxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-[(2R)-2- | HPLC (Method 6):<br>Rt = 5.11 min;<br>LC-MS (Method 19):<br>Rt = 3.06 min, |

| | |
|---|---|
| amino-4-benzyloxycarbonylamino-butyryl]-L-isoleucyl-L-allothreonyl-glycyl-L-seryl-L-serine $C^{1.11}$-$N^{3.3}$-lactam<br>Yield: 160 mg (crude product) from exemplary compound 426A (120 mg of crude product) and exemplary compound 10A according to procedure 13. | MS (ESIpos):<br>m/z (%) = 737.1 (100) $[M + 2H]^{2+}$,<br>1472.8 (20) $[M + H]^+$,<br>MS (ESIneg):<br>m/z (%) = 1471.8 (100) $[M - H]^-$. |

454A

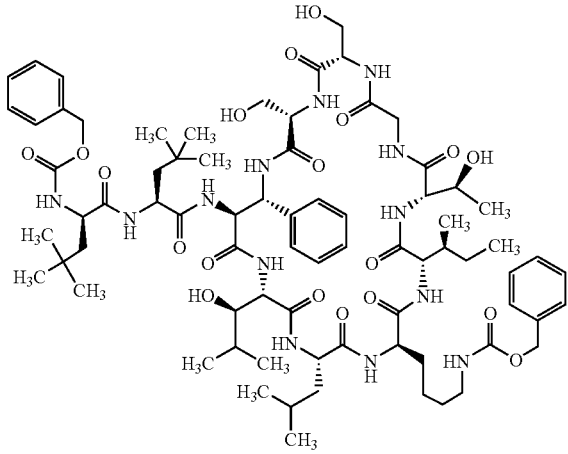

| | |
|---|---|
| $[N^2$-(Benzyloxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-($N^6$-benzyloxycarbonyl-D-lysyl)-L-isoleucyl-L-allothreonyl-glycyl-L-seryl-L-serine $C^{1.11}$-$N^{3.3}$-lactam<br>Yield: 29 mg (80% pure, 82% of theory) from exemplary compound 427A (21 mg, 19 µmol) and exemplary compound 10A according to procedure 13. | HPLC (Method 6):<br>$R_t$ = 5.01 min;<br>LC-MS (Method 52):<br>$R_t$ = 2.48 min,<br>MS (ESIpos):<br>m/z (%) = 751.3 (100) $[M + 2H]^{2+}$,<br>1502.0 (80) $[M + H]^+$,<br>MS (ESIneg):<br>m/z (%) = 1545.1 (90) $[M + HCOO^-]^-$;<br>HR-TOF-MS:<br>$C_{75}H_{114}N_{13}O_{19}$ calc. 1500.8349, found 1500.8326 $[M + H]^+$. |

455A

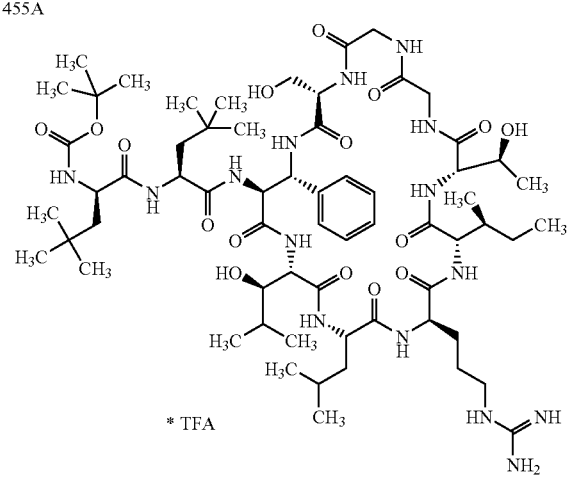

| | |
|---|---|
| $[N^2$-(tert.-Butoxycarbonyl)-3-tert-butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-glycyl-L-serine $C^{1.11}$-$N^{3.3}$-lactam trifluoroacetate | HPLC (Method 6):<br>$R_t$ = 4.43 min;<br>LC-MS (Method 19):<br>$R_t$ = 2.14 min,<br>MS (ESIpos):<br>m/z (%) = 1330.9 (10) $[M + H]^+$; |

| | |
|---|---|
| Yield: 177 mg (92% of theory) from exemplary compound 428A (160 mg, 133 µmol) and exemplary compound 8A according to procedure 13. | HR-TOF-MS:<br>$C_{63}H_{108}N_{15}O_{16}$ calc. 1330.8093, found 1330.8109 $[M + H]^+$. |

456A

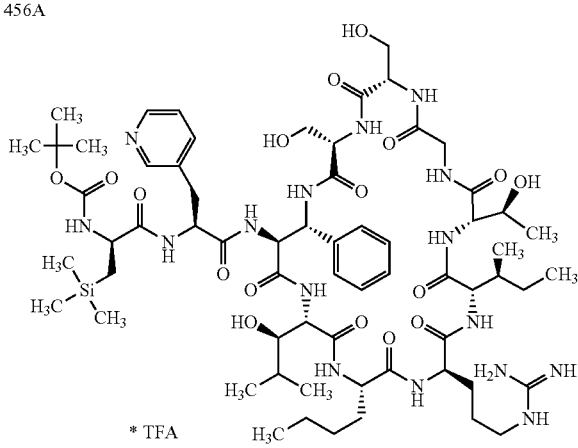

| | |
|---|---|
| $[N^2$-(tert.-Butoxycarbonyl)-3-trimethylsilyl-D-alanyl]-[3-(3-pyridyl)-L-alanyl]-[(3R)-3-amino-L-phenylalanyl]-[(3R)-3-hydroxy-L-leucyl]-L-norleucyl-D-arginyl-L-isoleucyl-L-allothreonyl-glycyl-L-alanyl-L-serine $C^{1.11}$-$N^{3.3}$-lactam trifluoroacetate<br>Yield: 45 mg (60% pure, 52% of theory) from exemplary compound 429A (76 mg, 52% pure, 32 µmol) and exemplary compound 274A according to procedure 13, purification according to method 45. | HPLC (Method 6):<br>$R_t$ = 3.83 min;<br>LC-MS (Method 19):<br>$R_t$ = 1.96 min,<br>MS (ESIpos):<br>m/z (%) = 691.6 (100) $[M + 2H]^{2+}$,<br>1381.7 (5) $[M + H]^+$,<br>MS (ESIneg):<br>m/z (%) = 1380.7 (100) $[M - H]^-$;<br>HR-TOF-MS:<br>$C_{64}H_{105}N_{16}O_{16}Si$ calc. 1381.7659, found 1381.7666 $[M + H]^+$. |

457A

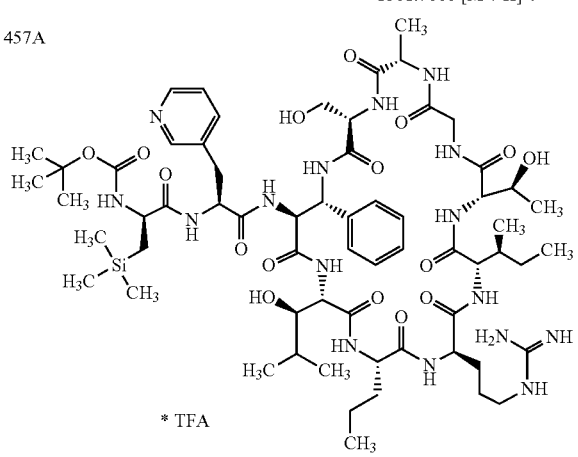

| | |
|---|---|
| $[N^2$-(tert.-Butoxycarbonyl)-3-trimethylsilyl-D-alanyl]-[3-(3-pyridyl)-L-alanyl]-[(3R)-3-amino-L-phenylalanyl]-[(3R)-3-hydroxy-L-leucyl]-L-norvalyl-D-arginyl-L-isoleucyl-L-allothreonyl-glycyl-L-alanyl-L-serine $C^{1.11}$-$N^{3.3}$-lactam trifluoroacetate<br>Yield: 41 mg (52% pure, 32% of theory) from exemplary compound 430A (50 mg, 42% pure, 32 µmol) and exemplary compound 274A according to procedure 13, purification according to method 45. | HPLC (Method 6):<br>$R_t$ = 3.73 min;<br>LC-MS (Method 19):<br>$R_t$ = 1.91 min,<br>MS (ESIpos):<br>m/z (%) = 685.4 (100) $[M + 2H]^{2+}$,<br>1368.8 (30) $[M + H]^+$,<br>MS (ESIneg):<br>m/z (%) = 1367.7 (30) $[M - H]^-$;<br>HR-TOF-MS:<br>$C_{63}H_{103}N_{16}O_{16}Si$ calc. 1367.7502, found 1367.7495 $[M + H]^+$. |

-continued

458A

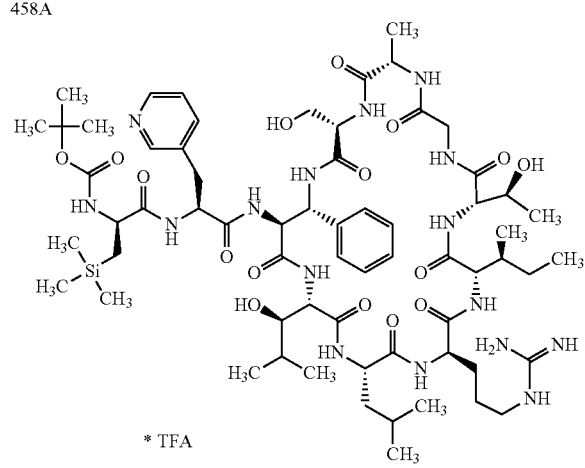

* TFA

[N²-(tert.-Butoxycarbonyl)-3-trimethylsilyl-D-alanyl]-[3-(3-pyridyl)-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-alanyl-L-serine $C^{1.11}$-$N^{3.3}$-lactam trifluoroacetate
Yield: 45 mg (60% pure, 36% of theory) from exemplary compound 230A (49 mg, 46% pure, 32 μmol) and exemplary compound 274A according to procedure 13, purification according to method 45.

HPLC (Method 6):
$R_t$ = 3.83 min;
LC-MS (Method 19):
$R_t$ = 1.97 min,
MS (ESIpos):
m/z (%) = 691.9 (100)
$[M + 2H]^{2+}$,
1381.7 (20) $[M + H]^+$,
MS (ESIneg):
m/z (%) = 1379.7 (100)
$[M - H]^-$;
HR-TOF-MS:
$C_{64}H_{105}N_{16}O_{16}Si$ calc.
1381.7569, found
1381.7683 $[M + H]^+$.

Example 459A tert-Butyl [(phenylsulfonyl)(pyridin-3-yl)methyl]carbamate

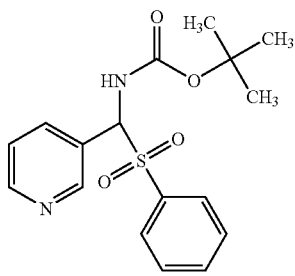

Pyridine-3-carbaldehyde (5.36 g, 50 mmol), tert-butyl carbamate (11.7 g, 100 mmol, 2 equivalents), sodiumphenylsulfinate (20.36 g, 124 mmol, 2.48 equivalents), formic acid (1.89 ml, 2.30 g, 1 equivalent), methanol (55 ml) and water (111 ml) are mixed and vigorously stirred at room temperature for 3 d. The product precipitates in the form of colorless crystals which are collected by filtration, washed with water and a little MTBE and dried in vacuo. Yield: 4.10 g (24% of theory).

LC-MS (Method 51): $R_t$=2.51 min, MS (ESIpos): m/z (%)=349.3 (100) $[M+H]^+$.

Example 460A tert-Butyl [(pyridin-3-yl)methylene]carbamate

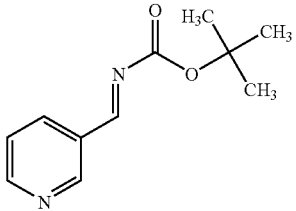

Potassium carbonate (4.78 g, 34 mmol, 6 equivalents) is heat-dried in vacuo and covered with a layer of THF (70 mL). The mixture is heated to reflux for 16 h, then allowed to cool and filtered through a layer of celite. The filtrate is concentrated and the oily residue (1.33 g of crude product, quant.) is reacted further without purification.

Example 461A

Ethyl rac-threo-3-[(tert-butoxycarbonyl)amino]-$N^2$-(diphenylmethylene)-3-pyridin-3-yl-alaninate

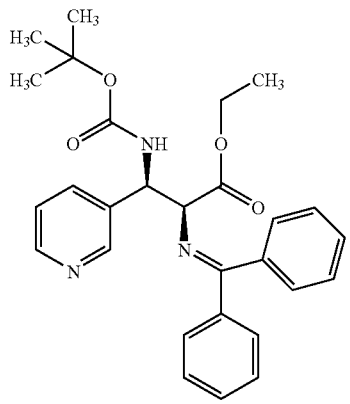

The reaction takes place based on a method for the addition of copper enolates onto sulfonylimines: L. Bernardi, A. Gothelf, R. G. Hazell, K. A. Jørgensen, *J. Org. Chem.* 2003, 68, 2583-2591. tert-Butyl [(1E)-phenylmethylene]carbamate can be prepared according to the literature: A. Klepacz, A. Zwierzak, *Tetrahedron Lett.* 2002 43; 1079-1080.

Freshly activated 3 Å molecular sieves, tetrakis(acetonitrile)copper(I) hexafluorophosphate (179 mg, 0.48 mmol, 0.1 equivalent) and (R)-(+)-2-(2-(diphenylphosphino)phenyl)-4-phenyl-2-oxazoline (329 mg, 0.53 mmol, 0.11 equivalents) are provided under argon, and abs. THF (41 ml) is added. Triethylamine (67 μl, 49 mg, 0.48 mmol, 0.1 equivalent) is then pipetted in. The mixture is cooled to −20° C. and, as soon as this temperature is reached, ethyl N-(diphenylmethylene) glycinate (1.29 g, 4.81 mmol) and exemplary compound 459A (1.19 g, 5.77 mmol, 1.2 equivalents) are added. The mixture is stirred for 16 h, during which it is slowly allowed to reach room temperature. Silica gel (about 15 g) is then added, and the solvent is distilled off in vacuo. The residue is chromatographed with cyclohexane-ethyl acetate 9+1 (Biotage 40M with ZIF-SIM 35). The title compound is obtained in a yield of 1.85 g (95% pure, 77% of theory).

LC-MS (Method 51): $R_t$=3.55 min MS (ESIpos): m/z (%)=474.3 (100) [M+H]$^+$.

Example 462A

Ethyl rac-threo-3-[(tert-butoxycarbonyl)amino]-3-pyridin-3-yl-alaninate Trifluoroacetate

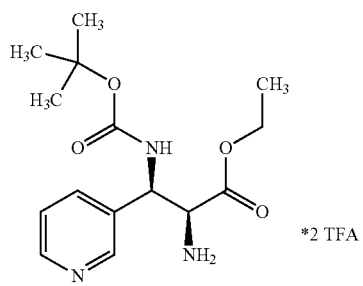

The title compound from example 461A (350 mg, 0.74 mmol) is dissolved in acetonitrile (9.33 ml) and, 187 µl of TFA (2.42 mmol, 3.3 equivalents) and water (187 µl, 10.4 µmol, 14 equivalents) are added and the mixture is left to stand at 4° C. for 16 h. All the volatile constituents of the reaction mixture are distilled off in vacuo, and the residue is purified by chromatography (method 34). Yield: 366 mg (92% of theory).

HPLC (Method 6): $R_t$=3.03 min.

LC-MS (Method 22): $R_t$=2.32 min, MS (ESIpos): m/z (%)=310.0 (80) [M+H]$^+$.

HR-TOF-MS: $C_{15}H_{24}N_3O_4$ calc. 310.1762, found 310.1767 [M+H]$^+$.

Example 463A

Ethyl rac-threo-3-[(tert-butoxycarbonyl)amino]-N$^2$-(benzyloxy)carbonylamino-3-pyridin-3-yl-alaninate

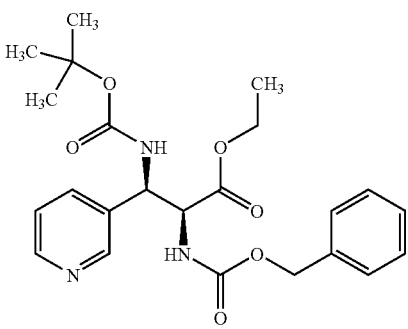

Exemplary compound 462A (366 mg, 0.68 mmol) and benzyloxycarbonylsuccinimide (209 mg, 0.82 mmol, 1.2 equivalents) are dissolved in 5 ml of dichloromethane-water (4+1), and the mixture is cooled to 0° C. While stirring vigorously, sodium bicarbonate (86 mg, 1.03 mmol, 1.5 equivalents) and tetrabutylammonium bromide (11 mg, 34 µmol, 0.05 equivalents) are added, and the mixture is stirred vigorously at room temperature for 16 h. The organic phase is separated off, washed with conc. NaCl, dried over sodium sulfate and concentrated. The crude product is chromatographed (method 34). Yield: 314 mg (84% pure, 0.60 mmol, 88% of theory) of the title compound.

$R_f$=0.076 (CyHex-EtOAc 9+1).

HPLC (Method 54): $R_t$=4.33 min (erythro diastereomer) and 4.52 min (threo diastereomer).

LC-MS (Method 19): $R_t$=2.71 min, MS (ESIpos): m/z (%)=409.3 (30) [M+H]$^+$, erythro isomer and $R_t$=2.75 min, MS (ESIpos): m/z (%)=409.0 (70) [M+H]$^+$ threo isomer).

$^1$H NMR (400 MHz, d$_6$-DMSO) δ (ppm)=0.71-0.86 (m, 6H), 1.16 (t, J=7.1 Hz, 3H), 1.34 (s, 9H), 1.59 (m, 1H), 3.70 (ddd, J=3.4, J$^1$=J$^2$=10.3 Hz, 1H), 3.99-4.08 (m, 2H), 4.32 (dd, J=3.4, J=9.5 Hz, 1H), 5.03 (d, J=12.4 Hz, 1H), 5.10 (d, J=12.4 Hz, 1H), 6.62 (d, J=10.5 Hz, 1H), 7.31-7.40 (m, 5H), 7.44 (d, J=9.3 Hz, 1H).

HR-TOF-MS: $C_{21}H_{33}N_2O_6$ calc. 409.2334, found 409.2329 [M+H]$^+$.

Example 464A (3R)-3-[(tert-Butoxycarbonyl)amino]-N$^2$-(benzyloxy)carbonylamino-3-pyridin-3-yl-L-alanine

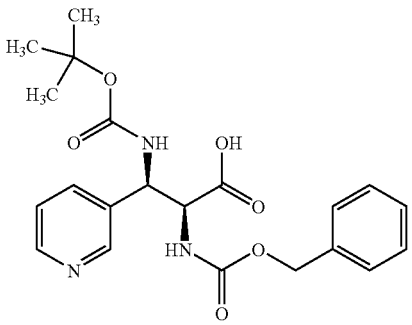

The title compound from example 463A (314 mg, 0.56 mmol) is dissolved in a THF-water mixture (2+1, 17 ml) at 0° C., lithium hydroxide monohydrate (25 mg, 0.59 mmol, 1.1 equivalents) is added, and the mixture is stirred at 0° C. for 3 h. The THF is then distilled off, and the aqueous residue is lyophilized and then purified by chromatography (method 44). The product is separated by chromatography on a chiral phase according to method 58. The enantiomers of the threo diastereomer and those of the minor erythro diastereomer are each obtained separately thereby. The e.e. of the main isomer (title compound) after the chiral chromatography is determined by method 59, and is 100%. The yield of the title compound is 113 mg (38% of theory based on the starting compound 463A.

HPLC (Method 6): $R_t$=3.53 min.

Chiral HPLC (Method 59): $R_t$=4.71 min.

LC-MS (Method 19): $R_t$=1.85 min, MS (ESIpos): m/z (%)=416.2 (100) [M+H]$^+$, MS (ESIneg): m/z (%)=414.1.2 (100) [M−H]$^-$.

HR-TOF-MS: $C_{21}H_{26}N_3O_6$ calc. 416.1817, found 416.1808 [M+H]$^+$.

Example 465A

Pentafluorophenyl (3R)-3-[(tert-butoxycarbonyl)amino]-N²-(benzyloxy)carbonylamino-3-pyridin-3-yl-L-alaninate

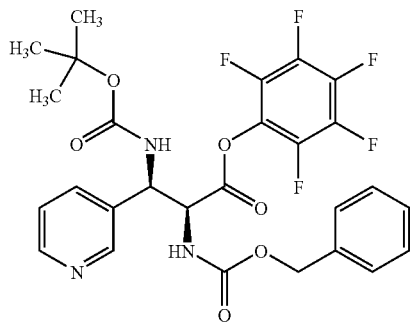

Exemplary compound 464A (63 mg, 119 µmol) and pentafluorophenol (24 mg, 131 µmol, 1.1 equivalents) are dissolved in dichloromethane (0.8 ml) at room temperature, EDCI (25 mg, 131 µmol, 1.1 equivalents) is then added, and the mixture is left to stand in a refrigerator for about 12 h. The solvent is subsequently distilled off in vacuo, and the residue is purified by chromatography (method 44). The title compound is obtained in a yield of 47 mg (51% of theory) as a colorless solid.

HPLC (Method 54): $R_t$=4.49 min.

LC-MS (Method 19): $R_t$=2.74 min, MS (ESIpos): m/z (%)=582.2 (40) $[M+H]^+$.

HR-TOF-MS: $C_{27}H_{25}N_3O_6F_5$ calc. 582.1659, found 582.1647 $[M+H]^+$.

Compounds 466A-470A listed in the following table were prepared by the indicated procedures from the indicated starting materials.

466A

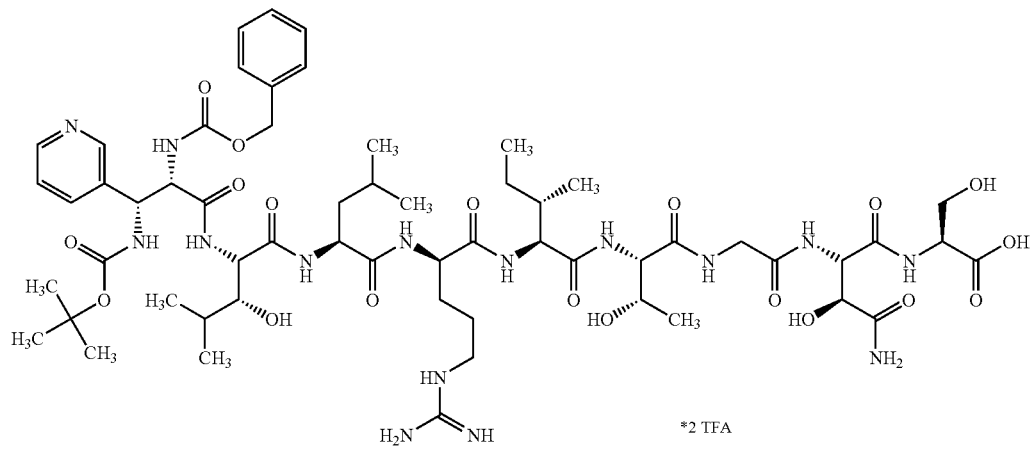

[(3R)-N²-(Benzyloxycarbonyl)-3-{(tert-butoxycarbonyl)amino}-3-(pyridin-3-yl)-L-alanyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine bistrifluoroacetate
Yield: 51 mg (49% of theory) from exemplary compound 3A (76 mg, 68 µmol) and 465A according to procedure 10, purification according to method 45

*2 TFA

HPLC (Method 6): $R_t$ = 3.42 min; LC-MS (Method 19): $R_t$ = 1.75 min, MS (ESIpos): m/z (%) = 652.1 (100) $[M + 2H]^{2+}$, 1302.7 (5) $[M + H]^+$; MS (ESIneg) m/z (%) = 1300.7 (100) $[M - H]^-$; HR-TOF-MS: $C_{58}H_{92}N_{15}O_{19}$ calc. 1302.6689, found 1302.6661 $[M + H]^+$.

467A

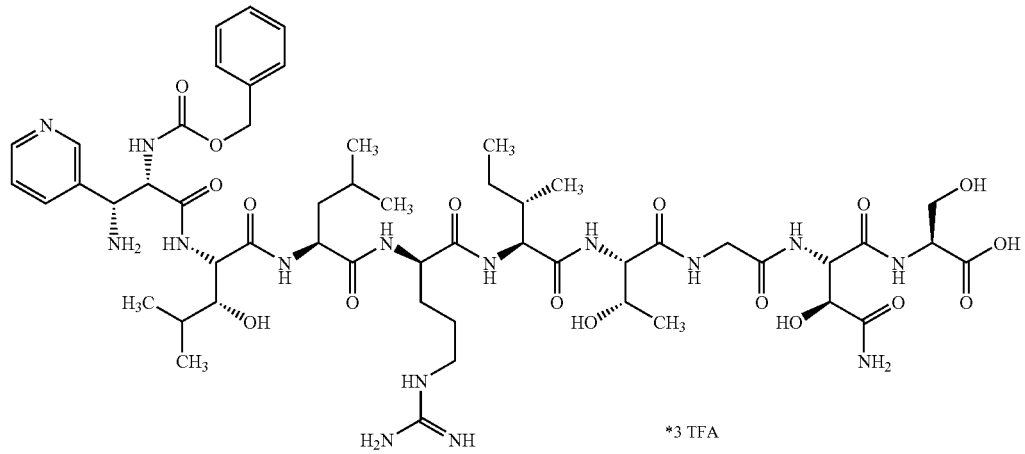

[(3R)-N²-(Benzyloxycarbonyl)-3-amino-3-(pyridin-3-yl)-L-alanyl]-[(3R)-3-hydroxy-L-leucyl]-L-leucyl-D-arginyl-L-isoleucyl-L-allothreonyl-glycyl-[(3R)-3-

*3 TFA

HPLC (Method 6): $R_t$ = 3.12 min; LC-MS (Method 52): $R_t$ = 0.91 min, MS (ESIpos): m/z (%) = 602.0 (100) $[M + 2H]^{2+}$, 1202.7 (5)

hydroxy-L-asparaginyl]-L-serine bistrifluoroacetate
Yield: 52 mg (quant.) as a colorless solid from 51 mg of exemplary compound 466A according to procedure 2, crude product reacted further without purification.

[M + H]$^+$, MS (ESIneg): m/z (%) =1200.8 (100) [M − H]$^−$; HR-TOF-MS: C$_{53}$H$_{84}$N$_{15}$O$_{17}$ calc. 1202.6165, found 1202.6160 [M + H]$^+$.

468A

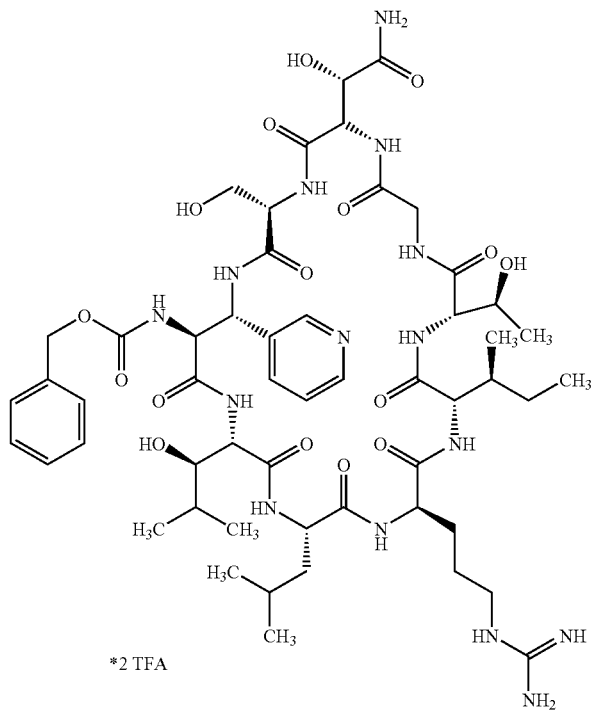

*2 TFA

[(3R)-N$^2$-(Benzyloxycarbonyl)-3-amino-3-(pyridin-3-yl)-L-alanyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine C$^{1.9}$-N$^{3.1}$-lactam bis-trifluoroacetate
Yield: 29 mg (61% of theory) from exemplary compound 467A (52 mg, 34 μmol) according to procedure 11, purification according to method 45.

HPLC (Method 6): R$_t$ = 3.38 min; LC-MS (Method 19): R$_t$ = 1.58 min, MS (ESIpos): m/z (%) = 592.9 (100) [M + 2H]$^{2+}$, 1184.7 (5) [M + H]$^+$, MS (ESIneg): m/z (%) = 1182.6 (100) [M − H]$^−$; HR-TOF-MS: C$_{53}$H$_{82}$N$_{15}$O$_{16}$ calc. 1184.6059, found 1184.6088 [M + H]$^+$.

469A

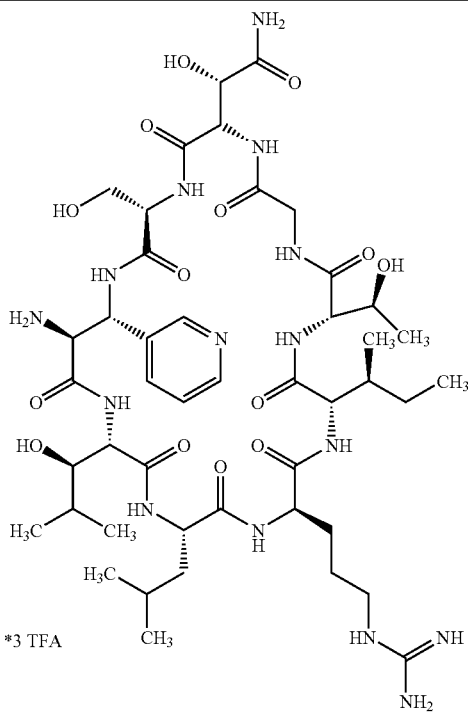

*3 TFA

[(3R)-3-Amino-3-(pyridin-3-yl)-L-alanyl]-[(3R)-3-hydroxy-L-leucyl]-L-leucyl-D-arginyl-L-isoleucyl-L-allothreonyl-glycyl-[(3R)-3-hydroxy-L-asparaginyl]-L-C$^{1.9}$-N$^{3.1}$-lactam tristrifluoroacetate
Yield: 65 mg (96% of theory) from exemplary compound 468A (65 mg, 46 μmol) according to procedure 4.

HPLC (Method 6): R$_t$ = 2.84 min; LC-MS (Method 22): R$_t$ = 2.13 min, MS (ESIpos): m/z (%) = 526.2 (100) [M + 2H]$^{2+}$, 1050.6 (30) [M + H]$^+$, MS (ESIneg): m/z (%) = 1048.6 (100) [M − H]$^−$; HR-TOF-MS: C$_{45}$H$_{76}$N$_{15}$O$_{14}$ calc. 1050.5691, found 1050.5670 [M + H]$^+$.

470A

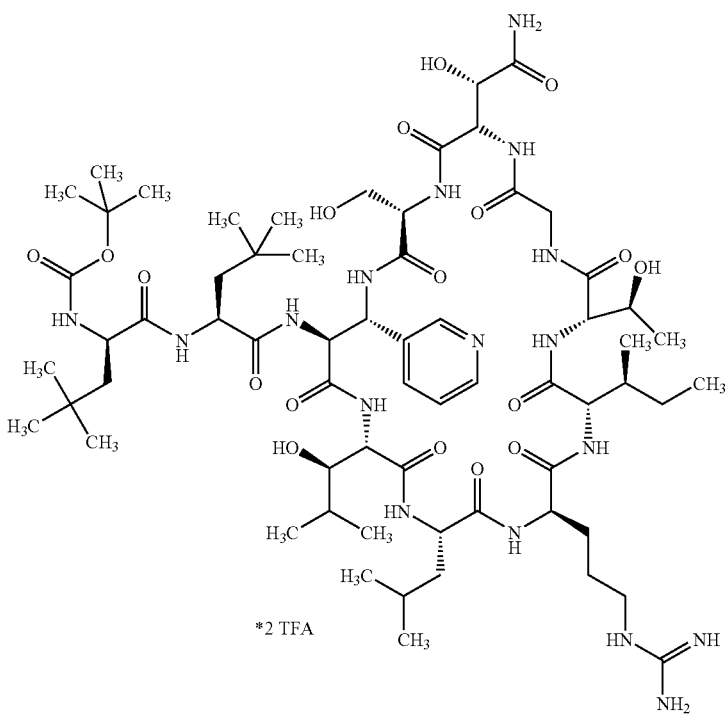

*2 TFA

[N$^2$-(tert.-Butoxycarbonyl)-3-tert-butyl-D-alanyl]-[3-tert-butyl-L-alanyl]-[(3R)-3-amino-3-(pyridin-3-yl)-L-alanyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine C$^{1.11}$-N$^{3.3}$-lactam HPLC (Method 6): R$_t$ = 4.13 min; LC-MS (Method 19): R$_t$ = 2.12 min, MS (ESIpos): m/z (%) = 703.1 (100) [M + 2H]$^{2+}$, 1404.8 (5) [M + H]$^+$, MS (ESIneg): m/z (%) = 1402.8 (100) [M − H]$^−$; HR-TOF-MS: C$_{64}$H$_{110}$N$_{17}$O$_{18}$ calc.

bistrifluoroacetate
Yield: 30 mg (60% of theory) from exemplary compound 469A (65 mg, 47 µmol) and exemplary compound 8A according to procedure 13, chromatography according to method 45.

1404.8210, found 1404.8215 [M + H]$^+$.

Exemplary Embodiments

Example 1

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-asparaginyl-L-serine $C^{1.11}$-$N^{3.3}$-lactam bistrifluoroacetate HR-TOF-MS (Method 24): $C_{60}H_{103}N_{16}O_{15}$ [M+H]$^+$ found 1287.7810, calc. 1287.7784.

Example 2

D-Leucyl-L-leucyl-[(3R)-3-amino-L-phenylalanyl]-[(3R)-3-hydroxy-L-leucyl]-L-leucyl-D-arginyl-L-isoleucyl-L-threonyl-glycyl-L-asparaginyl-L-serine $C^{1.11}$-$N^{3.3}$-lactam bistrifluoroacetate

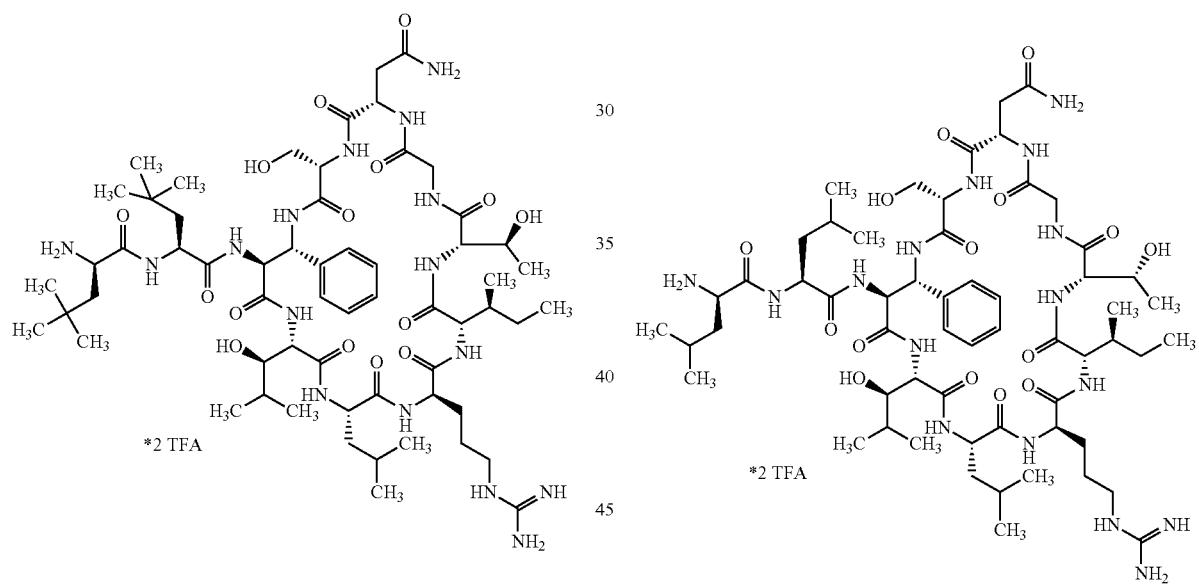

The protecting group is removed from the benzyloxycarbonyl-protected peptide (example 53A, 1.5 mg, 0.89 µmol) in dioxane and in aq. 0.1% TFA (1 ml, 10 equivalents) by hydrogenolysis according to procedure 4 after 1 h. 1.3 mg (96.6% of theory) of product are obtained after fine purification by preparative HPLC (method 26).

Alternatively, the amine (example 1) is liberated from the compound of example 58A (13.0 mg, 8.47 µmol) after the hydrogenolytic cleavage of the ester (procedure 4) in methanol (5 ml) using 0.1 N hydrochloric acid (508 µl, 1.9 mg, 50.79 µmol, 6 eq.). After chromatography (method 26), 12.0 mg (93.5% of theory) of the title compound are isolated.

HPLC (Method 9) $R_t$=14.73 min.

LC-MS (Method 18): $R_t$=1.71 min; MS (ESIpos): m/z (%)=1288 (3) [M+H]$^+$, 644 (100) [M+2H]$^{2+}$; MS (ESIneg.): m/z (%) 1286 (50) [M−H]$^-$, 642 (38) [M−2H]$^{2-}$, 1332 (100).

The title compound is prepared from the benzyloxycarbonyl-protected peptide (example 73A, 33.0 mg, 21.89 µmol) after the hydrogenolytic ester cleavage (procedure 4) in methanol (10 ml) and 0.1 N aq. hydrochloric acid (219 µl, 0.8 mg, 21.89 µmol, 1 eq.). Fine purification takes place by preparative HPLC (method 26) and 18.1 mg (56.1% of theory) of product are isolated.

HPLC (Method 9) $R_t$=14.15 min.

LC-MS (Method 18): $R_t$=1.52 min; MS (ESIpos): m/z (%)=1259 (5) [M+H]$^+$, 630 (100) [M+2H]$^{2+}$; MS (ESIneg.): m/z (%)=1257 (100) [M−H]$^-$, 628 (28) [M−2H]$^{2-}$.

HR-TOF-MS (Method 24): $C_{58}H_{100}N_{16}O_{15}$ [M+H]$^+$ found 1259.7454, calc. 1259.7471.

Example 3

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-ornityl-L-isoleucyl-L-allothreonyl-glycyl-L-asparaginyl-L-serine $C^{1.11}$-$N^{3.3}$-lactam bistrifluoroacetate

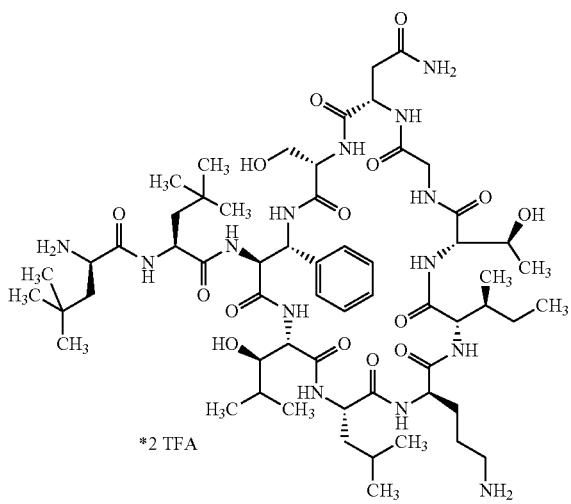

*2 TFA

The title compound is prepared from the benzyloxycarbonyl-protected peptide (example 81A, 20.0 mg, 13.21 µmol) after the hydrogenolytic ester cleavage (procedure 4) in methanol (10 ml) and 0.1 N aq. hydrochloric acid (198 µl, 0.7 mg, 19.8 µmol, 1.5 eq.). Fine purification takes place by preparative HPLC (method 26), and 17.9 mg (91.9% of theory) of product are isolated.

HPLC (Method 9) $R_t$=15.51 min.

LC-MS (Method 18): $R_t$=1.57 min; MS (ESIpos): m/z (%)=1245 (13) [M+H]$^+$, 623 (100) [M+2H]$^{2+}$; MS (ESIneg.): m/z (%)=1243 (100) [M−H]$^-$.

HR-TOF-MS (Method 24): $C_{59}H_{102}N_{14}O_{15}$ [M+H]$^+$ found 1245.7560, calc. 1245.7566.

Example 4

[3-tert-Butyl-D-alanyl]-[3-tert-butyl-L-alanyl]-[(3R)-3-amino-O-methyl-L-tyrosyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam bistrifluoroacetate

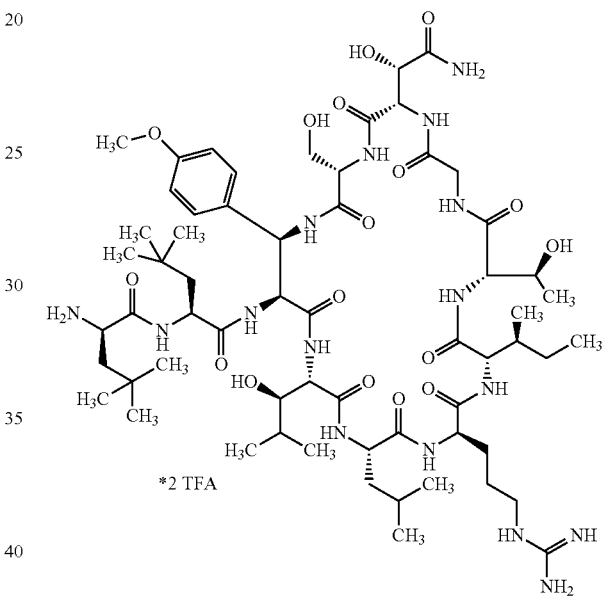

*2 TFA

The compound of example 112A (23 mg, 14.5 µmol) is reacted according to procedure 5. After purification by chromatography by means of preparative HPLC (method 43) 17 mg (75% of theory) of product are obtained by freeze drying.

HPLC/UV-Vis (Method 5): $R_t$=3.69 min.

HPLC/UV-Vis (Method 4): $R_t$=3.95 min.

LC-MS (Method 18): $R_t$=1.71 min; MS (ESIpos): m/z (%)=667 (100) [M+2H]$^{2+}$, 1333 (2) [M+H]$^+$; MS (ESIneg.): m/z (%) 1331 (100) [M−H]$^-$.

Example 5

[3-tert-Butyl-D-alanyl]-[3-tert-butyl-L-alanyl]-[(3R)-3-amino-4-(dimethylaminophenyl)-L-alanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam tristrifluoroacetate

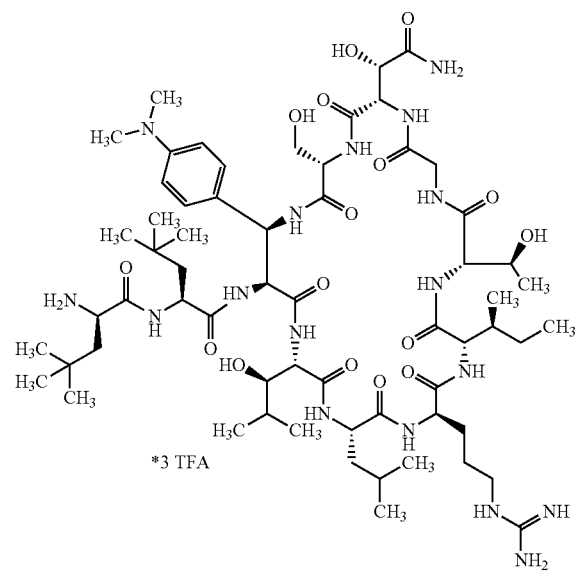

*3 TFA

The compound of example 128A (105 mg, 66% purity, 41 μmol) is dissolved in 30% TFA in dichloromethane (4 ml) and stirred at RT for 20 min. The mixture is then concentrated in vacuo and the residue is purified by chromatography (method 44 with modified gradient: 0-2 min 10% B, ramp, 38 min 60% B). 49 mg (29 μmol, 70% of theory) of the title compound are obtained.

HPLC (Method 7): $R_t$=3.62 min.

LC-MS (Method 20): $R_t$=1.72 min, MS (ESIpos.): m/z (%) 450.0 (100) [M+3H]$^{3+}$, 674.4 (40) [M+2H]$^{2+}$.

HR-TOF-MS (Method 24): $C_{62}H_{108}N_{17}O_{16}$ [M+H]$^+$ calc. 1346.8155, found 1346.8130.

Example 6

[3-Trimethylsilyl-D-alanyl]-[3-tert-butyl-L-alanyl]-[(3R)-3-amino-4-(dimethylamino-phenyl)-L-alanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam tristrifluoroacetate

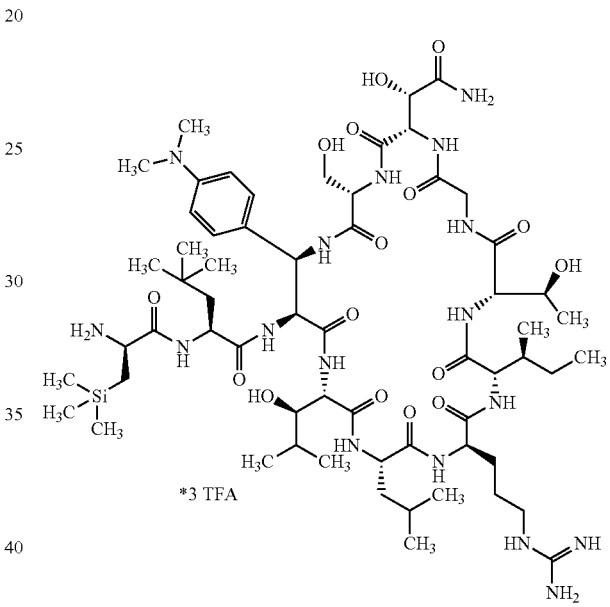

*3 TFA

The compound of example 133A (126 mg, 82 μmol) is dissolved in 30% TFA in dichloromethane (4 ml) and stirred at RT for 20 min. The mixture is then concentrated in vacuo and the residue is purified by chromatography (method 44 with modified gradient: 0-2 min 10% B, ramp, 38 min 60% B). 78 mg (46 μmol, 56% of theory) of the title compound are obtained.

HPLC (Method 7): $R_t$=3.69 min.

LC-MS (Method 20): $R_t$=1.66 min, MS (ESIpos.): m/z (%) 682.3 (100) [M+2H]$^{2+}$, 1364.1 (2) [M+H]$^+$.

HR-TOF-MS (Method 24): $C_{61}H_{108}N_{17}O_{16}Si$ [M+H]$^+$ calc. 1362.7924, found 1362.7949.

Example 7

D-Phenylalanyl-L-phenylalanyl-[(3R)-3-amino-L-alanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}-N^{3.3}$-lactam bistrifluoroacetate

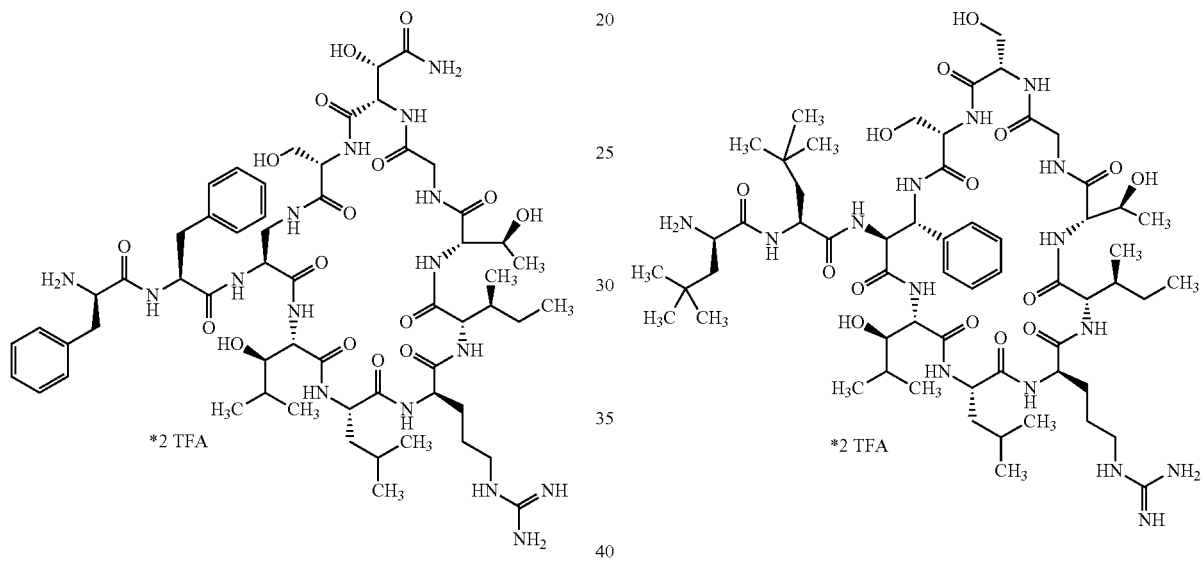

*2 TFA

The target compound is prepared from the compound of example 144A (0.3 mg, 0.20 µmol) as described in procedure 1. After fine purification by gel chromatography (method 45, eluent: methanol), 0.1 mg (23.3% of theory) of product is isolated.

HPLC (Method 12): $R_t$=5.74 min.

LC-MS (Method 18): $R_t$=1.57 min, MS (ESIpos.): m/z (%)=1268 (2) [M+H]$^+$, 634 (100) [M+2H]$^{2+}$; MS (ESIpos.): m/z (%)=1266 (50) [M–H]$^-$, 632 (22) [M–2H]$^{2-}$, 1312 (100) [M–H+HCO$_2$H]$^-$.

MALDI-MS (Method 25): $C_{58}H_{92}N_{16}O_{16}$ [M+H]$^+$ calc. 1267.68, found 1267.65.

Example 8

[3-tert-Butyl-D-alanyl]-[3-tert-Butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-seryl-L-serine $C^{1.11}-N^{3.3}$-lactam bistrifluoroacetate

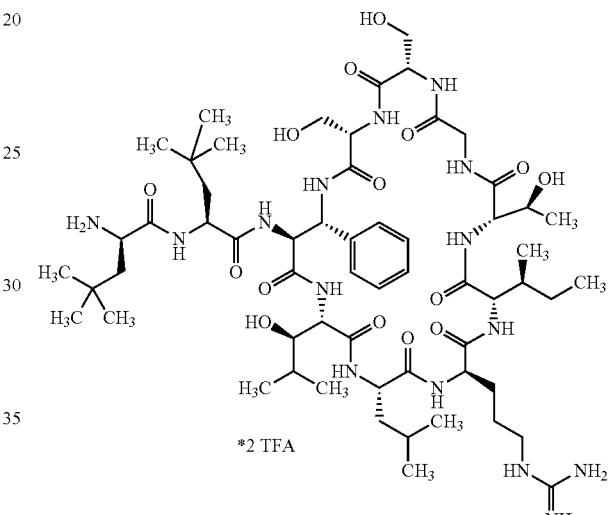

*2 TFA

The compound of example 233A (4 mg, 3 µmol) is dissolved in methanol (1 ml). 17 µl of 1 M hydrochloric acid and 10% palladium-carbon (2 mg) are added and the mixture is hydrogenated under atmospheric pressure at room temperature for 2 h. The solution is filtered to remove the catalyst and concentrated. After purification by chromatography (method 44) 2.2 mg (1.5 µmol 53% of theory) of the title compound are obtained.

HPLC (Method 5): $R_t$=4.45 min.

LC-MS (Method 20): $R_t$=1.45 min, MS (ESIpos): m/z (%) 631.1 (100) [M+2H]$^{2+}$, 1260.9 (3) [M+H]$^+$.

HR-TOF-MS (Method 24): $C_{59}H_{102}N_{15}O_{15}$ calc. 1260.7675, found 1260.7670 [M+H]$^+$.

Example 9

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[3-(3-pyridyl)-L-alanyl]-L-serine $C^{1.11}$-$N^{3.3}$-lactam tristrifluoroacetate

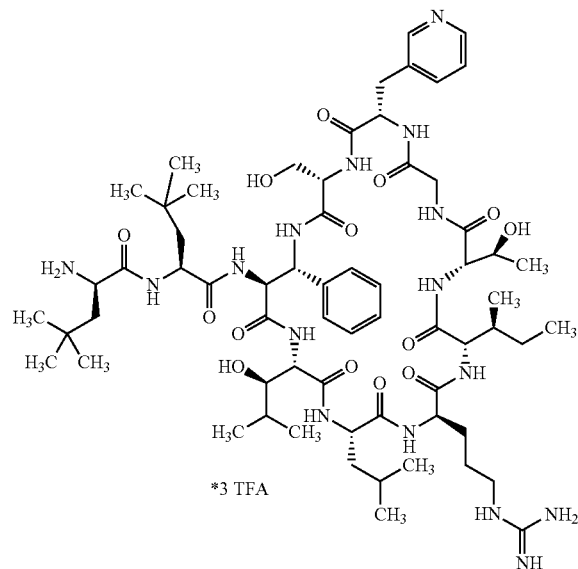

According to the method for preparing the compound of example 233A the title compound is obtained in a yield of 4 mg (32% of theory) from the compound of example 226A (12 mg, 13 µmol).

HPLC (Method 5): $R_t$=3.60 min.

LC-MS (Method 19): $R_t$=1.43 min, MS (ESIpos): m/z (%)=661.5 (100) [M+2H]$^{2+}$, 1321.8 (10) [M+H]$^+$.

HR-TOF-MS (Method 24): $C_{64}H_{105}N_{16}O_{14}$ calc. 1321.7991, found 1321.7955 [M+H]$^+$.

Example 10

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-phenyalanyl-L-serine $C^{1.11}$-$N^{3.3}$-lactam bistrifluoroacetate

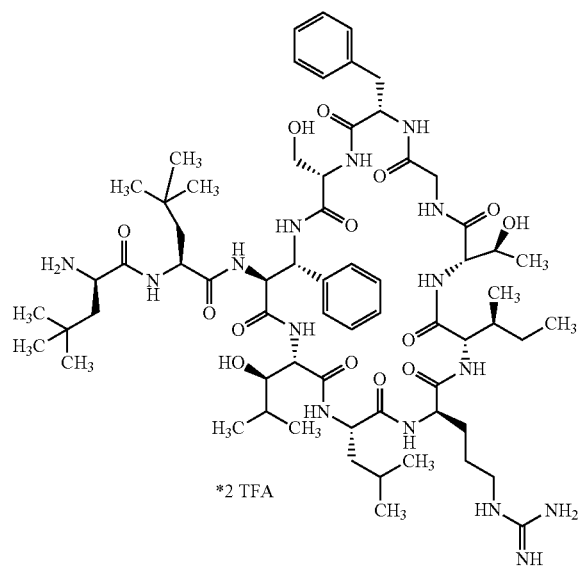

The compound of example 235A is reacted according to general procedure 2 with 1 ml of the reagent solution for 1 h, and the product is purified according to a modified method 44 (gradient: 0 min 25% B, ramp, 35-38 min 35% B). The title compound is obtained in a yield of 10 mg (50% of theory).

HPLC (Method 5): $R_t$=3.41 min.

LC-MS (Method 19): $R_t$=1.57 min, MS (ESIpos): m/z (%)=661.1 (100) [M+2H]$^{2+}$, 1320.8 (5) [M+H]$^+$; MS (ESIneg): m/z (%)=1318.6 (90) [M−H]$^-$.

HR-TOF-MS (Method 24): $C_{65}H_{106}N_{15}O_{14}$ calc. 1320.8039, found 1320.8042 [M+H]$^+$.

Example 11

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[L-threonyl]-L-serine $C^{1.11}$-$N^{3.2}$-lactam bistrifluoroacetate

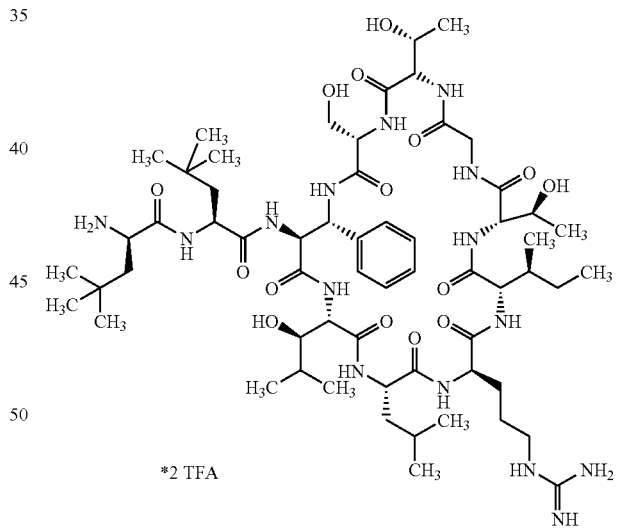

The compound of example 236A is reacted according to general procedure 2 with 1 ml of the reagent solution for 30 min, and the product is purified according to method 44. The title compound is obtained in a yield of 3 mg (27% of theory).

HPLC (Method 5): $R_t$=3.73 min.

LC-MS (Method 19): $R_t$=1.53 min, MS (ESIpos): m/z (%)=638.0 (100) [M+2H]$^{2+}$.

HR-TOF-MS (Method 24): $C_{60}H_{103}N_{15}O_{15}$ calc. 1274.7831, found 1274.7827 [M+H]$^+$.

Example 12

[3-tert-Butyl-D-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-allothreonyl-L-serine $C^{1.11}$-$N^{3.3}$-lactam bistrifluoroacetate

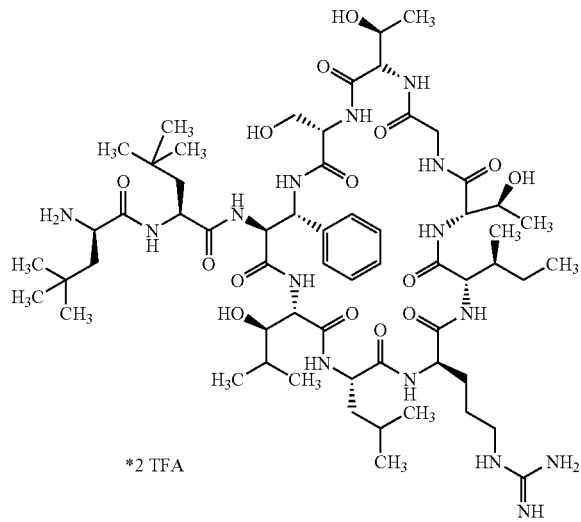

The compound of example 237A (47 mg, 24 µmol) is reacted according to general procedure 2 with 1 ml of the reagent solution for 30 min, and the product is purified according to method 44. The title compound is obtained in a yield of 21 mg (57% of theory).

HPLC (Method 6): $R_t$=3.43 min.

LC-MS (Method 19): $R_t$=1.52 min, MS (ESIpos): m/z (%)=638.1 (100) [M+2H]$^{2+}$; MS (ESIneg): m/z (%)=1273.6 [M]$^-$.

HR-TOF-MS (Method 24): $C_{60}H_{103}N_{15}O_{15}$ calc. 1274.7831, found 1274.7800 [M+H]$^+$.

Example 13

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-alanyl-L-serine $C^{1.11}$-$N^{3.3}$-lactam bistrifluoroacetate

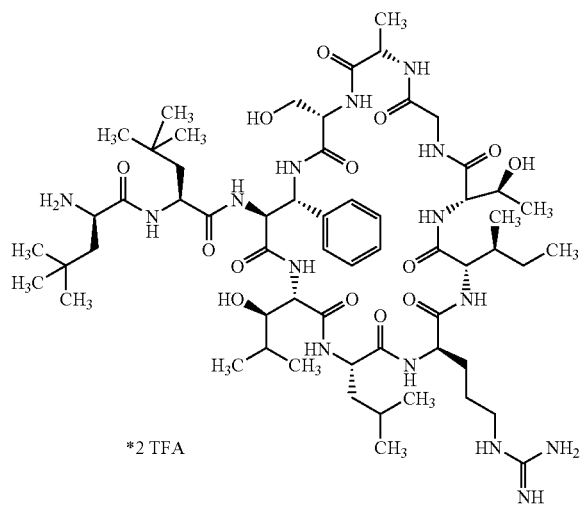

The compound of example 238A is reacted according to general procedure 2 with 1 ml of the reagent solution for 30 min, and the product is purified according to method 44. A further fine purification is then carried out: column: Waters Symmetry-Prep™ C-18, 7 µm, 300 mm×19 mm; eluent A: water+0.05% TFA, eluent B: acetonitrile+0.05% TFA: flow rate: 10 ml/min; A:B 65/35 isocratic. The title compound is obtained in a yield of 8 mg (20% of theory).

HPLC (Method 5): $R_t$=3.71 min.

LC-MS (Method 19): $R_t$=1.49 min, MS (ESIpos): m/z (%)=623.2 (100) [M+2H]$^{2+}$.

HR-TOF-MS (Method 24): $C_{59}H_{101}N_{15}O_{14}$ calc. 1244.7726, found 1244.7748 [M+H]$^+$.

Example 14

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-seryl-glycyl-[(3S)-3-hydroxy-L-asparaginyl]-L-serine $C^{1.11}$-$N^{3.3}$-lactam bistrifluoroacetate

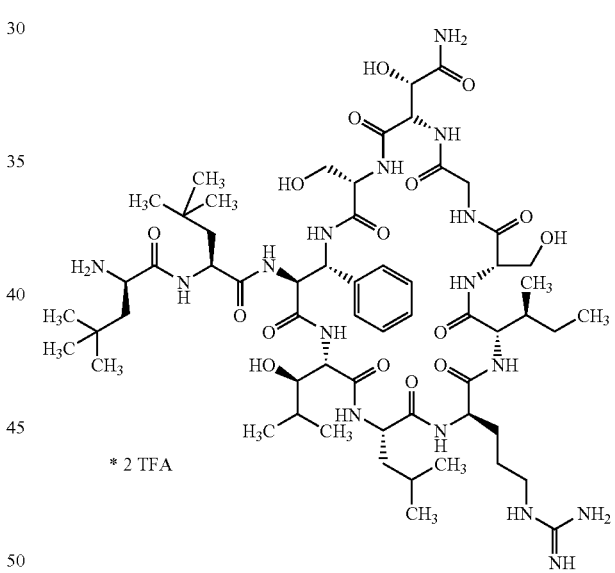

The compound of example 239A is reacted according to general procedure 2 with 1 ml of the reagent solution for 1 h, and the product is purified according to method 44. A further fine purification is then carried out: column: Waters Symmetry-Prep™ C-18, 7 µm, 300 mm×19 mm; eluent A: water+0.05% TFA, eluent B: acetonitrile+0.05% TFA: flow rate: 10 ml/min; A:B 65/35 isocratic. The title compound is obtained in a yield of 9 mg (6 µmol, 35% of theory).

HPLC (Method 5): $R_t$=3.63 min.

LC-MS (Method 19): $R_t$=1.43 min, MS (ESIpos): m/z (%)=643.7 (100) [M+2H]$^{2+}$, 1289.8 (10) [M+H]$^+$.

HR-TOF-MS (Method 24): $C_{59}H_{101}N_{16}O_{16}$ calc. 1289.7576, found 1289.7578 [M+H]$^+$.

Example 15

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-asparaginyl-L-serine-$C^{1.11}$-$N^{3.3}$-lactam-bistrifluoroacetate

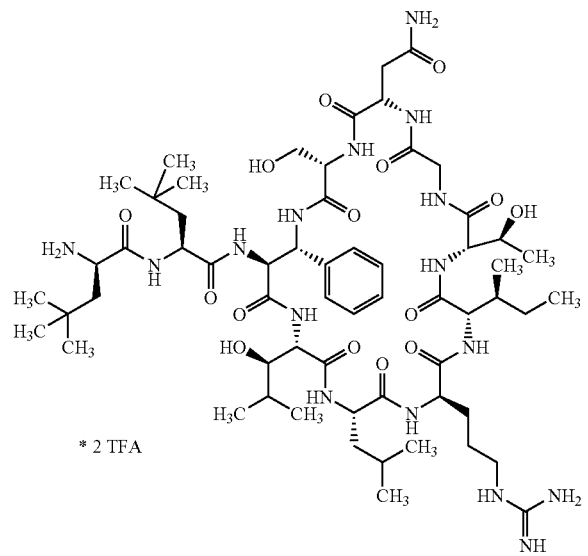

* 2 TFA

The compound of example 240A is reacted according to general procedure 2 with 1 ml of the reagent solution for 1 h, and the product is purified several times according to method 44. The title compound is obtained in a yield of 1.1 mg (6 µmol, 3.5% of theory).

HPLC (Method 5): $R_t$=3.41 min.
LC-MS (Method 22): $R_t$=2.90 min, MS (ESIpos): m/z (%)=645 (100) $[M+2H]^{2+}$, 1288 (10) $[M+H]^+$.
HR-TOF-MS (Method 24): $C_{60}H_{103}N_{16}O_{15}$ calc. 1287.7784, found 1287.7786 $[M+H]^+$.

Example 16

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-alanine $C^{1.11}$-$N^{3.3}$-lactam bistrifluoroacetate

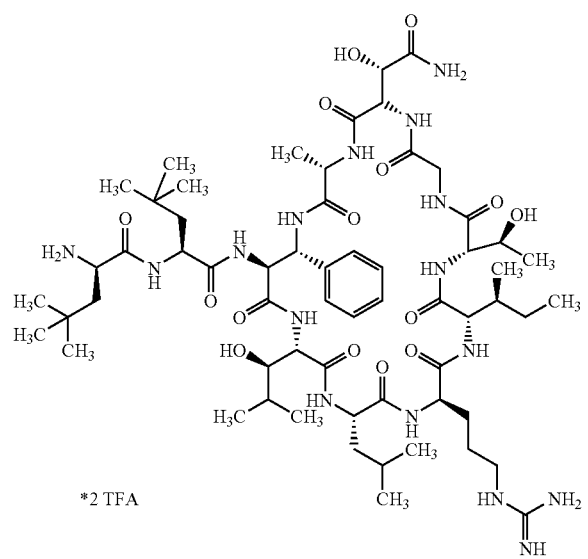

*2 TFA

The compound of example 253A is reacted according to general procedure 2 with 2 ml of the reagent solution for 1 h, and the product is purified according to method 44. The product is fine purified according to a variant of method 34 (use of eluent A:eluent B 3:2; isocratic instead of the gradient). The title compound is obtained in a yield of 22 mg (36% of theory).

HPLC (Method 6): $R_t$=3.43 min.
LC-MS (Method 22): $R_t$=2.90 min, MS (ESIpos): m/z (%)=645 (100) $[M+2H]^{2+}$, 1288 (60) $[M+H]^+$; MS (ESIneg): m/z (%)=1286 (100) $[M-H]^-$.
HR-TOF-MS (Method 24): $C_{60}H_{103}N_{16}O_{15}$ calc. 1287.7784, found 1287.7800 $[M+H]^+$.

Example 17

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-D-alanyl-[(3S)-3-hydroxy-L-asparaginyl]-L-serine $C^{1.11}$-$N^{3.3}$-lactam bistrifluoroacetate

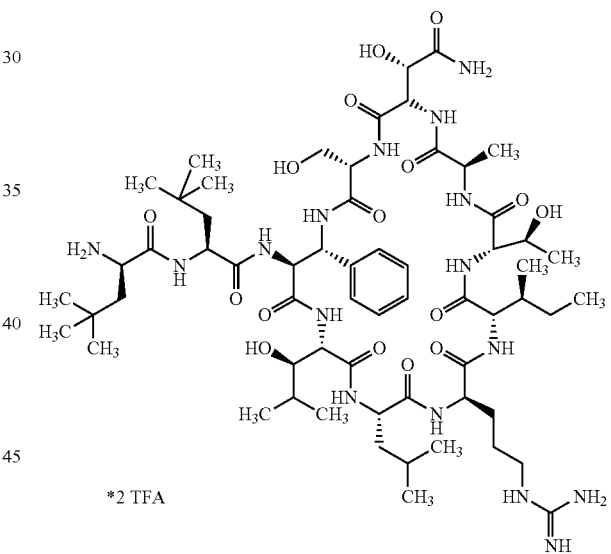

*2 TFA

The compound of example 267A (34 mg of crude product, about 6 µmol) is reacted according to general procedure 2 with 1 ml of the reagent solution for 30 min. The product is obtained pure by chromatography twice according to method 33. The title compound is obtained in a yield of 6 mg (65% of theory).

HPLC (Method 6): $R_t$=3.42 min.
LC-MS (Method 22): $R_t$=2.90 min, MS (ESIpos): m/z (%)=660 (100) $[M+2H]^{2+}$, 1317.8 (10) $[M+H]^+$; MS (ESIneg): m/z (%)=1315.8 (100) $[M-H]^-$.
HR-TOF-MS (Method 24): $C_{61}H_{105}N_{16}O_{16}$ calc. 1317.7889, found 1317.7892 $[M+H]^+$.

Compounds 19-44 shown in the following table were prepared according to the indicated procedures from the indicated starting materials.

| Exemplary embodiment No. | Name Yield, Synthesis Method | Structure Analysis |
|---|---|---|
| 19 | | 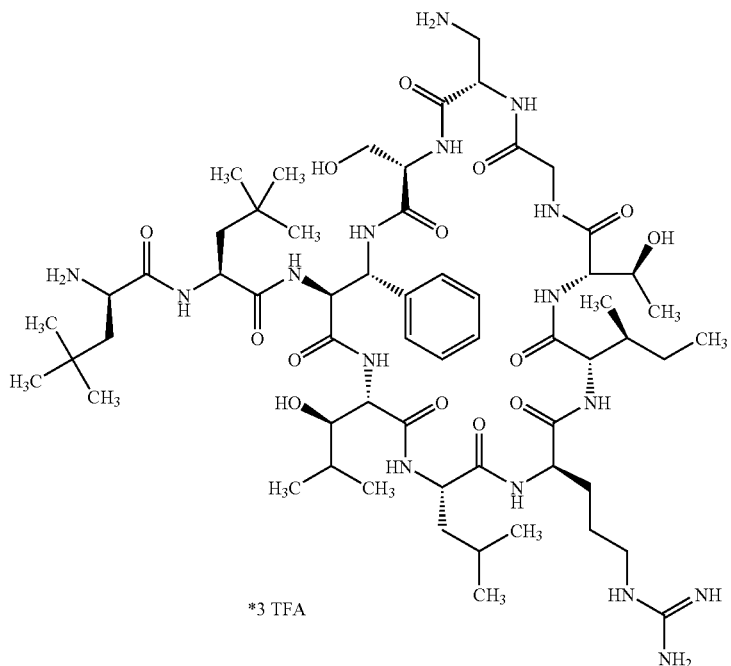 *3 TFA |
| | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(2S)-2,3-diaminopropionyl]-L-serine $C^{1.11}$-$N^{3.3}$-lactam tristrifluoroacetate<br>Yield: 120 mg (44% of theory) from exemplary compound 432A (273 mg, 172 µmol) according to procedure 2, purification according to method 44 | HPLC (Method 6): $R_t$ = 3.34 min; LC-MS (Method 19): $R_t$ = 1.38 min, MS (ESIpos): m/z (%) = 630.5 (100) $[M + 2H]^{2+}$, 1259.8 (10) $[M + H]^+$, MS (ESIneg): m/z (%) = 1257.8 (30) $[M - H]^-$, 1304.7 (100) $[M + HCOO^-]^-$; HR-TOF-MS: $C_{59}H_{103}N_{16}O_{14}$ calc. 1259.7835, found 1259.7811 $[M + H]^+$. |
| 20 | | 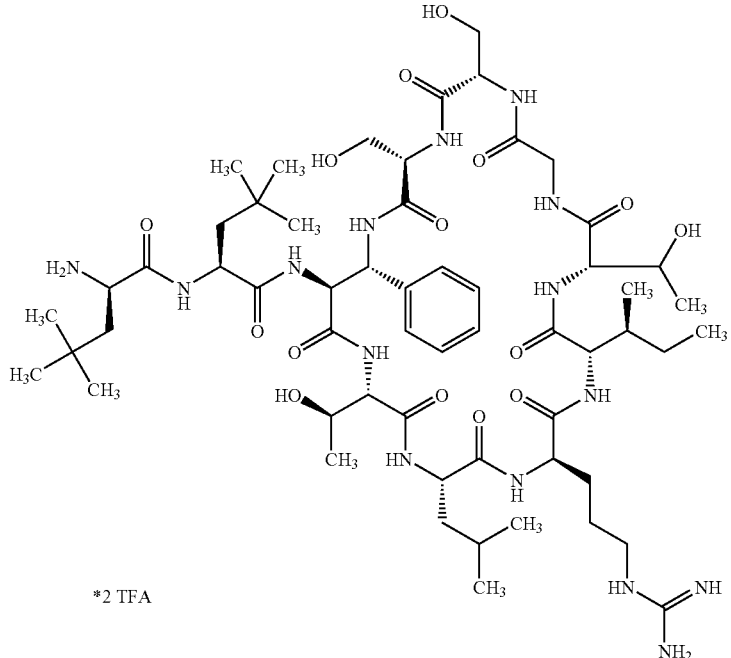 *2 TFA |
| | [3-tert-Butyl-D-alanyl]-[3-tert-butyl-L-alanyl]-[(3R)-3-amino-L-phenylalanyl]-L-threonyl-L-leucyl-D-arginyl-L-isoleucyl-L-allothreonyl- | HPLC (Method 6): $R_t$ = 3.45 min; LC-MS (Method 19): $R_t$ = 1.52 min, MS (ESIpos): m/z (%) = 617.1 (100) $[M + 2H]^{2+}$, 1232.9 |

| Exemplary embodiment No. | Structure Name Yield, Synthesis Method | Analysis |
|---|---|---|
| | glycyl-L-serine $C^{1.11}$-$N^{3.3}$-lactam bistrifluoroacetate<br>Yield: 1.1 mg (17% of theory) from exemplary compound 433A (6 mg, 4 μmol) according to procedure 2, multiple purification according to method 33. | (10) $[M + H]^+$, MS (ESIneg): m/z (%) = 1230.9 (100) $[M + H]^+$, 1277.0 (80) $[M + HCOO^-]^-$; HR-TOF-MS: $C_{57}H_{98}N_{15}O_{15}$ calc. 1232.7362, found 1232.7371 $[M + H]^+$. |
| 21 | 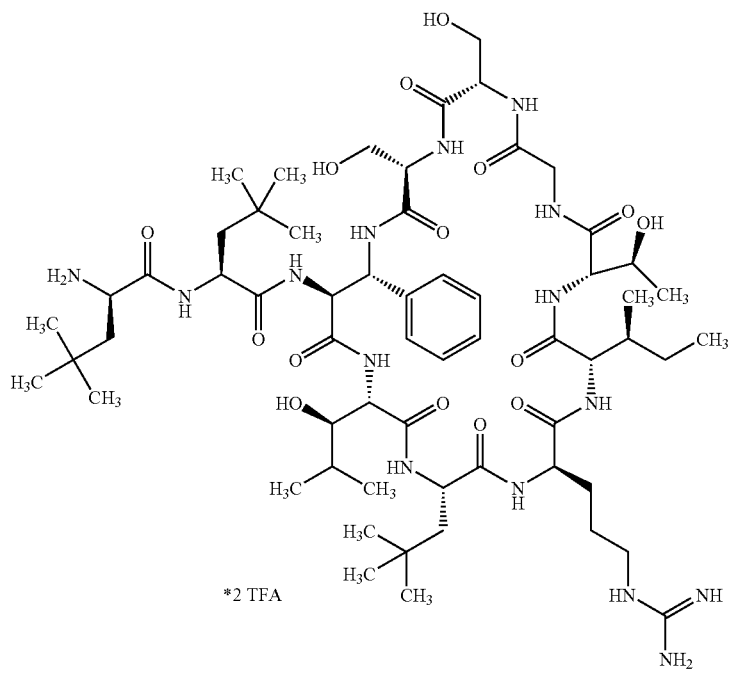[3-tert-Butyl-D-alanyl]-[3-tert-butyl-L-alanyl]-[(3R)-3-amino-L-phenylalanyl]-[(3R)-3-hydroxy-L-leucyl]-[3-tert-butyl-L-alanyl]-D-arginyl-L-isoleucyl-L-allothreonyl-glycyl-L-seryl-L-serine $C^{1.11}$-$N^{3.3}$-lactam bistrifluoroacetate<br>Yield: 6.5 mg (25% of theory) from exemplary compound 434A (22 mg, 16 μmol) according to procedure 2, purification according to method 44. | HPLC (Method 6): $R_t$ = 3.52 min; LC-MS (Method 19): $R_t$ = 1.58 min, MS (ESIpos): m/z (%) = 638.3 (100) $[M + 2H]^{2+}$, 1275.2 (5) $[M + H]^+$, MS (ESIneg): m/z (%) = 1273.0 (100) $[M - H]^-$; HR-TOF-MS: $C_{60}H_{104}N_{15}O_{15}$ calc. 1274.7831, found 1274.7804 $[M + H]^+$. |

| Exemplary embodiment No. | Name Yield, Synthesis Method | Structure Analysis |
|---|---|---|
| 22 | | 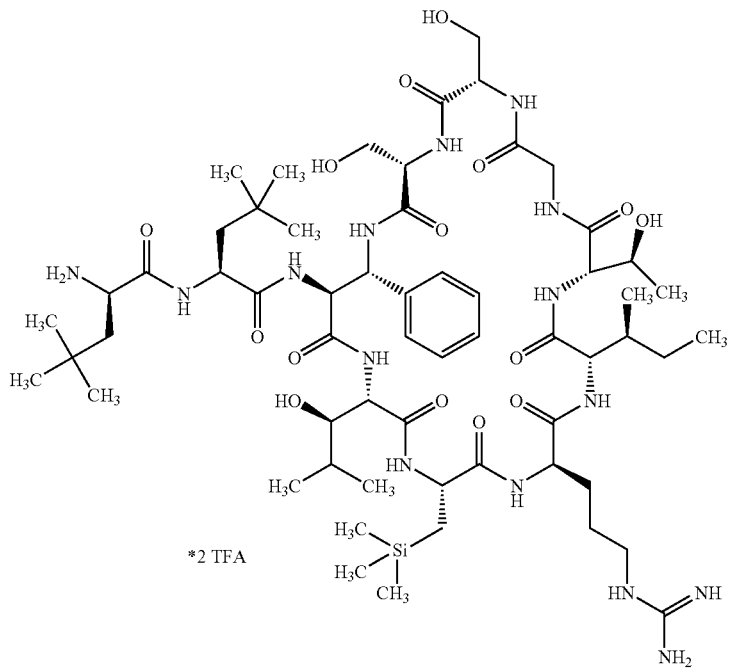 |
| | [3-tert-Butyl-D-alanyl]-[3-tert-butyl-L-alanyl]-[(3R)-3-amino-L-phenylalanyl]-[(3R)-3-hydroxy-L-leucyl]-[3-trimethylsilyl-L-alanyl]-D-arginyl-L-isoleucyl-L-allothreonyl-glycyl-L-seryl-L-serine $C^{1.11}$-$N^{3.3}$-lactam bistrifluoroacetate<br>Yield: 13 mg (42% of theory) from exemplary compound 435A (29 mg, 20 μmol) according to procedure 2, purification according to method 44. | HPLC (Method 6): $R_t$ = 3.58 min; LC-MS (Method 19): $R_t$ = 646.1 (100) $[M + 2H]^{2+}$, 1291.1 (5) $[M + H]^+$ min, MS (ESIpos): m/z (%) =, MS (ESIneg): m/z (%) = 1289.0 (30)m–, 1335.0 (100) $[M + HCOO^-]^-$; HR-TOF-MS: $C_{59}H_{104}N_{15}O_{15}Si$ calc. 1290.7601, found 1290.7576 $[M + H]^+$. |
| 23 | | 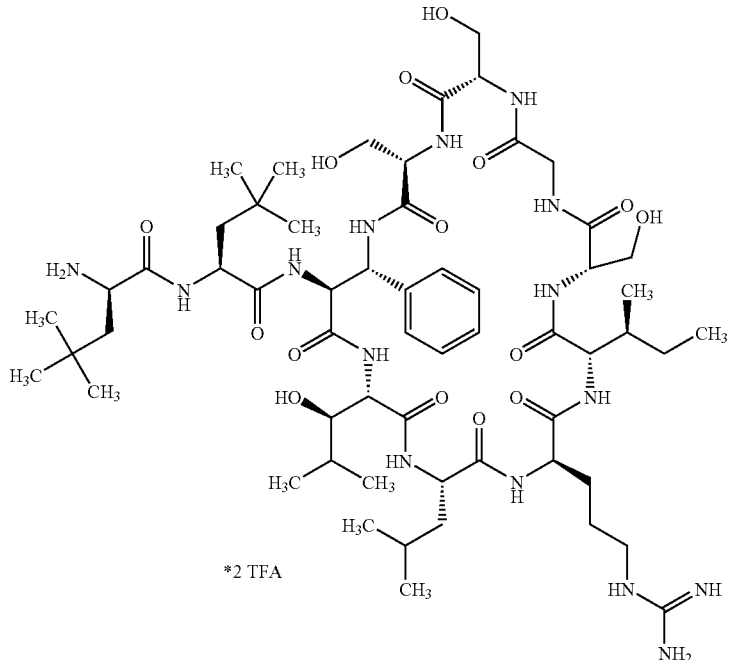 |
| | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L- | HPLC (Method 6): $R_t$ = 3.44 min; LC-MS (Method 19): $R_t$ = 1.67 min, MS (ESIpos): m/z (%) = 624.0 (100) $[M + 2H]^{2+}$, 1246.8 |

| Exemplary embodiment No. | Name Yield, Synthesis Method | Structure Analysis |
|---|---|---|
| | isoleucyl-L-seryl-glycyl-L-seryl-L-serine $C^{1.11}$-$N^{3.3}$-lactam bistrifluoroacetate<br>Yield: 13 mg (54% of theory) from exemplary compound 436A (23 mg, 16 µmol) according to procedure 2, purification according to a variation of method 44 (ramp only to 60% acetonitrile). | (5) $[M + H]^+$, MS (ESIneg): m/z (%) = 1244.8 (80) $[M − H]^−$, 1290.8 (100) $[M + HCOO^−]^−$; HR-TOF-MS: $C_{58}H_{100}N_{15}O_{15}$ calc. 1246.7518, found 1246.7500 $[M + H]^+$. |
| 24 | | |

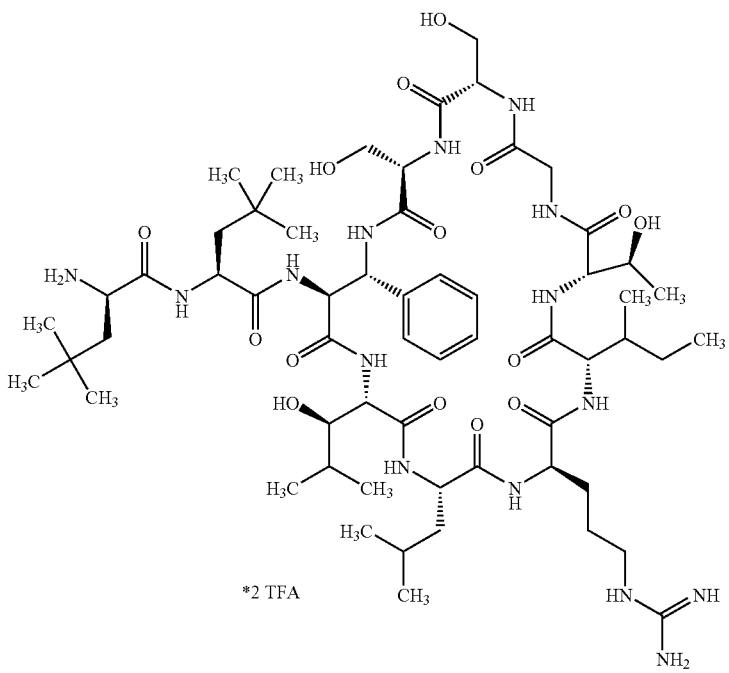

*2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-valyl-L-allothreonyl-glycyl-L-seryl-L-serine $C^{1.11}$-$N^{3.3}$-lactam bistrifluoroacetate
Yield: 13 mg (44% of theory) from exemplary compound 437A (73 mg, 20 µmol) according to procedure 2, purification according to a variation of method 44 (ramp only to 60% acetonitrile).

HPLC (Method 6): $R_t$ = 3.42 min; LC-MS (Method 19): $R_t$ = 1.47 min, MS (ESIpos): m/z (%) = 624.1 (100) $[M + 2H]^{2+}$, 1246.7 (10) $[M + H]^+$, MS (ESIneg): m/z (%) = 1290.7 (50) $[M + HCOO^−]^−$; HR-TOF-MS: $C_{58}H_{100}N_{15}O_{15}$ calc. 1246.7518, found 1246.7512 $[M + H]^+$.

| Exemplary embodiment No. | Name Yield, Synthesis Method | Structure Analysis |
|---|---|---|

25

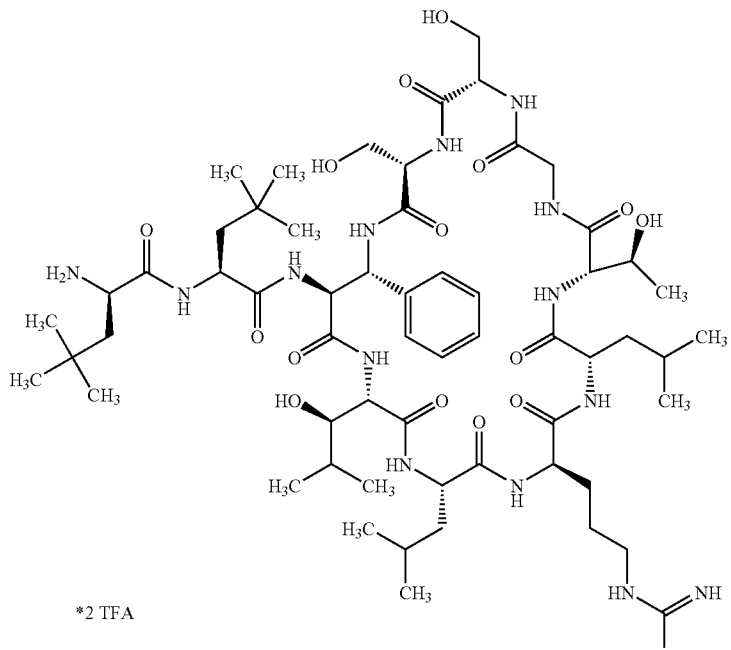

*2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-leucyl-L-allothreonyl-glycyl-L-seryl-L-serine $C^{1.11}$-$N^{3.3}$-lactam bistrifluoroacetate
Yield: 8 mg (11% of theory) from exemplary compound 438A (72 mg, 49 μmol) according to procedure 2, multiple purification according to a variation of method 44 (ramp only to 60% acetonitrile).

HPLC (Method 6): $R_t$ = 3.49 min; LC-MS (Method 19): $R_t$ = 1.62 min, MS (ESIpos): m/z (%) = 631.2 (100) $[M + 2H]^{2+}$, 1260.9 (1) $[M + H]^+$, MS (ESIneg): m/z (%) = 1259.9 (90) $[M - H]^-$, 1305 $([M + HCOO]^-$; HR-TOF MS: $C_{59}H_{102}N_{15}O_{15}$ calc. 1260.7675, found 1260.7642 $[M + H]^+$.

26

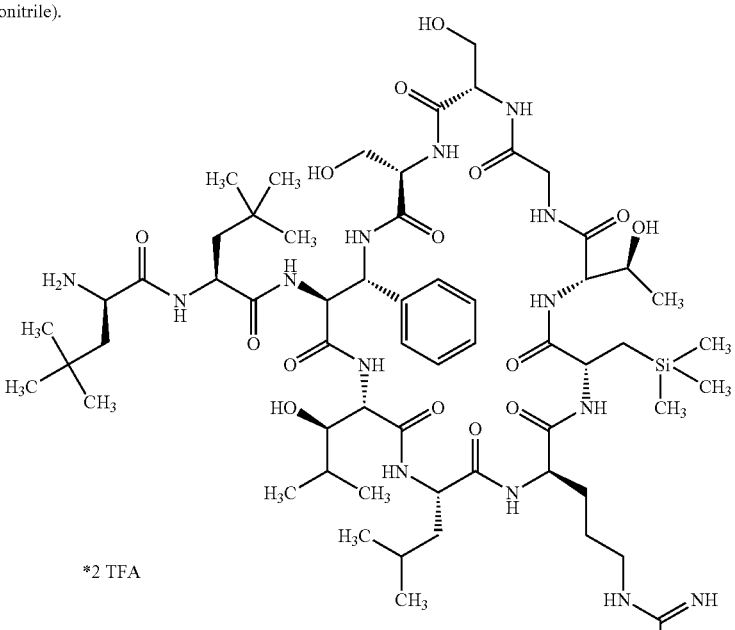

*2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-[3-

HPLC (Method 6): $R_t$ = 3.57 min; LC-MS (Method 19): $R_t$ = 1.69 min, MS (ESIpos): m/z (%) = 646.1 (100) $[M + 2H]^{2+}$, 1290.9

| Exemplary embodiment No. | Name Yield, Synthesis Method | Analysis |
|---|---|---|
| | trimethylsilyl-L-alanlyl]-L-allothreonyl-glycyl-L-seryl-L-serine $C^{1.11}$-$N^{3.3}$-lactam bistrifluoroacetate<br>Yield: 12mg (26% of theory) from exemplary compound 439A (74 mg, 30 µmol) according to procedure 2, multiple purification according to a variation of method 44 (ramp only to 60% acetonitrile). | (5) $[M + H]^+$, MS (ESIneg): m/z (%) = 1288.9 (90) $[M - H]^-$, 1336.0 (100) $[M + HCOO^-]^-$; HR-TOF-MS: $C_{59}H_{104}N_{15}O_{15}Si$ calc. 1290.7601, found 1290.7587 $[M + H^+]$. |
| 27 | 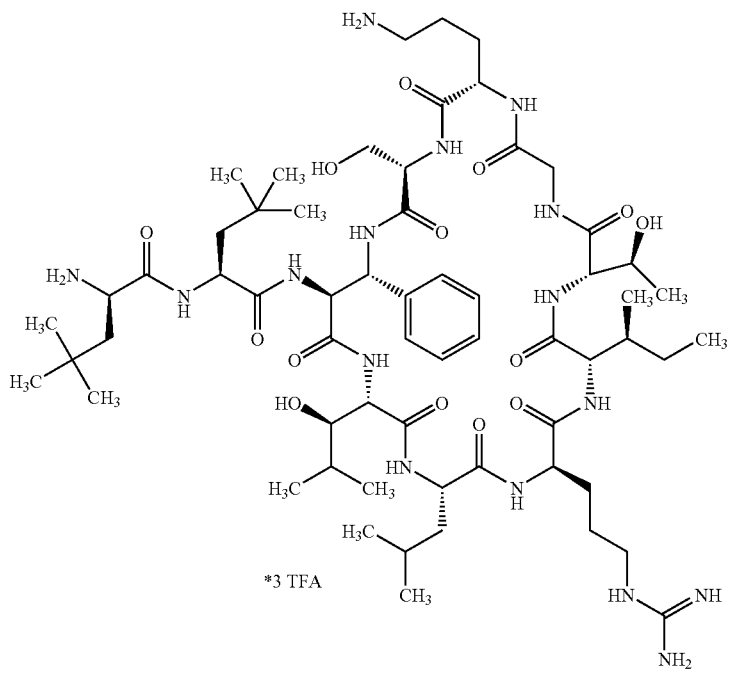<br>[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-ornithyl-L-serine $C^{1.11}$-$N^{3.3}$-lactam tristrifluoroacetate<br>Yield: 4 mg (6% of theory) from exemlary compound 441A (65 mg, 39 µmol) according to procedure 4, multiple purification according to a variation of method 44 (ramp only to 55% acetonitrile). | HPLC (Method 6): $R_t$ = 3.31 min; LC-MS (Method 19): $R_t$ = 1.50 min, MS (ESIpos): m/z (%) = 644.6 (100) $[M + 2H]^{2+}$, 1287.9 (5) $[M + H]^+$, MS (ESIneg): m/z (%) = 1285.9 (50) $[M - H]^-$; HR-TOF-MS: $C_{61}H_{104}N_{16}O_{14}$ calc. 1287.8148, found 1287.8126 $[M + H]^+$. |

| Exemplary embodiment No. | Name Yield, Synthesis Method | Structure Analysis |
|---|---|---|
| 28 | | 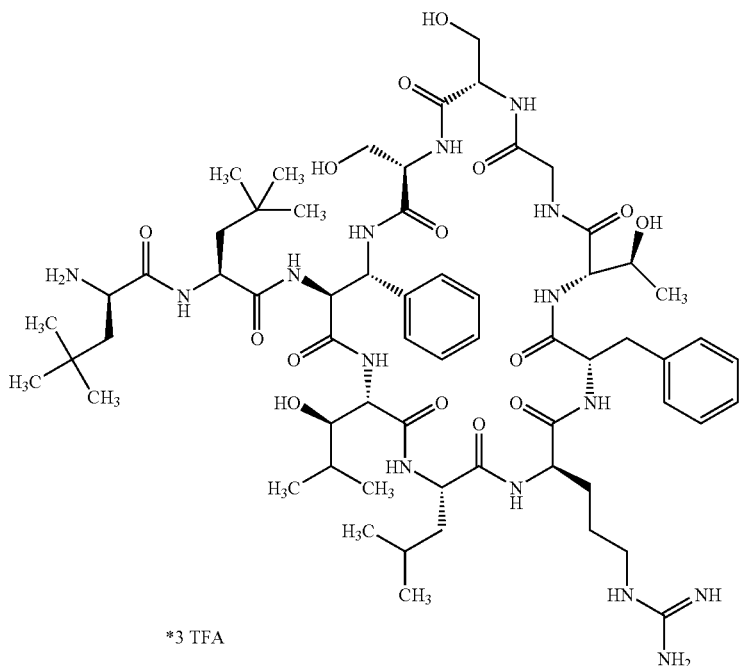 *3 TFA |
| | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-phenylalanyl-L-allothreonyl-glycyl-L-seryl-L-serine C$^{1.11}$-N$^{3.3}$-lactam bistrifluoroacetate Yield: 8 mg (67% of theory) from exemplary compound 442A (12 mg, 8 μmol) according to procedure 2, purification according to a variation of method 44 (ramp only to 60% acetonitrile). | HPLC (Method 6): R$_t$ = 3.45 min; LC-MS (Method 19): R$_t$ = 1.76 min, MS (ESIpos): m/z (%) = 648.1 (100) [M + 2H]$^{2+}$, 1294.8 (1) [M + H]$^+$, MS (ESIneg): m/z (%) = 1292.9 (70) [M − H]$^-$, 1338.6 (100) [M + HCOO$^-$]$^-$; HR-TOF-MS: C$_{62}$H$_{100}$N$_{15}$O$_{15}$ calc. 1294.7518, found 1294.7520 [M + H]$^+$. |
| 29 | | 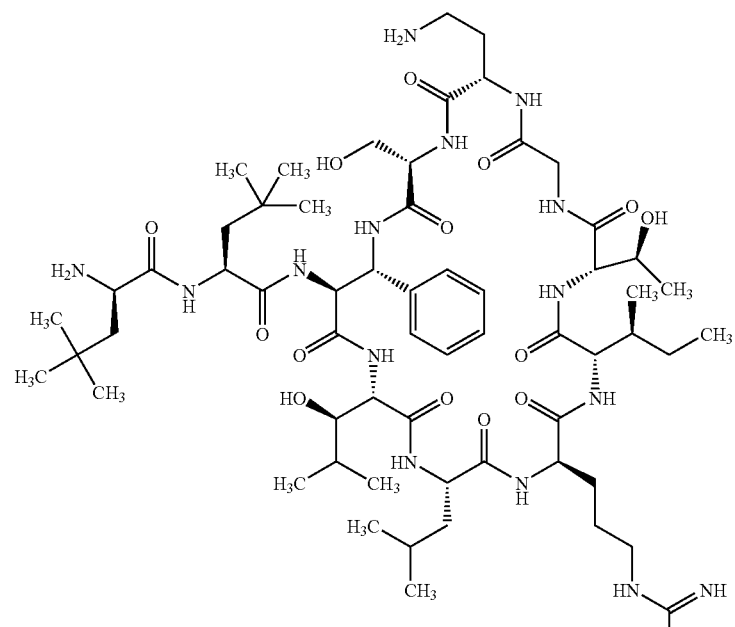 *3 TFA |
| | [3-tert-Butyl-D-alanyl]-[3-tert-butyl-L-alanyl]-[(3R)-3-amino-L-phenylalanyl]-[(3R)-3- | HPLC (Method 6): R$_t$ = 3.23 min; LC-MS (Method 19): R$_t$ = 1.45 min, MS (ESIpos): |

| Exemplary embodiment No. | Structure Name Yield, Synthesis Method | Analysis |
|---|---|---|
| | hydroxy-L-leucyl]-L-leucyl-D-arginyl-L-isoleucyl-L-allothreonyl-glycyl-[(2S)-2,4-diaminobutyryl]-L-serine $C^{1.11}$-$N^{3.3}$-lactam tristrifluoroacetate<br>Yield: 7 mg (10% of theory) from exemplary compound 444A (75 mg, 46 μmol) according to procedure 4, multiple purification according to a variation of method 44 (ramp only to 55% acetonitrile). | m/z (%) = 425.4 (100) $[M + 3H]^{3+}$, 637.6 (50) $[M + 2H]^{2+}$, 1273.9 (5) $[M + H]^+$, MS (ESIneg): m/z (%) = 1273.1 (70) $[M - H]^-$, 1318.1 (100) $[M + HCOO^-]^-$; HR-TOF-MS: $C_{60}H_{105}N_{16}O_{14}$ calc. 1273.7991, found 1273.8020 $[M + H]^+$. |
| 30 | 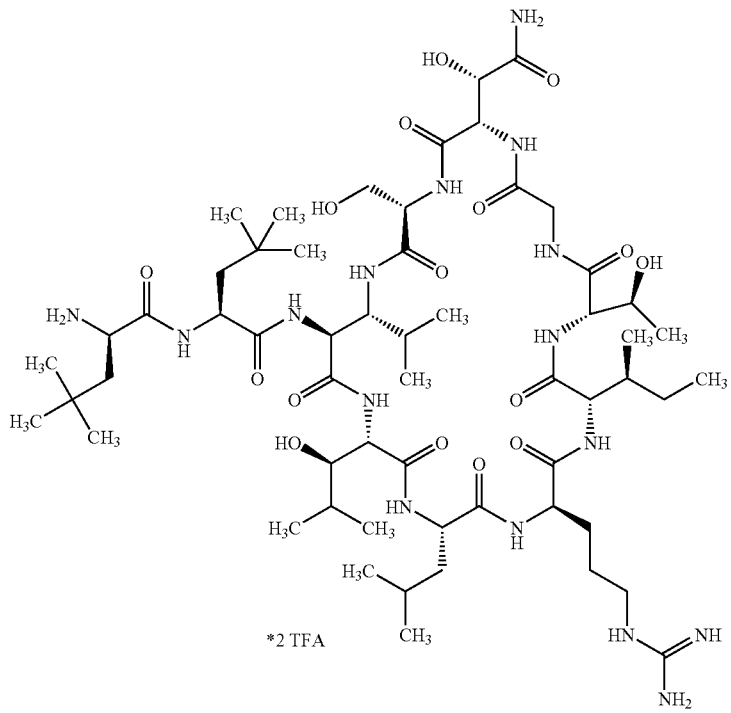<br>[3-tert-Butyl-D-alanyl]-[3-tert-butyl-L-alanyl]-[(3R)-3-amino-L-leucyl]-[(3R)-3-hydroxy-L-leucyl]-L-leucyl-D-arginyl-L-isoleucyl-L-allothreonyl-glycyl-[(3R)-3-hydroxy-L-asparaginyl]-L-serine $C^{1.11}$-$N^{3.3}$-lactam bistrifluoroacetate<br>Yield: 29 mg (53% of theory) from exemplary compound 445A (53 mg, 36 μmol) according to procedure 2, purification according to a variation of method 44 (ramp only to 60% acetonitrile). | HPLC (Method 6): $R_t$ = 3.43 min; LC-MS Method 19): $R_t$ = 1.52 min, MS (ESIpos): m/z (%) = 635.6 (100) $[M + 2H]^{2+}$, 1269.8 (10) $[M + H]^+$, MS (ESIneg): m/z (%) = 1267.8 (80) $[M - H]^-$, 1313.8 (80) $[M + HCOO^-]^-$; HR-TOF-MS: $C_{57}H_{105}N_{16}O_{16}$ calc. 1269.7889, found 1269.7886 $[M + H]^+$. |

-continued

| Exemplary embodiment No. | Name Yield, Synthesis Method | Structure Analysis |
|---|---|---|
| 31 | [3-tert-Butyl-D-alanyl]-[3-tert-butyl-L-alanyl]-[(3R)-3-amino-L-phenylalanyl]-[(3R)-3-hydroxy-L-leucyl]-L-norvalyl-D-arginyl-L-isoleucyl-L-allothreonyl-glycyl-L-seryl-L-serine $C^{1.11}$-$N^{3.3}$-lactam bistrifluoroacetate<br>Yield: 54 mg (27% of theory) from exemplary compound 446A (54 mg, 37 µmol) according to procedure 2, purification according to a variation of method 44 (ramp only to 60% acetonitrile). | 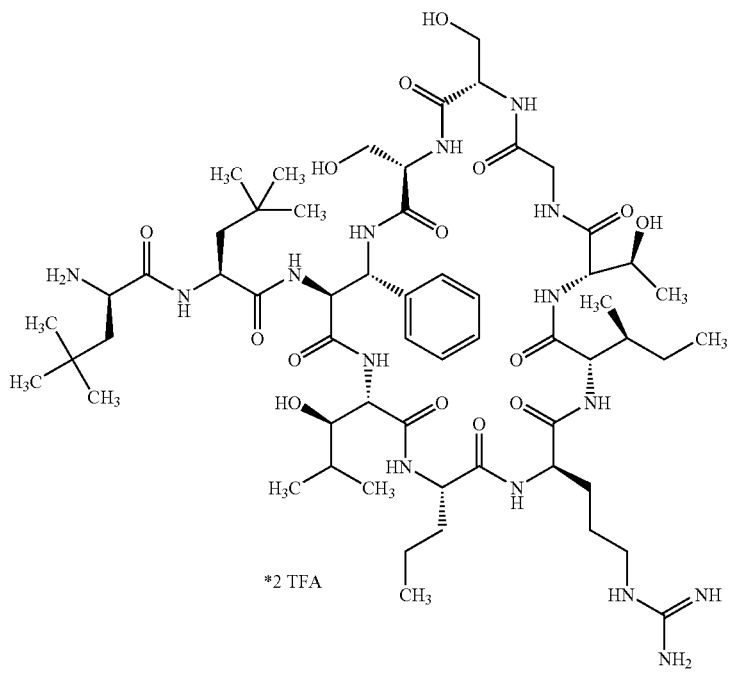<br>HPLC (Method 6): $R_t$ = 3.42 min; LC-MS (Method 51): $R_t$ = 2.15 min, MS (ESIpos): m/z (%) = 624.6 (100) $[M + 2H]^{2+}$, 1246.9 (1) $[M + H]^+$; HR-TOF-MS: $C_{58}H_{100}N_{15}O_{15}$ calc. 1246.7518, found 1246.7549 $[M + H]^+$. |
| 32 | [3-tert-Butyl-D-alanyl]-[3-tert-butyl-L-alanyl]-[(3R)-3-amino-L-phenylalanyl]-[(3R)-3-hydroxy-L-leucyl]-L-valyl-D-arginyl-L- | 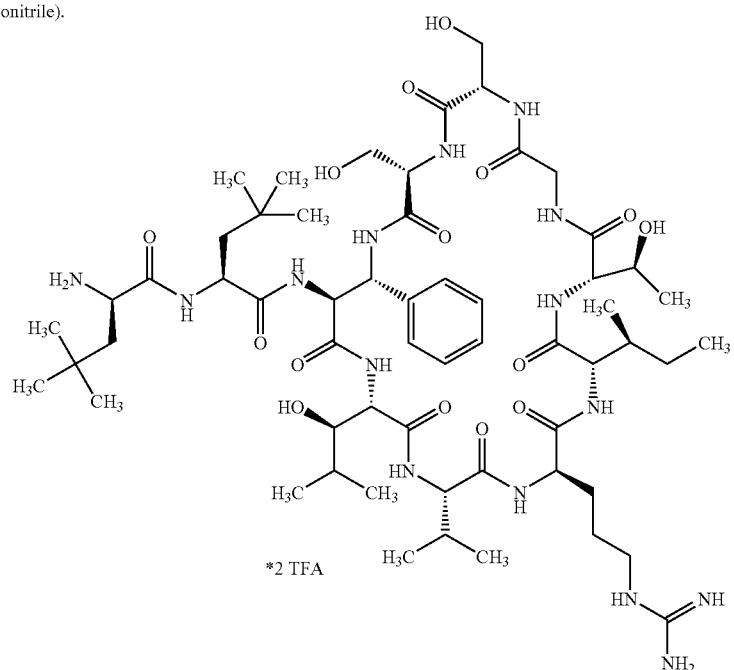<br>HPLC (Method 6): $R_t$ = 3.40 min; LC-MS (Method 19): $R_t$ = 1.51 min, MS (ESIpos): m/z (%) = 624.0 (100) $[M + 2H]^{2+}$, 1246.8 |

| Exemplary embodiment No. | Name Yield, Synthesis Method | Structure Analysis |
|---|---|---|
| | isoleucyl-L-allothreonyl-glycyl-L-seryl-L-serine $C^{1.11}$-$N^{3.3}$-lactam bistrifluoroacetate Yield: 20 mg (36% of theory) from exemplary compound 447A (54 mg, 37 µmol) according to procedure 2, purification according to a variation of method 44 (ramp only to 60% acetonitrile). | (10) $[M + H]^+$, MS (ESIneg): m/z (%) = 1244.8 (90) $[M - H]^-$, 1291.7 (100) $[M + HCOO^-]^-$; HR-TOF-MS: $C_{58}H_{100}N_{15}O_{15}$ calc. 1246.7518, found 1246.7494 $[M + H]^+$. |
| 33 | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-allothreonyl-D-seryl-L-seryl-L-serine $C^{1.11}$-$N^{3.3}$-lactam bistrifluoroacetate Yield: 21 mg (33% of theory) from exemplary compound 448A (64 mg, 43 µmol) according to procedure 2, purification according to a variation of method 44 (ramp only to 50% acetonitrile). | 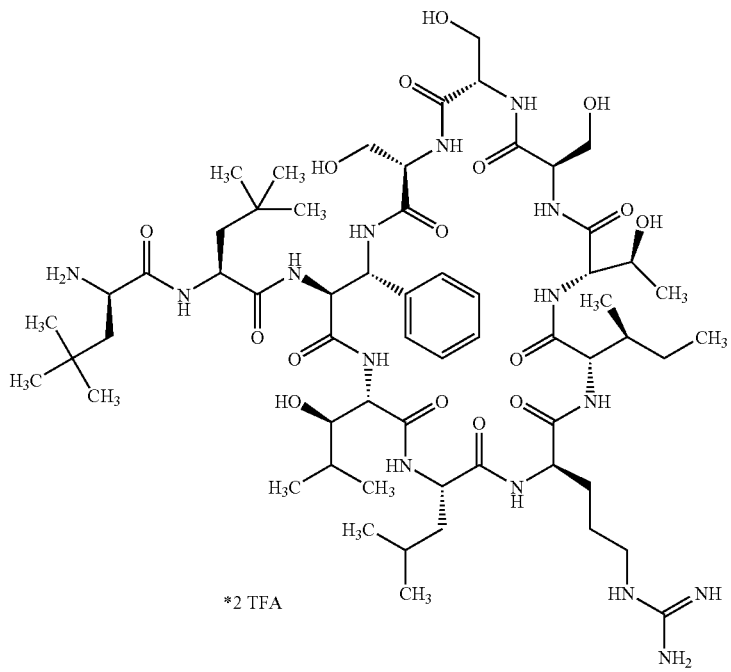 HPLC (Method 6): $R_t$ = 3.44 min; LC-MS (Method 19): $R_t$ = 1.54 min, MS (ESIpos): m/z (%) = 646.2 (100) $[M + 2H]^{2+}$, 1290.8 (10) $[M + H]^+$, MS (ESIneg): m/z (%) = 1289.8 (60) $[M - H]^-$, 1334.8 $[M + HCOO^-]^-$; HR-TOF-MS: $C_{60}H_{104}N_{15}O_{16}$ calc. 1290.7780, found 1290.7766 $[M + H^+]$. |

| Exemplary embodiment No. | Name Yield, Synthesis Method | Structure Analysis |
|---|---|---|
| 34 | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-valyl-glycyl-L-seryl-L-serine $C^{1.11}$-$N^{3.3}$-lactam bistrifluoroacetate Yield: 3.5 mg (10% of theory) from exemplary compound 449A (33 mg, 23 µmol) according to procedure 2, purification according to a variation of method 44 (ramp only to 50% acetonitrile). | 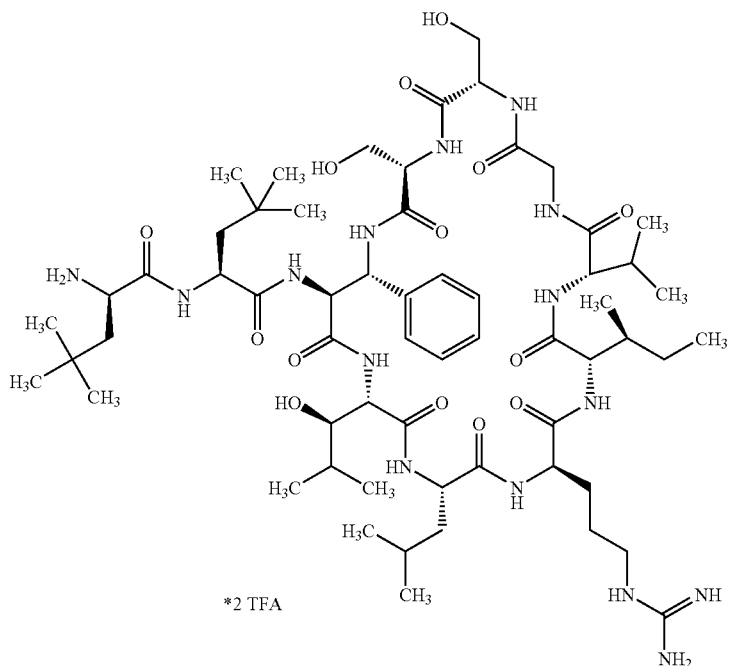 *2 TFA<br><br>HPLC (Method 6): $R_t$ = 3.46 min; LC-MS (Method 19): $R_t$ = 1.66 min, MS (ESIpos): m/z (%) = 630.0 (100) [M + 2H]$^{2+}$, 1258.8 (10) [M + H]$^+$, MS (ESIneg): m/z (%) = 1257.8 (90) [M − H]$^−$, 1303.8 (100) [M + HCOO$^−$]$^−$; HR-TOF-MS: $C_{60}H_{104}N_{15}O_{14}$ calc. 1258.7882, found 1258.7905 [M + H]$^+$. |
| 35 | [3-tert-Butyl-D-alanyl]-[3-tert-butyl-L-alanyl]-[(3R)-3-amino-L-phenylalanyl]-[(3R)-3-hydroxy-L-leucyl]-L-isoleucyl-D-arginyl-L- | 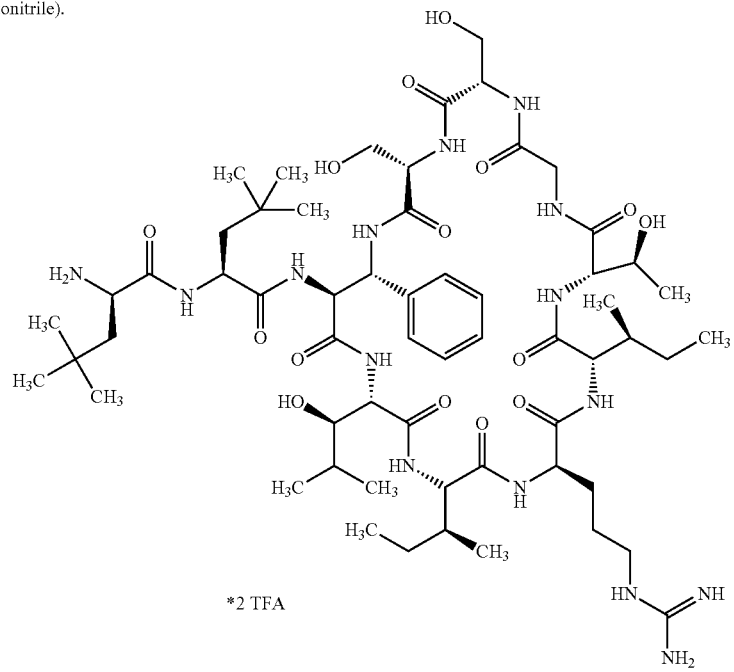 *2 TFA<br><br>HPLC (Method 53): $R_t$ = 5.76 min; LC-MS (Method 19): $R_t$ = 1.59 min, MS (ESIpos): m/z (%) = 631.2 (100) [M + 2H]$^{2+}$, 1260.8 |

| Exemplary embodiment No. | Name Yield, Synthesis Method | Analysis |
|---|---|---|
| | isoleucyl-L-allothreonyl-glycyl-L-seryl-L-serine $C^{1.11}$-$N^{3.3}$-lactam bistrifluoroacetate<br><br>Yield: 12 mg (70% of theory) from exemplary compound 450A (19 mg, 10 μmol) according to procedure 2, purification according to a variation of method 44 (ramp only to 70% acetonitrile). | (5) $[M + H]^+$, MS (ESIneg): m/z (%) = 1258.9 (100) $[M - H]^-$; HR-TOF-MS: $C_{59}H_{102}N_{15}O_{15}$ calc. 1260.7675, found 1260.7666 $[M + H]^+$. |
| 36 | 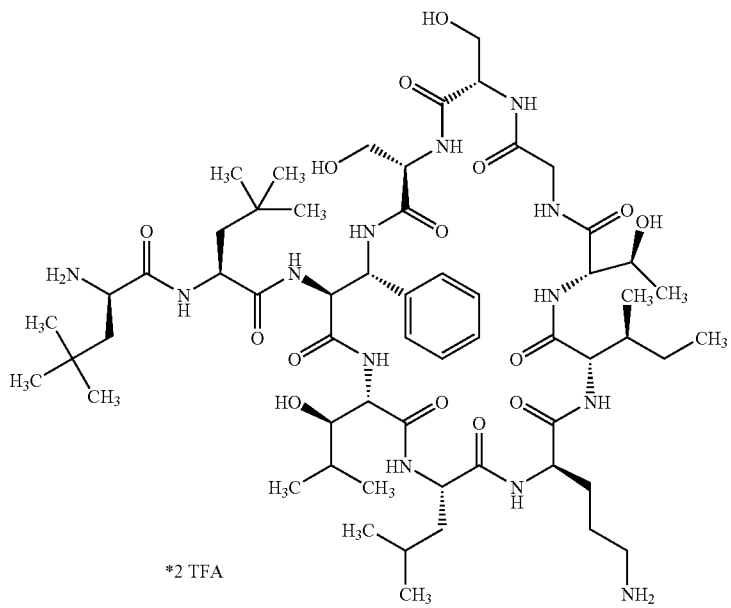<br><br>*2 TFA<br><br>[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-ornithyl-L-isoleucyl-L-allothreonyl-glycyl-L-seryl-L-serine $C^{1.11}$-$N^{3.3}$-lactam bistrifluoroacetate<br><br>Yield: 12 mg (25% of theory) from exemplary compound 451A (49 mg, 33 μmol) according to procedure 4, purification according to a variation of method 44 (ramp only to 35% acetonitrile). | HPLC (Method 6): $R_t$ = 3.43 min; LC-MS (Method 19): $R_t$ = 1.59 min, MS (ESIpos): m/z (%) = 610.1 (100) $[M + 2H]^{2+}$, 1218.8 (10) $[M + H]^+$, MS (ESIneg): m/z (%) = 1216.8 (100) $[M - H]^-$; HR-TOF-MS: $C_{58}H_{100}N_{13}O_{15}$ calc. 1218.7457, found 1218.7477 $[M + H]^+$. |

-continued

| Exemplary embodiment No. | Name Yield, Synthesis Method | Structure Analysis |
|---|---|---|

37

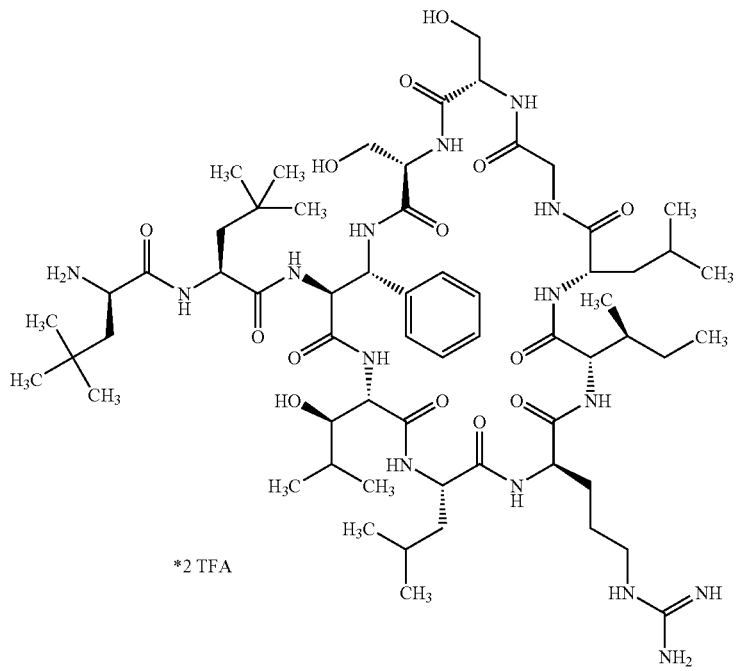

*2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-D-arginyl-L-isoleucyl-L-leucyl-glycyl-L-seryl-L-serine $C^{1.11}$-$N^{3.3}$-lactam bistrifluoroacetate
Yield: 15 mg (46% of theory) from exemplary compound 452A (42 mg, 22 μmol) according to procedure 2, purification according to a variation of method 33 (ramp only to 70% acetonitrile).

HPLC (Method 6): $R_t$ = 3.56 min; LC-MS (Method 52): $R_t$ = 1.22 min, MS (ESIpos): m/z (%) = 637.2 (100) $[M + 2H]^{2+}$, 1273.0 (5) $[M + H]^+$, MS (ESIneg): m/z (%) = 1271.1 (40) $[M - H]^-$, 1317.0 (100) $[M + HCOO]^-$; HR-TOF-MS: $C_{61}H_{106}N_{15}O_{14}$ calc. 1272.8039, found 1272.8015 $[M + H]^+$.

38

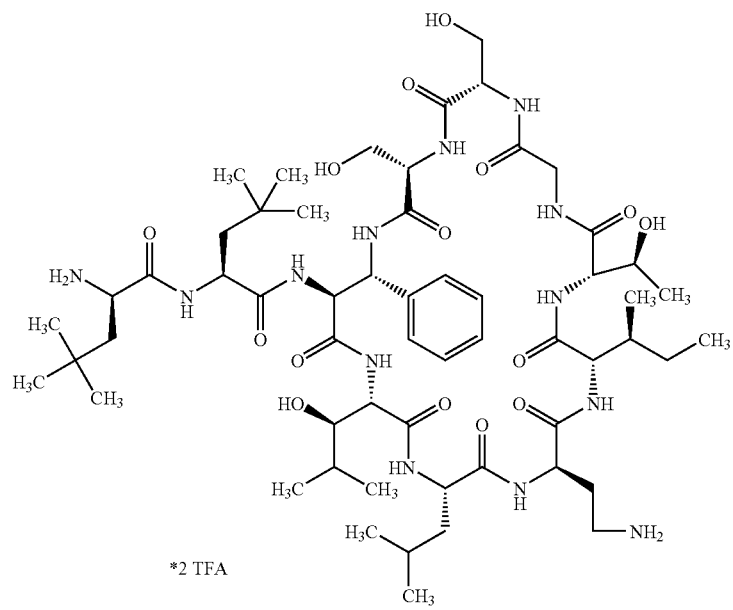

*2 TFA

[3-tert-Butyl-D-alanyl]-[3-tert-butyl-L-alanyl]-[(3R)-3-amino-L-phenylalanyl]-[(3R)-3-hydroxy-L-leucyl]-L-leucyl-[(2R)-2,4-diaminobutyryl]-L-isoleucyl-L-allothreonyl- HPLC (Method 6): $R_t$ = 3.42 min; LC-MS (Method 19): $R_t$ = 1.59 min, MS (ESIpos): m/z (%) = 603.0 (100) $[M + 2H]^{2+}$; 1204.8 (10) $[M + H]^+$, MS (ESIneg): m/z (%) =

| Exemplary embodiment No. | Name Yield, Synthesis Method | Structure Analysis |
|---|---|---|
| 39 | glycyl-L-seryl-L-serine $C^{1.11}$—$N^{3.3}$-lactam bistrifluoroacetate<br>Yield: 7 mg (40% of theory) from exemplary compound 453A (162 mg, (11% pure, 12 μmol) according to procedure 4, purification according to a variation of method 44 (ramp only to 35% acetonitrile). | 1202.8 (100) [M − H]⁻, 1248.8 (50) [M + HCOO]⁻; HR-TOF-MS: $C_{57}H_{98}N_{13}O_{15}$ calc. 1204.7300, found 1204.7329 [M + H]⁺. |
| | 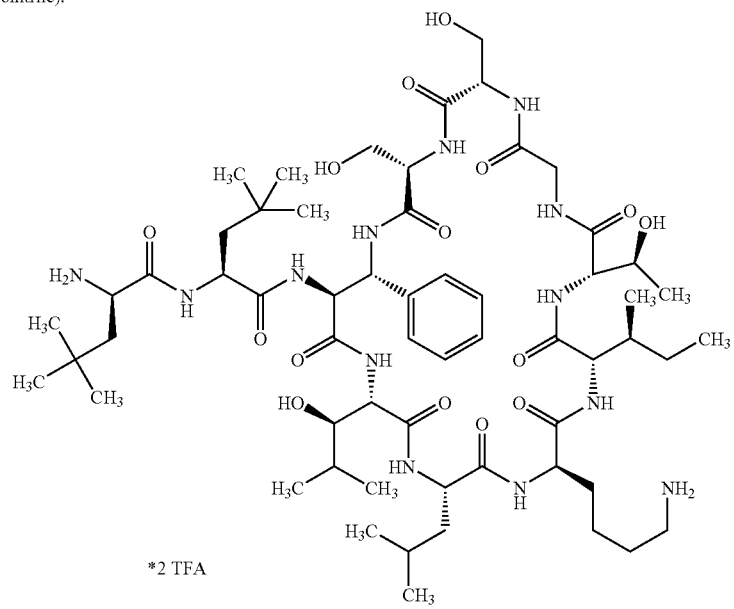  *2 TFA | |
| | [3-tert-Butyl-D-alanyl]-[3-tert-butyl-L-alanyl]-[(3R)-3-amino-L-phenylalanyl]-[(3R)-3-hydroxy-L-leucyl]-L-leucyl-D-lysyl-L-isoleucyl-L-allothreonyl-glycyl-L-seryl-L-serine $C^{1.11}$-$N^{3.3}$-lactam bistrifluoroacetate<br>Yield: 14 mg (62% of theory) from exemplary compound 454A (29 mg, 80% pure, 15 μmol) according to procedure 4, purification according to a variation of method 44 (ramp only to 70% acetonitrile). | HPLC (Method 53): $R_t$ = 5.66 min; LC-MS (Method 19): $R_t$ = 1.57 min, MS (ESIpos): m/z (%) = 617.1 (100) [M + 2H]²⁺, 1232.8 (10) [M + H]⁺, MS (ESIneg): m/z (%) = 1231.8 (100) [M − H]⁻, 1276.8 (50) [M + HCOO]⁻; HR-TOF-MS: $C_{59}H_{102}N_{13}O_{15}$ calc. 1232.7613, found 1232.7598 [M + H]⁺. |
| 40 | 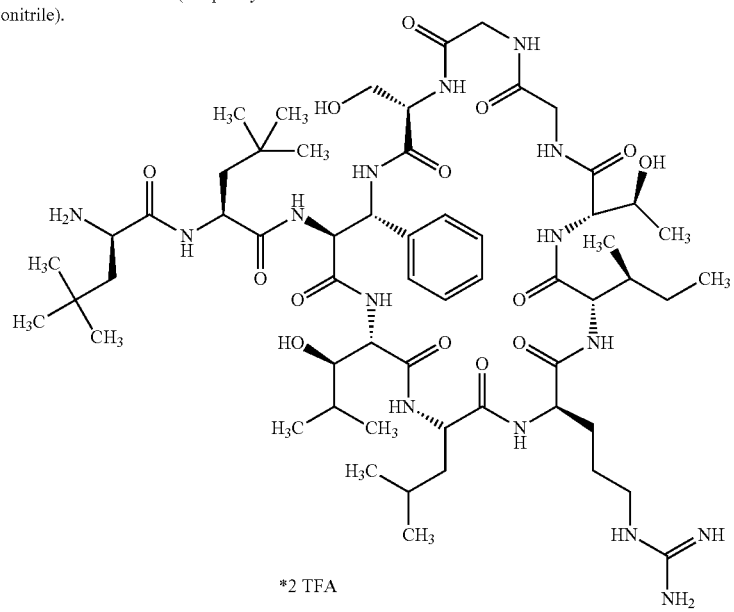  *2 TFA | |
| | [3-tert-Butyl-D-alanyl]-[3-tert-butyl-L-alanyl]-[(3R)-3-amino-L-phenylalanyl]-[(3R)-3- | HPLC (Method 6): $R_t$ = 3.47 min; LC-MS (Method 19): $R_t$ = 1.54 min, MS (ESIpos): |

| Exemplary embodiment No. | Name Yield, Synthesis Method | Structure Analysis |
|---|---|---|
| | hydroxy-L-leucyl]-L-leucyl-D-arginyl-L-isoleucyl-L-allothreonyl-glycyl-glycyl-L-serine $C^{1.11}$-$N^{3.3}$-lactam bistrifluoroacetate Yield: 13 mg (7% of theory) from exemplary compound 455A (177 mg, 123 µmol) according to procedure 2, purification according to a variation of method 33 (ramp only to 60% acetonitrile). | m/z (%) = 616.1 (100) $[M + 2H]^{2+}$, 1230.8 (10) $[M + H]^+$, MS (ESIneg): m/z (%) = 1228.9 (60) $[M − H]^−$, 1274.8 (100) $[M + HCOO^−]^−$; HR-TOF-MS: $C_{58}H_{100}N_{15}O_{14}$ calc. 1230.7569, found 1230.7570 $[M + H]^+$. |
| 41 | 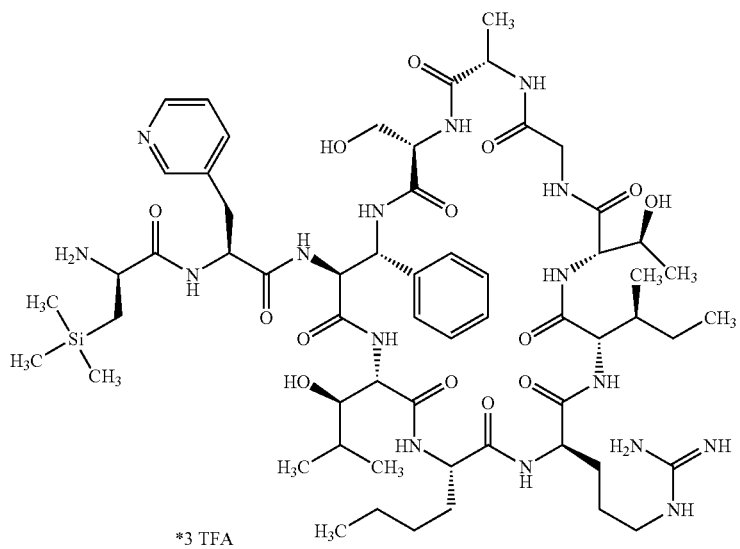 *3 TFA [3-Trimethylsilyl-D-alanyl]-[3-(3-pyridyl)-L-alanyl]-[(3R)-3-amino-L-phenylalanyl]-[(3R)-3-hydroxy-L-leucyl]-L-norleucyl-D-arginyl-L-isoleucyl-L-allothreonyl-glycyl-L-alanyl-L-serine $C^{1.11}$-$N^{3.3}$-lactam tristrifluoroacetate Yield: 13 mg (47% of theory) from exemplary compound 456A (45 mg, 60% pure, 17 µmol) according to procedure 2, purification according to a variation of method 44 (ramp only to 60% acetonitrile). | HPLC (Method 6): $R_t$ = 3.23 min; LC-MS (Method 19): $R_t$ = 1.41 min, MS (ESIpos): m/z (%) = 641.5 (100) $[M + 2H]^{2+}$, MS (ESIneg): m/z (%) = 1280.8 (100) $[M − H]^−$; HR-TOF-MS: $C_{59}H_{97}N_{16}O_{14}Si$ cal. 1281.7134, found 1281.7152 $[M + H]^+$. |
| 42 | 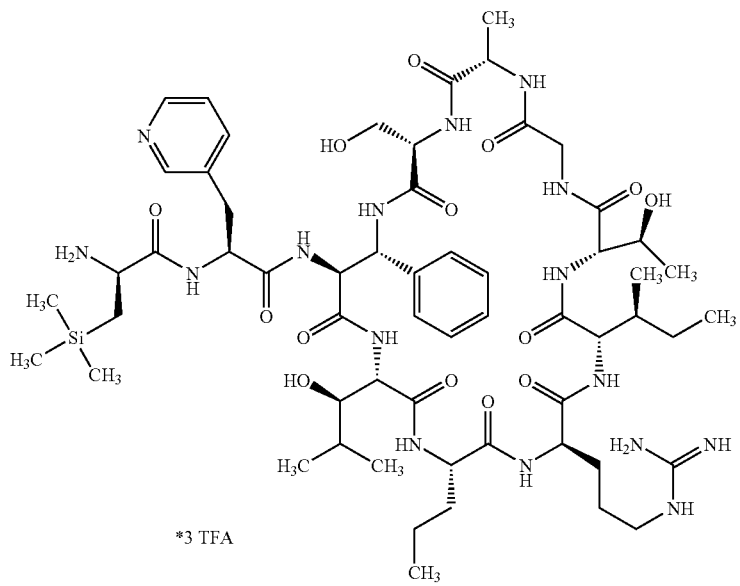 *3 TFA [3-Trimethylsilyl-D-alanyl]-[3-(3-pyridyl)-L-alanyl]-[(3R)-3-amino-L-phenylalanyl]-[(3R)-3- | HPLC (Method 6): $R_t$ = 3.16 min; LC-MS (Method 19): $R_t$ = 1.33 min, MS (ESIpos): |

| Exemplary embodiment No. | Name Yield, Synthesis Method | Analysis |
|---|---|---|
| | hydroxy-L-leucyl]-L-norvalyl-D-arginyl-L-isoleucyl-L-allothreonyl-glycyl-L-alanyl-L-serine $C^{1.11}$-$N^{3.3}$-lactam tristrifluoroacetate Yield: 15 mg (68% of theory) from exemplary compound 457A (41 mg, 51% pure, 13 µmol) and exemplary compound 274A according to procedure 2, purification according to a variation of method 44 (ramp only to 55% acetonitrile). | m/z (%) = 634.5 (100) $[M + 2H]^{2+}$, 1267.7 (10) $[M + H]^+$, MS (ESIneg): m/z (%) = 1265.8 (100) $[M - H]^-$, 1311.8 (40) $[M + HCOO]^-$; HR-TOF-MS: $C_{58}H_{95}N_{16}O_{14}Si$ calc. 1267.6978, found 1267.6979 $[M + H]^+$. |
| 43 | 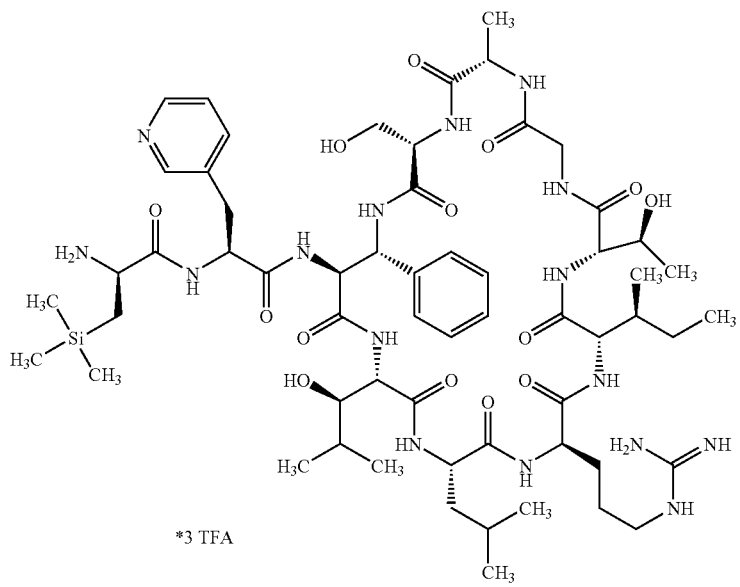<br>*3 TFA<br><br>[3-Trimethylsilyl-D-alanyl]-[3-(3-pyridyl)-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-L-alanyl-L-serine $C^{1.11}$-$N^{3.3}$-lactam tristrifluoroacetate Yield: 22 mg (79% of theory) from exemplary compound 458A (45 mg, 60% pure, 17 µmol) according to procedure 2, purification according to a variation of method 44 (ramp only to 60% acetonitrile). | HPLC (Method 6): $R_t$ = 3.22 min; LC-MS (Method 19): $R_t$ = 1.39 min, MS (ESIpos): m/z (%) = 641.6 (100) $[M + 2H]^{2+}$, 1281.7 (10) $[M + H]^+$, MS (ESIneg): m/z (%) = 1279.8 (100) $[M - H]^-$; HR-TOF-MS: $C_{59}H_{97}N_{16}O_{14}Si$ calc. 1281.7134, found 1281.7128 $[M + H]^+$. |

| Exemplary embodiment No. | Name Yield, Synthesis Method | Structure Analysis |
|---|---|---|
| 44 | [3-tert-Butyl-D-alanyl]-[3-tert-butyl-L-alanyl]-[(3R)-3-amino-3-(pyridin-3-yl)-L-alanyl]- [(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$-$N^{3.3}$-lactam tristrifluoroacetate<br>Yield: 10.6 mg (56% of theory) from exemplary compound 470A (30 mg, 60% pure, 11 μmol) according to procedure 2, purification according to a variation of method 44 (ramp only to 70% acetonitrile). | 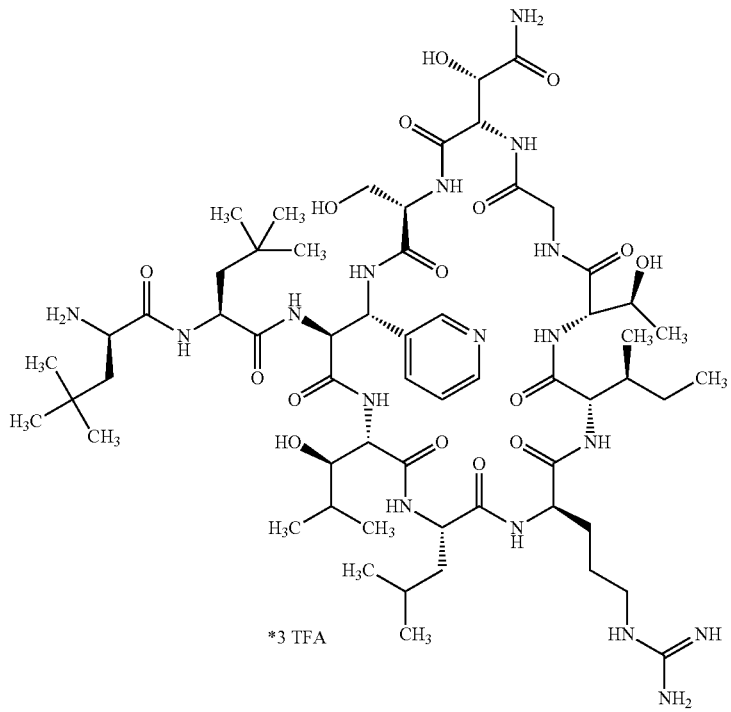<br>HPLC (Method 6): $R_t$ = 3.34 min; LC-MS (Method 19): $R_t$ = 1.53 min, MS (ESIpos): m/z (%) = 435.6 (100) $[M + 3H]^{3+}$, 653.0 (80, $[M + 2H]^{2+}$), 1304.8 (10) $[M + H]^+$, MS (ESIneg): m/z (%) = 1302.8 (100) $[M - H]^-$; HR-TOF-MS: $C_{59}H_{102}N_{17}O_{16}$ calc. 1304.7685, found 1304.7670 $[M + H]^+$. |

B. Assessment of the Physiological Activity

The in vitro effect of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Enterococcus faecalis* 27159, *E. faecium* 4147 and *Streptococcus pneumoniae* G9a are incubated with the described test substances in a 1:2 dilution series. The MIC determination is carried out with a cell count of $10^5$ microbes per ml in Isosensitest medium (Difco, Irvine/USA), with the exception of *S. pneumoniae* which is tested in BHI broth (Difco, Irvine/USA) with 10% bovine serum with a cell count of $10^6$ microbes per ml. The cultures are incubated at 37° C. for 18-24 hours, *S. pneumoniae* in the presence of 10% $CO_2$.

The MIC is defined as the lowest concentration of each substance at which no visible bacterial growth occurs any longer. The MIC values are reported in μg/ml.

Representative in vitro activity data for the compounds of the invention are shown in Table A:

TABLE A

| Example No. | MIC *S. aureus* 133 [μg/ml] | MIC *S. pneumoniae* G9a [μg/ml] | MIC *E. faecalis* ICB 27159 [μg/ml] |
|---|---|---|---|
| 13 | 0.25 | 0.5 | 0.5 |
| 14 | 0.25 | 0.125 | 0.5 |
| 23 | 0.5 | 0.25 | 1 |
| 35 | 0.25 | 0.5 | 1 |
| 41 | 0.25 | 0.25 | 2 |
| 44 | 0.25 | 0.125 | 0.5 |
| Lysobactin | 0.5 | 0.063 | 0.5 |

The suitability of the compounds of the invention for the treatment of bacterial infections can be shown in the following animal model:

Systemic Infection with *Staphylococcus aureus* 133:

Cells of *S. aureus* 133 are grown overnight in BHI broth (Oxoid, N.Y./USA). The overnight culture is diluted 1:100 in fresh BHI broth and incubated for 3 hours. The cells which are then in the logarithmic phase of growth are centrifuged off and washed twice with buffered physiological saline. Then a cell suspension in saline is adjusted photometrically to an extinction of 50 units. After a dilution step (1:15), this suspension is mixed 1:1 with a 10% mucin solution. 0.25 ml of this infection solution is administered intraperitoneally per 20 g mouse (equivalent to $1 \times 10^6$ microbes/mouse). Therapy takes place intraperitoneally or intravenously 30 minutes after the infection. Female CFW1 mice are used for the infection experiment. The survival of the animals is recorded over 6 days.

The properties of the compounds of the invention in relation to renal tolerability can be shown in the following animal model:

Mouse Model for Determining Nephrotoxic Effects:

Nephrotoxic side effects of the nonadepsipeptides are analyzed by histopathological examinations of the kidneys in mice after multiple administration of a particular dosage. For this purpose, 5-6 animals are treated daily either intravenously (i.v.) or intraperitoneally (i.p.) with substances which are dissolved in aqueous solution or with the addition of Solutol. Nephrotoxic effects are determined by optical microscopic assessment of hematoxylin and eosin (H&E) stained paraffin sections of the kidneys. A 'periodic acid Schiff' (PAS) reaction is optionally carried out to visualize glycoproteins better. Nephrotoxic effects are specified semiquantitatively for each animal as severities of the tubular basophilia and degeneration/regeneration occurring (severities: 0=no effect; 1=minimal effect; 2=slight effect; 3=moderate effect; 4=severe lesions). The average severity of the tubular degeneration/regeneration as well as the incidence (number of affected animals) is calculated for each animal group or derivative. Renal changes going beyond this, such as tubular dilatation as well as necroses and the accumulation of necrotic material, are likewise listed.

Rat Model for Determining Nephrotoxic Effects:

Nephrotoxic side effects of nonadepsipeptides are analyzed by histopathological examinations of the kidneys in rats after multiple administration of a particular dosage. For this purpose, 5 animals are treated daily intravenously (i.v.) with substances which are dissolved in saline or Ringer's lactate solution. Nephrotoxic effects are determined by optical microscopic assessment of hematoxylin and eosin (H&E) stained paraffin sections of the kidneys. A 'periodic acid Schiff' (PAS) reaction is optionally carried out to visualize glycoproteins better. Nephrotoxic effects are specified semiquantitatively for each animal as severities of the tubular basophilia and degeneration/regeneration occurring (severities: 0=no effect; 1=minimal effect; 2=slight effect; 3 moderate effect; 4=severe lesions). The average severity of the tubular degeneration/regeneration as well as the incidence (number of affected animals) is calculated for each animal group or derivative. Renal changes going beyond this, such as tubular dilatation as well as necroses and the accumulation of necrotic material, are likewise listed.

Principle of the Determination of the Free Fraction Via Transil:

The method described here for determining the free fraction ($f_u$) of a test substance is divided into 2 parts:

a) Determination of the Transil®/buffer distribution ratio ($MA_{buffer}$) by incubating the test substance in a Transil®-buffer (pH 7.4) dispersion and subsequently determining the concentration in the dispersion and in the buffer supernatant.

b) Determination of the Transil®/plasma distribution ratio ($MA_{plasma}$) by incubating the test substance in a Transil®-plasma dispersion and subsequently determining the concentration in the dispersion and in the plasma.

The quotient of the two distribution ratios yields $f_u$.

In the case of highly protein-bound substances, the plasma is usually diluted with isotonic phosphate buffer (pH 7.4) and subsequently suspended with Transil®. The determination of $f_u'$ (free fraction in diluted plasma) in this diluted protein solution takes place in analogy to the determination of $f_u$. The free fraction in undiluted plasma is calculated from $f_u'$ and the dilution factor.

Concerning this method, compare also: Schuhmacher, Joachim; Kohlsdorfer, Christian; Buehner, Klaus; Brandenburger, Tim; Kruk, Renate, "High-throughput determination of the free fraction of drugs strongly bound to plasma proteins." *Journal of Pharmaceutical Sciences* 2004, 93, 816-830.

Determination of the Membrane Affinity of a Test Substance after Distribution Between Transil® and Buffer ($MA_{buffer}$):

All incubations are carried out in suitable glass vessels, e.g. glass vials, ground-socket test tubes. The total volume is usually 0.5-5 ml, and the Transil® volume is 10-100 µl. If the membrane affinities are expected to be high, the Transil® dispersion can be diluted up to 20-fold with phosphate buffer of pH 7.4, e.g. Dulbecco's PBS. Phosphate buffer of pH 7.4 is provided in the incubation vessels, and the Transil® is, after thorough mixing, pipetted in. The test substance is pipetted in at a concentration of, for example, 200 ng/ml, n=6. The proportion of organic solvent should be $\leq$2%. The mixtures are incubated at room temperature for 30 min, e.g. on a mini-shaker at an angle of about 45°, at about 400 rpm. In order to determine the 100% value at least one aliquot of, for example, 100 µl is removed, and the remaining mixture is centrifuged at about 1800 g for about 10 min. At least 2 aliquots (e.g. 100 µl) of the supernatant are removed from each sample for the determination the concentration.

Determination of $MA_{plasma}$ in Undiluted or Diluted Plasma:

The total incubation volume and the added volume of Transil® depend on the expected free fraction. The total volume is usually 0.5-1 ml, and the Transil® volume is 10-100 µl. If the free fractions are very low, the plasma of the species to be investigated is diluted, with isotonic buffer solution, pH 7.4, e.g. 10-400-fold, and then Transil® is added. The subsequent procedure takes place as described above for the determination of the $MA_{buffer}$ values.

Principle of the Determination of the Free Fraction Via Ultrafiltration:

The plasma of the species to be investigated is filtered through a semipermeable membrane. The substance concentration in the filtrate is measured and the free fraction $f_u$ is calculated therefrom. The Centrifree micropartition system from Millipore/Amicon is used. The ultrafiltration membranes have a cut-off of 30 000 Da. 1 ml of plasma is doped with the substance in a concentration of about 1 µg/ml. The proportion of solvent should be <2%. After incubation at room temperature for 30 minutes, the plasma is pipetted into the ultrafiltration system and centrifuged at 1800 g for 10 minutes. The substance concentration in the ultrafiltrate ($C_u$; unbound substance concentration) and in the plasma before centrifugation (C; total substance concentration) is measured. The free fraction is calculated according to the formula: $f_u$ (%)=$C_u$/C*100.

Determination of the Chemical Stability in Stability Alkaline Aqueous Solution:

0.3 mg of the test substance are dissolved in a mixture of 0.25 ml of acetonitrile, 0.25 ml of DMSO and 0.5 ml of buffer of pH 7.8 (consisting of 111 mg (1 mmol) of calcium chloride, 7.91 g (100 mmol) of ammonium bicarbonate, 100 ml of acetonitrile ad 1000 ml) and left to stand at room temperature. A 5 μl aliquot is taken from the solution once an hour and analyzed by HPLC (method 57). The concentration of the test compound at time 0 h, indicated by the UV absorption (1E), is set equal to 100%, and the decrease over time is observed. At the same time, the increase in the ring-opened degradation product is observed.

Figure 2:
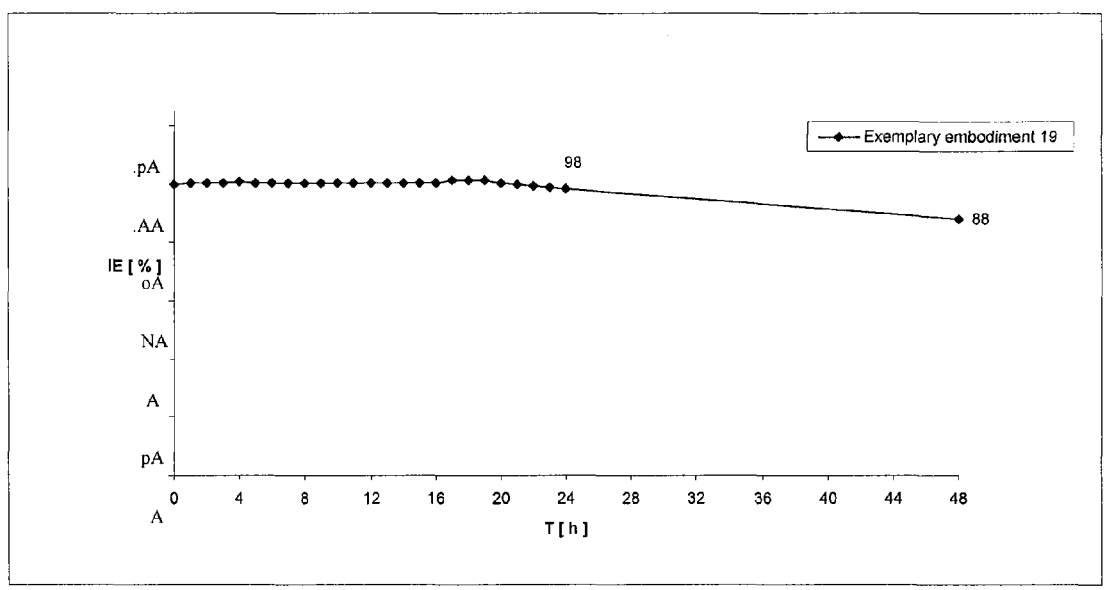
FIG. 2 A plot of the change in concentration of the compound of example 19 over time in an aqueous, slightly alkaline solution.
Figure 3:
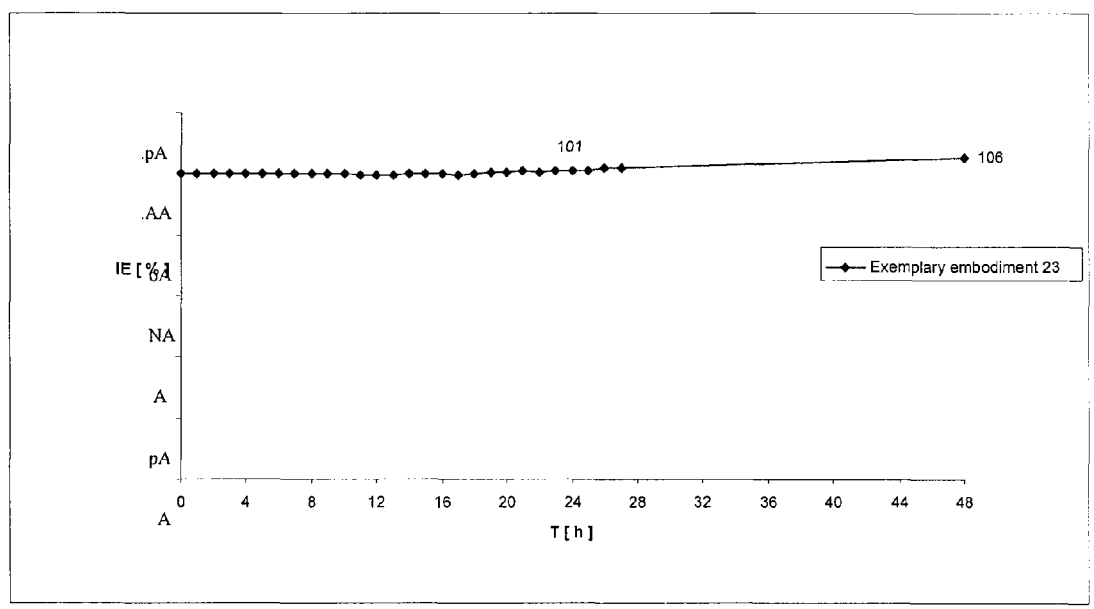
FIG. 3 A plot of the change in concentration of the compound of example 23 over time in an aqueous, slightly alkaline solution.
Figure 4:
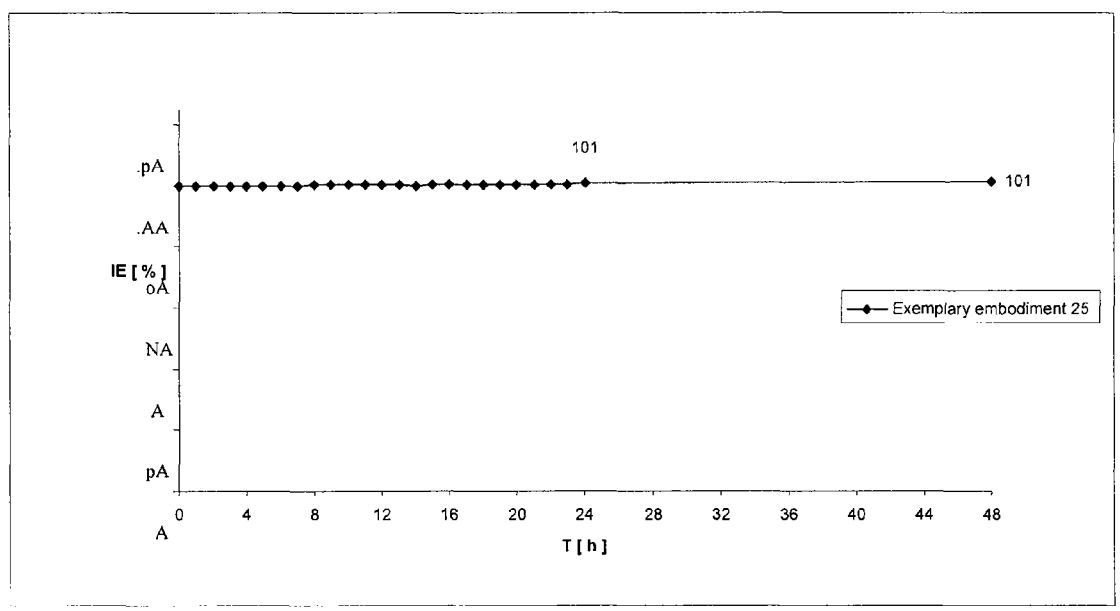
FIG. 4 A plot of the change in concentration of the compound of example 25 over time in an aqueous, slightly alkaline solution.
Figure 5:
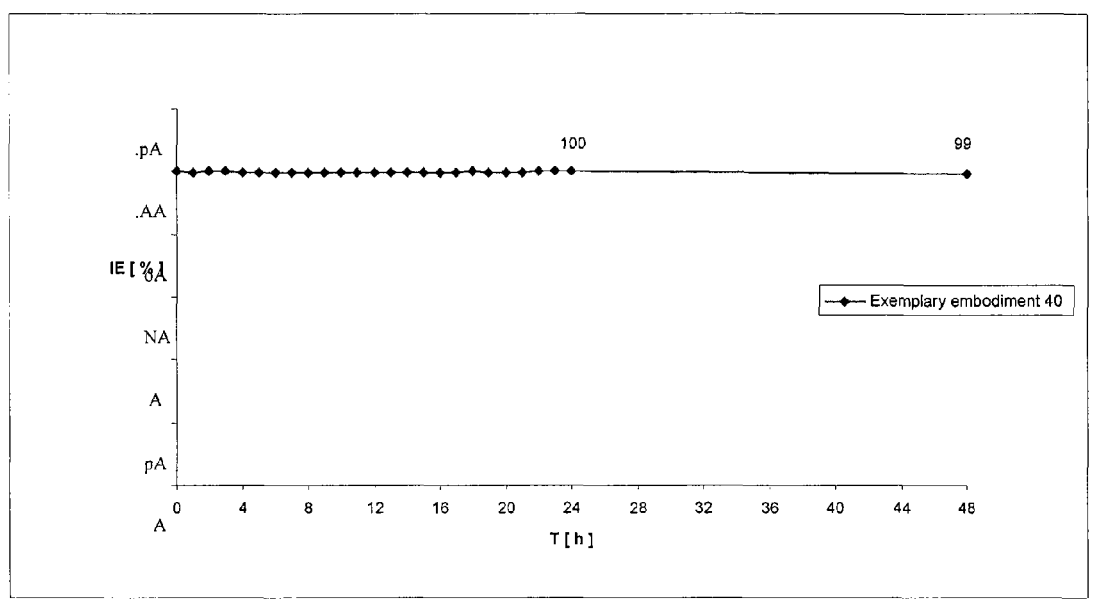
FIG. 5 A plot of the change in concentration of the compound of example 40 over time in an aqueous, slightly alkaline solution.

This assay provided the results shown in FIGS. 1-5. It is evident from the curves that the compounds of the invention are distinctly more stable in aqueous alkaline solution than lysobactin.

C. Exemplary Embodiments of Pharmaceutical Compositions

The compounds of the invention can be converted into pharmaceutical preparations in the following ways:

Tablet:
Composition:
 100 mg of the compound of example 1, 50 mg of lactose (monohydrate), 50 mg of maize starch (native), 10 mg of polyvinylpyrrolidone (PVP 25) (BASF, Ludwigshafen, Germany) and 2 mg of magnesium stearate.
Tablet weight 212 mg. Diameter 8 mm, radius of curvature 12 mm.
Production:
 The mixture of active ingredient, lactose and starch is granulated with a 5% solution (m/m) of the PVP in water. The granules are dried and then mixed with the magnesium stearate for 5 min. This mixture is compressed using a conventional tablet press (see above for format of the tablet). A compressive force of 15 kN is used as guideline for the compression.

Suspension which can be Administered Orally:
Composition:
 1000 mg of the compound of example 1, 1000 mg of ethanol (96%), 400 mg of Rhodigel (xanthan gum, FMC, Pennsylvania, USA) and 99 g of water.
 10 ml of oral suspension are equivalent to a single dose of 100 mg of the compound of the invention.
Production:
 The Rhodigel is suspended in ethanol, and the active ingredient is added to the suspension. The water is added while stirring. The mixture is stirred for about 6 h until the swelling of the Rhodigel is complete.

Solution which can be Administered Intravenously:
Composition:
 100-200 mg of the compound of example 1, 15 g of polyethylene glycol 400 and 250 g of water for injection.
Production:
 The compound of example 1 is dissolved together with polyethylene glycol 400 in the water with stirring. The solution is sterilized by filtration (pore diameter 0.22 μm) and dispensed into heat-sterilized infusion bottles under aseptic conditions. The latter are closed with infusion stoppers and crimped caps.

What is claimed is:
1. A compound of formula

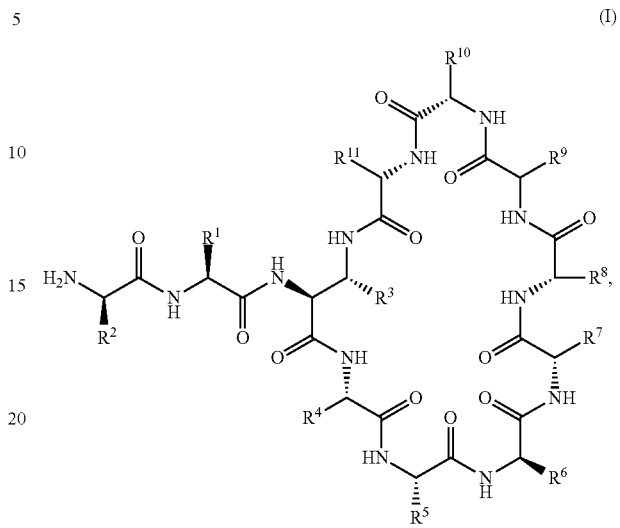

in which
$R^1$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl,
whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy,
$R^2$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl,
whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy,
$R^3$ represents hydrogen, $C_1$-$C_4$-alkyl, $C_3$-$C_7$-cycloalkyl, $C_3$-$C_7$-cycloalkylmethyl, phenyl, benzyl, 5- or 6-membered heteroaryl or 5- or 6-membered heteroarylmethyl,
whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl, $C_1$-$C_4$-alkylaminocarbonyl and 5- or 6-membered heterocyclyl which is bonded via nitrogen,
$R^4$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl,
whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^5$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^6$ represents $C_1$-$C_6$-alkyl, whereby alkyl is substituted with a substituent selected from the group consisting of amino, 1,4,5,6-tetrahydropyrimidin-2-ylamino, [amino-(imino)methyl]amino, 2-pyridyl, 3-pyridyl and 4-pyridyl, $R^7$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl or trimethylsilylmethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^8$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^9$ represents hydrogen, $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl or 2-amino-2-oxoethyl, whereby alkyl may be substituted with 1 to 3 substituents selected independently of one another from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^{10}$ represents hydrogen, $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^{11}$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, or one of the salts thereof, except a compound of formula

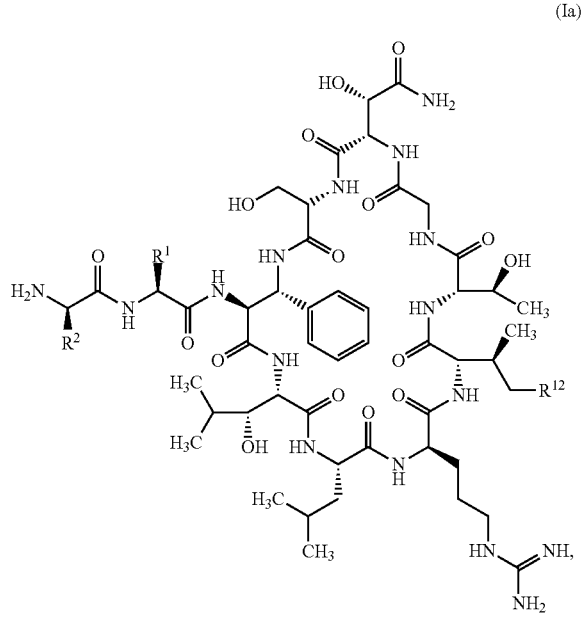

(Ia)

in which $R^1$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl, whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy, $R^2$ represents 2-methylprop-1-yl, 2,2-dimethylprop-1-yl, 2,2-dimethylbut-1-yl, trimethylsilylmethyl, benzyl, 2-pyridylmethyl, 3-pyridylmethyl, 2-thienylmethyl, 3-thienylmethyl or 1,3-thiazol-4-ylmethyl, whereby benzyl, 2-pyridylmethyl, 3-pyridylmethyl, 2-thienylmethyl, 3-thienylmethyl and 1,3-thiazol-4-ylmethyl may be substituted with 1 or 2 substituents selected independently of one another from the group consisting of halogen, trifluoromethyl, methyl and methoxy, and $R^{12}$ represents hydrogen or methyl, or one of the salts thereof.

2. The compound of claim 1, whereby $R^{10}$ represents $C_1$-$C_6$-alkyl, $C_3$-$C_7$-cycloalkyl, $C_3$-$C_7$-cycloalkylmethyl, phenyl, benzyl, 5- or 6-membered heteroaryl, 5- or 6-membered heteroarylmethyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl, cycloalkylmethyl, phenyl, benzyl, heteroaryl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, or one of the salts thereof.

3. The compound of claim 1, whereby $R^1$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^2$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^3$ represents $C_1$-$C_4$-alkyl, phenyl, benzyl, 2-pyridyl, 3-pyridyl or 4-pyridyl, whereby phenyl, benzyl, 2-pyridyl, 3-pyridyl and 4-pyridyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^4$ represents $C_1$-$C_6$-alkyl, $C_3$-$C_7$-cycloalkylmethyl, benzyl, 5- or 6-membered heteroarylmethyl or trimethylsilylmethyl, whereby alkyl may be substituted with a hydroxy substituent, and whereby cycloalkylmethyl, benzyl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^5$ represents $C_1$-$C_6$-alkyl, $C_3$-$C_7$-cycloalkylmethyl, phenyl, benzyl, 5- or 6-membered heteroarylmethyl or trimethylsilylmethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkylmethyl, phenyl, benzyl and heteroarylmethyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^6$ represents $C_1$-$C_6$-alkyl, whereby alkyl is substituted with a substituent selected from the group consisting of amino, 1,4,5,6-tetrahydropyrimidin-2-ylamino, [amino-(imino)methyl]amino, 2-pyridyl, 3-pyridyl and 4-pyridyl, $R^7$ represents $C_1$-$C_6$-alkyl, $C_3$-$C_7$-cycloalkylmethyl, phenyl, benzyl, 5- or 6-membered heteroarylmethyl or trimethylsilylmethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkylmethyl, phenyl, benzyl and heteroarylmethyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, $R^8$ represents $C_1$-$C_6$-alkyl, $C_3$-$C_7$-cycloalkylmethyl, benzyl, 5- or 6-membered heteroarylmethyl or trimethylsilylmethyl, whereby alkyl may be substituted with a hydroxy substituent, and whereby cycloalkylmethyl, benzyl and heteroarylmethyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy, $C_1$-$C_4$-alkylamino, hydroxycarbonyl, $C_1$-$C_4$-alkoxycarbonyl, aminocarbonyl and $C_1$-$C_4$-alkylaminocarbonyl, $R^9$ represents hydrogen, $C_1$-$C_6$-alkyl, $C_3$-$C_7$-cycloalkyl, phenyl, trimethylsilylmethyl or 2-amino-2-oxoethyl, whereby methyl may be substituted with a substituent selected from the group consisting of hydroxy, amino and mercapto, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, $R^{10}$ represents hydrogen, $C_1$-$C_6$-alkyl, $C_3$-$C_7$-cycloalkyl, phenyl, trimethylsilylmethyl, 2-amino-2-oxoethyl, 2-amino-1-hydroxy-2-oxoethyl, (aminosulfonyl)(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, $R^{11}$ represents methyl or ethyl, whereby methyl and ethyl may be substituted with a substituent selected from the group consisting of hydroxy, amino, mercapto, 1,4,5,6-tetrahydropyrimidin-2-ylamino and [amino(imino)methyl]amino, or one of the salts thereof, except the compounds of formula (Ia), in which $R^1$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, $R^2$ represents 2-methylprop-1-yl, 2,2-dimethylprop-1-yl, 2,2-dimethylbut-1-yl, trimethylsilylmethyl, benzyl, 2-pyridylmethyl or 3-pyridylmethyl, whereby benzyl, 2-pyridylmethyl and 3-pyridylmethyl may be substituted with 1 or 2 substituents selected independently of one another from the group consisting of halogen, trifluoromethyl and methyl, and $R^{12}$ represents hydrogen or methyl, or one of the salts thereof.

4. The compound of claim 3, whereby $R^1$ represents 2-methylprop-1-yl, 2,2-dimethylprop-1-yl, 2,2-dimethylbut-1-yl, trimethylsilylmethyl or benzyl, whereby benzyl may be substituted with 1 or 2 substituents selected independently of one another from the group consisting of halogen, trifluoromethyl and methyl, or one of the salts thereof.

5. The compound of claim 3, whereby $R^3$ represents phenyl, benzyl, 2-pyridyl, 3-pyridyl or 4-pyridyl, whereby phenyl, benzyl, 2-pyridyl, 3-pyridyl and 4-pyridyl may be substituted with 1 to 4 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-alkylamino, or one of the salts thereof.

6. The compound of claim 3, whereby $R^{10}$ represents $C_1$-$C_6$-alkyl, $C_3$-$C_7$-cycloalkyl, phenyl, trimethylsilylmethyl, 2-amino-2-oxoethyl, 2-amino-1-hydroxy-2-oxoethyl, (aminosulfonyl)-(hydroxy)methyl, 2-($C_1$-$C_4$-alkylamino)-2-oxoethyl or 2-($C_1$-$C_4$-alkylamino)-1-hydroxy-2-oxoethyl, whereby alkyl may be substituted with a substituent selected from the group consisting of halogen, hydroxy, amino, mercapto, 1,4,5,6-tetrahydropyrimidin-2-ylamino and [amino(imino)methyl]amino, and whereby cycloalkyl and phenyl may be substituted with 1 to 4 substituents selected independently of one another from the group consisting of halogen, cyano, hydroxy, amino, trifluoromethyl, trifluoromethoxy, $C_1$-$C_4$-alkyl, $C_1$-$C_4$-alkoxy and $C_1$-$C_4$-alkylamino, or one of the salts thereof.

7. The compound of claim 1, whereby $R^1$ represents 2,2-dimethylprop-1-yl, 2,2-dimethylbut-1-yl, trimethylsilylmethyl or 3-pyridylmethyl, $R^2$ represents 2,2-dimethylprop-1-yl, 2,2-dimethylbut-1-yl, trimethylsilylmethyl or 3-pyridylmethyl, $R^3$ represents $C_1$-$C_4$-alkyl, 3-pyridyl or phenyl, whereby 3-pyridyl or phenyl may be substituted with a substituent selected from the group consisting of halogen, cyano, methyl, methoxy, dimethylamino and diethylamino, $R^4$ represents —CH(OH)—$C_1$-$C_5$-alkyl or —CH(OH) phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, $R^5$ represents $C_1$-$C_6$-alkyl, $C_3$-$C_7$-cycloalkylmethyl, benzyl or trimethylsilylmethyl, $R^6$ represents linear $C_2$-$C_4$-alkyl, whereby alkyl is substituted with a substituent selected from the group consisting of amino, 1,4,5,6-tetrahydropyrimidin-2-ylamino and [amino(imino)methyl]amino, $R^7$ represents $C_1$-$C_6$-alkyl, $C_3$-$C_7$-cycloalkylmethyl, benzyl or trimethylsilylmethyl, $R^8$ represents $C_1$-$C_4$-alkyl, —CH$_2$—OH, —CH(OH)—$C_1$-$C_5$-alkyl or —CH(OH)-phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, and $R^9$ represents hydrogen, $C_1$-$C_6$-alkyl, hydroxymethyl or 2-amino-2-oxoethyl, $R^{10}$ represents hydrogen, $C_1$-$C_4$-alkyl, 2-amino-2-oxoethyl or 2-amino-1-hydroxy-2-oxoethyl, whereby $C_1$-$C_4$-alkyl may be substituted with a substituent selected from the group consisting of amino and hydroxy, with the exception that $R^{10}$ is not 4-aminobut-1-yl, $R^{11}$ represents methyl, whereby methyl is substituted with a substituent selected from the group consisting of hydroxy and amino, or one of the salts thereof, except the compounds of formula (Ia), in which $R^1$ represents 2,2-dimethylprop-1-yl, 2,2-dimethylbut-1-yl, trimethylsilylmethyl or 3-pyridylmethyl, $R^2$ represents 2,2-dimethylprop-1-yl, 2,2-dimethylbut-1-yl, trimethylsilylmethyl or 3-pyridylmethyl, and $R^{12}$ represents hydrogen or methyl, or one of the salts thereof.

8. The compound of claim 7, whereby $R^1$ represents 2,2-dimethylprop-1-yl, 2,2-dimethylbut-1-yl or trimethylsilylmethyl, or one of the salts thereof.

9. The compound of claim 7, whereby $R^2$ represents 2,2-dimethylprop-1-yl or 3-pyridylmethyl, or one of the salts thereof.

10. The compound of claim 7, whereby $R^3$ represents phenyl, whereby phenyl may be substituted with a substituent selected from the group consisting of halogen, cyano, methyl, methoxy, dimethylamino and diethylamino, or one of the salts thereof.

11. The compound of claim 7, whereby $R^8$ represents —CH(OH)—$C_1$-$C_5$-alkyl or —CH(OH)phenyl, whereby —CH(OH)phenyl may be substituted with 1 to 3 substituents selected independently of one another from the group consisting of halogen, cyano, trifluoromethyl, trifluoromethoxy, $C_1$-$C_4$-alkyl, $C_1$-$C_4$-alkoxy and $C_1$-$C_4$-dialkylamino, and or one of the salts thereof.

12. The compound of claim 7, whereby $R^{10}$ represents methyl, ethyl, 2-amino-2-oxoethyl or 2-amino-1-hydroxy-2-oxoethyl, whereby methyl and ethyl may be substituted with a hydroxy substituent, or one of the salts thereof.

13. A method for preparing a compound of formula (I) of claim 1, whereby

[A] a compound of formula

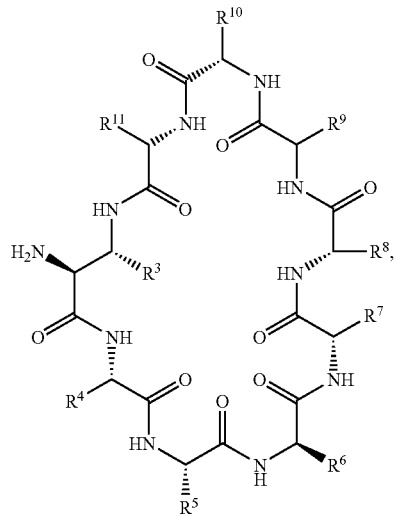

(II)

in which $R^3$, $R^4$, $R^5$, $R^6$, $R^7$, $R^8$, $R^9$, $R^{10}$ and $R^{11}$ have the meaning indicated in claim 1, is first reacted with a compound of formula

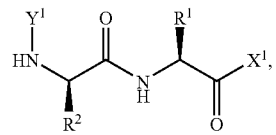

(III)

in which $R^1$ and $R^2$ have the meaning indicated in claim 1, $Y^1$ represents tert-butoxycarbonyl or benzyloxycarbonyl, and $X^1$ represents halogen or hydroxy, and subsequently with an acid, by hydrogenolysis or with an acid and by hydrogenolysis or

[B] a compound of formula

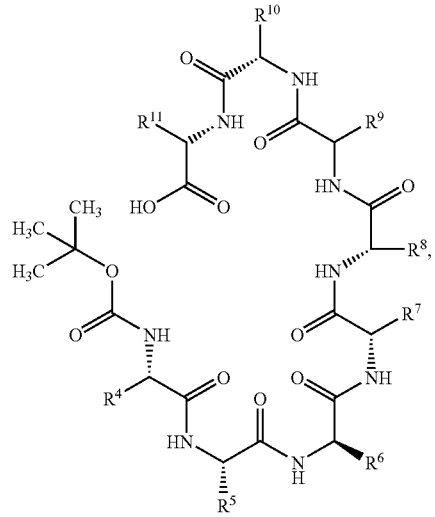

(IV)

in which $R^4$, $R^5$, $R^6$, $R^7$, $R^8$, $R^9$, $R^{10}$ and $R^{11}$ have the meaning indicated in claim 1, is first reacted with a compound of formula

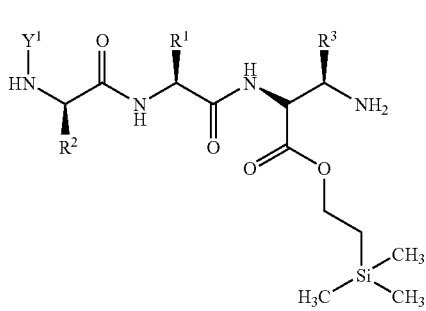
(V)

in which
R$^1$, R$^2$ and R$^3$ have the meaning indicated in claim 1, and Y$^1$ represents tert-butoxycarbonyl or benzyloxycarbonyl, and subsequently in a 4-stage synthesis
a) with a fluoride reagent such as tetrabutylammonium fluoride,
b) with an acid,
c) with a dehydrating reagent, where appropriate in the presence of a base,
and
d) by hydrogenolysis.

14. The method of claim 13, whereby the compound of formula (II) is prepared by reacting a compound of formula

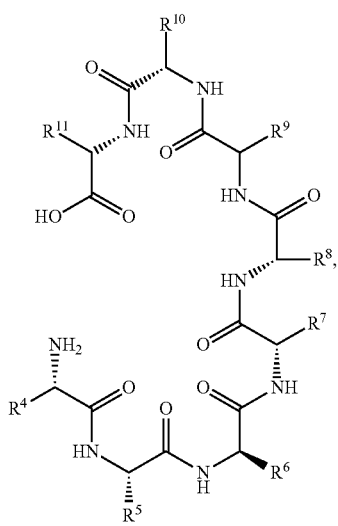
(VI)

first with a compound of formula

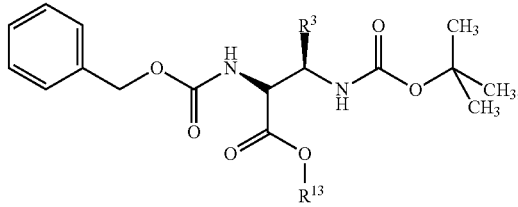
(VII)

in which

R$^{13}$ represents cyanomethyl, p-nitrophenyl, o-nitrophenyl, 2,4-dinitrophenyl, 2,4,5-trichlorophenyl, pentachlorophenyl, pentafluorophenyl (Pfp), N-hydroxyphthalimidyl, N-hydroxysuccinimidyl (O-Su), 1-hydroxypiperidinyl or 5-chloro-8-hydroxyquinolinyl, and subsequently in a 3-stage synthesis a) with an acid, b) with a dehydrating reagent, where appropriate in the presence of a base, and c) by hydrogenolysis.

15. A medicament which comprises a compound of claim 1 and at least one additional compound having antibacterial activity.

16. A medicament comprising a compound of claim 1 in combination with an inert, nontoxic, pharmaceutically acceptable excipient.

17. The medicament of claim 16 which is formulated for intravenous administration.

18. A method for controlling bacterial infections in humans or animals, which comprises administering an antibacterially effective amount of at least one compound of claim 1 or a medicament of claim 15 to the human or animal subject in need thereof.

19. The method of claim 18, wherein the compound or the medicament is administered orally or parenterally.

20. The method of claim 13, wherein X$^1$ represents bromine, chlorine, fluorine, or hydroxy.

* * * * *